(12) United States Patent
Yadav et al.

(10) Patent No.: US 7,273,746 B2
(45) Date of Patent: Sep. 25, 2007

(54) DIACYLGLYCEROL ACYLTRANSFERASES FOR ALTERATION OF POLYUNSATURATED FATTY ACIDS AND OIL CONTENT IN OLEAGINOUS ORGANISMS

(75) Inventors: Narendra S. Yadav, Chadds Ford, PA (US); Zhixiong Xue, Chadds Ford, PA (US); Hongxiang Zhang, Chadds Ford, PA (US)

(73) Assignee: E.I. duPont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/024,544

(22) Filed: Dec. 29, 2004

(65) Prior Publication Data

US 2006/0094086 A1     May 4, 2006

Related U.S. Application Data

(60) Provisional application No. 60/624,812, filed on Nov. 4, 2004.

(51) Int. Cl.
| | | |
|---|---|---|
| *C12N 1/16* | (2006.01) | |
| *C12N 1/13* | (2006.01) | |
| *C12N 1/19* | (2006.01) | |
| *C12N 1/18* | (2006.01) | |
| *C12N 9/10* | (2006.01) | |
| *C12P 21/06* | (2006.01) | |
| *C07H 21/04* | (2006.01) | |

(52) U.S. Cl. .............. 435/254.2; 435/252.3; 435/257.2; 435/254.11; 435/69.1; 435/6; 435/193; 435/134; 536/23.2

(58) Field of Classification Search ............ 435/193, 435/69.1, 254.11, 134; 536/23.3
See application file for complete search history.

(56) References Cited

U.S. PATENT DOCUMENTS

| | | |
|---|---|---|
| 6,100,077 A | 8/2000 | Sturley et al. |
| 6,344,548 B1 | 2/2002 | Farese, Jr. et al. |
| 6,552,250 B1 | 4/2003 | Nykiforuk et al. |
| 2004/0078836 A1 | 4/2004 | Farese, Jr. et al. |
| 2004/0088759 A1 | 5/2004 | Cahoon et al. |

OTHER PUBLICATIONS

U.S. Appl. No. 10/882,760, filed Jul. 1, 2004, Yadav et al.
Hongyuan Yang et al., Sterol Esterification in Yeast: A Two-Gene Process, Science, vol. 272:1353-1356, 1996.
Heidemarie Mullner et al., Dynamics of neutral lipid storage in yeast, Acta Biochimca Polonica, vol. 51:323-347, 2004.
D. Sorger et al., Triacylglycerol biosynthesis in yeast, Appl. Microbiol. Biotechnol., 61:289-299, 2003.
Line Sandager et al., Storage Lipid Synthesis Is Non-essential in Yeast, J. Biol. Chem., vol. 277(8):6478-6482, 2002.
Anders Dahlqvist et al., Phospholipid:diacylglycerol acyltransferase: An enzyme that catalyzes the acyl-CoA-independent formation of triacylglycerol in yeast and plants, PNAS, vol. 97(12):6487-6492, 2000.
L. Sandager et al., An acyl-CoA:cholesterol acyltranseferase (ACAT)-related gene is involved in the accumulation of triacylglycerols in *Saccharomyces cerevislae*, Biochemical Society Transactions, vol. 28(6):700-702, 2000.
Kathryn D. Lardizabal et al., DGAT2 Is a New Diacylglycerol Acyltransferase Gene Family, J. Biol. Chem., vol. 276(42):38862-38869, 2001.
National Center for Biotechnology Information General Identifier No. 41387496, Accession No. AY445635, Jul. 1, 2004, K. Giannoulia et al., Olive DGAT1 CDNA.
National Center for Biotechnology Information General Identifier No. 15099950, Accession No. AF384160, Oct. 16, 2001, S. Cases et al., Cloning of DGAT2, A Second Mammalian Diacylglycerol.
National Center for Biotechnology Information General Identifier No. 17865334, Accession No. NM_053437, Apr. 20, 2005. J. J. Liang et al., Overexpression of Human Diacylglycerol Acyltransferase 1, Acyl-CoA:Cholesterol Acyltransferase 1, or Acyl-CoA:Cholesterol Acyltransferase 2 Stimulates Secretion of Apolipoprotein B-Containing Lipoproteins in MCA-RH7777 Cells.
National Center for Biotechnology Information General Identifier No. 27819635, Accession No. NM_174693, Apr. 23, 2005, C. Kuhn et al., Evidence for Multiple Alleles at the DGAT1 Locus Better Explains a Quantitative Trait Locus With Major Effect on Milk Fat Content in Cattle.
National Center for Biotechnology Information General Identifier No. 21684669, Accession No. AY116586, Dec. 30, 2002, D. Nonneman et al., Linkage Mapping of Porcine DGAT1 to a Region of Chromosome 4 That Contains QTL for Growth and Fatness.
National Center for Biotechnology Information General Identifier No. 33113254, Accession No. AY327327, Nov. 3, 2004, F. Quittnat et al., on the Biogenesis of Lipid Bodies in Ancient Eukaryotes:Synthesis of Triacylglycerols by a Toxoplasma DGAT1-Related Enzyme.
National Center for Biotechnology Information General Identifier No. 33113252, Accession No. AY327326, Nov. 3, 2004, F. Quittnat et al., on the Biogenesis of Lipid Bodies in Ancient Eukaryotes:Synthesis of Triacylglycerols by a Toxoplasma DGAT1-Related Enzyme.

(Continued)

*Primary Examiner*—Rebecca E. Prouty
*Assistant Examiner*—Iqbal Chowdhury

(57) ABSTRACT

Acyltransferases are provided, suitable for use in the manufacture of microbial oils enriched in omega fatty acids in oleaginous yeast (e.g., *Yarrowia lipolytica*). Specifically, genes encoding diacylglycerol acyltransferase (DGAT1) have been isolated from *Y. lipolytica* and *Mortierella alpina*. These genes encode enzymes that participate in the terminal step in oil biosynthesis in yeast. Each is expected to play a key role in altering the quantity of polyunsaturated fatty acids produced in oils of oleaginous yeasts.

8 Claims, 28 Drawing Sheets

OTHER PUBLICATIONS

National Center for Biotechnology Information General Identifier No. 10803052, Accession No. AF298815, Oct. 16, 2000, S.-K. Hwang et al., Isolation of Perilla Frutescens Diacylglycerol Acyltransferase CDNA.

National Center for Biotechnology Information General Identifier No. 5579407, Accession No. AF164434, Nov. 30, 1999, C.L. Nykiforuk et al., Isolation and Characterization of a CDNA Encoding a Second Putative Diacylglycerol Acyltransferase From a Microspore-Derived Cell Suspension Culture of *Brassica napus* L. CV Jet NEUF.

National Center for Biotechnology Information General Identifier No. 34582301, Accession No. Q876L2, Mar. 15, 2004, R.B. Langkjaer et al., Yeast Genome Duplication was Followed by Asynchronous Differentation of Duplicated Genes.

National Center for Biotechnology Information General Identifier No. 1703371, Accession No. P53629, May 1, 2005, H. Yang et al., Sterol Esterification in Yeast:A Two-Gene Process.

National Center for Biotechnology Information General Identifier No. 1703372, Accession No. Q10269, May 1, 2005, V. Wood et al., The Genome Sequence of *Schizosaccharomyces pombe*.

|   |   |   | Consensus | SEQ ID NO: |
|---|---|---|---|---|
| 1 | — — — — — — — — — — — — — — — — — M S S S T — — — — — — | Nc DAGAT1 | 19 |
| 1 | — — — — — — — — — — — — — — — — — — M N S A T — — — — — — | Fm DAGAT1 | 20 |
| 1 | — — — — — — — — — — — — — — — — — — M T E S T — — — — — — | Ma DGAT1 | 18 |
| 1 | M A A A T A T G L D L A A Q E G A Q Q R R S T — — — — — — | Mg DAGAT1 | 21 |
| 1 | — — — — — — — — — — — — — — — — — — — — — — — — — — — — | An DAGAT1 | 22 |
| 1 | — — — — — — — — — — — — M E V R R R K I D V L K — — — — — | Yl DGAT1 | 14 |
| 1 | — — — — — — — — — — — — — M G D R G G A G S S — — — — — — | Mm DGAT1 | 129 |
| 1 | — — — — — — — — — — — — M A I S D E P E S V A T — — — — — | Gm DGAT1 | 130 |
| 1 | — — — — — — — — — — — — M A I L D S A G V T T V T E N G G G E | At DGAT1 | 131 |
| 1 | — — — — — — — — — — — — M V G S D G D G D G G G — — — — — | Os DGAT1 | 132 |
| 1 | — — — — — — — — — — — — M A I L D S P E I L D T S S S A D N | Pfdgat1 | 133 |
| 1 | — — — — — — — — — — — — M S K G N P D P H L P G S F L — — — — | Ta DGAT1 | 134 |

|   |   |   | Consensus |
|---|---|---|---|
| 6 | — — — — — — — — — — A T T T G L D P A V H T S N D — — — — — — | Nc DAGAT1 |
| 6 | — — — — — — — — — — — T T S T E T S N G S T S — — — — — — — — | Fm DAGAT1 |
| 6 | — — — — — — — — — — — T T T C A K E E G I A N — — — — — — — — | Ma DGAT1 |
| 24 | — — — — — — — — — — A T N Q S A D D D V T T N A D G — — — — — A | Mg DAGAT1 |
| 1 | — — — — — — — — — — — — — — — — — — — — — — — — — — — — | An DAGAT1 |
| 13 | — — — — — — — — — — A Q K N G Y E S G P P S R Q S — — — — — — | Yl DGAT1 |
| 11 | — — — — — — — R R R R T G S R - V S V Q G G S — — — — — | Mm DGAT1 |
| 13 | — A L N H S S L R R R P S - A T S T A G L F N S — — — — — | Gm DGAT1 |
| 20 | — F V D L D R L R R R K S R S D S S N G L L L S G S D N N S | At DGAT1 |
| 14 | — E A H A G G P R R R A G Q L R — — G R L R D E — — — — — — | Os DGAT1 |
| 20 | G A A H H T T L R R R Q S — A R S V P P L L D S D S N S L E | Pfdgat1 |
| 16 | — P S H G G P P P K P K T P P R T F R N L P S S — — — — — — | Ta DGAT1 |

|   |   |   | Consensus |
|---|---|---|---|
| 21 | — — — N — — — — — — — — — — — — — — — — — — — V I R R T H G T | Nc DAGAT1 |
| 18 | — — — — — — — — — — — — — — — — — — — — — — — V S K — — | Fm DAGAT1 |
| 18 | — — — — — — — — — — — — — — — — — — — — — — — — — — — — | Ma DGAT1 |
| 41 | A A A P — — — — — — — — — — — — — — — — S L K G T T A D | Mg DAGAT1 |
| 1 | — — — — — — — — — — — — — — — — — — — — — — — — — — — — | An DAGAT1 |
| 28 | — S Q P — — — — — — — — — — — — — — — — S S R A S S R T | Yl DGAT1 |
| 26 | — — — — — — — — — — — — — — — — — — — — G P K V E E D E | Mm DGAT1 |
| 35 | P E T T T D S S — — — — — — — — — — G D D L A K D S | Gm DGAT1 |
| 49 | P S D D V G A P A D V R — — — — — — D R I D S V V N D D A | At DGAT1 |
| 35 | — A A P — — — — — — — — — — — — — — — — G S P P R P R P | Os DGAT1 |
| 49 | A E S A I N D S E N V R N D A N L I E N L R G A V E S E N | Pfdgat1 |
| 39 | — S T H — — — — — — — — — — — — — — — — G P A P S V A A | Ta DGAT1 |

FIG. 8A

```
                                                                    Consensus    SEQ
                                                                                 ID NO:
 30  E N G S T P N D K A N A G G E P E T E T K R H S K K V - V R   Nc DAGAT       19
 21  R N G H D V T R T N G N G T T T T S P P K K A G - - - - -    Fm DAGAT       20
 18  - - - S A A L P D I P P K M E D L K S S R K T G - - - - -    Ma DGAT1       18
 53  T N G T S N G N G N G N V D E D E Q T K A L R K A - F T      Mg DAGAT       21
  1  - - - - - - - - - - - - - - - - M A T R K T A - - - - -      An DAGAT       22
 39  R N K H S S S T L S L S G L T M K V Q K K P A G P P A N S K   Yl DGAT1       14
 34  V R D A A V S P D L G A G G D A P A P A P A P A H T R D K D   Mm DGAT1      129
 51  G S D D S I N S D D - A A V N S Q - - Q Q N E K Q D T D F S   Gm DGAT1      130
 72  Q G T A N L A G D N N G G G D N N G G G R G G G E G R G N A   At DGAT1      131
 46  R P R P R G G D S N G R S V L R P G G G G R G G G G D F S    Os DGAT1      132
 79  E K Q E S Y G K E E - G A K V K E N G E T S N G N G T D V M   Pfdgat1       133
 50  A T I A T T P P S A S A A P L P P T V H G E A A H G A A A A   Ta DGAT1      134

S . . S                      Consensus
 59  S - - - - K Y R H V E A V H S Q S R P S C L S H D T T E S -   Nc DAGAT
 45  Q - - - - K Y R H V A A V H K K T R P S C L S H D S D A A -   Fm DAGAT
 39  S - - - - S Y K H T F P V H T K T I P S P L S K E A P P E -   Ma DGAT1
 82  R - - - - K Y R H V A L H S Q A R P S T L S H D S E A S -     Mg DAGAT
  8  - - - - - I Y R H A V A V H S Q V Q H S C L S R D S T K A -   An DAGAT
 69  T - - - - P F L H I K P V H T C C S T S M L S R D Y D G S N   Yl DGAT1
 64  G R T S V G D G Y W D L R C H R L Q D S L F S S D S G F S -   Mm DGAT1
 78  V L K - F A Y R P S V P A H R K V K E S P L S S D T I F R -   Gm DGAT1
102  D A T - F T Y R P S V P A H R R A R E S P L S S D A I F K -   At DGAT1
 76  A - - - F T F R A A A P V H R K A K E S P L S S D A I F K -   Os DGAT1
108  A V K - F T F R P A A P A H R K N K E S P L S S D A I F K -   Pfdgat1
 80  A R R D A L L P G V G A A H R R V K E S P L S S D A I F R -   Ta DGAT1

. . . . G . . N . . . . L                                   Consensus
 84  P S F L G F R N L M V I V L A N N S H - - - - - - - - Q Y G   Nc DAGAT
 70  P S F I G F R N L M V I V L G I Y H I - - - - - G M S Q F D   Fm DAGAT
 64  - S Y R G F V N L G M L L L F G N N I R L I I E N Y L K Y G   Ma DGAT1
107  P S F V G F R N L M V I V L - - - - - - - - - - - - - - -    Mg DAGAT
 32  T S F I G F R N L M V V V L V A M N L R L V I E N F L K Y G   An DAGAT
 95  P S F K G F K N I G M I I L I V G N - - - - - - - - - - -    Yl DGAT1
 93  N - Y R G I L N W C V V M L I L S N A R L F L E N L I K Y G   Mm DGAT1
106  Q S H A G L F N L C I V V L V A V N S R L I I E N L M K Y G   Gm DGAT1
130  Q S H A G L F N L C V V L I A V N S R L I I E N L M K Y G    At DGAT1
102  Q S H A G L F N L C I V V L V A V N S R L I I E N L M K Y G   Os DGAT1
136  Q S H A G L F N L C I V V L V A V N S R L I I E N L M K Y G   Pfdgat1
109  Q S H A G L L N L C I V V L I A V N S R L I I E N L M K Y G   Ta DGAT1
     Motif #1
```

FIG. 8B

|     |                                                                   | Consensus | SEQ ID NO: |
|-----|-------------------------------------------------------------------|-----------|------------|
| 106 | V L I C I - - G C H D F R K S D - - I N L G L L Y F L I P         | Nc DAGAT  | 19 |
| 95  | S E Q P I - - D T A S Y R - Q D - - I F L G L L Y F L I P         | Fm DAGAT  | 20 |
| 93  | F L S I - - P G S S V S K Q D - - W I L A A L T H A I L P         | Ma DGAT1  | 18 |
| 121 | - - - - - - - - - - - - - - - - - - - - - - - - - - - - - -      | Mg DAGAT  | 21 |
| 62  | V L I C I - - R C H D Y R K Q D - - V V I G A I L F A L V P       | An DAGAT  | 22 |
| 113 | - - L R L - - A F E N Y L K Y G - - I S N P F F D P K I T P       | Yl DGAT1  | 14 |
| 122 | I L V D P - I Q V V S L F L K D P Y S W P A P C V I I A S N       | Mm DGAT1  | 129 |
| 136 | W L I K S G F W F S S K S L R D - - - W P L F M C C L S L V       | Gm DGAT1  | 130 |
| 160 | W L I R T D F W F S S R S L R D - - - W P L F M C W I S L S       | At DGAT1  | 131 |
| 132 | L L I R A G F W F N D K S L R D - - - W P L L M C C L S L P       | Os DGAT1  | 132 |
| 166 | W L I K S G F W F S S T S L R D - - - W P L L M C C L S L P       | Pfdgat1   | 133 |
| 139 | L L I R A G F W F S A R S L G D - - - W P L L M C C L T L P       | Ta DGAT1  | 134 |

|     |                                                             | Consensus |
|-----|-------------------------------------------------------------|-----------|
| 132 | C H L F I A Y I I E Y Y A A V Q A R A E R N V S A S E - - - | Nc DAGAT  |
| 120 | C H L L A A Y L I E L A A A Q Q A R G - - - - - S - - -     | Fm DAGAT  |
| 119 | V N L I L A Y K L E S W A K E R A V G Y R K R R S D E P I A | Ma DGAT1  |
| 121 | - - - - - - - - E L L A A Q Q A R N S R - - - G Y F - - -   | Mg DAGAT  |
| 88  | C Q L L C S Y F I E L A A S R H A Q R - - - - - - - - - -   | An DAGAT  |
| 137 | S E W Q L S G - - L L I V V A Y A H I - - - - - - - - - -   | Yl DGAT1  |
| 151 | I F V V A A F Q I E K R L A V G A L T - - - - - - - - - -   | Mm DGAT1  |
| 163 | V F P F A A F I V E K L A Q R K C I P - - - - - - - - - -   | Gm DGAT1  |
| 187 | I F P L A A F T V E K L V L Q K Y I S - - - - - - - - - -   | At DGAT1  |
| 159 | A F P L G A F A V E K L A F N N V I T - - - - - - - - - -   | Os DGAT1  |
| 193 | V F A L A S F L V E K L V K L N Y I P - - - - - - - - - -   | Pfdgat1   |
| 166 | I F P L A A L M T E K W A Q R K L I R - - - - - - - - - -   | Ta DGAT1  |

|     |                                                             | Consensus |
|-----|-------------------------------------------------------------|-----------|
| 159 | - - - Q N A K E H Q H Q D G T N S P T E E Q H R K F Q - - - | Nc DAGAT  |
| 140 | - - - - - - L K R Y N D S A S G G P S D Q E R K K F H - - - | Fm DAGAT  |
| 149 | Q E S T K A V X A G D N D A I K T T K P A K A Q D L T P E A | Ma DGAT1  |
| 136 | - - - N R G R T G S S R D G S T S P T E D E S R R F V - - - | Mg DAGAT  |
| 107 | - - - - - - V I G R A K K Q D K D R I L N E S K - - - - - - | An DAGAT  |
| 154 | - - - - - - L M A Y A I E S A A K L L F L S S K - - - - - - | Yl DGAT1  |
| 170 | - - - - - - - - - - - - - - - - - - - - - - - - - - - - -  | Mm DGAT1  |
| 182 | - - - - - - - - - - - - - - - - - - - - - - - - - - - - -  | Gm DGAT1  |
| 206 | - - - - - - - - - - - - - - - - - - - - - - - - - - - - -  | At DGAT1  |
| 178 | - - - - - - - - - - - - - - - - - - - - - - - - - - - - -  | Os DGAT1  |
| 212 | - - - - - - - - - - - - - - - - - - - - - - - - - - - - -  | Pfdgat1   |
| 185 | - - - - - - - - - - - - - - - - - - - - - - - - - - - - -  | Ta DGAT1  |

FIG. 8C

```
                     . . . . . . . . . H . . . . . . . . . . . . . . . . . . . .   Consensus      SEQ
                                                                                                  ID NO:
183 - - - S T W K L V R L L H A I N V T T A L V L T S Y V V Y Y   Nc DAGAT:        19
161 - - - K T W V I V A W A H L F N I T L A L V L T T W V V Y F   Fm DAGAT:        20
179 L A R K E Q S T V G W L H V F N L F T I V A W P S F M S Y F   Ma DGAT1         18
160 - - - S T W K L I A L V H G I N V N S A L I T T Y T V Y F     Mg DAGAT:        21
125 - - - R T W F A I A L L H S I I S F F G L A A T S Y V I F Y   An DAGAT:        22
172 - - - H H Y M A V G L L H T M N T L S S I S L L S Y V V Y Y   Yl DGAT1         14
170 - - - - - E Q M G L L L H V V N L A T I I C F P A A V A L L   Mm DGAT1        129
182 - - - - - E P V V V V L H I I I T S T S L F Y P V L V I L R   Gm DGAT1        130
206 - - - - - E P V G I F L H I I I T M T E V L Y P V Y V T L R   At DGAT1        131
178 - - - - - D A V A T C L H I F L S T T E I V Y P V L V I L K   Os DGAT1        132
212 - - - - - E W V A V F L H V T I T T V E I L F P V V V I L R   Pfdgat1         133
185 - - - - - D H V S I L L H I I I T T T V L I Y P V V V I L K   Ta DGAT1        134

. . . . . . . . . . . . . . . . . . L K . . S . . . .         Consensus

210 H I H H P L I G T L T E V H A - I V V W L K T A S Y A F T N   Nc DAGAT:
188 K I H H P L I G T L T E M H A - I A V W L K T A S Y A F T N   Fm DAGAT:
209 M I Y H P F V A M S C L M N G - L I L F L K M T S F A L V N   Ma DGAT1
187 H I H H P L I G T L T E M H A - V I V W L K T A S Y A F T N   Mg DGAT:
152 Y V N H P G I G T V C E V Q V - I I V S L K S S Y A L T N     An DAGAT:
199 Y L P N P V A G T I V E F V A - V I L S L K L A S Y A L T N   Yl DGAT1
195 V E S I T P V G S V F A L A S Y S I M F L K L Y S Y R D V N   Mm DGAT1
207 C D S A F V S G V T L M L F S - C V V W L K L V S Y A H T N   Gm DGAT1
231 C D S A F L S G V T L M L L T - C I V W L K L V S Y A H T S   At DGAT1
203 C D S A V L S G F L L I F I A - C I V W L K L V S F A H T N   Os DGAT1
237 C D S A V L S G V T L M L F A - C T V W L K L V S Y A H T N   Pfdgat1
210 C E S A V L S G F V L M F I A - S I T W L K L V S F A H T N   Ta DGAT1

. . . . . . R . . . . . . . . . . . . . . . . . . . . .       Consensus

239 - - - R D L R H A Y L H P A R - - - - - - - - - - - - - - -   Nc DAGAT:
217 - - - R D L R H A Y L H P V E - - - - - - - - - - - - - - -   Fm DAGAT:
238 - - - Q E L R A A Y I F G T P V D T F Q H M A K V H D I S -   Ma DGAT1
216 - - - R D L R H A Y L H P V K - - - - - - - - - - - - - - -   Mg DAGAT:
181 - - - R D L R R A M L G S P S - - - - - - - - - - - - - - -   An DAGAT:
228 - - - S D L R K A A I H A Q K L D K T Q D D N E K E S T S S   Yl DGAT1
225 L W C R Q R R V K A K A V S T - - - - - - - - - - - - - - -   Mm DGAT1
236 - - - Y D M R A L T K L V - - - - - - - - - - - - - - - - -   Gm DGAT1
260 - - - Y D I R S L A N A A - - - - - - - - - - - - - - - - -   At DGAT1
232 - - - H D I R Q L T M G G - - - - - - - - - - - - - - - - -   Os DGAT1
266 - - - Y D L R V L A K S L - - - - - - - - - - - - - - - - -   Pfdgat1
239 - - - Y D I R I L S Q S I - - - - - - - - - - - - - - - - -   Ta DGAT1
```

FIG. 8D

```
                                                              Consensus      SEQ
                                                                            ID NO:
251 - - - - - - - - - - - G E L D A L P G L Y A E C P Y P E N I T  Nc DAGAT:  19
229 - - - - - - - - - - - G E R E L V P E L Y T Q C P Y P Q N I T  Fm DAGAT:  20
264 - - - - - - G - - - K D L T K K E I F Q Y D I Q Y P D N I T    Ma DGAT1   18
228 - - - - - - - - - - - G E L D A L P E L Y K Q C P Y P N N I T  Mg DAGAT:  21
193 - - - - - - - - - - - A D S D - I P E L Y R S C P Y P R N I T  An DAGAT:  22
255 S S S S D D A E T L A D I D V I P A Y Y A Q L P Y P Q N V T    Yl DGAT1   14
240 - - - - - - - - - - - G K K V S G A A A Q Q A V S Y P D N L T  Mm DGAT1   129
246 - - - - - - - - - - E K G E A L L D T L N M D Y P Y N V S      Gm DGAT1   130
270 - - - - - - - - - - - D K - - - - - - A N P E V S Y Y V S      At DGAT1   131
242 - - - - - - - - - - K K V D N E L S T V D M D N L Q P P T      Os DGAT1   132
276 - - - - - - - - - - - D K W E A M S R Y W N L D Y A Y D V S    Pfdgat1    133
249 - - - - - - - - - - E K G A T H G S S I D E E N I K G P T      Ta DGAT1   134
                                                    Motif #2

. . . . . Y F . . A P T L . Y . . . . P . . . . . R . . . .   Consensus

271 M G N L C Y F W W A P T L V Y Q P V Y P R T A K I R W S F V  Nc DAGAT:
249 F S N L A Y F W W A P T L V Y Q P V Y P R T D K I R W G F V  Fm DAGAT:
285 L K N I G Y F W L A P T L C Y Q P S Y P R T T V F R K S F F  Ma DGAT1
248 M K N L C Y F W W A P T L I Y Q P V Y P R S G R I R W V F F  Mg DAGAT:
212 L G N L A Y F L W A P T L V Y Q P V Y P R T P R I R W S F V  An DAGAT:
285 L S N L L Y F W F A P T L V Y Q P V Y P K T E R I R P K H V  Yl DGAT1
260 Y R D L Y Y F I F A P T L C Y E L N F P R S P R I R K R F L  Mm DGAT1
265 F K S L A Y F L V A P T L C Y Q P S Y P R T P Y I R K G W L  Gm DGAT1
282 L K S L A Y F M V A P T L C Y Q P S Y P R S A C I R K G W V  At DGAT1
261 L G N L I Y F M M A P T L C Y Q P S Y P R T S C V R K G W L  Os DGAT1
295 F K S L A Y F M V A P T L C Y Q P S Y P R T A C I R K G W V  Pfdgat1
268 I N S V V Y F M L A P T L C Y Q P S Y P R T A F I R K G W V  Ta DGAT1

. . . . . . . . . . . . . . . . . Q . . . P . . . . . .   Consensus

301 A K R C G E V I C L S V F I W F L S A Q Y A T P V L R N S L  Nc DAGAT:
279 A K R V G E I F G L S V F I W V A S A Q Y A A P V L R N S L  Fm DAGAT:
315 L K R V A E I V T C L G M M Y F L V E Q Y A T P T L Q N S V  Ma DGAT1
278 F K R V A E V F C L S V C I W F L S A Q Y A T P V L V N S L  Mg DAGAT:
242 G K R L F E F V C L S V V M W L L S A Q Y A A P L L R N A T  An DAGAT:
315 I R N L F E L V S L C M L I Q F L I F Q Y A Y P I M Q S C L  Yl DGAT1
290 L R R V L E M L F F T Q L Q V G L I Q Q W M V P T I Q N S M  Mm DGAT1
295 F R Q L V K L I I F T G V M G F I I D Q Y I N P I V Q N S Q  Gm DGAT1
312 A R Q F A K L V I F T G F M G F I I E Q Y I N P I V R N S K  At DGAT1
291 I R Q I I L Y L I F T G L Q G F I I E Q Y I N P I V V N S Q  Os DGAT1
325 V R Q L I K L V I F T G L M G F I I E Q Y I N P I V Q N S Q  Pfdgat1
298 T R Q L I K C V V F T G L M G F I I E Q Y I N P I V Q N S K  Ta DGAT1
                                                Motif #3
```

FIG. 8E

|     |   |   |   |   |   |   |   |   |   |   |   |   |   | E |   |   |   | K | L |   |   |   |   |   |   |   |   | W | L |   | Consensus |     | SEQ ID NO: |
|---|---|---|---|---|---|---|---|---|---|---|---|---|---|---|---|---|---|---|---|---|---|---|---|---|---|---|---|---|---|---|---|---|---|
| 331 | D | K | I | A | S | - | - | L | D | I | P | S | I | V | E | R | L | L | K | L | S | T | I | S | L | I | I | W | L | A | Nc DAGAT | 19 |
| 309 | D | K | I | A | S | - | - | L | D | L | M | S | I | L | E | R | L | L | K | L | S | T | I | S | L | A | I | W | L | A | Fm DAGAT | 20 |
| 345 | R | A | F | D | E | - | - | L | A | F | G | T | I | L | E | R | V | L | K | L | S | T | T | S | V | I | I | W | L | L | Ma DGAT1 | 18 |
| 308 | D | K | I | A | S | - | - | L | D | M | P | A | I | L | E | R | L | L | K | L | S | T | I | S | L | A | I | W | L | A | Mg DAGAT | 21 |
| 272 | Q | K | I | A | T | - | - | L | D | I | A | S | I | L | E | R | G | L | K | L | S | T | I | S | L | V | I | W | L | A | An DAGAT | 22 |
| 345 | A | L | F | F | Q | P | K | L | D | Y | A | N | I | S | E | R | L | M | K | L | A | S | V | S | M | M | V | W | L | I | Yl DGAT1 | 14 |
| 320 | K | P | F | K | D | M | - | - | D | Y | S | R | I | I | E | R | L | L | K | L | A | V | P | N | H | L | I | W | L | I | Mm DGAT1 | 129 |
| 325 | H | P | L | K | G | - | - | - | N | L | L | Y | A | T | E | R | V | L | K | L | S | V | P | N | L | Y | V | W | L | C | Gm DGAT1 | 130 |
| 342 | H | P | L | K | G | - | - | - | D | L | L | Y | A | I | E | R | V | L | K | L | S | V | P | N | L | Y | V | W | L | C | At DGAT1 | 131 |
| 321 | H | P | L | K | G | - | - | - | G | L | L | N | A | V | E | T | V | L | K | L | S | L | P | N | V | Y | L | W | L | C | Os DGAT1 | 132 |
| 355 | H | P | L | K | G | - | - | - | N | L | L | Y | A | I | E | R | V | L | K | L | S | V | P | N | L | Y | V | W | L | C | Pfdgat1 | 133 |
| 328 | H | P | L | N | G | - | - | - | N | F | L | D | A | I | E | R | V | L | K | L | S | V | P | T | L | Y | V | W | L | C | Ta DGAT1 | 134 |

Motif #4

|     | . | F |   |   | . | F |   |   |   |   |   |   | . | A | E |   |   | . | F |   | . | R |   | . | . | Y | . |   | W | W | N | Consensus |
|---|---|---|---|---|---|---|---|---|---|---|---|---|---|---|---|---|---|---|---|---|---|---|---|---|---|---|---|---|---|---|---|---|
| 359 | G | F | F | A | L | F | Q | S | F | L | N | A | L | A | E | V | T | R | F | A | D | R | S | F | Y | D | E | W | W | N | Nc DAGAT |
| 337 | G | F | F | A | L | F | Q | S | F | L | N | A | L | A | E | V | L | R | F | G | D | R | S | F | Y | D | D | W | W | N | Fm DAGAT |
| 373 | M | F | Y | T | F | F | H | S | F | F | N | A | L | A | E | A | L | Y | F | G | D | R | R | F | Y | L | A | W | W | N | Ma DGAT1 |
| 336 | G | F | F | A | L | F | Q | S | F | L | N | A | L | A | E | I | T | R | F | G | D | R | S | F | Y | E | A | W | W | N | Mg DAGAT |
| 300 | G | F | Y | A | L | F | Q | S | L | L | N | G | L | A | E | I | M | R | F | G | D | R | E | F | Y | T | D | W | W | N | An DAGAT |
| 375 | G | F | Y | A | F | F | Q | N | G | L | N | L | I | A | E | L | T | C | F | G | N | R | T | F | Y | Q | Q | W | W | N | Yl DGAT1 |
| 348 | F | F | Y | W | F | F | H | S | C | L | N | A | V | A | E | L | L | Q | F | G | D | R | E | F | Y | R | D | W | W | N | Mm DGAT1 |
| 352 | M | F | Y | C | F | F | H | L | W | L | N | I | L | A | E | L | L | R | F | G | D | R | E | F | Y | K | D | W | W | N | Gm DGAT1 |
| 369 | M | F | Y | C | F | F | H | L | W | L | N | I | L | A | E | L | L | C | F | G | D | R | E | F | Y | K | D | W | W | N | At DGAT1 |
| 348 | M | F | Y | A | F | F | H | L | W | L | S | I | L | A | E | I | L | R | F | G | D | R | E | F | Y | K | D | W | W | N | Os DGAT1 |
| 382 | M | F | Y | C | F | F | H | L | W | L | N | I | L | A | E | L | L | C | F | G | D | R | E | F | Y | K | D | W | W | N | Pfdgat1 |
| 355 | M | F | Y | S | F | F | H | L | W | L | N | I | L | A | E | L | L | R | F | G | D | R | E | F | Y | K | D | W | W | N | Ta DGAT1 |

|     |   |   |   |   |   |   |   |   | W |   |   | W | N | . | P | V |   |   |   |   |   |   | H | . | Y | . | P |   |   |   |   | Consensus |
|---|---|---|---|---|---|---|---|---|---|---|---|---|---|---|---|---|---|---|---|---|---|---|---|---|---|---|---|---|---|---|---|---|
| 389 | S | E | S | L | G | V | Y | W | R | T | W | N | K | P | V | Y | Q | Y | F | K | R | H | V | Y | S | P | M | R | S | R | Nc DAGAT |
| 367 | S | E | S | L | G | A | Y | W | R | T | W | N | K | P | V | Y | T | Y | F | K | R | H | L | Y | M | P | M | I | G | R | Fm DAGAT |
| 403 | A | T | G | V | G | M | Y | W | K | T | W | N | S | P | V | Y | T | F | F | K | R | H | V | Y | L | P | L | I | T | S | Ma DGAT1 |
| 366 | S | E | S | L | G | V | Y | W | R | T | W | N | K | P | V | Y | Q | Y | F | K | R | H | V | Y | S | P | M | L | G | R | Mg DAGAT |
| 330 | S | P | S | F | G | V | Y | W | R | S | W | N | R | P | V | Y | I | F | M | K | R | H | V | Y | M | P | L | V | T | R | An DAGAT |
| 405 | S | R | S | I | G | Q | Y | W | T | L | W | N | K | P | V | N | Q | Y | F | R | H | H | V | Y | V | P | L | L | A | R | Yl DGAT1 |
| 378 | A | E | S | V | T | Y | F | W | Q | N | W | N | I | P | V | H | K | W | C | I | R | H | F | Y | K | P | M | L | R | H | Mm DGAT1 |
| 382 | A | K | T | V | E | D | Y | W | R | M | W | N | M | P | V | H | K | W | M | I | R | H | L | Y | F | P | C | L | R | H | Gm DGAT1 |
| 399 | A | K | S | V | G | D | Y | W | R | M | W | N | M | P | V | H | K | W | M | V | R | H | I | Y | F | P | C | L | R | S | At DGAT1 |
| 378 | A | K | T | I | D | E | Y | W | R | K | W | N | M | P | V | H | K | W | V | V | R | H | I | Y | F | P | C | M | R | N | Os DGAT1 |
| 412 | A | R | T | V | E | E | Y | W | R | M | W | N | M | P | V | H | K | W | M | V | R | H | I | Y | C | P | C | L | Q | N | Pfdgat1 |
| 385 | A | K | T | V | E | E | Y | W | R | M | W | N | M | P | V | H | K | W | I | V | R | H | I | Y | F | P | C | I | R | N | Ta DGAT1 |

Motif #6   Motif #5

FIG. 8F

|     |   |   |   |   |   |   |   |   |   |   |   |   |   |   |   |   |   |   |   |   | Consensus | SEQ ID NO: |
|-----|---|---|---|---|---|---|---|---|---|---|---|---|---|---|---|---|---|---|---|---|-----------|------------|
|     | . | . | . | . | A | . | . | . | F | . | . | S | A | . | . | H | E | . | . | . | . . . P . . | |
| 419 | G | W | S | N | A | T | A | S | L | A | V | F | F | L | S | A | V | L | H | E | L L V G V P T H N L | Nc DAGAT: 19 |
| 397 | G | W | S | P | Q | A | A | S | F | F | V | F | L | V | S | A | I | L | H | E | I L V G V P T H N I | Fm DAGAT: 20 |
| 433 | G | T | S | P | M | V | A | S | I | V | I | F | L | I | S | A | V | L | H | E | I L I G F P T H M I | Ma DGAT1 18 |
| 396 | G | W | A | P | R | T | A | S | A | S | V | F | L | I | S | A | V | L | H | E | I L V G V P T H N I | Mg DAGAT: 21 |
| 360 | G | W | N | F | T | L | A | G | T | V | V | F | A | V | S | A | V | L | H | E | I L V G V P T H N L | An DAGAT: 22 |
| 435 | G | M | S | R | F | N | A | S | V | V | V | F | F | S | A | V | I | H | E | L | L V G I P T H N I | Yl DGAT1 14 |
| 408 | G | S | S | K | W | V | A | R | T | G | V | F | L | T | S | A | F | F | H | E | Y L V S V P L R M F | Mm DGAT1 129 |
| 412 | G | L | P | K | A | A | A | L | L | I | A | F | L | V | S | A | L | F | H | E | L C I A V P C H I F | Gm DGAT1 130 |
| 429 | K | I | P | K | T | L | A | I | I | I | A | F | L | V | S | A | V | F | H | E | L C I A V P C R L F | At DGAT1 131 |
| 408 | G | I | S | K | E | V | A | V | L | I | S | F | L | V | S | A | V | L | H | E | I C V A V P C R I L | Os DGAT1 132 |
| 442 | G | I | P | K | I | V | A | V | L | I | A | F | L | V | S | A | I | F | H | E | L C V A V P C Q I F | Pfdgat1 133 |
| 415 | G | L | S | K | G | C | A | I | L | I | A | F | L | V | S | A | V | F | H | E | L C I A V P C H I F | Ta DGAT1 134 |

Motif #7

|     |   |   |   |   |   |   |   |   |   |   |   |   |   |   |   |   |   |   |   |   | Consensus | |
|-----|---|---|---|---|---|---|---|---|---|---|---|---|---|---|---|---|---|---|---|---|-----------|---|
|     | . | . | . | A | . | . | . | . | . | . | . | Q | . | P | L | . | . | . | . | . | . . . . . . | |
| 449 | I | G | V | A | F | L | G | M | F | L | Q | L | P | L | I | Q | F | T | K | P | L E - K K T S P N G | Nc DAGAT: |
| 427 | I | G | V | A | F | L | G | M | F | L | Q | L | P | L | I | H | L | T | K | P | L E N M K L G H T G | Fm DAGAT: |
| 463 | Y | G | Y | A | F | A | G | M | F | L | Q | I | P | L | I | I | L | T | R | P | L E K W R G T G S G | Ma DGAT1 |
| 426 | I | G | V | A | F | M | G | M | F | L | Q | V | P | L | I | I | L | T | A | P | L E - K R K S P T G | Mg DAGAT: |
| 390 | I | G | V | A | S | I | A | M | M | F | Q | L | P | L | I | L | L | T | A | P | F E - R F K S P L G | An DAGAT: |
| 465 | I | G | A | A | F | F | G | M | M | S | Q | V | P | L | I | M | A | T | E | N | L Q - H I N S S L G | Yl DGAT1 |
| 438 | R | L | W | A | F | T | A | M | M | A | Q | V | P | L | A | W | I | V | G | - | - - - - - R F F Q | Mm DGAT1 |
| 442 | K | L | W | A | F | G | G | I | M | F | Q | V | P | L | V | L | I | T | N | Y | L Q - - - N K F R N | Gm DGAT1 |
| 459 | K | L | W | A | F | L | G | I | M | F | Q | V | P | L | V | F | I | T | N | Y | L Q - - - E R F G - | At DGAT1 |
| 438 | K | F | W | A | F | L | G | I | M | L | Q | I | P | L | I | V | L | T | A | Y | L K - - - S K F R D | Os DGAT1 |
| 472 | K | F | W | A | F | S | G | I | M | L | Q | V | P | L | V | I | V | T | N | Y | L Q - - - E K F K N | Pfdgat1 |
| 445 | K | L | W | A | F | S | G | I | M | F | Q | I | P | L | L | F | L | T | K | Y | L Q - - - D K F K N | Ta DGAT1 |

..Motif #7

|     |   |   |   |   |   |   |   |   |   |   |   |   |   |   |   |   |   |   |   |   | Consensus | |
|-----|---|---|---|---|---|---|---|---|---|---|---|---|---|---|---|---|---|---|---|---|-----------|---|
|     | . | . | . | G | N | . | . | . | W | . | . | . | . | . | . | G | Q | P | . | . | . . . Y . . . . | |
| 478 | K | L | L | G | N | I | I | F | W | V | S | F | T | I | F | G | Q | P | F | A | A L M Y F Y A - - W | Nc DAGAT: |
| 457 | K | I | V | G | N | T | I | F | W | V | S | F | T | I | F | G | Q | P | F | A | A L M Y F Y A - - W | Fm DAGAT: |
| 493 | - | - | L | G | N | M | I | F | W | V | S | F | T | I | L | G | Q | P | A | C | A L L Y Y Y H - - W | Ma DGAT1 |
| 455 | K | L | I | G | N | S | I | F | W | V | S | F | T | I | F | G | Q | P | L | A | A L M Y F Y A - - W | Mg DAGAT: |
| 419 | K | A | I | G | N | S | F | W | V | T | F | C | V | V | G | Q | P | L | G | A | L L Y F F A - - W | An DAGAT: |
| 494 | P | F | L | G | N | C | A | F | W | F | T | F | - | F | L | G | Q | P | T | C | A F L Y Y L A - - Y | Yl DGAT1 |
| 461 | G | N | Y | G | N | A | A | V | W | V | T | L | - | I | I | G | Q | P | V | A | V L M Y V H D Y Y V | Mm DGAT1 |
| 469 | S | M | V | G | N | M | I | F | W | F | I | F | S | I | L | G | Q | P | M | C | V L L Y Y H D - - L | Gm DGAT1 |
| 485 | S | T | V | G | N | M | I | F | W | F | I | F | C | I | F | G | Q | P | M | C | V L L Y Y H D - - L | At DGAT1 |
| 465 | T | M | V | G | N | M | I | F | W | F | F | F | C | I | Y | G | Q | P | M | C | L L L Y Y H D - - V | Os DGAT1 |
| 499 | S | M | V | G | N | M | M | F | W | C | F | F | C | I | F | G | Q | P | M | C | V L L Y Y H D - - L | Pfdgat1 |
| 472 | T | M | V | G | N | M | I | F | W | F | F | F | S | I | V | G | Q | P | M | C | V L L Y Y H D - - V | Ta DGAT1 |

Motif #8

FIG. 8G

|  |  | Consensus | SEQ ID NO: |
|---|---|---|---|
| 506 Q A K Y G S V S K M T T S Q Q L V Q Q G Q G T C P P L V | Nc DAGAT | 19 |
| 485 Q A K Y G S V T D S G F S I S | Fm DAGAT | 20 |
| 519 T K R H M D V | Ma DGAT1 | 18 |
| 483 Q A K Y G S V S K M G Y A T S K A A L T N | Mg DAGAT | 21 |
| 447 Q A K Y G S V S Q T H P | An DAGAT | 22 |
| 521 N Y K Q N Q | Yl DGAT1 | 14 |
| 490 L N Y D A P V G V | Mm DGAT1 | 129 |
| 497 M N R K G K L D | Gm DGAT1 | 130 |
| 513 M N R K G S M S | At DGAT1 | 131 |
| 493 M N R I E K A R | Os DGAT1 | 132 |
| 527 M N R K A S A R | Pfdgat1 | 133 |
| 500 M N R Q A Q T N G | Ta DGAT1 | 134 |

FIG. 8H

SEQUENCE LISTING

```
<160> NUMBER OF SEQ ID NOS: 175

<210> SEQ ID NO 1
<211> LENGTH: 2119
<212> TYPE: DNA
<213> ORGANISM: Yarrowia lipolytica
<220> FEATURE:
<221> NAME/KEY: CDS
<222> LOCATION: (291)..(1835)
<223> OTHER INFORMATION: DGAT2 opening reading frame, comprising 2
      smaller internal opening reading frames
<220> FEATURE:
<221> NAME/KEY: misc_feature
<222> LOCATION: (291)..(293)
<223> OTHER INFORMATION: initiation codon ('ATG')
<220> FEATURE:
<221> NAME/KEY: misc_feature
<222> LOCATION: (456)..(458)
<223> OTHER INFORMATION: initiation codon ('ATG')
<220> FEATURE:
<221> NAME/KEY: misc_feature
<222> LOCATION: (768)..(770)
<223> OTHER INFORMATION: initiation codon ('ATG')

<400> SEQUENCE: 1
aaacgcaccc actgctcgtc ctccttgctc ctcgaaaccg actcctctac acacgtcaaa        60
tccgaggttg aaatcttccc cacatttggc agccaaacca gcatcccca gcaacctcgc       120 acagcgccga aatcgacctg tcgacttggc cacaaaaaaa agcaccggct ctgcaacagt       180
tctcacgacc aattacgtac aagtacgaaa tcgttcgtgg accgtgactg ataagctccc       240 acttttctt ctaacaacag gcaacagaca agtcacacaa aacaaaagct atg act           296
                                                       Met Thr
                                                         1 atc gac tca caa tac tac aag tcg cga gac aaa aac gac acg gca ccc        344
Ile Asp Ser Gln Tyr Tyr Lys Ser Arg Asp Lys Asn Asp Thr Ala Pro
        5                  10                  15 aaa atc gcg gga atc cga tat gcc ccg cta tcg aca cca tta ctc aac        392
Lys Ile Ala Gly Ile Arg Tyr Ala Pro Leu Ser Thr Pro Leu Leu Asn
 20                  25                  30 cga tgt gag acc ttc tct ctg gtc tgg cac att ttc agc att ccc act        440
Arg Cys Glu Thr Phe Ser Leu Val Trp His Ile Phe Ser Ile Pro Thr
35                  40                  45                  50 ttc ctc aca att ttc atg cta tgc tgc gca att cca ctg ctc tgg cca        488
Phe Leu Thr Ile Phe Met Leu Cys Cys Ala Ile Pro Leu Leu Trp Pro
                55                  60                  65 ttt gtg att gcg tat gta gtg tac gct gtt aaa gac gac tcc ccg tcc        536
Phe Val Ile Ala Tyr Val Val Tyr Ala Val Lys Asp Asp Ser Pro Ser
            70                  75                  80 aac gga gga gtg gtc aag cga tac tcg cct att tca aga aac ttc ttc        584
Asn Gly Gly Val Val Lys Arg Tyr Ser Pro Ile Ser Arg Asn Phe Phe
        85                  90                  95 atc tgg aag ctc ttt ggc cgc tac ttc ccc ata act ctg cac aag acg        632
Ile Trp Lys Leu Phe Gly Arg Tyr Phe Pro Ile Thr Leu His Lys Thr
        100                 105                 110 gtg gat ctg gag ccc acg cac aca tac tac cct ctg gac gtc cag gag        680
Val Asp Leu Glu Pro Thr His Thr Tyr Tyr Pro Leu Asp Val Gln Glu
115                 120                 125                 130
```

-continued

```
tat cac ctg att gct gag aga tac tgg ccg cag aac aag tac ctc cga      728
Tyr His Leu Ile Ala Glu Arg Tyr Trp Pro Gln Asn Lys Tyr Leu Arg
            135                 140                 145 gca atc atc tcc acc atc gag tac ttt ctg ccc gcc ttc atg aaa cgg      776
Ala Ile Ile Ser Thr Ile Glu Tyr Phe Leu Pro Ala Phe Met Lys Arg
        150                 155                 160 tct ctt tct atc aac gag cag gag cag cct gcc gag cga gat cct ctc      824
Ser Leu Ser Ile Asn Glu Gln Glu Gln Pro Ala Glu Arg Asp Pro Leu
            165                 170                 175 ctg tct ccc gtt tct ccc agc tct ccg ggt tct caa cct gac aag tgg      872
Leu Ser Pro Val Ser Pro Ser Pro Gly Ser Gln Pro Asp Lys Trp
        180                 185                 190 att aac cac gac agc aga tat agc cgt gga gaa tca tct ggc tcc aac      920
Ile Asn His Asp Ser Arg Tyr Ser Arg Gly Glu Ser Ser Gly Ser Asn
195                 200                 205                 210 ggc cac gcc tcg ggc tcc gaa ctt aac ggc aac ggc aac aat ggc acc      968
Gly His Ala Ser Gly Ser Glu Leu Asn Gly Asn Gly Asn Asn Gly Thr
            215                 220                 225 act aac cga cga cct ttg tcg tcc gcc tct gct ggc tcc act gca tct     1016
Thr Asn Arg Arg Pro Leu Ser Ser Ala Ser Ala Gly Ser Thr Ala Ser
        230                 235                 240 gat tcc acg ctt ctt aac ggg tcc ctc aac tcc tac gcc aac cag atc     1064
Asp Ser Thr Leu Leu Asn Gly Ser Leu Asn Ser Tyr Ala Asn Gln Ile
            245                 250                 255 att ggc gaa aac gac cca cag ctg tcg ccc aca aaa ctc aag ccc act     1112
Ile Gly Glu Asn Asp Pro Gln Leu Ser Pro Thr Lys Leu Lys Pro Thr
        260                 265                 270 ggc aga aaa tac atc ttc ggc tac cac ccc cac ggc att atc ggc atg     1160
Gly Arg Lys Tyr Ile Phe Gly Tyr His Pro His Gly Ile Ile Gly Met
275                 280                 285                 290 gga gcc ttt ggt gga att gcc acc gag gga gct gga tgg tcc aag ctc     1208
Gly Ala Phe Gly Gly Ile Ala Thr Glu Gly Ala Gly Trp Ser Lys Leu
            295                 300                 305 ttt ccg ggc atc cct gtt tct ctt atg act ctc acc aac aac ttc cga     1256
Phe Pro Gly Ile Pro Val Ser Leu Met Thr Leu Thr Asn Asn Phe Arg
        310                 315                 320 gtg cct ctc tac aga gag tac ctc atg agt ctg gga gtc gct tct gtc     1304
Val Pro Leu Tyr Arg Glu Tyr Leu Met Ser Leu Gly Val Ala Ser Val
            325                 330                 335 tcc aag aag tcc tgc aag gcc ctc ctc aag cga aac cag tct atc tgc     1352
Ser Lys Lys Ser Cys Lys Ala Leu Leu Lys Arg Asn Gln Ser Ile Cys
        340                 345                 350 att gtc gtt ggt gga gca cag gaa agt ctt ctg gcc aga ccc ggt gtc     1400
Ile Val Val Gly Gly Ala Gln Glu Ser Leu Leu Ala Arg Pro Gly Val
355                 360                 365                 370 atg gac ctg gtg cta ctc aag cga aag ggt ttt gtt cga ctt ggt atg     1448
Met Asp Leu Val Leu Leu Lys Arg Lys Gly Phe Val Arg Leu Gly Met
            375                 380                 385 gag gtc gga aat gtc gcc ctt gtt ccc atc atg gcc ttt ggt gag aac     1496
Glu Val Gly Asn Val Ala Leu Val Pro Ile Met Ala Phe Gly Glu Asn
        390                 395                 400 gac ctc tat gac cag gtt agc aac gac aag tcg tcc aag ctg tac cga     1544
Asp Leu Tyr Asp Gln Val Ser Asn Asp Lys Ser Ser Lys Leu Tyr Arg
            405                 410                 415 ttc cag cag ttt gtc aag aac ttc ctt gga ttc acc ctt cct ttg atg     1592
Phe Gln Gln Phe Val Lys Asn Phe Leu Gly Phe Thr Leu Pro Leu Met
        420                 425                 430 cat gcc cga ggc gtc ttc aac tac gat gtc ggt ctt gtc ccc tac agg     1640
His Ala Arg Gly Val Phe Asn Tyr Asp Val Gly Leu Val Pro Tyr Arg
```

```
              435                 440                 445                 450
cga ccc gtc aac att gtg gtt ggt tcc ccc att gac ttg cct tat ctc          1688
Arg Pro Val Asn Ile Val Val Gly Ser Pro Ile Asp Leu Pro Tyr Leu
                    455                 460                 465 cca cac ccc acc gac gaa gaa gtg tcc gaa tac cac gac cga tac atc          1736
Pro His Pro Thr Asp Glu Glu Val Ser Glu Tyr His Asp Arg Tyr Ile
                470                 475                 480 gcc gag ctg cag cga atc tac aac gag cac aag gat gaa tat ttc atc          1784
Ala Glu Leu Gln Arg Ile Tyr Asn Glu His Lys Asp Glu Tyr Phe Ile
            485                 490                 495 gat tgg acc gag gag ggc aaa gga gcc cca gag ttc cga atg att gag          1832
Asp Trp Thr Glu Glu Gly Lys Gly Ala Pro Glu Phe Arg Met Ile Glu
500                 505                 510 taa ggaaaactgc ctgggttagg caaatagcta atgagtattt ttttgatggc              1885
aaccaaatgt agaaagaaaa aaaaaaaaaa agaaaaaaaa aagagaatat tatatctatg        1945
taattctatt aaaagctctg ttgagtgagc ggaataaata ctgttgaaga ggggattgtg        2005
tagagatctg tttactcaat ggcaaactca tctgggggag atccttccac tgtgggaagc        2065
tcctggatag cctttgcatc ggggttcaag aagaccattg tgaacagccc ttga             2119

<210> SEQ ID NO 2
<211> LENGTH: 514
<212> TYPE: PRT
<213> ORGANISM: Yarrowia lipolytica

<400> SEQUENCE: 2

Met Thr Ile Asp Ser Gln Tyr Tyr Lys Ser Arg Asp Lys Asn Asp Thr
1               5                   10                  15

Ala Pro Lys Ile Ala Gly Ile Arg Tyr Ala Pro Leu Ser Thr Pro Leu
            20                  25                  30

Leu Asn Arg Cys Glu Thr Phe Ser Leu Val Trp His Ile Phe Ser Ile
        35                  40                  45

Pro Thr Phe Leu Thr Ile Phe Met Leu Cys Cys Ala Ile Pro Leu Leu
    50                  55                  60

Trp Pro Phe Val Ile Ala Tyr Val Val Tyr Ala Val Lys Asp Asp Ser
65                  70                  75                  80

Pro Ser Asn Gly Gly Val Val Lys Arg Tyr Ser Pro Ile Ser Arg Asn
                85                  90                  95

Phe Phe Ile Trp Lys Leu Phe Gly Arg Tyr Phe Pro Ile Thr Leu His
            100                 105                 110

Lys Thr Val Asp Leu Glu Pro Thr His Thr Tyr Tyr Pro Leu Asp Val
        115                 120                 125

Gln Glu Tyr His Leu Ile Ala Glu Arg Tyr Trp Pro Gln Asn Lys Tyr
    130                 135                 140

Leu Arg Ala Ile Ile Ser Thr Ile Glu Tyr Phe Leu Pro Ala Phe Met
145                 150                 155                 160

Lys Arg Ser Leu Ser Ile Asn Glu Gln Glu Gln Pro Ala Glu Arg Asp
                165                 170                 175

Pro Leu Leu Ser Pro Val Ser Pro Ser Pro Gly Ser Gln Pro Asp
            180                 185                 190

Lys Trp Ile Asn His Asp Ser Arg Tyr Ser Arg Gly Glu Ser Ser Gly
        195                 200                 205

Ser Asn Gly His Ala Ser Gly Ser Glu Leu Asn Gly Asn Gly Asn Asn
    210                 215                 220

Gly Thr Thr Asn Arg Arg Pro Leu Ser Ser Ala Ser Ala Gly Ser Thr
```

```
                225                 230                 235                 240
Ala Ser Asp Ser Thr Leu Leu Asn Gly Ser Leu Asn Ser Tyr Ala Asn
                    245                 250                 255
Gln Ile Ile Gly Glu Asn Asp Pro Gln Leu Ser Pro Thr Lys Leu Lys
                260                 265                 270
Pro Thr Gly Arg Lys Tyr Ile Phe Gly Tyr His Pro His Gly Ile Ile
                275                 280                 285
Gly Met Gly Ala Phe Gly Gly Ile Ala Thr Glu Gly Ala Gly Trp Ser
        290                 295                 300
Lys Leu Phe Pro Gly Ile Pro Val Ser Leu Met Thr Leu Thr Asn Asn
305                 310                 315                 320
Phe Arg Val Pro Leu Tyr Arg Glu Tyr Leu Met Ser Leu Gly Val Ala
                325                 330                 335
Ser Val Ser Lys Lys Ser Cys Lys Ala Leu Leu Lys Arg Asn Gln Ser
                340                 345                 350
Ile Cys Ile Val Val Gly Gly Ala Gln Glu Ser Leu Leu Ala Arg Pro
            355                 360                 365
Gly Val Met Asp Leu Val Leu Leu Lys Arg Lys Gly Phe Val Arg Leu
        370                 375                 380
Gly Met Glu Val Gly Asn Val Ala Leu Val Pro Ile Met Ala Phe Gly
385                 390                 395                 400
Glu Asn Asp Leu Tyr Asp Gln Val Ser Asn Asp Lys Ser Ser Lys Leu
                405                 410                 415
Tyr Arg Phe Gln Gln Phe Val Lys Asn Phe Leu Gly Phe Thr Leu Pro
            420                 425                 430
Leu Met His Ala Arg Gly Val Phe Asn Tyr Asp Val Gly Leu Val Pro
            435                 440                 445
Tyr Arg Arg Pro Val Asn Ile Val Val Gly Ser Pro Ile Asp Leu Pro
        450                 455                 460
Tyr Leu Pro His Pro Thr Asp Glu Glu Val Ser Glu Tyr His Asp Arg
465                 470                 475                 480
Tyr Ile Ala Glu Leu Gln Arg Ile Tyr Asn Glu His Lys Asp Glu Tyr
                485                 490                 495
Phe Ile Asp Trp Thr Glu Glu Gly Lys Gly Ala Pro Glu Phe Arg Met
            500                 505                 510
Ile Glu

<210> SEQ ID NO 3
<211> LENGTH: 1380
<212> TYPE: DNA
<213> ORGANISM: Yarrowia lipolytica

<400> SEQUENCE: 3
atgctatgct gcgcaattcc actgctctgg ccatttgtga ttgcgtatgt agtgtacgct      60
gttaaagacg actccccgtc caacggagga gtggtcaagc gatactcgcc tatttcaaga    120
aacttcttca tctggaagct ctttggccgc tacttcccca taactctgca caagacggtg    180
gatctggagc ccacgcacac atactaccct ctggacgtcc aggagtatca cctgattgct    240
gagagatact ggccgcagaa caagtacctc cgagcaatca tctccaccat cgagtacttt    300 ctgccgcct tcatgaaacg gtctctttct atcaacgagc aggagcagcc tgccgagcga    360
gatcctctcc tgtctcccgt ttctcccagc tctccgggtt ctcaacctga caagtggatt    420
aaccacgaca gcagatatag ccgtggagaa tcatctggct ccaacggcca cgcctcgggc    480
```

-continued

```
tccgaactta acggcaacgg caacaatggc accactaacc gacgacctt  gtcgtccgcc    540
tctgctggct ccactgcatc tgattccacg cttcttaacg ggtccctcaa ctcctacgcc    600
aaccagatca ttggcgaaaa cgacccacag ctgtcgccca caaaactcaa gcccactggc    660
agaaaataca tcttcggcta ccaccccac ggcattatcg catgggagc ctttggtgga     720
attgccaccg agggagctgg atggtccaag ctctttccgg gcatccctgt ttctcttatg    780
actctcacca caacttccg agtgcctctc tacagagagt acctcatgag tctgggagtc    840
gcttctgtct ccaagaagtc ctgcaaggcc ctcctcaagc gaaaccagtc tatctgcatt    900
gtcgttggtg gagcacagga aagtcttctg gccagaccg gtgtcatgga cctggtgcta    960
ctcaagcgaa agggttttgt tcgacttggt atggaggtcg gaaatgtcgc ccttgttccc   1020
atcatggcct ttggtgagaa cgacctctat gaccaggtta gcaacgacaa gtcgtccaag   1080
ctgtaccgat ccagcagtt tgtcaagaac ttccttggat tcaccctt c tttgatgcat   1140
gcccgaggcg tcttcaacta cgatgtcggt cttgtcccct acaggcgacc cgtcaacatt   1200
gtggttggtt ccccccattga cttgccttat ctcccacacc ccaccgacga agaagtgtcc   1260
gaataccacg accgatacat cgccgagctg cagcgaatct acaacgagca caaggatgaa   1320
tatttcatcg attggaccga ggagggcaaa ggagccccag agttccgaat gattgagtaa   1380
```

<210> SEQ ID NO 4
<211> LENGTH: 459
<212> TYPE: PRT
<213> ORGANISM: Yarrowia lipolytica

<400> SEQUENCE: 4

```
Met Leu Cys Cys Ala Ile Pro Leu Leu Trp Pro Phe Val Ile Ala Tyr
1               5                   10                  15

Val Val Tyr Ala Val Lys Asp Asp Ser Pro Ser Asn Gly Gly Val Val
            20                  25                  30

Lys Arg Tyr Ser Pro Ile Ser Arg Asn Phe Phe Ile Trp Lys Leu Phe
        35                  40                  45

Gly Arg Tyr Phe Pro Ile Thr Leu His Lys Thr Val Asp Leu Glu Pro
    50                  55                  60

Thr His Thr Tyr Tyr Pro Leu Asp Val Gln Glu Tyr His Leu Ile Ala
65                  70                  75                  80

Glu Arg Tyr Trp Pro Gln Asn Lys Tyr Leu Arg Ala Ile Ile Ser Thr
                85                  90                  95

Ile Glu Tyr Phe Leu Pro Ala Phe Met Lys Arg Ser Leu Ser Ile Asn
            100                 105                 110

Glu Gln Glu Gln Pro Ala Glu Arg Asp Pro Leu Leu Ser Pro Val Ser
        115                 120                 125

Pro Ser Ser Pro Gly Ser Gln Pro Asp Lys Trp Ile Asn His Asp Ser
    130                 135                 140

Arg Tyr Ser Arg Gly Glu Ser Ser Gly Ser Asn Gly His Ala Ser Gly
145                 150                 155                 160

Ser Glu Leu Asn Gly Asn Gly Asn Asn Gly Thr Thr Asn Arg Arg Pro
                165                 170                 175

Leu Ser Ser Ala Ser Ala Gly Ser Thr Ala Ser Asp Ser Thr Leu Leu
            180                 185                 190

Asn Gly Ser Leu Asn Ser Tyr Ala Asn Gln Ile Ile Gly Glu Asn Asp
        195                 200                 205

Pro Gln Leu Ser Pro Thr Lys Leu Lys Pro Thr Gly Arg Lys Tyr Ile
    210                 215                 220
```

```
Phe Gly Tyr His Pro His Gly Ile Ile Gly Met Gly Ala Phe Gly Gly
225                 230                 235                 240

Ile Ala Thr Glu Gly Ala Gly Trp Ser Lys Leu Phe Pro Gly Ile Pro
            245                 250                 255

Val Ser Leu Met Thr Leu Thr Asn Asn Phe Arg Val Pro Leu Tyr Arg
            260                 265                 270

Glu Tyr Leu Met Ser Leu Gly Val Ala Ser Val Ser Lys Lys Ser Cys
            275                 280                 285

Lys Ala Leu Leu Lys Arg Asn Gln Ser Ile Cys Ile Val Val Gly Gly
290                 295                 300

Ala Gln Glu Ser Leu Leu Ala Arg Pro Gly Val Met Asp Leu Val Leu
305                 310                 315                 320

Leu Lys Arg Lys Gly Phe Val Arg Leu Gly Met Glu Val Gly Asn Val
                325                 330                 335

Ala Leu Val Pro Ile Met Ala Phe Gly Glu Asn Asp Leu Tyr Asp Gln
                340                 345                 350

Val Ser Asn Asp Lys Ser Ser Lys Leu Tyr Arg Phe Gln Gln Phe Val
            355                 360                 365

Lys Asn Phe Leu Gly Phe Thr Leu Pro Leu Met His Ala Arg Gly Val
370                 375                 380

Phe Asn Tyr Asp Val Gly Leu Val Pro Tyr Arg Arg Pro Val Asn Ile
385                 390                 395                 400

Val Val Gly Ser Pro Ile Asp Leu Pro Tyr Leu Pro His Pro Thr Asp
                405                 410                 415

Glu Glu Val Ser Glu Tyr His Asp Arg Tyr Ile Ala Glu Leu Gln Arg
            420                 425                 430

Ile Tyr Asn Glu His Lys Asp Glu Tyr Phe Ile Asp Trp Thr Glu Glu
                435                 440                 445

Gly Lys Gly Ala Pro Glu Phe Arg Met Ile Glu
450                 455

<210> SEQ ID NO 5
<211> LENGTH: 1068
<212> TYPE: DNA
<213> ORGANISM: Yarrowia lipolytica

<400> SEQUENCE: 5
atgaaacggt ctctttctat caacgagcag gagcagcctg ccgagcgaga tcctctcctg      60
tctcccgttt ctcccagctc tccgggttct caacctgaca agtggattaa ccacgacagc    120
agatatagcc gtggagaatc atctggctcc aacggccacg cctcgggctc cgaacttaac    180
ggcaacggca acaatggcac cactaaccga cgacctttgt cgtccgcctc tgctggctcc    240
actgcatctg attccacgct tcttaacggg tccctcaact cctacgccaa ccagatcatt    300
ggcgaaaacg acccacagct gtcgcccaca aaactcaagc ccactggcag aaaatacatc    360
ttcggctacc accccacgg cattatcggc atgggagcct tggtggaat gccaccgag      420 ggagctggat ggtccaagct ctttccgggc atccctgttt ctcttatgac tctcaccaac    480
aacttccgag tgcctctcta cagagagtac ctcatgagtc tgggagtcgc ttctgtctcc    540
aagaagtcct gcaaggccct cctcaagcga accagtcta tctgcattgt cgttggtgga    600
gcacaggaaa gtcttctggc cagacccggt gtcatggacc tggtgctact caagcgaaag    660
ggttttgttc gacttggtat ggaggtcgga aatgtcgccc ttgttcccat catggccttt    720
ggtgagaacg acctctatga ccaggttagc aacgacaagt cgtccaagct gtaccgattc    780
```

```
cagcagtttg tcaagaactt ccttggattc acccttcctt tgatgcatgc ccgaggcgtc    840
ttcaactacg atgtcggtct tgtcccctac aggcgacccg tcaacattgt ggttggttcc    900
cccattgact tgccttatct cccacacccc accgacgaag aagtgtccga ataccacgac    960
cgatacatcg ccgagctgca gcgaatctac aacgagcaca aggatgaata tttcatcgat   1020
tggaccgagg agggcaaagg agccccagag ttccgaatga ttgagtaa                1068
```

```
<210> SEQ ID NO 6
<211> LENGTH: 355
<212> TYPE: PRT
<213> ORGANISM: Yarrowia lipolytica

<400> SEQUENCE: 6
```

```
Met Lys Arg Ser Leu Ser Ile Asn Glu Gln Glu Gln Pro Ala Glu Arg
1               5                   10                  15

Asp Pro Leu Leu Ser Pro Val Ser Pro Ser Pro Gly Ser Gln Pro
            20                  25                  30

Asp Lys Trp Ile Asn His Asp Ser Arg Tyr Ser Arg Gly Glu Ser Ser
        35                  40                  45

Gly Ser Asn Gly His Ala Ser Gly Ser Glu Leu Asn Gly Asn Gly Asn
    50                  55                  60

Asn Gly Thr Thr Asn Arg Arg Pro Leu Ser Ser Ala Ser Ala Gly Ser
65                  70                  75                  80

Thr Ala Ser Asp Ser Thr Leu Leu Asn Gly Ser Leu Asn Ser Tyr Ala
                85                  90                  95

Asn Gln Ile Ile Gly Glu Asn Asp Pro Gln Leu Ser Pro Thr Lys Leu
            100                 105                 110

Lys Pro Thr Gly Arg Lys Tyr Ile Phe Gly Tyr His Pro His Gly Ile
        115                 120                 125

Ile Gly Met Gly Ala Phe Gly Gly Ile Ala Thr Glu Gly Ala Gly Trp
    130                 135                 140

Ser Lys Leu Phe Pro Gly Ile Pro Val Ser Leu Met Thr Leu Thr Asn
145                 150                 155                 160

Asn Phe Arg Val Pro Leu Tyr Arg Glu Tyr Leu Met Ser Leu Gly Val
                165                 170                 175

Ala Ser Val Ser Lys Lys Ser Cys Lys Ala Leu Leu Lys Arg Asn Gln
            180                 185                 190

Ser Ile Cys Ile Val Val Gly Ala Gln Glu Ser Leu Leu Ala Arg
        195                 200                 205

Pro Gly Val Met Asp Leu Val Leu Leu Lys Arg Lys Gly Phe Val Arg
    210                 215                 220

Leu Gly Met Glu Val Gly Asn Val Ala Leu Val Pro Ile Met Ala Phe
225                 230                 235                 240

Gly Glu Asn Asp Leu Tyr Asp Gln Val Ser Asn Asp Lys Ser Ser Lys
                245                 250                 255

Leu Tyr Arg Phe Gln Gln Phe Val Lys Asn Phe Leu Gly Phe Thr Leu
            260                 265                 270

Pro Leu Met His Ala Arg Gly Val Phe Asn Tyr Asp Val Gly Leu Val
        275                 280                 285

Pro Tyr Arg Arg Pro Val Asn Ile Val Val Gly Ser Pro Ile Asp Leu
    290                 295                 300

Pro Tyr Leu Pro His Pro Thr Asp Glu Glu Val Ser Glu Tyr His Asp
305                 310                 315                 320
```

```
Arg Tyr Ile Ala Glu Leu Gln Arg Ile Tyr Asn Glu His Lys Asp Glu
            325                 330                 335

Tyr Phe Ile Asp Trp Thr Glu Glu Gly Lys Gly Ala Pro Glu Phe Arg
            340                 345                 350

Met Ile Glu
        355

<210> SEQ ID NO 7
<211> LENGTH: 2326
<212> TYPE: DNA
<213> ORGANISM: Yarrowia lipolytica
<220> FEATURE:
<221> NAME/KEY: misc_feature
<222> LOCATION: (2271)..(2271)
<223> OTHER INFORMATION: n is a, c, g, or t

<400> SEQUENCE: 7
tattaatatt atgctcttca tgcaccagca aaataaccga aacgcgcata tgatagtggg      60
attctcgatt tgcccggcag acaaacgccg ctaaaatcgc cacagtatcg aattttaatt    120
gaatacgaac gtcaattccg gcttatcctt ctagcagttg tctcccgcag ctcgctccat    180
gactaatcat tcacgcgaca tgtctcagct accccggtct ggctcatgta aaaaagtgt     240 aatcggcttt tttccggttg atcacaacca tcaatgacac aacctgtgaa tcggaaggcg    300
actgtcgagc gggtcgagcc agcagtggag gtggctgact ccgagtccga ggccaagacc    360
gacgtccacg ttcaccacca tcatcaccac cacaagcgaa aatccgtcaa gggcaagatt    420
ctcaacttct tcacccgaag tcgacgtatc accttcgtcc tcggcgccgt ggtcggtgtg    480
atagccgcgg gatactacgc tgcgccaccg gagctcagca ttgatatcga tgctcttctc    540
ggcgacttgc cctcgttcga ctttgacgct ctatctctcg acaacttgtc catggacagt    600
gtgtcggact tgtacaaga catgaaatcg cggtttccga ccaagattct gcaggaggcg    660
gccaagatcg agaagcacca gaaaagcgaa cagaaggctg cccctttttgc tgtgggcaag    720 gctatgaaga gcgagggact caacgccaag tacccggtgg tgctggtgcc cggcgtcatc    780
tccacgggac tggagagctg gtccctggag ggaaccgagg agtgtcccac cgagtcgcac    840
ttcagaaagc gaatgtgggg ctcctggtac atgatccgag tcatgctgct ggacaagtac    900
tgctggctgc agaacctgat gctggacaca gagaccggtc tagaccctcc ccatttcaag    960
ctgcgagccg cccaggggatt tgcctccgcc gacttcttta tggcaggcta ctggctgtgg   1020
aacaagctgc tcgagaacct ggctgttatt ggatacgata cggatacaat gtctgctgcg   1080
gcgtacgact ggagactgtc ctaccctgat ttggagcacc gagacggata cttctccaag   1140
ctcaaagctt caatcgaaga gactaagcgt atgacaggtg agaagacagt tctgacgggc   1200
cattccatgg gctcccaggt catcttctac ttcatgaagt gggctgaggc cgagggatat   1260
ggaggaggag gtcccaactg ggtcaatgac catattgaat cctttgtcga catttccggc   1320
tccatgctgg gtactcccaa gaccctggtt gctcttctgt ctggagaaat gaaggatacc   1380
gtgcagctga acgcgatggc tgtgtatgga ctggagcagt tcttctctcg acgagagcga   1440
gccgatctgc tgcgaacatg gggaggaatt gcttccatga ttcccaaggg tggtaaggct   1500
atctggggtg atcattctgg agccctgat gacgagcccg gccagaatgt caccttttggc   1560 aacttcatca agttcaagga gtccttgacc gagtactctg ctaagaacct caccatggat   1620
gaaaccgttg acttcctgta ttctcagtct cccgagtggt ttgtgaaccg aaccgagggt   1680
gcttactcct ttggaattgc caagactcga agcaggttga gcagaatga aagcgaccct   1740
```

-continued

```
tctacctgga gcaaccctct ggaagctgct ctccccaatg cccccgatct caagatctac    1800
tgcttctatg gagtcggtaa ggataccgag cgagcctact actaccagga tgagcccaat    1860
cccgagcaga ccaacttgaa cgtcagtatc gctggaaacg accctgatgg tgtgcttatg    1920
ggtcagggcg atggaaccgt ctcccttgtg acccatacca tgtgtcaccg atggaaggac    1980
gagaattcca agttcaaccc tggtaacgcc caggtcaagg ttgtggagat gttgcaccag    2040
cctgatcgac ttgatattcg aggcggtgct cagactgccg agcatgtgga cattctgggg    2100
cgttctgagt tgaacgagat ggttctgaag gtggctagtg gaaagggaaa tgagattgaa    2160
gagagagtca tctccaacat tgatgagtgg gtgtggaaga ttgatctcgg cagcaattag    2220
agagtccgtt ttgtagagta atatgttttg tatatcacac tgatggagaa nggcgttcga    2280
tttctcatga ttccatgtgg ttgtttaatg agcacgtaga acgacg                  2326
```

<210> SEQ ID NO 8
<211> LENGTH: 648
<212> TYPE: PRT
<213> ORGANISM: Yarrowia lipolytica

<400> SEQUENCE: 8

```
Met Thr Gln Pro Val Asn Arg Lys Ala Thr Val Glu Arg Val Glu Pro
1               5                   10                  15

Ala Val Glu Val Ala Asp Ser Glu Ser Glu Ala Lys Thr Asp Val His
            20                  25                  30

Val His His His His His His Lys Arg Lys Ser Val Lys Gly Lys
        35                  40                  45

Ile Leu Asn Phe Phe Thr Arg Ser Arg Arg Ile Thr Phe Val Leu Gly
    50                  55                  60

Ala Val Val Gly Val Ile Ala Ala Gly Tyr Tyr Ala Ala Pro Pro Glu
65                  70                  75                  80

Leu Ser Ile Asp Ile Asp Ala Leu Leu Gly Asp Leu Pro Ser Phe Asp
                85                  90                  95

Phe Asp Ala Leu Ser Leu Asp Asn Leu Ser Met Asp Ser Val Ser Asp
            100                 105                 110

Phe Val Gln Asp Met Lys Ser Arg Phe Pro Thr Lys Ile Leu Gln Glu
        115                 120                 125

Ala Ala Lys Ile Glu Lys His Gln Lys Ser Glu Gln Lys Ala Ala Pro
    130                 135                 140

Phe Ala Val Gly Lys Ala Met Lys Ser Glu Gly Leu Asn Ala Lys Tyr
145                 150                 155                 160

Pro Val Val Leu Val Pro Gly Val Ile Ser Thr Gly Leu Glu Ser Trp
                165                 170                 175

Ser Leu Glu Gly Thr Glu Glu Cys Pro Thr Glu Ser His Phe Arg Lys
            180                 185                 190

Arg Met Trp Gly Ser Trp Tyr Met Ile Arg Val Met Leu Leu Asp Lys
        195                 200                 205

Tyr Cys Trp Leu Gln Asn Leu Met Leu Asp Thr Glu Thr Gly Leu Asp
    210                 215                 220

Pro Pro His Phe Lys Leu Arg Ala Ala Gln Gly Phe Ala Ser Ala Asp
225                 230                 235                 240

Phe Phe Met Ala Gly Tyr Trp Leu Trp Asn Lys Leu Leu Glu Asn Leu
                245                 250                 255

Ala Val Ile Gly Tyr Asp Thr Asp Thr Met Ser Ala Ala Ala Tyr Asp
            260                 265                 270
```

```
Trp Arg Leu Ser Tyr Pro Asp Leu Glu His Arg Asp Gly Tyr Phe Ser
        275                 280                 285

Lys Leu Lys Ala Ser Ile Glu Glu Thr Lys Arg Met Thr Gly Glu Lys
    290                 295                 300

Thr Val Leu Thr Gly His Ser Met Gly Ser Gln Val Ile Phe Tyr Phe
305                 310                 315                 320

Met Lys Trp Ala Glu Ala Glu Gly Tyr Gly Gly Gly Pro Asn Trp
                325                 330                 335

Val Asn Asp His Ile Glu Ser Phe Val Asp Ile Ser Gly Ser Met Leu
                340                 345                 350

Gly Thr Pro Lys Thr Leu Val Ala Leu Leu Ser Gly Glu Met Lys Asp
                355                 360                 365

Thr Val Gln Leu Asn Ala Met Ala Val Tyr Gly Leu Glu Gln Phe Phe
                370                 375                 380

Ser Arg Arg Glu Arg Ala Asp Leu Leu Arg Thr Trp Gly Gly Ile Ala
385                 390                 395                 400

Ser Met Ile Pro Lys Gly Gly Lys Ala Ile Trp Gly Asp His Ser Gly
                405                 410                 415

Ala Pro Asp Asp Glu Pro Gly Gln Asn Val Thr Phe Gly Asn Phe Ile
                420                 425                 430

Lys Phe Lys Glu Ser Leu Thr Glu Tyr Ser Ala Lys Asn Leu Thr Met
                435                 440                 445

Asp Glu Thr Val Asp Phe Leu Tyr Ser Gln Ser Pro Glu Trp Phe Val
    450                 455                 460

Asn Arg Thr Glu Gly Ala Tyr Ser Phe Gly Ile Ala Lys Thr Arg Lys
465                 470                 475                 480

Gln Val Glu Gln Asn Glu Lys Arg Pro Ser Thr Trp Ser Asn Pro Leu
                485                 490                 495

Glu Ala Ala Leu Pro Asn Ala Pro Asp Leu Lys Ile Tyr Cys Phe Tyr
                500                 505                 510

Gly Val Gly Lys Asp Thr Glu Arg Ala Tyr Tyr Gln Asp Glu Pro
                515                 520                 525

Asn Pro Glu Gln Thr Asn Leu Asn Val Ser Ile Ala Gly Asn Asp Pro
    530                 535                 540

Asp Gly Val Leu Met Gly Gln Gly Asp Gly Thr Val Ser Leu Val Thr
545                 550                 555                 560

His Thr Met Cys His Arg Trp Lys Asp Glu Asn Ser Lys Phe Asn Pro
                565                 570                 575

Gly Asn Ala Gln Val Lys Val Val Glu Met Leu His Gln Pro Asp Arg
                580                 585                 590

Leu Asp Ile Arg Gly Gly Ala Gln Thr Ala Glu His Val Asp Ile Leu
                595                 600                 605

Gly Arg Ser Glu Leu Asn Glu Met Val Leu Lys Val Ala Ser Gly Lys
    610                 615                 620

Gly Asn Glu Ile Glu Glu Arg Val Ile Ser Asn Ile Asp Glu Trp Val
625                 630                 635                 640

Trp Lys Ile Asp Leu Gly Ser Asn
                645
```

<210> SEQ ID NO 9
<211> LENGTH: 1632
<212> TYPE: DNA
<213> ORGANISM: Yarrowia lipolytica
<220> FEATURE:
<221> NAME/KEY: misc_feature
<223> OTHER INFORMATION: strain CLIB99, chromosome F
<300> PUBLICATION INFORMATION:
<308> DATABASE ACCESSION NUMBER: GenBank NC_006072, bases 974607-976238, locus_tag="YALI0F06578g"
<309> DATABASE ENTRY DATE: 2004-07-30
<313> RELEVANT RESIDUES: (1)..(1632)

<400> SEQUENCE: 9

```
atggccacac tccaccccga agacgccgca ggacggcccg tgcgacgacg acctcgtccc      60
tccagttcgg gcggctccag atcgccgtcc accaaacgac actcgatagt gcgggagcat     120
ctcggagaag agctcaatgt gcccgacggc aggaaatgg acctgggcca ggtcaacaag      180
aacctcaatg ccgcatacgc caaggccgag aaggactcgg acgacgagaa ggaaaagaag     240
gaggagggcg tggtggacga gctgccagag aagtattcct accctcgatt ctcaaagaac     300
aaccgacgct acagattcac cgacatcaag ttcaagccaa caccgtcgat tctcgacaag     360
ttcgcccaca aggactcgga gttcttggc ttctacaccc tgctgtggat ggtgtttgcc      420
ttctgcgtct tccgaaccgg cctgctcaac tacacaaacg aaggcatcct gttccggggc     480
cagatttttcg ccattctcag caaagatctc tggaaagtcg cattggtcga tctgggcatg   540
tacctgacca cctatctgtc tgtgtttctg caattggccg tcaagcacgg tctggtcgac    600
tggaactcgt ttggctggat catccagaac gtgcaccaga ccctgttcct cttcttctac    660
ctttgggtcg ccaagtcgag taacctgcct tggatcggta acatcttcat tgtgcttcat    720
gcctttgtca tgctcatgaa acaacactcg tacgccttct acaatggcta cctatggact    780
gtcgaggacg agctctccca cgcaaagcag cgtctcaccg aagacattcc tgtttcagag    840
aaggaggatc tcaagctgga catcgagttc tgcgagacag agctcaaggt ccaatccaga    900
cacacccctt tccccaccaa catcaccttt tctaactact tctggtactc catgttccca    960
acgctcgtct acgaaattga gttccctcga accccccgaa tcaagtggac atacgtgctg   1020
gagaaggtcg ccgcagtctt tggcgtcttc ttccttatga tctgggtcgc agagtcgtac   1080
ctgtatcccc ctgtggtggc tgttattcaa atgcgagacg aaccttctg gaacaaggtc    1140
cgaatctatc ccatttttcct gtcggacatt ctgctgccct ttgtcattga gtacatgctt   1200
gttttctaca tcatctggga cgccattctc aacggcattg ccgagctcac tcgcttcgcc   1260
gacagagact tttatggccc ctggtggaac tgtaccagct gggagcagtt tagccgagaa   1320
tggaacattc ctgtctacca gttcctcaag cgacacgtct accactcgtc catctctgct   1380
ttcaagttct ccaagggcgc agctaccctc accaccttct gctgtcttc tcttgtccac   1440
gagctggtca tgtttgccat ctttaagaag ttccgaggat acctgctgtt gctgcagatg   1500
acccagctgc cctggccat gctgcagaaa accaaatgga tccaggacag accgttttt   1560
ggcaacgctt tcttctggtt ctcgctcatg atcggacctt ctctcatgtg ttccatgtac   1620
ctcctcttct aa                                                        1632
```

<210> SEQ ID NO 10
<211> LENGTH: 543
<212> TYPE: PRT
<213> ORGANISM: Yarrowia lipolytica
<220> FEATURE:
<221> NAME/KEY: MISC_FEATURE
<223> OTHER INFORMATION: strain CLIB99, chromosome F
<300> PUBLICATION INFORMATION:
<308> DATABASE ACCESSION NUMBER: GenBank NC_006072, locus_tag="YALI0F06578g"
<309> DATABASE ENTRY DATE: 2004-07-30
<313> RELEVANT RESIDUES: (1)..(543)

<400> SEQUENCE: 10

```
Met Ala Thr Leu His Pro Glu Asp Ala Ala Gly Arg Pro Val Arg Arg
1               5                   10                  15

Arg Pro Arg Pro Ser Ser Gly Gly Ser Arg Ser Pro Ser Thr Lys
            20                  25                  30

Arg His Ser Ile Val Arg Glu His Leu Gly Glu Glu Leu Asn Val Pro
                35                  40                  45

Asp Gly Gln Glu Met Asp Leu Gly Gln Val Asn Lys Asn Leu Asn Ala
    50                  55                  60

Ala Tyr Ala Lys Ala Glu Lys Asp Ser Asp Glu Lys Glu Lys Lys
65                  70                  75                  80

Glu Glu Gly Val Val Asp Glu Leu Pro Glu Lys Tyr Ser Tyr Pro Arg
                85                  90                  95

Phe Ser Lys Asn Asn Arg Arg Tyr Arg Phe Thr Asp Ile Lys Phe Lys
                100                 105                 110

Pro Thr Pro Ser Ile Leu Asp Lys Phe Ala His Lys Asp Ser Glu Phe
            115                 120                 125

Phe Gly Phe Tyr Thr Leu Leu Trp Met Val Phe Ala Phe Cys Val Phe
130                 135                 140

Arg Thr Gly Leu Leu Asn Tyr Thr Asn Glu Gly Ile Leu Phe Arg Gly
145                 150                 155                 160

Gln Ile Phe Ala Ile Leu Ser Lys Asp Leu Trp Lys Val Ala Leu Val
                165                 170                 175

Asp Leu Gly Met Tyr Leu Thr Thr Tyr Leu Ser Val Phe Leu Gln Leu
            180                 185                 190

Ala Val Lys His Gly Leu Val Asp Trp Asn Ser Phe Gly Trp Ile Ile
                195                 200                 205

Gln Asn Val His Gln Thr Leu Phe Leu Phe Phe Tyr Leu Trp Val Ala
    210                 215                 220

Lys Ser Ser Asn Leu Pro Trp Ile Gly Asn Ile Phe Ile Val Leu His
225                 230                 235                 240

Ala Phe Val Met Leu Met Lys Gln His Ser Tyr Ala Phe Tyr Asn Gly
                245                 250                 255

Tyr Leu Trp Thr Val Glu Asp Glu Leu Ser His Ala Lys Gln Arg Leu
            260                 265                 270

Thr Glu Asp Ile Pro Val Ser Glu Lys Glu Asp Leu Lys Leu Asp Ile
        275                 280                 285

Glu Phe Cys Glu Thr Glu Leu Lys Val Gln Ser Arg His Thr Pro Phe
290                 295                 300

Pro Thr Asn Ile Thr Phe Ser Asn Tyr Phe Trp Tyr Ser Met Phe Pro
305                 310                 315                 320

Thr Leu Val Tyr Glu Ile Glu Phe Pro Arg Thr Pro Arg Ile Lys Trp
                325                 330                 335

Thr Tyr Val Leu Glu Lys Val Ala Ala Val Phe Gly Val Phe Phe Leu
            340                 345                 350

Met Ile Trp Val Ala Glu Ser Tyr Leu Tyr Pro Pro Val Val Ala Val
                355                 360                 365

Ile Gln Met Arg Asp Glu Pro Phe Trp Asn Lys Val Arg Ile Tyr Pro
    370                 375                 380

Ile Phe Leu Ser Asp Ile Leu Leu Pro Phe Val Ile Glu Tyr Met Leu
385                 390                 395                 400

Val Phe Tyr Ile Ile Trp Asp Ala Ile Leu Asn Gly Ile Ala Glu Leu
                405                 410                 415
```

```
Thr Arg Phe Ala Asp Arg Asp Phe Tyr Gly Pro Trp Trp Asn Cys Thr
            420                 425                 430

Ser Trp Glu Gln Phe Ser Arg Glu Trp Asn Ile Pro Val Tyr Gln Phe
        435                 440                 445

Leu Lys Arg His Val Tyr His Ser Ser Ile Ser Ala Phe Lys Phe Ser
    450                 455                 460

Lys Gly Ala Ala Thr Leu Thr Thr Phe Leu Leu Ser Ser Leu Val His
465                 470                 475                 480

Glu Leu Val Met Phe Ala Ile Phe Lys Lys Phe Arg Gly Tyr Leu Leu
                485                 490                 495

Leu Leu Gln Met Thr Gln Leu Pro Leu Ala Met Leu Gln Lys Thr Lys
            500                 505                 510

Trp Ile Gln Asp Arg Pro Val Phe Gly Asn Ala Phe Phe Trp Phe Ser
            515                 520                 525

Leu Met Ile Gly Pro Ser Leu Met Cys Ser Met Tyr Leu Leu Phe
            530                 535                 540

<210> SEQ ID NO 11
<211> LENGTH: 1581
<212> TYPE: DNA
<213> ORGANISM: Yarrowia lipolytica
<220> FEATURE:
<221> NAME/KEY: misc_feature
<223> OTHER INFORMATION: strain CLIB99, chromosome D
<300> PUBLICATION INFORMATION:
<308> DATABASE ACCESSION NUMBER: GenBank CR382130, bases
      1026155-1027735, locus_tag="YALI0D07986g"
<309> DATABASE ENTRY DATE: 2005-04-17
<313> RELEVANT RESIDUES: (1)..(1581)

<400> SEQUENCE: 11
atggaagtcc gacgacgaaa aatcgacgtg ctcaaggccc agaaaaacgg ctacgaatcg     60
ggcccaccat ctcgacaatc gtcgcagccc tcctcaagag catcgtccag aacccgcaac    120
aaacactcct cgtccaccct gtcgctcagc ggactgacca tgaaagtcca gaagaaacct    180
gcgggacccc cggcgaactc caaaacgcca ttcctacaca tcaagcccgt gcacacgtgc    240
tgctccacat caatgctttc gcgcgattat gacggctcca accccagctt caagggcttc    300
aaaaacatcg gcatgatcat tctcattgtg gaaatctac ggctcgcatt cgaaaactac    360
ctcaaatacg gcatttccaa cccgttcttc gaccccaaaa ttactccttc cgagtggcag    420
ctctcaggct tgctccatagt cgtggcctac gcacatatcc tcatggccta cgctattgag    480
agcgctgcca agctgctgtt cctctctagc aaacaccact acatggccgt ggggcttctg    540
cataccatga acactttgtc gtccatctcg ttgctgtcct acgtcgtcta ctactacctg    600
cccaaccccg tggcaggcac aatagtcgag tttgtggccg ttattctgtc tctcaaactc    660
gcctcatacg ccctcactaa ctcggatctc cgaaaagccg caattcatgc ccagaagctc    720
gacaagacgc aagacgataa cgaaaaggaa tccacctcgt cttcctcttc ttcagatgac    780
gcagagactt tggcagacat tgacgtcatt cctgcatact acgcacagct gccctacccc    840
cagaatgtga cgctgtcgaa cctgctgtac ttctggtttg ctcccacact ggtctaccag    900
cccgtgtacc ccaagacgga gcgtattcga cccaagcacg tgatccgaaa cctgtttgag    960
ctcgtctctc tgtgcatgct tattcagttt ctcatcttcc agtacgccta ccccatcatg   1020
cagtcgtgtc tggctctgtt cttccagccc aagctcgatt atgccaacat ctccgagcgc   1080
ctcatgaagt tggcctccgt gtctatgatg gtctggctca ttggattcta cgctttcttc   1140
```

-continued

```
cagaacggtc tcaatcttat tgccgagctc acctgttttg gaaacagaac cttctaccag    1200
cagtggtgga attcccgctc cattggccag tactggactc tatggaacaa gccagtcaac    1260
cagtacttta gacaccacgt ctacgtgcct cttctcgctc ggggcatgtc gcggttcaat    1320
gcgtcggtgg tggttttctt tttctccgcc gtcatccatg aactgcttgt cggcatcccc    1380
actcacaaca tcatcggagc cgccttcttc ggcatgatgt cgcaggtgcc tctgatcatg    1440
gctactgaga accttcagca tattaactcc tctctgggcc ccttccttgg caactgtgca    1500
ttctggttca ccttttcct gggacaaccc acttgtgcat tcctttatta tctggcttac     1560
aactacaagc agaaccagta g                                              1581
```

<210> SEQ ID NO 12
<211> LENGTH: 526
<212> TYPE: PRT
<213> ORGANISM: Yarrowia lipolytica
<220> FEATURE:
<221> NAME/KEY: MISC_FEATURE
<223> OTHER INFORMATION: strain CLIB99, chromosome D
<300> PUBLICATION INFORMATION:
<308> DATABASE ACCESSION NUMBER: GenBank CR382130,
    locus_tag="YALI0D07986g"
<309> DATABASE ENTRY DATE: 2005-04-17
<313> RELEVANT RESIDUES: (1)..(526)

<400> SEQUENCE: 12

```
Met Glu Val Arg Arg Arg Lys Ile Asp Val Leu Lys Ala Gln Lys Asn
1               5                   10                  15

Gly Tyr Glu Ser Gly Pro Pro Ser Arg Gln Ser Ser Gln Pro Ser Ser
            20                  25                  30

Arg Ala Ser Ser Arg Thr Arg Asn Lys His Ser Ser Ser Thr Leu Ser
        35                  40                  45

Leu Ser Gly Leu Thr Met Lys Val Gln Lys Lys Pro Ala Gly Pro Pro
    50                  55                  60

Ala Asn Ser Lys Thr Pro Phe Leu His Ile Lys Pro Val His Thr Cys
65                  70                  75                  80

Cys Ser Thr Ser Met Leu Ser Arg Asp Tyr Asp Gly Ser Asn Pro Ser
                85                  90                  95

Phe Lys Gly Phe Lys Asn Ile Gly Met Ile Ile Leu Ile Val Gly Asn
            100                 105                 110

Leu Arg Leu Ala Phe Glu Asn Tyr Leu Lys Tyr Gly Ile Ser Asn Pro
        115                 120                 125

Phe Phe Asp Pro Lys Ile Thr Pro Ser Glu Trp Gln Leu Ser Gly Leu
    130                 135                 140

Leu Ile Val Val Ala Tyr Ala His Ile Leu Met Ala Tyr Ala Ile Glu
145                 150                 155                 160

Ser Ala Ala Lys Leu Leu Phe Leu Ser Ser Lys His His Tyr Met Ala
                165                 170                 175

Val Gly Leu Leu His Thr Met Asn Thr Leu Ser Ser Ile Ser Leu Leu
            180                 185                 190

Ser Tyr Val Val Tyr Tyr Leu Pro Asn Pro Val Ala Gly Thr Ile
        195                 200                 205

Val Glu Phe Val Ala Val Ile Leu Ser Leu Lys Leu Ala Ser Tyr Ala
    210                 215                 220

Leu Thr Asn Ser Asp Leu Arg Lys Ala Ala Ile His Ala Gln Lys Leu
225                 230                 235                 240

Asp Lys Thr Gln Asp Asp Asn Glu Lys Glu Ser Thr Ser Ser Ser Ser
                245                 250                 255
```

```
Ser Ser Asp Asp Ala Glu Thr Leu Ala Asp Ile Asp Val Ile Pro Ala
        260                 265                 270
Tyr Tyr Ala Gln Leu Pro Tyr Pro Gln Asn Val Thr Leu Ser Asn Leu
        275                 280                 285
Leu Tyr Phe Trp Phe Ala Pro Thr Leu Val Tyr Gln Pro Val Tyr Pro
        290                 295                 300
Lys Thr Glu Arg Ile Arg Pro Lys His Val Ile Arg Asn Leu Phe Glu
305                 310                 315                 320
Leu Val Ser Leu Cys Met Leu Ile Gln Phe Leu Ile Phe Gln Tyr Ala
                325                 330                 335
Tyr Pro Ile Met Gln Ser Cys Leu Ala Leu Phe Phe Gln Pro Lys Leu
        340                 345                 350
Asp Tyr Ala Asn Ile Ser Glu Arg Leu Met Lys Leu Ala Ser Val Ser
        355                 360                 365
Met Met Val Trp Leu Ile Gly Phe Tyr Ala Phe Phe Gln Asn Gly Leu
        370                 375                 380
Asn Leu Ile Ala Glu Leu Thr Cys Phe Gly Asn Arg Thr Phe Tyr Gln
385                 390                 395                 400
Gln Trp Trp Asn Ser Arg Ser Ile Gly Gln Tyr Trp Thr Leu Trp Asn
                405                 410                 415
Lys Pro Val Asn Gln Tyr Phe Arg His His Val Tyr Val Pro Leu Leu
                420                 425                 430
Ala Arg Gly Met Ser Arg Phe Asn Ala Ser Val Val Phe Phe Phe
        435                 440                 445
Ser Ala Val Ile His Glu Leu Leu Val Gly Ile Pro Thr His Asn Ile
450                 455                 460
Ile Gly Ala Ala Phe Phe Gly Met Met Ser Gln Val Pro Leu Ile Met
465                 470                 475                 480
Ala Thr Glu Asn Leu Gln His Ile Asn Ser Ser Leu Gly Pro Phe Leu
                485                 490                 495
Gly Asn Cys Ala Phe Trp Phe Thr Phe Phe Leu Gly Gln Pro Thr Cys
                500                 505                 510
Ala Phe Leu Tyr Tyr Leu Ala Tyr Asn Tyr Lys Gln Asn Gln
                515                 520                 525

<210> SEQ ID NO 13
<211> LENGTH: 1578
<212> TYPE: DNA
<213> ORGANISM: Yarrowia lipolytica

<400> SEQUENCE: 13
atggaggtcc gacgacgaaa gatagacgtg ctcaaggccc agaaaaacgg ctacgaatcg      60
ggcccaccat ctcgacaatc gtcgcagccc tcctcaagag catcgtccag aacccgcaac     120
aaacactcct cgtccaccct gtcgctcagc ggactgacca tgaaagtcca agagaaacct     180
gcgggacccc cggcgaactc caaaacgcca ttcctacaca tcaagcccgt gcacacgtgc     240
tgctccacat caatgctttc gcgcgattat gacggctcca accccagctt caagggcttc     300
aaaaacatcg gcatgatcat tctcattgtg ggaaatctac ggctcgcatt cgaaaactac     360
ctcaaatacg gcatttccaa cccgttcttc gaccccaaaa ttactccttc cgagtggcag     420
ctctcaggct tgctcatagt cgtggcctac gcacatatcc tcatggccta cgctattgag     480
agcgctgcca agctgctgtt cctctctagc aaacaccact acatggccgt ggggcttctg     540
cataccatga acactttgtc gtccatctcg ttgctgtcct acgtcgtcta ctactacctg     600
```

```
cccaaccccg tggcaggcac aatagtcgag tttgtggccg ttattctgtc tctcaaactc      660
gcctcatacg ccctcactaa ctcggatctc cgaaaagccg caattcatgc ccagaagctc      720
gacaagacgc aagacgataa cgaaaaggaa tccacctcgt cttcctcttc ttcagatgac      780
gcagagactt tggcagacat tgacgtcatt cctgcatact acgcacagct gccctacccc      840
cagaatgtga cgctgtcgaa cctgctgtac ttctggtttg ctcccacact ggtctaccag      900
cccgtgtacc ccaagacgga gcgtattcga cccaagcacg tgatccgaaa cctgtttgag      960
ctcgtctctc tgtgcatgct tattcagttt ctcatcttcc agtacgccta ccccatcatg     1020
cagtcgtgtc tggctctgtt cttccagccc aagctcgatt atgccaacat ctccgagcgc     1080
ctcatgaagt tggcctccgt gtctatgatg gtctggctca ttggattcta cgctttcttc     1140
cagaacggtc tcaatcttat tgccgagctc acctgttttg gaaacagaac cttctaccag     1200
cagtggtgga attcccgctc cattggccag tactggactc tatggaacaa gccagtcaac     1260
cagtacttta gacaccacgt ctacgtgcct cttctcgctc ggggcatgtc gcggttcaat     1320
gcgtcggtgg tggttttctt tttctccgcc gtcatccatg aactgcttgt cggcatcccc     1380
actcacaaca tcatcggagc cgccttcttc ggcatgatgt cgcaggtgcc tctgatcatg     1440
gctactgaga accttcagca tattaactcc tctctgggcc ccttccttgg caactgtgca     1500
ttctggttca ccttttcct gggacaaccc acttgtgcat tcctttacta tttggcctac     1560
aactacaagc agaaccag                                                   1578
```

<210> SEQ ID NO 14
<211> LENGTH: 526
<212> TYPE: PRT
<213> ORGANISM: Yarrowia lipolytica
<220> FEATURE:
<221> NAME/KEY: misc_feature
<222> LOCATION: (518)..(518)
<223> OTHER INFORMATION: Xaa can be any naturally occurring amino acid

<400> SEQUENCE: 14

```
Met Glu Val Arg Arg Arg Lys Ile Asp Val Leu Lys Ala Gln Lys Asn
1               5                   10                  15

Gly Tyr Glu Ser Gly Pro Pro Ser Arg Gln Ser Ser Gln Pro Ser Ser
            20                  25                  30

Arg Ala Ser Ser Arg Thr Arg Asn Lys His Ser Ser Ser Thr Leu Ser
        35                  40                  45

Leu Ser Gly Leu Thr Met Lys Val Gln Lys Lys Pro Ala Gly Pro Pro
    50                  55                  60

Ala Asn Ser Lys Thr Pro Phe Leu His Ile Lys Pro Val His Thr Cys
65                  70                  75                  80

Cys Ser Thr Ser Met Leu Ser Arg Asp Tyr Asp Gly Ser Asn Pro Ser
                85                  90                  95

Phe Lys Gly Phe Lys Asn Ile Gly Met Ile Ile Leu Ile Val Gly Asn
            100                 105                 110

Leu Arg Leu Ala Phe Glu Asn Tyr Leu Lys Tyr Gly Ile Ser Asn Pro
        115                 120                 125

Phe Phe Asp Pro Lys Ile Thr Pro Ser Glu Trp Gln Leu Ser Gly Leu
    130                 135                 140

Leu Ile Val Val Ala Tyr Ala His Ile Leu Met Ala Tyr Ala Ile Glu
145                 150                 155                 160

Ser Ala Ala Lys Leu Leu Phe Leu Ser Ser Lys His His Tyr Met Ala
                165                 170                 175
```

```
Val Gly Leu Leu His Thr Met Asn Thr Leu Ser Ser Ile Ser Leu Leu
            180                 185                 190

Ser Tyr Val Val Tyr Tyr Leu Pro Asn Pro Val Ala Gly Thr Ile
        195                 200                 205

Val Glu Phe Val Ala Val Ile Leu Ser Leu Lys Leu Ala Ser Tyr Ala
    210                 215                 220

Leu Thr Asn Ser Asp Leu Arg Lys Ala Ile His Ala Gln Lys Leu
225                 230                 235                 240

Asp Lys Thr Gln Asp Asp Asn Glu Lys Glu Ser Thr Ser Ser Ser
                245                 250                 255

Ser Ser Asp Asp Ala Glu Thr Leu Ala Asp Ile Asp Val Ile Pro Ala
            260                 265                 270

Tyr Tyr Ala Gln Leu Pro Tyr Pro Gln Asn Val Thr Leu Ser Asn Leu
            275                 280                 285

Leu Tyr Phe Trp Phe Ala Pro Thr Leu Val Tyr Gln Pro Val Tyr Pro
        290                 295                 300

Lys Thr Glu Arg Ile Arg Pro Lys His Val Ile Arg Asn Leu Phe Glu
305                 310                 315                 320

Leu Val Ser Leu Cys Met Leu Ile Gln Phe Leu Ile Phe Gln Tyr Ala
                325                 330                 335

Tyr Pro Ile Met Gln Ser Cys Leu Ala Leu Phe Phe Gln Pro Lys Leu
            340                 345                 350

Asp Tyr Ala Asn Ile Ser Glu Arg Leu Met Lys Leu Ala Ser Val Ser
            355                 360                 365

Met Met Val Trp Leu Ile Gly Phe Tyr Ala Phe Phe Gln Asn Gly Leu
    370                 375                 380

Asn Leu Ile Ala Glu Leu Thr Cys Phe Gly Asn Arg Thr Phe Tyr Gln
385                 390                 395                 400

Gln Trp Trp Asn Ser Arg Ser Ile Gly Gln Tyr Trp Thr Leu Trp Asn
                405                 410                 415

Lys Pro Val Asn Gln Tyr Phe Arg His His Val Tyr Val Pro Leu Leu
            420                 425                 430

Ala Arg Gly Met Ser Arg Phe Asn Ala Ser Val Val Phe Phe
            435                 440                 445

Ser Ala Val Ile His Glu Leu Leu Val Gly Ile Pro Thr His Asn Ile
    450                 455                 460

Ile Gly Ala Ala Phe Phe Gly Met Met Ser Gln Val Pro Leu Ile Met
465                 470                 475                 480

Ala Thr Glu Asn Leu Gln His Ile Asn Ser Ser Leu Gly Pro Phe Leu
                485                 490                 495

Gly Asn Cys Ala Phe Trp Phe Thr Phe Phe Leu Gly Gln Pro Thr Cys
            500                 505                 510

Ala Phe Leu Tyr Tyr Xaa Ala Tyr Asn Tyr Lys Gln Asn Gln
            515                 520                 525

<210> SEQ ID NO 15
<211> LENGTH: 1632
<212> TYPE: DNA
<213> ORGANISM: Yarrowia lipolytica

<400> SEQUENCE: 15
atggccacac tccaccccga agacgccgca ggacggcccg tgcgacgacg acctcgtccc      60
tccagttcgg gcggtccag atcgccgtcc accaaacgac actcgatagt gcgggagcat     120
```

-continued

```
ctcggagaag agctcaatgt gcccgacggc caggaaatgg acctgggcca ggtcaacaag    180
aacctcaatg ccgcatacgc caaggccgag aaggactcgg acgacgagaa ggaaaagaag    240
gaggagggcg tggtggacga gctgccagag aagtattcct accctcgatt ctcaaagaac    300
aaccgacgct acagattcac cgacatcaag ttcaagccaa caccgtcgat tctcgacaag    360
ttcgcccaca aggactcgga gttctttggc ttctacaccc tgctgtggat ggtgtttgcc    420
ttctgcgtct tccgaaccgg cctgctcaac tacacaaacg aaggcatcct gttccggggc    480
cagattttcg ccattctcag caaagatctc tggaaagtcg cattggtcga tctgggcatg    540
tacctgacca cctatctgtc tgtgtttctg caattggccg tcaagcacgg tctggtcgac    600
tggaactcgt ttggctggat catccagaac gtgcaccaga ccctgttcct cttcttctac    660
ctttgggtcg ccaagtcgag taacctgcct tggatcggta acatcttcat tgtgcttcat    720
gcctttgtca tgctcatgaa acaacactcg tacgccttct acaatggcta cctatggact    780
gtcgaggaca agctctccca cgcaaagcag cgtctcaccg aagacattcc tgtttcagag    840
aaggaggatc tcaagctgga catcgagttc tgcgagacag agctcaaggt ccaatccaga    900 cacaccccctt tccccaccaa catcacccttt tctaactact tctggtactc catgttccca    960
acgctcgtct acgaaattga gttccctcga accccccgaa tcaagtggac atacgtgctg   1020
gagaaggtcg ccgcagtctt tggcgtcttc ttccttatga tctgggtcgc agagtcgtac   1080
ctgtatcccc ctgtggtggc tgttattcaa atgcgagacg aacccttctg gaacaaggtc   1140
cgaatctatc ccattttcct gtcggacatt ctgctgccct tgtcattga gtacatgctt   1200 gttttctaca tcatctggga cgccattctc aacggcattg ccgagctcac tcgcttcgcc   1260
gacagagact tttatggccc ctggtggaac tgtaccagct gggagcagtt tagccgagaa   1320
tggaacattc ctgtctacca gttcctcaag cgacacgtct accactcgtc catctctgct   1380
ttcaagttct ccaagggcgc agctaccctc accaccttct gctgtcttc tcttgtccac   1440 gagctggtca tgtttgccat ctttaagaag ttccgaggat acctgctgtt gctgcagatg   1500
acccagctgc ccctggccat gctgcagaaa accaaatgga tccaggacag acccgttttt   1560
ggcaacgctt tcttctggtt ctcgctcatg atcggacctt ctctcatgtg ttccatgtac   1620
ctcctcttct aa                                                        1632
```

<210> SEQ ID NO 16
<211> LENGTH: 543
<212> TYPE: PRT
<213> ORGANISM: Yarrowia lipolytica

<400> SEQUENCE: 16

```
Met Ala Thr Leu His Pro Glu Asp Ala Ala Gly Arg Pro Val Arg Arg
1               5                   10                  15

Arg Pro Arg Pro Ser Ser Gly Gly Ser Arg Ser Pro Ser Thr Lys
            20                  25                  30

Arg His Ser Ile Val Arg Glu His Leu Gly Glu Glu Leu Asn Val Pro
        35                  40                  45

Asp Gly Gln Glu Met Asp Leu Gly Gln Val Asn Lys Asn Leu Asn Ala
    50                  55                  60

Ala Tyr Ala Lys Ala Glu Lys Asp Ser Asp Asp Glu Lys Glu Lys Lys
65                  70                  75                  80

Glu Glu Gly Val Val Asp Glu Leu Pro Glu Lys Tyr Ser Tyr Pro Arg
                85                  90                  95

Phe Ser Lys Asn Asn Arg Arg Tyr Arg Phe Thr Asp Ile Lys Phe Lys
```

-continued

```
            100                 105                 110
Pro Thr Pro Ser Ile Leu Asp Lys Phe Ala His Lys Asp Ser Glu Phe
        115                 120                 125

Phe Gly Phe Tyr Thr Leu Leu Trp Met Val Phe Ala Phe Cys Val Phe
    130                 135                 140

Arg Thr Gly Leu Leu Asn Tyr Thr Asn Glu Gly Ile Leu Phe Arg Gly
145                 150                 155                 160

Gln Ile Phe Ala Ile Leu Ser Lys Asp Leu Trp Lys Val Ala Leu Val
                165                 170                 175

Asp Leu Gly Met Tyr Leu Thr Thr Tyr Leu Ser Val Phe Leu Gln Leu
            180                 185                 190

Ala Val Lys His Gly Leu Val Asp Trp Asn Ser Phe Gly Trp Ile Ile
        195                 200                 205

Gln Asn Val His Gln Thr Leu Phe Leu Phe Phe Tyr Leu Trp Val Ala
    210                 215                 220

Lys Ser Ser Asn Leu Pro Trp Ile Gly Asn Ile Phe Ile Val Leu His
225                 230                 235                 240

Ala Phe Val Met Leu Met Lys Gln His Ser Tyr Ala Phe Tyr Asn Gly
                245                 250                 255

Tyr Leu Trp Thr Val Glu Asp Glu Leu Ser His Ala Lys Gln Arg Leu
            260                 265                 270

Thr Glu Asp Ile Pro Val Ser Glu Lys Glu Asp Leu Lys Leu Asp Ile
        275                 280                 285

Glu Phe Cys Glu Thr Glu Leu Lys Val Gln Ser Arg His Thr Pro Phe
    290                 295                 300

Pro Thr Asn Ile Thr Phe Ser Asn Tyr Phe Trp Tyr Ser Met Phe Pro
305                 310                 315                 320

Thr Leu Val Tyr Glu Ile Glu Phe Pro Arg Thr Pro Arg Ile Lys Trp
                325                 330                 335

Thr Tyr Val Leu Glu Lys Val Ala Ala Val Phe Gly Val Phe Phe Leu
            340                 345                 350

Met Ile Trp Val Ala Glu Ser Tyr Leu Tyr Pro Pro Val Val Ala Val
        355                 360                 365

Ile Gln Met Arg Asp Glu Pro Phe Trp Asn Lys Val Arg Ile Tyr Pro
    370                 375                 380

Ile Phe Leu Ser Asp Ile Leu Leu Pro Phe Val Ile Glu Tyr Met Leu
385                 390                 395                 400

Val Phe Tyr Ile Ile Trp Asp Ala Ile Leu Asn Gly Ile Ala Glu Leu
                405                 410                 415

Thr Arg Phe Ala Asp Arg Asp Phe Tyr Gly Pro Trp Trp Asn Cys Thr
            420                 425                 430

Ser Trp Glu Gln Phe Ser Arg Glu Trp Asn Ile Pro Val Tyr Gln Phe
        435                 440                 445

Leu Lys Arg His Val Tyr His Ser Ser Ile Ser Ala Phe Lys Phe Ser
    450                 455                 460

Lys Gly Ala Ala Thr Leu Thr Thr Phe Leu Leu Ser Ser Leu Val His
465                 470                 475                 480

Glu Leu Val Met Phe Ala Ile Phe Lys Lys Phe Arg Gly Tyr Leu Leu
                485                 490                 495

Leu Leu Gln Met Thr Gln Leu Pro Leu Ala Met Leu Gln Lys Thr Lys
            500                 505                 510

Trp Ile Gln Asp Arg Pro Val Phe Gly Asn Ala Phe Phe Trp Phe Ser
        515                 520                 525
```

Leu Met Ile Gly Pro Ser Leu Met Cys Ser Met Tyr Leu Leu Phe
    530                 535                 540

<210> SEQ ID NO 17
<211> LENGTH: 1578
<212> TYPE: DNA
<213> ORGANISM: Mortierella alpina
<220> FEATURE:
<221> NAME/KEY: misc_feature
<222> LOCATION: (466)..(466)
<223> OTHER INFORMATION: n is a, c, g, or t

<400> SEQUENCE: 17

| | | | | | |
|---|---|---|---|---|---|
| atgacagagt | cgacaacaac | gacatgtgca | aaggaggagg | gcattgccaa | cagcgctgct | 60 |
| ttgcctgaca | ttcccccaaa | gatggaagac | ctcaagtcct | ccaggaagac | cggctcttct | 120 |
| tacaagcaca | ccttccccgt | ccatacaaaa | accatcccca | gcccattgtc | taaagaggca | 180 |
| cctccagaga | gctatcgtgg | attcgtcaac | ctcggcatgc | tcctactttt | cggcaacaac | 240 |
| atccgattga | tcatcgagaa | ttacctcaaa | tacggcttcc | tgctctcaat | ccctggatca | 300 |
| agcgtctcga | agcaggactg | gatcctggct | gccctcaccc | acgccatcct | acccgtcaac | 360 |
| ctcatcctgg | cctacaagct | tgagagctgg | gccaaggaga | gagccgtcgg | ctatcgcaag | 420 |
| cgtcgatctg | acgaacccat | tgcccaggaa | tcaaccaagg | ccgtgncagc | aggagataat | 480 |
| gacgctatca | aaaccacaaa | acccgccaag | gcccaggatc | tcacacccga | ggcccttgca | 540 |
| aggaaggaac | aatcgaccgt | gggctggctc | catgtcttca | atctgttcac | catcgttgcc | 600 |
| tggccctcct | tcatgtccta | ctttatgatc | taccaccct | tcgtggccat | gtcctgcctc | 660 |
| atgaacggac | ttatcctctt | cctcaaaatg | acctcctttg | cgcttgtgaa | ccaggagctc | 720 |
| cgagcagcct | acatctttgg | aacacccgtg | gacacgttcc | agcacatggc | taaagtgcac | 780 |
| gacatctctg | gcaaggacct | gacaaagaag | gagatcttcc | agtatgacat | ccagtacccc | 840 |
| gacaacatca | ccctcaagaa | cattggctat | ttctggctcg | ccccacgct | ctgctaccag | 900 |
| ccatcatacc | caaggacgac | cgtcttccgc | aaatccttct | tcctcaagcg | tgtggccgag | 960 |
| atcgtgacct | gtctgggcat | gatgtacttt | ttagtcgagc | agtacgccac | ccccacccctg | 1020 |
| cagaactcgg | tccgagcatt | cgatgagttg | gcgttcggca | ccattctgga | gagagtgctg | 1080 |
| aagctgagca | ccaccagtgt | catcatctgg | ctactcatgt | tctacacctt | tttccactcg | 1140 |
| ttctttaatg | ctcttgcaga | ggcactgtac | tttggagacc | gtcgcttcta | tctcgcctgg | 1200 |
| tggaatgcca | ctggtgtcgg | catgtactgg | aagacgtgga | actcgcccgt | ctacaccttc | 1260 |
| ttcaaacgcc | acgtatacct | gccctgatc | acctctggca | cctctcccat | ggtcgcctcg | 1320 |
| atcgtcatct | tcctcatctc | ggctgtcttg | cacgagatct | tgatcggctt | ccccactcat | 1380 |
| atgatctatg | gatacgcatt | cgccggcatg | ttcctccaga | tcccgctgat | cattctgacc | 1440 |
| cgaccccctcg | aaaatggcg | aggcaccgga | tcgggtctcg | gcaacatgat | cttctgggtc | 1500 |
| tcgttcacca | tcctgggcca | gccagcgtgt | gcgctgctct | actactacca | ctggaccaag | 1560 |
| cgccatatgg | atgtttga | | | | | 1578 |

<210> SEQ ID NO 18
<211> LENGTH: 525
<212> TYPE: PRT
<213> ORGANISM: Mortierella alpina
<220> FEATURE:
<221> NAME/KEY: misc_feature
<222> LOCATION: (156)..(156)
<223> OTHER INFORMATION: Xaa can be any naturally occurring amino acid

<400> SEQUENCE: 18

```
Met Thr Glu Ser Thr Thr Thr Cys Ala Lys Glu Glu Gly Ile Ala
1               5                   10                  15

Asn Ser Ala Ala Leu Pro Asp Ile Pro Pro Lys Met Glu Asp Leu Lys
            20                  25                  30

Ser Ser Arg Lys Thr Gly Ser Ser Tyr Lys His Thr Phe Pro Val His
            35                  40                  45

Thr Lys Thr Ile Pro Ser Pro Leu Ser Lys Glu Ala Pro Pro Glu Ser
            50                  55                  60

Tyr Arg Gly Phe Val Asn Leu Gly Met Leu Leu Phe Gly Asn Asn
65                  70                  75                  80

Ile Arg Leu Ile Ile Glu Asn Tyr Leu Lys Tyr Gly Phe Leu Leu Ser
                85                  90                  95

Ile Pro Gly Ser Ser Val Ser Lys Gln Asp Trp Ile Leu Ala Ala Leu
            100                 105                 110

Thr His Ala Ile Leu Pro Val Asn Leu Ile Leu Ala Tyr Lys Leu Glu
            115                 120                 125

Ser Trp Ala Lys Glu Arg Ala Val Gly Tyr Arg Lys Arg Arg Ser Asp
            130                 135                 140

Glu Pro Ile Ala Gln Glu Ser Thr Lys Ala Val Xaa Ala Gly Asp Asn
145                 150                 155                 160

Asp Ala Ile Lys Thr Thr Lys Pro Ala Lys Ala Gln Asp Leu Thr Pro
                165                 170                 175

Glu Ala Leu Ala Arg Lys Glu Gln Ser Thr Val Gly Trp Leu His Val
            180                 185                 190

Phe Asn Leu Phe Thr Ile Val Ala Trp Pro Ser Phe Met Ser Tyr Phe
            195                 200                 205

Met Ile Tyr His Pro Phe Val Ala Met Ser Cys Leu Met Asn Gly Leu
            210                 215                 220

Ile Leu Phe Leu Lys Met Thr Ser Phe Ala Leu Val Asn Gln Glu Leu
225                 230                 235                 240

Arg Ala Ala Tyr Ile Phe Gly Thr Pro Val Asp Thr Phe Gln His Met
                245                 250                 255

Ala Lys Val His Asp Ile Ser Gly Lys Asp Leu Thr Lys Lys Glu Ile
            260                 265                 270

Phe Gln Tyr Asp Ile Gln Tyr Pro Asp Asn Ile Thr Leu Lys Asn Ile
            275                 280                 285

Gly Tyr Phe Trp Leu Ala Pro Thr Leu Cys Tyr Gln Pro Ser Tyr Pro
            290                 295                 300

Arg Thr Thr Val Phe Arg Lys Ser Phe Leu Lys Arg Val Ala Glu
305                 310                 315                 320

Ile Val Thr Cys Leu Gly Met Met Tyr Phe Leu Val Glu Gln Tyr Ala
                325                 330                 335

Thr Pro Thr Leu Gln Asn Ser Val Arg Ala Phe Asp Glu Leu Ala Phe
            340                 345                 350

Gly Thr Ile Leu Glu Arg Val Leu Lys Leu Ser Thr Thr Ser Val Ile
            355                 360                 365

Ile Trp Leu Leu Met Phe Tyr Thr Phe His Ser Phe Asn Ala
            370                 375                 380

Leu Ala Glu Ala Leu Tyr Phe Gly Asp Arg Arg Phe Tyr Leu Ala Trp
385                 390                 395                 400

Trp Asn Ala Thr Gly Val Gly Met Tyr Trp Lys Thr Trp Asn Ser Pro
```

-continued

```
                    405                 410                 415
Val Tyr Thr Phe Phe Lys Arg His Val Tyr Leu Pro Leu Ile Thr Ser
                420                 425                 430

Gly Thr Ser Pro Met Val Ala Ser Ile Val Ile Phe Leu Ile Ser Ala
            435                 440                 445

Val Leu His Glu Ile Leu Ile Gly Phe Pro Thr His Met Ile Tyr Gly
        450                 455                 460

Tyr Ala Phe Ala Gly Met Phe Leu Gln Ile Pro Leu Ile Ile Leu Thr
465                 470                 475                 480

Arg Pro Leu Glu Lys Trp Arg Gly Thr Gly Ser Gly Leu Gly Asn Met
                485                 490                 495

Ile Phe Trp Val Ser Phe Thr Ile Leu Gly Gln Pro Ala Cys Ala Leu
            500                 505                 510

Leu Tyr Tyr Tyr His Trp Thr Lys Arg His Met Asp Val
        515                 520                 525

<210> SEQ ID NO 19
<211> LENGTH: 533
<212> TYPE: PRT
<213> ORGANISM: Neurospora crassa
<220> FEATURE:
<221> NAME/KEY: MISC_FEATURE
<223> OTHER INFORMATION: strain OR74A
<300> PUBLICATION INFORMATION:
<308> DATABASE ACCESSION NUMBER: GenBank Accession No. XP_322121
<309> DATABASE ENTRY DATE: 2005-01-26
<313> RELEVANT RESIDUES: (1)..(533)

<400> SEQUENCE: 19

Met Ser Ser Thr Ala Thr Thr Thr Gly Leu Asp Pro Ala Val His
1               5                   10                  15

Thr Ser Asn Asp Asn Val Ile Arg Arg Thr His Gly Thr Glu Asn Gly
                20                  25                  30

Ser Thr Pro Asn Asp Lys Ala Asn Ala Gly Gly Glu Pro Glu Thr Glu
            35                  40                  45

Thr Lys Arg His Ser Lys Lys Val Val Arg Ser Lys Tyr Arg His Val
        50                  55                  60

Glu Ala Val His Ser Gln Ser Arg Pro Ser Cys Leu Ser His Asp Thr
65                  70                  75                  80

Thr Glu Ser Pro Ser Phe Leu Gly Phe Arg Asn Leu Met Val Ile Val
                85                  90                  95

Leu Ala Asn Asn Ser His Gln Tyr Gly Val Leu Ile Cys Ile Gly Cys
            100                 105                 110

His Asp Phe Arg Lys Ser Asp Ile Asn Leu Gly Leu Leu Tyr Phe
        115                 120                 125

Leu Ile Pro Cys His Leu Phe Ile Ala Tyr Ile Ile Glu Tyr Tyr Ala
130                 135                 140

Ala Val Gln Ala Arg Ala Glu Arg Asn Val Ser Ala Ser Glu Gln Asn
145                 150                 155                 160

Ala Lys Glu His Gln His Gln Asp Gly Thr Asn Ser Pro Thr Glu Glu
                165                 170                 175

Gln His Arg Lys Phe Gln Ser Thr Trp Lys Leu Val Arg Leu Leu His
            180                 185                 190

Ala Ile Asn Val Thr Thr Ala Leu Val Leu Thr Ser Tyr Val Val Tyr
        195                 200                 205

Tyr His Ile His His Pro Leu Ile Gly Thr Leu Thr Glu Val His Ala
    210                 215                 220
```

-continued

```
Ile Val Val Trp Leu Lys Thr Ala Ser Tyr Ala Phe Thr Asn Arg Asp
225                 230                 235                 240

Leu Arg His Ala Tyr Leu His Pro Ala Arg Gly Glu Leu Asp Ala Leu
                245                 250                 255

Pro Gly Leu Tyr Ala Glu Cys Pro Tyr Pro Glu Asn Ile Thr Met Gly
                260                 265                 270

Asn Leu Cys Tyr Phe Trp Trp Ala Pro Thr Leu Val Tyr Gln Pro Val
            275                 280                 285

Tyr Pro Arg Thr Ala Lys Ile Arg Trp Ser Phe Val Ala Lys Arg Cys
290                 295                 300

Gly Glu Val Ile Cys Leu Ser Val Phe Ile Trp Phe Leu Ser Ala Gln
305                 310                 315                 320

Tyr Ala Thr Pro Val Leu Arg Asn Ser Leu Asp Lys Ile Ala Ser Leu
                325                 330                 335

Asp Ile Pro Ser Ile Val Glu Arg Leu Leu Lys Leu Ser Thr Ile Ser
                340                 345                 350

Leu Ile Ile Trp Leu Ala Gly Phe Phe Ala Leu Phe Gln Ser Phe Leu
            355                 360                 365

Asn Ala Leu Ala Glu Val Thr Arg Phe Ala Asp Arg Ser Phe Tyr Asp
370                 375                 380

Glu Trp Trp Asn Ser Glu Ser Leu Gly Val Tyr Trp Arg Thr Trp Asn
385                 390                 395                 400

Lys Pro Val Tyr Gln Tyr Phe Lys Arg His Val Tyr Ser Pro Met Arg
                405                 410                 415

Ser Arg Gly Trp Ser Asn Ala Thr Ala Ser Leu Ala Val Phe Phe Leu
            420                 425                 430

Ser Ala Val Leu His Glu Leu Leu Val Gly Val Pro Thr His Asn Leu
            435                 440                 445

Ile Gly Val Ala Phe Leu Gly Met Phe Leu Gln Leu Pro Leu Ile Gln
450                 455                 460

Phe Thr Lys Pro Leu Glu Lys Lys Thr Ser Pro Asn Gly Lys Leu Leu
465                 470                 475                 480

Gly Asn Ile Ile Phe Trp Val Ser Phe Thr Ile Phe Gly Gln Pro Phe
                485                 490                 495

Ala Ala Leu Met Tyr Phe Tyr Ala Trp Gln Ala Lys Tyr Gly Ser Val
                500                 505                 510

Ser Lys Met Thr Thr Ser Gln Gln Leu Val Gln Gln Gly Gln Gly Thr
            515                 520                 525

Cys Pro Pro Leu Val
            530
```

<210> SEQ ID NO 20
<211> LENGTH: 499
<212> TYPE: PRT
<213> ORGANISM: Gibberella zeae PH-1
<300> PUBLICATION INFORMATION:
<308> DATABASE ACCESSION NUMBER: GenBank Accession No. EAA77624
<309> DATABASE ENTRY DATE: 2004-02-13
<313> RELEVANT RESIDUES: (1)..(499)

<400> SEQUENCE: 20

```
Met Asn Ser Ala Thr Thr Thr Ser Thr Glu Thr Ser Asn Gly Ser Thr
1               5                   10                  15

Ser Val Ser Lys Arg Asn Gly His Asp Val Thr Arg Thr Asn Gly Asn
            20                  25                  30
```

-continued

```
Gly Thr Thr Thr Thr Ser Pro Pro Lys Lys Ala Gly Gln Lys Tyr Arg
         35                  40                  45

His Val Ala Ala Val His Lys Lys Thr Arg Pro Ser Cys Leu Ser His
     50                  55                  60

Asp Ser Asp Ala Ala Pro Ser Phe Ile Gly Phe Arg Asn Leu Met Val
 65                  70                  75                  80

Ile Val Leu Gly Ile Tyr His Ile Gly Met Ser Gln Phe Asp Ser Glu
                 85                  90                  95

Gln Pro Ile Asp Thr Ala Ser Tyr Arg Gln Asp Ile Phe Leu Gly Leu
                100                 105                 110

Leu Leu Tyr Phe Leu Ile Pro Cys His Leu Leu Ala Ala Tyr Leu Ile
             115                 120                 125

Glu Leu Ala Ala Ala Gln Gln Ala Arg Gly Ser Leu Lys Arg Tyr Asn
         130                 135                 140

Asp Ser Ala Ser Gly Gly Pro Ser Asp Gln Glu Arg Lys Lys Phe His
145                 150                 155                 160

Lys Thr Trp Val Ile Val Ala Trp Ala His Leu Phe Asn Ile Thr Leu
                165                 170                 175

Ala Leu Val Leu Thr Thr Trp Val Val Tyr Phe Lys Ile His His Pro
             180                 185                 190

Leu Ile Gly Thr Leu Thr Glu Met His Ala Ile Ala Val Trp Leu Lys
         195                 200                 205

Thr Ala Ser Tyr Ala Phe Thr Asn Arg Asp Leu Arg His Ala Tyr Leu
         210                 215                 220

His Pro Val Glu Gly Glu Arg Glu Leu Val Pro Glu Leu Tyr Thr Gln
225                 230                 235                 240

Cys Pro Tyr Pro Gln Asn Ile Thr Phe Ser Asn Leu Ala Tyr Phe Trp
                245                 250                 255

Trp Ala Pro Thr Leu Val Tyr Gln Pro Val Tyr Pro Arg Thr Asp Lys
             260                 265                 270

Ile Arg Trp Gly Phe Val Ala Lys Arg Val Gly Glu Ile Phe Gly Leu
         275                 280                 285

Ser Val Phe Ile Trp Val Ala Ser Gln Tyr Ala Ala Pro Val Leu
         290                 295                 300

Arg Asn Ser Leu Asp Lys Ile Ala Ser Leu Asp Leu Met Ser Ile Leu
305                 310                 315                 320

Glu Arg Leu Leu Lys Leu Ser Thr Ile Ser Leu Ala Ile Trp Leu Ala
                325                 330                 335

Gly Phe Phe Ala Leu Phe Gln Ser Phe Leu Asn Ala Leu Ala Glu Val
             340                 345                 350

Leu Arg Phe Gly Asp Arg Ser Phe Tyr Asp Asp Trp Trp Asn Ser Glu
         355                 360                 365

Ser Leu Gly Ala Tyr Trp Arg Thr Trp Asn Lys Pro Val Tyr Thr Tyr
    370                 375                 380

Phe Lys Arg His Leu Tyr Met Pro Met Ile Gly Arg Gly Trp Ser Pro
385                 390                 395                 400

Gln Ala Ala Ser Phe Phe Val Phe Leu Val Ser Ala Ile Leu His Glu
                405                 410                 415

Ile Leu Val Gly Val Pro Thr His Asn Ile Ile Gly Val Ala Phe Leu
             420                 425                 430

Gly Met Phe Leu Gln Leu Pro Leu Ile His Leu Thr Lys Pro Leu Glu
         435                 440                 445

Asn Met Lys Leu Gly His Thr Gly Lys Ile Val Gly Asn Thr Ile Phe
```

```
                   450                 455                 460
Trp Val Ser Phe Thr Ile Phe Gly Gln Pro Phe Ala Ala Leu Met Tyr
465                 470                 475                 480

Phe Tyr Ala Trp Gln Ala Lys Tyr Gly Ser Val Thr Asp Ser Gly Phe
                485                 490                 495

Ser Ile Ser

<210> SEQ ID NO 21
<211> LENGTH: 503
<212> TYPE: PRT
<213> ORGANISM: Magnaporthe grisea 70-15
<300> PUBLICATION INFORMATION:
<308> DATABASE ACCESSION NUMBER: GenBank Accession No. EAA52634
<309> DATABASE ENTRY DATE: 2003-10-31
<313> RELEVANT RESIDUES: (1)..(503)

<400> SEQUENCE: 21

Met Ala Ala Thr Ala Thr Gly Leu Asp Leu Ala Ala Gln Glu Gly
1               5                   10                  15

Ala Gln Gln Arg Arg Ser Thr Ala Thr Asn Gln Ser Ala Asp Asp Asp
                20                  25                  30

Val Thr Thr Asn Ala Asp Gly Ala Ala Ala Pro Ser Leu Lys Gly
            35                  40                  45

Thr Thr Ala Asp Thr Asn Gly Thr Ser Asn Gly Asn Gly Asn Gly Asn
    50                  55                  60

Gly Asn Val Asp Glu Asp Glu Gln Thr Lys Ala Leu Arg Lys Ala Phe
65                  70                  75                  80

Thr Arg Lys Tyr Arg His Val Ala Ala Leu His Ser Gln Ala Arg Pro
                85                  90                  95

Ser Thr Leu Ser His Asp Ser Glu Ala Ser Pro Ser Phe Val Gly Phe
            100                 105                 110

Arg Asn Leu Met Val Ile Val Leu Glu Leu Leu Ala Ala Gln Gln Ala
        115                 120                 125

Arg Asn Ser Arg Gly Tyr Phe Asn Arg Gly Arg Thr Gly Ser Ser Arg
    130                 135                 140

Asp Gly Ser Thr Ser Pro Thr Glu Asp Glu Ser Arg Arg Phe Val Ser
145                 150                 155                 160

Thr Trp Lys Leu Ile Ala Leu Val His Gly Ile Asn Val Asn Ser Ala
                165                 170                 175

Leu Leu Ile Thr Thr Tyr Thr Val Tyr Phe His Ile His Pro Leu
            180                 185                 190

Ile Gly Thr Leu Thr Glu Met His Ala Val Ile Val Trp Leu Lys Thr
        195                 200                 205

Ala Ser Tyr Ala Phe Thr Asn Arg Asp Leu Arg His Ala Tyr Leu His
    210                 215                 220

Pro Val Lys Gly Glu Leu Asp Ala Leu Pro Glu Leu Tyr Lys Gln Cys
225                 230                 235                 240

Pro Tyr Pro Asn Asn Ile Thr Met Lys Asn Leu Cys Tyr Phe Trp Trp
                245                 250                 255

Ala Pro Thr Leu Ile Tyr Gln Pro Val Tyr Pro Arg Ser Gly Arg Ile
            260                 265                 270

Arg Trp Val Phe Phe Lys Arg Val Ala Glu Val Phe Cys Leu Ser
        275                 280                 285

Val Cys Ile Trp Phe Leu Ser Ala Gln Tyr Ala Thr Pro Val Leu Val
    290                 295                 300
```

```
Asn Ser Leu Asp Lys Ile Ala Ser Leu Asp Met Pro Ala Ile Leu Glu
305                 310                 315                 320

Arg Leu Leu Lys Leu Ser Thr Ile Ser Leu Ala Ile Trp Leu Ala Gly
                325                 330                 335

Phe Phe Ala Leu Phe Gln Ser Phe Leu Asn Ala Leu Ala Glu Ile Thr
            340                 345                 350

Arg Phe Gly Asp Arg Ser Phe Tyr Glu Ala Trp Trp Asn Ser Glu Ser
        355                 360                 365

Leu Gly Val Tyr Trp Arg Thr Trp Asn Lys Pro Val Tyr Gln Tyr Phe
    370                 375                 380

Lys Arg His Val Tyr Ser Pro Met Leu Gly Arg Gly Trp Ala Pro Arg
385                 390                 395                 400

Thr Ala Ser Ala Ser Val Phe Leu Ile Ser Ala Val Leu His Glu Ile
                405                 410                 415

Leu Val Gly Val Pro Thr His Asn Ile Ile Gly Val Ala Phe Met Gly
            420                 425                 430

Met Phe Leu Gln Val Pro Leu Ile Ile Leu Thr Ala Pro Leu Glu Lys
        435                 440                 445

Arg Lys Ser Pro Thr Gly Lys Leu Ile Gly Asn Ser Ile Phe Trp Val
    450                 455                 460

Ser Phe Thr Ile Phe Gly Gln Pro Leu Ala Ala Leu Met Tyr Phe Tyr
465                 470                 475                 480

Ala Trp Gln Ala Lys Tyr Gly Ser Val Ser Lys Met Gly Tyr Ala Thr
                485                 490                 495

Ser Lys Ala Ala Leu Thr Asn
                500

<210> SEQ ID NO 22
<211> LENGTH: 458
<212> TYPE: PRT
<213> ORGANISM: Aspergillus nidulans FGSC A4
<300> PUBLICATION INFORMATION:
<308> DATABASE ACCESSION NUMBER: GenBank Accession No. EAA57945
<309> DATABASE ENTRY DATE: 2004-09-09
<313> RELEVANT RESIDUES: (1)..(458)

<400> SEQUENCE: 22

Met Ala Thr Arg Lys Thr Ala Ile Tyr Arg His Ala Val Ala Val His
1               5                   10                  15

Ser Gln Val Gln His Ser Cys Leu Ser Arg Asp Ser Thr Lys Ala Thr
                20                  25                  30

Ser Phe Ile Gly Phe Arg Asn Leu Met Val Val Leu Val Ala Met
            35                  40                  45

Asn Leu Arg Leu Val Ile Glu Asn Phe Leu Lys Tyr Gly Val Leu Ile
        50                  55                  60

Cys Ile Arg Cys His Asp Tyr Arg Lys Gln Asp Val Val Ile Gly Ala
65                  70                  75                  80

Ile Leu Phe Ala Leu Val Pro Cys Gln Leu Leu Cys Ser Tyr Phe Ile
                85                  90                  95

Glu Leu Ala Ala Ser Arg His Ala Gln Arg Val Ile Gly Arg Ala Lys
            100                 105                 110

Lys Gln Asp Lys Asp Arg Ile Leu Asn Glu Ser Lys Arg Thr Trp Phe
        115                 120                 125

Ala Ile Ala Leu Leu His Ser Ile Ile Ser Phe Phe Gly Leu Ala Ala
    130                 135                 140

Thr Ser Tyr Val Ile Phe Tyr Tyr Val Asn His Pro Gly Ile Gly Thr
```

```
                145                 150                 155                 160
Val Cys Glu Val Gln Val Ile Ile Val Ser Leu Lys Ser Tyr Ser Tyr
                    165                 170                 175
Ala Leu Thr Asn Arg Asp Leu Arg Arg Ala Met Leu Gly Ser Pro Ser
                180                 185                 190
Ala Asp Ser Asp Ile Pro Glu Leu Tyr Arg Ser Cys Pro Tyr Pro Arg
            195                 200                 205
Asn Ile Thr Leu Gly Asn Leu Ala Tyr Phe Leu Trp Ala Pro Thr Leu
        210                 215                 220
Val Tyr Gln Pro Val Tyr Pro Arg Thr Pro Arg Ile Arg Trp Ser Phe
225                 230                 235                 240
Val Gly Lys Arg Leu Phe Glu Phe Val Cys Leu Ser Val Val Met Trp
                245                 250                 255
Leu Leu Ser Ala Gln Tyr Ala Ala Pro Leu Leu Arg Asn Ala Thr Gln
                260                 265                 270
Lys Ile Ala Thr Leu Asp Ile Ala Ser Ile Leu Glu Arg Gly Leu Lys
            275                 280                 285
Leu Ser Thr Ile Ser Leu Val Ile Trp Leu Ala Gly Phe Tyr Ala Leu
        290                 295                 300
Phe Gln Ser Leu Leu Asn Gly Leu Ala Glu Ile Met Arg Phe Gly Asp
305                 310                 315                 320
Arg Glu Phe Tyr Thr Asp Trp Trp Asn Ser Pro Ser Phe Gly Val Tyr
                325                 330                 335
Trp Arg Ser Trp Asn Arg Pro Val Tyr Ile Phe Met Lys Arg His Val
                340                 345                 350
Tyr Met Pro Leu Val Thr Arg Gly Trp Asn Pro Thr Leu Ala Gly Thr
            355                 360                 365
Val Val Phe Ala Val Ser Ala Val Leu His Glu Ile Leu Val Gly Val
        370                 375                 380
Pro Thr His Asn Leu Ile Gly Val Ala Ser Ile Ala Met Met Phe Gln
385                 390                 395                 400
Leu Pro Leu Ile Leu Leu Thr Ala Pro Phe Glu Arg Phe Lys Ser Pro
                405                 410                 415
Leu Gly Lys Ala Ile Gly Asn Ser Phe Phe Trp Val Thr Phe Cys Val
                420                 425                 430
Val Gly Gln Pro Leu Gly Ala Leu Leu Tyr Phe Phe Ala Trp Gln Ala
            435                 440                 445
Lys Tyr Gly Ser Val Ser Gln Thr His Pro
        450                 455

<210> SEQ ID NO 23
<211> LENGTH: 8
<212> TYPE: PRT
<213> ORGANISM: Artificial Sequence
<220> FEATURE:
<223> OTHER INFORMATION: Fungal DGAT1 motif #1
<220> FEATURE:
<221> NAME/KEY: MISC_FEATURE
<222> LOCATION: (1)..(1)
<223> OTHER INFORMATION: Xaa = F or Y
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
```

```
<221> NAME/KEY: MISC_FEATURE
<222> LOCATION: (7)..(7)
<223> OTHER INFORMATION: Xaa = L or I
<220> FEATURE:
<221> NAME/KEY: MISC_FEATURE
<222> LOCATION: (8)..(8)
<223> OTHER INFORMATION: Xaa = M or G

<400> SEQUENCE: 23

Xaa Xaa Gly Phe Xaa Asn Xaa Xaa
1               5

<210> SEQ ID NO 24
<211> LENGTH: 7
<212> TYPE: PRT
<213> ORGANISM: Artificial Sequence
<220> FEATURE:
<223> OTHER INFORMATION: Fungal DGAT1 motif #2
<220> FEATURE:
<221> NAME/KEY: MISC_FEATURE
<222> LOCATION: (1)..(1)
<223> OTHER INFORMATION: Xaa = P or Q
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa = I or V

<400> SEQUENCE: 24

Xaa Tyr Pro Xaa Asn Xaa Thr
1               5

<210> SEQ ID NO 25
<211> LENGTH: 7
<212> TYPE: PRT
<213> ORGANISM: Artificial Sequence
<220> FEATURE:
<223> OTHER INFORMATION: Fungal DGAT1 motif #3
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa = L or M

<400> SEQUENCE: 25

Gln Tyr Ala Xaa Pro Xaa Xaa
1               5

<210> SEQ ID NO 26
<211> LENGTH: 11
<212> TYPE: PRT
<213> ORGANISM: Artificial Sequence
<220> FEATURE:
<223> OTHER INFORMATION: Fungal DGAT1 motif #4
<220> FEATURE:
<221> NAME/KEY: MISC_FEATURE
<222> LOCATION: (3)..(3)
<223> OTHER INFORMATION: Xaa = A or S
<220> FEATURE:
<221> NAME/KEY: MISC_FEATURE
<222> LOCATION: (4)..(4)
<223> OTHER INFORMATION: Xaa = T or S
<220> FEATURE:
```

```
<221> NAME/KEY: MISC_FEATURE
<222> LOCATION: (5)..(5)
<223> OTHER INFORMATION: Xaa = can not be P
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: Xaa = I or V

<400> SEQUENCE: 26

Lys Leu Xaa Xaa Xaa Ser Xaa Xaa Xaa Trp Leu
1               5                   10

<210> SEQ ID NO 27
<211> LENGTH: 7
<212> TYPE: PRT
<213> ORGANISM: Artificial Sequence
<220> FEATURE:
<223> OTHER INFORMATION: Fungal DGAT1 motif #5
<220> FEATURE:
<221> NAME/KEY: MISC_FEATURE
<222> LOCATION: (3)..(3)
<223> OTHER INFORMATION: Xaa = Y or N
<220> FEATURE:
<221> NAME/KEY: MISC_FEATURE
<222> LOCATION: (4)..(4)
<223> OTHER INFORMATION: Xaa = Q or T or I
<220> FEATURE:
<221> NAME/KEY: MISC_FEATURE
<222> LOCATION: (5)..(5)
<223> OTHER INFORMATION: Xaa = Y or F
<220> FEATURE:
<221> NAME/KEY: MISC_FEATURE
<222> LOCATION: (6)..(6)
<223> OTHER INFORMATION: Xaa = F or M
<220> FEATURE:
<221> NAME/KEY: MISC_FEATURE
<222> LOCATION: (7)..(7)
<223> OTHER INFORMATION: Xaa = K or R

<400> SEQUENCE: 27

Pro Val Xaa Xaa Xaa Xaa Xaa
1               5

<210> SEQ ID NO 28
<211> LENGTH: 10
<212> TYPE: PRT
<213> ORGANISM: Artificial Sequence
<220> FEATURE:
<223> OTHER INFORMATION: Fungal DGAT1 motif #6
<220> FEATURE:
<221> NAME/KEY: MISC_FEATURE
<222> LOCATION: (3)..(3)
<223> OTHER INFORMATION: Xaa = K or R or S
<220> FEATURE:
<221> NAME/KEY: MISC_FEATURE
<222> LOCATION: (6)..(6)
<223> OTHER INFORMATION: Xaa = Y or N
<220> FEATURE:
<221> NAME/KEY: MISC_FEATURE
<222> LOCATION: (7)..(7)
<223> OTHER INFORMATION: Xaa can not be K
<220> FEATURE:
<221> NAME/KEY: MISC_FEATURE
<222> LOCATION: (8)..(8)
<223> OTHER INFORMATION: Xaa = Y or F
<220> FEATURE:
<221> NAME/KEY: MISC_FEATURE
<222> LOCATION: (9)..(9)
<223> OTHER INFORMATION: Xaa = F or M
<220> FEATURE:
<221> NAME/KEY: MISC_FEATURE
```

```
<222> LOCATION: (10)..(10)
<223> OTHER INFORMATION: Xaa = K or R

<400> SEQUENCE: 28

Trp Asn Xaa Pro Val Xaa Xaa Xaa Xaa Xaa
1               5                   10

<210> SEQ ID NO 29
<211> LENGTH: 11
<212> TYPE: PRT
<213> ORGANISM: Artificial Sequence
<220> FEATURE:
<223> OTHER INFORMATION: Fungal DGAT1 motif #7
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: MISC_FEATURE
<222> LOCATION: (10)..(10)
<223> OTHER INFORMATION: Xaa = I or Y

<400> SEQUENCE: 29

Leu Xaa Gly Xaa Pro Thr His Xaa Xaa Xaa Gly
1               5                   10

<210> SEQ ID NO 30
<211> LENGTH: 7
<212> TYPE: PRT
<213> ORGANISM: Artificial Sequence
<220> FEATURE:
<223> OTHER INFORMATION: Fungal DGAT1 motif #8
<220> FEATURE:
<221> NAME/KEY: MISC_FEATURE
<222> LOCATION: (2)..(2)
<223> OTHER INFORMATION: Xaa = L or F
<220> FEATURE:
<221> NAME/KEY: MISC_FEATURE
<222> LOCATION: (3)..(3)
<223> OTHER INFORMATION: Xaa = L or M
<220> FEATURE:
<221> NAME/KEY: MISC_FEATURE
<222> LOCATION: (5)..(5)
<223> OTHER INFORMATION: Xaa = F or Y
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa = A or H

<400> SEQUENCE: 30

Ala Xaa Xaa Tyr Xaa Xaa Xaa
1               5

<210> SEQ ID NO 31
<211> LENGTH: 8
<212> TYPE: PRT
<213> ORGANISM: Artificial Sequence
<220> FEATURE:
<223> OTHER INFORMATION: Universal DGAT1 motif #1
<220> FEATURE:
<221> NAME/KEY: misc_feature
```

```
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid

<400> SEQUENCE: 31

Xaa Xaa Gly Xaa Xaa Asn Xaa Xaa
 1               5

<210> SEQ ID NO 32
<211> LENGTH: 7
<212> TYPE: PRT
<213> ORGANISM: Artificial Sequence
<220> FEATURE:
<223> OTHER INFORMATION: Universal DGAT1 motif #3
<220> FEATURE:
<221> NAME/KEY: MISC_FEATURE
<222> LOCATION: (2)..(2)
<223> OTHER INFORMATION: Xaa = Y or W
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid

<400> SEQUENCE: 32

Gln Xaa Xaa Xaa Pro Xaa Xaa
 1               5

<210> SEQ ID NO 33
<211> LENGTH: 11
<212> TYPE: PRT
<213> ORGANISM: Artificial Sequence
<220> FEATURE:
<223> OTHER INFORMATION: Universal DGAT1 motif #4
<220> FEATURE:
<221> NAME/KEY: MISC_FEATURE
<222> LOCATION: (3)..(3)
<223> OTHER INFORMATION: Xaa = A or S
<220> FEATURE:
<221> NAME/KEY: misc_feature
<222> LOCATION: (4)..(9)
<223> OTHER INFORMATION: Xaa can be any naturally occurring amino acid

<400> SEQUENCE: 33

Lys Leu Xaa Xaa Xaa Xaa Xaa Xaa Xaa Trp Leu
 1               5                  10

<210> SEQ ID NO 34
<211> LENGTH: 7
<212> TYPE: PRT
<213> ORGANISM: Artificial Sequence
<220> FEATURE:
<223> OTHER INFORMATION: Universal DGAT1 motif #5
<220> FEATURE:
<221> NAME/KEY: misc_feature
<222> LOCATION: (3)..(7)
<223> OTHER INFORMATION: Xaa can be any naturally occurring amino acid

<400> SEQUENCE: 34

Pro Val Xaa Xaa Xaa Xaa Xaa
 1               5
```

```
<210> SEQ ID NO 35
<211> LENGTH: 10
<212> TYPE: PRT
<213> ORGANISM: Artificial Sequence
<220> FEATURE:
<223> OTHER INFORMATION: Universal DGAT1 motif #6
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(10)
<223> OTHER INFORMATION: Xaa can be any naturally occurring amino acid

<400> SEQUENCE: 35

Trp Asn Xaa Pro Val Xaa Xaa Xaa Xaa Xaa
1               5                   10

<210> SEQ ID NO 36
<211> LENGTH: 11
<212> TYPE: PRT
<213> ORGANISM: Artificial Sequence
<220> FEATURE:
<223> OTHER INFORMATION: Universal DGAT1 motif #7
<220> FEATURE:
<221> NAME/KEY: misc_feature
<222> LOCATION: (1)..(4)
<223> OTHER INFORMATION: Xaa can be any naturally occurring amino acid
<220> FEATURE:
<221> NAME/KEY: misc_feature
<222> LOCATION: (6)..(11)
<223> OTHER INFORMATION: Xaa can be any naturally occurring amino acid

<400> SEQUENCE: 36

Xaa Xaa Xaa Xaa Pro Xaa Xaa Xaa Xaa Xaa Xaa
1               5                   10

<210> SEQ ID NO 37
<211> LENGTH: 7
<212> TYPE: PRT
<213> ORGANISM: Artificial Sequence
<220> FEATURE:
<223> OTHER INFORMATION: Universal DGAT1 motif #8
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (2)..(2)
<223> OTHER INFORMATION: Xaa = L or F
<220> FEATURE:
<221> NAME/KEY: MISC_FEATURE
<222> LOCATION: (3)..(3)
<223> OTHER INFORMATION: Xaa = L or M
<220> FEATURE:
<221> NAME/KEY: misc_feature
<222> LOCATION: (5)..(7)
<223> OTHER INFORMATION: Xaa can be any naturally occurring amino acid

<400> SEQUENCE: 37

Xaa Xaa Xaa Tyr Xaa Xaa Xaa
1               5

<210> SEQ ID NO 38
<211> LENGTH: 7
<212> TYPE: PRT
<213> ORGANISM: Artificial Sequence
<220> FEATURE:
<223> OTHER INFORMATION: Fungal DGAT2 motif
<220> FEATURE:
```

```
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<300> PUBLICATION INFORMATION:
<302> TITLE: Diacylglycerol acyltransferase nucleic acid sequences and
      associated products
<310> PATENT DOCUMENT NUMBER: US 2004/0107459 A1
<311> PATENT FILING DATE: 2003-07-31
<312> PUBLICATION DATE: 2004-06-03
<313> RELEVANT RESIDUES: (1)..(7)

<400> SEQUENCE: 38

Phe Xaa Xaa Pro Xaa Tyr Arg
1               5

<210> SEQ ID NO 39
<211> LENGTH: 19
<212> TYPE: DNA
<213> ORGANISM: Artificial Sequence
<220> FEATURE:
<223> OTHER INFORMATION: Primer TEF5'

<400> SEQUENCE: 39
agagaccggg ttggcggcg                                                    19

<210> SEQ ID NO 40
<211> LENGTH: 30
<212> TYPE: DNA
<213> ORGANISM: Artificial Sequence
<220> FEATURE:
<223> OTHER INFORMATION: Primer TEF3'

<400> SEQUENCE: 40 ttggatccctt tgaatgattc ttatactcag                                       30

<210> SEQ ID NO 41
<211> LENGTH: 29
<212> TYPE: DNA
<213> ORGANISM: Artificial Sequence
<220> FEATURE:
<223> OTHER INFORMATION: Primer XPR5'

<400> SEQUENCE: 41
tttccgcggc ccgagattcc ggcctcttc                                         29

<210> SEQ ID NO 42
<211> LENGTH: 31
<212> TYPE: DNA
<213> ORGANISM: Artificial Sequence
<220> FEATURE:
<223> OTHER INFORMATION: Primer XPR3'

<400> SEQUENCE: 42
tttccgcgga cacaatatct ggtcaaattt c                                      31

<210> SEQ ID NO 43
<211> LENGTH: 39
<212> TYPE: DNA
<213> ORGANISM: Artificial Sequence
<220> FEATURE:
<223> OTHER INFORMATION: Primer YL5

<400> SEQUENCE: 43 ccccccctcga ggtcgatggt gtcgataagc ttgatatcg                             39
```

```
<210> SEQ ID NO 44
<211> LENGTH: 39
<212> TYPE: DNA
<213> ORGANISM: Artificial Sequence
<220> FEATURE:
<223> OTHER INFORMATION: Primer YL6

<400> SEQUENCE: 44
cgatatcaag cttatcgaca ccatcgacct cgaggggggg                    39

<210> SEQ ID NO 45
<211> LENGTH: 35
<212> TYPE: DNA
<213> ORGANISM: Artificial Sequence
<220> FEATURE:
<223> OTHER INFORMATION: Primer YL9

<400> SEQUENCE: 45
tggtaaataa atgatgtcga ctcaggcgac gacgg                         35

<210> SEQ ID NO 46
<211> LENGTH: 35
<212> TYPE: DNA
<213> ORGANISM: Artificial Sequence
<220> FEATURE:
<223> OTHER INFORMATION: Primer YL10

<400> SEQUENCE: 46
ccgtcgtcgc ctgagtcgac atcatttatt tacca                         35

<210> SEQ ID NO 47
<211> LENGTH: 37
<212> TYPE: DNA
<213> ORGANISM: Artificial Sequence
<220> FEATURE:
<223> OTHER INFORMATION: Primer YL7

<400> SEQUENCE: 47
caaccgattt cgacagttaa ttaataaattt gaatcga                      37

<210> SEQ ID NO 48
<211> LENGTH: 37
<212> TYPE: DNA
<213> ORGANISM: Artificial Sequence
<220> FEATURE:
<223> OTHER INFORMATION: Primer YL8

<400> SEQUENCE: 48
tcgattcaaa ttattaatta actgtcgaaa tcggttg                       37

<210> SEQ ID NO 49
<211> LENGTH: 36
<212> TYPE: DNA
<213> ORGANISM: Artificial Sequence
<220> FEATURE:
<223> OTHER INFORMATION: Primer YL3

<400> SEQUENCE: 49
gtataagaat cattccaccat ggatccacta gttcta                       36

<210> SEQ ID NO 50
<211> LENGTH: 36
<212> TYPE: DNA
<213> ORGANISM: Artificial Sequence
<220> FEATURE:
```

```
<223> OTHER INFORMATION: Primer YL4

<400> SEQUENCE: 50
tagaactagt ggatccatgg tgaatgattc ttatac                                    36

<210> SEQ ID NO 51
<211> LENGTH: 30
<212> TYPE: DNA
<213> ORGANISM: Artificial Sequence
<220> FEATURE:
<223> OTHER INFORMATION: Primer YL1

<400> SEQUENCE: 51
cagtgccaaa agccaaggca ctgagctcgt                                           30

<210> SEQ ID NO 52
<211> LENGTH: 31
<212> TYPE: DNA
<213> ORGANISM: Artificial Sequence
<220> FEATURE:
<223> OTHER INFORMATION: Primer YL2

<400> SEQUENCE: 52
gacgagctca gtgccttggc ttttggcact g                                         31

<210> SEQ ID NO 53
<211> LENGTH: 33
<212> TYPE: DNA
<213> ORGANISM: Artificial Sequence
<220> FEATURE:
<223> OTHER INFORMATION: Primer YL61

<400> SEQUENCE: 53
acaattccac acaacgtacg agccggaagc ata                                       33

<210> SEQ ID NO 54
<211> LENGTH: 33
<212> TYPE: DNA
<213> ORGANISM: Artificial Sequence
<220> FEATURE:
<223> OTHER INFORMATION: Primer YL62

<400> SEQUENCE: 54
tatgcttccg gctcgtacgt tgtgtggaat tgt                                       33

<210> SEQ ID NO 55
<211> LENGTH: 8196
<212> TYPE: DNA
<213> ORGANISM: Artificial Sequence
<220> FEATURE:
<223> OTHER INFORMATION: Plasmid pY20

<400> SEQUENCE: 55
tggagctcca gcttttgttc cctttagtga gggttaattt cgagcttggc gtaatcatgg          60
tcatagctgt ttcctgtgtg aaattgttat ccgctcacaa ttccacacaa catacgagcc         120
ggaagcataa agtgtaaagc ctggggtgcc taatgagtga gctaactcac attaattgcg         180
ttgcgctcac tgcccgcttt ccagtcggga acctgtcgt gccagctgca ttaatgaatc          240
ggccaacgcg cggggagagg cggtttgcgt attgggcgct cttccgcttc ctcgctcact         300
gactcgctgc gctcggtcgt tcggctgcgg cgagcggtat cagctcactc aaaggcggta         360
atacggttat ccacagaatc aggggataac gcaggaaaga acatgtgagc aaaaggccag         420
caaaaggcca ggaaccgtaa aaaggccgcg ttgctggcgt ttttccatag gctccgcccc         480
```

-continued

```
cctgacgagc atcacaaaaa tcgacgctca agtcagaggt ggcgaaaccc gacaggacta    540
taaagatacc aggcgtttcc ccctggaagc tccctcgtgc gctctcctgt tccgaccctg    600
ccgcttaccg gatacctgtc cgcctttctc ccttcgggaa gcgtggcgct ttctcatagc    660
tcacgctgta ggtatctcag ttcggtgtag gtcgttcgct ccaagctggg ctgtgtgcac    720
gaaccccccg ttcagcccga ccgctgcgcc ttatccggta actatcgtct tgagtccaac    780
ccggtaagac acgacttatc gccactggca gcagccactg gtaacaggat tagcagagcg    840
aggtatgtag gcggtgctac agagttcttg aagtggtggc ctaactacgg ctacactaga    900
aggacagtat ttggtatctg cgctctgctg aagccagtta ccttcggaaa aagagttggt    960
agctcttgat ccggcaaaca accaccgctg gtagcggtg gttttttgt ttgcaagcag    1020 cagattacgc gcagaaaaaa aggatctcaa gaagatcctt tgatctttc tacgggtct    1080 gacgctcagt ggaacgaaaa ctcacgttaa gggattttgg tcatgagatt atcaaaaagg    1140
atcttcacct agatcctttt aaattaaaaa tgaagtttta aatcaatcta agtatatat    1200 gagtaaactt ggtctgacag ttaccaatgc ttaatcagtg aggcacctat ctcagcgatc    1260
tgtctatttc gttcatccat agttgcctga ctccccgtcg tgtagataac tacgatacgg    1320
gagggcttac catctggccc cagtgctgca atgataccgc gagacccacg ctcaccggct    1380
ccagatttat cagcaataaa ccagccagcc ggaagggccg agcgcagaag tggtcctgca    1440
actttatccg cctccatcca gtctattaat tgttgccggg aagctagagt aagtagttcg    1500
ccagttaata gtttgcgcaa cgttgttgcc attgctacag gcatcgtggt gtcacgctcg    1560
tcgtttggta tggcttcatt cagctccggt tcccaacgat caaggcgagt tacatgatcc    1620
cccatgttgt gcaaaaaagc ggttagctcc ttcggtcctc cgatcgttgt cagaagtaag    1680
ttggccgcag tgttatcact catggttatg gcagcactgc ataattctct tactgtcatg    1740
ccatccgtaa gatgcttttc tgtgactggt gagtactcaa ccaagtcatt ctgagaatag    1800
tgtatgcggc gaccgagttg ctcttgcccg gcgtcaatac gggataatac cgcgccacat    1860
agcagaactt taaaagtgct catcattgga aaacgttctt cggggcgaaa actctcaagg    1920
atcttaccgc tgttgagatc cagttcgatg taacccactc gtgcacccaa ctgatcttca    1980
gcatctttta ctttcaccag cgtttctggg tgagcaaaaa caggaaggca aaatgccgca    2040
aaaaagggaa taagggcgac acggaaatgt tgaatactca tactcttcct ttttcaatat    2100
tattgaagca tttatcaggg ttattgtctc atgagcggat acatatttga atgtatttag    2160
aaaaataaac aaatagggt tccgcgcaca tttccccgaa aagtgccacc tgacgcgccc    2220
tgtagcggcg cattaagcgc ggcgggtgtg gtggttacgc gcagcgtgac cgctacactt    2280
gccagcgccc tagcgcccgc tcctttcgct ttcttccctt cctttctcgc cacgttcgcc    2340
ggctttcccc gtcaagctct aaatcggggg ctccctttag ggttccgatt tagtgcttta    2400
cggcacctcg accccaaaaa acttgattag ggtgatggtt cacgtagtgg gccatcgccc    2460
tgatagacgg ttttttcgccc tttgacgttg gagtccacgt tctttaatag tggactcttg    2520
ttccaaactg gaacaacact caaccctatc tcggtctatt cttttgattt ataagggatt    2580
ttgccgattt cggcctattg gttaaaaaat gagctgattt aacaaaaatt taacgcgaat    2640
tttaacaaaa tattaacgct tacaatttcc attcgccatt caggctgcgc aactgttggg    2700
aagggcgatc ggtgcgggcc tcttcgctat tacgccagct ggcgaaaggg ggatgtgctg    2760
caaggcgatt aagttgggta acgccagggt tttcccagtc acgacgttgt aaaacgacgg    2820
```

```
ccagtgaatt gtaatacgac tcactatagg gcgaattggg taccgggccc ccctcgagg   2880 tcgacggtat cgataagctt gatatcgaat tcatgtcaca caaaccgatc ttcgcctcaa   2940
ggaaacctaa ttctacatcc gagagactgc cgagatccag tctacactga ttaattttcg   3000
ggccaataat ttaaaaaaat cgtgttatat aatattatat gtattatata tatacatcat   3060
gatgatactg acagtcatgt cccattgcta aatagacaga ctccatctgc cgcctccaac   3120
tgatgttctc aatatttaag gggtcatctc gcattgttta ataataaaca gactccatct   3180
accgcctcca aatgatgttc tcaaaatata ttgtatgaac ttattttat tacttagtat     3240 tattagacaa cttacttgct ttatgaaaaa cacttcctat ttaggaaaca atttataatg   3300
gcagttcgtt catttaacaa tttatgtaga ataaatgtta taaatgcgta tgggaaatct   3360
taaatatgga tagcataaat gatatctgca ttgcctaatt cgaaatcaac agcaacgaaa   3420
aaaatccctt gtacaacata aatagtcatc gagaaatatc aactatcaaa gaacagctat   3480
tcacacgtta ctattgagat tattattgga cgagaatcac acactcaact gtctttctct   3540
cttctagaaa tacaggtaca agtatgtact attctcattg ttcatacttc tagtcatttc   3600
atcccacata ttccttggat ttctctccaa tgaatgacat tctatcttgc aaattcaaca   3660
attataataa gatataccaa agtagcggta tagtggcaat caaaaagctt ctctggtgtg   3720
cttctcgtat ttattttat tctaatgatc cattaaaggt atatatttat ttcttgttat    3780
ataatccttt tgtttattac atgggctgga tacataaagg tattttgatt taatttttg    3840 cttaaattca atcccccctc gttcagtgtc aactgtaatg gtaggaaatt accatacttt   3900
tgaagaagca aaaaaaatga aagaaaaaaa aaatcgtatt tccaggttag acgttccgca   3960
gaatctagaa tgcggtatgc ggtacattgt tcttcgaacg taaaagttgc gctccctgag   4020
atattgtaca ttttgctttt tacaagtaca agtacatcgt acaactatgt actactgttg   4080
atgcatccac aacagtttgt tttgttttt tttgttttt ttttttctaa tgattcatta    4140
ccgctatgta tacctacttg tacttgtagt aagccgggtt attggcgttc aattaatcat   4200
agacttatga atctgcacgg tgtgcgctgc gagttacttt tagcttatgc atgctacttg   4260
ggtgtaatat tgggatctgt tcggaaatca acggatgctc aaccgatttc gacagtaata   4320
atttgaatcg aatcggagcc taaaatgaac ccgagtatat ctcataaaat tctcggtgag   4380
aggtctgtga ctgtcagtac aaggtgcctt cattatgccc tcaaccttac catacctcac   4440
tgaatgtagt gtacctctaa aaatgaaata cagtgccaaa agccatggca ctgagctcgt   4500
ctaacggact tgatatacaa ccaattaaaa caaatgaaaa gaaatacagt tctttgtatc   4560
atttgtaaca attaccctgt acaaactaag gtattgaaat cccacaatat tcccaaagtc   4620 caccccttc caaattgtca tgcctacaac tcatatacca agcactaacc taccaaacac    4680
cactaaaacc ccacaaaata tatcttaccg aatatacagt aacaagctac caccacactc   4740
gttgggtgca gtcgccagct taaagatatc tatccacatc agccacaact cccttccttt   4800
aataaaccga ctacacccctt ggctattgag gttatgagtg aatatactgt agacaagaca  4860 cttttcaagaa gactgtttcc aaaacgtacc actgtcctcc actacaaaca cacccaatct  4920
gcttcttcta gtcaaggttg ctacaccggt aaattataaa tcatcatttc attagcaggg   4980
cagggccctt tttatagagt cttatacact agcggaccct gccggtagac caacccgcag   5040
gcgcgtcagt ttgctccttc catcaatgcg tcgtagaaac gacttactcc ttcttgagca   5100
gctccttgac cttgttggca acaagtctcc gacctcggag gtggaggaag agcctccgat   5160
atcggcggta gtgataccag cctcgacgga ctccttgacg gcagcctcaa cagcgtcacc   5220
```

-continued

```
ggcgggcttc atgttaagag agaacttgag catcatggcg gcagacagaa tggtggcaat    5280
ggggttgacc ttctgcttgc cgagatcggg ggcagatccg tgacagggct cgtacagacc    5340
gaacgcctcg ttggtgtcgg gcagagaagc cagagaggcg gagggcagca gacccagaga    5400
accggggatg acggaggcct cgtcggagat gatatcgcca aacatgttgg tggtgatgat    5460
gataccattc atcttggagg gctgcttgat gaggatcatg gcggccgagt cgatcagctg    5520
gtggttgagc tcgagctggg ggaattcgtc cttgaggact cgagtgacag tctttcgcca    5580
aagtcgagag gaggccagca cgttggcctt gtcaagagac cacacgggaa gagggggtt    5640 gtgctgaagg gccaggaagg cggccattcg ggcaattcgc tcaacctcag gaacggagta    5700
ggtctcggtg tcgaagcgca cgccagatcc gtcatcctcc tttcgctctc caaagtagat    5760
acctccgacg agctctcgga caatgatgaa gtcggtgccc tcaacgtttc ggatggggga    5820
gagatcggcg agcttgggcg acagcagctg gcagggtcgc aggttggcgt acaggttcag    5880
gtcctttcgc agcttgagga gaccctgctc gggtcgcacg tcggttcgtc cgtcgggagt    5940
ggtccatacg tgttggcag cgcctccgac agcaccgagc ataatagagt cagccttcg    6000 gcagatgtcg agagtagcgt cggtgatggg ctcgccctcc ttctcaatgg cagctcctcc    6060
aatgagtcgg tcctcaaaca caaactcggt gccggaggcc tcagcaacag acttgagcac    6120
cttgacggcc tcggcaatca cctcggggcc acagaagtcg ccgccgagaa gaacaatctt    6180 cttgagtca gtcttggtct tcttagtttc gggttccatt gtggatgtgt gtggttgtat    6240
gtgtgatgtg gtgtgtggag tgaaaatctg tggctggcaa acgctcttgt atatatacgc    6300
acttttgccc gtgctatgtg gaagactaaa cctccgaaga ttgtgactca ggtagtgcgg    6360
tatcggctag ggacccaaac cttgtcgatg ccgatagcgc tatcgaacgt accccagccg    6420
gccgggagta tgtcggaggg gacatacgag atcgtcaagg gtttgtggcc aactggtaaa    6480
taaatgatga ctcaggcgac gacggaattc ctgcagccca tctgcagaat tcaggagaga    6540
ccgggttggc ggcgtatttg tgtcccaaaa acagcccca attgccccaa ttgaccccaa    6600
attgacccag tagcgggccc aacccggcg agagcccct tcaccccaca tatcaaacct    6660 ccccggttc ccacacttgc cgttaagggc gtagggtact gcagtctgga atctacgctt    6720
gttcagactt tgtactagtt tctttgtctg gccatccggg taaccatgc cggacgcaaa    6780 atagactact gaaaatttt ttgctttgtg gttgggactt tagccaaggg tataaaagac    6840
caccgtcccc gaattacctt tcctcttctt ttctctctct ccttgtcaac tcacacccga    6900
aatcgttaag catttccttc tgagtataag aatcattcaa aggatccact agttctagag    6960
cggccgctta aaccatgaaa aagcctgaac tcaccgcgac gtctgtcgag aagtttctga    7020
tcgaaaagtt cgacagcgtc tccgacctga tgcagctctc ggagggcgaa gaatctcgtg    7080
ctttcagctt cgatgtagga gggcgtggat atgtcctgcg ggtaaatagc tgcgccgatg    7140
gtttctacaa agatcgttat gtttatcggc actttgcatc ggccgcgctc ccgattccgg    7200
aagtgcttga cattggggaa ttcagcgaga gcctgaccta ttgcatctcc cgccgtgcac    7260
agggtgtcac gttgcaagac ctgcctgaaa ccgaactgcc cgctgttctg cagccggtcg    7320
cggaggccat ggatgcgatc gctgcggccg atcttagcca gacgagcggg ttcggcccat    7380
tcggaccgca aggaatcggt caatacacta catggcgtga tttcatatgc gcgattgctg    7440
atccccatgt gtatcactgg caaactgtga tggacgacac cgtcagtgcg tccgtcgcgc    7500
aggctctcga tgagctgatg ctttgggccg aggactgccc cgaagtccgg cacctcgtgc    7560
```

-continued

```
acgcggattt cggctccaac aatgtcctga cggacaatgg ccgcataaca gcggtcattg    7620
actggagcga ggcgatgttc ggggattccc aatacgaggt cgccaacatc ttcttctgga    7680
ggccgtggtt ggcttgtatg gagcagcaga cgcgctactt cgagcggagg catccggagc    7740
ttgcaggatc gccgcggctc cgggcgtata tgctccgcat tggtcttgac caactctatc    7800
agagcttggt tgacggcaat tcgatgatg cagcttgggc gcagggtcga tgcgacgcaa    7860
tcgtccgatc cggagccggg actgtcgggc gtacacaaat cgcccgcaga agcgcggccg    7920
tctggaccga tggctgtgta gaagtactcg ccgatagtgg aaaccgacgc cccagcactc    7980
gtccgagggc aaaggaatag tgaggtacct aaagcggccg ccaccgcggc ccgagattcc    8040
ggcctcttcg gccgccaagc gacccgggtg gacgtctaga ggtacctagc aattaacaga    8100
tagtttgccg gtgataattc tcttaacctc ccacactcct ttgacataac gatttatgta    8160
acgaaactga aatttgacca gatattgtgt ccgcgg                               8196
```

<210> SEQ ID NO 56
<211> LENGTH: 1026
<212> TYPE: DNA
<213> ORGANISM: Escherichia coli

<400> SEQUENCE: 56

```
atgaaaaagc ctgaactcac cgcgacgtct gtcgagaagt ttctgatcga aaagttcgac      60
agcgtctccg acctgatgca gctctcggag ggcgaagaat ctcgtgcttt cagcttcgat     120
gtaggagggc gtggatatgt cctgcgggta aatagctgcg ccgatggttt ctacaaagat     180
cgttatgttt atcggcactt tgcatcggcc gcgctcccga ttccggaagt gcttgacatt     240
ggggaattca gcgagagcct gacctattgc atctcccgcc gtgcacaggg tgtcacgttg     300
caagacctgc ctgaaaccga actgcccgct gttctgcagc cggtcgcgga ggccatggat     360
gcgatcgctg cggccgatct tagccagacg agcgggttcg gcccattcgg accgcaagga     420
atcggtcaat acactacatg gcgtgatttc atatgcgcga ttgctgatcc ccatgtgtat     480
cactggcaaa ctgtgatgga cgacaccgtc agtgcgtccg tcgcgcaggc tctcgatgag     540
ctgatgcttt gggccgagga ctgccccgaa gtccggcacc tcgtgcacgc ggatttcggc     600
tccaacaatg tcctgacgga caatggccgc ataacagcgg tcattgactg gagcgaggcg     660
atgttcgggg attcccaata cgaggtcgcc aacatcttct tctggaggcc gtggttggct     720
tgtatggagc agcagacgcg ctacttcgag cggaggcatc cggagcttgc aggatcgccg     780
cggctccggg cgtatatgct ccgcattggt cttgaccaac tctatcagag cttggttgac     840
ggcaatttcg atgatgcagc ttgggcgcag ggtcgatgcg acgcaatcgt ccgatccgga     900
gccgggactg tcggcgtac acaaatcgcc cgcagaagcg cggccgtctg gaccgatggc     960
tgtgtagaag tactcgccga tagtggaaac cgacgcccca gcactcgtcc gagggcaaag    1020
gaatag                                                                1026
```

<210> SEQ ID NO 57
<211> LENGTH: 341
<212> TYPE: PRT
<213> ORGANISM: Escherichia coli

<400> SEQUENCE: 57

```
Met Lys Lys Pro Glu Leu Thr Ala Thr Ser Val Glu Lys Phe Leu Ile
1               5                   10                  15

Glu Lys Phe Asp Ser Val Ser Asp Leu Met Gln Leu Ser Glu Gly Glu
            20                  25                  30
```

```
Glu Ser Arg Ala Phe Ser Phe Asp Val Gly Gly Arg Gly Tyr Val Leu
        35                  40                  45
Arg Val Asn Ser Cys Ala Asp Gly Phe Tyr Lys Asp Arg Tyr Val Tyr
    50                  55                  60
Arg His Phe Ala Ser Ala Ala Leu Pro Ile Pro Glu Val Leu Asp Ile
65                  70                  75                  80
Gly Glu Phe Ser Glu Ser Leu Thr Tyr Cys Ile Ser Arg Arg Ala Gln
                85                  90                  95
Gly Val Thr Leu Gln Asp Leu Pro Glu Thr Glu Leu Pro Ala Val Leu
            100                 105                 110
Gln Pro Val Ala Glu Ala Met Asp Ala Ile Ala Ala Asp Leu Ser
        115                 120                 125
Gln Thr Ser Gly Phe Gly Pro Phe Gly Pro Gln Ile Gly Gln Tyr
    130                 135                 140
Thr Thr Trp Arg Asp Phe Ile Cys Ala Ile Ala Asp Pro His Val Tyr
145                 150                 155                 160
His Trp Gln Thr Val Met Asp Asp Thr Val Ser Ala Ser Val Ala Gln
                165                 170                 175
Ala Leu Asp Glu Leu Met Leu Trp Ala Glu Asp Cys Pro Glu Val Arg
            180                 185                 190
His Leu Val His Ala Asp Phe Gly Ser Asn Asn Val Leu Thr Asp Asn
        195                 200                 205
Gly Arg Ile Thr Ala Val Ile Asp Trp Ser Glu Ala Met Phe Gly Asp
    210                 215                 220
Ser Gln Tyr Glu Val Ala Asn Ile Phe Phe Trp Arg Pro Trp Leu Ala
225                 230                 235                 240
Cys Met Glu Gln Gln Thr Arg Tyr Phe Glu Arg Arg His Pro Glu Leu
                245                 250                 255
Ala Gly Ser Pro Arg Leu Arg Ala Tyr Met Leu Arg Ile Gly Leu Asp
            260                 265                 270
Gln Leu Tyr Gln Ser Leu Val Asp Gly Asn Phe Asp Asp Ala Ala Trp
        275                 280                 285
Ala Gln Gly Arg Cys Asp Ala Ile Val Arg Ser Gly Ala Gly Thr Val
    290                 295                 300
Gly Arg Thr Gln Ile Ala Arg Arg Ser Ala Ala Val Trp Thr Asp Gly
305                 310                 315                 320
Cys Val Glu Val Leu Ala Asp Ser Gly Asn Arg Arg Pro Ser Thr Arg
                325                 330                 335
Pro Arg Ala Lys Glu
            340

<210> SEQ ID NO 58
<211> LENGTH: 1710
<212> TYPE: DNA
<213> ORGANISM: Yarrowia lipolytica

<400> SEQUENCE: 58
gtcgacgagt atctgtctga ctcgtcattg ccgcctttgg agtacgactc caactatgag     60
tgtgcttgga tcactttgac gatacattct tcgttggagg ctgtgggtct gacagctgcg    120
ttttcggcgc ggttggccga caacaatatc agctgcaacg tcattgctgg ctttcatcat    180
gatcacattt tgtcggcaa aggcgacgcc cagagagcca ttgacgttct ttctaatttg    240
gaccgatagc cgtatagtcc agtctatcta taagttcaac taactcgtaa ctattaccat    300
```

-continued

```
aacatatact tcactgcccc agataaggtt ccgataaaaa gttctgcaga ctaaatttat    360
ttcagtctcc tcttcaccac caaaatgccc tcctacgaag ctcgagctaa cgtccacaag    420
tccgcctttg ccgctcgagt gctcaagctc gtggcagcca agaaaaccaa cctgtgtgct    480
tctctggatg ttaccaccac caaggagctc attgagcttg ccgataaggt cggaccttat    540
gtgtgcatga tcaagaccca tatcgacatc attgacgact tcacctacgc cggcactgtg    600
ctccccctca aggaacttgc tcttaagcac ggtttcttcc tgttcgagga cagaaagttc    660
gcagatattg caacactgt caagcaccag tacaagaacg tgtctaccg aatcgccgag    720 tggtccgata tcaccaacgc ccacggtgta cccggaaccg gaatcattgc tggcctgcga    780
gctggtgccg aggaaactgt ctctgaacag aagaaggagg acgtctctga ctacgagaac    840
tcccagtaca aggagttcct ggtcccctct cccaacgaga gctggccag aggtctgctc    900 atgctggccg agctgtcttg caagggctct ctggccactg gcgagtactc caagcagacc    960
attgagcttg cccgatccga ccccgagttt gtggttggct tcattgccca gaaccgacct    1020
aagggcgact ctgaggactg gcttattctg accccggg tgggtcttga cgacaaggga    1080
gacgctctcg acagcagta ccgaactgtt gaggatgtca tgtctaccgg aacggatatc    1140
ataattgtcg gccgaggtct gtacggccag aaccgagatc ctattgagga ggccaagcga    1200
taccagaagg ctggctggga ggcttaccag aagattaact gttagaggtt agactatgga    1260
tatgtcattt aactgtgtat atagagagcg tgcaagtatg gagcgcttgt tcagcttgta    1320
tgatggtcag acgacctgtc tgatcgagta tgtatgatac tgcacaacct gtgtatccgc    1380
atgatctgtc caatggggca tgttgttgtg tttctcgata cggagatgct gggtacaagt    1440
agctaatacg attgaactac ttatacttat atgaggcttg aagaaagctg acttgtgtat    1500
gacttattct caactacatc cccagtcaca ataccaccac tgcactacca ctacaccaaa    1560
accatgatca aaccacccat ggacttcctg gaggcagaag aacttgttat ggaaaagctc    1620
aagagagaga agccaagata ctatcaagac atgtgtcgca acttcaagga ggaccaagct    1680
ctgtacaccg agaaacaggc ctttgtcgac                                    1710
```

<210> SEQ ID NO 59
<211> LENGTH: 286
<212> TYPE: PRT
<213> ORGANISM: Yarrowia lipolytica

<400> SEQUENCE: 59

```
Met Pro Ser Tyr Glu Ala Arg Ala Asn Val His Lys Ser Ala Phe Ala
1               5                   10                  15

Ala Arg Val Leu Lys Leu Val Ala Ala Lys Lys Thr Asn Leu Cys Ala
            20                  25                  30

Ser Leu Asp Val Thr Thr Thr Lys Glu Leu Ile Glu Leu Ala Asp Lys
        35                  40                  45

Val Gly Pro Tyr Val Cys Met Ile Lys Thr His Ile Asp Ile Ile Asp
    50                  55                  60

Asp Phe Thr Tyr Ala Gly Thr Val Leu Pro Leu Lys Glu Leu Ala Leu
65                  70                  75                  80

Lys His Gly Phe Phe Leu Phe Glu Asp Arg Lys Phe Ala Asp Ile Gly
                85                  90                  95

Asn Thr Val Lys His Gln Tyr Lys Asn Gly Val Tyr Arg Ile Ala Glu
            100                 105                 110

Trp Ser Asp Ile Thr Asn Ala His Gly Val Pro Gly Thr Gly Ile Ile
        115                 120                 125
```

```
Ala Gly Leu Arg Ala Gly Ala Glu Glu Thr Val Ser Glu Gln Lys Lys
            130                 135                 140

Glu Asp Val Ser Asp Tyr Glu Asn Ser Gln Tyr Lys Glu Phe Leu Val
145                 150                 155                 160

Pro Ser Pro Asn Glu Lys Leu Ala Arg Gly Leu Leu Met Leu Ala Glu
                165                 170                 175

Leu Ser Cys Lys Gly Ser Leu Ala Thr Gly Glu Tyr Ser Lys Gln Thr
            180                 185                 190

Ile Glu Leu Ala Arg Ser Asp Pro Glu Phe Val Val Gly Phe Ile Ala
            195                 200                 205

Gln Asn Arg Pro Lys Gly Asp Ser Glu Asp Trp Leu Ile Leu Thr Pro
    210                 215                 220

Gly Val Gly Leu Asp Asp Lys Gly Asp Ala Leu Gly Gln Gln Tyr Arg
225                 230                 235                 240

Thr Val Glu Asp Val Met Ser Thr Gly Thr Asp Ile Ile Ile Val Gly
                245                 250                 255

Arg Gly Leu Tyr Gly Gln Asn Arg Asp Pro Ile Glu Glu Ala Lys Arg
            260                 265                 270

Tyr Gln Lys Ala Gly Trp Glu Ala Tyr Gln Lys Ile Asn Cys
        275                 280                 285

<210> SEQ ID NO 60
<211> LENGTH: 35
<212> TYPE: DNA
<213> ORGANISM: Artificial Sequence
<220> FEATURE:
<223> OTHER INFORMATION: Primer KU5

<400> SEQUENCE: 60
tttgcccggg cgagtatctg tctgactcgt cattg                          35

<210> SEQ ID NO 61
<211> LENGTH: 33
<212> TYPE: DNA
<213> ORGANISM: Artificial Sequence
<220> FEATURE:
<223> OTHER INFORMATION: Primer KU3

<400> SEQUENCE: 61
aaagcccggg caaaggcctg tttctcggtg tac                            33

<210> SEQ ID NO 62
<211> LENGTH: 29
<212> TYPE: DNA
<213> ORGANISM: Artificial Sequence
<220> FEATURE:
<223> OTHER INFORMATION: Primer P7
<220> FEATURE:
<221> NAME/KEY: misc_feature
<222> LOCATION: (24)..(24)
<223> OTHER INFORMATION: n is a, c, g, or t

<400> SEQUENCE: 62
aactacatct tcggctayca yccncaygg                                 29

<210> SEQ ID NO 63
<211> LENGTH: 10
<212> TYPE: PRT
<213> ORGANISM: Artificial Sequence
<220> FEATURE:
<223> OTHER INFORMATION: DGAT2 Consensus Sequence
```

```
<400> SEQUENCE: 63

Asn Tyr Ile Phe Gly Tyr His Pro His Gly
1               5                   10

<210> SEQ ID NO 64
<211> LENGTH: 29
<212> TYPE: DNA
<213> ORGANISM: Artificial Sequence
<220> FEATURE:
<223> OTHER INFORMATION: Primer P8
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 64
agggactcgg aggcgccgcc ncanacdat                              29

<210> SEQ ID NO 65
<211> LENGTH: 10
<212> TYPE: PRT
<213> ORGANISM: Artificial Sequence
<220> FEATURE:
<223> OTHER INFORMATION: DGAT2 Consensus Sequence

<400> SEQUENCE: 65

Ile Val Val Gly Gly Ala Ser Glu Ser Leu
1               5                   10

<210> SEQ ID NO 66
<211> LENGTH: 23
<212> TYPE: DNA
<213> ORGANISM: Artificial Sequence
<220> FEATURE:
<223> OTHER INFORMATION: Primer P80

<400> SEQUENCE: 66
gggcatccct gtttctctta tga                                   23

<210> SEQ ID NO 67
<211> LENGTH: 23
<212> TYPE: DNA
<213> ORGANISM: Artificial Sequence
<220> FEATURE:
<223> OTHER INFORMATION: Primer P81

<400> SEQUENCE: 67
aacttccgag tgcctctcta cag                                   23

<210> SEQ ID NO 68
<211> LENGTH: 24
<212> TYPE: DNA
<213> ORGANISM: Artificial Sequence
<220> FEATURE:
<223> OTHER INFORMATION: LinkAmp Primer 1

<400> SEQUENCE: 68
aggcacagtc gaggacttat ccta                                  24

<210> SEQ ID NO 69
<211> LENGTH: 29
<212> TYPE: DNA
<213> ORGANISM: Artificial Sequence
```

```
<220> FEATURE:
<223> OTHER INFORMATION: Primer P95

<400> SEQUENCE: 69
ggcaagctta ttgtcgttgg tggagcaca                                        29

<210> SEQ ID NO 70
<211> LENGTH: 35
<212> TYPE: DNA
<213> ORGANISM: Artificial Sequence
<220> FEATURE:
<223> OTHER INFORMATION: Primer P96

<400> SEQUENCE: 70
aattccacca gatctgtcgt ggtattcgga cactt                                 35

<210> SEQ ID NO 71
<211> LENGTH: 39
<212> TYPE: DNA
<213> ORGANISM: Artificial Sequence
<220> FEATURE:
<223> OTHER INFORMATION: Primer P97

<400> SEQUENCE: 71
ataccacgac agatctggtg gaattgccac cgagggagc                             39

<210> SEQ ID NO 72
<211> LENGTH: 30
<212> TYPE: DNA
<213> ORGANISM: Artificial Sequence
<220> FEATURE:
<223> OTHER INFORMATION: Primer P98

<400> SEQUENCE: 72
gcggaattcg cagatagact ggtttcgctt                                       30

<210> SEQ ID NO 73
<211> LENGTH: 22
<212> TYPE: DNA
<213> ORGANISM: Artificial Sequence
<220> FEATURE:
<223> OTHER INFORMATION: Primer P115

<400> SEQUENCE: 73
aactacatct tcggctatca cc                                               22

<210> SEQ ID NO 74
<211> LENGTH: 22
<212> TYPE: DNA
<213> ORGANISM: Artificial Sequence
<220> FEATURE:
<223> OTHER INFORMATION: Primer P116

<400> SEQUENCE: 74
tgaacaagcg tagattccag ac                                               22

<210> SEQ ID NO 75
<211> LENGTH: 22
<212> TYPE: DNA
<213> ORGANISM: Artificial Sequence
<220> FEATURE:
<223> OTHER INFORMATION: Primer P112

<400> SEQUENCE: 75
cacccttgct cggcgatgta tc                                               22
```

<210> SEQ ID NO 76
<211> LENGTH: 29
<212> TYPE: DNA
<213> ORGANISM: Artificial Sequence
<220> FEATURE:
<223> OTHER INFORMATION: Primer P26
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 76
atgctggaca aggagaccgg nctngaycc                              29

<210> SEQ ID NO 77
<211> LENGTH: 10
<212> TYPE: PRT
<213> ORGANISM: Artificial Sequence
<220> FEATURE:
<223> OTHER INFORMATION: PDAT Consensus Sequence

<400> SEQUENCE: 77

Met Leu Asp Lys Glu Thr Gly Leu Asp Pro
1               5                   10

<210> SEQ ID NO 78
<211> LENGTH: 33
<212> TYPE: DNA
<213> ORGANISM: Artificial Sequence
<220> FEATURE:
<223> OTHER INFORMATION: Primer P27
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t

<400> SEQUENCE: 78
ccagatgacg tcgccgccct tgggnarcat nga                         33

<210> SEQ ID NO 79
<211> LENGTH: 11
<212> TYPE: PRT
<213> ORGANISM: Artificial Sequence
<220> FEATURE:
<223> OTHER INFORMATION: PDAT Consensus Sequence

<400> SEQUENCE: 79

Ser Met Leu Pro Lys Gly Gly Glu Val Ile Trp
1               5                   10

<210> SEQ ID NO 80
<211> LENGTH: 34
<212> TYPE: DNA
<213> ORGANISM: Artificial Sequence
<220> FEATURE:
<223> OTHER INFORMATION: Primer P39

<400> SEQUENCE: 80
ggcggtaccg gatcctcaat cgaagagact aagc                        34

<210> SEQ ID NO 81
<211> LENGTH: 30
<212> TYPE: DNA
<213> ORGANISM: Artificial Sequence
<220> FEATURE:
<223> OTHER INFORMATION: Primer P42

<400> SEQUENCE: 81
ccggaattca gctttgagct tggagaagta                                      30

<210> SEQ ID NO 82
<211> LENGTH: 5105
<212> TYPE: DNA
<213> ORGANISM: Artificial Sequence
<220> FEATURE:
<223> OTHER INFORMATION: Plasmid pLV13
<220> FEATURE:
<221> NAME/KEY: misc_feature
<222> LOCATION: (4446)..(4446)
<223> OTHER INFORMATION: n is a, c, g, or t

<400> SEQUENCE: 82
gtacgagccg gaagcataaa gtgtaaagcc tggggtgcct aatgagtgag ctaactcaca     60
ttaattgcgt tgcgctcact gcccgctttc cagtcgggaa acctgtcgtg ccagctgcat    120
taatgaatcg gccaacgcgc ggggagaggc ggtttgcgta ttgggcgctc ttccgcttcc    180
tcgctcactg actcgctgcg ctcggtcgtt cggctgcggc gagcggtatc agctcactca    240
aaggcggtaa tacggttatc cacagaatca ggggataacg caggaaagaa catgtgagca    300
aaaggccagc aaaaggccag gaaccgtaaa aaggccgcgt tgctggcgtt tttccatagg    360
ctccgccccc ctgacgagca tcacaaaaat cgacgctcaa gtcagaggtg gcgaaacccg    420
acaggactat aaagatacca ggcgtttccc cctggaagct ccctcgtgcg ctctcctgtt    480
ccgaccctgc cgcttaccgg atacctgtcc gcctttctcc cttcgggaag cgtggcgctt    540
tctcatagct cacgctgtag gtatctcagt tcggtgtagg tcgttcgctc caagctgggc    600
tgtgtgcacg aaccccccgt tcagcccgac cgctgcgcct tatccggtaa ctatcgtctt    660
gagtccaacc cggtaagaca cgacttatcg ccactggcag cagccactgg taacaggatt    720
agcagagcga ggtatgtagg cggtgctaca gagttcttga agtggtggcc taactacggc    780
tacactagaa ggacagtatt tggtatctgc gctctgctga agccagttac cttcggaaaa    840
agagttggta gctcttgatc cggcaaacaa accaccgctg gtagcggtgg tttttttgtt    900
tgcaagcagc agattacgcg cagaaaaaaa ggatctcaag aagatccttt gatcttttct    960
acggggtctg acgctcagtg gaacgaaaac tcacgttaag ggattttggt catgagatta   1020
tcaaaaagga tcttcaccta gatcctttta aattaaaaat gaagttttaa atcaatctaa   1080
agtatatatg agtaaacttg gtctgacagt taccaatgct taatcagtga ggcacctatc   1140
tcagcgatct gtctatttcg ttcatccata gttgcctgac tccccgtcgt gtagataact   1200
acgatacggg agggcttacc atctggcccc agtgctgcaa tgataccgcg agacccacgc   1260
tcaccggctc cagatttatc agcaataaac cagccagccg gaagggccga gcgcagaagt   1320
ggtcctgcaa ctttatccgc ctccatccag tctattaatt gttgccggga agctagagta   1380
agtagttcgc cagttaatag tttgcgcaac gttgttgcca ttgctacagg catcgtggtg   1440
tcacgctcgt cgtttggtat ggcttcattc agctccggtt cccaacgatc aaggcgagtt   1500
acatgatccc ccatgttgtg caaaaaagcg gttagctcct tcggtcctcc gatcgttgtc   1560
agaagtaagt tggccgcagt gttatcactc atggttatgg cagcactgca taattctctt   1620

```
actgtcatgc catccgtaag atgctttct gtgactggtg agtactcaac caagtcattc    1680
tgagaatagt gtatgcggcg accgagttgc tcttgcccgg cgtcaatacg ggataatacc    1740
gcgccacata gcagaacttt aaaagtgctc atcattggaa aacgttcttc ggggcgaaaa    1800
ctctcaagga tcttaccgct gttgagatcc agttcgatgt aacccactcg tgcacccaac    1860
tgatcttcag catcttttac tttcaccagc gtttctgggt gagcaaaaac aggaaggcaa    1920
aatgccgcaa aaagggaat aagggcgaca cggaaatgtt gaatactcat actcttcctt    1980
tttcaatatt attgaagcat ttatcagggt tattgtctca tgagcggata catatttgaa    2040
tgtatttaga aaataaaca aatagggggtt ccgcgcacat ttccccgaaa agtgccacct    2100
gacgcgccct gtagcggcgc attaagcgcg gcgggtgtgg tggttacgcg cagcgtgacc    2160
gctacacttg ccagcgccct agcgcccgct cctttcgctt tcttcccttc ctttctcgcc    2220
acgttcgccg gctttccccg tcaagctcta aatcggggggc tccctttagg gttccgattt    2280
agtgctttac ggcacctcga cccccaaaaaa cttgattagg gtgatggttc acgtagtggg    2340
ccatcgccct gatagacggt ttttcgccct tgacgttgg agtccacgtt ctttaatagt    2400
ggactcttgt tccaaactgg aacaacactc aaccctatct cggtctattc ttttgattta    2460
taagggattt tgccgatttc ggcctattgg ttaaaaaatg agctgattta caaaaatttt    2520
aacgcgaatt ttaacaaaat attaacgctt acaatttcca ttcgccattc aggctgcgca    2580
actgttggga agggcgatta agtcatacac aagtcagctt cttcgagcc tcatataagt    2640
ataagtagtt caacgtatta gcactgtacc cagcatctcc gtatcgagaa acacaacaac    2700
atgccccatt ggacagatca tgcggataca caggttgtgc agtatcatac atactcgatc    2760
agacaggtcg tctgaccatc atacaagctg aacaagcgct ccatacttgc acgtctctcta    2820
tatacacagt taaattacat atccatagtc taacctctaa cagttaatct tctggtaagc    2880
ctcccagcca gccttctggt atcgcttggc ctcctcaata ggatctcggt tctggccgta    2940
cagacctcgg ccgacaatta tgatatccgt tccggtagac atgacatcct caacagttcg    3000
gtactgctgt ccgagagcgt ctcccttgtc gtcaagaccc accccggggg tcagaataag    3060
ccagtcctca gagtcgccct taggtcggtt ctgggcaatg aagccaacca caaactcggg    3120
gtcggatcgg gcaagctcaa tggtctgctt ggagtactcg ccagtggcca gagagccctt    3180
gcaagacagc tcggccagca tgagcagacc tctggccagc ttctcgttgg gagagggggac    3240
taggaactcc ttgtactggg agttctcgta gtcagagacg tcctccttct tctgttcaga    3300
gacagtttcc tcggcaccag ctcgcaggcc agcaatgatt ccggttccgg gtacaccgtg    3360
ggcgttggtg atatcggacc actcggcgat tcggtgacac cggtactggt gcttgacagt    3420
gttgccaata tctgcgaact ttctgtcctc gaacaggaag aaaccgtgct aagagcaag    3480
ttccttgagg gggagcacag tgccggcgta ggtgaagtcg tcaatgatgt cgatatgggt    3540
tttgatcatg cacacataag gtccgacctt atcggcaagc tcaatgagct ccttggtggt    3600
ggtaacatcc agagaagcac acaggttggt tttcttggct gccacgagct tgagcactcg    3660
agcggcaaag gcggacttgt ggacgttagc tcgagcttcg taggaggggca ttttggtggt    3720
gaagaggaga ctgaaataaa tttagtctgc agaacttttt atcggaacct tatctggggc    3780
agtgaagtat atgttatggt aatagttacg agttagttga acttatagat agactggact    3840
atacggctat cggtccaaat tagaaagaac gtcaatggct ctctgggcgt cgcctttgcc    3900
gacaaaaatg tgatcatgat gaaagccagc aatgacgttg cagctgatat tgttgtcggc    3960
caaccgcgcc gaaaacgcag ctgtcagacc cacagcctcc aacgaagaat gtatcgtcaa    4020
```

-continued

```
agtgatccaa gcacactcat agttggagtc gtactccaaa ggcggcaatg acgagtcaga    4080
cagatactcg tcgactcagg cgacgacgga attcagcttt gagcttggag aagtatccgt    4140
ctcggtgctc caaatcaggg taggacagtc tccagtcgta cgccgcagca gacattgtat    4200
ccgtatcgta tccaataaca gccaggttct cgagcagctt gttccacagc cagtagcctg    4260
ccataaagaa gtcggcggag gcaaatccct gggcggctcg cagcttgaaa tggggagggt    4320
ctagaccggt ctctgtgtcc agcatcaggt tctgcagcca gcagtacttg tccagcagca    4380
tgactcggat catgtaccag gagccccaca ttcgctttct gaagtgcgac tcggtgggac    4440
actccnyggt tccctccagg gaccagctct ccagtcccgt ggagatgacg ccgggcacca    4500
gcaccaccgg gtacttggcg ttgagtccct cgctcttcat agccttgccc acagcaaaag    4560
gggcagcctt ctgttcgctt ttctggtgct tctcgatctt gagatctaga atacagaagt    4620
caacggttca tccatggtga ggtcttagca gagtactcgg tcaagactcc ttgaacttga    4680
tgaagttgcc aaaggtgaca ttctggccgg gctcgtcatc aggggctcca gaatgatcac    4740
cccagatagc cttaccaccc ttgggaatca tggaagcaat tcctccccat gttcgcagca    4800
gatcggctcg ctctcgtcga gagaagaact gctccagtcc atacacagcc atcgcgttca    4860
gctgcacggt atccttcatt tctccagaca gaagagcaac cagggtcttg ggagtaccca    4920
gcatggagcc ggaaatgtcg acaaaggatt caatatggtc attgacccag ttgggacctc    4980
ctcctccata tccctcggcc tcagcccact tcatgaagta aagatgacc tgggagccca    5040 tggaatggcc cgtcagaact gtcttctcac ctgtcatacg cttagtctct tcgattgagg    5100
atccg                                                                5105
```

<210> SEQ ID NO 83
<211> LENGTH: 41
<212> TYPE: DNA
<213> ORGANISM: Artificial Sequence
<220> FEATURE:
<223> OTHER INFORMATION: Primer P41

<400> SEQUENCE: 83
cttctgtatt ctagatctca agatcgagaa gcaccagaaa a                        41

<210> SEQ ID NO 84
<211> LENGTH: 48
<212> TYPE: DNA
<213> ORGANISM: Artificial Sequence
<220> FEATURE:
<223> OTHER INFORMATION: Primer P40

<400> SEQUENCE: 84
gcttctcgat cttgagatct agaatacaga agtcaacggt tcatccat                 48

<210> SEQ ID NO 85
<211> LENGTH: 22
<212> TYPE: DNA
<213> ORGANISM: Artificial Sequence
<220> FEATURE:
<223> OTHER INFORMATION: Primer P51

<400> SEQUENCE: 85
tagatagact ggactatacg gc                                             22

<210> SEQ ID NO 86
<211> LENGTH: 20
<212> TYPE: DNA

```
<213> ORGANISM: Artificial Sequence
<220> FEATURE:
<223> OTHER INFORMATION: Primer P52

<400> SEQUENCE: 86
gactgtccta ccctgatttg                                               20

<210> SEQ ID NO 87
<211> LENGTH: 33
<212> TYPE: DNA
<213> ORGANISM: Artificial Sequence
<220> FEATURE:
<223> OTHER INFORMATION: Primer P37

<400> SEQUENCE: 87
ccaggtacca agatcgagaa gcaccagaaa agc                                33

<210> SEQ ID NO 88
<211> LENGTH: 36
<212> TYPE: DNA
<213> ORGANISM: Artificial Sequence
<220> FEATURE:
<223> OTHER INFORMATION: Primer P38

<400> SEQUENCE: 88
ctcgaattca gaatacagaa gtcaacggtt catcca                             36

<210> SEQ ID NO 89
<211> LENGTH: 23
<212> TYPE: DNA
<213> ORGANISM: Artificial Sequence
<220> FEATURE:
<223> OTHER INFORMATION: Primer P79

<400> SEQUENCE: 89
tctctgtaga gaggcactcg gaa                                           23

<210> SEQ ID NO 90
<211> LENGTH: 23
<212> TYPE: DNA
<213> ORGANISM: Artificial Sequence
<220> FEATURE:
<223> OTHER INFORMATION: Primer P84

<400> SEQUENCE: 90
tgacgccggg caccagcacc acc                                           23

<210> SEQ ID NO 91
<211> LENGTH: 24
<212> TYPE: DNA
<213> ORGANISM: Artificial Sequence
<220> FEATURE:
<223> OTHER INFORMATION: Primer P85

<400> SEQUENCE: 91
gtcacctttg gcaacttcat caag                                          24

<210> SEQ ID NO 92
<211> LENGTH: 41
<212> TYPE: DNA
<213> ORGANISM: Artificial Sequence
<220> FEATURE:
<223> OTHER INFORMATION: Primer P201

<400> SEQUENCE: 92
ctcgcggccg ccatggaggt ccgacgacga aarathgayg t                       41
```

<210> SEQ ID NO 93
<211> LENGTH: 46
<212> TYPE: DNA
<213> ORGANISM: Artificial Sequence
<220> FEATURE:
<223> OTHER INFORMATION: Primer P203
<220> FEATURE:
<221> NAME/KEY: misc_feature
<222> LOCATION: (38)..(38)
<223> OTHER INFORMATION: n is a, c, g, or t

<400> SEQUENCE: 93
gaggcggccg ctactggttc tgcttgtagt tgtaggcnar rtarta                46

<210> SEQ ID NO 94
<211> LENGTH: 44
<212> TYPE: DNA
<213> ORGANISM: Artificial Sequence
<220> FEATURE:
<223> OTHER INFORMATION: Primer P214

<400> SEQUENCE: 94
atctcgacaa tcgtcgcagc cctcctcaag agcatcgtcc agaa                  44

<210> SEQ ID NO 95
<211> LENGTH: 42
<212> TYPE: DNA
<213> ORGANISM: Artificial Sequence
<220> FEATURE:
<223> OTHER INFORMATION: Primer P215

<400> SEQUENCE: 95
cgaacagatc ccaatattac atgaggcgag tttgagagac ag                    42

<210> SEQ ID NO 96
<211> LENGTH: 44
<212> TYPE: DNA
<213> ORGANISM: Artificial Sequence
<220> FEATURE:
<223> OTHER INFORMATION: Primer P216

<400> SEQUENCE: 96
aactggtatt taaatgatgt ccccaagacg gagcgtattc gacc                  44

<210> SEQ ID NO 97
<211> LENGTH: 40
<212> TYPE: DNA
<213> ORGANISM: Artificial Sequence
<220> FEATURE:
<223> OTHER INFORMATION: Primer P217

<400> SEQUENCE: 97
gtagttgtag gctaggtagt aaaggaatgc acaagtgggt                       40

<210> SEQ ID NO 98
<211> LENGTH: 42
<212> TYPE: DNA
<213> ORGANISM: Artificial Sequence
<220> FEATURE:
<223> OTHER INFORMATION: Primer P218

<400> SEQUENCE: 98
ctgtctctca aactcgcctc atgtaatatt gggatctgtt cg                    42

<210> SEQ ID NO 99

```
<211> LENGTH: 40
<212> TYPE: DNA
<213> ORGANISM: Artificial Sequence
<220> FEATURE:
<223> OTHER INFORMATION: Primer P219

<400> SEQUENCE: 99
cgaatacgct ccgtcttggg gacatcattt aaataccagt                40

<210> SEQ ID NO 100
<211> LENGTH: 20
<212> TYPE: DNA
<213> ORGANISM: Artificial Sequence
<220> FEATURE:
<223> OTHER INFORMATION: Primer P226

<400> SEQUENCE: 100
cgacgaaaaa ttgacgtgct                                      20

<210> SEQ ID NO 101
<211> LENGTH: 20
<212> TYPE: DNA
<213> ORGANISM: Artificial Sequence
<220> FEATURE:
<223> OTHER INFORMATION: Primer P227

<400> SEQUENCE: 101
gatttccgaa cagatcccaa                                      20

<210> SEQ ID NO 102
<211> LENGTH: 54
<212> TYPE: DNA
<213> ORGANISM: Artificial Sequence
<220> FEATURE:
<223> OTHER INFORMATION: Primer P205
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t

<400> SEQUENCE: 102
ctcgcggccg ccatggccac cctgcaccccc gargaygcng cnggnmgncc ngtn     54

<210> SEQ ID NO 103
<211> LENGTH: 55
<212> TYPE: DNA
<213> ORGANISM: Artificial Sequence
<220> FEATURE:
<223> OTHER INFORMATION: Primer P208
<220> FEATURE:
<221> NAME/KEY: misc_feature
```

```
<222> LOCATION: (44)..(44)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t

<400> SEQUENCE: 103
gaggcggccg ctagaacagc aggtacatgg agcacatcag gganggnccd atcat        55

<210> SEQ ID NO 104
<211> LENGTH: 42
<212> TYPE: DNA
<213> ORGANISM: Artificial Sequence
<220> FEATURE:
<223> OTHER INFORMATION: Primer P220

<400> SEQUENCE: 104
tccaccaaac gacactcgat agtgcgggag catctcggag aa                      42

<210> SEQ ID NO 105
<211> LENGTH: 40
<212> TYPE: DNA
<213> ORGANISM: Artificial Sequence
<220> FEATURE:
<223> OTHER INFORMATION: Primer P221

<400> SEQUENCE: 105
gaacagatcc caatattaca ccaaggcagg ttactcgact                         40

<210> SEQ ID NO 106
<211> LENGTH: 42
<212> TYPE: DNA
<213> ORGANISM: Artificial Sequence
<220> FEATURE:
<223> OTHER INFORMATION: Primer P222

<400> SEQUENCE: 106
gccaactggt atttaaatga tgttccatgt tccccacgct cg                      42

<210> SEQ ID NO 107
<211> LENGTH: 40
<212> TYPE: DNA
<213> ORGANISM: Artificial Sequence
<220> FEATURE:
<223> OTHER INFORMATION: Primer P223

<400> SEQUENCE: 107
acatggagca catcagggar ggacckatca tgagcgagaa                         40

<210> SEQ ID NO 108
<211> LENGTH: 42
<212> TYPE: DNA
<213> ORGANISM: Artificial Sequence
<220> FEATURE:
<223> OTHER INFORMATION: Primer P224

<400> SEQUENCE: 108
caagtcgagt aacctgcctt ggtgtaatat tgggatctgt tc                      42

<210> SEQ ID NO 109
<211> LENGTH: 41
<212> TYPE: DNA
<213> ORGANISM: Artificial Sequence
<220> FEATURE:
<223> OTHER INFORMATION: Primer P225
```

-continued

```
<400> SEQUENCE: 109
acgagcgtgg ggaacatgga acatcattta aataccagtt g                    41

<210> SEQ ID NO 110
<211> LENGTH: 12649
<212> TYPE: DNA
<213> ORGANISM: Artificial Sequence
<220> FEATURE:
<223> OTHER INFORMATION: Plasmid pKUNF12T6E
<220> FEATURE:
<221> NAME/KEY: misc_feature
<222> LOCATION: (2507)..(2507)
<223> OTHER INFORMATION: n is a, c, g, or t
<220> FEATURE:
<221> NAME/KEY: misc_feature
<222> LOCATION: (2512)..(2515)
<223> OTHER INFORMATION: n is a, c, g, or t

<400> SEQUENCE: 110
taaccctcac taaagggaac aaaagctgga gctccaccgc ggacacaata tctggtcaaa    60
tttcagtttc gttacataaa tcgttatgtc aaaggagtgt gggaggttaa gagaattatc   120
accggcaaac tatctgttaa ttgctaggta cctctagacg tccacccggg tcgcttggcg   180
gccgaagagg ccggaatctc gggccgcggt ggcggccgct tagttggtct tggacttctt   240
gggcttcttc aggtaggact ggacaaagaa gttgccgaac agagcgagca gggtgatcat   300
gtacacgccg agcagctgga ccagagcctg agggtagtcg caggggaaga ggtagtcgta   360
cagggactgc accagcatag ccatgaactg ggtcatctgc agagtggtga tgtagggctt   420
gatgggcttg acgaagccga agccctgaga ggaaaagaag tagtaggcgt acatgacggt   480
gtggacgaag gagttgagga tgacggagaa gtaggcgtcg ccaccaggag cgtacttggc   540
aatagcccac cagatggcga gatggtggc atggtggtac acgtgcagga aggagacctg   600
gttgaacttc ttgcacagga tcatgatagc ggtgtccagg aactcgtagg ccttggagac   660
gtagaacacg tagacgattc gggacatgcc ctgagcgtgg gactcgttgc ccttctccat   720
gtcgttgccg aagaccttgt agccacccag gatagcctgt cggatggtct cgacgcacat   780
gtagagggac agtccgaaga ggaacaggtt gtggagcagc ttgatggtct tcagctcgaa   840
gggcttctcc atctgcttca tgatgggaat gccgaagagc agcatggcca tgtagccgac   900
ctcgaaggcg agcatggtgg agacgtccat catgggcaga ccgtcggtca gagcgtaggg   960
cttagctccg tccatccact ggtcgacacc ggtctcgact cgtccgacca cgtcgtccca  1020
gacagaggag ttggccatgg tgaatgattc ttatactcag aaggaaatgc ttaacgattt  1080
cgggtgtgag ttgacaagga gagagagaaa agaagaggaa aggtaattcg gggacggtgg  1140
tcttttatac ccttggctaa agtcccaacc acaaagcaaa aaattttca gtagtctatt  1200 ttgcgtccgg catgggttac ccggatggcc agacaaagaa actagtacaa agtctgaaca  1260
agcgtagatt ccagactgca gtaccctacg cccttaacgg caagtgtggg aaccggggga  1320
ggtttgatat gtggggtgaa gggggctctc gccggggttg ggcccgctac tgggtcaatt  1380
tggggtcaat tggggcaatt ggggctgttt tttgggacac aaatacgccg ccaacccggt  1440
ctctcctgaa ttctgcatcg atcgaggaag aggacaagcg gctgcttctt aagtttgtga  1500
catcagtatc caaggcacca ttgcaaggat tcaaggcttt gaacccgtca tttgccattc  1560
gtaacgctgg tagacaggtt gatcggttcc ctacggcctc cacctgtgtc aatcttctca  1620
agctgcctga ctatcaggac attgatcaac ttcggaagaa acttttgtat gccattcgat  1680
cacatgctgg tttcgatttg tcttagagga acgcatatac agtaatcata gagaataaac  1740
```

```
gatattcatt tattaaagta gatagttgag gtagaagttg taaagagtga taaatagcgg    1800
ccgcgcctac ttaagcaacg ggcttgataa cagcgggggg ggtgcccacg ttgttgcggt    1860
tgcggaagaa cagaacaccc ttaccagcac cctcggcacc agcgctgggc tcaacccact    1920
ggcacatacg cgcactgcgg tacatggcgc ggatgaagcc acgaggacca tcctggacat    1980
cagcccggta gtgcttgccc atgatgggct taatggcctc ggtggcctcg tccgcgttgt    2040
agaaggggat gctgctgacg tagtggtgga ggacatgagt ctcgatgatg ccgtggagaa    2100
ggtggcggcc gatgaagccc atctcacggt caatggtagc agcggcacca cggacgaagt    2160
tccactcgtc gttggtgtag tggggaaggg tagggtcggt gtgctggagg aaggtgatgg    2220
caacgagcca gtggttaacc cagaggtagg gaacaaagta ccagatggcc atgttgtaga    2280
aaccgaactt ctgaacgagg aagtacagag cagtggccat cagaccgata ccaatatcgc    2340
tgaggacgat gagcttagcg tcactgttct cgtacagagg gctgcgggga tcgaagtggt    2400
taacaccacc gccgaggccg ttatgcttgc ccttgccgcg accctcacgc tggcgctcgt    2460
ggtagttgtg gccggtaaca ttggtgatga ggtagttggg ccagccnacg annnnctcag    2520
taagatgagc gagctcgtgg gtcatctttc cgagacgagt agcctgctgc tcgcgggttc    2580
ggggaacgaa gaccatgtca cgctccatgt tgccagtggc cttgtggtgc tttcggtggg    2640
agatttgcca gctgaagtag gggacaagga gggaagagtg aagaacccag ccagtaatgt    2700
cgttgatgat gcgagaatcg gagaaagcac cgtgaccgca ctcatgggca ataacccaga    2760
gaccagtacc gaaaagaccc tgaagaacgg tgtacacggc ccacagacca gcgcgggcgg    2820
gggtggaggg gatatattcg ggggtcacaa agttgtacca gatgctgaaa gtggtagtca    2880
ggaggacaat gtcgcggagg atataaccgt atcccttgag agcggagcgc ttgaagcagt    2940
gcttagggat ggcattgtag atgtccttga tggtaaagtc gggaacctcg aactggttgc    3000
cgtaggtgtc gagcatgaca ccatactcgg acttgggctt ggcgatatca acctcggaca    3060
tggacgagag cgatgtggaa gaggccgagt ggcgggggaga gtctgaagga gagacggcgg    3120
cagactcaga atccgtcaca gtagttgagg tgacggtgcg tctaagcgca gggttctgct    3180
tgggcagagc cgaagtggac gccatggaga gctgggttag tttgtgtaga gagtgtgtgt    3240
tgctagcgac tttcggattg tgtcattaca caaaacgcgt cgtctcgaca ctgatcttgt    3300
cgtggatact cacggctcgg acatcgtcgc cgacgatgac accggacttt cgcttaagga    3360
cgtcagtaac aggcattgtg tgatgtgtag tttagatttc gaatctgtgg ggaaagaaag    3420 gaaaaagag actggcaacc gattgggaga gccactgttt atatataccc tagacaagcc    3480
ccccgcttgt aagatgttgg tcaatgtaaa ccagtattaa ggttggcaag tgcaggagaa    3540
gcaaggtgtg ggtaccgagc aatggaaatg tgcggaaggc aaaaaaatga ggccacggcc    3600
tattgtcggg gctatatcca gggggcgatt gaagtacact aacatgacat gtgtccacag    3660
accctcaatc tggcctgatg agccaaatcc atacgcgctt tcgcagctct aaaggctata    3720
acaagtcaca ccaccctgct cgacctcagc gccctcactt tttgttaaga caaactgtac    3780
acgctgttcc agcgttttct gcctgcacct ggtgggacat ttggtgcaac ctaaagtgct    3840
cggaacctct gtggtgtcca gatcagcgca gcagttccga ggtagttttg aggcccttag    3900
atgatgcaat ggtgtcagtc gctggatcac gagtcttaat ggcagtattc gttcttattt    3960
gtgccattga gccccgttat cctcgtatct tctacccccc atcccatccc tttgttggtg    4020
caaccctacc catttattgt tgggtgcagc ccaaccgacg tggagagctt ggcttggcca    4080
```

```
tataaaaagg ccccccccta gtggcaatgg cagaaagtca gctgtgagtt gttgaatttg    4140
tcatctaggc ggcctggccg tcttctccgg ggcaattgtt cctctatagt actgcgtaca    4200
ctgtttaaac agtgtacgca gatctgcgac acggaattc ctgcagccca tctgcagaat     4260
tcaggagaga ccgggttggc ggcgtatttg tgtcccaaaa acagcccca attgccccaa     4320
ttgaccccaa attgacccag tagcgggccc aaccccggcg agagcccct tcaccccaca     4380
tatcaaacct cccccggttc ccacacttgc cgttaagggc gtagggtact gcagtctgga    4440
atctacgctt gttcagactt tgtactagtt tctttgtctg gccatccggg taacccatgc    4500
cggacgcaaa atagactact gaaaattttt ttgctttgtg gttgggactt tagccaaggg    4560
tataaaagac caccgtcccc gaattacctt tcctcttctt ttctctctct ccttgtcaac    4620
tcacacccga aatcgttaag catttccttc tgagtataag aatcattcac catggctgcc    4680
gctccctctg tgcgaacctt tacccgagcc gaggttctga acgctgaggc tctgaacgag    4740
ggcaagaagg acgctgaggc tccctttcctg atgatcatcg acaacaaggt gtacgacgtc    4800
cgagagttcg tccctgacca tcctggaggc tccgtgattc tcacccacgt tggcaaggac    4860
ggcaccgacg tctttgacac ctttcatccc gaggctgctt gggagactct cgccaacttc    4920
tacgttggag acattgacga gtccgaccga gacatcaaga acgatgactt tgccgctgag    4980
gtccgaaagc tgcgaacccct gttccagtct ctcggctact acgactcctc taaggcctac    5040
tacgccttca aggtctcctt caacctctgc atctgggac tgtccaccgt cattgtggcc     5100
aagtgggtc agacctccac cctcgccaac gtgctctctg ctgccctgct cggcctgttc    5160
tggcagcagt gcggatggct ggctcacgac tttctgcacc accaggtctt ccaggaccga    5220
ttctggggtt atctcttcgg agccttcctg ggaggtgtct gccagggctt ctcctcttcc    5280
tggtggaagg acaagcacaa cactcaccat gccgctccca acgtgcatgg cgaggatcct    5340
gacattgaca cccaccctct cctgacctgg tccgagcacg ctctggagat gttctccgac    5400
gtccccgatg aggagctgac ccgaatgtgg tctcgattca tggtcctgaa ccagacctgg    5460
ttctacttcc ccattctctc cttcgctcga ctgtcttggt gcctccagtc cattctcttt    5520
gtgctgccca acggtcaggc tcacaagccc tccggagctc gagtgcccat ctccctggtc    5580
gagcagctgt ccctcgccat gcactggacc tggtacctcg ctaccatgtt cctgttcatc    5640
aaggatcctg tcaacatgct cgtgtacttc ctggtgtctc aggctgtgtg cggaaacctg    5700
ctcgccatcg tgttctccct caaccacaac ggtatgcctg tgatctccaa ggaggaggct    5760
gtcgacatgg attcttcttttac caagcagatc atcactggtc gagatgtcca tcctggactg    5820
ttcgccaact ggttcaccgg tggcctgaac taccagatcg agcatcacct gttcccttcc    5880
atgcctcgac acaacttctc caagatccag cctgccgtcg agaccctgtg caagaagtac    5940
aacgtccgat accacaccac tggtatgatc gagggaactg ccgaggtctt ctcccgactg    6000
aacgaggtct ccaaggccac ctccaagatg ggcaaggctc agtaagcggc cgcatgagaa    6060
gataaatata taaatacatt gagatattaa atgcgctaga ttagagagcc tcatactgct    6120
cggagagaag ccaagacgag tactcaaagg ggattacacc atccatatcc acagacacaa    6180
gctgggaaa ggttctatat acactttccg gaataccgta gtttccgatg ttatcaatgg     6240
gggcagccag gatttcaggc acttcggtgt ctcggggtga aatggcgttc ttggcctcca    6300
tcaagtcgta ccatgtcttc atttgcctgt caaagtaaaa cagaagcaga tgaagaatga    6360
acttgaagtg aaggaatta aattgccccg gagaagacgg ccaggccgcc tagatgacaa     6420
attcaacaac tcacagctga cttttctgcca ttgccactag ggggggggcct ttttatatgg   6480
```

```
ccaagccaag ctctccacgt cggttgggct gcacccaaca ataaatgggt agggttgcac    6540
caacaaaggg atgggatggg gggtagaaga tacgaggata acgggctca atggcacaaa    6600 taagaacgaa tactgccatt aagactcgtg atccagcgac tgacaccatt gcatcatcta    6660
agggcctcaa aactacctcg gaactgctgc gctgatctgg acaccacaga ggttccgagc    6720
actttaggtt gcaccaaatg tcccaccagg tgcaggcaga aaacgctgga acagcgtgta    6780
cagtttgtct taacaaaaag tgagggcgct gaggtcgagc agggtggtgt gacttgttat    6840 agccttttaga gctgcgaaag cgcgtatgga tttggctcat caggccagat tgagggtctg    6900
tggacacatg tcatgttagt gtacttcaat cgcccctgg atatagcccc gacaataggc    6960
cgtggcctca ttttttttgcc ttccgcacat ttccattgct cggtacccac accttgcttc    7020
tcctgcactt gccaacctta atactggttt acattgacca acatcttaca agcgggggc    7080 ttgtctaggg tatatataaa cagtggctct cccaatcgt tgccagtctc ttttttcctt    7140
tctttcccca cagattcgaa atctaaacta cacatcacac aatgcctgtt actgacgtcc    7200
ttaagcgaaa gtccggtgtc atcgtcggcg acgatgtccg agccgtgagt atccacgaca    7260
agatcagtgt cgagacgacg cgttttgtgt aatgacacaa tccgaaagtc gctagcaaca    7320
cacactctct acacaaacta acccagctct ccatggagtc cattgctccc ttcctgccct    7380
ccaagatgcc tcaggacctg ttcatggacc tcgccagcgc tatcggtgtc cgagctgctc    7440
cctacgtcga tcccctggag gctgccctgg ttgcccaggc cgagaagtac attcccacca    7500
ttgtccatca cactcgaggc ttcctggttg ccgtggagtc tccccctggct cgagagctgc    7560 ctctgatgaa ccccttccac gtgctcctga tcgtgctcgc ctacctggtc accgtgtttg    7620
tgggtatgca gatcatgaag aactttgaac gattcgaggt caagaccttc tccctcctgc    7680
acaacttctg tctggtctcc atctccgcct acatgtgcgg tggcatcctg tacgaggctt    7740
atcaggccaa ctatggactg tttgagaacg ctgccgatca caccttcaag ggtctcccta    7800
tggctaagat gatctggctc ttctacttct ccaagatcat ggagtttgtc gacaccatga    7860
tcatggtcct caagaagaac aaccgacaga tttcctttct gcacgtgtac caccactctt    7920
ccatcttcac catctggtgg ctggtcacct tcgttgctcc caacggtgaa gcctacttct    7980
ctgctgccct gaactccttc atccacgtca tcatgtacgg ctactacttt ctgtctgccc    8040
tgggcttcaa gcaggtgtcg ttcatcaagt tctacatcac tcgatcccag atgacccagt    8100
tctgcatgat gtctgtccag tcttcctggg acatgtacgc catgaaggtc cttggccgac    8160
ctggataccc cttcttcatc accgctctgc tctggttcta catgtggacc atgctcggtc    8220
tcttctacaa cttttaccga aagaacgcca agctcgccaa gcaggccaag gctgacgctg    8280
ccaaggagaa ggccagaaag ctccagtaag cggccgcaag tgtggatggg gaagtgagtg    8340
cccggttctg tgtgcacaat tggcaatcca agatggatgg attcaacaca gggatatagc    8400
gagctacgtg gtggtgcgag atatagcaa cggatattta tgtttgacac ttgagaatgt    8460
acgatacaag cactgtccaa gtacaatact aaacatactg tacatactca tactcgtacc    8520
cgggcaacgg tttcacttga gtgcagtggc tagtgctctt actcgtacag tgtgcaatac    8580
tgcgtatcat agtctttgat gtatatcgta ttcattcatg ttagttgcgt acgaagtcgt    8640
caatgatgtc gatatggtt ttgatcatgc acacataagg tccgacccta tcggcaagct    8700
caatgagctc cttggtggtg gtaacatcca gagaagcaca caggttggtt ttcttggctg    8760
ccacgagctt gagcactcga gcggcaaagg cggacttgtg gacgttagct cgagcttcgt    8820
```

```
aggagggcat tttggtggtg aagaggagac tgaaataaat ttagtctgca gaactttta     8880
tcggaacctt atctggggca gtgaagtata tgttatggta atagttacga gttagttgaa    8940
cttatagata gactggacta tacggctatc ggtccaaatt agaaagaacg tcaatggctc    9000
tctgggcgtc gcctttgccg acaaaaatgt gatcatgatg aaagccagca atgacgttgc    9060
agctgatatt gttgtcggcc aaccgcgccg aaaacgcagc tgtcagaccc acagcctcca    9120
acgaagaatg tatcgtcaaa gtgatccaag cacactcata gttggagtcg tactccaaag    9180
gcggcaatga cgagtcagac agatactcgt cgacctttc cttgggaacc accaccgtca     9240
gcccttctga ctcacgtatt gtagccaccg acacaggcaa cagtccgtgg atagcagaat    9300
atgtcttgtc ggtccatttc tcaccaactt taggcgtcaa gtgaatgttg cagaagaagt    9360
atgtgccttc attgagaatc ggtgttgctg atttcaataa agtcttgaga tcagtttggc    9420
gcgccagctg cattaatgaa tcggccaacg cgcggggaga ggcggtttgc gtattgggcg    9480
ctcttccgct tcctgctca ctgactcgct gcgctcggtc gttcggctgc ggcgagcggt      9540
atcagctcac tcaaaggcgg taatacggtt atccacagaa tcagggata acgcaggaaa     9600
gaacatgtga gcaaaaggcc agcaaaaggc caggaaccgt aaaaaggccg cgttgctggc    9660
gttttccat aggctccgcc cccctgacga gcatcacaaa aatcgacgct caagtcagag      9720
gtggcgaaac ccgacaggac tataaagata ccaggcgttt ccccctggaa gctccctcgt    9780
gcgctctcct gttccgaccc tgccgcttac cggatacctg tccgcctttc tcccttcggg    9840
aagcgtggcg ctttctcata gctcacgctg taggtatctc agttcggtgt aggtcgttcg    9900
ctccaagctg ggctgtgtgc acgaaccccc cgttcagccc gaccgctgcg ccttatccgg    9960
taactatcgt cttgagtcca acccggtaag acacgactta tcgccactgg cagcagccac   10020
tggtaacagg attagcagag cgaggtatgt aggcggtgct acagagttct tgaagtggtg   10080
gcctaactac ggctacacta agaacagt atttggtatc tgcgctctgc tgaagccagt      10140
taccttcgga aaagagttg gtagctcttg atccggcaaa caaaccaccg ctggtagcgg     10200
tggttttttt gtttgcaagc agcagattac gcgcagaaaa aaggatctc aagaagatcc      10260
tttgatcttt tctacggggt ctgacgctca gtggaacgaa aactcacgtt aagggatttt   10320
ggtcatgaga ttatcaaaaa ggatcttcac ctagatcctt ttaaattaaa aatgaagtttt  10380
taaatcaatc taaagtatat atgagtaaac ttggtctgac agttaccaat gcttaatcag   10440
tgaggcacct atctcagcga tctgtctatt tcgttcatcc atagttgcct gactccccgt   10500
cgtgtagata actacgatac gggagggctt accatctggc cccagtgctg caatgatacc   10560
gcgagaccca cgctcaccgg ctccagattt atcagcaata aaccagccag ccggaagggc   10620
cgagcgcaga agtggtcctg caactttatc cgcctccatc cagtctatta attgttgccg   10680
ggaagctaga gtaagtagtt cgccagttaa tagtttgcgc aacgttgttg ccattgctac   10740
aggcatcgtg gtgtcacgct cgtcgtttgg tatggcttca ttcagctccg gttcccaacg   10800
atcaaggcga gttacatgat cccccatgtt gtgcaaaaaa gcggttagct ccttcggtcc   10860
tccgatcgtt gtcagaagta agttggccgc agtgttatcc tcatggtta tggcagcact    10920
gcataattct cttactgtca tgccatccgt aagatgcttt tctgtgactg gtgagtactc   10980
aaccaagtca ttctgagaat agtgtatgcg gcgaccgagt tgctcttgcc cggcgtcaat   11040
acgggataat accgcgccac atagcagaac tttaaaagtg ctcatcattg gaaaacgttc   11100
ttcggggcga aaactctcaa ggatcttacc gctgttgaga tccagttcga tgtaacccac   11160
tcgtgcaccc aactgatctt cagcatcttt tactttcacc agcgtttctg ggtgagcaaa   11220
```

-continued

```
aacaggaagg caaaatgccg caaaaaaggg aataagggcg acacggaaat gttgaatact    11280
catactcttc cttttttcaat attattgaag catttatcag ggttattgtc tcatgagcgg    11340
atacatattt gaatgtattt agaaaaataa acaaatgggg gttccgcgca catttccccg    11400
aaaagtgcca cctgatgcgg tgtgaaatac cgcacagatg cgtaaggaga aaataccgca    11460
tcaggaaatt gtaagcgtta atattttgtt aaaattcgcg ttaaattttt gttaaatcag    11520 ctcattttt aaccaatagg ccgaaatcgg caaaatccct tataaatcaa agaatagac     11580 cgagataggg ttgagtgttg ttccagtttg gaacaagagt ccactattaa agaacgtgga    11640
ctccaacgtc aaagggcgaa aaaccgtcta tcagggcgat ggcccactac gtgaaccatc    11700
accctaatca gttttttgg ggtcgaggtg ccgtaaagca ctaaatcgga accctaaagg    11760
gagcccccga tttagagctt gacggggaaa gccggcgaac gtggcgagaa aggaagggaa    11820
gaaagcgaaa ggagcgggcg ctagggcgct ggcaagtgta gcggtcacgc tgcgcgtaac    11880
caccacaccc gccgcgctta atgcgccgct acagggcgcg tccattcgcc attcaggctg    11940
cgcaactgtt gggaagggcg atcggtgcgg gcctcttcgc tattacgcca gctggcgaaa    12000
gggggatgtg ctgcaaggcg attaagttgg gtaacgccag ggttttccca gtcacgacgt    12060
tgtaaaacga cggccagtga attgtaatac gactcactat agggcgaatt gggcccgacg    12120
tcgcatgcag tggtggtatt gtgactgggg atgtagttga gaataagtca tacacaagtc    12180
agctttcttc gagcctcata taagtataag tagttcaacg tattagcact gtacccagca    12240
tctccgtatc gagaaacaca acaacatgcc ccattggaca gatcatgcgg atacacaggt    12300
tgtgcagtat catacatact cgatcagaca ggtcgtctga ccatcataca agctgaacaa    12360
gcgctccata cttgcacgct ctctatatac acagttaaat tacatatcca tagtctaacc    12420
tctaacagtt aatcttctgg taagcctccc agccagcctt ctggtatcgc ttggcctcct    12480
caataggatc tcggttctgg ccgtacagac ctcggccgac aattatgata tccgttccgg    12540
tagacatgac atcctcaaca gttcggtact gctgtccgag agcgtctccc ttgtcgtcaa    12600
gacccacccc gggggtcaga ataagccagt cctcagagtc gcccttaat               12649
```

<210> SEQ ID NO 111
<211> LENGTH: 973
<212> TYPE: DNA
<213> ORGANISM: Yarrowia lipolytica
<220> FEATURE:
<221> NAME/KEY: misc_feature
<223> OTHER INFORMATION: Promoter FBAIN

<400> SEQUENCE: 111

```
aaattgcccc ggagaagacg gccaggccgc ctagatgaca aattcaacaa ctcacagctg      60
actttctgcc attgccacta ggggggggcc ttttttatatg gccaagccaa gctctccacg    120
tcggttgggc tgcacccaac aataaatggg tagggttgca ccaacaaagg gatgggatgg    180
ggggtagaag atacgaggat aacggggctc aatggcacaa ataagaacga atactgccat    240
taagactcgt gatccagcga ctgacaccat tgcatcatct aagggcctca aaactacctc    300
ggaactgctg cgctgatctg gacaccacag aggttccgag cactttaggt tgcaccaaat    360
gtcccaccag gtgcaggcag aaaacgctgg aacagcgtgt acagtttgtc ttaacaaaaa    420
gtgagggcgc tgaggtcgag cagggtggtg tgacttgtta tagcctttag agctgcgaaa    480
gcgcgtatgg atttggctca tcaggccaga ttgagggtct gtggacacat gtcatgttag    540
tgtacttcaa tcgcccctg gatatagccc cgacaatagg ccgtggcctc atttttttgc     600
```

```
cttccgcaca tttccattgc tcggtaccca caccttgctt ctcctgcact tgccaacctt        660
aatactggtt tacattgacc aacatcttac aagcggggg cttgtctagg gtatatataa         720
acagtggctc tcccaatcgg ttgccagtct cttttttcct ttctttcccc acagattcga        780
aatctaaact acacatcaca caatgcctgt tactgacgtc cttaagcgaa agtccggtgt        840
catcgtcggc gacgatgtcc gagccgtgag tatccacgac aagatcagtg tcgagacgac        900
gcgttttgtg taatgacaca atccgaaagt cgctagcaac acacactctc tacacaaact        960
aacccagctc tcc                                                           973
```

<210> SEQ ID NO 112
<211> LENGTH: 957
<212> TYPE: DNA
<213> ORGANISM: Mortierella alpina
<220> FEATURE:
<221> NAME/KEY: misc_feature
<223> OTHER INFORMATION: synthetic elongase 1 (codon-optimized)

<400> SEQUENCE: 112

```
atggagtcca ttgctcccctt cctgccctcc aagatgcctc aggacctgtt catggacctc        60
gccagcgcta tcggtgtccg agctgctccc tacgtcgatc ccctggaggc tgccctggtt        120
gcccaggccg agaagtacat tcccaccatt gtccatcaca ctcgaggctt cctggttgcc        180
gtggagtctc ccctggctcg agagctgcct ctgatgaacc ccttccacgt gctcctgatc        240
gtgctcgcct acctggtcac cgtgtttgtg ggtatgcaga tcatgaagaa ctttgaacga        300 tcgaggtca agaccttctc cctcctgcac aacttctgtc tggtctccat ctccgcctac         360
atgtgcggtg gcatcctgta cgaggcttat caggccaact atggactgtt tgagaacgct        420
gccgatcaca ccttcaaggg tctccctatg gctaagatga tctggctctt ctacttctcc        480
aagatcatgg agtttgtcga caccatgatc atggtcctca agaagaacaa ccgacagatt        540
tcctttctgc acgtgtacca ccactcttcc atcttcacca tctggtggct ggtcaccttc        600
gttgctccca acggtgaagc ctacttctct gctgccctga actccttcat ccacgtcatc        660
atgtacggct actactttct gtctgccctg ggcttcaagc aggtgtcgtt catcaagttc        720
tacatcactc gatcccagat gacccagttc tgcatgatgt ctgtccagtc ttcctgggac        780
atgtacgcca tgaaggtcct tggccgacct ggataccccct tcttcatcac cgctctgctc        840
tggttctaca tgtggaccat gctcggtctc ttctacaact tttaccgaaa gaacgccaag        900
ctcgccaagc aggccaaggc tgacgctgcc aaggagaagg ccagaaagct ccagtaa          957
```

<210> SEQ ID NO 113
<211> LENGTH: 318
<212> TYPE: PRT
<213> ORGANISM: Mortierella alpina
<300> PUBLICATION INFORMATION:
<308> DATABASE ACCESSION NUMBER: GenBank Accession No. AX464731
<309> DATABASE ENTRY DATE: 2002-07-16
<313> RELEVANT RESIDUES: (1)..(318)

<400> SEQUENCE: 113

```
Met Glu Ser Ile Ala Pro Phe Leu Pro Ser Lys Met Pro Gln Asp Leu
1               5                   10                  15

Phe Met Asp Leu Ala Thr Ala Ile Gly Val Arg Ala Ala Pro Tyr Val
            20                  25                  30

Asp Pro Leu Glu Ala Ala Leu Val Ala Gln Ala Glu Lys Tyr Ile Pro
        35                  40                  45
```

```
Thr Ile Val His His Thr Arg Gly Phe Leu Val Ala Val Glu Ser Pro
 50                  55                  60

Leu Ala Arg Glu Leu Pro Leu Met Asn Pro Phe His Val Leu Leu Ile
 65                  70                  75                  80

Val Leu Ala Tyr Leu Val Thr Val Phe Val Gly Met Gln Ile Met Lys
                 85                  90                  95

Asn Phe Glu Arg Phe Glu Val Lys Thr Phe Ser Leu Leu His Asn Phe
                100                 105                 110

Cys Leu Val Ser Ile Ser Ala Tyr Met Cys Gly Gly Ile Leu Tyr Glu
            115                 120                 125

Ala Tyr Gln Ala Asn Tyr Gly Leu Phe Glu Asn Ala Ala Asp His Thr
130                 135                 140

Phe Lys Gly Leu Pro Met Ala Lys Met Ile Trp Leu Phe Tyr Phe Ser
145                 150                 155                 160

Lys Ile Met Glu Phe Val Asp Thr Met Ile Met Val Leu Lys Lys Asn
                165                 170                 175

Asn Arg Gln Ile Ser Phe Leu His Val Tyr His His Ser Ser Ile Phe
                180                 185                 190

Thr Ile Trp Trp Leu Val Thr Phe Val Ala Pro Asn Gly Glu Ala Tyr
            195                 200                 205

Phe Ser Ala Ala Leu Asn Ser Phe Ile His Val Ile Met Tyr Gly Tyr
210                 215                 220

Tyr Phe Leu Ser Ala Leu Gly Phe Lys Gln Val Ser Phe Ile Lys Phe
225                 230                 235                 240

Tyr Ile Thr Arg Ser Gln Met Thr Gln Phe Cys Met Met Ser Val Gln
                245                 250                 255

Ser Ser Trp Asp Met Tyr Ala Met Lys Val Leu Gly Arg Pro Gly Tyr
            260                 265                 270

Pro Phe Phe Ile Thr Ala Leu Leu Trp Phe Tyr Met Trp Thr Met Leu
275                 280                 285

Gly Leu Phe Tyr Asn Phe Tyr Arg Lys Asn Ala Lys Leu Ala Lys Gln
290                 295                 300

Ala Lys Ala Asp Ala Ala Lys Glu Lys Ala Arg Lys Leu Gln
305                 310                 315
```

<210> SEQ ID NO 114
<211> LENGTH: 1374
<212> TYPE: DNA
<213> ORGANISM: Mortierella alpina
<220> FEATURE:
<221> NAME/KEY: misc_feature
<223> OTHER INFORMATION: synthetic delta-6 desaturase (codon-optimized)

<400> SEQUENCE: 114

```
atggctgccg ctccctctgt gcgaaccttt acccgagccg aggttctgaa cgctgaggct    60
ctgaacgagg gcaagaagga cgctgaggct cccttcctga tgatcatcga caacaaggtg   120
tacgacgtcc gagagttcgt ccctgaccat cctggaggct ccgtgattct cacccacgtt   180
ggcaaggacg gcaccgacgt ctttgacacc tttcatcccg aggctgcttg ggagactctc   240
gccaacttct acgttggaga cattgacgag tccgaccgag acatcaagaa cgatgacttt   300
gccgctgagg tccgaaagct gcgaaccctg ttccagtctc tcggctacta cgactcctct   360
aaggcctact acgccttcaa ggtctccttc aacctctgca tctggggact gtccaccgtc   420
attgtggcca gtgggggtca gactccacc ctcgccaacg tgctctctgc tgccctgctc   480
ggcctgttct ggcagcagtg cggatggctg gctcacgact ttctgcacca ccaggtcttc   540
```

```
caggaccgat tctggggtga tctcttcgga gccttcctgg gaggtgtctg ccagggcttc      600
tcctcttcct ggtggaagga caagcacaac actcaccatg ccgctcccaa cgtgcatggc      660
gaggatcctg acattgacac ccaccctctc ctgacctggt ccgagcacgc tctggagatg      720
ttctccgacg tccccgatga ggagctgacc cgaatgtggt ctcgattcat ggtcctgaac      780
cagacctggt tctacttccc cattctctcc ttcgctcgac tgtcttggtg cctccagtcc      840
attctctttg tgctgcccaa cggtcaggct cacaagccct ccggagctcg agtgcccatc      900
tccctggtcg agcagctgtc cctcgccatg cactggacct ggtacctcgc taccatgttc      960
ctgttcatca aggatcctgt caacatgctc gtgtacttcc tggtgtctca ggctgtgtgc     1020
ggaaacctgc tcgccatcgt gttctccctc aaccacaacg gtatgcctgt gatctccaag     1080
gaggaggctg tcgacatgga tttctttacc aagcagatca tcactggtcg agatgtccat     1140
cctggactgt tcgccaactg gttcaccggt ggcctgaact accagatcga gcatcacctg     1200
ttcccttcca tgcctcgaca caacttctcc aagatccagc tgccgtcga gaccctgtgc     1260 aagaagtaca acgtccgata ccacaccact ggtatgatcg agggaactgc cgaggtcttc     1320
tcccgactga acgaggtctc caaggccacc tccaagatgg gcaaggctca gtaa           1374
```

<210> SEQ ID NO 115
<211> LENGTH: 457
<212> TYPE: PRT
<213> ORGANISM: Mortierella alpina
<300> PUBLICATION INFORMATION:
<308> DATABASE ACCESSION NUMBER: GenBank Accession No. AF465281
<309> DATABASE ENTRY DATE: 2002-02-04
<313> RELEVANT RESIDUES: (1)..(457)

<400> SEQUENCE: 115

```
Met Ala Ala Ala Pro Ser Val Arg Thr Phe Thr Arg Ala Glu Val Leu
1               5                   10                  15

Asn Ala Glu Ala Leu Asn Glu Gly Lys Lys Asp Ala Glu Ala Pro Phe
            20                  25                  30

Leu Met Ile Ile Asp Asn Lys Val Tyr Asp Val Arg Glu Phe Val Pro
        35                  40                  45

Asp His Pro Gly Gly Ser Val Ile Leu Thr His Val Gly Lys Asp Gly
    50                  55                  60

Thr Asp Val Phe Asp Thr Phe His Pro Glu Ala Ala Trp Glu Thr Leu
65                  70                  75                  80

Ala Asn Phe Tyr Val Gly Asp Ile Asp Glu Ser Asp Arg Asp Ile Lys
                85                  90                  95

Asn Asp Asp Phe Ala Ala Glu Val Arg Lys Leu Arg Thr Leu Phe Gln
            100                 105                 110

Ser Leu Gly Tyr Tyr Asp Ser Ser Lys Ala Tyr Tyr Ala Phe Lys Val
        115                 120                 125

Ser Phe Asn Leu Cys Ile Trp Gly Leu Ser Thr Val Ile Val Ala Lys
    130                 135                 140

Trp Gly Gln Thr Ser Thr Leu Ala Asn Val Leu Ser Ala Ala Leu Leu
145                 150                 155                 160

Gly Leu Phe Trp Gln Gln Cys Gly Trp Leu Ala His Asp Phe Leu His
                165                 170                 175

His Gln Val Phe Gln Asp Arg Phe Trp Gly Asp Leu Phe Gly Ala Phe
            180                 185                 190

Leu Gly Gly Val Cys Gln Gly Phe Ser Ser Ser Trp Trp Lys Asp Lys
        195                 200                 205
```

```
His Asn Thr His His Ala Ala Pro Asn Val His Gly Glu Asp Pro Asp
        210                 215                 220
Ile Asp Thr His Pro Leu Leu Thr Trp Ser Glu His Ala Leu Glu Met
225                 230                 235                 240
Phe Ser Asp Val Pro Asp Glu Glu Leu Thr Arg Met Trp Ser Arg Phe
                245                 250                 255
Met Val Leu Asn Gln Thr Trp Phe Tyr Phe Pro Ile Leu Ser Phe Ala
            260                 265                 270
Arg Leu Ser Trp Cys Leu Gln Ser Ile Leu Phe Val Leu Pro Asn Gly
        275                 280                 285
Gln Ala His Lys Pro Ser Gly Ala Arg Val Pro Ile Ser Leu Val Glu
    290                 295                 300
Gln Leu Ser Leu Ala Met His Trp Thr Trp Tyr Leu Ala Thr Met Phe
305                 310                 315                 320
Leu Phe Ile Lys Asp Pro Val Asn Met Leu Val Tyr Phe Leu Val Ser
                325                 330                 335
Gln Ala Val Cys Gly Asn Leu Leu Ala Ile Val Phe Ser Leu Asn His
            340                 345                 350
Asn Gly Met Pro Val Ile Ser Lys Glu Glu Ala Val Asp Met Asp Phe
        355                 360                 365
Phe Thr Lys Gln Ile Ile Thr Gly Arg Asp Val His Pro Gly Leu Phe
    370                 375                 380
Ala Asn Trp Phe Thr Gly Gly Leu Asn Tyr Gln Ile Glu His His Leu
385                 390                 395                 400
Phe Pro Ser Met Pro Arg His Asn Phe Ser Lys Ile Gln Pro Ala Val
                405                 410                 415
Glu Thr Leu Cys Lys Lys Tyr Asn Val Arg Tyr His Thr Thr Gly Met
            420                 425                 430
Ile Glu Gly Thr Ala Glu Val Phe Ser Arg Leu Asn Glu Val Ser Lys
        435                 440                 445
Ala Thr Ser Lys Met Gly Lys Ala Gln
    450                 455

<210> SEQ ID NO 116
<211> LENGTH: 1001
<212> TYPE: DNA
<213> ORGANISM: Yarrowia lipolytica
<220> FEATURE:
<221> NAME/KEY: misc_feature
<223> OTHER INFORMATION: Promoter FBA

<400> SEQUENCE: 116
taaacagtgt acgcagtact atagaggaac aattgccccg gagaagacgg ccaggccgcc      60
tagatgacaa attcaacaac tcacagctga ctttctgcca ttgccactag ggggggcctt     120
tttatatggc caagccaagc tctccacgtc ggttgggctg cacccaacaa taaatgggta     180
gggttgcacc aacaaaggga tgggatgggg ggtagaagat acgaggataa cggggctcaa     240
tggcacaaat aagaacgaat actgccatta agactcgtga tccagcgact gacaccattg     300
catcatctaa gggcctcaaa actacctcgg aactgctgcg ctgatctgga caccacagag     360
gttccgagca ctttaggttg caccaaatgt cccaccaggt gcaggcagaa aacgctggaa     420
cagcgtgtac agtttgtctt aacaaaaagt gagggcgctg aggtcgagca gggtggtgtg     480
acttgttata gcctttagag ctgcgaaagc gcgtatggat ttggctcatc aggccagatt     540
gagggtctgt ggacacatgt catgttagtg tacttcaatc gccccctgga tatagccccg     600
```

```
acaataggcc gtggcctcat tttttgcct tccgcacatt tccattgctc ggtacccaca      660
ccttgcttct cctgcacttg ccaaccttaa tactggttta cattgaccaa catcttacaa      720 gcgggggct tgtctagggt atatataaac agtggctctc ccaatcggtt gccagtctct      780
tttttccttt ctttccccac agattcgaaa tctaaactac acatcacaca atgcctgtta      840
ctgacgtcct taagcgaaag tccggtgtca tcgtcggcga cgatgtccga gccgtgagta      900
tccacgacaa gatcagtgtc gagacgacgc gttttgtgta atgacacaat ccgaaagtcg      960
ctagcaacac acactctcta cacaaactaa cccagctctc c                        1001
```

<210> SEQ ID NO 117
<211> LENGTH: 1434
<212> TYPE: DNA
<213> ORGANISM: Fusarium monoliforme
<220> FEATURE:
<221> NAME/KEY: misc_feature
<223> OTHER INFORMATION: delta-12 desaturase

<400> SEQUENCE: 117

```
atggcgtcca cttcggctct gcccaagcag aaccctgcgc ttagacgcac cgtcacctca       60
actactgtga cggattctga gtctgccgcc gtctctcctt cagactctcc ccgccactcg      120
gcctcttcca catcgctctc gtccatgtcc gaggttgata tcgccaagcc caagtccgag      180
tatggtgtca tgctcgacac ctacggcaac cagttcgagg ttcccgactt taccatcaag      240
gacatctaca atgccatccc taagcactgc ttcaagcgct ccgctctcaa gggatacggt      300
tatatcctcc gcgacattgt cctcctgact accactttca gcatctggta caactttgtg      360
acccccgaat atatccctc caccccgcc cgcgctggtc tgtgggccgt gtacaccgtt      420
cttcagggtc ttttcggtac tggtctctgg gttattgccc atgagtgcgg tcacggtgct      480
ttctccgatt ctcgcatcat caacgacatt actggctggg ttcttcactc ttccctcctt      540
gtcccctact tcagctggca aatctcccac cgaaagcacc acaaggccac tggcaacatg      600
gagcgtgaca tggtcttcgt tccccgaacc cgcgagcagc aggctactcg tctcggaaag      660
atgacccacg agctcgctca tcttactgag gagaccccg ctttcactct tctcatgctc      720
gtccttcagc agctcgttgg ctggcccaac tacctcatca ccaatgttac cggccacaac      780
taccacgagc gccagcgtga gggtcgcggc aagggcaagc ataacggcct cggcggtggt      840
gttaaccact cgatccccg cagccctctg tacgagaaca gtgacgctaa gctcatcgtc      900
ctcagcgata ttggtatcgg tctgatggcc actgctctgt acttcctcgt tcagaagttc      960
ggtttctaca acatggccat ctggtacttt gttccctacc tctgggttaa ccactggctc     1020
gttgccatca ccttcctcca gcacaccgac cctaccttc cccactacac caacgacgag     1080
tggaacttcg tccgtggtgc cgctgctacc attgaccgtg agatgggctt catcggccgc     1140
caccttctcc acggcatcat cgagactcat gtcctccacc actacgtcag cagcatcccc     1200
ttctacaacg cggacgaggc caccgaggcc attaagccca tcatgggcaa gcactaccgg     1260
gctgatgtcc aggatggtcc tcgtggcttc atccgcgcca tgtaccgcag tgcgcgtatg     1320
tgccagtggg ttgagcccag cgctggtgcc gagggtgctg gtaagggtgt tctgttcttc     1380
cgcaaccgca acaacgtggg cacccccccc gctgttatca agcccgttgc ttaa           1434
```

<210> SEQ ID NO 118
<211> LENGTH: 477
<212> TYPE: PRT
<213> ORGANISM: Fusarium monoliforme

```
<400> SEQUENCE: 118

Met Ala Ser Thr Ser Ala Leu Pro Lys Gln Asn Pro Ala Leu Arg Arg
1               5                   10                  15

Thr Val Thr Ser Thr Val Thr Asp Ser Glu Ser Ala Ala Val Ser
            20                  25                  30

Pro Ser Asp Ser Pro Arg His Ser Ala Ser Ser Thr Ser Leu Ser Ser
            35                  40                  45

Met Ser Glu Val Asp Ile Ala Lys Pro Lys Ser Glu Tyr Gly Val Met
    50                  55                  60

Leu Asp Thr Tyr Gly Asn Gln Phe Glu Val Pro Asp Phe Thr Ile Lys
65                  70                  75                  80

Asp Ile Tyr Asn Ala Ile Pro Lys His Cys Phe Lys Arg Ser Ala Leu
                85                  90                  95

Lys Gly Tyr Gly Tyr Ile Leu Arg Asp Ile Val Leu Leu Thr Thr Thr
            100                 105                 110

Phe Ser Ile Trp Tyr Asn Phe Val Thr Pro Glu Tyr Ile Pro Ser Thr
            115                 120                 125

Pro Ala Arg Ala Gly Leu Trp Ala Val Tyr Thr Val Leu Gln Gly Leu
            130                 135                 140

Phe Gly Thr Gly Leu Trp Val Ile Ala His Glu Cys Gly His Gly Ala
145                 150                 155                 160

Phe Ser Asp Ser Arg Ile Ile Asn Asp Ile Thr Gly Trp Val Leu His
                165                 170                 175

Ser Ser Leu Leu Val Pro Tyr Phe Ser Trp Gln Ile Ser His Arg Lys
            180                 185                 190

His His Lys Ala Thr Gly Asn Met Glu Arg Asp Met Val Phe Val Pro
            195                 200                 205

Arg Thr Arg Glu Gln Gln Ala Thr Arg Leu Gly Lys Met Thr His Glu
            210                 215                 220

Leu Ala His Leu Thr Glu Glu Thr Pro Ala Phe Thr Leu Leu Met Leu
225                 230                 235                 240

Val Leu Gln Gln Leu Val Gly Trp Pro Asn Tyr Leu Ile Thr Asn Val
                245                 250                 255

Thr Gly His Asn Tyr His Glu Arg Gln Arg Glu Gly Arg Gly Lys Gly
            260                 265                 270

Lys His Asn Gly Leu Gly Gly Val Asn His Phe Asp Pro Arg Ser
            275                 280                 285

Pro Leu Tyr Glu Asn Ser Asp Ala Lys Leu Ile Val Leu Ser Asp Ile
            290                 295                 300

Gly Ile Gly Leu Met Ala Thr Ala Leu Tyr Phe Leu Val Gln Lys Phe
305                 310                 315                 320

Gly Phe Tyr Asn Met Ala Ile Trp Tyr Phe Val Pro Tyr Leu Trp Val
                325                 330                 335

Asn His Trp Leu Val Ala Ile Thr Phe Leu Gln His Thr Asp Pro Thr
            340                 345                 350

Leu Pro His Tyr Thr Asn Asp Glu Trp Asn Phe Val Arg Gly Ala Ala
            355                 360                 365

Ala Thr Ile Asp Arg Glu Met Gly Phe Ile Gly Arg His Leu Leu His
            370                 375                 380

Gly Ile Ile Glu Thr His Val Leu His His Tyr Val Ser Ser Ile Pro
385                 390                 395                 400

Phe Tyr Asn Ala Asp Glu Ala Thr Glu Ala Ile Lys Pro Ile Met Gly
```

```
                    405                 410                 415
Lys His Tyr Arg Ala Asp Val Gln Asp Gly Pro Arg Gly Phe Ile Arg
            420                 425                 430

Ala Met Tyr Arg Ser Ala Arg Met Cys Gln Trp Val Glu Pro Ser Ala
            435                 440                 445

Gly Ala Glu Gly Ala Gly Lys Gly Val Leu Phe Phe Arg Asn Arg Asn
        450                 455                 460

Asn Val Gly Thr Pro Pro Ala Val Ile Lys Pro Val Ala
465                 470                 475

<210> SEQ ID NO 119
<211> LENGTH: 819
<212> TYPE: DNA
<213> ORGANISM: Thraustochytrium aureum
<220> FEATURE:
<221> NAME/KEY: misc_feature
<223> OTHER INFORMATION: synthetic elongase (codon-optimized)

<400> SEQUENCE: 119
atggccaact cctctgtctg ggacgacgtg gtcggacgag tcgagaccgg tgtcgaccag      60
tggatggacg gagctaagcc ctacgctctg accgacggtc tgcccatgat ggacgtctcc     120
accatgctcg ccttcgaggt cggctacatg gccatgctgc tcttcggcat tcccatcatg     180
aagcagatgg agaagcccct cgagctgaag accatcaagc tgctccacaa cctgttcctc     240
ttcggactgt ccctctacat gtgcgtcgag accatccgac aggctatcct gggtggctac     300
aaggtcttcg caacgacat ggagaagggc aacgagtccc acgctcaggg catgtcccga     360
atcgtctacg tgttctacgt ctccaaggcc tacgagttcc tggacaccgc tatcatgatc     420
ctgtgcaaga agttcaacca ggtctccttc ctgcacgtgt accaccatgc caccatcttc     480
gccatctggt gggctattgc caagtacgct cctggtggcg acgcctactt ctccgtcatc     540
ctcaactcct cgtccacac cgtcatgtac gcctactact tctttttcctc tcagggcttc     600 ggcttcgtca agcccatcaa gccctacatc accactctgc agatgaccca gttcatggct     660
atgctggtgc agtccctgta cgactacctc ttccccgtgcg actaccctca ggctctggtc     720
cagctgctcg gcgtgtacat gatcacccctg ctcgctctgt tcggcaactt ctttgtccag     780
tcctacctga agaagcccaa gaagtccaag accaactaa                              819

<210> SEQ ID NO 120
<211> LENGTH: 272
<212> TYPE: PRT
<213> ORGANISM: Thraustochytrium aureum

<400> SEQUENCE: 120

Met Ala Asn Ser Ser Val Trp Asp Asp Val Val Gly Arg Val Glu Thr
1               5                   10                  15

Gly Val Asp Gln Trp Met Asp Gly Ala Lys Pro Tyr Ala Leu Thr Asp
            20                  25                  30

Gly Leu Pro Met Met Asp Val Ser Thr Met Leu Ala Phe Glu Val Gly
        35                  40                  45

Tyr Met Ala Met Leu Leu Phe Gly Ile Pro Ile Met Lys Gln Met Glu
    50                  55                  60

Lys Pro Phe Glu Leu Lys Thr Ile Lys Leu Leu His Asn Leu Phe Leu
65                  70                  75                  80

Phe Gly Leu Ser Leu Tyr Met Cys Val Glu Thr Ile Arg Gln Ala Ile
                85                  90                  95
```

```
Leu Gly Gly Tyr Lys Val Phe Gly Asn Asp Met Glu Lys Gly Asn Glu
            100                 105                 110

Ser His Ala Gln Gly Met Ser Arg Ile Val Tyr Val Phe Tyr Val Ser
            115                 120                 125

Lys Ala Tyr Glu Phe Leu Asp Thr Ala Ile Met Ile Leu Cys Lys Lys
            130                 135                 140

Phe Asn Gln Val Ser Phe Leu His Val Tyr His His Ala Thr Ile Phe
145                 150                 155                 160

Ala Ile Trp Trp Ala Ile Ala Lys Tyr Ala Pro Gly Gly Asp Ala Tyr
                165                 170                 175

Phe Ser Val Ile Leu Asn Ser Phe His Thr Val Met Tyr Ala Tyr
            180                 185                 190

Tyr Phe Phe Ser Ser Gln Gly Phe Gly Phe Val Lys Pro Ile Lys Pro
            195                 200                 205

Tyr Ile Thr Thr Leu Gln Met Thr Gln Phe Met Ala Met Leu Val Gln
            210                 215                 220

Ser Leu Tyr Asp Tyr Leu Phe Pro Cys Asp Tyr Pro Gln Ala Leu Val
225                 230                 235                 240

Gln Leu Leu Gly Val Tyr Met Ile Thr Leu Leu Ala Leu Phe Gly Asn
                245                 250                 255

Phe Phe Val Gln Ser Tyr Leu Lys Pro Lys Lys Ser Lys Thr Asn
            260                 265                 270

<210> SEQ ID NO 121
<211> LENGTH: 10945
<212> TYPE: DNA
<213> ORGANISM: Artificial Sequence
<220> FEATURE:
<223> OTHER INFORMATION: Plasmid pDMW232

<400> SEQUENCE: 121
aattcctgca gcccatcgat caggagagac cgggttggcg gcgtatttgt gtcccaaaaa     60
acagccccaa ttgccccaat tgaccccaaa ttgacccagt agcgggccca acccggcga    120
gagcccccctt caccccacat atcaaacctc ccccggttcc cacacttgcc gttaagggcg    180
tagggtactg cagtctggaa tctacgcttg ttcagacttt gtactagttt ctttgtctgg    240
ccatccgggt aacccatgcc ggacgcaaaa tagactactg aaaatttttt tgctttgtgg    300
ttgggacttt agccaagggt ataaaagacc accgtccccg aattaccttt cctcttcttt    360
tctctctctc cttgtcaact cacacccgaa atcgttaagc atttccttct gagtataaga    420
atcattcacc atgggaacgg accaaggaaa accttcacc tgggaagagc tggcggccca    480
taacaccaag gacgacctac tcttggccat ccgcggcagg gtgtacgatg tcacaaagtt    540
cttgagccgc catcctggtg gagtggacac tctcctgctc ggagctggcc gagatgttac    600
tccggtcttt gagatgtatc acgcgtttgg ggctgcagat gccattatga agaagtacta    660
tgtcggtaca ctggtctcga tgagctgcc catcttcccg gagccaacgg tgttccacaa    720
aaccatcaag acgagagtcg agggctactt tacggatcgg aacattgatc caagaatag    780
accagagatc tggggacgat acgctcttat ctttggatcc ttgatcgctt cctactacgc    840
gcagctcttt gtgcctttcg ttgtcgaacg cacatggctt caggtggtgt ttgcaatcat    900
catgggattt gcgtgcgcac aagtcggact caaccctctt catgatgcgt ctcactttcc    960
agtgacccac aaccccactg tctggaagat tctgggagcc acgcacgact ttttcaacgg   1020
agcatcgtac ctggtgtgga tgtaccaaca tatgctcggc catcacccct acaccaacat   1080
```

```
tgctggagca gatcccgacg tgtcgacgtc tgagcccgat gttcgtcgta tcaagcccaa    1140
ccaaaagtgg tttgtcaacc acatcaacca gcacatgttt gttcctttcc tgtacggact    1200
gctggcgttc aaggtgcgca ttcaggacat caacattttg tactttgtca agaccaatga    1260
cgctattcgt gtcaatccca tctcgacatg gcacactgtg atgttctggg gcggcaaggc    1320
tttctttgtc tggtatcgcc tgattgttcc cctgcagtat ctgccctgg gcaaggtgct    1380 gctcttgttc acggtcgcgg acatggtgtc gtcttactgg ctggcgctga ccttccaggc    1440
gaaccacgtt gttgaggaag ttcagtggcc gttgcctgac gagaacggga tcatccaaaa    1500
ggactgggca gctatgcagg tcgagactac gcaggattac gcacacgatt cgcacctctg    1560
gaccagcatc actggcagct tgaactacca ggctgtgcac catctgttcc ccaacgtgtc    1620
gcagcaccat tatcccgata ttctggccat catcaagaac acctgcagcg agtacaaggt    1680
tccataccct gtcaaggata cgttttggca agcatttgct tcacatttgg agcacttgcg    1740
tgttcttgga ctccgtccca aggaagagta ggcagctaag cggccgcatg agaagataaa    1800
tatataaata cattgagata ttaaatgcgc tagattagag agcctcatac tgctcggaga    1860
gaagccaaga cgagtactca aaggggatta ccaccatccat atccacagac acaagctggg    1920
gaaaggttct atatacactt tccggaatac cgtagtttcc gatgttatca atgggggcag    1980
ccaggatttc aggcacttcg gtgtctcggg gtgaaatggc gttcttggcc tccatcaagt    2040
cgtaccatgt cttcatttgc ctgtcaaagt aaaacagaag cagatgaaga atgaacttga    2100
agtgaaggaa tttaaattgc cccggagaag acggccaggc cgcctagatg acaaattcaa    2160
caactcacag ctgactttct gccattgcca ctagggggg gcctttttat atggccaagc    2220
caagctctcc acgtcggttg ggctgcaccc aacaataaat gggtagggtt gcaccaacaa    2280
agggatggga tgggggtag aagatacgag gataacgggg ctcaatggca caaataagaa    2340
cgaatactgc cattaagact cgtgatccag cgactgacac cattgcatca tctaagggcc    2400
tcaaaactac ctcggaactg ctgcgctgat ctggacacca cagaggttcc gagcacttta    2460
ggttgcacca aatgtcccac caggtgcagg cagaaaacgc tggaacagcg tgtacagttt    2520
gtcttaacaa aaagtgaggg cgctgaggtc gagcagggtg gtgtgacttg ttatagcctt    2580
tagagctgcg aaagcgcgta tggatttggc tcatcaggcc agattgaggg tctgtggaca    2640
catgtcatgt tagtgtactt caatcgcccc ctggatatag ccccgacaat aggccgtggc    2700 ctcattttt tgccttccgc acatttccat tgctcggtac ccacaccttg cttctcctgc    2760
acttgccaac cttaatactg gtttacattg accaacatct tacaagcggg gggcttgtct    2820
agggtatata taaacagtgg ctctcccaat cggttgccag tctctttttt cctttctttc    2880
cccacagatt cgaaatctaa actacacatc acacaatgcc tgttactgac gtccttaagc    2940
gaaagtccgg tgtcatcgtc ggcgacgatg tccgagccgt gagtatccac gacaagatca    3000
gtgtcgagac gacgcgtttt gtgtaatgac acaatccgaa agtcgctagc aacacacact    3060
ctctacacaa actaacccag ctctccatgg gaacggacca aggaaaaacc ttcacctggg    3120
aagagctggc ggcccataac accaaggacg acctactctt ggccatccgc ggcagggtgt    3180
acgatgtcac aaagttcttg agccgccatc ctggtggagt ggacactctc ctgctcggag    3240
ctggccgaga tgttactccg gtctttgaga tgtatcacgc gtttgggct gcagatgcca    3300 ttatgaagaa gtactatgtc ggtacactgg tctcgaatga gctgcccatc ttcccggagc    3360
caacggtgtt ccacaaaacc atcaagacga gagtcgaggg ctactttacg gatcggaaca    3420
ttgatcccaa gaatagacca gagatctggg gacgatacgc tcttatcttt ggatccttga    3480
```

```
tcgcttccta ctacgcgcag ctctttgtgc ctttcgttgt cgaacgcaca tggcttcagg    3540
tggtgtttgc aatcatcatg ggatttgcgt gcgcacaagt cggactcaac cctcttcatg    3600
atgcgtctca cttttcagtg acccacaacc ccactgtctg gaagattctg ggagccacgc    3660
acgacttttt caacggagca tcgtacctgg tgtggatgta ccaacatatg ctcggccatc    3720
acccctacac caacattgct ggagcagatc ccgacgtgtc gacgtctgag cccgatgttc    3780
gtcgtatcaa gcccaaccaa aagtggtttg tcaaccacat caaccagcac atgtttgttc    3840
ctttcctgta cggactgctg gcgttcaagg tgcgcattca ggacatcaac attttgtact    3900
ttgtcaagac caatgacgct attcgtgtca atcccatctc gacatggcac actgtgatgt    3960 tctgggcgg caaggctttc tttgtctggt atcgcctgat tgttccctg cagtatctgc    4020 ccctgggcaa ggtgctgctc ttgttcacgg tcgcggacat ggtgtcgtct tactggctgg    4080
cgctgacctt ccaggcgaac cacgttgttg aggaagttca gtggccgttg cctgacgaga    4140
acgggatcat ccaaaaggac tgggcagcta tgcaggtcga gactacgcag gattacgcac    4200
acgattcgca cctctggacc agcatcactg gcagcttgaa ctaccaggct gtgcaccatc    4260
tgttccccaa cgtgtcgcag caccattatc ccgatattct ggccatcatc aagaacacct    4320
gcagcgagta caaggttcca taccttgtca aggatacgtt ttggcaagca tttgcttcac    4380
atttggagca cttgcgtgtt cttggactcc gtcccaagga agagtaggca gctaagcggc    4440
cgcaagtgtg gatggggaag tgagtgcccg gttctgtgtg cacaattggc aatccaagat    4500
ggatggattc aacacaggga tatagcgagc tacgtggtgg tgcgaggata tagcaacgga    4560
tatttatgtt tgacacttga gaatgtacga tacaagcact gtccaagtac aatactaaac    4620
atactgtaca tactcatact cgtacccggg caacggtttc acttgagtgc agtggctagt    4680
gctcttactc gtacagtgtg caatactgcg tatcatagtc tttgatgtat atcgtattca    4740
ttcatgttag ttgcgtacgc caccattctg tctgccgcca tgatgctcaa gttctctctt    4800
aacatgaagc ccgccggtga cgctgttgag gctgccgtca aggagtccgt cgaggctggt    4860
atcactaccg ccgatatcgg aggctcttcc tccacctccg aggtcggaga cttgttgcca    4920
acaaggtcaa ggagctgctc aagaaggagt aagtcgtttc tacgacgcat tgatggaagg    4980
agcaaactga cgcgcctgcg ggttggtcta ccggcagggt ccgctagtgt ataagactct    5040
ataaaagggg ccctgccctg ctaatgaaat gatgatttat aatttaccgg tgtagcaacc    5100
ttgactagaa gaagcagatt gggtgtgttt gtagtggagg acagtggtac gttttggaaa    5160
cagtcttctt gaaagtgtct tgtctacagt atattcactc ataacctcaa tagccaaggg    5220
tgtagtcggt ttattaaagg aagggagttg tggctgatgt ggatagatat ctttaagctg    5280
gcgactgcac ccaacgagtg tggtggtagc ttgttactgt atattcggta agatatattt    5340
tgtgggtttt tagtggtgtt tggtaggtta gtgcttggta tatgagttgt aggcatgaca    5400
atttggaaag gggtggactt tgggaatatt gtgggatttc aataccttag tttgtacagg    5460
gtaattgtta caaatgatac aaagaactgt atttctttc atttgttta attggttgta    5520 tatcaagtcc gttagacgag ctcagtgggc gcgccagctg cattaatgaa tcggccaacg    5580
cgcggggaga ggcggtttgc gtattgggcg ctcttccgct tcctcgctca ctgactcgct    5640
gcgctcggtc gttcggctgc ggcgagcggt atcagctcac tcaaaggcgg taatacggtt    5700
atccacagaa tcaggggata acgcaggaaa gaacatgtga gcaaaaggcc agcaaaaggc    5760
caggaaccgt aaaaaggccg cgttgctggc gtttttccat aggctccgcc cccctgacga    5820
```

-continued

| | |
|---|---|
| gcatcacaaa aatcgacgct caagtcagag gtggcgaaac ccgacaggac tataaagata | 5880 |
| ccaggcgttt ccccctggaa gctccctcgt gcgctctcct gttccgaccc tgccgcttac | 5940 |
| cggatacctg tccgccttc tcccttcggg aagcgtggcg ctttctcata gctcacgctg | 6000 |
| taggtatctc agttcggtgt aggtcgttcg ctccaagctg ggctgtgtgc acgaaccccc | 6060 |
| cgttcagccc gaccgctgcg ccttatccgg taactatcgt cttgagtcca acccggtaag | 6120 |
| acacgactta tcgccactgg cagcagccac tggtaacagg attagcagag cgaggtatgt | 6180 |
| aggcggtgct acagagttct tgaagtggtg gcctaactac ggctacacta gaagaacagt | 6240 |
| atttggtatc tgcgctctgc tgaagccagt taccttcgga aaagagttg gtagctcttg | 6300 |
| atccggcaaa caaccaccg ctggtagcgg tggtttttt gtttgcaagc agcagattac | 6360 |
| gcgcagaaaa aaaggatctc aagaagatcc tttgatcttt tctacggggt ctgacgctca | 6420 |
| gtggaacgaa aactcacgtt aagggatttt ggtcatgaga ttatcaaaaa ggatcttcac | 6480 |
| ctagatcctt ttaaattaaa aatgaagttt taaatcaatc taaagtatat atgagtaaac | 6540 |
| ttggtctgac agttaccaat gcttaatcag tgaggcacct atctcagcga tctgtctatt | 6600 |
| tcgttcatcc atagttgcct gactccccgt cgtgtagata actacgatac gggagggctt | 6660 |
| accatctggc cccagtgctg caatgatacc gcgagaccca cgctcaccgg ctccagattt | 6720 |
| atcagcaata aaccagccag ccggaagggc cgagcgcaga agtggtcctg caactttatc | 6780 |
| cgcctccatc cagtctatta attgttgccg ggaagctaga gtaagtagtt cgccagttaa | 6840 |
| tagtttcgc aacgttgttg ccattgctac aggcatcgtg gtgtcacgct cgtcgtttgg | 6900 |
| tatggcttca ttcagctccg gttcccaacg atcaaggcga gttacatgat cccccatgtt | 6960 |
| gtgcaaaaaa gcggttagct ccttcggtcc tccgatcgtt gtcagaagta agttggccgc | 7020 |
| agtgttatca ctcatggtta tggcagcact gcataattct cttactgtca tgccatccgt | 7080 |
| aagatgcttt tctgtgactg gtgagtactc aaccaagtca ttctgagaat agtgtatgcg | 7140 |
| gcgaccgagt tgctcttgcc cggcgtcaat acgggataat accgcgccac atagcagaac | 7200 |
| tttaaaagtg ctcatcattg gaaaacgttc ttcggggcga aaactctcaa ggatcttacc | 7260 |
| gctgttgaga tccagttcga tgtaacccac tcgtgcaccc aactgatctt cagcatcttt | 7320 |
| tactttcacc agcgtttctg ggtgagcaaa aacaggaagg caaaatgccg caaaaaaggg | 7380 |
| aataagggcg acacggaaat gttgaatact catactcttc cttttcaat attattgaag | 7440 |
| catttatcag ggttattgtc tcatgagcgg atacatattt gaatgtattt agaaaaataa | 7500 |
| acaaataggg gttccgcgca catttccccg aaaagtgcca cctgatgcgg tgtgaaatac | 7560 |
| cgcacagatg cgtaaggaga aaataccgca tcaggaaatt gtaagcgtta atattttgtt | 7620 |
| aaaattcgcg ttaaattttt gttaaatcag ctcattttt aaccaatagg ccgaaatcgg | 7680 |
| caaaatccct tataaatcaa agaatagacc gagataggg ttgagtgttg ttccagtttg | 7740 |
| gaacaagagt ccactattaa agaacgtgga ctccaacgtc aaagggcgaa aaaccgtcta | 7800 |
| tcagggcgat ggcccactac gtgaaccatc accctaatca agttttttgg ggtcgaggtg | 7860 |
| ccgtaaagca ctaaatcgga acctaaagg gagcccccga tttagagctt gacggggaaa | 7920 |
| gccggcgaac gtggcgagaa aggaagggaa gaaagcgaaa ggagcgggcg ctagggcgct | 7980 |
| ggcaagtgta gcggtcacgc tgcgcgtaac caccacaccc gccgcgctta atgcgccgct | 8040 |
| acagggcgcg tccattcgcc attcaggctg cgcaactgtt gggaagggcg atcggtgcgg | 8100 |
| gcctcttcgc tattacgcca gctggcgaaa ggggatgtg ctgcaaggcg attaagttgg | 8160 |
| gtaacgccag ggttttccca gtcacgacgt tgtaaaacga cggccagtga attgtaatac | 8220 |

```
gactcactat agggcgaatt gggcccgacg tcgcatgcta tcggcatcga caaggtttgg    8280
gtccctagcc gataccgcac tacctgagtc acaatcttcg gaggtttagt cttccacata    8340
gcacgggcaa aagtgcgtat atatacaaga gcgtttgcca gccacagatt ttcactccac    8400
acaccacatc acacatacaa ccacacacat ccacaatgga acccgaaact aagaagacca    8460
agactgactc caagaagatt gttcttctcg gcggcgactt ctgtggcccc gaggtgattg    8520
ccgaggccgt caaggtgctc aagtctgttg ctgaggcctc cggcaccgag tttgtgtttg    8580
aggaccgact cattggagga gctgccattg agaaggaggg cgagcccatc accgacgcta    8640
ctctcgacat ctgccgaaag gctgactcta ttatgctcgg tgctgtcgga ggcgctgcca    8700
acaccgtatg gaccactccc gacggacgaa ccgacgtgcg acccgagcag ggtctcctca    8760
agctgcgaaa ggacctgaac ctgtacgcca acctgcgacc ctgccagctg ctgtcgccca    8820
agctcgccga tctctccccc atccgaaacg ttgagggcac cgacttcatc attgtccgag    8880
agctcgtcgg aggtatctac tttggagagc gaaaggagga tgacggatct ggcgtcgctt    8940
ccgacaccga gacctactcc gttaattaat ttgaatcgaa tcgatgagcc taaaatgaac    9000
ccgagtatat ctcataaaat tctcggtgag aggtctgtga ctgtcagtac aaggtgcctt    9060
cattatgccc tcaaccttac catacctcac tgaatgtagt gtacctctaa aaatgaaata    9120
cagtgccaaa agccaaggca ctgagctcgt ctaacggact tgatatacaa ccaattaaaa    9180
caaatgaaaa gaaatacagt tctttgtatc atttgtaaca attaccctgt acaaactaag    9240
gtattgaaat cccacaatat tcccaaagtc caccccttc caaattgtca tgcctacaac    9300
tcatatacca agcactaacc taccgtttaa acagtgtacg cagatctggt gtagtggtag    9360
tgcagtggtg gtattgtgac tggggatgta gttgagaata agtcatacac aagtcagctt    9420
tcttcgagcc tcatataagt ataagtagtt caacgtatta gcactgtacc cagcatctcc    9480
gtatcgagaa acacaacaac atgccccatt ggacagatca tgcggataca caggttgtgc    9540
agtatcatac atactcgatc agacaggtcg tctgaccatc atacaagctg aacaagcgct    9600
ccatacttgc acgctctcta tatacacagt taaattacat atccatagtc taacctctaa    9660
cagttaatct tctggtaagc ctcccagcca gccttctggt atcgcttggc ctcctcaata    9720
ggatctcggt tctggccgta cagacctcgg ccgacaatta tgatatccgt tccggtagac    9780
atgacatcct caacagttcg gtactgctgt ccgagagcgt ctcccttgtc gtcaagaccc    9840
accccggggg tcagaataag ccagtcctca gagtcgccct taggtcggtt ctgggcaatg    9900
aagccaacca caaactcggg gtcggatcgg gcaagctcaa tggtctgctt ggagtactcg    9960
ccagtggcca gagagccctt gcaagacagc tcggccagca tgagcagacc tctggccagc   10020
ttctcgttgg gagagggggac taggaactcc ttgtactggg agttctcgta gtcagagacg   10080
tcctccttct tctgttcaga dacagtttcc tcggcaccag ctcgcaggcc agcaatgatt   10140
ccggttccgg gtacaccgtg ggcgttggtg atatcggacc actcggcgat tcggtgacac   10200
cggtactggt gcttgacagt gttgccaata tctgcgaact ttctgtcctc gaacaggaag   10260
aaaccgtgct taagagcaag ttccttgagg gggagcacag tgccggcgta ggtgaagtcg   10320
tcaatgatgt cgatatgggt tttgatcatg cacacataag gtccgaccc atcggcaagc   10380 tcaatgagct ccttggtggt ggtaacatcc agagaagcac acaggttggt tttcttggct   10440
gccacgagct tgagcactcg agcggcaaag gcggacttgt ggacgttagc tcgagcttcg   10500
taggagggca ttttggtggt gaagaggaga ctgaaataaa tttagtctgc agaacttttt   10560
```

-continued

```
atcggaacct tatctggggc agtgaagtat atgttatggt aatagttacg agttagttga    10620
acttatagat agactggact atacggctat cggtccaaat tagaaagaac gtcaatggct    10680
ctctgggcgt cgcctttgcc gacaaaaatg tgatcatgat gaaagccagc aatgacgttg    10740
cagctgatat tgttgtcggc caaccgcgcc gaaaacgcag ctgtcagacc cacagcctcc    10800
aacgaagaat gtatcgtcaa agtgatccaa gcacactcat agttggagtc gtactccaaa    10860
ggcggcaatg acgagtcaga cagatactcg tcgacctttt ccttgggaac caccaccgtc    10920
agcccttctg actcacgtat tgtag                                          10945
```

<210> SEQ ID NO 122
<211> LENGTH: 1341
<212> TYPE: DNA
<213> ORGANISM: Mortierella alpina
<220> FEATURE:
<221> NAME/KEY: misc_feature
<223> OTHER INFORMATION: delta-5 desaturase
<300> PUBLICATION INFORMATION:
<308> DATABASE ACCESSION NUMBER: GenBank Accession No. AF067654
<309> DATABASE ENTRY DATE: 1998-11-11
<313> RELEVANT RESIDUES: (1)..(1341)

<400> SEQUENCE: 122

```
atgggaacgg accaaggaaa aaccttcacc tgggaagagc tggcggccca taacaccaag      60
gacgacctac tcttggccat ccgcggcagg gtgtacgatg tcacaaagtt cttgagccgc     120
catcctggtg gagtggacac tctcctgctc ggagctggcc gagatgttac tccggtcttt     180
gagatgtatc acgcgtttgg ggctgcagat gccattatga agaagtacta tgtcggtaca     240
ctggtctcga atgagctgcc catcttcccg gagccaacgg tgttccacaa aaccatcaag     300
acgagagtcg agggctactt tacggatcgg aacattgatc ccaagaatag accagagatc     360
tggggacgat acgctcttat ctttggatcc ttgatcgctt cctactacgc gcagctcttt     420 gtgccttttcg ttgtcgaacg cacatggctt caggtggtgt ttgcaatcat catgggattt     480
gcgtgcgcac aagtcggact caaccctctt catgatgcgt ctcactttttc agtgacccac     540 aaccccactg tctggaagat tctgggagcc acgcacgact ttttcaacgg agcatcgtac     600
ctggtgtgga tgtaccaaca tatgctcggc catcaccect acaccaacat tgctggagca     660
gatcccgacg tgtcgacgtc tgagcccgat gttcgtcgta tcaagcccaa ccaaaagtgg     720
tttgtcaacc acatcaacca gcacatgttt gttccttttcc tgtacggact gctggcgttc     780
aaggtgcgca ttcaggacat caacatttttg tactttgtca agaccaatga cgctattcgt     840
gtcaatccca tctcgacatg gcacactgtg atgttctggg gcggcaaggc tttctttgtc     900
tggtatcgcc tgattgttcc cctgcagtat ctgccccctgg gcaaggtgct gctcttgttc     960
acggtcgcgg acatggtgtc gtcttactgg ctggcgctga ccttccaggc gaaccacgtt    1020
gttgaggaag ttcagtggcc gttgcctgac gagaacggga tcatccaaaa ggactgggca    1080
gctatgcagg tcgagactac gcaggattac gcacacgatt cgcacctctg gaccagcatc    1140
actggcagct tgaactacca ggctgtgcac catctgttcc ccaacgtgtc gcagcaccat    1200
tatcccgata ttctggccat catcaagaac acctgcagcg agtacaaggt tccataccct    1260
gtcaaggata cgttttggca agcatttgct tcacatttgg agcacttgcg tgttcttgga    1320
ctccgtccca aggaagagta g                                              1341
```

<210> SEQ ID NO 123
<211> LENGTH: 446
<212> TYPE: PRT

<213> ORGANISM: Mortierella alpina
<300> PUBLICATION INFORMATION:
<308> DATABASE ACCESSION NUMBER: GenBank Accession No. AF067654
<309> DATABASE ENTRY DATE: 1998-11-11
<313> RELEVANT RESIDUES: (1)..(446)

<400> SEQUENCE: 123

```
Met Gly Thr Asp Gln Gly Lys Thr Phe Thr Trp Glu Leu Ala Ala
1               5                   10                  15

His Asn Thr Lys Asp Asp Leu Leu Ala Ile Arg Gly Arg Val Tyr
                20                  25                  30

Asp Val Thr Lys Phe Leu Ser Arg His Pro Gly Gly Val Asp Thr Leu
                35                  40                  45

Leu Leu Gly Ala Gly Arg Asp Val Thr Pro Val Phe Glu Met Tyr His
    50                  55                  60

Ala Phe Gly Ala Ala Asp Ala Ile Met Lys Lys Tyr Tyr Val Gly Thr
65                  70                  75                  80

Leu Val Ser Asn Glu Leu Pro Ile Phe Pro Glu Pro Thr Val Phe His
                85                  90                  95

Lys Thr Ile Lys Thr Arg Val Glu Gly Tyr Phe Thr Asp Arg Asn Ile
                100                 105                 110

Asp Pro Lys Asn Arg Pro Glu Ile Trp Gly Arg Tyr Ala Leu Ile Phe
            115                 120                 125

Gly Ser Leu Ile Ala Ser Tyr Tyr Ala Gln Leu Phe Val Pro Phe Val
    130                 135                 140

Val Glu Arg Thr Trp Leu Gln Val Val Phe Ala Ile Ile Met Gly Phe
145                 150                 155                 160

Ala Cys Ala Gln Val Gly Leu Asn Pro Leu His Asp Ala Ser His Phe
                165                 170                 175

Ser Val Thr His Asn Pro Thr Val Trp Lys Ile Leu Gly Ala Thr His
                180                 185                 190

Asp Phe Phe Asn Gly Ala Ser Tyr Leu Val Trp Met Tyr Gln His Met
            195                 200                 205

Leu Gly His His Pro Tyr Thr Asn Ile Ala Gly Ala Asp Pro Asp Val
    210                 215                 220

Ser Thr Ser Glu Pro Asp Val Arg Arg Ile Lys Pro Asn Gln Lys Trp
225                 230                 235                 240

Phe Val Asn His Ile Asn Gln His Met Phe Val Pro Phe Leu Tyr Gly
                245                 250                 255

Leu Leu Ala Phe Lys Val Arg Ile Gln Asp Ile Asn Ile Leu Tyr Phe
                260                 265                 270

Val Lys Thr Asn Asp Ala Ile Arg Val Asn Pro Ile Ser Thr Trp His
                275                 280                 285

Thr Val Met Phe Trp Gly Gly Lys Ala Phe Phe Val Trp Tyr Arg Leu
    290                 295                 300

Ile Val Pro Leu Gln Tyr Leu Pro Leu Gly Lys Val Leu Leu Leu Phe
305                 310                 315                 320

Thr Val Ala Asp Met Val Ser Ser Tyr Trp Leu Ala Leu Thr Phe Gln
                325                 330                 335

Ala Asn His Val Val Glu Glu Val Gln Trp Pro Leu Pro Asp Glu Asn
                340                 345                 350

Gly Ile Ile Gln Lys Asp Trp Ala Ala Met Gln Val Glu Thr Thr Gln
            355                 360                 365

Asp Tyr Ala His Asp Ser His Leu Trp Thr Ser Ile Thr Gly Ser Leu
370                 375                 380
```

```
Asn Tyr Gln Ala Val His His Leu Phe Pro Asn Val Ser Gln His His
385                 390                 395                 400

Tyr Pro Asp Ile Leu Ala Ile Ile Lys Asn Thr Cys Ser Glu Tyr Lys
            405                 410                 415

Val Pro Tyr Leu Val Lys Asp Thr Phe Trp Gln Ala Phe Ala Ser His
            420                 425                 430

Leu Glu His Leu Arg Val Leu Gly Leu Arg Pro Lys Glu Glu
        435                 440                 445

<210> SEQ ID NO 124
<211> LENGTH: 12690
<212> TYPE: DNA
<213> ORGANISM: Artificial Sequence
<220> FEATURE:
<223> OTHER INFORMATION: Plasmid pZP3L37

<400> SEQUENCE: 124
aaataccagt tggccacaaa cccttgacga tctcgtatgt cccctccgac atactcccgg      60
ccggctgggg tacgttcgat agcgctatcg gcatcgacaa ggtttgggtc cctagccgat    120
accgcactac ctgagtcaca atcttcggag gtttagtctt ccacatagca cgggcaaaag    180
tgcgtatata tacaagagcg tttgccagcc acagattttc actccacaca ccacatcaca    240
catacaacca cacacatcca caatggaacc cgaaactaag aagaccaaga ctgactccaa    300
gaagattgtt cttctcggcg gcgacttctg tggccccgag gtgattgccg aggccgtcaa    360
ggtgctcaag tctgttgctg aggcctccgg caccgagttt gtgtttgagg accgactcat    420
tggaggagct gccattgaga aggagggcga gcccatcacc gacgctactc tcgacatctg    480
ccgaaaggct gactctatta tgctcggtgc tgtcggaggc gctgccaaca ccgtatggac    540
cactcccgac ggacgaaccg acgtgcgacc cgagcagggt ctcctcaagc tgcgaaagga    600
cctgaacctg tacgccaacc tgcgaccctg ccagctgctg tcgcccaagc tcgccgatct    660
ctcccccatc cgaaacgttg agggcaccga cttcatcatt gtccgagagc tcgtcggagg    720
tatctacttt ggagagcgaa aggaggatga cggatctggc gtcgcttccg acaccgagac    780
ctactccgtt cctgaggttg agcgaattgc ccgaatggcc gccttcctgg cccttcagca    840
caaccccccct cttcccgtgt ggtctcttga caaggccaac gtgctggcct cctctcgact    900
ttggcgaaag actgtcactc gagtcctcaa ggacgaattc ccccagctcg agctcaacca    960
ccagctgatc gactcggccg ccatgatcct catcaagcag ccctccaaga tgaatggtat   1020
catcatcacc accaacatgt tggcgatat catctccgac gaggcctccg tcatccccgg   1080
ttctctgggt ctgctgccct ccgcctctct ggcttctctg cccgacacca acgaggcgtt   1140
cggtctgtac gagccctgtc acggatctgc ccccgatctc ggcaagcaga aggtcaaccc   1200
cattgccacc attctgtctg ccgccatgat gctcaagttc tctcttaaca tgaagcccgc   1260
cggtgacgct gttgaggctg ccgtcaagga gtccgtcgag gctggtatca ctaccgccga   1320
tatcggaggc tcttcctcca cctccgaggt cggagacttg ttgccaacaa ggtcaaggag   1380
ctgctcaaga aggagtaagt cgtttctacg acgcattgat ggaaggagca aactgacgcg   1440
cctgcgggtt ggtctaccgg cagggtccgc tagtgtataa gactctataa aagggccct    1500
gccctgctaa tgaaatgatg atttataatt taccggtgta gcaaccttga ctagaagaag   1560
cagattgggt gtgtttgtag tggaggacag tggtacgttt tggaaacagt cttcttgaaa   1620
gtgtcttgtc tacagtatat tcactcataa cctcaatagc caagggtgta gtcggtttat   1680
```

-continued

```
taaaggaagg gagttgtggc tgatgtggat agatatcttt aagctggcga ctgcacccaa    1740
cgagtgtggt ggtagcttgt tagatctgta tattcggtaa gatatatttt gtggggtttt    1800
agtggtgttt aaacagtgta cgcagtacta tagaggaaca attgccccgg agaagacggc    1860
caggccgcct agatgacaaa ttcaacaact cacagctgac tttctgccat tgccactagg    1920 gggggggcctt tttatatggc caagccaagc tctccacgtc ggttgggctg cacccaacaa    1980
taaatgggta gggttgcacc aacaaaggga tgggatgggg ggtagaagat acgaggataa    2040
cggggctcaa tggcacaaat aagaacgaat actgccatta agactcgtga tccagcgact    2100
gacaccattg catcatctaa gggcctcaaa actacctcgg aactgctgcg ctgatctgga    2160
caccacagag gttccgagca ctttaggttg caccaaatgt cccaccaggt gcaggcagaa    2220
aacgctggaa cagcgtgtac agtttgtctt aacaaaaagt gagggcgctg aggtcgagca    2280
gggtggtgtg acttgttata gcctttagag ctgcgaaagc gcgtatggat ttggctcatc    2340
aggccagatt gagggtctgt ggacacatgt catgttagtg tacttcaatc gcccctgga    2400 tatagccccg acaataggcc gtggcctcat ttttttgcct tccgcacatt tccattgctc    2460
ggtacccaca ccttgcttct cctgcacttg ccaaccttaa tactggttta cattgaccaa    2520
catcttacaa gcggggggct tgtctagggt atatataaac agtggctctc ccaatcggtt    2580
gccagtctct ttttttcctt cttttcccac agattcgaaa tctaaactac acatcacaca    2640
atgcctgtta ctgacgtcct taagcgaaag tccggtgtca tcgtcggcga cgatgtccga    2700
gccgtgagta tccacgacaa gatcagtgtc gagacgacgc gttttgtgta atgacacaat    2760
ccgaaagtcg ctagcaacac acactctcta cacaaactaa cccagctctc catggctgag    2820
gataagacca aggtcgagtt ccctaccctg actgagctga agcactctat ccctaacgct    2880
tgctttgagt ccaacctcgg actctcgctc tactacactg cccgagcgat cttcaacgca    2940
tctgcctctg ctgctctgct ctacgctgcc cgatctactc ccttcattgc cgataacgtt    3000
ctgctccacg ctctggtttg cgccacctac atctacgtgc agggtgtcat cttctggggt    3060
ttctttaccg tcggtcacga ctgtggtcac tctgccttct cccgatacca ctccgtcaac    3120
ttcatcattg gctgcatcat gcactctgcc attctgactc ccttcgagtc ctggcgagtg    3180
acccaccgac accatcacaa gaacactggc aacattgata aggacgagat cttctaccct    3240
catcggtccg tcaaggacct ccaggacgtg cgacaatggg tctacaccct cggaggtgct    3300
tggtttgtct acctgaaggt cggatatgct cctcgaacca tgtcccactt tgacccctgg    3360
gaccctctcc tgcttcgacg agcctccgct gtcatcgtgt ccctcggagt ctgggctgcc    3420
ttcttcgctg cctacgccta cctcacatac tcgctcggct ttgccgtcat gggcctctac    3480
tactatgctc ctctctttgt cttttgcttcg ttcctcgtca ttactacctt cttgcatcac    3540
aacgacgaag ctactccctg gtacggtgac tcggagtgga cctacgtcaa gggcaacctg    3600
agctccgtcg accgatcgta cggagctttc gtggacaacc tgtctcacca cattggcacc    3660
caccaggtcc atcacttgtt ccctatcatt ccccactaca agctcaacga agccaccaag    3720
cactttgctg ccgcttaccc tcacctcgtg agacgtaacg acgagcccat cattactgcc    3780
ttcttcaaga ccgctcacct ctttgtcaac tacggagctg tgcccgagac tgctcagatt    3840
ttcaccctca aagagtctgc cgctgcagcc aaggccaaga gcgactaagc ggccgctatt    3900
tatcactctt tacaacttct acctcaacta tctactttaa taaatgaata tcgtttattc    3960
tctatgatta ctgtatatgc gttcctctaa gacaaatcga aaccagcatg tgatcgaatg    4020
gcatacaaaa gtttcttccg aagttgatca atgtcctgat agtcaggcag cttgagaaga    4080
```

```
ttgacacagg tggaggccgt agggaaccga tcaacctgtc taccagcgtt acgaatggca    4140
aatgacgggt tcaaagcctt gaatccttgc aatggtgcct tggatactga tgtcacaaac    4200
ttaagaagca gccgcttgtc ctcttcctcg atcgatcagg agagaccggg ttggcggcgt    4260
atttgtgtcc caaaaaacag ccccaattgc cccaattgac cccaaattga cccagtagcg    4320
ggcccaaccc cggcgagagc ccccttcacc ccacatatca aacctccccc ggttcccaca    4380
cttgccgtta agggcgtagg gtactgcagt ctggaatcta cgcttgttca gactttgtac    4440
tagtttcttt gtctggccat ccgggtaacc catgccggac gcaaaataga ctactgaaaa    4500
ttttttttgct ttgtggttgg actttagcc aagggtataa aagaccaccg tccccgaatt    4560
acctttcctc ttcttttctc tctctccttg tcaactcaca cccgaaatcg ttaagcattt    4620
ccttctgagt ataagaatca ttcaccatgg ctgaggataa gaccaaggtc gagttcccta    4680
ccctgactga gctgaagcac tctatcccta acgcttgctt tgagtccaac ctcggactct    4740
cgctctacta cactgcccga gcgatcttca acgcatctgc ctctgctgct ctgctctacg    4800
ctgcccgatc tactcccttc attgccgata acgttctgct ccacgctctg gtttgcgcca    4860
cctacatcta cgtgcagggt gtcatcttct ggggtttctt taccgtcggt cacgactgtg    4920
gtcactctgc cttctcccga taccactccg tcaacttcat cattggctgc atcatgcact    4980
ctgccattct gactcccttc gagtcctggc gagtgaccca ccgacaccat cacaagaaca    5040
ctggcaacat tgataaggac gagatcttct accctcatcg gtccgtcaag gacctccagg    5100
acgtgcgaca atgggtctac accctcggag gtgcttggtt tgtctacctg aaggtcggat    5160
atgctcctcg aaccatgtcc cactttgacc cctgggaccc tctcctgctt cgacgagcct    5220
ccgctgtcat cgtgtccctc ggagtctggg ctgccttctt cgctgcctac gcctacctca    5280
catactcgct cggctttgcc gtcatgggcc tctactacta tgctcctctc tttgtctttg    5340
cttcgttcct cgtcattact accttcttgc atcacaacga cgaagctact ccctggtacg    5400
gtgactcgga gtggaccctac gtcaagggca acctgagctc cgtcgaccga tcgtacggag    5460
cttttcgtgga caacctgtct caccacattg gcacccacca ggtccatcac ttgttcccta    5520
tcattcccca ctacaagctc aacgaagcca ccaagcactt tgctgccgct taccctcacc    5580
tcgtgagacg taacgacgag cccatcatta ctgccttctt caagaccgct cacctctttg    5640
tcaactacgg agctgtgccc gagactgctc agattttcac cctcaaagag tctgccgctg    5700
cagccaaggc caagagcgac taagcggccg caagtgtgga tggggaagtg agtgcccggt    5760
tctgtgtgca caattggcaa tccaagatgg atggattcaa cacagggata tagcgagcta    5820
cgtggtggtg cgaggatata gcaacggata tttatgtttg acacttgaga atgtacgata    5880
caagcactgt ccaagtacaa tactaaacat actgtacata ctcatactcg tacccgggca    5940
acggtttcac ttgagtgcag tggctagtgc tcttactcgt acagtgtgca atactgcgta    6000
tcatagtctt tgatgtatat cgtattcatt catgttagtt gcgtacggtg tgtatcgtag    6060
aggtagtgac gtgttgtcca cagggcgact gtgtccgtgt atatatatat tcctcggccc    6120
gagcttattt gtgtggggtt gaggaaatca aaccaaatcg gtagtcagag aaataaaaca    6180
aaagaaata aaagaaata gaggacgcac aacgccatca ccgtcggaga gacaggagaa    6240
gggaaaatgg gcaaaaatgc ccttatcaca cccgcccgct tgtgctctc attcggctcc    6300
cacaagagcc tcttgtcctg gttccccccc cccacatttt aacacccac acgacgttgc    6360
tgcacgtgga atttcggcc gaaaacctgt ggggtactta cttttggcac tggagagaag    6420
```

```
catctgggat tttgggaacc taggcagaag atgaggaaaa aaataagagg aaccgttgtg   6480
agcttgctta tcagtgtcat atactccccc ctccttgcgt ttttgcgtct ttccccccta   6540
tttttcaaat tttgcgattt tttttctctt tttttccgct tttttccgct tttttttttgg  6600 ccggctttta tccatttctc caagccgagg atcacatcta tgcagcccag tccgttggag   6660
catatctgcg gtagagtttc ggaacggcgt taagcactgt gtccgggtcg gtctggaacg   6720
agattgagcg ggaaattcgg gggaataaga ccaccgttgg actccccgca atgaggagat   6780
caagatgtgc ttttcagaat tctgattggt ggcgcgccag ctgcattaat gaatcggcca   6840
acgcgcgggg agaggcggtt tgcgtattgg gcgctcttcc gcttcctcgc tcactgactc   6900
gctgcgctcg gtcgttcggc tgcggcgagc ggtatcagct cactcaaagg cggtaatacg   6960
gttatccaca gaatcagggg ataacgcagg aaagaacatg tgagcaaaag gccagcaaaa   7020
ggccaggaac cgtaaaaagg ccgcgttgct ggcgtttttc cataggctcc gcccccctga   7080
cgagcatcac aaaaatcgac gctcaagtca gaggtggcga acccgacag gactataaag    7140 ataccaggcg tttccccctg gaagctccct cgtgcgctct cctgttccga ccctgccgct   7200
taccggatac ctgtccgcct ttctcccttc gggaagcgtg gcgctttctc atagctcacg   7260
ctgtaggtat ctcagttcgg tgtaggtcgt tcgctccaag ctgggctgtg tgcacgaacc   7320
ccccgttcag cccgaccgct gcgccttatc cggtaactat cgtcttgagt ccaacccggt   7380
aagacacgac ttatcgccac tggcagcagc cactggtaac aggattagca gagcgaggta   7440
tgtaggcggt gctacagagt tcttgaagtg gtggcctaac tacggctaca ctagaagaac   7500
agtatttggt atctgcgctc tgctgaagcc agttaccttc ggaaaaagag ttggtagctc   7560
ttgatccggc aaacaaacca ccgctggtag cggtggtttt tttgtttgca agcagcagat   7620
tacgcgcaga aaaaaggat ctcaagaaga tcctttgatc ttttctacgg ggtctgacgc    7680
tcagtggaac gaaaactcac gttaagggat tttggtcatg agattatcaa aaaggatctt   7740
cacctagatc cttttaaatt aaaaatgaag ttttaaatca atctaaagta tatatgagta   7800
aacttggtct gacagttacc aatgcttaat cagtgaggca cctatctcag cgatctgtct   7860
atttcgttca tccatagttg cctgactccc cgtcgtgtag ataactacga tacgggaggg   7920
cttaccatct ggccccagtg ctgcaatgat accgcgagac ccacgctcac cggctccaga   7980
tttatcagca ataaaccagc cagccggaag ggccgagcgc agaagtggtc ctgcaacttt   8040
atccgcctcc atccagtcta ttaattgttg ccgggaagct agagtaagta gttcgccagt   8100
taatagtttg cgcaacgttg ttgccattgc tacaggcatc gtggtgtcac gctcgtcgtt   8160
tggtatggct tcattcagct ccggttccca acgatcaagg cgagttacat gatcccccat   8220
gttgtgcaaa aaagcggtta gctccttcgg tcctccgatc gttgtcagaa gtaagttggc   8280
cgcagtgtta tcactcatgg ttatggcagc actgcataat tctcttactg tcatgccatc   8340
cgtaagatgc ttttctgtga ctggtgagta ctcaaccaag tcattctgag aatagtgtat   8400
gcggcgaccg agttgctctt gcccggcgtc aatacgggat aataccgcgc cacatagcag   8460
aactttaaaa gtgctcatca ttggaaaacg ttcttcgggg cgaaaactct caaggatctt   8520
accgctgttg agatccagtt cgatgtaacc cactcgtgca cccaactgat cttcagcatc   8580
ttttactttc accagcgttt ctgggtgagc aaaaacagga aggcaaaatg ccgcaaaaaa   8640
gggaataagg gcgacacgga aatgttgaat actcatactc ttcctttttc aatattattg   8700
aagcatttat cagggttatt gtctcatgag cggatacata tttgaatgta tttagaaaaa   8760
taaacaaata ggggttccgc gcacatttcc ccgaaaagtg ccacctgatg cggtgtgaaa   8820
```

-continued

```
taccgcacag atgcgtaagg agaaaatacc gcatcaggaa attgtaagcg ttaatatttt    8880
gttaaaattc gcgttaaatt tttgttaaat cagctcattt tttaaccaat aggccgaaat    8940
cggcaaaatc ccttataaat caaaagaata gaccgagata gggttgagtg ttgttccagt    9000
ttggaacaag agtccactat taaagaacgt ggactccaac gtcaaagggc gaaaaaccgt    9060
ctatcagggc gatggcccac tacgtgaacc atcaccctaa tcaagttttt tggggtcgag    9120
gtgccgtaaa gcactaaatc ggaaccctaa agggagcccc cgatttagag cttgacgggg    9180
aaagccggcg aacgtggcga gaaggaagg gaagaaagcg aaaggagcgg gcgctagggc    9240
gctggcaagt gtagcggtca cgctgcgcgt aaccaccaca cccgccgcgc ttaatgcgcc    9300
gctacagggc gcgtccattc gccattcagg ctgcgcaact gttgggaagg gcgatcggtg    9360
cgggcctctt cgctattacg ccagctggcg aaaggggat gtgctgcaag gcgattaagt    9420
tgggtaacgc cagggttttc ccagtcacga cgttgtaaaa cgacggccag tgaattgtaa    9480
tacgactcac tatagggcga attgggcccg acgtcgcatg cgtcgagata tcgacattgt    9540
tccatctcca gtttaacccc aacttatcga gagtatttgt gagacacgca ataaatgaat    9600
ttataccaat caaatccata ttctacgctg tctacatata gatacttttt gtcatctctt    9660
gccctactat ttcgtcgata tatgaaggat acgccaaccg aacccatact ccacgctaca    9720
cacgcgcctt ttcacgcatt tctggggaaa atagacaccc ttggtgtcac ctgaagaata    9780
tgaaagaaga tattcattgt attgagctgt agatctgtgt atttcttgac ctcatcaatg    9840
acttctgggc tctttacctc gaatcatggt ggtactgtac cacatctcaa caccttgtag    9900
cacacctatg ggaaaattga gactatgaat ggattcccgt gcccgtatta ctctactaat    9960
ttgatcttgg aacgcgaaaa tacgtttcta ggactccaaa gaatctcaac tcttgtcctt    10020
actaaatata ctaccccatag ttgatggttt acttgaacag agaggacatg ttcacttgac    10080
ccaaagtttc tcgcatctct tggatatttg aacaacggcg tccactgacc gtcagttatc    10140
cagtcacaaa accccacat tcatacattc ccatgtacgt ttacaaagtt ctcaattcca    10200
tcgtgcaaat caaaatcaca tctattcatt catcatatat aaacccatca tgtctactaa    10260
cactcacaac tccatagaaa acatcgactc agaacacacg ctccatctat tcctcgtcca    10320
gctcgcaaat gtcgtcatct taattaaaag gcgttgaaac agaatgagcc agacagcaag    10380
gacaaggtgg ccaacagcaa ggagtccaaa aagccctcta ttgacgagat ccacgatgtt    10440
attgctcatg aggtttccga gctcgatgct gggaagaaga agtgatttgt atataagaaa    10500
taaatgagat atagtaaagg agtgcaagag aatggcaagg tggtcaaatt ctatattact    10560
tgcagtcact ggttcctcgt tgacatgaat gaagttaccg ttggcatagc tgatttaata    10620
tataactgtc caactaactc tcacctagat ataacccatg tgtgtgtttc caatcatcaa    10680
tgcggccgct tagtcgctct tggccttggc tgcagcggca gactcttgta gggtgaaaat    10740
ctgagcagtc tcgggcacag ctccgtagtt gacaaagagg tgagcggtct tgaagaaggc    10800
agtaatgatg ggctcgtcgt tacgtctcac gaggtgaggg taagcggcag caaagtgctt    10860
ggtggcttcg ttgagcttgt agtggggaat gatagggaac aagtgatgga cctggtgggt    10920
gccaatgtgg tgagacaggt tgtccacgaa agctccgtac gatcggtcga cggagctcag    10980
gttgcccttg acgtaggtcc actccgagtc accgtaccag ggagtagctt cgtcgttgtg    11040
atgcaagaag gtagtaatga cgaggaacga agcaaagaca aagagaggag catagtagta    11100
gaggcccatg acggcaaagc cgagcgagta tgtgaggtag gcgtaggcag cgaagaaggc    11160
```

-continued

| | | | | |
|---|---|---|---|---|
| agcccagact | ccgagggaca | cgatgacagc | ggaggctcgt | cgaagcagga gagggtccca | 11220 |
| ggggtcaaag | tgggacatgg | ttcgaggagc | atatccgacc | ttcaggtaga caaaccaagc | 11280 |
| acctccgagg | gtgtagaccc | attgtcgcac | gtcctggagg | tccttgacgg accgatgagg | 11340 |
| gtagaagatc | tcgtccttat | caatgttgcc | agtgttcttg | tgatggtgtc ggtgggtcac | 11400 |
| tcgccaggac | tcgaagggag | tcagaatggc | agagtgcatg | atgcagccaa tgatgaagtt | 11460 |
| gacggagtgg | tatcgggaga | aggcagagtg | accacagtcg | tgaccgacgg taaagaaacc | 11520 |
| ccagaagatg | acaccctgca | cgtagatgta | ggtggcgcaa | accagagcgt ggagcagaac | 11580 |
| gttatcggca | atgaagggag | tagatcgggc | agcgtagagc | agagcagcag aggcagatgc | 11640 |
| gttgaagatc | gctcgggcag | tgtagtagag | cgagagtccg | aggttggact caaagcaagc | 11700 |
| gttagggata | gagtgcttca | gctcagtcag | ggtagggaac | tcgaccttgg tcttatcctc | 11760 |
| agccatggta | ccagagctgg | gttagtttgt | gtagagagtg | tgtgttgcta gcgactttcg | 11820 |
| gattgtgtca | ttacacaaaa | cgcgtcgtct | cgacactgat | cttgtcgtgg atactcacgg | 11880 |
| ctcggaattc | tgtgatgtgt | agtttagatt | tcgaatctgt | ggggaaagaa aggaaaaaag | 11940 |
| agactggcaa | ccgattggga | gagccactgt | ttatatatac | cctagacaag ccccccgctt | 12000 |
| gtaagatgtt | ggtcaatgta | aaccagtatt | aaggttggca | agtgcaggag aagcaaggtg | 12060 |
| tgggtaccga | gcaatggaaa | tgtgcggaag | gcaaaaaaat | gaggccacgg cctattgtcg | 12120 |
| gggctatatc | caggggggcga | ttgaagtaca | ctaacatgac | atgtgtccac agaccctcaa | 12180 |
| tctggcctga | tgagccaaat | ccatacgcgc | tttcgcagct | ctaaaggcta taacaagtca | 12240 |
| caccaccctg | ctcgacctca | gcgccctcac | tttttgttaa | gacaaactgt acacgctgtt | 12300 |
| ccagcgtttt | ctgcctgcac | ctggtgggac | atttggtgca | acctaaagtg ctcggaacct | 12360 |
| ctgtggtgtc | cagatcagcg | cagcagttcc | gaggtagttt | tgaggcccct agatgatgca | 12420 |
| atggtgtcag | tcgctggatc | acgagtctta | atggcagtat | tcgttcttat ttgtgccatt | 12480 |
| gagccccgtt | atcctcgtat | cttctacccc | ccatcccatc | cctttgttgg tgcaaccct | 12540 |
| cccatttatt | gttgggtgca | gcccaaccga | cgtgggagagc | ttggcttggc catataaaaa | 12600 |
| ggcccccccc | tagtggcaat | ggcagaaagt | cagctgtgag | ttgttgaatt tgtcatctag | 12660 |
| gcggcctggc | cgtcttctcc | ggggcaattt | | | 12690 |

<210> SEQ ID NO 125
<211> LENGTH: 1077
<212> TYPE: DNA
<213> ORGANISM: Saprolegnia diclina
<220> FEATURE:
<221> NAME/KEY: misc_feature
<223> OTHER INFORMATION: synthetic delta-17 desaturase (codon-optimized)

<400> SEQUENCE: 125

| | | | | |
|---|---|---|---|---|
| atggctgagg | ataagaccaa | ggtcgagttc | cctaccctga | ctgagctgaa gcactctatc | 60 |
| cctaacgctt | gctttgagtc | caacctcgga | ctctcgctct | actacactgc ccgagcgatc | 120 |
| ttcaacgcat | ctgcctctgc | tgctctgctc | tacgctgccc | gatctactcc cttcattgcc | 180 |
| gataacgttc | tgctccacgc | tctggtttgc | gccacctaca | tctacgtgca gggtgtcatc | 240 |
| ttctggggtt | tctttaccgt | cggtcacgac | tgtggtcact | ctgccttctc ccgataccac | 300 |
| tccgtcaact | tcatcattgg | ctgcatcatg | cactctgcca | ttctgactcc cttcgagtcc | 360 |
| tgcgagtga | cccaccgaca | ccatcacaag | aacactggca | acattgataa ggacgagatc | 420 |
| ttctacccctc | atcggtccgt | caaggacctc | caggacgtgc | gacaatgggt ctacaccctc | 480 |

```
ggaggtgctt ggtttgtcta cctgaaggtc ggatatgctc ctcgaaccat gtcccacttt        540 gaccctggg  acctctcct  gcttcgacga gcctccgctg tcatcgtgtc cctcggagtc        600
tgggctgcct tcttcgctgc ctacgcctac ctcacatact cgctcggctt tgccgtcatg        660
ggcctctact actatgctcc tctctttgtc tttgcttcgt tcctcgtcat tactaccttc        720
ttgcatcaca acgacgaagc tactccctgg tacggtgact cggagtggac ctacgtcaag        780
ggcaacctga gctccgtcga ccgatcgtac ggagctttcg tggacaacct gtctcaccac        840
attggcaccc accaggtcca tcacttgttc cctatcattc cccactacaa gctcaacgaa        900
gccaccaagc actttgctgc cgcttaccct cacctcgtga cgtaacga cgagcccatc         960 attactgcct tcttcaagac cgctcacctc tttgtcaact acggagctgt gcccgagact       1020
gctcagattt tcaccctcaa agagtctgcc gctgcagcca aggccaagag cgactaa         1077
```

<210> SEQ ID NO 126
<211> LENGTH: 358
<212> TYPE: PRT
<213> ORGANISM: Saprolegnia diclina
<220> FEATURE:
<221> NAME/KEY: MISC_FEATURE
<223> OTHER INFORMATION: strain: ATCC #56851

<400> SEQUENCE: 126

```
Met Ala Glu Asp Lys Thr Lys Val Glu Phe Pro Thr Leu Thr Glu Leu
1               5                   10                  15

Lys His Ser Ile Pro Asn Ala Cys Phe Glu Ser Asn Leu Gly Leu Ser
            20                  25                  30

Leu Tyr Tyr Thr Ala Arg Ala Ile Phe Asn Ala Ser Ala Ser Ala Ala
        35                  40                  45

Leu Leu Tyr Ala Ala Arg Ser Thr Pro Phe Ile Ala Asp Asn Val Leu
    50                  55                  60

Leu His Ala Leu Val Cys Ala Thr Tyr Ile Tyr Val Gln Gly Val Ile
65                  70                  75                  80

Phe Trp Gly Phe Phe Thr Val Gly His Asp Cys Gly His Ser Ala Phe
                85                  90                  95

Ser Arg Tyr His Ser Val Asn Phe Ile Ile Gly Cys Ile Met His Ser
            100                 105                 110

Ala Ile Leu Thr Pro Phe Glu Ser Trp Arg Val Thr His Arg His His
        115                 120                 125

His Lys Asn Thr Gly Asn Ile Asp Lys Asp Glu Ile Phe Tyr Pro His
    130                 135                 140

Arg Ser Val Lys Asp Leu Gln Asp Val Arg Gln Trp Val Tyr Thr Leu
145                 150                 155                 160

Gly Gly Ala Trp Phe Val Tyr Leu Lys Val Gly Tyr Ala Pro Arg Thr
                165                 170                 175

Met Ser His Phe Asp Pro Trp Asp Pro Leu Leu Leu Arg Arg Ala Ser
            180                 185                 190

Ala Val Ile Val Ser Leu Gly Val Trp Ala Ala Phe Phe Ala Ala Tyr
        195                 200                 205

Ala Tyr Leu Thr Tyr Ser Leu Gly Phe Ala Val Met Gly Leu Tyr Tyr
    210                 215                 220

Tyr Ala Pro Leu Phe Val Phe Ala Ser Phe Leu Val Ile Thr Thr Phe
225                 230                 235                 240

Leu His His Asn Asp Glu Ala Thr Pro Trp Tyr Gly Asp Ser Glu Trp
                245                 250                 255
```

-continued

```
       Thr Tyr Val Lys Gly Asn Leu Ser Ser Val Asp Arg Ser Tyr Gly Ala
                       260                 265                 270

Phe Val Asp Asn Leu Ser His His Ile Gly Thr His Gln Val His His
                   275                 280                 285

Leu Phe Pro Ile Ile Pro His Tyr Lys Leu Asn Glu Ala Thr Lys His
               290                 295                 300

Phe Ala Ala Ala Tyr Pro His Leu Val Arg Arg Asn Asp Glu Pro Ile
       305                 310                 315                 320

Ile Thr Ala Phe Phe Lys Thr Ala His Leu Phe Val Asn Tyr Gly Ala
                       325                 330                 335

Val Pro Glu Thr Ala Gln Ile Phe Thr Leu Lys Glu Ser Ala Ala Ala
                   340                 345                 350

Ala Lys Ala Lys Ser Asp
               355
```

<210> SEQ ID NO 127
<211> LENGTH: 924
<212> TYPE: DNA
<213> ORGANISM: Yarrowia lipolytica
<220> FEATURE:
<221> NAME/KEY: misc_feature
<223> OTHER INFORMATION: Promoter FBAINm

<400> SEQUENCE: 127

```
aaattgcccc ggagaagacg gccaggccgc ctagatgaca aattcaacaa ctcacagctg    60
actttctgcc attgccacta gggggggggcc ttttatatg gccaagccaa gctctccacg   120
tcggttgggc tgcacccaac aataaatggg tagggttgca ccaacaaagg gatgggatgg   180
ggggtagaag atacgaggat aacggggctc aatggcacaa ataagaacga atactgccat   240
taagactcgt gatccagcga ctgacaccat gcatcatct aagggcctca aaactacctc    300
ggaactgctg cgctgatctg gacaccacag aggttccgag cactttaggt tgcaccaaat   360
gtcccaccag gtgcaggcag aaaacgctgg aacagcgtgt acagtttgtc ttaacaaaaa   420
gtgagggcgc tgaggtcgag cagggtggtg tgacttgtta tagcctttag agctgcgaaa   480
gcgcgtatgg atttggctca tcaggccaga ttgagggtct gtggacacat gtcatgttag   540
tgtacttcaa tcgcccccctg gatatagccc cgacaatagg ccgtggcctc attttttgc    600
cttccgcaca tttccattgc tcggtaccca caccttgctt ctcctgcact tgccaacctt   660
aatactggtt tacattgacc aacatcttac aagcgggggg cttgtctagg gtatatataa   720
acagtggctc tcccaatcgg ttgccagtct cttttttcct ttctttcccc acagattcga   780
aatctaaact acacatcaca gaattccgag ccgtgagtat ccacgacaag atcagtgtcg   840
agacgacgcg ttttgtgtaa tgacacaatc gaaagtcgc tagcaacaca cactctctac    900
acaaactaac ccagctctgg tacc                                          924
```

<210> SEQ ID NO 128
<211> LENGTH: 8194
<212> TYPE: DNA
<213> ORGANISM: Artificial Sequence
<220> FEATURE:
<223> OTHER INFORMATION: Plasmid pY37/F15

<400> SEQUENCE: 128

```
ggccgcacaa tggcgactcg acagcgaact gccaccactg ttgtggtcga ggaccttccc    60
aaggtcactc ttgaggccaa gtctgaacct gtgttccccg atatcaagac catcaaggat   120
gccattcccg cgcactgctt ccagccctcg ctcgtcacct cattctacta cgtcttccgc   180
```

-continued

```
gattttgcca tggtctctgc cctcgtctgg gctgctctca cctacatccc cagcatcccc      240
gaccagaccc tccgcgtcgc agcttggatg gtctacggct tcgtccaggg tctgttctgc      300
accggtgtct ggattctcgg ccatgagtgc ggccacggtg ctttctctct ccacggaaag      360
gtcaacaatg tgaccggctg gttcctccac tcgttcctcc tcgtccccta cttcagctgg      420
aagtactctc accaccgcca ccaccgcttc accggccaca tggatctcga catggctttc      480
gtccccaaga ctgagcccaa gccctccaag tcgctcatga ttgctggcat tgacgtcgcc      540
gagcttgttg aggacacccc cgctgctcag atggtcaagc tcatcttcca ccagcttttc      600
ggatggcagg cgtacctctt cttcaacgct agctctggca agggcagcaa gcagtgggag      660
cccaagactg gcctctccaa gtggttccga gtcagtcact tcgagcctac cagcgctgtc      720
ttccgcccca acgaggccat cttcatcctc atctccgata tcggtcttgc tctaatggga      780
actgctctgt actttgcttc caagcaagtt ggtgtttcga ccattctctt cctctacctt      840
gttccctacc tgtgggttca ccactggctc gttgccatta cctacctcca ccaccaccac      900
accgagctcc ctcactacac cgctgagggc tggacctacg tcaagggagc tctcgccact      960
gtcgaccgtg agtttggctt catcggaaag cacctcttcc acggtatcat tgagaagcac     1020
gttgttcacc atctcttccc taagatcccc ttctacaagg ctgacgaggc caccgaggcc     1080
atcaagcccg tcattggcga ccactactgc cacgacgacc gaagcttcct gggccagctg     1140
tggaccatct tcggcacgct caagtacgtc gagcacgacc ctgcccgacc cggtgccatg     1200
cgatggaaca aggactaggc taggcggccg ccaccgcggc ccgaattccg gcctcttcgg     1260
ccgccaagcg acccgggtgg acgtctagag gtacctagca attaacagat agtttgccgg     1320
tgataattct cttaacctcc cacactcctt tgacataacg atttatgtaa cgaaactgaa     1380
atttgaccag atattgtgtc cgcggtggag ctccagcttt tgttcccttt agtgagggtt     1440
aatttcgagc ttggcgtaat catggtcata gctgtttcct gtgtgaaatt gttatccgct     1500
cacaattcca cacaacgtac gagccggaag cataaagtgt aaagcctggg gtgcctaatg     1560
agtgagctaa ctcacattaa ttgcgttgcg ctcactgccc gctttccagt cgggaaacct     1620
gtcgtgccag ctgcattaat gaatcggcca acgcgcgggg agaggcggtt tgcgtattgg     1680
gcgctcttcc gcttcctcgc tcactgactc gctgcgctcg tcgttcggc tgcggcgagc      1740 ggtatcagct cactcaaagg cggtaatacg gttatccaca gaatcagggg ataacgcagg     1800
aaagaacatg tgagcaaaag gccagcaaaa ggccaggaac cgtaaaaagg ccgcgttgct     1860
ggcgtttttc cataggctcc gcccccctga cgagcatcac aaaaatcgac gctcaagtca     1920
gaggtggcga aacccgacag gactataaag ataccaggcg tttccccctg gaagctccct     1980
cgtgcgctct cctgttccga ccctgccgct taccggatac ctgtccgcct ttctcccttc     2040
gggaagcgtg cgctttctc atagctcacg ctgtaggtat ctcagttcgg tgtaggtcgt      2100
tcgctccaag ctgggctgtg tgcacgaacc cccgttcag cccgaccgct gcgccttatc      2160
cggtaactat cgtcttgagt ccaacccggt aagacacgac ttatcgccac tggcagcagc     2220
cactggtaac aggattagca gagcgaggta tgtaggcggt gctacagagt tcttgaagtg     2280
gtggcctaac tacggctaca ctagaaggac agtatttggt atctgcgctc tgctgaagcc     2340
agttaccttc ggaaaaagag ttggtagctc ttgatccggc aaacaaacca ccgctggtag     2400
cggtggtttt tttgtttgca agcagcagat tacgcgcaga aaaaaaggat ctcaagaaga     2460
tcctttgatc ttttctacgg ggtctgacgc tcagtggaac gaaaactcac gttaagggat     2520
```

```
tttggtcatg agattatcaa aaaggatctt cacctagatc cttttaaatt aaaaatgaag    2580
ttttaaatca atctaaagta tatatgagta aacttggtct gacagttacc aatgcttaat    2640
cagtgaggca cctatctcag cgatctgtct atttcgttca tccatagttg cctgactccc    2700
cgtcgtgtag ataactacga tacgggaggg cttaccatct ggccccagtg ctgcaatgat    2760
accgcgagac ccacgctcac cggctccaga tttatcagca ataaaccagc cagccggaag    2820
ggccgagcgc agaagtggtc ctgcaacttt atccgcctcc atccagtcta ttaattgttg    2880
ccgggaagct agagtaagta gttcgccagt taatagtttg cgcaacgttg ttgccattgc    2940
tacaggcatc gtggtgtcac gctcgtcgtt tggtatggct tcattcagct ccggttccca    3000
acgatcaagg cgagttacat gatcccccat gttgtgcaaa aaagcggtta gctccttcgg    3060
tcctccgatc gttgtcagaa gtaagttggc cgcagtgtta tcactcatgg ttatggcagc    3120
actgcataat tctcttactg tcatgccatc cgtaagatgc ttttctgtga ctggtgagta    3180
ctcaaccaag tcattctgag aatagtgtat gcggcgaccg agttgctctt gcccggcgtc    3240
aatacgggat aataccgcgc cacatagcag aactttaaaa gtgctcatca ttggaaaacg    3300
ttcttcgggg cgaaaactct caaggatctt accgctgttg agatccagtt cgatgtaacc    3360
cactcgtgca cccaactgat cttcagcatc ttttactttc accagcgttt ctgggtgagc    3420
aaaaacagga aggcaaaatg ccgcaaaaaa gggaataagg gcgacacgga aatgttgaat    3480
actcatactc ttcctttttc aatattattg aagcatttat cagggttatt gtctcatgag    3540
cggatacata tttgaatgta tttagaaaaa taaacaaata ggggttccgc gcacatttcc    3600
ccgaaaagtg ccacctgacg cgccctgtag cggcgcatta agcgcggcgg gtgtggtggt    3660
tacgcgcagc gtgaccgcta cacttgccag cgccctagcg cccgctcctt tcgctttctt    3720
cccttccttt ctcgccacgt tcgccggctt tccccgtcaa gctctaaatc ggggctccc    3780 tttagggttc cgatttagtg ctttacggca cctcgacccc aaaaaacttg attagggtga    3840
tggttcacgt agtgggccat cgccctgata gacggttttt cgccctttga cgttggagtc    3900
cacgttcttt aatagtggac tcttgttcca aactggaaca acactcaacc ctatctcggt    3960
ctattctttt gatttataag ggattttgcc gatttcggcc tattggttaa aaaatgagct    4020
gatttaacaa aaatttaacg cgaattttaa caaatatta acgcttacaa tttccattcg    4080
ccattcaggc tgcgcaactg ttgggaaggg cgatcggtgc gggcctcttc gctattacgc    4140
cagctggcga aggggggatg tgctgcaagg cgattaagtt gggtaacgcc agggttttcc    4200
cagtcacgac gttgtaaaac gacggccagt gaattgtaat acgactcact ataggcgaa    4260 ttgggtaccg ggccccccct cgaggtcgat ggtgtcgata gcttgatat cgaattcatg    4320 tcacacaaac cgatcttcgc ctcaaggaaa cctaattcta catccgagag actgccgaga    4380
tccagtctac actgattaat tttcgggcca ataatttaaa aaaatcgtgt tatataatat    4440
tatatgtatt atatatatac atcatgatga tactgacagt catgtcccat tgctaaatag    4500
acagactcca tctgccgcct ccaactgatg ttctcaatat ttaaggggtc atctcgcatt    4560
gtttaataat aaacagactc catctaccgc ctccaaatga tgttctcaaa atatattgta    4620
tgaacttatt tttattactt agtattatta gacaacttac ttgctttatg aaaaacactt    4680
cctatttagg aaacaattta taatggcagt tcgttcattt aacaatttat gtagaataaa    4740
tgttataaat gcgtatggga aatcttaaat atggatagca taaatgatat ctgcattgcc    4800
taattcgaaa tcaacagcaa cgaaaaaaat cccttgtaca acataaatag tcatcgagaa    4860
atatcaacta tcaaagaaca gctattcaca cgttactatt gagattatta ttggacgaga    4920
```

-continued

```
atcacacact caactgtctt tctctcttct agaaatacag gtacaagtat gtactattct    4980
cattgttcat acttctagtc atttcatccc acatattcct tggatttctc tccaatgaat    5040
gacattctat cttgcaaatt caacaattat aataagatat accaaagtag cggtatagtg    5100
gcaatcaaaa agcttctctg gtgtgcttct cgtatttatt tttattctaa tgatccatta    5160
aaggtatata tttatttctt gttatataat ccttttgttt attacatggg ctggatacat    5220
aaaggtattt tgatttaatt ttttgcttaa attcaatccc ccctcgttca gtgtcaactg    5280
taatggtagg aaattaccat acttttgaag aagcaaaaaa aatgaaagaa aaaaaaaatc    5340
gtatttccag gttagacgtt ccgcagaatc tagaatgcgg tatgcggtac attgttcttc    5400
gaacgtaaaa gttgcgctcc ctgagatatt gtacattttt gcttttacaa gtacaagtac    5460
atcgtacaac tatgtactac tgttgatgca tccacaacag tttgttttgt ttttttttgt    5520
tttttttttt tctaatgatt cattaccgct atgtatacct acttgtactt gtagtaagcc    5580
gggttattgg cgttcaatta atcatagact tatgaatctg cacggtgtgc gctgcgagtt    5640
acttttagct tatgcatgct acttgggtgt aatattggga tctgttcgga atcaacgga    5700
tgctcaaccg atttcgacag taattaatta agtcatacac aagtcagctt tcttcgagcc    5760
tcatataagt ataagtagtt caacgtatta gcactgtacc cagcatctcc gtatcgagaa    5820
acacaacaac atgccccatt ggacagatca tgcggataca caggttgtgc agtatcatac    5880
atactcgatc agacaggtcg tctgaccatc ataagctg aacaagcgct ccatacttgc     5940
acgctctcta tatacacagt taaattacat atccatagtc taacctctaa cagttaatct    6000
tctggtaagc ctcccagcca gccttctggt atcgcttggc ctcctcaata ggatctcggt    6060
tctggccgta cagacctcgg ccgacaatta tgatatccgt tccggtagac atgacatcct    6120
caacagttcg gtactgctgt ccgagagcgt ctcccttgtc gtcaagaccc accccggggg    6180
tcagaataag ccagtcctca gagtcgccct taggtcggtt ctgggcaatg aagccaacca    6240
caaactcggg gtcggatcgg gcaagctcaa tggtctgctt ggagtactcg ccagtggcca    6300
gagagcccct tgcaagacagc tcggccagca tgagcagacc tctggccagc ttctcgttgg    6360
gagaggggac taggaactcc ttgtactggg agttctcgta gtcagagacg tcctccttct    6420
tctgttcaga gacagtttcc tcggcaccag ctcgcaggcc agcaatgatt ccggttccgg    6480
gtacaccgtg ggcgttggtg atatcggacc actcggcgat tcggtgacac cggtactggt    6540
gcttgacagt gttgccaata tctgcgaact ttctgtcctc gaacaggaag aaaccgtgct    6600
taagagcaag ttccttgagg gggagcacag tgccggcgta ggtgaagtcg tcaatgatgt    6660
cgatatgggt tttgatcatg cacacataag gtccgacctt atcggcaagc tcaatgagct    6720
ccttggtggt ggtaacatcc agagaagcac acaggttggt tttcttggct gccacgagct    6780
tgagcactcg agcggcaaag gcggacttgt ggacgttagc tcgagcttcg taggagggca    6840
ttttggtggt gaagaggaga ctgaaataaa tttagtctgc agaactttt atcggaacct     6900
tatctggggc agtgaagtat atgttatggt aatagttacg agttagttga acttatagat    6960
agactggact atacggctat cggtccaaat tagaaagaac gtcaatggct ctctgggcgt    7020
cgcctttgcc gacaaaaatg tgatcatgat gaaagccagc aatgacgttg cagctgatat    7080
tgttgtcggc caaccgcgcc gaaaacgcag ctgtcagacc cacagcctcc aacgaagaat    7140
gtatcgtcaa agtgatccaa gcacactcat agttggagtc gtactccaaa ggcggcaatg    7200
acgagtcaga cagatactcg tcgacgcagt aggatgtcct gcacgggtct ttttgtgggg    7260
```

-continued

```
tgtggagaaa ggggtgcttg gagatggaag ccggtagaac cgggctgctt gtgcttggag    7320
atggaagccg gtagaaccgg gctgcttggg gggatttggg gccgctgggc tccaaagagg    7380
ggtaggcatt tcgttggggt tacgtaattg cggcatttgg gtcctgcgcg catgtcccat    7440
tggtcagaat tagtccggat aggagactta tcagccaatc acagcgccgg atccacctgt    7500
aggttgggtt gggtgggagc acccctccac agagtagagt caaacagcag cagcaacatg    7560
atagttgggg gtgtgcgtgt taaaggaaaa aaaagaagct tgggttatat tcccgctcta    7620
tttagaggtt gcgggataga cgccgacgga gggcaatggc gccatggaac cttgcggata    7680
tcgatacgcc gcggcggact gcgtccgaac cagctccagc agcgtttttt ccgggccatt    7740
gagccgactg cgaccccgcc aacgtgtctt ggcccacgca ctcatgtcat gttggtgttg    7800
ggaggccact ttttaagtag cacaaggcac ctagctcgca gcaaggtgtc cgaaccaaag    7860
aagcggctgc agtggtgcaa acggggcgga aacggcggga aaaagccacg ggggcacgaa    7920
ttgaggcacc ccctcgaatt tgagacgagt cacggcccca ttcgcccgcg caatggctcg    7980
ccaacgcccg gtcttttgca ccacatcagg ttaccccaag ccaaaccttt gtgttaaaaa    8040
gcttaacata ttataccgaa cgtaggtttg ggcgggcttg ctccgtctgt ccaaggcaac    8100
atttatataa gggtctgcat cgccggctca attgaatctt ttttcttctt ctcttctcta    8160
tattcattct tgaattaaac acacatcaat ccgc                                 8194
```

<210> SEQ ID NO 129
<211> LENGTH: 10448
<212> TYPE: DNA
<213> ORGANISM: Artificial Sequence
<220> FEATURE:
<223> OTHER INFORMATION: Plasmid pKO2UM26E

<400> SEQUENCE: 129

```
cgattgcccc ggagaagacg gccaggccgc ctagatgaca aattcaacaa ctcacagctg      60
actttctgcc attgccacta gggggggggcc tttttatatg gccaagccaa gctctccacg     120
tcggttgggc tgcacccaac aataaatggg tagggttgca ccaacaaagg gatgggatgg     180
ggggtagaag atacgaggat aacggggctc aatggcacaa ataagaacga atactgccat     240
taagactcgt gatccagcga ctgacaccat tgcatcatct aagggcctca aaactacctc     300
ggaactgctg cgctgatctg gacaccacag aggttccgag cactttaggt tgcaccaaat     360
gtcccaccag gtgcaggcag aaaacgctgg aacagcgtgt acagtttgtc ttaacaaaaa     420
gtgagggcgc tgaggtcgag cagggtggtg tgacttgtta tagcctttag agctgcgaaa     480
gcgcgtatgg atttggctca tcaggccaga ttgagggtct gtggacacat gtcatgttag     540
tgtacttcaa tcgcccctg gatatagccc cgacaatagg ccgtggcctc atttttttgc      600
cttccgcaca tttccattgc tcggtaccca caccttgctt ctcctgcact tgccaacctt     660
aatactggtt tacattgacc aacatcttac aagcgggggg cttgtctagg gtatatataa     720
acagtggctc tcccaatcgg ttgccagtct cttttttcct ttctttcccc acagattcga     780
aatctaaact acacatcaca caatgcctgt tactgacgtc cttaagcgaa agtccggtgt     840
catcgtcggc gacgatgtcc gagccgtgag tatccacgac aagatcagtg tcgagacgac     900
gcgttttgtg taatgacaca atccgaaagt cgctagcaac acacactctc tacacaaact     960
aacccagctc tccatggtga agtccaagcg acaggctctg cccctcacca tcgacggaac    1020
tacctacgac gtctccgctt gggtgaactt ccacctggt ggagctgaaa tcattgagaa    1080
ctaccaggga cgagatgcta ctgacgcctt catggttatg cactctcagg aagccttcga    1140
```

-continued

```
caagctcaag cgaatgccca agatcaaccc ctcctccgag ctgcctcccc aggctgccgt    1200
caacgaagct caggaggatt tccgaaagct ccgagaagag ctgatcgcca ctggcatgtt    1260
tgacgcctct cccctctggt actcgtacaa gatctccacc accctgggtc ttggcgtgct    1320
tggatacttc ctgatggtcc agtaccagat gtacttcatt ggtgctgtgc tgctcggtat    1380
gcactaccag caaatgggat ggctgtctca tgacatctgc caccaccaga ccttcaagaa    1440
ccgaaactgg aataacctcg tgggtctggt ctttggcaac ggactccagg gcttctccgt    1500
gacctggtgg aaggacagac acaacgccca tcattctgct accaacgttc agggtcacga    1560
tcccgacatt gataacctgc ctctgctcgc ctggtccgag gacgatgtca ctcgagcttc    1620
tcccatctcc cgaaagctca ttcagttcca acagtactat ttcctggtca tctgtattct    1680
cctgcgattc atctggtgtt tccagtctgt gctgaccgtt cgatcctca aggaccgaga    1740 caaccagttc taccgatctc agtacaagaa agaggccatt ggactcgctc tgcactggac    1800
tctcaagacc ctgttccacc tcttctttat gccctccatc ctgacctcgc tcctggtgtt    1860
ctttgtttcc gagctcgtcg gtggcttcgg aattgccatc gtggtcttca tgaaccacta    1920
ccctctggag aagatcggtg attccgtctg ggacggacat ggcttctctg tgggtcagat    1980
ccatgagacc atgaacattc gacgaggcat cattactgac tggttctttg gaggcctgaa    2040
ctaccagatc gagcaccatc tctggcccac cctgcctcga cacaacctca ctgccgtttc    2100
ctaccaggtg aacagctgt gccagaagca caacctcccc taccgaaacc ctctgcccca    2160
tgaaggtctc gtcatcctgc tccgatacct ggccgtgttc gctcgaatgg ccgagaagca    2220
gcccgctggc aaggctctct aagcggccgc attgatgatt ggaaacacac acatgggtta    2280
tatctaggtg agagttagtt ggacagttat atattaaatc agctatgcca acggtaactt    2340
cattcatgtc aacgaggaac cagtgactgc aagtaatata gaatttgacc accttgccat    2400
tctcttgcac tcctttacta tatctcattt atttcttata tacaaatcac ttcttcttcc    2460
cagcatcgag ctcggaaacc tcatgagcaa taacatcgtg gatctcgtca atagagggct    2520
ttttggactc cttgctgttg gccacctttgt ccttgctgtc tggctcattc tgtttcaacg    2580 cctttaatt aagtcataca caagtcagct ttcttcgagc ctcatataag tataagtagt    2640
tcaacgtatt agcactgtac ccagcatctc cgtatcgaga aacacaacaa catgccccat    2700
tggacagatc atgcggatac acaggttgtg cagtatcata catactcgat cagacaggtc    2760
gtctgaccat catacaagct gaacaagcgc tccatacttg cacgctctct atatacacag    2820
ttaaattaca tatccatagt ctaacctcta acagttaatc ttctggtaag cctcccagcc    2880
agccttctgg tatcgcttgg cctcctcaat aggatctcgg ttctggccgt acagacctcg    2940
gccgacaatt atgatatccg ttccggtaga catgacatcc tcaacagttc ggtactgctg    3000
tccgagagcg tctcccttgt cgtcaagacc caccccgggg gtcagaataa gccagtcctc    3060
agagtcgccc ttaggtcggt tctgggcaat gaagccaacc acaaactcgg ggtcggatcg    3120
ggcaagctca atggtctgct tggagtactc gccagtggcc agagagccct tgcaagacag    3180
ctcggccagc atgagcagac ctctggccag cttctcgttg ggagaggggga ctaggaactc    3240 cttgtactgg gagttctcgt agtcagagac gtcctcctc ttctgttcag agacagtttc    3300
ctcggcacca gctcgcaggc cagcaatgat tccggttccg ggtacaccgt gggcgttggt    3360
gatatcggac cactcggcga ttcggtgaca ccggtactgg tgcttgacag tgttgccaat    3420
atctgcgaac tttctgtcct cgaacaggaa gaaaccgtgc ttaagagcaa gttccttgag    3480
```

```
ggggagcaca gtgccggcgt aggtgaagtc gtcaatgatg tcgatatggg ttttgatcat    3540
gcacacataa ggtccgacct tatcggcaag ctcaatgagc tccttggtgg tggtaacatc    3600
cagagaagca cacaggttgg ttttcttggc tgccacgagc ttgagcactc gagcggcaaa    3660
ggcggacttg tggacgttag ctcgagcttc gtaggagggc attttggtgg tgaagaggag    3720
actgaaataa atttagtctg cagaactttt tatcggaacc ttatctgggg cagtgaagta    3780
tatgttatgg taatagttac gagttagttg aacttataga tagactggac tatacggcta    3840
tcggtccaaa ttagaaagaa cgtcaatggc tctctgggcg tcgcctttgc cgacaaaaat    3900
gtgatcatga tgaaagccag caatgacgtt gcagctgata ttgttgtcgg ccaaccgcgc    3960
cgaaaacgca gctgtcagac ccacagcctc caacgaagaa tgtatcgtca agtgatcca    4020 agcacactca tagttggagt cgtactccaa aggcggcaat gacgagtcag acagatactc    4080
gtcgactcag gcgacgacgg aattcctgca gcccatctgc agaattcagg agagaccggg    4140
ttggcggcgt atttgtgtcc caaaaaacag ccccaattgc cccggagaag acggccaggc    4200
cgcctagatg acaaattcaa caactcacag ctgactttct gccattgcca ctaggggggg    4260 gccttttat atggccaagc caagctctcc acgtcggttg ggctgcaccc aacaataaat    4320
gggtagggtt gcaccaacaa agggatggga tgggggtag aagatacgag gataacgggg    4380
ctcaatggca caaataagaa cgaatactgc cattaagact cgtgatccag cgactgacac    4440
cattgcatca tctaagggcc tcaaaactac ctcggaactg ctgcgctgat ctggacacca    4500
cagaggttcc gagcacttta ggttgcacca aatgtcccac caggtgcagg cagaaaacgc    4560
tggaacagcg tgtacagttt gtcttaacaa aaagtgaggg cgctgaggtc gagcagggtg    4620
gtgtgacttt ttatagcctt tagagctgcg aaagcgcgta tggatttggc tcatcaggcc    4680
agattgaggg tctgtggaca catgtcatgt tagtgtactt caatcgcccc ctggatatag    4740
ccccgacaat aggccgtggc ctcattttt tgccttccgc acatttccat tgctcggtac    4800
ccacaccttg cttctcctgc acttgccaac cttaatactg gtttacattg accaacatct    4860
tacaagcggg gggcttgtct agggtatata taaacagtgg ctctcccaat cggttgccag    4920
tctctttttt cctttctttc cccacagatt cgaaatctaa actacacatc acacaatgcc    4980
tgttactgac gtccttaagc gaaagtccgg tgtcatcgtc ggcgacgatg tccgagccgt    5040
gagtatccac gacaagatca gtgtcgagac gacgcgtttt gtgtaatgac acaatccgaa    5100
agtcgctagc aacacacact ctctacacaa actaacccag ctctccatgg ctctggccaa    5160
cgacgctggc gagcgaatct gggctgccgt caccgatccc gaaatcctca ttggcacctt    5220
ctcctacctg ctcctgaagc ctctcctgcg aaactctggt ctcgtggacg agaagaaagg    5280
agcctaccga acctccatga tctggtacaa cgtcctcctg gctctcttct ctgccctgtc    5340
cttctacgtg actgccaccg ctctcggctg ggactacggt actggagcct ggctgcgaag    5400
acagaccggt gatactcccc agcctctctt tcagtgtccc tctcctgtct gggactccaa    5460
gctgttcacc tggactgcca aggccttcta ctattctaag tacgtggagt acctcgacac    5520
cgcttggctg gtcctcaagg gcaagcgagt gtcctttctg caggccttcc atcactttgg    5580
agctccctgg gacgtctacc tcggcattcg actgcacaac gagggtgtgt ggatcttcat    5640
gttctttaac tcgttcattc acaccatcat gtacacctac tatggactga ctgccgctgg    5700
ctacaagttc aaggccaagc ctctgatcac tgccatgcag atttgccagt cgtcggtgg    5760 cttttctcctg gtctgggact acatcaacgt tccctgcttc aactctgaca agggcaagct    5820
gttctcctgg gctttcaact acgcctacgt cggatctgtc tttctcctgt tctgtcactt    5880
```

```
cttttaccag gacaacctgg ccaccaagaa atccgctaag gctggtaagc agctttagcg   5940
gccgcaagtg tggatgggga agtgagtgcc cggttctgtg tgcacaattg caatccaag    6000
atggatggat tcaacacagg gatatagcga gctacgtggt ggtgcgagga tatagcaacg   6060
gatatttatg tttgacactt gagaatgtac gatacaagca ctgtccaagt acaatactaa   6120
acatactgta catactcata ctcgtacccg gcaacggtt tcacttgagt gcagtggcta    6180
gtgctcttac tcgtacagtg tgcaatactg cgtatcatag tctttgatgt atatcgtatt   6240
cattcatgtt agttgcgtac gagccggaag cataaagtgt aaagcctggg gtgcctaatg   6300
agtgagctaa ctcacattaa ttgcgttgcg ctcactgccc gctttccagt cgggaaacct   6360
gtcgtgccag ctgcattaat gaatcggcca acgcgcgggg agaggcggtt tgcgtattgg   6420
gcgctcttcc gcttcctcgc tcactgactc gctgcgctcg tcgttcggc tgcggcgagc    6480
ggtatcagct cactcaaagg cggtaatacg gttatccaca gaatcagggg ataacgcagg   6540
aaagaacatg tgagcaaaag gccagcaaaa ggccaggaac cgtaaaaagg ccgcgttgct   6600
ggcgtttttc cataggctcc gcccccctga cgagcatcac aaaaatcgac gctcaagtca   6660
gaggtggcga acccgacag gactataaag ataccaggcg tttccccctg gaagctccct    6720
cgtgcgctct cctgttccga ccctgccgct taccggatac ctgtccgcct ttctcccttc   6780
gggaagcgtg gcgctttctc atagctcacg ctgtaggtat ctcagttcgg tgtaggtcgt   6840
tcgctccaag ctgggctgtg tgcacgaacc ccccgttcag cccgaccgct gcgccttatc   6900
cggtaactat cgtcttgagt ccaacccggt aagacacgac ttatcgccac tggcagcagc   6960
cactggtaac aggattagca gagcgaggta tgtaggcggt gctacagagt tcttgaagtg   7020
gtggcctaac tacggctaca ctagaaggac agtatttggt atctgcgctc tgctgaagcc   7080
agttaccttc ggaaaaagag ttggtagctc ttgatccggc aaacaaacca ccgctggtag   7140
cggtggtttt tttgtttgca agcagcagat tacgcgcaga aaaaaaggat ctcaagaaga   7200
tcctttgatc ttttctacgg ggtctgacgc tcagtggaac gaaaactcac gttaagggat   7260
tttggtcatg agattatcaa aaaggatctt cacctagatc cttttaaatt aaaaatgaag   7320
ttttaaatca atctaaagta tatatgagta aacttggtct gacagttacc aatgcttaat   7380
cagtgaggca cctatctcag cgatctgtct atttcgttca tccatagttg cctgactccc   7440
cgtcgtgtag ataactacga tacgggaggg cttaccatct ggccccagtg ctgcaatgat   7500
accgcgagac ccacgctcac cggctccaga tttatcagca ataaaccagc cagccggaag   7560
ggccgagcgc agaagtggtc ctgcaacttt atccgcctcc atccagtcta ttaattgttg   7620
ccgggaagct agagtaagta gttcgccagt taatagtttg cgcaacgttg ttgccattgc   7680
tacaggcatc gtggtgtcac gctcgtcgtt tggtatggct tcattcagct ccggttccca   7740
acgatcaagg cgagttacat gatcccccat gttgtgcaaa aaagcggtta gctccttcgg   7800
tcctccgatc gttgtcagaa gtaagttggc cgcagtgtta tcactcatgg ttatggcagc   7860
actgcataat tctcttactg tcatgccatc cgtaagatgc ttttctgtga ctggtgagta   7920
ctcaaccaag tcattctgag aatagtgtat gcggcgaccg agttgctctt gcccggcgtc   7980
aatacgggat aataccgcgc cacatagcag aactttaaaa gtgctcatca ttggaaaacg   8040
ttcttcgggg cgaaaactct caaggatctt accgctgttg agatccagtt cgatgtaacc   8100
cactcgtgca cccaactgat cttcagcatc ttttactttc accagcgttt ctgggtgagc   8160
aaaaacagga aggcaaaatg ccgcaaaaaa gggaataagg gcgacacgga aatgttgaat   8220
```

```
actcatactc ttcctttttc aatattattg aagcatttat cagggttatt gtctcatgag    8280
cggatacata tttgaatgta tttagaaaaa taaacaaata ggggttccgc gcacatttcc    8340
ccgaaaagtg ccacctgacg cgccctgtag cggcgcatta agcgcggcgg gtgtggtggt    8400
tacgcgcagc gtgaccgcta cacttgccag cgccctagcg cccgctcctt tcgctttctt    8460
cccttccttt ctcgccacgt tcgccggctt tccccgtcaa gctctaaatc gggggctccc    8520
tttagggttc cgatttagtg ctttacggca cctcgacccc aaaaaacttg attagggtga    8580
tggttcacgt agtgggccat cgccctgata cacggttttt cgccctttga cgttggagtc    8640
cacgttcttt aatagtggac tcttgttcca aactggaaca acactcaacc ctatctcggt    8700
ctattctttt gatttataag ggattttgcc gatttcggcc tattggttaa aaaatgagct    8760
gatttaacaa aaatttaacg cgaattttaa caaaatatta acgcttacaa tttccattcg    8820
ccattcaggc tgcgcaactg ttgggaaggg cgatcggtgc gggcctcttc gctattacgc    8880
cagctggcga aggggggatg tgctgcaagg cgattaagtt gggtaacgcc agggttttcc    8940
cagtcacgac gttgtaaaac gacggccagt gaattgtaat acgactcact atagggcgaa    9000
ttgggtaccg ggccccccct cgaggtcgat ggtgtcgata agcttgatat cgaattcatg    9060
tcacacaaac cgatcttcgc ctcaaggaaa cctaattcta catccgagag actgccgaga    9120
tccagtctac actgattaat tttcgggcca ataatttaaa aaaatcgtgt tatataatat    9180
tatatgtatt atatatatac atcatgatga tactgacagt catgtcccat tgctaaatag    9240
acagactcca tctgccgcct ccaactgatg ttctcaatat ttaagggtc atctcgcatt     9300
gtttaataat aaacagactc catctaccgc ctccaaatga tgttctcaaa atatattgta    9360
tgaacttatt tttattactt agtattatta gacaacttac ttgctttatg aaaaacactt    9420
cctatttagg aaacaattta taatggcagt tcgttcattt aacaatttat gtagaataaa    9480
tgttataaat gcgtatggga atcttaaat atggatagca taaatgatat ctgcattgcc    9540
taattcgaaa tcaacagcaa cgaaaaaaat cccttgtaca acataaatag tcatcgagaa    9600
atatcaacta tcaaagaaca gctattcaca cgttactatt gagattatta ttggacgaga    9660
atcacacact caactgtctt tctctcttct agaaatacag gtacaagtat gtactattct    9720
cattgttcat acttctagtc atttcatccc acatattcct tggatttctc tccaatgaat    9780
gacattctat cttgcaaatt caacaattat aataagatat accaaagtag cggtatagtg    9840
gcaatcaaaa agcttctctg gtgtgcttct cgtatttatt tttattctaa tgatccatta    9900
aaggtatata tttatttctt gttatataat ccttttgttt attacatggg ctggatacat    9960
aaagtatttt tgatttaatt ttttgcttaa attcaatccc ccctcgttca gtgtcaactg   10020
taatggtagg aaattaccat acttttgaag aagcaaaaaa aatgaaagaa aaaaaaaatc   10080
gtatttccag gttagacgtt ccgcagaatc tagaatgcgg tatgcggtac attgttcttc   10140
gaacgtaaaa gttcgctccc tgagatattg tacatttttt gctttacaa gtacaagtac    10200
atcgtacaac tatgtactac tgttgatgca tccacaacag tttgtttttgt ttttttttgt   10260
ttttttttt tctaatgatt cattaccgct atgtatacct acttgtactt gtagtaagcc    10320
gggttattgg cgttcaatta atcatagact tatgaatctg cacggtgtgc gctgcgagtt   10380
actttttagct tatgcatgct acttgggtgt aatattggga tctgttcgga aatcaacgga   10440
tgctcaat                                                            10448
```

<210> SEQ ID NO 130
<211> LENGTH: 1936

-continued

```
<212> TYPE: DNA
<213> ORGANISM: Yarrowia lipolytica
<220> FEATURE:
<221> NAME/KEY: CDS
<222> LOCATION: (283)..(1539)
<223> OTHER INFORMATION: delta-12 desaturase

<400> SEQUENCE: 130
cgtagttata tacaagaggt agatgcgtgc tggtgttaga ggggctctca ggattaggag      60
gaaaatttga cattggccct caacatataa cctcgggtgt gcctctgttt accctcagct     120
tttgcttgtc cccaagtcag tcacgccagg ccaaaaaggt tggtggattg acagggagaa     180
aaaaaaaagc ctagtgggtt taaactcgag gtaagacatt gaaatatata ccggtcggca     240
tcctgagtcc ctttctcgta ttccaacaga ccgaccatag aa atg gat tcg acc        294
                                                Met Asp Ser Thr
                                                  1 acg cag acc aac acc ggc acc ggc aag gtg gcc gtg cag ccc ccc acg       342
Thr Gln Thr Asn Thr Gly Thr Gly Lys Val Ala Val Gln Pro Pro Thr
  5                  10                  15                  20 gcc ttc att aag ccc att gag aag gtg tcc gag ccc gtc tac gac acc       390
Ala Phe Ile Lys Pro Ile Glu Lys Val Ser Glu Pro Val Tyr Asp Thr
                 25                  30                  35 ttt ggc aac gag ttc act cct cca gac tac tct atc aag gat att ctg       438
Phe Gly Asn Glu Phe Thr Pro Pro Asp Tyr Ser Ile Lys Asp Ile Leu
     40                  45                  50 gat gcc att ccc cag gag tgc tac aag cgg tcc tac gtt aag tcc tac       486
Asp Ala Ile Pro Gln Glu Cys Tyr Lys Arg Ser Tyr Val Lys Ser Tyr
 55                  60                  65 tcg tac gtg gcc cga gac tgc ttc ttt atc gcc gtt ttt gcc tac atg       534
Ser Tyr Val Ala Arg Asp Cys Phe Phe Ile Ala Val Phe Ala Tyr Met
 70                  75                  80 gcc tac gcg tac ctg cct ctt att ccc tcg gct tcc ggc cga gct gtg       582
Ala Tyr Ala Tyr Leu Pro Leu Ile Pro Ser Ala Ser Gly Arg Ala Val
85                  90                  95                 100 gcc tgg gcc atg tac tcc att gtc cag ggt ctg ttt ggc acc ggt ctg       630
Ala Trp Ala Met Tyr Ser Ile Val Gln Gly Leu Phe Gly Thr Gly Leu
                105                 110                 115 tgg gtt ctt gcc cac gag tgt ggc cac tct gct ttc tcc gac tct aac       678
Trp Val Leu Ala His Glu Cys Gly His Ser Ala Phe Ser Asp Ser Asn
            120                 125                 130 acc gtc aac aac gtc acc gga tgg gtt ctg cac tcc tcc atg ctg gtc       726
Thr Val Asn Asn Val Thr Gly Trp Val Leu His Ser Ser Met Leu Val
        135                 140                 145 cct tac tac gcc tgg aag ctg acc cac tcc atg cac cac aag tcc act       774
Pro Tyr Tyr Ala Trp Lys Leu Thr His Ser Met His His Lys Ser Thr
    150                 155                 160 ggt cac ctc acc cgt gat atg gtg ttt gtg ccc aag gac cga aag gag       822
Gly His Leu Thr Arg Asp Met Val Phe Val Pro Lys Asp Arg Lys Glu
165                 170                 175                 180 ttt atg gag aac cga ggc gcc cat gac tgg tct gag ctt gct gag gac       870
Phe Met Glu Asn Arg Gly Ala His Asp Trp Ser Glu Leu Ala Glu Asp
                185                 190                 195 gct ccc ctc atg acc ctc tac ggc ctc atc acc cag cag gtg ttt gga       918
Ala Pro Leu Met Thr Leu Tyr Gly Leu Ile Thr Gln Gln Val Phe Gly
            200                 205                 210 tgg cct ctg tat ctg ctg tct tac gtt acc gga cag aag tac ccc aag       966
Trp Pro Leu Tyr Leu Leu Ser Tyr Val Thr Gly Gln Lys Tyr Pro Lys
        215                 220                 225 ctc aac aaa tgg gct gtc aac cac ttc aac ccc aac gcc ccg ctg ttt      1014
Leu Asn Lys Trp Ala Val Asn His Phe Asn Pro Asn Ala Pro Leu Phe
```

-continued

```
                    230                 235                 240
gag aag aag gac tgg ttc aac atc tgg atc tct aac gtc ggt att ggt         1062
Glu Lys Lys Asp Trp Phe Asn Ile Trp Ile Ser Asn Val Gly Ile Gly
245                 250                 255                 260 atc acc atg tcc gtc atc gca tac tcc atc aac cga tgg ggc ctg gct         1110
Ile Thr Met Ser Val Ile Ala Tyr Ser Ile Asn Arg Trp Gly Leu Ala
                265                 270                 275 tcc gtc acc ctc tac tac ctg atc ccc tac ctg tgg gtc aac cac tgg         1158
Ser Val Thr Leu Tyr Tyr Leu Ile Pro Tyr Leu Trp Val Asn His Trp
            280                 285                 290 ctg gtg gcc atc acc tac ctg cag cac acc gac ccc act ctg ccc cac         1206
Leu Val Ala Ile Thr Tyr Leu Gln His Thr Asp Pro Thr Leu Pro His
        295                 300                 305 tac cac gcc gac cag tgg aac ttc acc cga gga gcc gcc gcc acc atc         1254
Tyr His Ala Asp Gln Trp Asn Phe Thr Arg Gly Ala Ala Ala Thr Ile
    310                 315                 320 gac cga gag ttt ggc ttc atc ggc tcc ttc tgc ttc cat gac atc atc         1302
Asp Arg Glu Phe Gly Phe Ile Gly Ser Phe Cys Phe His Asp Ile Ile
325                 330                 335                 340 gag acc cac gtt ctg cac cac tac gtg tct cga att ccc ttc tac aac         1350
Glu Thr His Val Leu His His Tyr Val Ser Arg Ile Pro Phe Tyr Asn
                345                 350                 355 gcc cga atc gcc act gag aag atc aag aag gtc atg ggc aag cac tac         1398
Ala Arg Ile Ala Thr Glu Lys Ile Lys Lys Val Met Gly Lys His Tyr
            360                 365                 370 cga cac gac gac acc aac ttc atc aag tct ctt tac act gtc gcc cga         1446
Arg His Asp Asp Thr Asn Phe Ile Lys Ser Leu Tyr Thr Val Ala Arg
        375                 380                 385 acc tgc cag ttt gtt gaa ggt aag gaa ggc att cag atg ttt aga aac         1494
Thr Cys Gln Phe Val Glu Gly Lys Glu Gly Ile Gln Met Phe Arg Asn
    390                 395                 400 gtc aat gga gtc gga gtt gct cct gac ggc ctg cct tct aaa aag             1539
Val Asn Gly Val Gly Val Ala Pro Asp Gly Leu Pro Ser Lys Lys
405                 410                 415 tagagctaga aatgttattt gattgtgttt taactgaaca gcaccgagcc cgaggctaag       1599
ccaagcgaag ccgaggggtt gtgtagtcca tggacgtaac gagtaggcga tatcaccgca       1659
ctcggcactg cgtgtctgcg ttcatgggcg aagtcacatt acgctgacaa ccgttgtagt       1719 ttcccttag tatcaatact gttacaagta ccggtctcgt actcgtactg atacgaatct       1779
gtgggaagaa gtcaccccta tcagaccttc atactgatgt ttcggatatc aatagaactg       1839
gcatagagcc gttaaagaag tttcacttaa tcactccaac cctcctactt gtagattcaa       1899
gcagatcgat aagatggatt tgatggtcag tgctagc                                1936
```

<210> SEQ ID NO 131
<211> LENGTH: 419
<212> TYPE: PRT
<213> ORGANISM: Yarrowia lipolytica

<400> SEQUENCE: 131

```
Met Asp Ser Thr Thr Gln Thr Asn Thr Gly Thr Gly Lys Val Ala Val
1               5                   10                  15

Gln Pro Pro Thr Ala Phe Ile Lys Pro Ile Glu Lys Val Ser Glu Pro
            20                  25                  30

Val Tyr Asp Thr Phe Gly Asn Glu Phe Thr Pro Pro Asp Tyr Ser Ile
        35                  40                  45

Lys Asp Ile Leu Asp Ala Ile Pro Gln Glu Cys Tyr Lys Arg Ser Tyr
    50                  55                  60
```

```
Val Lys Ser Tyr Ser Tyr Val Ala Arg Asp Cys Phe Ile Ala Val
 65                  70                  75                  80

Phe Ala Tyr Met Ala Tyr Ala Tyr Leu Pro Leu Ile Pro Ser Ala Ser
             85                  90                  95

Gly Arg Ala Val Ala Trp Ala Met Tyr Ser Ile Val Gln Gly Leu Phe
            100                 105                 110

Gly Thr Gly Leu Trp Val Leu Ala His Glu Cys Gly His Ser Ala Phe
        115                 120                 125

Ser Asp Ser Asn Thr Val Asn Asn Val Thr Gly Trp Val Leu His Ser
    130                 135                 140

Ser Met Leu Val Pro Tyr Tyr Ala Trp Lys Leu Thr His Ser Met His
145                 150                 155                 160

His Lys Ser Thr Gly His Leu Thr Arg Asp Met Val Phe Val Pro Lys
                165                 170                 175

Asp Arg Lys Glu Phe Met Glu Asn Arg Gly Ala His Asp Trp Ser Glu
            180                 185                 190

Leu Ala Glu Asp Ala Pro Leu Met Thr Leu Tyr Gly Leu Ile Thr Gln
        195                 200                 205

Gln Val Phe Gly Trp Pro Leu Tyr Leu Leu Ser Tyr Val Thr Gly Gln
    210                 215                 220

Lys Tyr Pro Lys Leu Asn Lys Trp Ala Val Asn His Phe Asn Pro Asn
225                 230                 235                 240

Ala Pro Leu Phe Glu Lys Lys Asp Trp Phe Asn Ile Trp Ile Ser Asn
                245                 250                 255

Val Gly Ile Gly Ile Thr Met Ser Val Ile Ala Tyr Ser Ile Asn Arg
            260                 265                 270

Trp Gly Leu Ala Ser Val Thr Leu Tyr Tyr Leu Ile Pro Tyr Leu Trp
        275                 280                 285

Val Asn His Trp Leu Val Ala Ile Thr Tyr Leu Gln His Thr Asp Pro
    290                 295                 300

Thr Leu Pro His Tyr His Ala Asp Gln Trp Asn Phe Thr Arg Gly Ala
305                 310                 315                 320

Ala Ala Thr Ile Asp Arg Glu Phe Gly Phe Ile Gly Ser Phe Cys Phe
                325                 330                 335

His Asp Ile Ile Glu Thr His Val Leu His His Tyr Val Ser Arg Ile
            340                 345                 350

Pro Phe Tyr Asn Ala Arg Ile Ala Thr Glu Lys Ile Lys Lys Val Met
        355                 360                 365

Gly Lys His Tyr Arg His Asp Asp Thr Asn Phe Ile Lys Ser Leu Tyr
    370                 375                 380

Thr Val Ala Arg Thr Cys Gln Phe Val Glu Gly Lys Glu Gly Ile Gln
385                 390                 395                 400

Met Phe Arg Asn Val Asn Gly Val Gly Val Ala Pro Asp Gly Leu Pro
                405                 410                 415

Ser Lys Lys
```

<210> SEQ ID NO 132
<211> LENGTH: 1130
<212> TYPE: DNA
<213> ORGANISM: Yarrowia lipolytica
<220> FEATURE:
<221> NAME/KEY: misc_feature
<223> OTHER INFORMATION: GPAT promoter

<400> SEQUENCE: 132

```
caactttct  tgtcgacctg  agataccgag  gttgcgcagg  ggatcaactt  ttgtgtctca      60
gagggaccca  agtgcgtacg  gagagtacag  tacatactgt  agctaacggt  agcaggcgaa     120
ctactggtac  atacctcccc  cggaatatgt  acaggcataa  tgcgtatctg  tgggacatgt     180
ggtcgttgcg  ccattatgta  agcagcgtgt  actcctctga  ctgtccatat  ggtttgctcc     240
atctcaccct  catcgttttc  attgttcaca  ggcggccaca  aaaaaactgt  cttctctcct     300
tctctcttcg  ccttagtcta  ctcggaccag  ttttagttta  gcttggcgcc  actggataaa     360
tgagacctca  ggccttgtga  tgaggaggtc  acttatgaag  catgttagga  ggtgcttgta     420
tggatagaga  agcacccaaa  ataataagaa  taataataaa  acaggggggcg ttgtcatttc     480
atatcgtgtt  ttcaccatca  atacacctcc  aaacaatgcc  cttcatgtgg  ccagccccaa     540
tattgtcctg  tagttcaact  ctatgcagct  cgtatcttat  tgagcaagta  aaactctgtc     600
agccgatatt  gcccgacccg  cgacaagggt  caacaaggtg  gtgtaaggcc  ttcgcagaag     660
tcaaaactgt  gccaaacaaa  catctagagt  ctctttggtg  tttctcgcat  atatttaatc     720
ggctgtctta  cgtatttggc  ctcggtaccg  gactaatttc  ggatcatccc  caatacgctt     780
tttcttcgca  gctgtcaaca  gtgtccatga  tctatccacc  taaatgggtc  atatgaggcg     840
tataatttcg  tggtgctgat  aataattccc  atatatttga  cacaaaactt  cccccccctag    900
acatacatct  cacaatctca  cttcttgtgc  ttctgtcaca  catctcctcc  agctgacttc     960
aactcacacc  tctgccccag  ttggtctaca  gcggtataag  gtttctccgc  atagaggtgc    1020
accactcctc  ccgatacttg  tttgtgtgac  ttgtgggtca  cgacatatat  atctacacac    1080
attgcgccac  cctttggttc  ttccagcaca  acaaaaacac  gacacgctaa                1130
```

<210> SEQ ID NO 133
<211> LENGTH: 1203
<212> TYPE: DNA
<213> ORGANISM: Mortieralla isabellina
<220> FEATURE:
<221> NAME/KEY: CDS
<222> LOCATION: (1)..(1203)
<223> OTHER INFORMATION: delta-12 desaturase
<300> PUBLICATION INFORMATION:
<308> DATABASE ACCESSION NUMBER: GenBank Accession No. AF417245
<309> DATABASE ENTRY DATE: 2001-10-11
<313> RELEVANT RESIDUES: (1)..(1203)

<400> SEQUENCE: 133

```
atg gca cct ccc aac act atc gat gcc ggc ttg acc cag cgt cat atc       48
Met Ala Pro Pro Asn Thr Ile Asp Ala Gly Leu Thr Gln Arg His Ile
1               5                   10                  15 acc acc acg gcc gcc cca acc tcg gcc aag ccc gct ttc gag cgc aac       96
Thr Thr Thr Ala Ala Pro Thr Ser Ala Lys Pro Ala Phe Glu Arg Asn
            20                  25                  30 tac cag ctc ccc gag ttc act atc aag gag atc cga gag tgc atc cct      144
Tyr Gln Leu Pro Glu Phe Thr Ile Lys Glu Ile Arg Glu Cys Ile Pro
        35                  40                  45 gcc cac tgc ttt gag cgc tcc ggt ctt cgt ggt ctc tgc cac gtt gcc      192
Ala His Cys Phe Glu Arg Ser Gly Leu Arg Gly Leu Cys His Val Ala
    50                  55                  60 att gat ctg acc tgg gcc tcg ctc ttg ttc ctg gct gca acc cag atc      240
Ile Asp Leu Thr Trp Ala Ser Leu Leu Phe Leu Ala Ala Thr Gln Ile
65                  70                  75                  80 gac aag ttc gag aac ccc ttg atc cgc tat ctg gcc tgg cct gcg tac      288
Asp Lys Phe Glu Asn Pro Leu Ile Arg Tyr Leu Ala Trp Pro Ala Tyr
                85                  90                  95
```

```
tgg atc atg cag ggc att gtc tgc acc ggc ata tgg gtg ctg gcc cac      336
Trp Ile Met Gln Gly Ile Val Cys Thr Gly Ile Trp Val Leu Ala His
        100                 105                 110 gag tgc ggt cac cag tcc ttc tcg acc tcc aag act ctc aac aac acc      384
Glu Cys Gly His Gln Ser Phe Ser Thr Ser Lys Thr Leu Asn Asn Thr
            115                 120                 125 gtc ggc tgg atc ctg cac tcg atg ctc ttg gtc ccc tac cac tcc tgg      432
Val Gly Trp Ile Leu His Ser Met Leu Leu Val Pro Tyr His Ser Trp
130                 135                 140 aga atc tcg cac tcg aag cac cac aag gcc act ggc cac atg acc aag      480
Arg Ile Ser His Ser Lys His His Lys Ala Thr Gly His Met Thr Lys
145                 150                 155                 160 gac cag gtc ttt gtt ccc aag acc cgc tcc cag gtt ggt ttg cct ccc      528
Asp Gln Val Phe Val Pro Lys Thr Arg Ser Gln Val Gly Leu Pro Pro
                165                 170                 175 aag gag agc gct gct gct gcc gtt caa gag gag gac atg tcc gtg cac      576
Lys Glu Ser Ala Ala Ala Ala Val Gln Glu Glu Asp Met Ser Val His
            180                 185                 190 ctg gat gag gag gcc cct att gtg act ttg ttc tgg atg gtg atc cag      624
Leu Asp Glu Glu Ala Pro Ile Val Thr Leu Phe Trp Met Val Ile Gln
        195                 200                 205 ttc ctg ttc gga tgg cct gca tac ctg atc atg aac gcc tct ggt cag      672
Phe Leu Phe Gly Trp Pro Ala Tyr Leu Ile Met Asn Ala Ser Gly Gln
210                 215                 220 gac tat ggc cgc tgg acc tcg cac ttc cac act tac tcg ccc atc ttt      720
Asp Tyr Gly Arg Trp Thr Ser His Phe His Thr Tyr Ser Pro Ile Phe
225                 230                 235                 240 gag ccc cgc aac ttc ttc gac att atc atc tcg gat ctc ggt gtg ttg      768
Glu Pro Arg Asn Phe Phe Asp Ile Ile Ile Ser Asp Leu Gly Val Leu
                245                 250                 255 gct gcc ctc ggt gcc ctg atc tac gct tcc atg cag ctg tcg ctc ttg      816
Ala Ala Leu Gly Ala Leu Ile Tyr Ala Ser Met Gln Leu Ser Leu Leu
            260                 265                 270 acc gtg acc aag tac tac atc atc ccg tac ctg ttt gtc aac ttt tgg      864
Thr Val Thr Lys Tyr Tyr Ile Ile Pro Tyr Leu Phe Val Asn Phe Trp
        275                 280                 285 ttg gtc ctg att act ttc ttg cag cac acc gac ccc aag ctg ccc cat      912
Leu Val Leu Ile Thr Phe Leu Gln His Thr Asp Pro Lys Leu Pro His
290                 295                 300 tac cgt gag ggt gcc tgg aac ttc cag cgt gga gcc ctc tgc acc gtt      960
Tyr Arg Glu Gly Ala Trp Asn Phe Gln Arg Gly Ala Leu Cys Thr Val
305                 310                 315                 320 gac cgc tcg ttt ggc aag ttc ttg gac cat atg ttc cac ggc atc gtc     1008
Asp Arg Ser Phe Gly Lys Phe Leu Asp His Met Phe His Gly Ile Val
                325                 330                 335 cat acc cat gtg gcc cat cac ttg ttc tcg cag atg ccg ttc tac cat     1056
His Thr His Val Ala His His Leu Phe Ser Gln Met Pro Phe Tyr His
            340                 345                 350 gct gaa gaa gct acc tac cat ctc aag aaa ctg ctg gga gag tac tac     1104
Ala Glu Glu Ala Thr Tyr His Leu Lys Lys Leu Leu Gly Glu Tyr Tyr
        355                 360                 365 gtt tac gac cca tcc ccg atc gtc gtt gcg gtc tgg agg tcg ttc cgc     1152
Val Tyr Asp Pro Ser Pro Ile Val Val Ala Val Trp Arg Ser Phe Arg
370                 375                 380 gag tgc cga ttc gtg gag gat cat gga gac gtg gtc ttt ttc aag aag     1200
Glu Cys Arg Phe Val Glu Asp His Gly Asp Val Val Phe Phe Lys Lys
385                 390                 395                 400 taa                                                                  1203
```

-continued

```
<210> SEQ ID NO 134
<211> LENGTH: 400
<212> TYPE: PRT
<213> ORGANISM: Mortieralla isabellina

<400> SEQUENCE: 134

Met Ala Pro Pro Asn Thr Ile Asp Ala Gly Leu Thr Gln Arg His Ile
1               5                   10                  15

Thr Thr Thr Ala Ala Pro Thr Ser Ala Lys Pro Ala Phe Glu Arg Asn
            20                  25                  30

Tyr Gln Leu Pro Glu Phe Thr Ile Lys Glu Ile Arg Glu Cys Ile Pro
        35                  40                  45

Ala His Cys Phe Glu Arg Ser Gly Leu Arg Gly Leu Cys His Val Ala
    50                  55                  60

Ile Asp Leu Thr Trp Ala Ser Leu Leu Phe Leu Ala Ala Thr Gln Ile
65                  70                  75                  80

Asp Lys Phe Glu Asn Pro Leu Ile Arg Tyr Leu Ala Trp Pro Ala Tyr
                85                  90                  95

Trp Ile Met Gln Gly Ile Val Cys Thr Gly Ile Trp Val Leu Ala His
            100                 105                 110

Glu Cys Gly His Gln Ser Phe Ser Thr Ser Lys Thr Leu Asn Asn Thr
        115                 120                 125

Val Gly Trp Ile Leu His Ser Met Leu Leu Val Pro Tyr His Ser Trp
    130                 135                 140

Arg Ile Ser His Ser Lys His His Lys Ala Thr Gly His Met Thr Lys
145                 150                 155                 160

Asp Gln Val Phe Val Pro Lys Thr Arg Ser Gln Val Gly Leu Pro Pro
                165                 170                 175

Lys Glu Ser Ala Ala Ala Val Gln Glu Glu Asp Met Ser Val His
            180                 185                 190

Leu Asp Glu Glu Ala Pro Ile Val Thr Leu Phe Trp Met Val Ile Gln
        195                 200                 205

Phe Leu Phe Gly Trp Pro Ala Tyr Leu Ile Met Asn Ala Ser Gly Gln
    210                 215                 220

Asp Tyr Gly Arg Trp Thr Ser His Phe His Thr Tyr Ser Pro Ile Phe
225                 230                 235                 240

Glu Pro Arg Asn Phe Phe Asp Ile Ile Ile Ser Asp Leu Gly Val Leu
                245                 250                 255

Ala Ala Leu Gly Ala Leu Ile Tyr Ala Ser Met Gln Leu Ser Leu Leu
            260                 265                 270

Thr Val Thr Lys Tyr Tyr Ile Ile Pro Tyr Leu Phe Val Asn Phe Trp
        275                 280                 285

Leu Val Leu Ile Thr Phe Leu Gln His Thr Asp Pro Lys Leu Pro His
    290                 295                 300

Tyr Arg Glu Gly Ala Trp Asn Phe Gln Arg Gly Ala Leu Cys Thr Val
305                 310                 315                 320

Asp Arg Ser Phe Gly Lys Phe Leu Asp His Met Phe His Gly Ile Val
                325                 330                 335

His Thr His Val Ala His His Leu Phe Ser Gln Met Pro Phe Tyr His
            340                 345                 350

Ala Glu Ala Thr Tyr His Leu Lys Lys Leu Leu Gly Glu Tyr Tyr
        355                 360                 365

Val Tyr Asp Pro Ser Pro Ile Val Val Ala Val Trp Arg Ser Phe Arg
    370                 375                 380
```

| Glu | Cys | Arg | Phe | Val | Glu | Asp | His | Gly | Asp | Val | Val | Phe | Phe | Lys | Lys |
|---|---|---|---|---|---|---|---|---|---|---|---|---|---|---|---|
| 385 | | | | 390 | | | | | 395 | | | | | 400 | |

<210> SEQ ID NO 135
<211> LENGTH: 1521
<212> TYPE: DNA
<213> ORGANISM: Mortierella alpina
<220> FEATURE:
<221> NAME/KEY: misc_feature
<223> OTHER INFORMATION: delta-6 desaturase
<300> PUBLICATION INFORMATION:
<308> DATABASE ACCESSION NUMBER: GenBank Accession No. AB070555
<309> DATABASE ENTRY DATE: 2004-07-28
<313> RELEVANT RESIDUES: (1)..(1521)

<400> SEQUENCE: 135

| acaacgtgct | cttgtcctca | gaagactgtt | gtgctcttcc | ttccaccacc | ccaagcactc | 60 |
|---|---|---|---|---|---|---|
| tctcacccca | agcactgcct | gccatgacca | ccagcgaccc | atctgtcaga | gcgttcacac | 120 |
| gctcagaagt | gttgcacgcc | gatgccttga | acgagggcaa | aaagaacgcc | gaggcaccgt | 180 |
| ttctcatgat | catcgacaac | aaggtctacg | atgtgcgcga | gtttatcccc | gaccatcctg | 240 |
| gtgggagcgt | cattttgacc | cacgtaggca | aggacggcac | cgacgttttc | gagaccttcc | 300 |
| atcctgaggc | tgcttgggag | acgctcgcca | atttttatgt | cggtgacatt | gtagaatccg | 360 |
| atcgcgccat | cgagaacgac | gagtttgcag | ctgaggttcg | taagctgcgg | acattgtttt | 420 |
| attctttggg | ctactacgac | tcatccaagg | tttactacgc | cttcaaggtc | tcgttcaacc | 480 |
| tctgcatctg | gggcctgtct | gcattcattg | ttgccaaatg | gggccagacc | tcgaccctcg | 540 |
| caaacgtgat | atcagcctca | ctcctgggtg | tcttttggca | acagtgcggt | tggctcgccc | 600 |
| atgatttctt | gcaccatcag | gtctttcacg | atcgattctg | gggcgatctg | ttcggtgcat | 660 |
| ttctcggcgg | agtctgtcaa | ggtttctcct | cgtcctggtg | gaaggacaaa | cacaacaccc | 720 |
| accacgcggc | gcccaatgtc | catggagagg | atcccgatat | cgacacacat | ccgcttttga | 780 |
| cgtggagtga | gcatgcgctc | gagatgtttt | cggatgtgcc | cgatgaggag | cttacccaaa | 840 |
| tgtggtcccg | gtttatggtt | ctgaaccagg | cctggttta | ctttcccatt | ctgtcatttg | 900 |
| cccgcctgtc | ctggtgcatc | cagtcgattc | tttttgtgct | accgaacgga | caggcacaca | 960 |
| aacctgcggg | ggctcgggtt | cccatctcgc | tggtggagca | attgtcgttg | gcgatgcact | 1020 |
| ggacctggta | cctggcaacc | atgttcctgt | tcatcaagga | tcccgtcaac | atgatggtgt | 1080 |
| atttcttggt | ctcgcaagct | gtctgcggca | acctgttagc | gattgtgttc | tcgctgaacc | 1140 |
| ataacggtat | gcctgtgatc | tcgcaggagg | aagcggtcga | gatggatttc | ttcacaaagc | 1200 |
| agatcattac | gggtcgtgat | gtctacccgg | gttggtttgc | agactggttc | acgggtggat | 1260 |
| tgaactatca | gattgaacac | catctgttcc | cgtcgatgcc | tcgacaccat | ttctcaagaa | 1320 |
| tccagcccgc | ggttgaatcg | ctgtgcaaga | agtacgggt | ccgataccat | acgacgggga | 1380 |
| tgattgctgg | caccgcagag | gtcttttcgc | gactgaacga | ggtgtcccag | gctgcaagca | 1440 |
| agctcggcaa | gtctgcttga | gtctttcatg | tcctcaagtt | gattctagat | acttattttc | 1500 |
| gcagacttct | atcgataaat | t | | | | 1521 |

<210> SEQ ID NO 136
<211> LENGTH: 458
<212> TYPE: PRT
<213> ORGANISM: Mortierella alpina
<300> PUBLICATION INFORMATION:
<308> DATABASE ACCESSION NUMBER: GenBank Accession No. AB070555
<309> DATABASE ENTRY DATE: 2004-07-28
<313> RELEVANT RESIDUES: (1)..(458)

<400> SEQUENCE: 136

```
Met Thr Thr Ser Asp Pro Ser Val Arg Ala Phe Thr Arg Ser Glu Val
1               5                   10                  15

Leu His Ala Asp Ala Leu Asn Glu Gly Lys Lys Asn Ala Glu Ala Pro
            20                  25                  30

Phe Leu Met Ile Ile Asp Asn Lys Val Tyr Asp Val Arg Glu Phe Ile
            35                  40                  45

Pro Asp His Pro Gly Gly Ser Val Ile Leu Thr His Val Gly Lys Asp
        50                  55                  60

Gly Thr Asp Val Phe Glu Thr Phe His Pro Glu Ala Ala Trp Glu Thr
65                  70                  75                  80

Leu Ala Asn Phe Tyr Val Gly Asp Ile Val Glu Ser Asp Arg Ala Ile
                85                  90                  95

Glu Asn Asp Glu Phe Ala Ala Glu Val Arg Lys Leu Arg Thr Leu Phe
            100                 105                 110

Tyr Ser Leu Gly Tyr Tyr Asp Ser Ser Lys Val Tyr Ala Phe Lys
        115                 120                 125

Val Ser Phe Asn Leu Cys Ile Trp Gly Leu Ser Ala Phe Ile Val Ala
    130                 135                 140

Lys Trp Gly Gln Thr Ser Thr Leu Ala Asn Val Ile Ser Ala Ser Leu
145                 150                 155                 160

Leu Gly Val Phe Trp Gln Gln Cys Gly Trp Leu Ala His Asp Phe Leu
                165                 170                 175

His His Gln Val Phe His Asp Arg Phe Trp Gly Asp Leu Phe Gly Ala
            180                 185                 190

Phe Leu Gly Gly Val Cys Gln Gly Phe Ser Ser Trp Trp Lys Asp
        195                 200                 205

Lys His Asn Thr His His Ala Ala Pro Asn Val His Gly Glu Asp Pro
    210                 215                 220

Asp Ile Asp Thr His Pro Leu Leu Thr Trp Ser Glu His Ala Leu Glu
225                 230                 235                 240

Met Phe Ser Asp Val Pro Asp Glu Glu Leu Thr Gln Met Trp Ser Arg
                245                 250                 255

Phe Met Val Leu Asn Gln Ala Trp Phe Tyr Phe Pro Ile Leu Ser Phe
            260                 265                 270

Ala Arg Leu Ser Trp Cys Ile Gln Ser Ile Leu Phe Val Leu Pro Asn
        275                 280                 285

Gly Gln Ala His Lys Pro Ala Gly Ala Arg Val Pro Ile Ser Leu Val
    290                 295                 300

Glu Gln Leu Ser Leu Ala Met His Trp Thr Trp Tyr Leu Ala Thr Met
305                 310                 315                 320

Phe Leu Phe Ile Lys Asp Pro Val Asn Met Met Val Tyr Phe Leu Val
                325                 330                 335

Ser Gln Ala Val Cys Gly Asn Leu Leu Ala Ile Val Phe Ser Leu Asn
            340                 345                 350

His Asn Gly Met Pro Val Ile Ser Gln Glu Ala Val Glu Met Asp
        355                 360                 365

Phe Phe Thr Lys Gln Ile Ile Thr Gly Arg Asp Val Tyr Pro Gly Trp
    370                 375                 380

Phe Ala Asp Trp Phe Thr Gly Gly Leu Asn Tyr Gln Ile Glu His His
385                 390                 395                 400

Leu Phe Pro Ser Met Pro Arg His His Phe Ser Lys Ile Gln Pro Ala
```

```
                    405                 410                 415
        Val Glu Ser Leu Cys Lys Lys Tyr Gly Val Arg Tyr His Thr Thr Gly
                420                 425                 430

Met Ile Ala Gly Thr Ala Glu Val Phe Ser Arg Leu Asn Glu Val Ser
                435                 440                 445

Gln Ala Ala Ser Lys Leu Gly Lys Ser Ala
            450                 455

<210> SEQ ID NO 137
<211> LENGTH: 4313
<212> TYPE: DNA
<213> ORGANISM: Artificial Sequence
<220> FEATURE:
<223> OTHER INFORMATION: Plasmid pZKUM

<400> SEQUENCE: 137
taatcgagct tggcgtaatc atggtcatag ctgtttcctg tgtgaaattg ttatccgctc      60
acaattccac acaacatacg agccggaagc ataaagtgta aagcctgggg tgcctaatga    120
gtgagctaac tcacattaat tgcgttgcgc tcactgcccg ctttccagtc gggaaacctg    180
tcgtgccagc tgcattaatg aatcggccaa cgcgcgggga gaggcggttt gcgtattggg    240
cgctcttccg cttcctcgct cactgactcg ctgcgctcgg tcgttcggct gcggcgagcg    300
gtatcagctc actcaaaggc ggtaatacgg ttatccacag aatcagggga taacgcagga    360
aagaacatgt gagcaaaagg ccagcaaaag gccaggaacc gtaaaaaggc cgcgttgctg    420 gcgttttttcc ataggctccg cccccctgac gagcatcaca aaaatcgacg ctcaagtcag    480
aggtggcgaa acccgacagg actataaaga taccaggcgt ttccccctgg aagctccctc    540
gtgcgctctc ctgttccgac cctgccgctt accggatacc tgtccgcctt tctcccttcg    600
ggaagcgtgg cgctttctca tagctcacgc tgtaggtatc tcagttcggt gtaggtcgtt    660
cgctccaagc tgggctgtgt gcacgaaccc cccgttcagc ccgaccgctg cgccttatcc    720
ggtaactatc gtcttgagtc aacccggta agacacgact tatcgccact ggcagcagcc    780
actggtaaca ggattagcag agcgaggtat gtaggcggtg ctacagagtt cttgaagtgg    840
tggcctaact acggctacac tagaaggaca gtatttggta tctgcgctct gctgaagcca    900
gttaccttcg gaaaaagagt tggtagctct tgatccggca acaaaccac cgctggtagc    960 ggtggttttt ttgtttgcaa gcagcagatt acgcgcagaa aaaaggatc tcaagaagat   1020 cctttgatct tttctacggg gtctgacgct cagtggaacg aaaactcacg ttaagggatt   1080
ttggtcatga gattatcaaa aaggatcttc acctagatcc ttttaaatta aaaatgaagt   1140
tttaaatcaa tctaaagtat atatgagtaa acttggtctg acagttacca atgcttaatc   1200
agtgaggcac ctatctcagc gatctgtcta tttcgttcat ccatagttgc ctgactcccc   1260
gtcgtgtaga taactacgat acgggagggc ttaccatctg gccccagtgc tgcaatgata   1320
ccgcgagacc cacgctcacc ggctccagat ttatcagcaa taaaccagcc agccggaagg   1380
gccgagcgca gaagtggtcc tgcaacttta tccgcctcca tccagtctat taattgttgc   1440
cgggaagcta gagtaagtag ttcgccagtt aatagtttgc gcaacgttgt tgccattgct   1500
acaggcatcg tggtgtcacg ctcgtcgttt ggtatggctt cattcagctc cggttcccaa   1560
cgatcaaggc gagttacatg atccccccatg ttgtgcaaaa aagcggttag ctccttcggt   1620
cctccgatcg ttgtcagaag taagttggcc gcagtgttat cactcatggt tatggcagca   1680
ctgcataatt ctcttactgt catgccatcc gtaagatgct tttctgtgac tggtgagtac   1740
```

```
tcaaccaagt cattctgaga atagtgtatg cggcgaccga gttgctcttg cccggcgtca    1800
atacgggata ataccgcgcc acatagcaga actttaaaag tgctcatcat tggaaaacgt    1860
tcttcgggc  gaaaactctc aaggatctta ccgctgttga gatccagttc gatgtaaccc    1920
actcgtgcac ccaactgatc ttcagcatct tttactttca ccagcgtttc tgggtgagca    1980
aaaacaggaa ggcaaaatgc cgcaaaaaag ggaataaggg cgacacggaa atgttgaata    2040
ctcatactct tccttttca  atattattga agcatttatc agggttattg tctcatgagc    2100
ggatacatat ttgaatgtat ttagaaaaat aaacaaatag gggttccgcg cacatttccc    2160
cgaaaagtgc cacctgacgc gccctgtagc ggcgcattaa gcgcggcggg tgtggtggtt    2220
acgcgcagcg tgaccgctac acttgccagc gccctagcgc ccgctccttt cgctttcttc    2280
ccttcctttc tcgccacgtt cgccggcttt ccccgtcaag ctctaaatcg ggggctccct    2340
ttagggttcc gatttagtgc tttacggcac ctcgacccca aaaaacttga ttagggtgat    2400
ggttcacgta gtgggccatc gccctgatag acggtttttc gccctttgac gttggagtcc    2460
acgttcttta atagtggact cttgttccaa actggaacaa cactcaaccc tatctcggtc    2520
tattcttttg atttataagg gattttgccg atttcggcct attggttaaa aaatgagctg    2580
atttaacaaa aatttaacgc gaattttaac aaaatattaa cgcttacaat tccattcgc    2640
cattcaggct gcgcaactgt tgggaagggc gatcggtgcg ggcctcttcg ctattacgcc    2700
agctggcgaa aggggatgt  gctgcaaggc gattaagttg ggtaacgcca gggttttccc    2760
agtcacgacg ttgtaaaacg acggccagtg aattgtaata cgactcacta tagggcgaat    2820
tgggtaccgg gcccccctc  gaggtcgacg agtatctgtc tgactcgtca ttgccgcctt    2880
tggagtacga ctccaactat gagtgtgctt ggatcacttt gacgatacat tcttcgttgg    2940
aggctgtggg tctgacagct gcgttttcgg cgcggttggc cgacaacaat atcagctgca    3000
acgtcattgc tggctttcat catgatcaca tttttgtcgg caaaggcgac gcccagagag    3060
ccattgacgt tctttctaat ttggaccgat agccgtatag tccagtctat ctataagttc    3120
aactaactcg taactattac cataacatat acttcactgc cccagataag gttccgataa    3180
aaagttctgc agactaaatt tatttcagtc tcctcttcac caccaaaatg ccctcctacg    3240
aagctcgagt gctcaagctc gtggcagcca agaaaaccaa cctgtgtgct tctctggatg    3300
ttaccaccac caaggagctc attgagcttg ccgataaggt cggaccttat gtgtgcatga    3360
tcaaaaccca tatcgacatc attgacgact tcacctacgc cggcactgtg ctccccctca    3420
aggaacttgc tcttaagcac ggtttcttcc tgttcgagga cagaaagttc gcagatattg    3480
gcaacactgt caagcaccag taccggtgtc accgaatcgc cgagtggtcc gatatcacca    3540
acgcccacgg tgtacccgga accggaatcg attgctggcc tgcgagctgg tgcgtacgag    3600
gaaactgtct ctgaacagaa gaaggaggac gtctctgact acgagaactc ccagtacaag    3660
gagttcctag tccctctcc  caacgagaag ctggccagag tctgctcat  gctggccgag    3720
ctgtcttgca agggctctct ggccactggc gagtactcca agcagaccat tgagcttgcc    3780
cgatccgacc ccgagtttgt ggttggcttc attgcccaga accgacctaa gggcgactct    3840
gaggactggc ttattctgac ccccggggtg ggtcttgacg acaagggaga cgctctcgga    3900
cagcagtacc gaactgttga ggatgtcatg tctaccggaa cggatatcat aattgtcggc    3960
cgaggtctgt acggccagaa ccgagatcct attgaggagg ccaagcgata ccagaaggct    4020
ggctgggagg cttaccagaa gattaactgt tagaggttag actatggata tgtaatttaa    4080
ctgtgtatat agagagcgtg caagtatgga gcgcttgttc agcttgtatg atggtcagac    4140
```

-continued

| | |
|---|---|
| gacctgtctg atcgagtatg tatgatactg cacaacctgt gtatccgcat gatctgtcca | 4200 |
| atggggcatg ttgttgtgtt tctcgatacg gagatgctgg gtacagtgct aatacgttga | 4260 |
| actacttata cttatatgag gctcgaagaa agctgacttg tgtatgactt aat | 4313 |

<210> SEQ ID NO 138
<211> LENGTH: 10838
<212> TYPE: DNA
<213> ORGANISM: Artificial Sequence
<220> FEATURE:
<223> OTHER INFORMATION: Plasmid pKO2UF2PE
<220> FEATURE:
<221> NAME/KEY: misc_feature
<222> LOCATION: (1615)..(1618)
<223> OTHER INFORMATION: n is a, c, g, or t
<220> FEATURE:
<221> NAME/KEY: misc_feature
<222> LOCATION: (1623)..(1623)
<223> OTHER INFORMATION: n is a, c, g, or t

<400> SEQUENCE: 138

| | |
|---|---|
| aaattgcccc ggagaagacg gccaggccgc ctagatgaca aattcaacaa ctcacagctg | 60 |
| actttctgcc attgccacta gggggggggcc tttttatatg gccaagccaa gctctccacg | 120 |
| tcggttgggc tgcacccaac aataaatggg taggttgca ccaacaaagg gatgggatgg | 180 |
| ggggtagaag atacgaggat aacggggctc aatggcacaa ataagaacga atactgccat | 240 |
| taagactcgt gatccagcga ctgacaccat tgcatcatct aagggcctca aaactacctc | 300 |
| ggaactgctg cgctgatctg gacaccacag aggttccgag cactttaggt tgcaccaaat | 360 |
| gtcccaccag gtgcaggcag aaaacgctgg aacagcgtgt acagtttgtc ttaacaaaaa | 420 |
| gtgagggcgc tgaggtcgag cagggtggtg tgacttgtta tagcctttag agctgcgaaa | 480 |
| gcgcgtatgg atttggctca tcaggccaga ttgagggtct gtggacacat gtcatgttag | 540 |
| tgtacttcaa tcgcccctg gatatagccc cgacaatagg ccgtggcctc attttttgc | 600 |
| cttccgcaca tttccattgc tcgatacca caccttgctt ctcctgcact tgccaacctt | 660 |
| aatactggtt tacattgacc aacatcttac aagcgggggg cttgtctagg gtatatataa | 720 |
| acagtggctc tcccaatcgg ttgccagtct cttttttcct ttctttcccc acagattcga | 780 |
| aatctaaact acacatcaca gaattccgag ccgtgagtat ccacgacaag atcagtgtcg | 840 |
| agacgacgcg ttttgtgtaa tgacacaatc cgaaagtcgc tagcaacaca cactctctac | 900 |
| acaaactaac ccagctctgg taccatggcg tccacttcgg ctctgcccaa gcagaaccct | 960 |
| gcgcttagac gcaccgtcac ctcaactact gtgacggatt ctgagtctgc cgccgtctct | 1020 |
| ccttcagact ctccccgcca ctcggcctct tccacatcgc tctcgtccat gtccgaggtt | 1080 |
| gatatcgcca agcccaagtc cgagtatggt gtcatgctcg acacctacgg caaccagttc | 1140 |
| gaggttcccg actttaccat caaggacatc tacaatgcca tccctaagca ctgcttcaag | 1200 |
| cgctccgctc tcaagggata cggttatatc ctccgcgaca ttgtcctcct gactaccact | 1260 |
| ttcagcatct ggtacaactt tgtgaccccc gaatatatcc cctccacccc cgcccgcgct | 1320 |
| ggtctgtggg ccgtgtacac cgttcttcag ggtcttttcg gtactggtct ctgggttatt | 1380 |
| gcccatgagt gcggtcacgg tgcttttctcc gattctcgca tcatcaacga cattactggc | 1440 |
| tgggttcttc actcttccct ccttgtcccc tacttcagct ggcaaatctc ccaccgaaag | 1500 |
| caccacaagg ccactggcaa catggagcgt gacatggtct tcgttcccg aacccgcgag | 1560 |
| cagcaggcta ctcgtctcgg aaagatgacc cacgagctcg ctcatcttac tgagnnnntc | 1620 |

```
gtnggctggc ccaactacct catcaccaat gttaccggcc acaactacca cgagcgccag   1680
cgtgagggtc gcggcaaggg caagcataac ggcctcggcg gtggtgttaa ccacttcgat   1740
ccccgcagcc ctctgtacga gaacagtgac gctaagctca tcgtcctcag cgatattggt   1800
atcggtctga tggccactgc tctgtacttc ctcgttcaga agttcggttt ctacaacatg   1860
gccatctggt actttgttcc ctacctctgg gttaaccact ggctcgttgc catcaccttc   1920
ctccagcaca ccgaccctac ccttccccac tacaccaacg acgagtggaa cttcgtccgt   1980
ggtgccgctg ctaccattga ccgtgagatg ggcttcatcg gccgccacct tctccacggc   2040
atcatcgaga ctcatgtcct ccaccactac gtcagcagca tccccttcta caacgcggac   2100
gaggccaccg aggccattaa gcccatcatg ggcaagcact accgggctga tgtccaggat   2160
ggtcctcgtg gcttcatccg cgccatgtac cgcagtgcgc gtatgtgcca gtgggttgag   2220
cccagcgctg gtgccgaggg tgctggtaag ggtgttctgt tcttccgcaa ccgcaacaac   2280
gtgggcaccc ccccgctgt tatcaagccc gttgcttaag taggcgcggc cgcaagtgtg   2340
gatggggaag tgagtgcccg gttctgtgtg cacaattggc aatccaagat ggatggattc   2400
aacacaggga tatagcgagc tacgtggtgg tgcgaggata tagcaacgga tatttatgtt   2460
tgacacttga gaatgtacga tacaagcact gtccaagtac aatactaaac atactgtaca   2520
tactcatact cgtacccggg caacggtttc acttgagtgc agtggctagt gctcttactc   2580
gtacagtgtg caatactgcg tatcatagtc tttgatgtat atcgtattca ttcatgttag   2640
ttgcgtacgg gtgaagcttc cactggtcgg cgtggtagtg gggcagagtg gggtcggtgt   2700
gctgcaggta ggtgatggcc acgagccagt ggttgaccca caggtagggg atcaggtagt   2760
agagggtgac ggaagccagg ccccatcggt tgatggagta tgcgatgacg gacatggtga   2820
taccaatacc gacgttagag atccagatgt tgaaccagtc cttcttctca aacagcgggg   2880 cgttgggggtt gaagtggttg acagcccatt tgttgagctt ggggtacttc tgtccggtaa   2940
cgtaagacag cagatacaga ggccatccaa acacctgctg ggtgatgagg ccgtagaggg   3000
tcatgagggg agcgtcctca gcaagctcag accagtcatg ggcgcctcgg ttctccataa   3060
actcctttcg gtccttgggc acaaacacca tatcacgggt gaggtgacca gtggacttgt   3120
ggtgcatgga gtgggtcagc ttccaggcgt agtaagggac cagcatggag gagtgcagaa   3180
cccatccggt gacgttgttg acggtgttag agtcggagaa agcagagtgg ccacactcgt   3240
gggcaagaac ccacagaccg gtgccaaaca gaccctggac aatggagtac atggcccagg   3300
ccacagctcg gccggaagcc gagggaataa gaggcaggta cgcgtaggcc atgtaggcaa   3360
aaacggcgat aaagaagcag gcgcgccagc tgcattaatg aatcggccaa cgcgcgggga   3420
gaggcggttt gcgtattggg cgctcttccg cttcctcgct cactgactcg ctgcgctcgg   3480
tcgttcggct gcggcgagcg gtatcagctc actcaaaggc ggtaatacgg ttatccacag   3540
aatcagggga taacgcagga agaacatgt gagcaaaagg ccagcaaaag gccaggaacc   3600
gtaaaaaggc cgcgttgctg gcgtttttcc ataggctccg ccccctgac gagcatcaca   3660 aaaatcgacg ctcaagtcag aggtggcgaa acccgacagg actataaaga taccaggcgt   3720
ttccccctgg aagctccctc gtgcgctctc ctgttccgac cctgccgctt accggatacc   3780
tgtccgcctt tctcccttcg ggaagcgtgg cgctttctca tagctcacgc tgtaggtatc   3840
tcagttcggt gtaggtcgtt cgctccaagc tgggctgtgt gcacgaaccc cccgttcagc   3900
ccgaccgctg cgccttatcc ggtaactatc gtcttgagtc caacccggta agacacgact   3960
tatcgccact ggcagcagcc actggtaaca ggattagcag agcgaggtat gtaggcggtg   4020
```

```
ctacagagtt cttgaagtgg tggcctaact acggctacac tagaagaaca gtatttggta    4080
tctgcgctct gctgaagcca gttaccttcg aaaaagagt tggtagctct tgatccggca     4140
aacaaaccac cgctggtagc ggtggttttt ttgtttgcaa gcagcagatt acgcgcagaa    4200
aaaaggatc tcaagaagat cctttgatct tttctacggg gtctgacgct cagtggaacg    4260
aaaactcacg ttaagggatt ttggtcatga gattatcaaa aaggatcttc acctagatcc    4320
ttttaaatta aaaatgaagt tttaaatcaa tctaaagtat atatgagtaa acttggtctg    4380
acagttacca atgcttaatc agtgaggcac ctatctcagc gatctgtcta tttcgttcat    4440
ccatagttgc ctgactcccc gtcgtgtaga taactacgat acgggagggc ttaccatctg    4500
gccccagtgc tgcaatgata ccgcgagacc cacgctcacc ggctccagat ttatcagcaa    4560
taaaccagcc agccggaagg gccgagcgca gaagtggtcc tgcaacttta tccgcctcca    4620
tccagtctat taattgttgc cgggaagcta gagtaagtag ttcgccagtt aatagtttgc    4680
gcaacgttgt tgccattgct acaggcatcg tggtgtcacg ctcgtcgttt ggtatggctt    4740
cattcagctc cggttcccaa cgatcaaggc gagttacatg atcccccatg ttgtgcaaaa    4800
aagcggttag ctccttcggt cctccgatcg ttgtcagaag taagttggcc gcagtgttat    4860
cactcatggt tatggcagca ctgcataatt ctcttactgt catgccatcc gtaagatgct    4920
tttctgtgac tggtgagtac tcaaccaagt cattctgaga atagtgtatg cggcgaccga    4980
gttgctcttg cccggcgtca atacgggata ataccgcgcc acatagcaga actttaaaag    5040
tgctcatcat tggaaaacgt tcttcggggc gaaaactctc aaggatctta ccgctgttga    5100
gatccagttc gatgtaaccc actcgtgcac ccaactgatc ttcagcatct tttactttca    5160
ccagcgtttc tgggtgagca aaaacaggaa ggcaaaatgc cgcaaaaaag ggaataaggg    5220
cgacacggaa atgttgaata ctcatactct tcctttttca atattattga agcatttatc    5280
agggttattg tctcatgagc ggatacatat ttgaatgtat ttagaaaaat aaacaaatag    5340
gggttccgcg cacatttccc cgaaaagtgc cacctgatgc ggtgtgaaat accgcacaga    5400
tgcgtaagga gaaaataccg catcaggaaa ttgtaagcgt taatattttg ttaaaattcg    5460
cgttaaattt ttgttaaatc agctcatttt ttaaccaata ggccgaaatc ggcaaaatcc    5520
cttataaatc aaaagaatag accgagatag ggttgagtgt tgttccagtt tggaacaaga    5580
gtccactatt aaagaacgtg gactccaacg tcaaagggcg aaaaaccgtc tatcagggcg    5640
atggcccact acgtgaacca tcaccctaat caagttttt ggggtcgagg tgccgtaaag    5700
cactaaatcg gaaccctaaa gggagccccc gatttagagc ttgacgggga agccggcga    5760
acgtggcgag aaaggaaggg aagaaagcga aaggagcggg cgctagggcg ctggcaagtg    5820
tagcggtcac gctgcgcgta accaccacac ccgccgcgct taatgcgccg ctacagggcg    5880
cgtccattcg ccattcaggc tgcgcaactg ttgggaaggg cgatcggtgc gggcctcttc    5940
gctattacgc cagctggcga aggggggatg tgctgcaagg cgattaagtt gggtaacgcc    6000
agggttttcc cagtcacgac gttgtaaaac gacggccagt gaattgtaat acgactcact    6060
ataggcgaa ttgggcccga cgtcgcatgc ttgaatctac aagtaggagg gttggagtga    6120
ttaagtgaaa cttctttaac ggctctatgc cagttctatt gatatccgaa acatcagtat    6180
gaaggtctga taagggtgac ttcttcccac agattcgtat cagtacgagt acgagaccgg    6240
tacttgtaac agtattgata ctaaagggaa actacaacgg ttgtcagcgt aatgtgactt    6300
cgcccatgaa cgcagacacg cagtgccgag tgcggtgata tcgcctactc gttacgtcca    6360
```

```
tggactacac aaccccctcgg cttcgcttgg cttagcctcg ggctcggtgc tgttcagtta    6420
aaacacaatc aaataacatt tctacttttt agaaggcagg ccgtcaggag caactccgac    6480
tccattgacg tttctaaaca tctgaatgcc ttccttacct tcaacaaact ggcaggttcg    6540
ggcgacagtg taaagagact tgatgaagtt ggtgtcgtcg tgtcggtagt gcttgcccat    6600
gaccttcttg atcttctcag tggcgattcg ggcgttgtag aagggaattc cgtcgtcgcc    6660
tgagtcgacg agtatctgtc tgactcgtca ttgccgcctt tggagtacga ctccaactat    6720
gagtgtgctt ggatcacttt gacgatacat tcttcgttgg aggctgtggg tctgacagct    6780
gcgttttcgg cgcggttggc cgacaacaat atcagctgca acgtcattgc tggctttcat    6840
catgatcaca tttttgtcgg caaaggcgac gcccagagag ccattgacgt tctttctaat    6900
ttggaccgat agccgtatag tccagtctat ctataagttc aactaactcg taactattac    6960
cataacatat acttcactgc cccagataag gttccgataa aaagttctgc agactaaatt    7020
tatttcagtc tcctcttcac caccaaaatg ccctcctacg aagctcgagc taacgtccac    7080
aagtccgcct tgccgctcg agtgctcaag ctcgtggcag ccaagaaaac caacctgtgt    7140
gcttctctgg atgttaccac caccaaggag ctcattgagc ttccgataaa ggtcggacct    7200
tatgtgtgca tgatcaaaac ccatatcgac atcattgacg acttcaccta cgccggcact    7260
gtgctccccc tcaaggaact tgctcttaag cacggttttct tcctgttcga ggacagaaag    7320
ttcgcagata ttggcaacac tgtcaagcac cagtaccggt gtcaccgaat cgccgagtgg    7380
tccgatatca ccaacgccca cggtgtaccc ggaaccggaa tcattgctgg cctgcgagct    7440
ggtgccgagg aaactgtctc tgaacagaag aaggaggacg tctctgacta cgagaactcc    7500
cagtacaagg agttcctagt cccctctccc aacgagaagc tggccagagg tctgctcatg    7560
ctggccgagc tgtcttgcaa gggctctctg gccactggcg agtactccaa gcagaccatt    7620
gagcttgccc gatccgaccc cgagtttgtg gttggcttca ttgccagaa ccgacctaag    7680
ggcgactctg aggactggct tattctgacc cccggggtgg gtcttgacga caagggagac    7740
gctctcggac agcagtaccg aactgttgag gatgtcatgt ctaccggaac ggatatcata    7800
attgtcggcc gaggtctgta cggccagaac cgagatccta ttgaggaggc caagcgatac    7860
cagaaggctg gctgggaggc ttaccagaag attaactgtt agaggttaga ctatggatat    7920
gtaatttaac tgtgtatata gagagcgtgc aagtatggag cgcttgttca gcttgtatga    7980
tggtcagacg acctgtctga tcgagtatgt atgatactgc acaacctgtg tatccgcatg    8040
atctgtccaa tggggcatgt tgttgtgttt ctcgatacgg agatgctggg tacagtgcta    8100
atacgttgaa ctacttatac ttatatgagg ctcgaagaaa gctgacttgt gtatgactta    8160
attaatttga atcgaatcga tgagcctaaa atgaacccga gtatatctca taaaattctc    8220
ggtgagaggt ctgtgactgt cagtacaagg tgccttcatt atgccctcaa ccttaccata    8280
cctcactgaa tgtagtgtac ctctaaaaat gaaatacagt gccaaaagcc aaggcactga    8340
gctcgtctaa cggacttgat atacaaccaa ttaaaacaaa tgaaaagaaa tacagttctt    8400
tgtatcattt gtaacaatta ccctgtacaa actaaggtat tgaaatccca caatattccc    8460
aaagtccacc cctttccaaa ttgtcatgcc tacaactcat ataccaagca ctaacctacc    8520
gtttaaacag tgtacgcaga tcccgtcaac agttttatat atcgtagtta caaccatcaa    8580
cacttttttgg taagtgtacc attctatact ccaactggtc tgcaactgta caagtagaca    8640
tgttaatggt agttaataac atctacagca gaacctatgg taaagacatt gcatttttac    8700
aggaagtatc gtcctacacg ttgataaatc caaagatgcg gaacttcttc cacttttatc    8760
```

```
atcatcccct actcgtacac tcgtactctt tgttcgatcg cgattcattt ctataaataa    8820
tcttgtatgt acatgcggcc gcttactgga gctttctggc cttctccttg gcagcgtcag    8880
ccttggcctg cttggcgagc ttggcgttct ttcggtaaaa gttgtagaag agaccgagca    8940
tggtccacat gtagaaccag agcagagcgg tgatgaagaa ggggtatcca ggtcggccaa    9000
ggaccttcat ggcgtacatg tcccaggaag actggacaga catcatgcag aactgggtca    9060
tctgggatcg agtgatgtag aacttgatga acgacacctg cttgaagccc agggcagaca    9120
gaaagtagta gccgtacatg atgacgtgga tgaaggagtt cagggcagca gagaagtagg    9180
cttcaccgtt gggagcaacg aaggtgacca gccaccagat ggtgaagatg aagagtggt     9240 ggtacacgtg cagaaaggaa atctgtcggt tgttcttctt gaggaccatg atcatggtgt    9300
cgacaaactc catgatcttg gagaagtaga agagccagat catcttagcc ataggggagac   9360 ccttgaaggt gtgatcggca gcgttctcaa acagtccata gttggcctga taagcctcgt    9420
acaggatgcc accgcacatg taggcggaga tggagaccag acagaagttg tgcaggaggg    9480
agaaggtctt gacctcgaat cgttcaaagt tcttcatgat ctgcataccc acaaacacgg    9540
tgaccaggta ggcgagcacg atcaggagca cgtggaaggg gttcatcaga ggcagctctc    9600
gagccagggg agactccacg gcaaccagga agcctcgagt gtgatggaca atggtgggaa    9660
tgtacttctc ggcctgggca accagggcag cctccagggg atcgacgtag ggagcagctc    9720
ggacaccgat agcgctggcg aggtccatga acaggtcctg aggcatcttg gagggcagga    9780
agggagcaat ggactccatg gttagcgtgt cgtgttttg ttgtgctgga agaaccaaag     9840
ggtggcgcaa tgtgtgtaga tatatatgtc gtgacccaca agtcacacaa acaagtatcg    9900
ggaggagtgg tgcacctcta tgcggagaaa ccttataccg ctgtagacca actggggcag    9960
aggtgtgagt tgaagtcagc tggaggagat gtgtgacaga agcacaagaa gtgagattgt   10020
gagatgtatg tctaggggg gaagtttttgt gtcaaatata tgggaattat tatcagcacc    10080
acgaaattat acgcctcata tgacccattt aggtggatag atcatggaca ctgttgacag   10140
ctgcgaagaa aaagcgtatt ggggatgatc cgaaattagt ccggtaccga ggcgcaaata   10200
cgtaagacag ccgatwaaat atatgcgaga aacaccaaag agactctaga tgtttgtttg   10260
gcacagtttt gacttctgcg aaggccttac accaccttgt tgacccttgt cgcgggtcgg   10320
gcaatatcgg ctgacagagt tttacttgct caataagata cgagctgcat agagttgaac   10380
tacaggacaa tattggggct ggccacatga agggcattgt ttggaggtgt attgatggtg   10440
aaaacacgat atgaaatgac aacgcccctt gttttattat tattcttatt atttttgggtg   10500 cttctctatc catacaagca cctcctaaca tgcttcataa gtgacctcct catcacaagg   10560
cctgaggtct catttatcca gtggcgccaa gctaaactaa aactggtccg agtagactaa   10620
ggcgaagaga gaaggagaga agacagtttt tttgtggccg cctgtgaaca atgaaaacga   10680
tgagggtgag atggagcaaa ccatatggac agtcagagga gtacacgctg cttacataat   10740
ggcgcaacga ccacatgtcc cacagatacg cattatgcct gtacatattc cgggggaggt   10800
atgtaccagt agttcgcctg ctaccgttag ctacattt                           10838
```

<210> SEQ ID NO 139
<211> LENGTH: 5833
<212> TYPE: DNA
<213> ORGANISM: Artificial Sequence
<220> FEATURE:
<223> OTHER INFORMATION: Plasmid pZKUT16

<400> SEQUENCE: 139

```
gtacgaggaa actgtctctg aacagaagaa ggaggacgtc tctgactacg agaactccca      60
gtacaaggag ttcctagtcc cctctcccaa cgagaagctg ccagaggtc tgctcatgct      120
ggccgagctg tcttgcaagg gctctctggc cactggcgag tactccaagc agaccattga     180
gcttgcccga tccgaccccg agtttgtggt tggcttcatt gcccagaacc gacctaaggg     240
cgactctgag gactggctta ttctgacccc cggggtgggt cttgacgaca agggagacgc     300
tctcggacag cagtaccgaa ctgttgagga tgtcatgtct accggaacgg atatcataat     360
tgtcggccga ggtctgtacg ccagaaccg agatcctatt gaggaggcca agcgatacca     420
gaaggctggc tgggaggctt accagaagat taactgttag aggttagact atggatatgt     480
aatttaactg tgtatataga gagcgtgcaa gtatggagcg cttgttcagc ttgtatgatg     540
gtcagacgac ctgtctgatc gagtatgtat gatactgcac aacctgtgta tccgcatgat     600
ctgtccaatg gggcatgttg ttgtgtttct cgatacggag atgctgggta cagtgctaat     660
acgttgaact acttatactt atatgaggct cgaagaaagc tgacttgtgt atgacttaat     720
taatcgagct tggcgtaatc atggtcatag ctgtttcctg tgtgaaattg ttatccgctc     780
acaattccac acaacatacg agccggaagc ataaagtgta aagcctgggg tgcctaatga     840
gtgagctaac tcacattaat tgcgttgcgc tcactgcccg cttttccagtc gggaaacctg     900
tcgtgccagc tgcattaatg aatcggccaa cgcgcgggga gaggcggttt gcgtattggg     960
cgctcttccg cttcctcgct cactgactcg ctgcgctcgg tcgttcggct gcggcgagcg    1020
gtatcagctc actcaaaggc ggtaatacgg ttatccacag aatcagggga taacgcagga    1080
aagaacatgt gagcaaaagg ccagcaaaag gccaggaacc gtaaaaaggc cgcgttgctg    1140
gcgttttttcc ataggctccg cccccctgac gagcatcaca aaaatcgacg ctcaagtcag    1200
aggtggcgaa acccgacagg actataaaga taccaggcgt ttccccctgg aagctccctc    1260
gtgcgctctc ctgttccgac cctgccgctt accggatacc tgtccgcctt tctcccttcg    1320
ggaagcgtgg cgctttctca tagctcacgc tgtaggtatc tcagttcggt gtaggtcgtt    1380
cgctccaagc tgggctgtgt gcacgaaccc cccgttcagc ccgaccgctg cgccttatcc    1440
ggtaactatc gtcttgagtc aacccggta agacacgact tatcgccact ggcagcagcc    1500
actggtaaca ggattagcag agcgaggtat gtaggcggtg ctacagagtt cttgaagtgg    1560
tggcctaact acggctacac tagaaggaca gtatttggta tctgcgctct gctgaagcca    1620
gttaccttcg gaaaaagagt tggtagctct tgatccggca acaaaccac cgctggtagc    1680
ggtggttttt ttgtttgcaa gcagcagatt acgcgcagaa aaaaggatc tcaagaagat    1740
cctttgatct tttctacggg gtctgacgct cagtggaaca aaaactcacg ttaagggatt    1800
ttggtcatga gattatcaaa aaggatcttc acctagatcc ttttaaatta aaaatgaagt    1860
tttaaatcaa tctaaagtat atatgagtaa acttggtctg acagttacca atgcttaatc    1920
agtgaggcac ctatctcagc gatctgtcta tttcgttcat ccatagttgc ctgactcccc    1980
gtcgtgtaga taactacgat acgggagggc ttaccatctg gccccagtgc tgcaatgata    2040
ccgcgagacc cacgctcacc ggctccagat ttatcagcaa taaccagcc agccggaagg    2100
gccgagcgca gaagtggtcc tgcaacttta tccgcctcca tccagtctat taattgttgc    2160
cgggaagcta gagtaagtag ttcgccagtt aatagtttgc gcaacgttgt tgccattgct    2220
acaggcatcg tggtgtcacg ctcgtcgttt ggtatggctt cattcagctc cggttcccaa    2280
cgatcaaggc gagttacatg atccccccatg ttgtgcaaaa aagcggttag ctccttcggt    2340
```

```
cctccgatcg ttgtcagaag taagttggcc gcagtgttat cactcatggt tatggcagca   2400
ctgcataatt ctcttactgt catgccatcc gtaagatgct tttctgtgac tggtgagtac   2460
tcaaccaagt cattctgaga atagtgtatg cggcgaccga gttgctcttg cccggcgtca   2520
atacgggata ataccgcgcc acatagcaga actttaaaag tgctcatcat tggaaaacgt   2580
tcttcggggc gaaaactctc aaggatctta ccgctgttga gatccagttc gatgtaaccc   2640
actcgtgcac ccaactgatc ttcagcatct tttactttca ccagcgtttc tgggtgagca   2700
aaaacaggaa ggcaaaatgc cgcaaaaaag gaataagggc gacacggaaa tgttgaata   2760
ctcatactct tcctttttca atattattga agcatttatc agggttattg tctcatgagc   2820
ggatacatat ttgaatgtat ttagaaaaat aaacaaatag gggttccgcg cacatttccc   2880
cgaaaagtgc cacctgacgc gccctgtagc ggcgcattaa gcgcggcggg tgtggtggtt   2940
acgcgcagcg tgaccgctac acttgccagc gccctagcgc ccgctccttt cgctttcttc   3000
ccttcctttc tcgccacgtt cgccggcttt ccccgtcaag ctctaaatcg ggggctccct   3060
ttagggttcc gatttagtgc tttacggcac ctcgacccca aaaaacttga ttagggtgat   3120
ggttcacgta gtgggccatc gccctgatag acggtttttc gccctttgac gttggagtcc   3180
acgttcttta atagtggact cttgttccaa actggaacaa cactcaaccc tatctcggtc   3240
tattcttttg atttataagg gattttgccg atttcggcct attggttaaa aaatgagctg   3300
atttaacaaa aatttaacgc gaattttaac aaaatattaa cgcttacaat ttccattcgc   3360
cattcaggct gcgcaactgt tgggaagggc gatcggtgcg ggcctcttcg ctattacgcc   3420
agctggcgaa aggggggatgt gctgcaaggc gattaagttg ggtaacgcca gggttttccc   3480
agtcacgacg ttgtaaaacg acggccagtg aattgtaata cgactcacta tagggcgaat   3540
tgggtaccgg gccccccctc gaggtcgacg agtatctgtc tgactcgtca ttgccgcctt   3600
tggagtacga ctccaactat gagtgtgctt ggatcacttt gacgatacat tcttcgttgg   3660
aggctgtggg tctgacagct gcgttttcgg cgcggttggc cgacaacaat atcagctgca   3720
acgtcattgc tggctttcat catgatcaca ttttttgtcgg caaaggcgac gcccagagag   3780
ccattgacgt tctttctaat ttggaccgat agccgtatag tccagtctat ctataagttc   3840
aactaactcg taactattac cataacatat acttcactgc cccagataag gttccgataa   3900
aaagttctgc agactaaatt tatttcagtc tcctcttcac caccaaaatg ccctcctacg   3960
aagctcgagt gctcaagctc gtggcagcca agaaaaccaa cctgtgtgct tctctggatg   4020
ttaccaccac caaggagctc attgagcttg ccgataaggt cggaccttat gtgtgcatga   4080
tcaaaaccca tatcgacatc attgacgact cacctacgc cggcactgtg ctccccctca   4140
aggaacttgc tcttaagcac ggtttcttcc tgttcgagga cagaaagttc gcagatattg   4200
gcaacactgt caagcaccag taccggtgtc accgaatcgc cgagtggtcc gatatcacca   4260
acgcccacgg tgtacccgga accggaatcg atgcagaatt caggagagac cgggttggcg   4320
gcgtatttgt gtcccaaaaa acagcccaa ttgccccaat tgaccccaaa ttgacccagt   4380
agcgggccca acccggcga gagccccctt caccccacat atcaaacctc cccggttcc    4440
cacacttgcc gttaagggcg tagggtactg cagtctggaa tctacgcttg ttcagacttt   4500
gtactagttt cttttgtctgg ccatccgggt aacccatgcc ggacgcaaaa tagactactg   4560
aaaatttttt tgctttgtgg ttgggacttt agccaagggt ataaaagacc accgtccccg   4620
aattaccttt cctcttcttt tctctctctc cttgtcaact cacacccgaa atcgttaagc   4680
```

```
atttccttct gagtataaga atcattcacc atggacatgt ccgtcctgac tctccaagag    4740
tacgagttcg agaagcagtt caacgagaat gaagccatcc aatggatgca ggaaaactgg    4800
aagaaatcct tcctgttttc tgccctctac gctgccttta tctttggtgg acgacatctg    4860
atgaacaagc gagccaagtt tgagctgcga aaacctctcg tgctctggtc cctgaccctc    4920
gctgtcttct ctatcttcgg tgctctgcga actggagcct acatgctcta catcctgatg    4980
accaaaggcc tgaaacagtc tgtttgtgac cagtcctttt acaacggacc cgtctcgaaa    5040
ttctgggctt acgcctttgt gctctccaaa gctcccgaac ttggcgatac catcttcatc    5100
attctgcgaa agcagaaact catcttcctg cactggtatc accacatcac cgtcctcctg    5160
tactcttggt actcctacaa ggacatggtg gctggaggtg gctggttcat gactatgaac    5220
tacggtgtcc acgccgtgat gtactcctac tacgccctcc gagctgccgg tttccgagtc    5280
tctcgaaagt ttgccatgtt catcaccctg tcgcagatca ctcagatgct catgggctgt    5340
gtcattaact acctggtctt caactggatg cagcatgaca atgaccagtg ctactcccac    5400
tttcagaaca tcttctggtc ctctctcatg tacctctcct accttctgct cttctgccat    5460
ttcttctttg aggcctacat tggcaaagtg aagaaagcca ccaaggctga gtaagcggcc    5520
gcaagtgtgg atggggaagt gagtgcccgg ttctgtgtgc acaattggca atccaagatg    5580
gatggattca acacagggat atagcgagct acgtggtggt gcgaggatat agcaacggat    5640
atttatgttt gacacttgag aatgtacgat acaagcactg tccaagtaca atactaaaca    5700
tactgtacat actcatactc gtacccgggc aacggtttca cttgagtgca gtggctagtg    5760
ctcttactcg tacagtgtgc aatactgcgt atcatagtct ttgatgtata tcgtattcat    5820
tcatgttagt tgc                                                       5833
```

<210> SEQ ID NO 140
<211> LENGTH: 804
<212> TYPE: DNA
<213> ORGANISM: Rattus norvegicus
<220> FEATURE:
<221> NAME/KEY: misc_feature
<223> OTHER INFORMATION: synthetic C16 elongase (codon-optimized)

<400> SEQUENCE: 140

```
atggacatgt ccgtcctgac tctccaagag tacgagttcg agaagcagtt caacgagaat     60
gaagccatcc aatggatgca ggaaaactgg aagaaatcct tcctgttttc tgccctctac    120
gctgccttta tctttggtgg acgacatctg atgaacaagc gagccaagtt tgagctgcga    180
aaacctctcg tgctctggtc cctgaccctc gctgtcttct ctatcttcgg tgctctgcga    240
actggagcct acatgctcta catcctgatg accaaaggcc tgaaacagtc tgtttgtgac    300
cagtcctttt acaacggacc cgtctcgaaa ttctgggctt acgcctttgt gctctccaaa    360
gctcccgaac ttggcgatac catcttcatc attctgcgaa agcagaaact catcttcctg    420
cactggtatc accacatcac cgtcctcctg tactcttggt actcctacaa ggacatggtg    480
gctggaggtg gctggttcat gactatgaac tacggtgtcc acgccgtgat gtactcctac    540
tacgccctcc gagctgccgg tttccgagtc tctcgaaagt ttgccatgtt catcaccctg    600
tcgcagatca ctcagatgct catgggctgt gtcattaact acctggtctt caactggatg    660
cagcatgaca atgaccagtg ctactcccac tttcagaaca tcttctggtc ctctctcatg    720
tacctctcct accttctgct cttctgccat ttcttctttg aggcctacat tggcaaagtg    780
aagaaagcca ccaaggctga gtaa                                           804
```

<210> SEQ ID NO 141
<211> LENGTH: 267
<212> TYPE: PRT
<213> ORGANISM: Rattus norvegicus
<300> PUBLICATION INFORMATION:
<308> DATABASE ACCESSION NUMBER: GenBank Accession No. AB071986
<309> DATABASE ENTRY DATE: 2005-04-19
<313> RELEVANT RESIDUES: (1)..(267)

<400> SEQUENCE: 141

Met Asn Met Ser Val Leu Thr Leu Gln Glu Tyr Glu Phe Glu Lys Gln
1               5                   10                  15

Phe Asn Glu Asn Glu Ala Ile Gln Trp Met Gln Glu Asn Trp Lys Lys
            20                  25                  30

Ser Phe Leu Phe Ser Ala Leu Tyr Ala Ala Phe Ile Phe Gly Gly Arg
        35                  40                  45

His Leu Met Asn Lys Arg Ala Lys Phe Glu Leu Arg Lys Pro Leu Val
    50                  55                  60

Leu Trp Ser Leu Thr Leu Ala Val Phe Ser Ile Phe Gly Ala Leu Arg
65                  70                  75                  80

Thr Gly Ala Tyr Met Leu Tyr Ile Leu Met Thr Lys Gly Leu Lys Gln
                85                  90                  95

Ser Val Cys Asp Gln Ser Phe Tyr Asn Gly Pro Val Ser Lys Phe Trp
            100                 105                 110

Ala Tyr Ala Phe Val Leu Ser Lys Ala Pro Glu Leu Gly Asp Thr Ile
        115                 120                 125

Phe Ile Ile Leu Arg Lys Gln Lys Leu Ile Phe Leu His Trp Tyr His
    130                 135                 140

His Ile Thr Val Leu Leu Tyr Ser Trp Tyr Ser Tyr Lys Asp Met Val
145                 150                 155                 160

Ala Gly Gly Gly Trp Phe Met Thr Met Asn Tyr Gly Val His Ala Val
                165                 170                 175

Met Tyr Ser Tyr Tyr Ala Leu Arg Ala Ala Gly Phe Arg Val Ser Arg
            180                 185                 190

Lys Phe Ala Met Phe Ile Thr Leu Ser Gln Ile Thr Gln Met Leu Met
        195                 200                 205

Gly Cys Val Ile Asn Tyr Leu Val Phe Asn Trp Met Gln His Asp Asn
    210                 215                 220

Asp Gln Cys Tyr Ser His Phe Gln Asn Ile Phe Trp Ser Ser Leu Met
225                 230                 235                 240

Tyr Leu Ser Tyr Leu Leu Leu Phe Cys His Phe Phe Glu Ala Tyr
                245                 250                 255

Ile Gly Lys Val Lys Lys Ala Thr Lys Ala Glu
            260                 265

<210> SEQ ID NO 142
<211> LENGTH: 23
<212> TYPE: DNA
<213> ORGANISM: Artificial Sequence
<220> FEATURE:
<223> OTHER INFORMATION: Primer P239

<400> SEQUENCE: 142
ccatgaacac tttgtcgtcc atc        23

<210> SEQ ID NO 143
<211> LENGTH: 23
<212> TYPE: DNA

<213> ORGANISM: Artificial Sequence
<220> FEATURE:
<223> OTHER INFORMATION: Primer P240

<400> SEQUENCE: 143
aatcgagctt gggctggaag aac                                               23

<210> SEQ ID NO 144
<211> LENGTH: 7822
<212> TYPE: DNA
<213> ORGANISM: Artificial Sequence
<220> FEATURE:
<223> OTHER INFORMATION: Plasmid pZP217+Ura

<400> SEQUENCE: 144

| | | | | | |
|---|---|---|---|---|---|
| aaacggtagg | ttagtgcttg | gtatatgagt | tgtaggcatg | acaatttgga | aagggtggga | 60 |
| ctttgggaat | attgtgggat | ttcaatacct | tagtttgtac | agggtaattg | ttacaaatga | 120 |
| tacaaagaac | tgtatttctt | ttcatttgtt | ttaattggtt | gtatatcaag | tccgttagac | 180 |
| gagctcagtg | ccttggcttt | tggcactgta | tttcatttt | agaggtacac | tacattcagt | 240 |
| gaggtatggt | aaggttgagg | gcataatgaa | ggcaccttgt | actgacagtc | acagacctct | 300 |
| caccgagaat | tttatgagat | atactcgggt | tcattttagg | ctcatcgatc | aggagagacc | 360 |
| gggttggcgg | cgtatttgtg | tcccaaaaaa | cagccccaat | tgccccaatt | gaccccaaat | 420 |
| tgacccagta | gcgggcccaa | ccccggcgag | agcccccttc | accccacata | tcaaacctcc | 480 |
| cccggttccc | acacttgccg | ttaagggcgt | agggtactgc | agtctggaat | ctacgcttgt | 540 |
| tcagactttg | tactagtttc | tttgtctggc | catccgggta | acccatgccg | gacgcaaaat | 600 |
| agactactga | aaattttttt | gctttgtggt | tgggacttta | gccaagggta | taaaagacca | 660 |
| ccgtccccga | attacctttc | ctcttctttt | ctctctctcc | ttgtcaactc | acacccgaaa | 720 |
| tcgttaagca | tttccttctg | agtataagaa | tcattcacca | tggctgagga | taagaccaag | 780 |
| gtcgagttcc | ctaccctgac | tgagctgaag | cactctatcc | ctaacgcttg | ctttgagtcc | 840 |
| aacctcggac | tctcgctcta | ctacactgcc | cgagcgatct | tcaacgcatc | tgcctctgct | 900 |
| gctctgctct | acgctgcccg | atctactccc | ttcattgccg | ataacgttct | gctccacgct | 960 |
| ctggtttgcg | ccacctacat | ctacgtgcag | ggtgtcatct | tctggggttt | ctttaccgtc | 1020 |
| ggtcacgact | gtggtcactc | tgccttctcc | cgataccact | ccgtcaactt | catcattggc | 1080 |
| tgcatcatgc | actctgccat | tctgactccc | ttcgagtcct | ggcgagtgac | ccaccgacac | 1140 |
| catcacaaga | acactggcaa | cattgataag | gacgagatct | ctaccctca | tcggtccgtc | 1200 |
| aaggacctcc | aggacgtgcg | acaatgggtc | tacaccctcg | gaggtgcttg | gtttgtctac | 1260 |
| ctgaaggtcg | gatatgctcc | tcgaaccatg | tcccactttg | accctggga | ccctctcctg | 1320 |
| cttcgacgag | cctccgctgt | catcgtgtcc | ctcggagtct | gggctgcctt | cttcgctgcc | 1380 |
| tacgcctacc | tcacatactc | gctcggcttt | gccgtcatgg | gcctctacta | ctatgctcct | 1440 |
| ctctttgtct | ttgcttcgtt | cctcgtcatt | actaccttct | tgcatcacaa | cgacgaagct | 1500 |
| actccctggt | acggtgactc | ggagtggacc | tacgtcaagg | gcaacctgag | ctccgtcgac | 1560 |
| cgatcgtacg | gagctttcgt | ggacaacctg | tctcaccaca | ttggcaccca | ccaggtccat | 1620 |
| cacttgttcc | ctatcattcc | ccactacaag | ctcaacgaag | ccaccaagca | ctttgctgcc | 1680 |
| gcttaccctc | acctcgtgag | acgtaacgac | gagcccatca | ttactgcctt | cttcaagacc | 1740 |
| gctcacctct | ttgtcaacta | cggagctgtg | cccgagactg | ctcagatttt | cacccctcaaa | 1800 |
| gagtctgccg | ctgcagccaa | ggccaagagc | gactaagcgg | ccgcaagtgt | ggatggggaa | 1860 |

```
gtgagtgccc ggttctgtgt gcacaattgg caatccaaga tggatggatt caacacaggg    1920
atatagcgag ctacgtggtg gtgcgaggat atagcaacgg atatttatgt ttgacacttg    1980
agaatgtacg atacaagcac tgtccaagta caatactaaa catactgtac atactcatac    2040
tcgtacccgg gcaacggttt cacttgagtg cagtggctag tgctcttact cgtacagtgt    2100
gcaatactgc gtatcatagt ctttgatgta tatcgtattc attcatgtta gttgcgtacg    2160
ggcgtcgttg cttgtgtgat ttttgaggac ccatcccttt ggtatataag tatactctgg    2220
ggttaaggtt gcccgtgtag tctaggttat agttttcatg tgaaataccg agagccgagg    2280
gagaataaac gggggtattt ggacttgttt ttttcgcgga aaagcgtcga atcaaccctg    2340
cgggccttgc accatgtcca cgacgtgttt ctcgccccaa ttcgcccctt gcacgtcaaa    2400
attaggcctc catctagacc cctccataac atgtgactgt ggggaaaagt ataagggaaa    2460
ccatgcaacc atagacgacg tgaaagacgg ggaggaacca atggaggcca agaaatggg     2520 gtagcaacag tccaggagac agacaaggag acaaggagag ggcgcccgaa agatcggaaa    2580
aacaaacatg tccaattggg gcagtgacgg aaacgacacg gacacttcag tacaatggac    2640
cgaccatctc caagccaggg ttattccggt atcaccttgg ccgtaacctc ccgctggtac    2700
ctgatattgt acacgttcac attcaatata ctttcagcta caataagaga ggctgtttgt    2760
cgggcatgtg tgtccgtcgt atggggtgat gtccgagggc gaaattcgct acaagcttaa    2820
ctctggcgct tgtccagtat gaatagacaa gtcaagacca gtggtgccat gattgacagg    2880
gaggtacaag acttcgatac tcgagcatta ctcggacttg tggcgattga acagacgggc    2940
gatcgcttct cccccgtatt gccggcgcgc cagctgcatt aatgaatcgg ccaacgcgcg    3000
gggagaggcg gtttgcgtat tgggcgctct tccgcttcct cgctcactga ctcgctgcgc    3060
tcggtcgttc ggctgcggcg agcggtatca gctcactcaa aggcggtaat acggttatcc    3120
acagaatcag gggataacgc aggaaagaac atgtgagcaa aaggccagca aaaggccagg    3180
aaccgtaaaa aggccgcgtt gctggcgttt ttccataggc tccgcccccc tgacgagcat    3240
cacaaaaatc gacgctcaag tcagaggtgg cgaaacccga caggactata agataccag    3300 gcgtttcccc ctggaagctc cctcgtgcgc tctcctgttc cgaccctgcc gcttaccgga    3360
tacctgtccg cctttctccc ttcgggaagc gtggcgcttt ctcatagctc acgctgtagg    3420
tatctcagtt cggtgtaggt cgttcgctcc aagctgggct gtgtgcacga accccccgtt    3480
cagcccgacc gctgcgcctt atccggtaac tatcgtcttg agtccaaccc ggtaagacac    3540
gacttatcgc cactggcagc agccactggt aacaggatta gcagagcgag gtatgtaggc    3600
ggtgctacag agttcttgaa gtggtggcct aactacggct acactagaag aacagtattt    3660
ggtatctgcg ctctgctgaa gccagttacc ttcggaaaaa gagttggtag ctcttgatcc    3720
ggcaaacaaa ccaccgctgg tagcggtggt ttttttgttt gcaagcagca gattacgcgc    3780
agaaaaaaag gatctcaaga agatccttt gatcttttcta cggggtctga cgctcagtgg    3840
aacgaaaact cacgttaagg gattttggtc atgagattat caaaaaggat cttcacctag    3900
atccttttaa attaaaaatg aagttttaaa tcaatctaaa gtatatatga gtaaacttgg    3960
tctgacagtt accaatgctt aatcagtgag gcacctatct cagcgatctg tctatttcgt    4020
tcatccatag ttgcctgact ccccgtcgtg tagataacta cgatacggga gggcttacca    4080
tctggcccca gtgctgcaat gataccgcga gacccacgct caccggctcc agatttatca    4140
gcaataaacc agccagccgg aagggccgag cgcagaagtg gtcctgcaac tttatccgcc    4200
```

```
tccatccagt ctattaattg ttgccgggaa gctagagtaa gtagttcgcc agttaatagt    4260
ttgcgcaacg ttgttgccat tgctacaggc atcgtggtgt cacgctcgtc gtttggtatg    4320
gcttcattca gctccggttc ccaacgatca aggcgagtta catgatcccc catgttgtgc    4380
aaaaaagcgg ttagctcctt cggtcctccg atcgttgtca gaagtaagtt ggccgcagtg    4440
ttatcactca tggttatggc agcactgcat aattctctta ctgtcatgcc atccgtaaga    4500
tgcttttctg tgactggtga gtactcaacc aagtcattct gagaatagtg tatgcggcga    4560
ccgagttgct cttgcccggc gtcaatacgg gataataccg cgccacatag cagaacttta    4620
aaagtgctca tcattggaaa acgttcttcg gggcgaaaac tctcaaggat cttaccgctg    4680
ttgagatcca gttcgatgta acccactcgt gcacccaact gatcttcagc atcttttact    4740
ttcaccagcg tttctgggtg agcaaaaaca ggaaggcaaa atgccgcaaa aaagggaata    4800
agggcgacac ggaaatgttg aatactcata ctcttccttt tcaatatta ttgaagcatt    4860 tatcagggtt attgtctcat gagcggatac atatttgaat gtatttagaa aaataaacaa    4920
ataggggttc cgcgcacatt tccccgaaaa gtgccacctg atgcggtgtg aaataccgca    4980
cagatgcgta aggagaaaat accgcatcag gaaattgtaa gcgttaatat tttgttaaaa    5040
ttcgcgttaa attttgttaa atcagctca ttttttaacc aataggccga atcggcaaa    5100 atcccttata aatcaaaaga atagaccgag ataggggttga gtgttgttcc agtttggaac    5160
aagagtccac tattaaagaa cgtggactcc aacgtcaaag ggcgaaaaac cgtctatcag    5220
ggcgatggcc cactacgtga accatcaccc taatcaagtt ttttgggggtc gaggtgccgt    5280 aaagcactaa atcggaaccc taaagggagc ccccgattta gagcttgacg gggaaagccg    5340
gcgaacgtgg cgagaagga agggaagaaa gcgaaggag cgggcgctag ggcgctggca    5400
agtgtagcgg tcacgctgcg cgtaaccacc acacccgccg cgcttaatgc gccgctacag    5460
ggcgcgtcca ttcgccattc aggctgcgca actgttggga agggcgatcg gtgcgggcct    5520
cttcgctatt acgccagctg gcgaaagggg gatgtgctgc aaggcgatta agttgggtaa    5580
cgccagggtt ttcccagtca cgacgttgta aaacgacggc cagtgaattg taatacgact    5640
cactataggg cgaattgggc cgacgtcgc atgcgctgat gacactttgg tctgaaagag    5700
atgcattttg aatcccaaac ttgcagtgcc caagtgacat acatctccgc gttttggaaa    5760
atgttcagaa acagttgatt gtgttggaat ggggaatggg gaatggaaaa atgactcaag    5820
tatcaattcc aaaaacttct ctggctggca gtacctactg tccatactac tgcattttct    5880
ccagtcaggc cactctatac tcgacgacac agtagtaaaa cccagataat ttcgacataa    5940
acaagaaaac agaccccaata atatttatat atagtcagcc gtttgtccag ttcagactgt    6000
aatagccgaa aaaaatcca aagtttctat tctaggaaaa tatattccaa tatttttaat    6060
tcttaatctc atttatttta ttctagcgaa atacatttca gctacttgag acatgtgata    6120
cccacaaatc ggattcggac tcggttgttc agaagagcat atggcattcg tgctcgcttg    6180
ttcacgtatt cttcctgttc catctcttgg ccgacaatca cacaaaaatg gggttttttt    6240
tttaattcta atgattcatt acagcaaaat tgagatatag cagaccacgt attccataat    6300
caccaaggaa gttcttgggc gtcttaatta agtcatacac aagtcagctt tcttcgagcc    6360
tcatataagt ataagtagtt caacgtatta gcactgtacc cagcatctcc gtatcgaaaa    6420
acacaacaac atgccccatt ggacagatca tgcggataca caggttgtgc agtatcatac    6480
atactcgatc agacaggtcg tctgaccatc atacaagctg aacaagcgct ccatacttgc    6540
acgctctcta tatacacagt taaattacat atccatagtc taacctctaa cagttaatct    6600
```

```
tctggtaagc ctcccagcca gccttctggt atcgcttggc ctcctcaata ggatctcggt    6660 tctgccgta cagacctcgg ccgacaatta tgatatccgt tccggtagac atgacatcct    6720
caacagttcg gtactgctgt ccgagagcgt ctcccttgtc gtcaagaccc accccggggg    6780
tcagaataag ccagtcctca gagtcgccct taggtcggtt ctgggcaatg aagccaacca    6840
caaactcggg gtcggatcgg gcaagctcaa tggtctgctt ggagtactcg ccagtggcca    6900
gagagccctt gcaagacagc tcggccagca tgagcagacc tctggccagc ttctcgttgg    6960
gagaggggac taggaactcc ttgtactggg agttctcgta gtcagagacg tcctcctttct    7020 tctgttcaga gacagtttcc tcggcaccag ctcgcaggcc agcaatgatt ccggttccgg    7080
gtacaccgtg ggcgttggtg atatcggacc actcggcgat tcggtgacac cggtactggt    7140
gcttgacagt gttgccaata tctgcgaact ttctgtcctc gaacaggaag aaaccgtgct    7200
taagagcaag ttccttgagg gggagcacag tgccggcgta ggtgaagtcg tcaatgatgt    7260
cgatatgggt tttgatcatg cacacataag gtccgacctt atcggcaagc tcaatgagct    7320
ccttggtggt ggtaacatcc agagaagcac acaggttggt tttcttggct gccacgagct    7380
tgagcactcg agcggcaaag gcggacttgt ggacgttagc tcgagcttcg taggagggca    7440
ttttggtggt gaagaggaga ctgaaataaa tttagtctgc agaacttttt atcggaacct    7500
tatctggggc agtgaagtat atgttatggt aatagttacg agttagttga acttatagat    7560
agactggact atacggctat cggtccaaat tagaaagaac gtcaatggct ctctgggcgt    7620
cgcctttgcc gacaaaaatg tgatcatgat gaaagccagc aatgacgttg cagctgatat    7680
tgttgtcggc caaccgcgcc gaaaacgcag ctgtcagacc cacagcctcc aacgaagaat    7740
gtatcgtcaa agtgatccaa gcacactcat agttggagtc gtactccaaa ggcggcaatg    7800
acgagtcaga cagatactcg tc                                             7822
```

<210> SEQ ID NO 145
<211> LENGTH: 39
<212> TYPE: DNA
<213> ORGANISM: Artificial Sequence
<220> FEATURE:
<223> OTHER INFORMATION: SMART IV oligonucleotide

<400> SEQUENCE: 145

```
aagcagtggt atcaacgcag agtggccatt acggccggg                           39
```

<210> SEQ ID NO 146
<211> LENGTH: 59
<212> TYPE: DNA
<213> ORGANISM: Artificial Sequence
<220> FEATURE:
<223> OTHER INFORMATION: CDSIII/3'PCR primer
<220> FEATURE:
<221> NAME/KEY: misc_feature
<222> LOCATION: (28)..(57)
<223> OTHER INFORMATION: thymidine (dT); see BD Biosciences Clontech's
      SMART cDNA technology
<220> FEATURE:
<221> NAME/KEY: misc_feature
<222> LOCATION: (59)..(59)
<223> OTHER INFORMATION: n is a, c, g, or t

<400> SEQUENCE: 146

```
attctagagg ccgaggcggc cgacatgttt tttttttttt tttttttttt ttttttvn      59
```

<210> SEQ ID NO 147
<211> LENGTH: 23

<212> TYPE: DNA
<213> ORGANISM: Artificial Sequence
<220> FEATURE:
<223> OTHER INFORMATION: 5'-PCR primer

<400> SEQUENCE: 147
aagcagtggt atcaacgcag agt                                            23

<210> SEQ ID NO 148
<211> LENGTH: 18
<212> TYPE: DNA
<213> ORGANISM: Artificial Sequence
<220> FEATURE:
<223> OTHER INFORMATION: Primer M13

<400> SEQUENCE: 148
tgtaaaacga cggccagt                                                  18

<210> SEQ ID NO 149
<211> LENGTH: 601
<212> TYPE: DNA
<213> ORGANISM: Mortierella alpina

<400> SEQUENCE: 149
gggcatgatg tacttttag tcgagcagta cgccaccccc accctgcaga actcggtccg       60
agcattcgat gagttggcgt tcggcaccat tctggagaga gtgctgaagc tgagcaccac     120
cagtgtcatc atctggctac tcatgttcta cacctttttc cactcgttct ttaatgctct    180
tgcagaggca ctgtactttg gagaccgtcg cttctatctc gcctggtgga atgccactgg    240
tgtcggcatg tactggaaga cgtggaactc gcccgtctac accttcttca aacgccacgt    300 ataccctgccc ctgatcacct ctggcaccte tcccatggtc gcctcgatcg tcatcttcct   360
catctcggct gtcttgcacg agatcttgat cggcttcccc actcatatga tctatggata    420
cgcattcgcc ggcatgttcc tccagatccc gctgatcatt ctgacccgac ccctcgaaaa    480
atggcgaggc accggatcgg gtctcggcaa catgatcttc tgggtctcgt tcaccatcct    540
gggccagcca gcgtgtgcgc tgctctacta ctaccactgg accaagcgcc atatggatgt    600
t                                                                   601

<210> SEQ ID NO 150
<211> LENGTH: 20
<212> TYPE: DNA
<213> ORGANISM: Artificial Sequence
<220> FEATURE:
<223> OTHER INFORMATION: Primer MARE2-N1

<400> SEQUENCE: 150
cctctgcaag agcattaaag                                                20

<210> SEQ ID NO 151
<211> LENGTH: 21
<212> TYPE: DNA
<213> ORGANISM: Artificial Sequence
<220> FEATURE:
<223> OTHER INFORMATION: Primer MARE2-N2

<400> SEQUENCE: 151
ttcagcactc tctccagaat g                                              21

<210> SEQ ID NO 152
<211> LENGTH: 44
<212> TYPE: DNA

```
<213> ORGANISM: Artificial Sequence
<220> FEATURE:
<223> OTHER INFORMATION: Genome Walker adaptor-1

<400> SEQUENCE: 152
gtaatacgac tagggcac gcgtggtcga cggcccgggc tggt                          44

<210> SEQ ID NO 153
<211> LENGTH: 8
<212> TYPE: DNA
<213> ORGANISM: Artificial Sequence
<220> FEATURE:
<223> OTHER INFORMATION: Genome Walker adaptor-2
<220> FEATURE:
<221> NAME/KEY: misc_feature
<222> LOCATION: (1)..(1)
<223> OTHER INFORMATION: 5' end is associated with a -PO4 group
<220> FEATURE:
<221> NAME/KEY: misc_feature
<222> LOCATION: (8)..(8)
<223> OTHER INFORMATION: 3' end is associated with a -H2N group

<400> SEQUENCE: 153 accagccc                                                                 8

<210> SEQ ID NO 154
<211> LENGTH: 22
<212> TYPE: DNA
<213> ORGANISM: Artificial Sequence
<220> FEATURE:
<223> OTHER INFORMATION: Primer AP1

<400> SEQUENCE: 154
gtaatacgac tcactatagg gc                                                22

<210> SEQ ID NO 155
<211> LENGTH: 19
<212> TYPE: DNA
<213> ORGANISM: Artificial Sequence
<220> FEATURE:
<223> OTHER INFORMATION: Primer AP2

<400> SEQUENCE: 155
actatagggc acgcgtggt                                                    19

<210> SEQ ID NO 156
<211> LENGTH: 1683
<212> TYPE: DNA
<213> ORGANISM: Mortierella alpina
<220> FEATURE:
<221> NAME/KEY: misc_feature
<222> LOCATION: (1093)..(1093)
<223> OTHER INFORMATION: n is a, c, g, or t

<400> SEQUENCE: 156
actatagggc acgcgtggtc gacggcccgg gctggtaaag attcgccac cccgcataca         60 ggtactcaca ctggcttcca tgcctacgct tacgagccaa ctcgattgca ctgttgcgtt       120
ccgtatcatg ccaacttgat gccataaaaa aaagatcctt tctttgcagc tcatgcttac       180
atgtctcatt gctcctccgt ttgctagggc atagtacagt tccccgccg ccatgacaga        240 gtcgacaaca acgacatgtg caaggagga gggcattgcc aacagcgctg ctttgcctga        300 cattcccca aagatggaag acctcaagtc ctccaggaag accggctctt cttacaagca        360
caccttcccc gtccatacaa aaaccatccc cagcccattg tctaaagagg cacctccaga       420
gagctatcgt ggattcgtca acctcggcag taagttccct ttcttatttt gcaccctgtt       480
```

```
cgataacact tcactctggg agtgaggagg tgtggccgtt gcgcacaact gggcggttcc    540
gttggaacaa gttgaatatg catgcatgca tgcagtgtga tacagtgtca tggagtcagt    600
acggcacagc ctcgctcagt ccttggatta ctcggacttc aacccaacca cagacggtgc    660
acacgttcag tttgagccgc gtctgaatgg cgatacacga gatagagagg cgccgtcgca    720
ttgaccccag agcagtgcaa acagcaatga ttggctgtgc agccccggta ccttcaattc    780
cttcgcttca tttcatgccg ctaaacatgt cactcctacg ttttccttg tggccgtcgc     840 ttagtgctcc tacttttcgg caacaacatc cgattgatca tcgagaatta cctcaaatac    900
ggcttcctgc tctcaatccc tggatcaagc gtctcgaagc aggactggat cctggctgcc    960
ctcacccacg ccatcctacc cgtcaacctc atcctggcct acaagcttga gagctgggcc   1020
aaggagagag ccgtcggcta tcgcaagcgt cgatctgacg aacccattgc ccaggaatca   1080
accaaggccg tgncagcagg agataatgac gctatcaaaa ccacaaaacc cgccaaggcc   1140
caggatctca cacccgaggc ccttgcaagg aaggaacaat cgaccgtggg ctggctccat   1200
gtcttcaatc tgttcaccat cgttgcctgg ccctccttca tgtcctactt tatgatctac   1260
caccccttcg tggccatgtc ctgcctcatg aacggactta tcctcttcct caaaatgacc   1320
tcctttgcgc ttgtgaacca ggagctccga gcagcctaca tctttggaac acccgtggac   1380
acgttccagc acatggctaa agtgcacgac atctctggca aggacctgac aaagaaggag   1440
atcttccagt atgacatcca gtaccccgac aacatcaccc tcaagaacat tggctatttc   1500
tggctcgccc ccacgctctg ctaccagcca tcatacccaa ggacgaccgt cttccgcaaa   1560
tccttcttcc tcaagcgtgt ggccgagatc gtgacctgtc tgggcatgat gtactttta    1620 gtcgagcagt acgccacccc caccctgcag aactcggtcc gagcattcga tgagttggcg   1680
ttc                                                                  1683
```

<210> SEQ ID NO 157
<211> LENGTH: 22
<212> TYPE: DNA
<213> ORGANISM: Artificial Sequence
<220> FEATURE:
<223> OTHER INFORMATION: Primer ARE-N3-1

<400> SEQUENCE: 157
agatcccgct gatcattctg ac                                               22

<210> SEQ ID NO 158
<211> LENGTH: 20
<212> TYPE: DNA
<213> ORGANISM: Artificial Sequence
<220> FEATURE:
<223> OTHER INFORMATION: Primer ARE-N3-2

<400> SEQUENCE: 158
gatcgggtct cggcaacatg                                                  20

<210> SEQ ID NO 159
<211> LENGTH: 37
<212> TYPE: DNA
<213> ORGANISM: Artificial Sequence
<220> FEATURE:
<223> OTHER INFORMATION: Primer AP

<400> SEQUENCE: 159
ggccacgcgt cgactagtac ttttttttttt tttttt                               37

```
<210> SEQ ID NO 160
<211> LENGTH: 49
<212> TYPE: DNA
<213> ORGANISM: Artificial Sequence
<220> FEATURE:
<223> OTHER INFORMATION: Primer UAP
<220> FEATURE:
<221> NAME/KEY: misc_feature
<222> LOCATION: (2)..(2)
<223> OTHER INFORMATION: N = uracil
<220> FEATURE:
<221> NAME/KEY: misc_feature
<222> LOCATION: (5)..(5)
<223> OTHER INFORMATION: N = uracil
<220> FEATURE:
<221> NAME/KEY: misc_feature
<222> LOCATION: (8)..(8)
<223> OTHER INFORMATION: N = uracil
<220> FEATURE:
<221> NAME/KEY: misc_feature
<222> LOCATION: (11)..(11)
<223> OTHER INFORMATION: N = uracil

<400> SEQUENCE: 160
cnacnacnac naggccacgc gtcgactagt acttttttttt tttttttt         49

<210> SEQ ID NO 161
<211> LENGTH: 184
<212> TYPE: DNA
<213> ORGANISM: Mortierella alpina

<400> SEQUENCE: 161
tttttttttt ttttttgttct taaaaaaact atgcgttctc ccattatctt tatatctatt    60
caaaaaaaat aataaagtcg gtcgtaagat tgaatcaaac atccatatgg cgcttggtcc   120
agtggtagta gtagagcagc gcacacgctg gctggcccag gatggtgaac gagacccaga   180
agat                                                                184

<210> SEQ ID NO 162
<211> LENGTH: 32
<212> TYPE: DNA
<213> ORGANISM: Artificial Sequence
<220> FEATURE:
<223> OTHER INFORMATION: Primer MACAT-F1

<400> SEQUENCE: 162
gatcccatgg cagagtcgac aacaacgaca tg                                  32

<210> SEQ ID NO 163
<211> LENGTH: 34
<212> TYPE: DNA
<213> ORGANISM: Artificial Sequence
<220> FEATURE:
<223> OTHER INFORMATION: Primer MACAT-R

<400> SEQUENCE: 163
gatcgcggcc gctcaaacat ccatatggcg cttg                                34

<210> SEQ ID NO 164
<211> LENGTH: 8165
<212> TYPE: DNA
<213> ORGANISM: Artificial Sequence
<220> FEATURE:
<223> OTHER INFORMATION: Plasmid pZUF17

<400> SEQUENCE: 164
gtacgagccg gaagcataaa gtgtaaagcc tggggtgcct aatgagtgag ctaactcaca    60
```

-continued

```
ttaattgcgt tgcgctcact gcccgctttc cagtcgggaa acctgtcgtg ccagctgcat      120
taatgaatcg gccaacgcgc ggggagaggc ggtttgcgta ttgggcgctc ttccgcttcc      180
tcgctcactg actcgctgcg ctcggtcgtt cggctgcggc gagcggtatc agctcactca      240
aaggcggtaa tacggttatc cacagaatca ggggataacg caggaaagaa catgtgagca      300
aaaggccagc aaaaggccag gaaccgtaaa aaggccgcgt tgctggcgtt tttccatagg      360
ctccgccccc ctgacgagca tcacaaaaat cgacgctcaa gtcagaggtg gcgaaacccg      420
acaggactat aaagatacca ggcgtttccc cctggaagct ccctcgtgcg ctctcctgtt      480
ccgaccctgc cgcttaccgg atacctgtcc gcctttctcc cttcgggaag cgtggcgctt      540
tctcatagct cacgctgtag gtatctcagt tcggtgtagg tcgttcgctc caagctgggc      600
tgtgtgcacg aaccccccgt tcagcccgac cgctgcgcct tatccggtaa ctatcgtctt      660
gagtccaacc cggtaagaca cgacttatcg ccactggcag cagccactgg taacaggatt      720
agcagagcga ggtatgtagg cggtgctaca gagttcttga agtggtggcc taactacggc      780
tacactagaa ggacagtatt tggtatctgc gctctgctga gccagttacc ttcggaaaa      840
agagttggta gctcttgatc cggcaaacaa accaccgctg gtagcggtgg ttttttttgtt      900
tgcaagcagc agattacgcg cagaaaaaaa ggatctcaag aagatccttt gatcttttct      960
acggggtctg acgctcagtg gaacgaaaac tcacgttaag ggattttggt catgagatta     1020
tcaaaagga tcttcaccta gatccttta aattaaaaat gaagttttaa atcaatctaa      1080
agtatatatg agtaaacttg gtctgacagt taccaatgct taatcagtga ggcacctatc     1140
tcagcgatct gtctatttcg ttcatccata gttgcctgac tccccgtcgt gtagataact     1200
acgatacggg agggcttacc atctggcccc agtgctgcaa tgataccgcg agacccacgc     1260
tcaccggctc cagatttatc agcaataaac cagccagccg aagggccga gcgcagaagt     1320
ggtcctgcaa ctttatccgc ctccatccag tctattaatt gttgccggga agctagagta     1380
agtagttcgc cagttaatag tttgcgcaac gttgttgcca ttgctacagg catcgtggtg     1440
tcacgctcgt cgtttggtat ggcttcattc agctccggtt cccaacgatc aaggcgagtt     1500
acatgatccc ccatgttgtg caaaaaagcg gttagctcct tcggtcctcc gatcgttgtc     1560
agaagtaagt tggccgcagt gttatcactc atggttatgg cagcactgca taattctctt     1620
actgtcatgc catccgtaag atgcttttct gtgactggtg agtactcaac caagtcattc     1680
tgagaatagt gtatgcggcg accgagttgc tcttgcccgg cgtcaatacg ggataatacc     1740
gcgccacata gcagaacttt aaaagtgctc atcattggaa aacgttcttc ggggcgaaaa     1800
ctctcaagga tcttaccgct gttgagatcc agttcgatgt aacccactcg tgcacccaac     1860
tgatcttcag catcttttac tttcaccagc gtttctgggt gagcaaaaac aggaaggcaa     1920
aatgccgcaa aaaagggaat aagggcgaca cggaaatgtt gaatactcat actcttcctt     1980
tttcaatatt attgaagcat ttatcagggt tattgtctca tgagcggata catatttgaa     2040
tgtatttaga aaataaaca atagggggtt ccgcgcacat ttccccgaaa agtgccacct     2100
gacgcgccct gtagcggcgc attaagcgcg gcgggtgtgg tggttacgcg cagcgtgacc     2160
gctacacttg ccagcgccct agcgcccgct cctttcgctt tcttcccttc ctttctcgcc     2220
acgttcgccg gctttccccg tcaagctcta aatcgggggc tccctttagg gttccgattt     2280
agtgctttac ggcacctcga cccaaaaaa cttgattagg gtgatggttc acgtagtggg     2340
ccatcgccct gatagacggt ttttcgccct ttgacgttgg agtccacgtt ctttaatagt     2400
```

```
ggactcttgt tccaaactgg aacaacactc aaccctatct cggtctattc ttttgattta    2460
taagggattt tgccgatttc ggcctattgg ttaaaaaatg agctgattta acaaaaattt    2520
aacgcgaatt ttaacaaaat attaacgctt acaatttcca ttcgccattc aggctgcgca    2580
actgttggga agggcgatcg gtgcgggcct cttcgctatt acgccagctg gcgaaagggg    2640
gatgtgctgc aaggcgatta agttgggtaa cgccagggtt ttcccagtca cgacgttgta    2700
aaacgacggc cagtgaattg taatacgact cactatagg cgaattgggt accgggcccc    2760
ccctcgaggt cgatggtgtc gataagcttg atatcgaatt catgtcacac aaaccgatct    2820
tcgcctcaag gaaacctaat tctacatccg agagactgcc gagatccagt ctacactgat    2880
taattttcgg gccaataatt taaaaaaatc gtgttatata atattatatg tattatatat    2940
atacatcatg atgatactga cagtcatgtc ccattgctaa atagacagac tccatctgcc    3000
gcctccaact gatgttctca atatttaagg ggtcatctcg cattgtttaa taataaacag    3060
actccatcta ccgcctccaa atgatgttct caaaatatat tgtatgaact tattttttatt    3120 acttagtatt attagacaac ttacttgctt tatgaaaaac acttcctatt taggaaacaa    3180
tttataatgg cagttcgttc atttaacaat ttatgtagaa taaatgttat aaatgcgtat    3240
gggaaatctt aaatatggat agcataaatg atatctgcat tgcctaattc gaaatcaaca    3300
gcaacgaaaa aaatcccttg tacaacataa atagtcatcg agaaatatca actatcaaag    3360
aacagctatt cacacgttac tattgagatt attattggac gagaatcaca cactcaactg    3420
tctttctctc ttctagaaat acaggtacaa gtatgtacta ttctcattgt tcatacttct    3480
agtcatttca tcccacatat tccttggatt tctctccaat gaatgacatt ctatcttgca    3540
aattcaacaa ttataataag atataccaaa gtagcggtat agtggcaatc aaaaagcttc    3600
tctggtgtgc ttctcgtatt tatttttatt ctaatgatcc attaaaggta tatatttatt    3660
tcttgttata taatccttt gtttattaca tgggctggat acataaaggt atttttgattt    3720 aatttttgc ttaaattcaa tcccccctcg ttcagtgtca actgtaatgg taggaaatta    3780
ccatactttt gaagaagcaa aaaaaatgaa agaaaaaaaa aatcgtatttt ccaggttaga    3840 cgttccgcag aatctagaat gcggtatgcg gtacattgtt cttcgaacgt aaaagttgcg    3900
ctccctgaga tattgtacat ttttgctttt acaagtacaa gtacatcgta caactatgta    3960
ctactgttga tgcatccaca acagtttgtt ttgtttttt ttgttttttt tttttctaat    4020
gattcattac cgctatgtat acctacttgt acttgtagta agccgggtta ttggcgttca    4080
attaatcata gacttatgaa tctgcacggt gtgcgctgcg agttacttt agcttatgca    4140 tgctacttgg gtgtaatatt gggatctgtt cggaaatcaa cggatgctca atcgatttcg    4200
acagtaatta attaagtcat acacaagtca gctttcttcg agcctcatat aagtataagt    4260
agttcaacgt attagcactg tacccagcat ctccgtatcg agaaacacaa caacatgccc    4320
cattggacag atcatgcgga tacacaggtt gtgcagtatc atacatactc gatcagacag    4380
gtcgtctgac catcatacaa gctgaacaag cgctccatac ttgcacgctc tctatataca    4440
cagttaaatt acatatccat agtctaacct ctaacagtta atcttctggt aagcctccca    4500
gccagccttc tggtatcgct tggcctcctc aataggatct cggttctggc cgtacagacc    4560
tcggccgaca attatgatat ccgttccggt agacatgaca tcctcaacag ttcggtactg    4620
ctgtccgaga gcgtctccct tgtcgtcaag acccaccccg ggggtcagaa taagccagtc    4680
ctcagagtcg ccottaggtc ggttctgggc aatgaagcca accacaaaact cggggtcgga    4740 tcgggcaagc tcaatggtct gcttggagta ctcgccagtg gccagagagc ccttgcaaga    4800
```

```
cagctcggcc agcatgagca gacctctggc cagcttctcg ttgggagagg ggactaggaa    4860
ctccttgtac tgggagttct cgtagtcaga gacgtcctcc ttcttctgtt cagagacagt    4920
ttcctcggca ccagctcgca ggccagcaat gattccggtt ccgggtacac cgtgggcgtt    4980
ggtgatatcg gaccactcgg cgattcggtg acaccggtac tggtgcttga cagtgttgcc    5040
aatatctgcg aactttctgt cctcgaacag gaagaaaccg tgcttaagag caagttcctt    5100 gaggggagc acagtgccgg cgtaggtgaa gtcgtcaatg atgtcgatat ggttttgat     5160 catgcacaca taaggtccga ccttatcggc aagctcaatg agctccttgg tggtggtaac    5220
atccagagaa gcacacaggt tggttttctt ggctgccacg agcttgagca ctcgagcggc    5280
aaaggcggac ttgtggacgt tagctcgagc ttcgtaggag ggcattttgg tggtgaagag    5340
gagactgaaa taaatttagt ctgcagaact ttttatcgga accttatctg gggcagtgaa    5400
gtatatgtta tggtaatagt tacgagttag ttgaacttat agatagactg gactatacgg    5460
ctatcggtcc aaattagaaa gaacgtcaat ggctctctgg gcgtcgcctt tgccgacaaa    5520
aatgtgatca tgatgaaagc cagcaatgac gttgcagctg atattgttgt cggccaaccg    5580
cgccgaaaac gcagctgtca gacccacagc ctccaacgaa gaatgtatcg tcaaagtgat    5640
ccaagcacac tcatagttgg agtcgtactc caaaggcggc aatgacgagt cagacagata    5700
ctcgtcgact caggcgacga cggaattcct gcagcccatc tgcagaattc aggagagacc    5760
gggttggcgg cgtatttgtg tcccaaaaaa cagccccaat tgcccggag aagacggcca    5820 ggccgcctag atgacaaatt caacaactca cagctgactt tctgccattg ccactagggg    5880 ggggccttt tatatggcca agccaagctc tccacgtcgg ttgggctgca cccaacaata    5940
aatgggtagg gttgcaccaa caaagggatg ggatggggg tagaagatac gaggataacg    6000
gggctcaatg gcacaaataa gaacgaatac tgccattaag actcgtgatc cagcgactga    6060
caccattgca tcatctaagg gcctcaaaac tacctcggaa ctgctgcgct gatctggaca    6120
ccacagaggt tccgagcact ttaggttgca ccaaatgtcc caccaggtgc aggcagaaaa    6180
cgctggaaca gcgtgtacag tttgtcttaa caaaaagtga gggcgctgag gtcgagcagg    6240
gtggtgtgac ttgttatagc ctttagagct gcgaaagcgc gtatggattt ggctcatcag    6300
gccagattga gggtctgtgg acacatgtca tgttagtgta cttcaatcgc ccctggata    6360 tagccccgac aataggccgt ggcctcattt ttttgccttc cgcacatttc cattgctcgg    6420
tacccacacc ttgcttctcc tgcacttgcc aaccttaata ctggtttaca ttgaccaaca    6480
tcttacaagc gggggcttg tctagggtat atataaacag tggctctccc aatcggttgc    6540
cagtctcttt tttcctttct ttccccacag attcgaaatc taaactacac atcacacaat    6600
gcctgttact gacgtcctta agcgaaagtc cggtgtcatc gtcggcgacg atgtccgagc    6660
cgtgagtatc cacgacaaga tcagtgtcga gacgacgcgt tttgtgtaat gacacaatcc    6720
gaaagtcgct agcaacacac actctctaca caaactaacc cagctctcca tggctgagga    6780
taagaccaag gtcgagttcc ctaccctgac tgagctgaag cactctatcc ctaacgcttg    6840
ctttgagtcc aacctcggac tctcgctcta ctacactgcc cgagcgatct tcaacgcatc    6900
tgcctctgct gctctgctct acgctgcccg atctactccc ttcattgccg ataacgttct    6960
gctccacgct ctggtttgcg ccacctacat ctacgtgcag ggtgtcatct tctgggggttt   7020 ctttaccgtc ggtcacgact gtggtcactc tgccttctcc cgataccact ccgtcaactt    7080
catcattggc tgcatcatgc actctgccat tctgactccc ttcgagtcct ggcgagtgac    7140
```

```
ccaccgacac catcacaaga acactggcaa cattgataag gacgagatct tctaccctca    7200
tcggtccgtc aaggacctcc aggacgtgcg acaatgggtc tacaccctcg gaggtgcttg    7260
gtttgtctac ctgaaggtcg gatatgctcc tcgaaccatg tcccactttg accccctggga   7320 ccctctcctg cttcgacgag cctccgctgt catcgtgtcc ctcggagtct gggctgcctt    7380
cttcgctgcc tacgcctacc tcacatactc gctcggcttt gccgtcatgg gcctctacta    7440
ctatgctcct ctctttgtct ttgcttcgtt cctcgtcatt actaccttct tgcatcacaa    7500
cgacgaagct actccctggt acggtgactc ggagtggacc tacgtcaagg gcaacctgag    7560
ctccgtcgac cgatcgtacg gagctttcgt ggacaacctg tctcaccaca ttggcaccca    7620
ccaggtccat cacttgttcc ctatcattcc ccactacaag ctcaacgaag ccaccaagca    7680
ctttgctgcc gcttaccctc acctcgtgag acgtaacgac gagcccatca ttactgcctt    7740
cttcaagacc gctcacctct ttgtcaacta cggagctgtg cccgagactg ctcagatttt    7800
caccctcaaa gagtctgccg ctgcagccaa ggccaagagc gactaagcgg ccgcaagtgt    7860
ggatggggaa gtgagtgccc ggttctgtgt gcacaattgg caatccaaga tggatggatt    7920
caacacaggg atatagcgag ctacgtggtg gtgcgaggat atagcaacgg atatttatgt    7980
ttgacacttg agaatgtacg atacaagcac tgtccaagta caatactaaa catactgtac    8040
atactcatac tcgtacccgg gcaacggttt cacttgagtg cagtggctag tgctcttact    8100
cgtacagtgt gcaatactgc gtatcatagt ctttgatgta tatcgtattc attcatgtta    8160
gttgc                                                                8165

<210> SEQ ID NO 165
<211> LENGTH: 8666
<212> TYPE: DNA
<213> ORGANISM: Artificial Sequence
<220> FEATURE:
<223> OTHER INFORMATION: Plasmid pMDGAT1-17
<220> FEATURE:
<221> NAME/KEY: misc_feature
<222> LOCATION: (467)..(467)
<223> OTHER INFORMATION: n is a, c, g, or t

<400> SEQUENCE: 165
catggcagag tcgacaacaa cgacatgtgc aaaggaggag ggcattgcca acagcgctgc     60
tttgcctgac attcccccaa agatggaaga cctcaagtcc tccaggaaga ccggctcttc    120
ttacaagcac accttccccg tccatacaaa aaccatcccc agcccattgt ctaaagaggc    180
acctccagag agctatcgtg gattcgtcaa cctcggcatg ctcctacttt tcggcaacaa    240
catccgattg atcatcgaga attacctcaa atacggcttc ctgctctcaa tccctggatc    300
aagcgtctcg aagcaggact ggatcctggc tgccctcacc cacgccatcc tacccgtcaa    360
cctcatcctg gcctacaagc ttgagagctg ggccaaggag agagccgtcg gctatcgcaa    420
gcgtcgatct gacgaaccca ttgcccagga atcaaccaag gccgtgncag caggagataa    480
tgacgctatc aaaaccacaa aacccgccaa ggcccaggat ctcacacccg aggcccttgc    540
aaggaaggaa caatcgaccg tgggctggct ccatgtcttc aatctgttca ccatcgttgc    600 ctggcctcc ttcatgtcct actttatgat ctaccacccc ttcgtggcca tgtcctgcct    660
catgaacgga cttatcctct tcctcaaaat gacctccttt gcgcttgtga accaggagct    720
ccgagcagcc tacatctttg gaacacccgt ggacacgttc cagcacatgg ctaaagtgca    780
cgacatctct ggcaaggacc tgacaaagaa ggagatcttc cagtatgaca tccagtaccc    840
cgacaacatc accctcaaga acattggcta tttctggctc gccccccacgc tctgctacca    900
```

-continued

```
gccatcatac ccaaggacga ccgtcttccg caaatccttc ttcctcaagc gtgtggccga    960
gatcgtgacc tgtctgggca tgatgtactt tttagtcgag cagtacgcca ccccacccct   1020
gcagaactcg gtccgagcat tcgatgagtt ggcgttcggc accattctgg agagagtgct   1080
gaagctgagc accaccagtg tcatcatctg gctactcatg ttctacacct ttttccactc   1140
gttctttaat gctcttgcag aggcactgta ctttggagac cgtcgcttct atctcgcctg   1200
gtggaatgcc actggtgtcg gcatgtactg gaagacgtgg aactcgcccg tctacacctt   1260
cttcaaacgc cacgtatacc tgcccctgat cacctctggc acctctccca tggtcgcctc   1320
gatcgtcatc ttcctcatct cggctgtctt gcacgagatc ttgatcggct tccccactca   1380
tatgatctat ggatacgcat cgccggcat gttcctccag atcccgctga tcattctgac   1440
ccgacccctc gaaaaatggc gaggcaccgg atcgggtctc ggcaacatga tcttctgggt   1500
ctcgttcacc atcctgggcc agccagcgtg tgcgctgctc tactactacc actggaccaa   1560
gcgccatatg gatgtttgag cggccgcaag tgtggatggg gaagtgagtg cccggttctg   1620
tgtgcacaat tggcaatcca agatggatgg attcaacaca gggatatagc gagctacgtg   1680
gtggtgcgag gatatagcaa cggatattta tgtttgacac ttgagaatgt acgatacaag   1740
cactgtccaa gtacaatact aaacatactg tacatactca tactcgtacc cgggcaacgg   1800
tttcacttga gtgcagtggc tagtgctctt actcgtacag tgtgcaatac tgcgtatcat   1860
agtctttgat gtatatcgta ttcattcatg ttagttgcgt acgagccgga agcataaagt   1920
gtaaagcctg gggtgcctaa tgagtgagct aactcacatt aattgcgttg cgctcactgc   1980
ccgctttcca gtcgggaaac ctgtcgtgcc agctgcatta atgaatcggc caacgcgcgg   2040
ggagaggcgg tttgcgtatt gggcgctctt ccgcttcctc gctcactgac tcgctgcgct   2100
cggtcgttcg gctgcggcga gcggtatcag ctcactcaaa ggcggtaata cggttatcca   2160
cagaatcagg ggataacgca ggaaagaaca tgtgagcaaa aggccagcaa aaggccagga   2220
accgtaaaaa ggccgcgttg ctggcgtttt tccataggct ccgcccccct gacgagcatc   2280
acaaaaatcg acgctcaagt cagaggtggc gaaacccgac aggactataa agataccagg   2340
cgtttccccc tggaagctcc ctcgtgcgct ctcctgttcc gaccctgccg cttaccggat   2400
acctgtccgc ctttctccct tcgggaagcg tggcgctttc tcatagctca cgctgtaggt   2460
atctcagttc ggtgtaggtc gttcgctcca agctgggctg tgtgcacgaa ccccccgttc   2520
agcccgaccg ctgcgcctta tccggtaact atcgtcttga gtccaacccg gtaagacacg   2580
acttatcgcc actggcagca gccactggta acaggattag cagagcgagg tatgtaggcg   2640
gtgctacaga gttcttgaag tggtggccta actacggcta cactagaagg acagtatttg   2700
gtatctgcgc tctgctgaag ccagttacct tcggaaaaag agttggtagc tcttgatccg   2760
gcaaacaaac caccgctggt agcggtggtt tttttgtttg caagcagcag attacgcgca   2820
gaaaaaaagg atctcaagaa gatcctttga tcttttctac ggggtctgac gctcagtgga   2880
acgaaaactc acgttaaggg attttggtca tgagattatc aaaaaggatc ttcacctaga   2940
tccttttaaa ttaaaaatga agttttaaat caatctaaag tatatatgag taaacttggt   3000
ctgacagtta ccaatgctta atcagtgagg cacctatctc agcgatctgt ctatttcgtt   3060
catccatagt tgcctgactc cccgtcgtgt agataactac gatacgggag ggcttaccat   3120
ctggccccag tgctgcaatg ataccgcgag acccacgctc accggctcca gatttatcag   3180
caataaacca gccagccgga agggccgagc gcagaagtgg tcctgcaact ttatccgcct   3240
```

```
ccatccagtc tattaattgt tgccgggaag ctagagtaag tagttcgcca gttaatagtt    3300
tgcgcaacgt tgttgccatt gctacaggca tcgtggtgtc acgctcgtcg tttggtatgg    3360
cttcattcag ctccggttcc caacgatcaa ggcgagttac atgatccccc atgttgtgca    3420
aaaaagcggt tagctccttc ggtcctccga tcgttgtcag aagtaagttg gccgcagtgt    3480
tatcactcat ggttatggca gcactgcata attctcttac tgtcatgcca tccgtaagat    3540
gcttttctgt gactggtgag tactcaacca agtcattctg agaatagtgt atgcggcgac    3600
cgagttgctc ttgcccggcg tcaatacggg ataataccgc gccacatagc agaactttaa    3660
aagtgctcat cattggaaaa cgttcttcgg ggcgaaaact ctcaaggatc ttaccgctgt    3720
tgagatccag ttcgatgtaa cccactcgtg cacccaactg atcttcagca tcttttactt    3780
tcaccagcgt ttctgggtga gcaaaaacag gaaggcaaaa tgccgcaaaa agggaataa    3840
gggcgacacg gaaatgttga atactcatac tcttcctttt tcaatattat tgaagcattt    3900
atcagggtta ttgtctcatg agcggataca tatttgaatg tatttagaaa aataaacaaa    3960
taggggttcc gcgcacattt ccccgaaaag tgccacctga cgcgccctgt agcggcgcat    4020
taagcgcggc gggtgtggtg gttacgcgca gcgtgaccgc tacacttgcc agcgccctag    4080
cgcccgctcc tttcgctttc ttcccttcct ttctcgccac gttcgccggc tttccccgtc    4140
aagctctaaa tcggggctc cctttagggt tccgatttag tgctttacgg cacctcgacc    4200
ccaaaaaact tgattagggt gatggttcac gtagtgggcc atcgccctga tagacggttt    4260
ttcgcccttt gacgttggag tccacgttct ttaatagtgg actcttgttc caaactggaa    4320
caacactcaa ccctatctcg gtctattctt ttgatttata agggattttg ccgatttcgg    4380
cctattggtt aaaaatgag ctgatttaac aaaaatttaa cgcgaatttt aacaaaatat    4440
taacgcttac aatttccatt cgccattcag gctgcgcaac tgttgggaag ggcgatcggt    4500
gcgggcctct tcgctattac gccagctggc gaaaggggga tgtgctgcaa ggcgattaag    4560
ttgggtaacg ccagggtttt cccagtcacg acgttgtaaa acgacggcca gtgaattgta    4620
atacgactca ctatagggcg aattgggtac cgggcccccc ctcgaggtcg atggtgtcga    4680
taagcttgat atcgaattca tgtcacacaa accgatcttc gcctcaagga aacctaattc    4740
tacatccgag agactgccga gatccagtct acactgatta attttcgggc caataattta    4800
aaaaaatcgt gttatataat attatatgta ttatatatat acatcatgat gatactgaca    4860
gtcatgtccc attgctaaat agacagactc catctgccgc ctccaactga tgttctcaat    4920
atttaagggg tcatctcgca ttgtttaata ataaacagac tccatctacc gcctccaaat    4980
gatgttctca aaatatattg tatgaactta ttttttattac ttagtattat tagacaactt    5040
acttgcttta tgaaaacac ttcctatttta ggaaacaatt tataatggca gttcgttcat    5100
ttaacaattt atgtagaata aatgttataa atgcgtatgg gaaatcttaa atatggatag    5160
cataaatgat atctgcattg cctaattcga atcaacagc aacgaaaaaa atcccttgta    5220
caacataaat agtcatcgag aaatatcaac tatcaaagaa cagctattca cacgttacta    5280
ttgagattat tattggacga gaatcacaca ctcaactgtc tttctctctt ctagaaatac    5340
aggtacaagt atgtactatt ctcattgttc atacttctag tcatttcatc ccacatattc    5400
cttggatttc tctccaatga atgacattct atcttgcaaa ttcaacaatt ataataagat    5460
ataccaaagt agcggtatag tgcaatcaa aaagcttctc tggtgtgctt ctcgtattta    5520
tttttattct aatgatccat taaaggtata tatttatttc ttgttatata atccttttgt    5580
ttattacatg ggctggatac ataaaggtat tttgatttaa ttttttgctt aaattcaatc    5640
```

-continued

```
ccccctcgtt cagtgtcaac tgtaatggta ggaaattacc atactttga agaagcaaaa    5700
aaaatgaaag aaaaaaaaaa tcgtatttcc aggttagacg ttccgcagaa tctagaatgc    5760
ggtatgcggt acattgttct tcgaacgtaa agttgcgct ccctgagata ttgtacattt     5820
ttgcttttac aagtacaagt acatcgtaca actatgtact actgttgatg catccacaac    5880
agtttgtttt gtttttttt gtttttttt tttctaatga ttcattaccg ctatgtatac      5940
ctacttgtac ttgtagtaag ccgggttatt ggcgttcaat taatcataga cttatgaatc    6000
tgcacggtgt gcgctgcgag ttacttttag cttatgcatg ctacttgggt gtaatattgg    6060
gatctgttcg gaaatcaacg gatgctcaat cgatttcgac agtaattaat taagtcatac    6120
acaagtcagc tttcttcgag cctcatataa gtataagtag ttcaacgtat tagcactgta    6180
cccagcatct ccgtatcgag aaacacaaca acatgcccca ttggacagat catgcggata    6240
cacaggttgt gcagtatcat acatactcga tcagacaggt cgtctgacca tcatacaagc    6300
tgaacaagcg ctccatactt gcacgctctc tatatacaca gttaaattac atatccatag    6360
tctaacctct aacagttaat cttctggtaa gcctcccagc cagccttctg gtatcgcttg    6420
gcctcctcaa taggatctcg gttctggccg tacagacctc ggccgacaat tatgatatcc    6480
gttccggtag acatgacatc ctcaacagtt cggtactgct gtccgagagc gtctcccttg    6540
tcgtcaagac ccaccccggg ggtcagaata agccagtcct cagagtcgcc cttaggtcgg    6600
ttctgggcaa tgaagccaac cacaaactcg gggtcggatc gggcaagctc aatggtctgc    6660
ttggagtact cgccagtggc cagagagccc ttgcaagaca gctcggccag catgagcaga    6720
cctctggcca gcttctcgtt gggagagggg actaggaact ccttgtactg ggagttctcg    6780
tagtcagaga cgtcctcctt cttctgttca gagacagttt cctcggcacc agctcgcagg    6840
ccagcaatga ttccggttcc gggtacaccg tgggcgttgg tgatatcgga ccactcggcg    6900
attcggtgac accggtactg gtgcttgaca gtgttgccaa tatctgcgaa ctttctgtcc    6960
tcgaacagga agaaaccgtg cttaagagca gttccttga gggggagcac agtgccggcg      7020
taggtgaagt cgtcaatgat gtcgatatgg gttttgatca tgcacacata aggtccgacc    7080
ttatcggcaa gctcaatgag ctccttggtg gtggtaacat ccagagaagc acacaggttg    7140
gttttcttgg ctgccacgag cttgagcact cgagcggcaa aggcggactt gtggacgtta    7200
gctcgagctt cgtaggaggg cattttggtg gtgaagagga gactgaaata aatttagtct    7260
gcagaacttt ttatcggaac cttatctggg gcagtgaagt atatgttatg gtaatagtta    7320
cgagttagtt gaacttatag atagactgga ctatacggct atcggtccaa attagaaaga    7380
acgtcaatgg ctctctgggc gtcgcctttg ccgacaaaaa tgtgatcatg atgaaagcca    7440
gcaatgacgt tgcagctgat attgttgtcg gccaaccgcg ccgaaaacgc agctgtcaga    7500
cccacagcct ccaacgaaga atgtatcgtc aaagtgatcc aagcacactc atagttggag    7560
tcgtactcca aaggcggcaa tgacgagtca gacagatact cgtcgactca ggcgacgacg    7620
gaattcctgc agcccatctg cagaattcag gagagaccgg gttggcggcg tatttgtgtc    7680
ccaaaaaaca gccccaattg ccccggagaa gacggccagg ccgcctagat gacaaattca    7740
acaactcaca gctgactttc tgccattgcc actaggggg ggccttttta tatggccaag      7800
ccaagctctc cacgtcggtt gggctgcacc caacaataaa tgggtagggt tgcaccaaca    7860
aagggatggg atgggggta gaagatacga ggataacggg gctcaatggc acaaataaga     7920
acgaatactg ccattaagac tcgtgatcca gcgactgaca ccattgcatc atctaagggc    7980
```

```
ctcaaaacta cctcggaact gctgcgctga tctggacacc acagaggttc cgagcacttt      8040
aggttgcacc aaatgtccca ccaggtgcag gcagaaaacg ctggaacagc gtgtacagtt      8100
tgtcttaaca aaaagtgagg cgcctgaggt cgagcagggt ggtgtgactt gttatagcct      8160
ttagagctgc gaaagcgcgt atggatttgg ctcatcaggc cagattgagg gtctgtggac      8220
acatgtcatg ttagtgtact tcaatcgccc cctggatata gccccgacaa taggccgtgg      8280
cctcattttt ttgccttccg cacatttcca ttgctcggta cccacacctt gcttctcctg      8340
cacttgccaa ccttaatact ggtttacatt gaccaacatc ttacaagcgg ggggcttgtc      8400
tagggtatat ataaacagtg gctctcccaa tcggttgcca gtctcttttt tccttctctt      8460
ccccacagat tcgaaatcta aactacacat cacacaatgc ctgttactga cgtccttaag      8520
cgaaagtccg gtgtcatcgt cggcgacgat gtccgagccg tgagtatcca cgacaagatc      8580
agtgtcgaga cgacgcgttt tgtgtaatga cacaatccga aagtcgctag caacacacac      8640
tctctacaca aactaaccca gctctc                                            8666

<210> SEQ ID NO 166
<211> LENGTH: 28
<212> TYPE: DNA
<213> ORGANISM: Artificial Sequence
<220> FEATURE:
<223> OTHER INFORMATION: Primer PZUF-mod1

<400> SEQUENCE: 166
gatcccatgg atccaggcct gttaacgg                                          28

<210> SEQ ID NO 167
<211> LENGTH: 32
<212> TYPE: DNA
<213> ORGANISM: Artificial Sequence
<220> FEATURE:
<223> OTHER INFORMATION: Primer PZUF-mod2

<400> SEQUENCE: 167
gatcgcggcc gcagacatga taagatacat tg                                     32

<210> SEQ ID NO 168
<211> LENGTH: 7323
<212> TYPE: DNA
<213> ORGANISM: Artificial Sequence
<220> FEATURE:
<223> OTHER INFORMATION: Plasmid pZUF-MOD-1

<400> SEQUENCE: 168
gtacgagccg gaagcataaa gtgtaaagcc tggggtgcct aatgagtgag ctaactcaca      60
ttaattgcgt tgcgctcact gcccgctttc cagtcgggaa acctgtcgtg ccagctgcat      120
taatgaatcg gccaacgcgc ggggagaggc ggtttgcgta ttgggcgctc ttccgcttcc      180
tcgctcactg actcgctgcg ctcggtcgtt cggctgcggc gagcggtatc agctcactca      240
aaggcggtaa tacggttatc cacagaatca ggggataacg caggaaagaa catgtgagca      300
aaaggccagc aaaaggccag gaaccgtaaa aaggccgcgt tgctggcgtt tttccatagg      360
ctccgccccc ctgacgagca tcacaaaaat cgacgctcaa gtcagaggtg gcgaaacccg      420
acaggactat aaagatacca ggcgtttccc cctggaagct ccctcgtgcg ctctcctgtt      480
ccgaccctgc cgcttaccgg atacctgtcc gcctttctcc cttcgggaag cgtggcgctt      540
tctcatagct cacgctgtag gtatctcagt tcggtgtagg tcgttcgctc caagctgggc      600
tgtgtgcacg aaccccccgt tcagcccgac cgctgcgcct tatccggtaa ctatcgtctt      660
```

-continued

```
gagtccaacc cggtaagaca cgacttatcg ccactggcag cagccactgg taacaggatt      720
agcagagcga ggtatgtagg cggtgctaca gagttcttga agtggtggcc taactacggc      780
tacactagaa ggacagtatt tggtatctgc gctctgctga agccagttac cttcggaaaa      840
agagttggta gctcttgatc cggcaaacaa accaccgctg gtagcggtgg ttttttttgtt     900 tgcaagcagc agattacgcg cagaaaaaaa ggatctcaag aagatccttt gatcttttct      960
acggggtctg acgctcagtg gaacgaaaac tcacgttaag ggattttggt catgagatta     1020
tcaaaaagga tcttcaccta gatcctttta aattaaaaat gaagttttaa atcaatctaa     1080
agtatatatg agtaaacttg gtctgacagt taccaatgct taatcagtga ggcacctatc     1140
tcagcgatct gtctatttcg ttcatccata gttgcctgac tccccgtcgt gtagataact     1200
acgatacggg agggcttacc atctggcccc agtgctgcaa tgataccgcg agacccacgc     1260
tcaccggctc cagatttatc agcaataaac cagccagccg gaagggccga gcgcagaagt     1320
ggtcctgcaa ctttatccgc ctccatccag tctattaatt gttgccggga agctagagta     1380
agtagttcgc cagttaatag tttgcgcaac gttgttgcca ttgctacagg catcgtggtg     1440
tcacgctcgt cgtttggtat ggcttcattc agctccggtt cccaacgatc aaggcgagtt     1500
acatgatccc ccatgttgtg caaaaaagcg gttagctcct tcggtcctcc gatcgttgtc     1560
agaagtaagt tggccgcagt gttatcactc atggttatgg cagcactgca taattctctt     1620
actgtcatgc catccgtaag atgcttttct gtgactggtg agtactcaac caagtcattc     1680
tgagaatagt gtatgcggcg accgagttgc tcttgcccgg cgtcaatacg ggataatacc     1740
gcgccacata gcagaacttt aaaagtgctc atcattggaa aacgttcttc ggggcgaaaa     1800
ctctcaagga tcttaccgct gttgagatcc agttcgatgt aacccactcg tgcacccaac     1860
tgatcttcag catcttttac tttcaccagc gtttctgggt gagcaaaaac aggaaggcaa     1920
aatgccgcaa aaaagggaat aagggcgaca cggaaatgtt gaatactcat actcttcctt     1980
tttcaatatt attgaagcat ttatcagggt tattgtctca tgagcggata catatttgaa     2040
tgtatttaga aaaataaaca aataggggtt ccgcgcacat ttccccgaaa agtgccacct     2100
gacgcgccct gtagcggcgc attaagcgcg gcgggtgtgg tggttacgcg cagcgtgacc     2160
gctacacttg ccagcgccct agcgcccgct cctttcgctt tcttcccttc ctttctcgcc     2220
acgttcgccg gctttccccg tcaagctcta aatcgggggc tccctttagg gttccgattt     2280
agtgctttac ggcacctcga ccccaaaaaa cttgattagg gtgatggttc acgtagtggg     2340
ccatcgccct gatagacggt ttttcgccct ttgacgttgg agtccacgtt ctttaatagt     2400
ggactcttgt tccaaactgg aacaacactc aaccctatct cggtctattc ttttgattta     2460
taagggattt tgccgatttc ggcctattgg ttaaaaaatg agctgattta acaaaaattt     2520
aacgcgaatt ttaacaaaat attaacgctt acaatttcca ttcgccattc aggctgcgca     2580
actgttggga agggcgatcg gtgcgggcct cttcgctatt acgccagctg gcgaaagggg     2640
gatgtgctgc aaggcgatta agttgggtaa cgccagggtt ttcccagtca cgacgttgta     2700
aaacgacggc cagtgaattg taatacgact cactataggg cgaattgggt accgggcccc     2760
ccctcgaggt cgatggtgtc gataagcttg atatcgaatt catgtcacac aaaccgatct     2820
tcgcctcaag gaaacctaat tctacatccg agagactgcc gagatccagt ctacactgat     2880
taattttcgg gccaataatt taaaaaaatc gtgttatata atattatatg tattatatat     2940
atacatcatg atgatactga cagtcatgtc ccattgctaa atagacagac tccatctgcc     3000
```

-continued

```
gcctccaact gatgttctca atatttaagg ggtcatctcg cattgtttaa taataaacag    3060
actccatcta ccgcctccaa atgatgttct caaaatatat tgtatgaact tatttttatt    3120
acttagtatt attagacaac ttacttgctt tatgaaaaac acttcctatt taggaaacaa    3180
tttataatgg cagttcgttc atttaacaat ttatgtagaa taaatgttat aaatgcgtat    3240
gggaaatctt aaatatggat agcataaatg atatctgcat tgcctaattc gaaatcaaca    3300
gcaacgaaaa aaatcccttg tacaacataa atagtcatcg agaaatatca actatcaaag    3360
aacagctatt cacacgttac tattgagatt attattggac gagaatcaca cactcaactg    3420
tctttctctc ttctagaaat acaggtacaa gtatgtacta ttctcattgt tcatacttct    3480
agtcatttca tcccacatat tccttggatt tctctccaat gaatgacatt ctatcttgca    3540
aattcaacaa ttataataag atataccaaa gtagcgtat agtggcaatc aaaaagcttc      3600
tctggtgtgc ttctcgtatt tatttttatt ctaatgatcc attaaaggta tatatttatt    3660
tcttgttata taatccttt gtttattaca tgggctggat acataaaggt attttgattt     3720
aattttttgc ttaaattcaa tcccccctcg ttcagtgtca actgtaatgg taggaaatta    3780
ccatactttt gaagaagcaa aaaaaatgaa agaaaaaaaa aatcgtattt ccaggttaga    3840
cgttccgcag aatctagaat gcggtatgcg gtacattgtt cttcgaacgt aaaagttgcg    3900
ctccctgaga tattgtacat ttttgctttt acaagtacaa gtacatcgta caactatgta    3960
ctactgttga tgcatccaca acagtttgtt ttgtttttt ttgttttttt tttttctaat     4020
gattcattac cgctatgtat acctacttgt acttgtagta agccgggtta ttggcgttca    4080
attaatcata gacttatgaa tctgcacggt gtgcgctgcg agttactttt agcttatgca    4140
tgctacttgg gtgtaatatt gggatctgtt cggaaatcaa cggatgctca atcgatttcg    4200
acagtaatta attaagtcat acacaagtca gctttcttcg agcctcatat aagtataagt    4260
agttcaacgt attagcactg tacccagcat ctccgtatcg agaaacacaa caacatgccc    4320
cattggacag atcatgcgga tacacaggtt gtgcagtatc atacatactc gatcagacag    4380
gtcgtctgac catcatacaa gctgaacaag cgctccatac ttgcacgctc tctatataca    4440
cagttaaatt acatatccat agtctaacct ctaacagtta atcttctggt aagcctccca    4500
gccagccttc tggtatcgct tggcctcctc aataggatct cggttctggc cgtacagacc    4560
tcggccgaca attatgatat ccgttccggt agacatgaca tcctcaacag ttcggtactg    4620
ctgtccgaga gcgtctccct tgtcgtcaag acccaccccg ggggtcagaa taagccagtc    4680
ctcagagtcg cccttaggtc ggttctgggc aatgaagcca accacaaact cggggtcgga    4740
tcgggcaagc tcaatggtct gcttggagta ctcgccagtg gccagagagc ccttgcaaga    4800
cagctcggcc agcatgagca gacctctggc cagcttctcg ttgggagagg ggactaggaa    4860
ctccttgtac tgggagttct cgtagtcaga gacgtcctcc ttcttctgtt cagagacagt    4920
ttcctcggca ccagctcgca ggccagcaat gattccggtt ccgggtacac cgtgggcgtt    4980
ggtgatatcg gaccactcgg cgattcggtg acaccggtac tggtgcttga cagtgttgcc    5040
aatatctgcg aactttctgt cctcgaacag gaagaaaccg tgcttaagag caagttcctt    5100
gaggggagc acagtgccgg cgtaggtgaa gtcgtcaatg atgtcgatat gggttttgat     5160
catgcacaca taaggtccga ccttatcggc aagctcaatg agctccttgg tggtggtaac    5220
atccagagaa gcacacaggt tggttttctt ggctgccacg agcttgagca ctcgagcggc    5280
aaaggcggac ttgtggacgt tagctcgagc ttcgtaggag ggcatttggg tggtgaagag    5340
gagactgaaa taaatttagt ctgcagaact ttttatcgga accttatctg gggcagtgaa    5400
```

-continued

```
gtatatgtta tggtaatagt tacgagttag ttgaacttat agatagactg gactatacgg    5460
ctatcggtcc aaattagaaa gaacgtcaat ggctctctgg gcgtcgcctt tgccgacaaa    5520
aatgtgatca tgatgaaagc cagcaatgac gttgcagctg atattgttgt cggccaaccg    5580
cgccgaaaac gcagctgtca gacccacagc ctccaacgaa gaatgtatcg tcaaagtgat    5640
ccaagcacac tcatagttgg agtcgtactc caaaggcggc aatgacgagt cagacagata    5700
ctcgtcgact caggcgacga cggaattcct gcagcccatc tgcagaattc aggagagacc    5760
gggttggcgg cgtatttgtg tcccaaaaaa cagccccaat tgccccggag aagacggcca    5820
ggccgcctag atgacaaatt caacaactca cagctgactt tctgccattg ccactagggg    5880 ggggccttttt tatatggcca agccaagctc tccacgtcgg ttgggctgca cccaacaata    5940
aatgggtagg gttgcaccaa caaagggatg ggatgggggg tagaagatac gaggataacg    6000
gggctcaatg gcacaaataa gaacgaatac tgccattaag actcgtgatc cagcgactga    6060
caccattgca tcatctaagg gcctcaaaac tacctcggaa ctgctgcgct gatctggaca    6120
ccacagaggt tccgagcact ttaggttgca ccaaatgtcc caccaggtgc aggcagaaaa    6180
cgctggaaca gcgtgtacag tttgtcttaa caaaaagtga gggcgctgag gtcgagcagg    6240
gtggtgtgac ttgttatagc ctttagagct gcgaaagcgc gtatggattt ggctcatcag    6300
gccagattga gggtctgtgg acacatgtca tgttagtgta cttcaatcgc ccctggata    6360 tagccccgac aataggccgt ggcctcattt ttttgccttc cgcacatttc cattgctcgg    6420
tacccacacc ttgcttctcc tgcacttgcc aaccttaata ctggtttaca ttgaccaaca    6480
tcttacaagc ggggggcttg tctagggtat atataaacag tggctctccc aatcggttgc    6540
cagtctcttt tttcctttct ttccccacag attcgaaatc taaactacac atcacacaat    6600
gcctgttact gacgtcctta agcgaaagtc cggtgtcatc gtcggcgacg atgtccgagc    6660
cgtgagtatc cacgacaaga tcagtgtcga gacgacgcgt tttgtgtaat gacacaatcc    6720
gaaagtcgct agcaacacac actctctaca caaactaacc cagctctcca tggatccagg    6780
cctgttaacg gccattacgg cctgcaggat ccgaaaaaac ctcccacacc tccccctgaa    6840
cctgaaacat aaaatgaatg caattgttgt tgttaacttg tttattgcag cttataatgg    6900
ttacaaataa agcaatagca tcacaaattt cacaaataaa gcatttttt cactgcattc    6960 tagttgtggt ttgtccaaac tcatcaatgt atcttatcat gtctgcggcc gcaagtgtgg    7020
atggggaagt gagtgcccgg ttctgtgtgc acaattggca atccaagatg gatggattca    7080
acacagggat atagcgagct acgtggtggt gcgaggatat agcaacggat atttatgttt    7140
gacacttgag aatgtacgat acaagcactg tccaagtaca atactaaaca tactgtacat    7200
actcatactc gtacccgggc aacggtttca cttgagtgca gtggctagtg ctcttactcg    7260
tacagtgtgc aatactgcgt atcatagtct ttgatgtata tcgtattcat tcatgttagt    7320
tgc                                                                  7323
```

<210> SEQ ID NO 169
<211> LENGTH: 388
<212> TYPE: PRT
<213> ORGANISM: Mus musculus
<300> PUBLICATION INFORMATION:
<308> DATABASE ACCESSION NUMBER: GenBank Accession No. AF384160
<309> DATABASE ENTRY DATE: 2001-10-16
<313> RELEVANT RESIDUES: (1)..(388)

<400> SEQUENCE: 169

-continued

```
Met Lys Thr Leu Ile Ala Ala Tyr Ser Gly Val Leu Arg Gly Glu Arg
1               5                   10                  15

Arg Ala Glu Ala Ala Arg Ser Glu Asn Lys Asn Lys Gly Ser Ala Leu
            20                  25                  30

Ser Arg Glu Gly Ser Gly Arg Trp Gly Thr Gly Ser Ser Ile Leu Ser
        35                  40                  45

Ala Leu Gln Asp Ile Phe Ser Val Thr Trp Leu Asn Arg Ser Lys Val
    50                  55                  60

Glu Lys Gln Leu Gln Val Ile Ser Val Leu Gln Trp Val Leu Ser Phe
65                  70                  75                  80

Leu Val Leu Gly Val Ala Cys Ser Val Ile Leu Met Tyr Thr Phe Cys
                85                  90                  95

Thr Asp Cys Trp Leu Ile Ala Val Leu Tyr Phe Thr Trp Leu Ala Phe
            100                 105                 110

Asp Trp Asn Thr Pro Lys Lys Gly Gly Arg Arg Ser Gln Trp Val Arg
        115                 120                 125

Asn Trp Ala Val Trp Arg Tyr Phe Arg Asp Tyr Phe Pro Ile Gln Leu
    130                 135                 140

Val Lys Thr His Asn Leu Leu Thr Thr Arg Asn Tyr Ile Phe Gly Tyr
145                 150                 155                 160

His Pro His Gly Ile Met Gly Leu Gly Ala Phe Cys Asn Phe Ser Thr
                165                 170                 175

Glu Ala Thr Glu Val Ser Lys Lys Phe Pro Gly Ile Arg Pro Tyr Leu
            180                 185                 190

Ala Thr Leu Ala Gly Asn Phe Arg Met Pro Val Leu Arg Glu Tyr Leu
        195                 200                 205

Met Ser Gly Gly Ile Cys Pro Val Asn Arg Asp Thr Ile Asp Tyr Leu
    210                 215                 220

Leu Ser Lys Asn Gly Ser Gly Asn Ala Ile Ile Ile Val Val Gly Gly
225                 230                 235                 240

Ala Ala Glu Ser Leu Ser Ser Met Pro Gly Lys Asn Ala Val Thr Leu
                245                 250                 255

Lys Asn Arg Lys Gly Phe Val Lys Leu Ala Leu Arg His Gly Ala Asp
            260                 265                 270

Leu Val Pro Thr Tyr Ser Phe Gly Glu Asn Glu Val Tyr Lys Gln Val
        275                 280                 285

Ile Phe Glu Glu Gly Ser Trp Gly Arg Trp Val Gln Lys Lys Phe Gln
    290                 295                 300

Lys Tyr Ile Gly Phe Ala Pro Cys Ile Phe His Gly Arg Gly Leu Phe
305                 310                 315                 320

Ser Ser Asp Thr Trp Gly Leu Val Pro Tyr Ser Lys Pro Ile Thr Thr
                325                 330                 335

Val Val Gly Glu Pro Ile Thr Val Pro Lys Leu Glu His Pro Thr Gln
            340                 345                 350

Lys Asp Ile Asp Leu Tyr His Ala Met Tyr Met Glu Ala Leu Val Lys
        355                 360                 365

Leu Phe Asp Asn His Lys Thr Lys Phe Gly Leu Pro Glu Thr Glu Val
    370                 375                 380

Leu Glu Val Asn
385

<210> SEQ ID NO 170
<211> LENGTH: 504
<212> TYPE: PRT
```

<213> ORGANISM: Glycine max
<300> PUBLICATION INFORMATION:
<302> TITLE: Plant diacyglycerol acyltransferases
<310> PATENT DOCUMENT NUMBER: US 20040088759
<311> PATENT FILING DATE: 2003-10-21
<312> PUBLICATION DATE: 2004-05-06
<313> RELEVANT RESIDUES: (1)..(504)

<400> SEQUENCE: 170

```
Met Ala Ile Ser Asp Glu Pro Glu Ser Val Ala Thr Ala Leu Asn His
1               5                   10                  15

Ser Ser Leu Arg Arg Arg Pro Ser Ala Thr Ser Thr Ala Gly Leu Phe
            20                  25                  30

Asn Ser Pro Glu Thr Thr Thr Asp Ser Ser Gly Asp Asp Leu Ala Lys
        35                  40                  45

Asp Ser Gly Ser Asp Asp Ser Ile Asn Ser Asp Asp Ala Ala Val Asn
    50                  55                  60

Ser Gln Gln Asn Glu Lys Gln Asp Thr Asp Phe Ser Val Leu Lys
65                  70                  75                  80

Phe Ala Tyr Arg Pro Ser Val Pro Ala His Arg Lys Val Lys Glu Ser
                85                  90                  95

Pro Leu Ser Ser Asp Thr Ile Phe Arg Gln Ser His Ala Gly Leu Phe
            100                 105                 110

Asn Leu Cys Ile Val Val Leu Val Ala Val Asn Ser Arg Leu Ile Ile
        115                 120                 125

Glu Asn Leu Met Lys Tyr Gly Trp Leu Ile Lys Ser Gly Phe Trp Phe
    130                 135                 140

Ser Ser Lys Ser Leu Arg Asp Trp Pro Leu Phe Met Cys Cys Leu Ser
145                 150                 155                 160

Leu Val Val Phe Pro Phe Ala Ala Phe Ile Val Glu Lys Leu Ala Gln
                165                 170                 175

Arg Lys Cys Ile Pro Glu Pro Val Val Val Leu His Ile Ile Ile
            180                 185                 190

Thr Ser Thr Ser Leu Phe Tyr Pro Val Leu Val Ile Leu Arg Cys Asp
        195                 200                 205

Ser Ala Phe Val Ser Gly Val Thr Leu Met Leu Phe Ser Cys Val Val
    210                 215                 220

Trp Leu Lys Leu Val Ser Tyr Ala His Thr Asn Tyr Asp Met Arg Ala
225                 230                 235                 240

Leu Thr Lys Leu Val Glu Lys Gly Glu Ala Leu Leu Asp Thr Leu Asn
                245                 250                 255

Met Asp Tyr Pro Tyr Asn Val Ser Phe Lys Ser Leu Ala Tyr Phe Leu
            260                 265                 270

Val Ala Pro Thr Leu Cys Tyr Gln Pro Ser Tyr Pro Arg Thr Pro Tyr
        275                 280                 285

Ile Arg Lys Gly Trp Leu Phe Arg Gln Leu Val Lys Leu Ile Ile Phe
    290                 295                 300

Thr Gly Val Met Gly Phe Ile Ile Asp Gln Tyr Ile Asn Pro Ile Val
305                 310                 315                 320

Gln Asn Ser Gln His Pro Leu Lys Gly Asn Leu Leu Tyr Ala Thr Glu
                325                 330                 335

Arg Val Leu Lys Leu Ser Val Pro Asn Leu Tyr Val Trp Leu Cys Met
            340                 345                 350

Phe Tyr Cys Phe Phe His Leu Trp Leu Asn Ile Leu Ala Glu Leu Leu
        355                 360                 365
```

-continued

```
Arg Phe Gly Asp Arg Glu Phe Tyr Lys Asp Trp Trp Asn Ala Lys Thr
    370                 375                 380

Val Glu Asp Tyr Trp Arg Met Trp Asn Met Pro Val His Lys Trp Met
385                 390                 395                 400

Ile Arg His Leu Tyr Phe Pro Cys Leu Arg His Gly Leu Pro Lys Ala
                405                 410                 415

Ala Ala Leu Leu Ile Ala Phe Leu Val Ser Ala Leu Phe His Glu Leu
            420                 425                 430

Cys Ile Ala Val Pro Cys His Ile Phe Lys Leu Trp Ala Phe Gly Gly
                435                 440                 445

Ile Met Phe Gln Val Pro Leu Val Leu Ile Thr Asn Tyr Leu Gln Asn
    450                 455                 460

Lys Phe Arg Asn Ser Met Val Gly Asn Met Ile Phe Trp Phe Ile Phe
465                 470                 475                 480

Ser Ile Leu Gly Gln Pro Met Cys Val Leu Leu Tyr Tyr His Asp Leu
                485                 490                 495

Met Asn Arg Lys Gly Lys Leu Asp
            500
```

<210> SEQ ID NO 171
<211> LENGTH: 520
<212> TYPE: PRT
<213> ORGANISM: Arabidopsis thaliana
<300> PUBLICATION INFORMATION:
<302> TITLE: Plant diacyglycerol acyltransferases
<310> PATENT DOCUMENT NUMBER: US20040088759
<311> PATENT FILING DATE: 2003-10-21
<312> PUBLICATION DATE: 2004-05-06
<313> RELEVANT RESIDUES: (1)..(520)

<400> SEQUENCE: 171

```
Met Ala Ile Leu Asp Ser Ala Gly Val Thr Thr Val Thr Glu Asn Gly
1               5                   10                  15

Gly Gly Glu Phe Val Asp Leu Asp Arg Leu Arg Arg Lys Ser Arg
            20                  25                  30

Ser Asp Ser Ser Asn Gly Leu Leu Leu Ser Gly Ser Asp Asn Asn Ser
            35                  40                  45

Pro Ser Asp Asp Val Gly Ala Pro Ala Asp Val Arg Asp Arg Ile Asp
    50                  55                  60

Ser Val Val Asn Asp Asp Ala Gln Gly Thr Ala Asn Leu Ala Gly Asp
65                  70                  75                  80

Asn Asn Gly Gly Gly Asp Asn Gly Gly Arg Gly Gly Glu
                85                  90                  95

Gly Arg Gly Asn Ala Asp Ala Thr Phe Thr Tyr Arg Pro Ser Val Pro
            100                 105                 110

Ala His Arg Arg Ala Arg Glu Ser Pro Leu Ser Ser Asp Ala Ile Phe
    115                 120                 125

Lys Gln Ser His Ala Gly Leu Phe Asn Leu Cys Val Val Leu Ile
    130                 135                 140

Ala Val Asn Ser Arg Leu Ile Ile Glu Asn Leu Met Lys Tyr Gly Trp
145                 150                 155                 160

Leu Ile Arg Thr Asp Phe Trp Phe Ser Arg Ser Leu Arg Asp Trp
                165                 170                 175

Pro Leu Phe Met Cys Trp Ile Ser Leu Ser Ile Phe Pro Leu Ala Ala
            180                 185                 190

Phe Thr Val Glu Lys Leu Val Leu Gln Lys Tyr Ile Ser Glu Pro Val
    195                 200                 205
```

-continued

```
Gly Ile Phe Leu His Ile Ile Thr Met Thr Glu Val Leu Tyr Pro
    210                 215                 220

Val Tyr Val Thr Leu Arg Cys Asp Ser Ala Phe Leu Ser Gly Val Thr
225                 230                 235                 240

Leu Met Leu Leu Thr Cys Ile Val Trp Leu Lys Leu Val Ser Tyr Ala
                245                 250                 255

His Thr Ser Tyr Asp Ile Arg Ser Leu Ala Asn Ala Ala Asp Lys Ala
            260                 265                 270

Asn Pro Glu Val Ser Tyr Tyr Val Ser Leu Lys Ser Leu Ala Tyr Phe
        275                 280                 285

Met Val Ala Pro Thr Leu Cys Tyr Gln Pro Ser Tyr Pro Arg Ser Ala
    290                 295                 300

Cys Ile Arg Lys Gly Trp Val Ala Arg Gln Phe Ala Lys Leu Val Ile
305                 310                 315                 320

Phe Thr Gly Phe Met Gly Phe Ile Ile Glu Gln Tyr Ile Asn Pro Ile
                325                 330                 335

Val Arg Asn Ser Lys His Pro Leu Lys Gly Asp Leu Leu Tyr Ala Ile
            340                 345                 350

Glu Arg Val Leu Lys Leu Ser Val Pro Asn Leu Tyr Val Trp Leu Cys
        355                 360                 365

Met Phe Tyr Cys Phe Phe His Leu Trp Leu Asn Ile Leu Ala Glu Leu
    370                 375                 380

Leu Cys Phe Gly Asp Arg Glu Phe Tyr Lys Asp Trp Trp Asn Ala Lys
385                 390                 395                 400

Ser Val Gly Asp Tyr Trp Arg Met Trp Asn Met Pro Val His Lys Trp
                405                 410                 415

Met Val Arg His Ile Tyr Phe Pro Cys Leu Arg Ser Lys Ile Pro Lys
            420                 425                 430

Thr Leu Ala Ile Ile Ile Ala Phe Leu Val Ser Ala Val Phe His Glu
        435                 440                 445

Leu Cys Ile Ala Val Pro Cys Arg Leu Phe Lys Leu Trp Ala Phe Leu
    450                 455                 460

Gly Ile Met Phe Gln Val Pro Leu Val Phe Ile Thr Asn Tyr Leu Gln
465                 470                 475                 480

Glu Arg Phe Gly Ser Thr Val Gly Asn Met Ile Phe Trp Phe Ile Phe
                485                 490                 495

Cys Ile Phe Gly Gln Pro Met Cys Val Leu Leu Tyr Tyr His Asp Leu
            500                 505                 510

Met Asn Arg Lys Gly Ser Met Ser
        515                 520

<210> SEQ ID NO 172
<211> LENGTH: 500
<212> TYPE: PRT
<213> ORGANISM: Oryza sativa
<300> PUBLICATION INFORMATION:
<302> TITLE: Plant diacyglycerol acyltransferases
<310> PATENT DOCUMENT NUMBER: US 20040088759
<311> PATENT FILING DATE: 2003-10-21
<312> PUBLICATION DATE: 2004-05-06
<313> RELEVANT RESIDUES: (1)..(500)

<400> SEQUENCE: 172

Met Val Gly Ser Asp Gly Asp Gly Asp Gly Gly Gly Glu Ala His
1               5                   10                  15

Ala Gly Gly Pro Arg Arg Arg Ala Gly Gln Leu Arg Gly Arg Leu Arg
```

```
                    20                  25                  30
Asp Glu Ala Ala Pro Gly Ser Pro Pro Arg Pro Arg Pro Arg Pro Arg
                35                  40                  45

Pro Arg Gly Gly Asp Ser Asn Gly Arg Ser Val Leu Arg Pro Gly Gly
    50                  55                  60

Gly Gly Gly Arg Gly Gly Gly Asp Phe Ser Ala Phe Thr Phe Arg
65                  70                  75                  80

Ala Ala Ala Pro Val His Arg Lys Ala Lys Glu Ser Pro Leu Ser Ser
                85                  90                  95

Asp Ala Ile Phe Lys Gln Ser His Ala Gly Leu Phe Asn Leu Cys Ile
                100                 105                 110

Val Val Leu Val Ala Val Asn Ser Arg Leu Ile Ile Glu Asn Leu Met
                115                 120                 125

Lys Tyr Gly Leu Leu Ile Arg Ala Gly Phe Trp Phe Asn Asp Lys Ser
                130                 135                 140

Leu Arg Asp Trp Pro Leu Leu Met Cys Cys Leu Ser Leu Pro Ala Phe
145                 150                 155                 160

Pro Leu Gly Ala Phe Ala Val Glu Lys Leu Ala Phe Asn Asn Val Ile
                165                 170                 175

Thr Asp Ala Val Ala Thr Cys Leu His Ile Phe Leu Ser Thr Thr Glu
                180                 185                 190

Ile Val Tyr Pro Val Leu Val Ile Leu Lys Cys Asp Ser Ala Val Leu
                195                 200                 205

Ser Gly Phe Leu Leu Ile Phe Ile Ala Cys Ile Val Trp Leu Lys Leu
                210                 215                 220

Val Ser Phe Ala His Thr Asn His Asp Ile Arg Gln Leu Thr Met Gly
225                 230                 235                 240

Gly Lys Lys Val Asp Asn Glu Leu Ser Thr Val Asp Met Asp Asn Leu
                245                 250                 255

Gln Pro Pro Thr Leu Gly Asn Leu Ile Tyr Phe Met Met Ala Pro Thr
                260                 265                 270

Leu Cys Tyr Gln Pro Ser Tyr Pro Arg Thr Ser Cys Val Arg Lys Gly
                275                 280                 285

Trp Leu Ile Arg Gln Ile Ile Leu Tyr Leu Ile Phe Thr Gly Leu Gln
                290                 295                 300

Gly Phe Ile Ile Glu Gln Tyr Ile Asn Pro Ile Val Val Asn Ser Gln
305                 310                 315                 320

His Pro Leu Lys Gly Gly Leu Leu Asn Ala Val Glu Thr Val Leu Lys
                325                 330                 335

Leu Ser Leu Pro Asn Val Tyr Leu Trp Leu Cys Met Phe Tyr Ala Phe
                340                 345                 350

Phe His Leu Trp Leu Ser Ile Leu Ala Glu Ile Leu Arg Phe Gly Asp
                355                 360                 365

Arg Glu Phe Tyr Lys Asp Trp Trp Asn Ala Lys Thr Ile Asp Glu Tyr
                370                 375                 380

Trp Arg Lys Trp Asn Met Pro Val His Lys Trp Val Val Arg His Ile
385                 390                 395                 400

Tyr Phe Pro Cys Met Arg Asn Gly Ile Ser Lys Glu Val Ala Val Leu
                405                 410                 415

Ile Ser Phe Leu Val Ser Ala Val Leu His Glu Ile Cys Val Ala Val
                420                 425                 430

Pro Cys Arg Ile Leu Lys Phe Trp Ala Phe Leu Gly Ile Met Leu Gln
                435                 440                 445
```

```
Ile Pro Leu Ile Val Leu Thr Ala Tyr Leu Lys Ser Lys Phe Arg Asp
    450                 455                 460

Thr Met Val Gly Asn Met Ile Phe Trp Phe Phe Phe Cys Ile Tyr Gly
465                 470                 475                 480

Gln Pro Met Cys Leu Leu Tyr Tyr His Asp Val Met Asn Arg Ile
                485                 490                 495

Glu Lys Ala Arg
            500

<210> SEQ ID NO 173
<211> LENGTH: 534
<212> TYPE: PRT
<213> ORGANISM: Perilla frutescens
<300> PUBLICATION INFORMATION:
<308> DATABASE ACCESSION NUMBER: GenBank Accession No. AF298815
<309> DATABASE ENTRY DATE: 2000-10-16
<313> RELEVANT RESIDUES: (1)..(534)

<400> SEQUENCE: 173

Met Ala Ile Leu Asp Ser Pro Glu Ile Leu Asp Thr Thr Ser Ser Ser
1               5                   10                  15

Ala Asp Asn Gly Ala Ala His His Thr Thr Leu Arg Arg Gln Ser
            20                  25                  30

Ala Arg Ser Val Pro Pro Leu Leu Asp Ser Asp Ser Asn Ser Leu Glu
        35                  40                  45

Ala Glu Ser Ala Ile Asn Asp Ser Glu Asn Val Arg Asn Asp Ala Asn
    50                  55                  60

Leu Ile Glu Asn Leu Arg Gly Gly Ala Val Glu Ser Glu Asn Glu Lys
65                  70                  75                  80

Gln Glu Ser Tyr Gly Lys Glu Gly Ala Lys Val Lys Glu Asn Gly
                85                  90                  95

Glu Thr Ser Asn Gly Asn Gly Thr Asp Val Met Ala Val Lys Phe Thr
                100                 105                 110

Phe Arg Pro Ala Ala Pro Ala His Arg Lys Asn Lys Glu Ser Pro Leu
        115                 120                 125

Ser Ser Asp Ala Ile Phe Lys Gln Ser His Ala Gly Leu Phe Asn Leu
130                 135                 140

Cys Ile Val Val Leu Val Ala Val Asn Ser Arg Leu Ile Ile Glu Asn
145                 150                 155                 160

Leu Met Lys Tyr Gly Trp Leu Ile Lys Ser Gly Phe Trp Phe Ser Ser
                165                 170                 175

Thr Ser Leu Arg Asp Trp Pro Leu Leu Met Cys Cys Leu Ser Leu Pro
            180                 185                 190

Val Phe Ala Leu Ala Ser Phe Leu Val Glu Lys Leu Val Lys Leu Asn
        195                 200                 205

Tyr Ile Pro Glu Trp Val Ala Val Phe Leu His Val Thr Ile Thr Thr
    210                 215                 220

Val Glu Ile Leu Phe Pro Val Val Ile Leu Arg Cys Asp Ser Ala
225                 230                 235                 240

Val Leu Ser Gly Val Thr Leu Met Leu Phe Ala Cys Thr Val Trp Leu
                245                 250                 255

Lys Leu Val Ser Tyr Ala His Thr Asn Tyr Asp Leu Arg Val Leu Ala
            260                 265                 270

Lys Ser Leu Asp Lys Trp Glu Ala Met Ser Arg Tyr Trp Asn Leu Asp
        275                 280                 285
```

```
Tyr Ala Tyr Asp Val Ser Phe Lys Ser Leu Ala Tyr Phe Met Val Ala
    290                 295                 300

Pro Thr Leu Cys Tyr Gln Pro Ser Tyr Pro Arg Thr Ala Cys Ile Arg
305                 310                 315                 320

Lys Gly Trp Val Val Arg Gln Leu Ile Lys Leu Val Ile Phe Thr Gly
                325                 330                 335

Leu Met Gly Phe Ile Ile Glu Gln Tyr Ile Asn Pro Ile Val Gln Asn
            340                 345                 350

Ser Gln His Pro Leu Lys Gly Asn Leu Leu Tyr Ala Ile Glu Arg Val
        355                 360                 365

Leu Lys Leu Ser Val Pro Asn Leu Tyr Val Trp Leu Cys Met Phe Tyr
    370                 375                 380

Cys Phe Phe His Leu Trp Leu Asn Ile Leu Ala Glu Leu Leu Cys Phe
385                 390                 395                 400

Gly Asp Arg Glu Phe Tyr Lys Asp Trp Trp Asn Ala Arg Thr Val Glu
                405                 410                 415

Glu Tyr Trp Arg Met Trp Asn Met Pro Val His Lys Trp Met Val Arg
            420                 425                 430

His Ile Tyr Cys Pro Cys Leu Gln Asn Gly Ile Pro Lys Ile Val Ala
        435                 440                 445

Val Leu Ile Ala Phe Leu Val Ser Ala Ile Phe His Glu Leu Cys Val
    450                 455                 460

Ala Val Pro Cys Gln Ile Phe Lys Phe Trp Ala Phe Ser Gly Ile Met
465                 470                 475                 480

Leu Gln Val Pro Leu Val Ile Val Thr Asn Tyr Leu Gln Glu Lys Phe
                485                 490                 495

Lys Asn Ser Met Val Gly Asn Met Met Phe Trp Cys Phe Phe Cys Ile
            500                 505                 510

Phe Gly Gln Pro Met Cys Val Leu Leu Tyr Tyr His Asp Leu Met Asn
        515                 520                 525

Arg Lys Ala Ser Ala Arg
    530

<210> SEQ ID NO 174
<211> LENGTH: 508
<212> TYPE: PRT
<213> ORGANISM: Triticum aestivum
<300> PUBLICATION INFORMATION:
<302> TITLE: Plant diacyglycerol acyltransferases
<310> PATENT DOCUMENT NUMBER: US 20040088759
<311> PATENT FILING DATE: 2003-10-21
<312> PUBLICATION DATE: 2004-05-06
<313> RELEVANT RESIDUES: (1)..(508)

<400> SEQUENCE: 174

Met Ser Lys Gly Asn Pro Asp Pro His Leu Pro Gly Ser Phe Leu Pro
1               5                   10                  15

Ser His Gly Gly Pro Pro Lys Pro Lys Thr Pro Pro Arg Thr Phe
            20                  25                  30

Arg Asn Leu Pro Ser Ser Thr His Gly Pro Ala Pro Ser Val Ala
        35                  40                  45

Ala Ala Thr Ile Ala Thr Thr Pro Ser Ala Ser Ala Pro Leu
    50                  55                  60

Pro Pro Thr Val His Gly Glu Ala His Gly Ala Ala Ala Ala
65                  70                  75                  80

Arg Arg Asp Ala Leu Leu Pro Gly Val Gly Ala Ala His Arg Arg Val
                85                  90                  95
```

-continued

```
Lys Glu Ser Pro Leu Ser Ser Asp Ala Ile Phe Arg Gln Ser His Ala
            100                 105                 110
Gly Leu Leu Asn Leu Cys Ile Val Val Leu Ile Ala Val Asn Ser Arg
            115                 120                 125
Leu Ile Ile Glu Asn Leu Met Lys Tyr Gly Leu Leu Ile Arg Ala Gly
            130                 135                 140
Phe Trp Phe Ser Ala Arg Ser Leu Gly Asp Trp Pro Leu Leu Met Cys
145                 150                 155                 160
Cys Leu Thr Leu Pro Ile Phe Pro Leu Ala Ala Leu Met Thr Glu Lys
                165                 170                 175
Trp Ala Gln Arg Lys Leu Ile Arg Asp His Val Ser Ile Leu Leu His
            180                 185                 190
Ile Ile Ile Thr Thr Thr Val Leu Ile Tyr Pro Val Val Ile Leu
            195                 200                 205
Lys Cys Glu Ser Ala Val Leu Ser Gly Phe Val Leu Met Phe Ile Ala
            210                 215                 220
Ser Ile Thr Trp Leu Lys Leu Val Ser Phe Ala His Thr Asn Tyr Asp
225                 230                 235                 240
Ile Arg Ile Leu Ser Gln Ser Ile Glu Lys Gly Ala Thr His Gly Ser
                245                 250                 255
Ser Ile Asp Glu Glu Asn Ile Lys Gly Pro Thr Ile Asn Ser Val Val
            260                 265                 270
Tyr Phe Met Leu Ala Pro Thr Leu Cys Tyr Gln Pro Ser Tyr Pro Arg
            275                 280                 285
Thr Ala Phe Ile Arg Lys Gly Trp Val Thr Arg Gln Leu Ile Lys Cys
            290                 295                 300
Val Val Phe Thr Gly Leu Met Gly Phe Ile Ile Glu Gln Tyr Ile Asn
305                 310                 315                 320
Pro Ile Val Gln Asn Ser Lys His Pro Leu Asn Gly Asn Phe Leu Asp
                325                 330                 335
Ala Ile Glu Arg Val Leu Lys Leu Ser Val Pro Thr Leu Tyr Val Trp
            340                 345                 350
Leu Cys Met Phe Tyr Ser Phe His Leu Trp Leu Asn Ile Leu Ala
            355                 360                 365
Glu Leu Leu Arg Phe Gly Asp Arg Glu Phe Tyr Lys Asp Trp Trp Asn
            370                 375                 380
Ala Lys Thr Val Glu Glu Tyr Trp Arg Met Trp Asn Met Pro Val His
385                 390                 395                 400
Lys Trp Ile Val Arg His Ile Tyr Phe Pro Cys Ile Arg Asn Gly Leu
                405                 410                 415
Ser Lys Gly Cys Ala Ile Leu Ile Ala Phe Leu Val Ser Ala Val Phe
            420                 425                 430
His Glu Leu Cys Ile Ala Val Pro Cys His Ile Phe Lys Leu Trp Ala
            435                 440                 445
Phe Ser Gly Ile Met Phe Gln Ile Pro Leu Leu Phe Leu Thr Lys Tyr
            450                 455                 460
Leu Gln Asp Lys Phe Lys Asn Thr Met Val Gly Asn Met Ile Phe Trp
465                 470                 475                 480
Phe Phe Phe Ser Ile Val Gly Gln Pro Met Cys Val Leu Leu Tyr Tyr
                485                 490                 495
His Asp Val Met Asn Arg Gln Ala Gln Thr Asn Gly
            500                 505
```

<210> SEQ ID NO 175
<211> LENGTH: 604
<212> TYPE: DNA
<213> ORGANISM: Mortierella alpina

<400> SEQUENCE: 175

```
gggggcatg atgtactttt tagtcgagca gtacgccacc cccaccctgc agaactcggt      60
ccgagcattc gatgagttgg cgttcggcac cattctggag agagtgctga agctgagcac    120
caccagtgtc atcatctggc tactcatgtt ctacacctttt ttccactcgt tcttaatgc    180
tcttgcagag gcactgtact ttggagaccg tcgcttctat ctcgcctggt ggaatgccac    240
tggtgtcggc atgtactgga agacgtggaa ctcgcccgtc tacaccttct tcaaacgcca    300
cgtatacctg ccctgatca cctctggcac ctctcccatg gtcgcctcga tcgtcatctt    360
cctcatctcg gctgtcttgc acgagatctt gatcggcttc cccactcata tgatctatgg    420
atacgcattc gccggcatgt tcctccagat cccgctgatc attctgaccc gacccctcga    480
aaaatggcga ggcaccggat cgggtctcgg caacatgatc ttctgggtct cgttcaccat    540
cctgggccag ccagcgtgtg cgctgctcta ctactaccac tggaccaagc gccatatgga    600
tgtt                                                                 604
```

DIACYLGLYCEROL ACYLTRANSFERASES FOR ALTERATION OF POLYUNSATURATED FATTY ACIDS AND OIL CONTENT IN OLEAGINOUS ORGANISMS

This application claims the benefit of U.S. Provisional Application 60/624,812, filed Nov. 4, 2004.

FIELD OF THE INVENTION

This invention is in the field of biotechnology. More specifically, this invention pertains to the identification of nucleic acid fragments encoding diacylglycerol acyltransferases (DGAT1) and acyl-CoA:sterol-acyltransferases. These enzymes are useful for altering the quantity of oil in oleaginous microorganisms, such as oleaginous yeasts.

BACKGROUND OF THE INVENTION

The present invention is directed toward the development of an oleaginous yeast that accumulates oils enriched in long-chain ω-3 and/or ω-6 polyunsaturated fatty acids ("PUFAs"; e.g., 18:3, 18:4, 20:3, 20:4, 20:5 and 22:6 fatty acids). Toward this end, the natural abilities of oleaginous yeast (mostly limited to 18:2 fatty acid production) have been enhanced by advances in genetic engineering, leading to the production of 20:4 (arachidonic acid, or "ARA"), 20:5 (eicosapentaenoic acid, or "EPA") and 22:6 (docosahexaenoic acid, or "DHA") PUFAs in transformant *Yarrowia lipolytica*. These ω-3 and ω-6 fatty acids were produced by introducing and expressing heterologous genes encoding the ω-3/ω-6 biosynthetic pathway in the oleaginous host (see co-pending U.S. patent application Ser. No. 10/840579, entirely incorporated herein by reference). However, in addition to developing techniques to introduce the appropriate fatty acid desaturases and elongases into these particular host organisms, it is also necessary to increase the transfer of PUFAs into storage lipid pools following their synthesis.

Most free fatty acids become esterified to coenzyme A (CoA), to yield acyl-CoAs. These molecules are then substrates for glycerolipid synthesis in the endoplasmic reticulum of the cell, where phosphatidic acid and diacylglycerol (DAG) are produced. Either of these metabolic intermediates may be directed to membrane phospholipids (e.g., phosphatidylglycerol, phosphatidylethanolamine, phosphatidylcholine) or DAG may be directed to form triacylglycerols (TAGs), the primary storage reserve of lipids in eukaryotic cells.

Two comprehensive mini-reviews on TAG biosynthesis in yeast, including details concerning the genes involved and the metabolic intermediates that lead to TAG synthesis are: D. Sorger and G. Daum, *Appl. Microbiol. Biotechnol.* 61:289-299 (2003); and H. Müllner and G. Daum, *Acta Biochimica Polonica*, 51(2):323-347 (2004). However, the authors acknowledge that most work performed thus far has focused on the yeast *Saccharomyces cerevisiae* and numerous questions regarding TAG formation and regulation remain.

Briefly, three pathways have been described for the synthesis of TAGs in *S. cerevisiae* (Sandager, L. et al., *J. Biol. Chem.* 277(8):6478-6482 (2002)). First, TAGs are mainly synthesized from DAG and acyl-CoAs by the activity of a diacylglycerol acyltransferase (i.e., DGAT2, encoded by the DGA1 gene). More recently, however, a phospholipid:diacylglycerol acyltransferase (i.e., PDAT, encoded by the LRO1 gene) has also been identified that is responsible for conversion of phospholipid and DAG to lysophospholipid and TAG, respectively, thus producing TAG via an acyl-CoA-independent mechanism (Dahlqvist et al., *PNAS.* 97(12):6487-6492 (2000)). Finally, two acyl-CoA:sterol-acyltransferases (encoded by the ARE1 and ARE2 genes) are known that utilize acyl-CoAs and sterols to produce sterol esters (and TAGs in low quantities; see Sandager, L. et al., *Biochem. Soc. Trans.* 28(6):700-702 (2000)). Together, PDAT and DGAT2 are responsible for approximately 95% of oil biosynthesis in *S. cerevisiae*.

Although homologs of each of the acyltransferase genes described above have been identified in various other organisms and disclosed in the public literature, few genes are available from organisms classified as oleaginous. With respect to yeast, those species included within the genera of *Yarrowia, Candida, Rhodotorula, Rhodosporidium, Cryptococcus, Trichosporon* and *Lipomyces* and that can accumulate at least 25% of their dry cell weight as oil are classified as oleaginous. Within this unique family of yeast, however, only two acyltransferases have been isolated and characterized. These include a DGAT2 and PDAT from *Yarrowia lipolytica* (see co-pending U.S. patent application Ser. No. 10/882,760, entirely incorporated herein by reference). However, in contrast to the findings in Saccharomyces cerevisiae, the *Y. lipolytica* DGAT2 and PDAT were discovered to only be partially responsible for the organism's total oil biosynthesis.

There remains a need there for to identify genes encoding diacylglycerol acyltransferases (DGAT1) and acyl-CoA:sterol-acyltransferases useful for expression in oleaginous yeast for the production of PFUA's. The present work was conducted to identify and characterize the additional gene(s) involved in oil biosynthesis in the oleaginous yeast, *Yarrowia lipolytica*. An understanding of the native mechanisms of oil biosynthesis in this organism is useful, prior to the development of techniques that modify the transfer of recombinantly produced fatty acids (e.g., long-chain PUFAs, such as ARA, EPA and DHA) to the storage lipid pools (i.e., TAG fraction) within transformant oleaginous yeast.

Applicants have solved the stated problem by isolating the genes encoding a diacylglycerol acyltransferase (DGAT1) and an acyl-CoA:sterol-acyltransferase (ARE2) from the oleaginous yeast, *Yarrowia lipolytica*. Together, the PDAT, DGAT2 and DGAT1 of *Yarrowia lipolytica* are responsible for up to ~95% of oil biosynthesis (while ARE2 may additionally be a minor contributor to oil biosynthesis). Additionally, an orthologous DGAT1 gene was cloned from *Mortierella alpina* (an oleaginous fungus) and four other fungal DGAT1 orthologs from public sequence databases (i.e., *Neurospora crassa, Gibberella zeae* PH-1, *Magnaporthe grisea* and *Aspergillus nidulans*) were identified. With these fungal DGAT1 protein sequences, the Applicants have discovered diagnostic features that will be useful to identify subsequent genes within this family of proteins. These DGAT1 genes will be useful to enable one to modify the transfer of long-chain free fatty acids (e.g., ω-3 and/or ω-6 fatty acids) to the TAG pool in oleaginous yeast.

SUMMARY OF THE INVENTION

The invention relates to the discovery of genes encoding acyltransferase enzymes. The genes and encoded enzymes are useful in manipulating the production of commercially useful oils in microorganisms, and particularly in oleaginous yeasts. Accordingly the invention provides an isolated nucleic acid molecule encoding a diacylglycerol acyltransferase 1 enzyme, selected from the group consisting of:
- (a) an isolated nucleic acid molecule encoding the amino acid sequence selected from the group consisting of SEQ ID NOs:14 and 18;
- (b) an isolated nucleic acid molecule that hybridizes with (a) under the following hybridization conditions: 0.1× SSC, 0.1% SDS, 65° C. and washed with 2×SSC, 0.1% SDS followed by 0.1×SSC, 0.1% SDS; or
- (c) an isolated nucleic acid molecule that is completely complementary to (a) or (b).

Similarly, the invention provides an isolated nucleic acid molecule encoding an acyl-CoA:sterol-acyltransferase, selected from the group consisting of:
- (a) an isolated nucleic acid molecule encoding the amino acid sequence as set forth in SEQ ID NO:16;
- (b) an isolated nucleic acid molecule that hybridizes with (a) under the following hybridization conditions: 0.1× SSC, 0.1% SDS, 65° C. and washed with 2×SSC, 0.1% SDS followed by 0.1×SSC, 0.1% SDS; or
- (c) an isolated nucleic acid molecule that is completely complementary to (a) or (b).

Additionally the invention provides polypeptides encoded by the isolated nucleic acid molecules of the invention as well as genetic chimera and host cells expressing the same.

In another embodiment the invention provides an isolated nucleic acid molecule encoding an amino acid motif selected from the group consisting of:
- a) SEQ ID NO:31;
- b) SEQ ID NO:32;
- c) SEQ ID NO:33;
- d) SEQ ID NO:34;
- e) SEQ ID NO:35;
- f) SEQ ID NO:36;
- g) SEQ ID NO:37;
- h) SEQ ID NO:23;
- i) SEQ ID NO:24;
- j) SEQ ID NO:25;
- k) SEQ ID NO:26;
- l) SEQ ID NO:27;
- m) SEQ ID NO:28;
- n) SEQ ID NO:29; and
- o) SEQ ID NO:30.

In another embodiment the invention provides an amino acid motif sequence selected from the group consisting of:
- a) SEQ ID NO:31;
- b) SEQ ID NO:32;
- c) SEQ ID NO:33;
- d) SEQ ID NO:34;
- e) SEQ ID NO:35;
- f) SEQ ID NO:36;
- g) SEQ ID NO:37;
- h) SEQ ID NO:23;
- i) SEQ ID NO:24;
- j) SEQ ID NO:25;
- k) SEQ ID NO:26;
- l) SEQ ID NO:27;
- m) SEQ ID NO:28;
- n) SEQ ID NO:29; and
- o) SEQ ID NO:30.

In a preferred embodiment the invention provides a method of increasing triacylglycerol content in a transformed host cell comprising:
- (a) providing a transformed host cell comprising:
  - (i) at least one gene encoding a diacylglycerol acyltransferase 1 enzyme having the amino acid sequence selected from the group consisting of SEQ ID NOs:14, 18, 19, 20, 21 and 22 under the control of suitable regulatory sequences; and,
  - (ii) a source of fatty acids;
- (b) growing the cell of step (a) under conditions whereby the at least one gene encoding a diacylglycerol acyltransferase 1 enzyme is expressed, resulting in the transfer of the fatty acids to triacylglycerol; and
- (c) optionally recovering the triacylglycerol of step (b).

In similar fashion the invention provides a method of increasing the ω-3 or ω-6 fatty acid content of triacylglycerols in a transformed host cell comprising:
- (a) providing a transformed host cell comprising:
  - (i) genes encoding a functional ω-3/ω-6 fatty acid biosynthetic pathway;
  - (ii) at least one gene encoding a diacylglycerol acyltransferase 1 enzyme having the amino acid sequence selected from the group consisting of SEQ ID NOs:14, 18, 19, 20, 21 and 22 under the control of suitable regulatory sequences;
- (b) growing the cell of step (a) under conditions whereby the genes of (i) and (ii) are expressed, resulting in the production of at least one ω-3 or ω-6 fatty acid and its transfer to triacylglycerol; and
- (c) optionally recovering the triacylglycerol of step (b).

Relatedly the invention provides a method of increasing triacylglycerol content in a transformed host cell comprising:
- (a) providing a transformed host cell comprising:
  - (i) at least one gene encoding a diacylglycerol acyltransferase 1 enzyme comprising all of the amino acid motifs as set forth in:
    1) SEQ ID NO:31;
    2) SEQ ID NO:32;
    3) SEQ ID NO:33;
    4) SEQ ID NO:34;
    5) SEQ ID NO:35;
    6) SEQ ID NO:36; and
    7) SEQ ID NO:37;
    under the control of suitable regulatory sequences; and,
  - (ii) a source of fatty acids;
- (b) growing the cell of step (a) under conditions whereby the at least one gene encoding a diacylglycerol acyltransferase 1 enzyme is expressed, resulting in the transfer of the fatty acids to triacylglycerol; and
- (c) optionally recovering the triacylglycerol of step (b).

In similar fashion the invention provides a method of increasing triacylglycerol content in a transformed host cell comprising:
- (a) providing a transformed host cell comprising:
  - (i) at least one gene encoding a diacylglycerol acyltransferase 1 enzyme comprising all of the amino acid motifs as set forth in:
    1) SEQ ID NO:23;
    2) SEQ ID NO:24;
    3) SEQ ID NO:25;
    4) SEQ ID NO:26;
    5) SEQ ID NO:27;
    6) SEQ ID NO:28;
    7) SEQ ID NO:29; and
    8) SEQ ID NO:30;
    under the control of suitable regulatory sequences; and,
  - (ii) a source of fatty acids;
- (b) growing the cell of step (a) under conditions whereby the at least one gene encoding a diacylglycerol acyltransferase 1 enzyme is expressed, resulting in the transfer of the fatty acids to triacylglycerol; and
- (c) optionally recovering the triacylglycerol of step (b).

Alternatively the invention provides a method of increasing the ω-3 or ω-6 fatty acid content of triacylglycerols in a transformed host cell comprising:
(a) providing a transformed host cell comprising:
   (i) genes encoding a functional ω-3/ω-6 fatty acid biosynthetic pathway; and
   (ii) at least one gene encoding a diacylglycerol acyltransferase 1 enzyme comprising all of the amino acid motifs as set forth in:
      1) SEQ ID NO:31;
      2) SEQ ID NO:32;
      3) SEQ ID NO:33;
      4) SEQ ID NO:34;
      5) SEQ ID NO:35;
      6) SEQ ID NO:36; and
      7) SEQ ID NO:37;
   under the control of suitable regulatory sequences;
(b) growing the cell of step (a) under conditions whereby the genes of (i) and (ii) are expressed, resulting in the production of at least one ω-3 or ω-6 fatty acid and its transfer to triacylglycerol; and
(c) optionally recovering the triacylglycerol of step (b).

In another embodiment the invention provides a method of increasing the ω-3 or ω-6 fatty acid content of triacylglycerols in a transformed host cell comprising:
(a) providing a transformed host cell comprising:
   (i) genes encoding a functional ω-3/ω-6 fatty acid biosynthetic pathway; and
   (ii) at least one gene encoding a diacylglycerol acyltransferase 1 enzyme comprising all of the amino acid motifs as set forth in:
      1) SEQ ID NO:23;
      2) SEQ ID NO:24;
      3) SEQ ID NO:25;
      4) SEQ ID NO:26;
      5) SEQ ID NO:27;
      6) SEQ ID NO:28;
      7) SEQ ID NO:29; and
      8) SEQ ID NO:30;
   under the control of suitable regulatory sequences;
(b) growing the cell of step (a) under conditions whereby the genes of (i) and (ii) are expressed, resulting in the production of at least one ω-3 or ω-6 fatty acid and its transfer to triacylglycerol; and
(c) optionally recovering the triacylglycerol of step (b).

In one embodiment the invention provides a method for the identification of a polypeptide having diacylglycerol acyltransferase 1 activity comprising:
a) obtaining the amino acid sequence of a polypeptide suspected of having diacylglycerol acyltransferase 1 activity; and,
b) identifying, in the amino acid sequence of the polypeptide of step (a), the presence of all of the amino acid motif sequences as set forth in:
   1) SEQ ID NO:31;
   2) SEQ ID NO:32;
   3) SEQ ID NO:33;
   4) SEQ ID NO:34;
   5) SEQ ID NO:35;
   6) SEQ ID NO:36; and
   7) SEQ ID NO:37;
wherein the presence of all of the motif sequences of step (a) in the polypeptide is indicative of diacylglycerol acyltransferase 1 activity.

In another embodiment the invention provides a method for the identification of a fungal polypeptide having diacylglycerol acyltransferase 1 activity comprising:
a) obtaining the amino acid sequence of a fungal polypeptide suspected of having diacylglycerol acyltransferase 1 activity; and,
b) identifying, in the amino acid sequence of the polypeptide of step (a), the presence of all of the amino acid motif sequences as set forth in:
   1) SEQ ID NO:23;
   2) SEQ ID NO:24;
   3) SEQ ID NO:25;
   4) SEQ ID NO:26;
   5) SEQ ID NO:27;
   6) SEQ ID NO:28;
   7) SEQ ID NO:29; and
   8) SEQ ID NO:30;
wherein the presence of all of the motif sequences of step (a) in the polypeptide is indicative of diacylglycerol acyltransferase 1 activity.

BRIEF DESCRIPTION OF THE DRAWINGS AND SEQUENCE DESCRIPTIONS

FIG. 4 provides plasmid maps for the following plasmids: (A) pY20; (B) pLV13; (C) pMDGAT1-17; and (D) pZUF-Mod-1.

Figure 5:
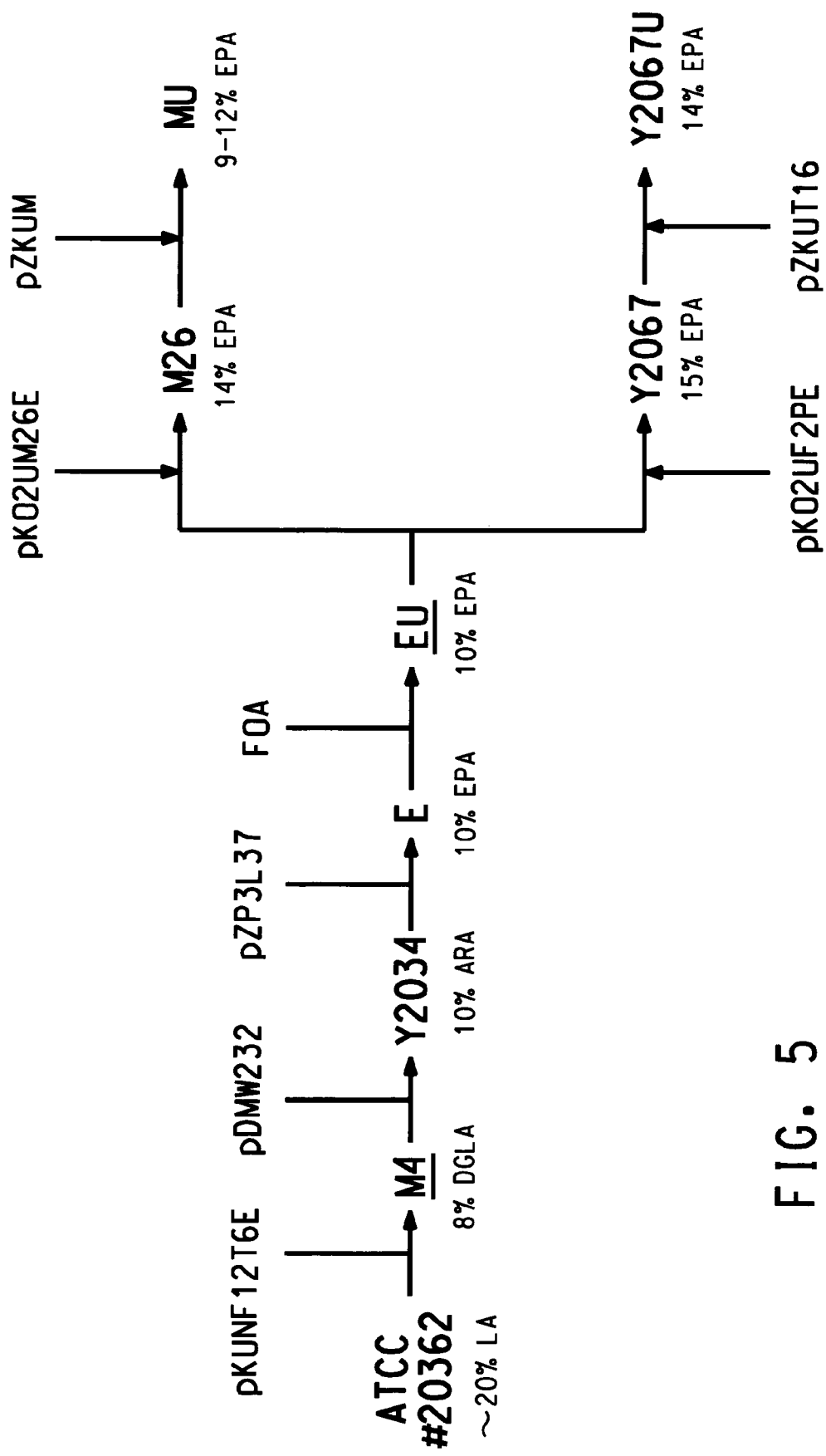

FIG. 5 diagrams the development of various *Yarrowia lipolytica* strains producing up to 15% EPA in the total lipid fraction.

FIG. 6 provides plasmid maps for the following: (A) pKUNF12T6E; (B) pDMW232; (C) pZP3L37; (D) pY37/F15; and (E) pKO2UM26E.

FIG. 7 provides plasmid maps for the following: (A) PZKUM; (B) pKO2UF2PE; (C) pZKUT16; (D) pZP2l7+Ura; and (E) pZUF17.

FIG. 8a, 8b, 8c, 8d, 8e, 8f, 8g and 8h are an alignment of DGAT1 proteins using the Megalign program of DNASTAR using Clustal W.

The invention can be more fully understood from the following detailed description and the accompanying sequence descriptions, which form a part of this application.

The following sequences comply with 37 C.F.R. §1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NOs:1-38, 112-115, 117-120, 122, 123, 125, 126, 130, 131, 133-136, 140, 141 and 169-174 are ORFs encoding genes or proteins (or portions thereof) or protein motifs, as identified in Table 1.

TABLE 1

Summary of Gene and Protein SEQ ID Numbers

| Description and Abbreviation | Nucleic acid SEQ ID NO. | Protein SEQ ID NO. |
|---|---|---|
| *Yarrowia lipolytica* DGAT2 ("Yl DGAT2") | 1 (2119 bp) | 2 (514 AA) |
|  | 3 (1380 bp) | 4 (459 AA) |
|  | 5 (1068 bp) | 6 (355 AA) |
| *Yarrowia lipolytica* PDAT ("Yl PDAT") | 7 (2326 bp) | 8 (648 AA) |
| *Yarrowia lipolytica* YALI-CDS2011.1 (see also GenBank Accession No. NC_006072, bases 974607-976238, locus_tag = "YALI0F06578g") | 9 (1632 bp) | 10 (543 AA) |
| *Yarrowia lipolytica* YALI-CDS2141.1 (see also GenBank Accession No. CR382130, bases 1026155-1027735, locus_tag = "YALI0D07986g") | 11 (1581 bp) | 12 (526 AA) |
| *Yarrowia lipolytica* DGAT1 ("Yl DGAT1") | 13 (1578 bp) | 14 (526 AA) |
| *Yarrowia lipolytica* ARE2 ("Yl ARE2") | 15 (1632 bp) | 16 (543 AA) |
| *Mortierella alpina* DGAT1 ("Ma DGAT1") | 17 (1578 bp) | 18 (525 AA) |
| *Mortierella alpina* DGAT1 - internal cDNA fragment | 175 (604 bp) | — |
| *Neurospora crassa* DGAT1 ("Nc DAGAT1") | — | 19 (533 AA) |
| *Gibberella zeae* DGAT1 ("Fm DAGAT1") | — | 20 (499 AA) |
| *Magnaporthe grisea* DGAT1 ("Mg DAGAT1") | — | 21 (503 AA) |
| *Aspergillus nidulans* DGAT1 ("An DAGAT1") | — | 22 (458 AA) |
| Fungal DGAT1 motif #1 | — | 23 |
| Fungal DGAT1 motif #2 | — | 24 |
| Fungal DGAT1 motif #3 | — | 25 |
| Fungal DGAT1 motif #4 | — | 26 |
| Fungal DGAT1 motif #5 | — | 27 |
| Fungal DGAT1 motif #6 | — | 28 |
| Fungal DGAT1 motif #7 | — | 29 |
| Fungal DGAT1 motif #8 | — | 30 |
| Universal DGAT1 motif #1 | — | 31 |
| Universal DGAT1 motif #3 | — | 32 |
| Universal DGAT1 motif #4 | — | 33 |
| Universal DGAT1 motif #5 | — | 34 |
| Universal DGAT1 motif #6 | — | 35 |
| Universal DGAT1 motif #7 | — | 36 |
| Universal DGAT1 motif #8 | — | 37 |
| Fungal DGAT2 motif | — | 38 |
| Synthetic elongase gene derived from *Mortierella alpina*, codon-optimized for expression in *Yarrowia lipolytica* | 112 (957 bp) | 113 (318 AA) |
| Synthetic Δ6 desaturase, derived from *Mortierella alpina*, codon-optimized for expression in *Yarrowia lipolytica* | 114 (1374 bp) | 115 (457 AA) |
| *Fusarium moniliforme* Δ12 desaturase | 117 (1434 bp) | 118 (477 AA) |
| Synthetic elongase gene derived from *Thraustochytrium aureum*, codon-optimized for expression in *Yarrowia lipolytica* | 119 (819 bp) | 120 (272 AA) |
| *Mortierella alpina* Δ5 desaturase | 122 (1341 bp) | 123 (446 AA) |
| Synthetic Δ17 desaturase gene derived from *Saprolegnia diclina*, codon-optimized for expression in *Yarrowia lipolytica* | 125 (1077 bp) | 126 (358 AA) |
| *Yarrowia lipolytica* Δ12 desaturase | 130 (1936 bp) | 131 (419 AA) |
| *Mortieralla isabellina* Δ12 desaturase | 133 (1203 bp) | 134 (400 AA) |
| *Mortierella alpina* Δ6 desaturase "B" | 135 (1521 bp) | 136 (458 AA) |
| Synthetic $C_{16}$ elongase gene derived from *Rattus norvegicus*, codon-optimized for expression in *Yarrowia lipolytica* | 140 (804 bp) | 141 (267 AA) |
| *Mus musculus* DGAT2 ("Mm DGAT1") | — | 169 (388 AA) |
| *Glycine max* DGAT1 ("Gm DGAT1") | — | 170 (504 AA) |
| *Arabidopsis thaliana* DGAT1 ("At DGAT1") | — | 171 (520 AA) |
| *Oryza sativa* DGAT1 ("Os DGAT1") | — | 172 (500 AA) |
| *Perilla frutescens* DGAT1 ("Pf DGAT1") | — | 173 (534 AA) |
| *Triticum aestivum* DGAT1 (Ta DGAT1") | — | 174 (508 AA) |

SEQ ID NOs:55, 82, 110, 121, 124, 128, 129, 137-139, 144, 164, 165 and 168 are plasmids as identified in Table 2.

TABLE 2

Summary of Plasmid SEQ ID Numbers

| Plasmid | Corresponding Figure | SEQ ID NO |
|---|---|---|
| pY20 | 4A | 55 (8,196 bp) |
| pLV13 | 4B | 82 (5,105 bp) |
| pKUNF12T6E | 6A | 110 (12,649 bp) |
| pDMW232 | 6B | 121 (10,945 bp |
| pZP3L37 | 6C | 124 (12,690 bp) |
| pY37/F15 | 6D | 128 (8,194 bp) |
| pKO2UM26E | 6E | 129 (10,448 bp) |
| pZKUM | 7A | 137 (4,313 bp) |
| pKO2UF2PE | 7B | 138 (10,838 bp) |
| pZKUT16 | 7C | 139 (5,833 bp) |
| pZP2I7 + Ura | 7D | 144 (7,822 bp) |
| pZUF17 | 7E | 164 (8,165 bp) |
| pMDGAT1-17 | 4C | 165 (8,666 bp) |
| pZUF-MOD-1 | 4D | 168 (7,323 bp) |

SEQ ID NOs:39 and 40 correspond to primers TEF5' and TEF3', respectively, used to isolate the TEF promoter.

SEQ ID NOs:41 and 42 correspond to primers XPR5' and XPR3', respectively, used to isolate the XPR2 transcriptional terminator.

SEQ ID NOs:43-54 correspond to primers YL5, YL6, YL9, YL10, YL7, YL8, YL3, YL4, YL1, YL2, YL61 and YL62, respectively, used for plasmid construction.

SEQ ID NO:56 corresponds to a 1 kB DNA fragment (amino acid sequence provided as SEQ ID NO:57) containing the *E. coli* hygromycin resistance gene.

SEQ ID NO:58 corresponds to a 1.7 kB DNA fragment containing the *Yarrowia* Ura3 gene (amino acid sequence provided as SEQ ID NO:59), which was amplified with primers KU5 and KU3 (SEQ ID NOs:60 and 61, respectively).

SEQ ID NOs:62 and 64 are the degenerate primers identified as P7 and P8, respectively, used for the isolation of a *Yarrowia lipolytica* DGAT2.

SEQ ID NOs:63 and 65 are the amino acid consensus sequences that correspond to the degenerate primers P7 and P8, respectively.

SEQ ID NOs:66-68 correspond to primers P80, P81 and LinkAmp Primer1, respectively, used for chromosome walking.

SEQ ID NOs:69-72 correspond to primers P95, P96, P97 and P98, respectively, used for targeted disruption of the *Y. lipolytica* DGAT2 gene.

SEQ ID NOs:73-75 correspond to primers P115, P116 and P112, respectively, used to screen for targeted integration of the disrupted *Y. lipolytica* DGAT2 gene.

SEQ ID NOs:76 and 78 are the degenerate primers identified as P26 and P27, respectively, used for the isolation of the *Y. lipolytica* PDAT.

SEQ ID NOs:77 and 79 are the amino acid consensus sequences that correspond to degenerate primers P26 and P27, respectively.

SEQ ID NOs:80, 81, 83 and 84 correspond to primers P39, P42, P41 and P40, respectively, used for targeted disruption of the *Y. lipolytica* PDAT gene.

SEQ ID NOs:85-88 correspond to primers P51, P52, P37 and P38, respectively, used to screen for targeted integration of the disrupted *Y. lipolytica* PDAT gene.

SEQ ID NO:89 corresponds to primer P79, used to amplify the full-length *Y. lipolytica* DGAT2 gene from rescued plasmids.

SEQ ID NOs:90 and 91 correspond to primers P84 and P85, respectively, used to amplify the full-length *Y. lipolytica* PDAT gene from rescued plasmids.

SEQ ID NOs:92 and 93 are the degenerate primers identified as P201 and P203, respectively, used for the isolation of the *Y. lipolytica* DGAT1.

SEQ ID NOs:94-99 correspond to primers P214, P215, P216, P217, P218 and P219, respectively, used for targeted disruption of the *Y. lipolytica* DGAT1 gene.

SEQ ID NOs:100 and 101 correspond to primers P226 and P227, respectively, used to screen for targeted integration of the disrupted *Y. lipolytica* DGAT1 gene.

SEQ ID NOs:102 and 103 are the degenerate primers identified as P205 and P208, respectively, used for isolation of the *Y. lipolytica* ARE2.

SEQ ID NOs:104-109 correspond to primers P220, P221, P222, P223, P224 and P225, respectively, used for targeted disruption of the *Y. lipolytica* ARE2 gene.

SEQ ID NOs:111, 116, 127 and 132 correspond to the following *Yarrowia lipolytica* promoters, respectively: fructose-bisphosphate aldolase+intron (FBAIN; 973 bp), fructose-bisphosphate aldolase (FBA; 1001 bp), fructose-bisphosphate aldolase+modified intron (FBAINm; 924 bp), glycerol-3-phosphate acyltransferase (GPAT; 1130 bp).

SEQ ID NOs:142 and 143 correspond to primers P239 and P240, respectively, used for sequencing of the *Y. lipolytica* DGAT1 ORF.

SEQ ID NOs:145-147 correspond to BD-Clontech Creator Smart® cDNA library kit primers SMART IV oligonucleotide, CDSIII/3' PCR primer and 5'-PCR primer.

SEQ ID NO:148 corresponds to the M13 forward primer used for sequencing of the *M. alpina* cDNA library.

SEQ ID NO:149 corresponds to the partial cDNA sequence (601 bp) encoding the putative *M. alpina* DGAT1 gene.

SEQ ID NOs:150 and 151 correspond to primers MARE2-N1 and MARE2-N2, respectively, used for cloning the 5'-end region of the putative *M. alpina* DGAT1 gene.

SEQ ID NOs:152 and 153 correspond to the Genome Walker adaptor from ClonTech's Universal GenomeWalker™ Kit, used for genome-walking.

SEQ ID NOs:154 and 155 correspond to primers AP1 and AP2, respectively, used for genome-walking to isolate the 5'-end region of the *M. alpina* DGAT1.

SEQ ID NO:156 corresponds to the 5'-end sequence (1683 bp) of the *M. alpina* DGAT1 cDNA fragment.

SEQ ID NOs:157 and 158 correspond to primers ARE-N3-1 and ARE-N3-2, respectively, used for cloning the 3'-end region of the putative *M. alpina* DGAT1 gene.

SEQ ID NOs:159 and 160 correspond to primers AP and UAP, respectively, used for genome-walking to isolate the 3'-end region of the *M. alpina* DGAT1.

SEQ ID NO:161 corresponds to the 3'-end sequence (184 bp) of the *M. alpina* DGAT1 cDNA fragment.

SEQ ID NOs:162 and 163 correspond to primers MACAT-F1 and MACAT-R, respectively, used for cloning of the *M. alpina* DGAT1 ORF.

SEQ ID NOs:166 and 167 correspond to primers pzuf-mod1 and pzuf-mod2, respectively, used for creating "control" plasmid pZUF-MOD-1.

DETAILED DESCRIPTION OF THE INVENTION

In accordance with the subject invention, Applicants have isolated and confirmed the identity of a *Yarrowia lipolytica* gene encoding a diacylglycerol acyltransferase (DGAT1) enzyme useful for transferring fatty acids into storage triacylglycerols (TAGs). Orthologous genes have also been isolated from *Mortierella alpina* and identified in *Neurospora crassa, Gibberella zeae* PH-1, *Magnaporthe grisea* and *Aspergillus nidulans*. Furthermore, the present invention provides motifs for readily identifying other DGAT1 genes from fungal organisms. In another embodiment, the *Yarrowia lipolytica* gene encoding an acyl-CoA:sterol-acyltransferase (ARE2) enzyme has been isolated. Each of these genes may be useful to alter the quantity of long chain polyunsaturated fatty acids (PUFAs) produced in transformant oleaginous yeasts.

The importance of PUFAs are undisputed. For example, certain PUFAs are important biological components of healthy cells and are recognized as: "essential" fatty acids that cannot be synthesized de novo in mammals and instead must be obtained either in the diet or derived by further desaturation and elongation of linoleic acid (LA) or α-linolenic acid (ALA); constituents of plasma membranes of cells, where they may be found in such forms as phospholipids or TAGs; necessary for proper development (particularly in the developing infant brain) and for tissue formation and repair; and, precursors to several biologically active eicosanoids of importance in mammals (e.g., prostacyclins, eicosanoids, leukotrienes, prostaglandins). Additionally, a high intake of long-chain ω-3 PUFAs produces cardiovascular protective effects (Dyerberg, J. et al., *Amer. J. Clin Nutr*. 28:958-966 (1975); Dyerberg, J. et al., *Lancet* 2(8081): 117-119 (Jul. 15, 1978); Shimokawa, H., *World Rev Nutr Diet*, 88:100-108 (2001); von Schacky, C. and Dyerberg, J., *World Rev Nutr Diet*, 88:90-99 (2001)). And, numerous other studies document wide-ranging health benefits conferred by administration of ω-3 and/or ω-6 fatty acids against a variety of symptoms and diseases (e.g., asthma, psoriasis, eczema, diabetes, cancer).

As such, the subject invention finds many applications. PUFAs, or derivatives thereof, accumulated by the methodology disclosed herein can be used as dietary substitutes, or supplements, particularly infant formulas, for patients undergoing intravenous feeding or for preventing or treating malnutrition. Alternatively, the purified PUFAs (or derivatives thereof) may be incorporated into cooking oils, fats or margarines formulated so that in normal use the recipient would receive the desired amount for dietary supplementation. The PUFAs may also be incorporated into infant formulas, nutritional supplements or other food products and may find use as anti-inflammatory or cholesterol lowering agents. Optionally, the compositions may be used for pharmaceutical use (human or veterinary). In this case, the PUFAs are generally administered orally but can be administered by any route by which they may be successfully absorbed, e.g., parenterally (e.g., subcutaneously, intramuscularly or intravenously), rectally, vaginally or topically (e.g., as a skin ointment or lotion).

Supplementation of humans or animals with PUFAs produced by recombinant means can result in increased levels of the added PUFAs, as well as their metabolic progeny. For example, treatment with ARA can result not only in increased levels of ARA, but also downstream products of ARA such as prostaglandins. Complex regulatory mechanisms can make it desirable to combine various PUFAs, or add different conjugates of PUFAs, in order to prevent, control or overcome such mechanisms to achieve the desired levels of specific PUFAs in an individual.

Definitions

In this disclosure, a number of terms and abbreviations are used.

The following definitions are provided.

"Open reading frame" is abbreviated ORF.

"Polymerase chain reaction" is abbreviated PCR.

"American Type Culture Collection" is abbreviated ATCC.

"Polyunsaturated fatty acid(s)" is abbreviated PUFA(s).

"Acyl-CoA:sterol-acyltransferase" is abbreviated ARE2.

"Phospholipid:diacylglycerol acyltransferase" is abbreviated PDAT.

"Diacylglycerol acyltransferase" is abbreviated DAG AT or DGAT.

"Diacylglycerol" is abbreviated DAG.

"Triacylglycerols" are abbreviated TAGs.

"Co-enzyme A" is abbreviated CoA.

The term "fatty acids" refers to long chain aliphatic acids (alkanoic acids) of varying chain length, from about $C_{12}$ to $C_{22}$ (although both longer and shorter chain-length acids are known). The predominant chain lengths are between $C_{16}$ and $C_{22}$. The structure of a fatty acid is represented by a simple notation system of "X:Y", where X is the total number of carbon (C) atoms in the particular fatty acid and Y is the number of double bonds.

Generally, fatty acids are classified as saturated or unsaturated. The term "saturated fatty acids" refers to those fatty acids that have no "double bonds" between their carbon backbone. In contrast, "unsaturated fatty acids" have "double bonds" along their carbon backbones (which are most commonly in the cis-configuration). "Monounsaturated fatty acids" have only one "double bond" along the carbon backbone (e.g., usually between the $9^{th}$ and $10^{th}$ carbon atom as for palmitoleic acid (16:1) and oleic acid (18:1)), while "polyunsaturated fatty acids" (or "PUFAs") have at least two double bonds along the carbon backbone (e.g., between the $9^{th}$ and $10^{th}$, and $12^{th}$ and $13^{th}$ carbon atoms for linoleic acid (18:2); and between the $9^{th}$ and $10^{th}$, $12^{th}$ and $13^{th}$, and $15^{th}$ and $16^{th}$ for α-linolenic acid (18:3)).

"PUFAs" can be classified into two major families (depending on the position (n) of the first double bond nearest the methyl end of the fatty acid carbon chain). Thus, the "omega-6 fatty acids" (ω-6 or n-6) have the first unsaturated double bond six carbon atoms from the omega (methyl) end of the molecule and additionally have a total of two or more double bonds, with each subsequent unsaturation occurring 3 additional carbon atoms toward the carboxyl end of the molecule. In contrast, the "omega-3 fatty acids" (ω-3 or n-3) have the first unsaturated double bond three carbon atoms away from the omega end of the molecule and additionally have a total of three or more double bonds, with each subsequent unsaturation occurring 3 additional carbon atoms toward the carboxyl end of the molecule.

For the purposes of the present disclosure, the omega-reference system will be used to indicate the number of carbons, the number of double bonds and the position of the double bond closest to the omega carbon, counting from the omega carbon (which is numbered 1 for this purpose). This nomenclature is shown below in Table 3, in the column titled "Shorthand Notation". The remainder of the Table summarizes the common names of ω-3 and ω-6 fatty acids, the abbreviations that will be used throughout the specification and each compounds' chemical name.

TABLE 3

Nomenclature Of Polyunsaturated Fatty Acids

| Common Name | Abbreviation | Chemical Name | Shorthand Notation |
|---|---|---|---|
| Linoleic | LA | cis-9,12-octadecadienoic | 18:2 ω-6 |
| γ-Linoleic | GLA | cis-6,9,12-octadecatrienoic | 18:3 ω-6 |
| Eicosadienoic | EDA | cis-11,14-eicosadienoic | 20:2 ω-6 |
| Dihomo-γ-Linoleic | DGLA | cis-8,11,14-eicosatrienoic | 20:3 ω-6 |
| Arachidonic | ARA | cis-5,8,11,14-eicosatetraenoic | 20:4 ω-6 |
| α-Linolenic | ALA | cis-9,12,15-octadecatrienoic | 18:3 ω-3 |
| Stearidonic | STA | cis-6,9,12,15-octadecatetraenoic | 18:4 ω-3 |
| Eicosatrienoic | ETrA | cis-11,14,17-eicosatrienoic | 20:3 ω-3 |
| Eicosatetraenoic | ETA | cis-8,11,14,17-eicosatetraenoic | 20:4 ω-3 |
| Eicosapentaenoic | EPA | cis-5,8,11,14,17-eicosapentaenoic | 20:5 ω-3 |
| Docosapentaenoic | DPA | cis-7,10,13,16,19-docosapentaenoic | 22:5 ω-3 |
| Docosahexaenoic | DHA | cis-4,7,10,13,16,19-docosahexaenoic | 22:6 ω-3 |

"Microbial oils" or "single cell oils" are those oils naturally produced by microorganisms (e.g., algae, oleaginous yeasts and filamentous fungi) during their lifespan. The term "oil" refers to a lipid substance that is liquid at 25° C. and usually polyunsaturated. In contrast, the term "fat" refers to a lipid substance that is solid at 25° C. and usually saturated.

"Lipid bodies" refer to lipid droplets that usually are bounded by specific proteins and a monolayer of phospholipid. These organelles are sites where most organisms transport/store neutral lipids. Lipid bodies are thought to arise from microdomains of the endoplasmic reticulum that contain TAG-biosynthesis enzymes; and, their synthesis and size appear to be controlled by specific protein components.

"Neutral lipids" refer to those lipids commonly found in cells in lipid bodies as storage fats and oils and are so called because at cellular pH, the lipids bear no charged groups. Generally, they are completely non-polar with no affinity for water. Neutral lipids generally refer to mono-, di-, and/or triesters of glycerol with fatty acids, also called monoacylglycerol, diacylglycerol or TAG, respectively (or collectively, acylglycerols). A hydolysis reaction must occur to release free fatty acids from acylglycerols.

The terms "triacylglycerol", "oil" and "TAGs" refer to neutral lipids composed of three fatty acyl residues esterified to a glycerol molecule (and such terms will be used interchangeably throughout the present disclosure herein). Such oils can contain long chain PUFAs, as well as shorter saturated and unsaturated fatty acids and longer chain saturated fatty acids. Thus, "oil biosynthesis" generically refers to the synthesis of TAGs in the cell.

The term "DAG AT" refers to a diacylglycerol acyltransferase (also known as an acyl-CoA-diacylglycerol acyltransferase or a diacylglycerol O-acyltransferase) (EC 2.3.1.20). This enzyme is responsible for the conversion of acyl-CoA and 1,2-diacylglycerol to TAG and CoA (thereby involved in the terminal step of TAG biosynthesis). Two families of DAG AT enzymes exist: DGAT1 and DGAT2. The former family shares homology with the acyl-CoA:cholesterol acyltransferase (ACAT) gene family, while the latter family is unrelated (Lardizabal et al., *J. Biol. Chem.* 276(42):38862-28869 (2001)).

The term "PDAT" refers to a phospholipid:diacylglycerol acyltransferase enzyme (EC 2.3.1.158). This enzyme is responsible for the transfer of an acyl group from the sn-2 position of a phospholipid to the sn-3 position of 1,2-diacylglycerol, thus resulting in lysophospholipid and TAG (thereby involved in the terminal step of TAG biosynthesis). This enzyme differs from DGAT (EC 2.3.1.20) by synthesizing TAG via an acyl-CoA-independent mechanism.

The term "ARE2" refers to an acyl-CoA:sterol-acyltransferase enzyme (EC 2.3.1.26; also known as a sterol-ester synthase 2 enzyme), catalyzing the following reaction: acyl-CoA+cholesterol=CoA+cholesterol ester.

The term "PUFA biosynthetic pathway enzyme" refers to any of the following enzymes (and genes which encode said enzymes) associated with the biosynthesis of a PUFA, including: a Δ4 desaturase, a Δ5 desaturase, a Δ6 desaturase, a Δ12 desaturase, a Δ15 desaturase, a Δ17 desaturase, a Δ9 desaturase, a Δ8 desaturase and/or an elongase(s).

Figure 2:
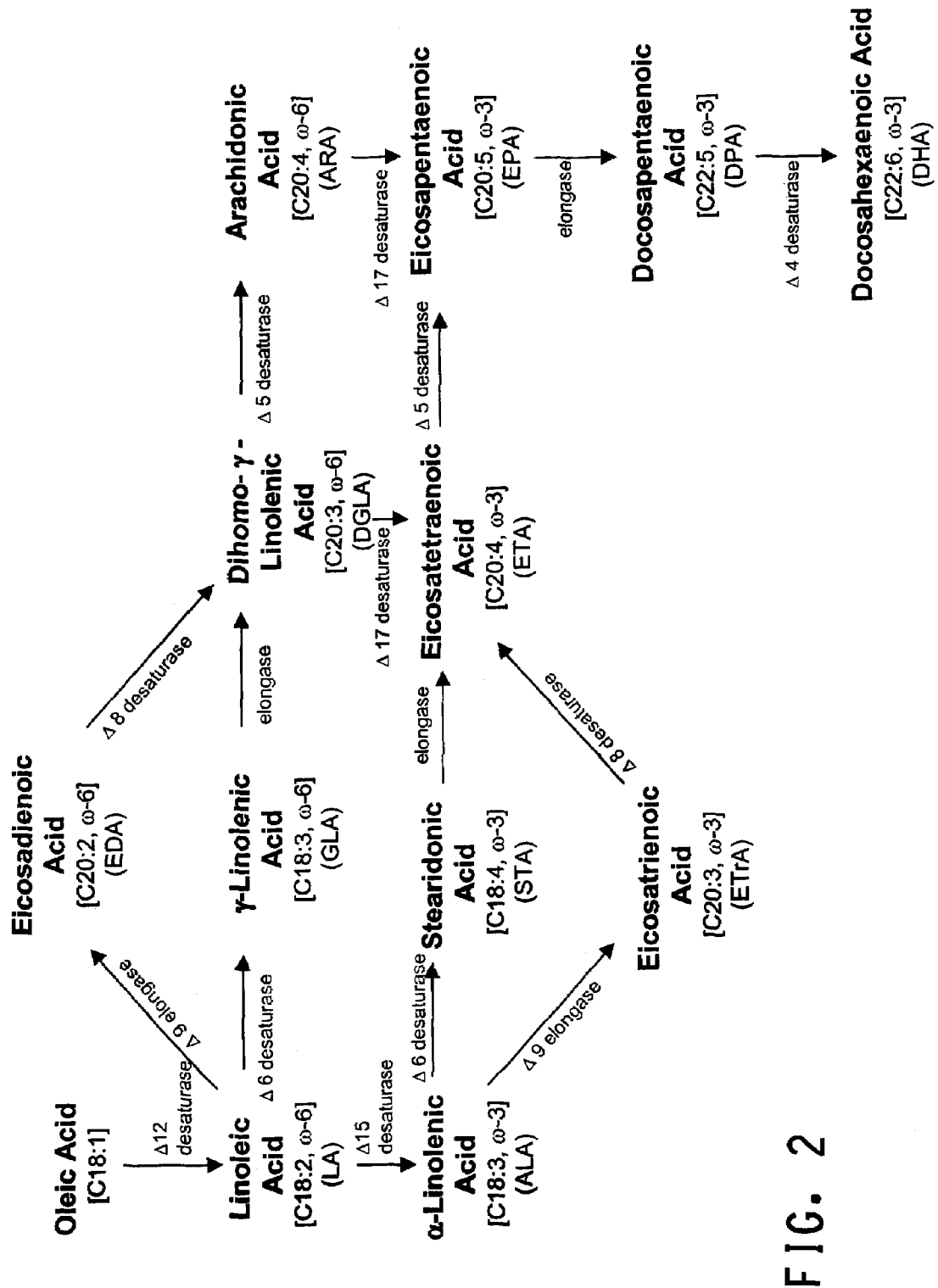
FIG. 2 illustrates the ω-3 and ω-6 fatty acid biosynthetic pathways.
Figure 3A:
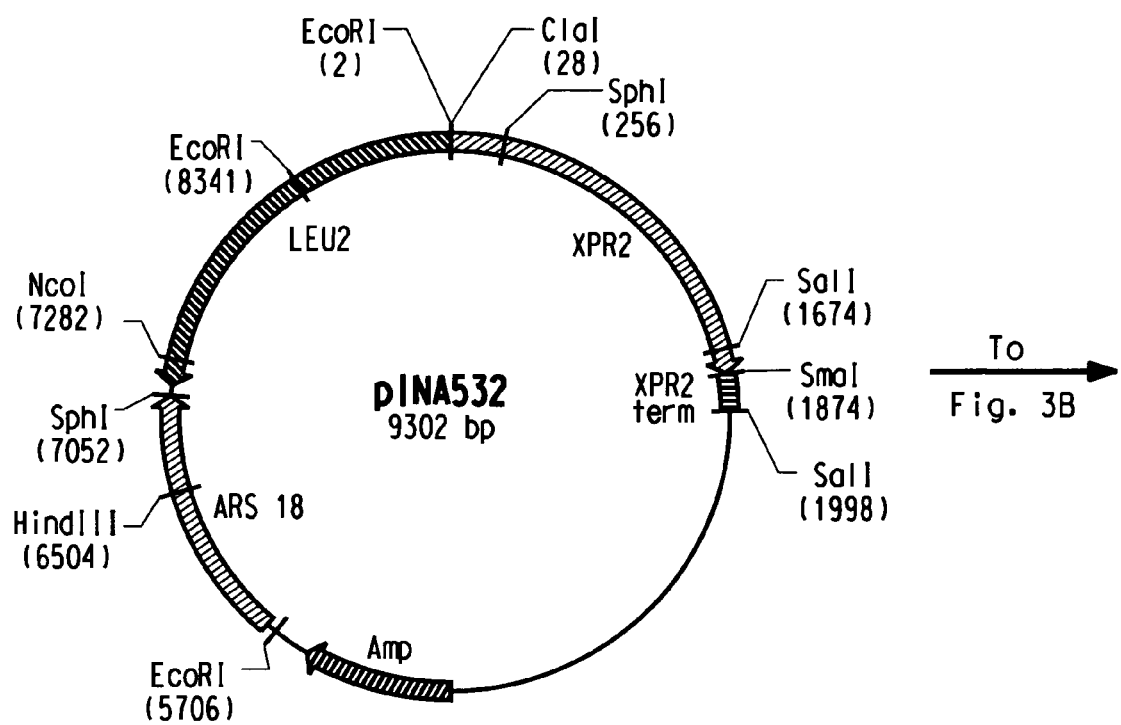
FIG. 3 illustrates the construction of plasmid vector pY5 for gene expression in *Yarrowia lipolytica*.
Figure 3A:
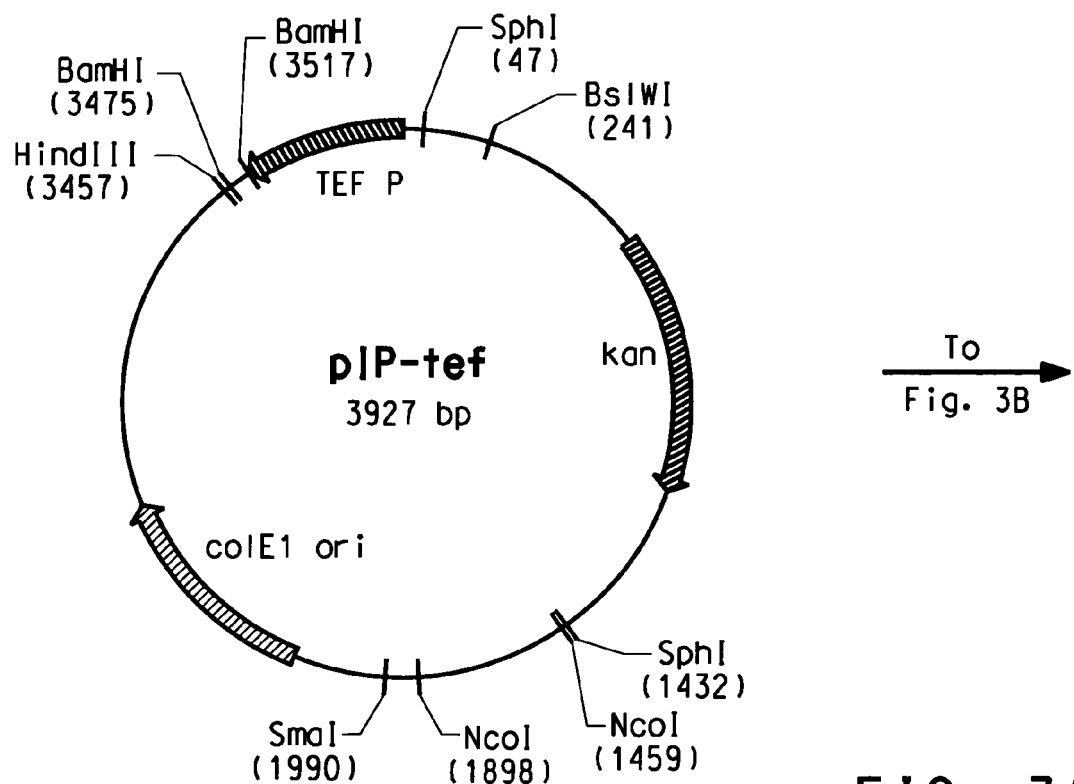
Figure 3B:
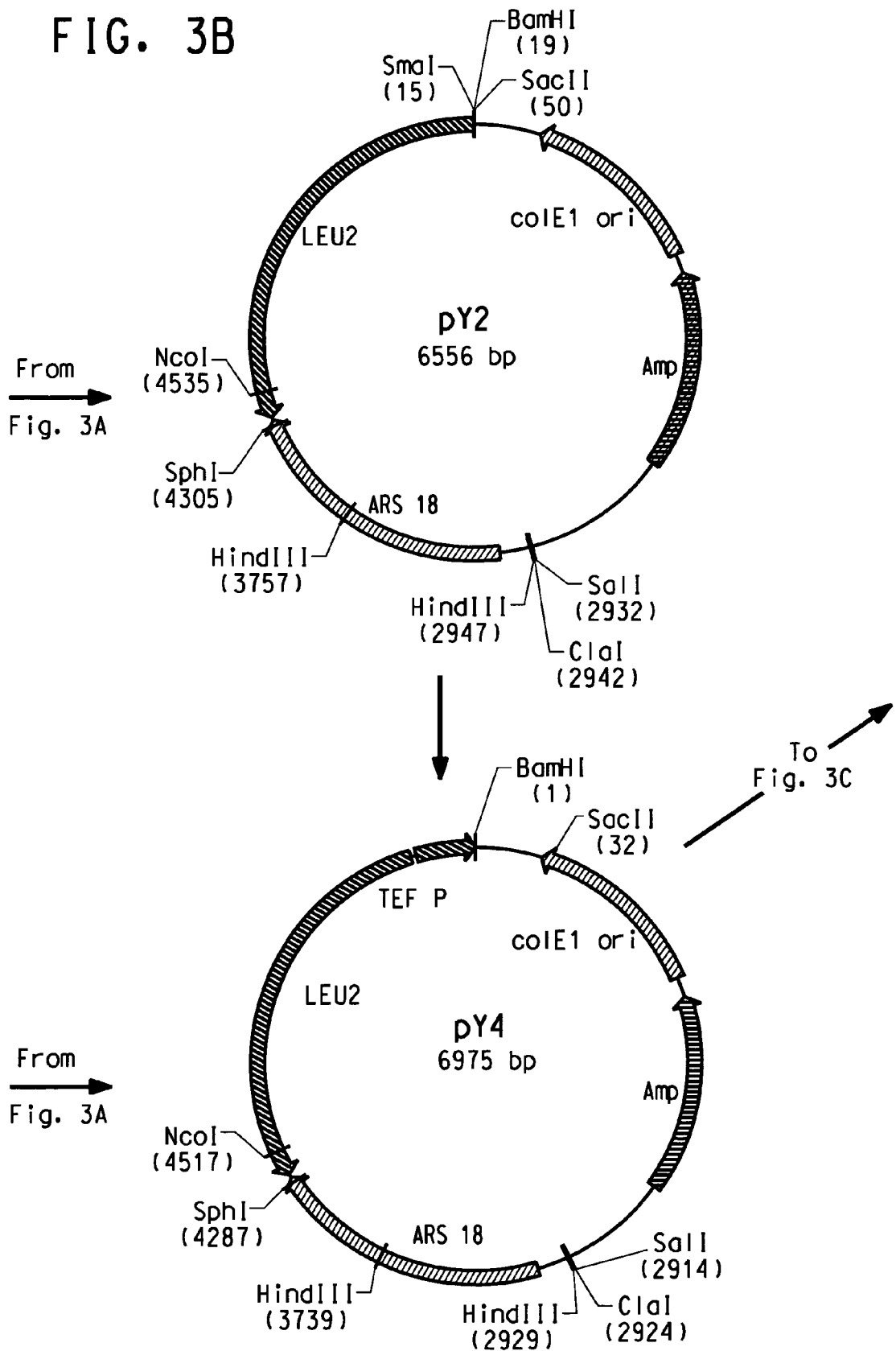
Figure 3C:
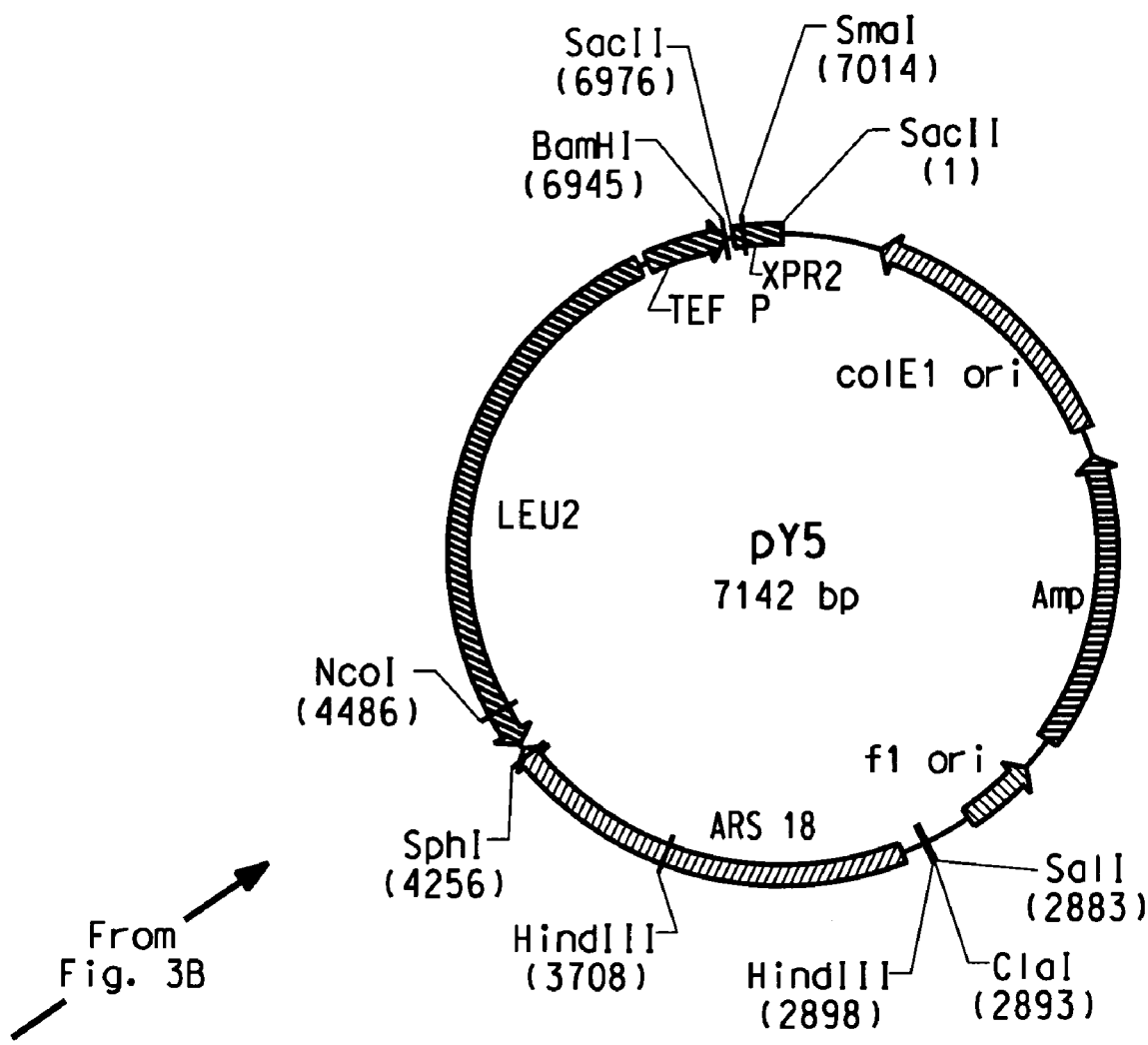
Figure 4A:
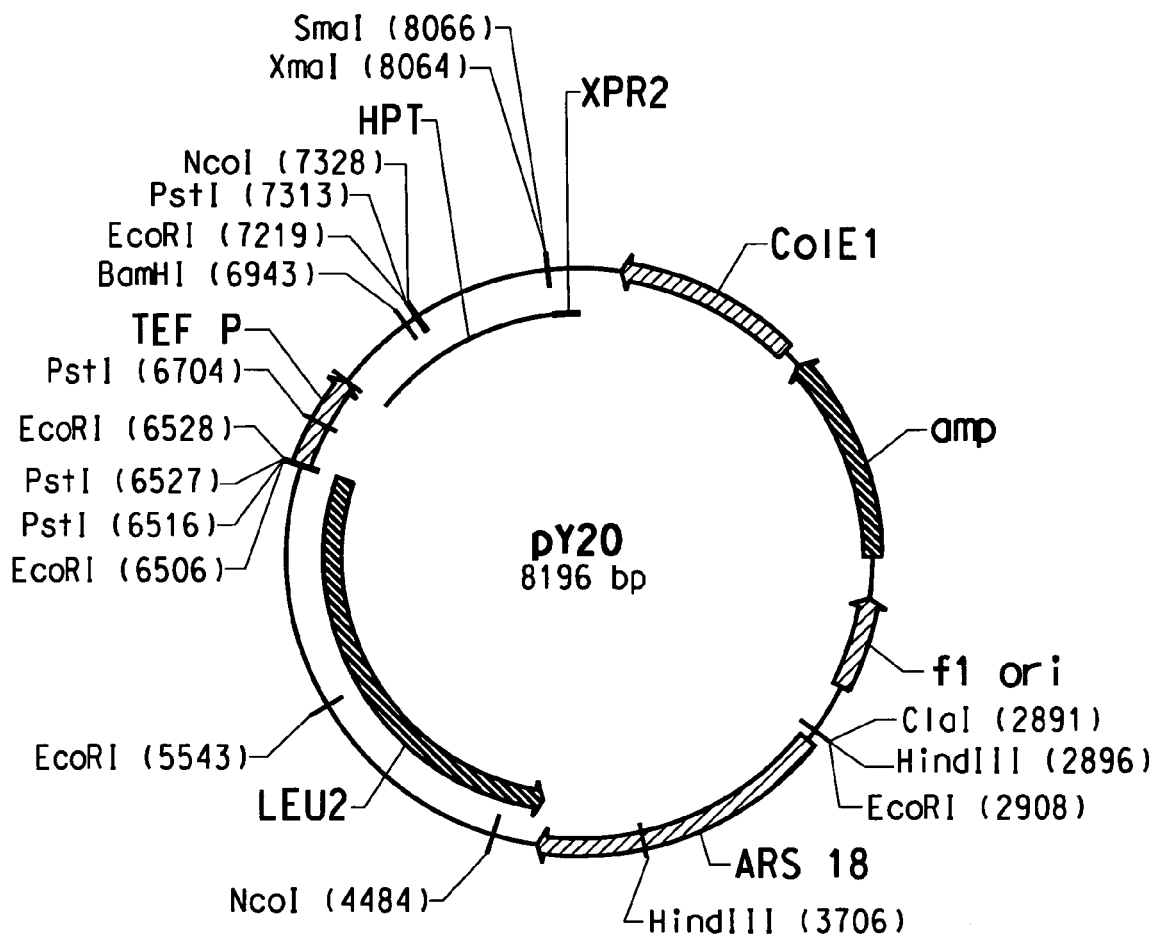
Figure 4B:
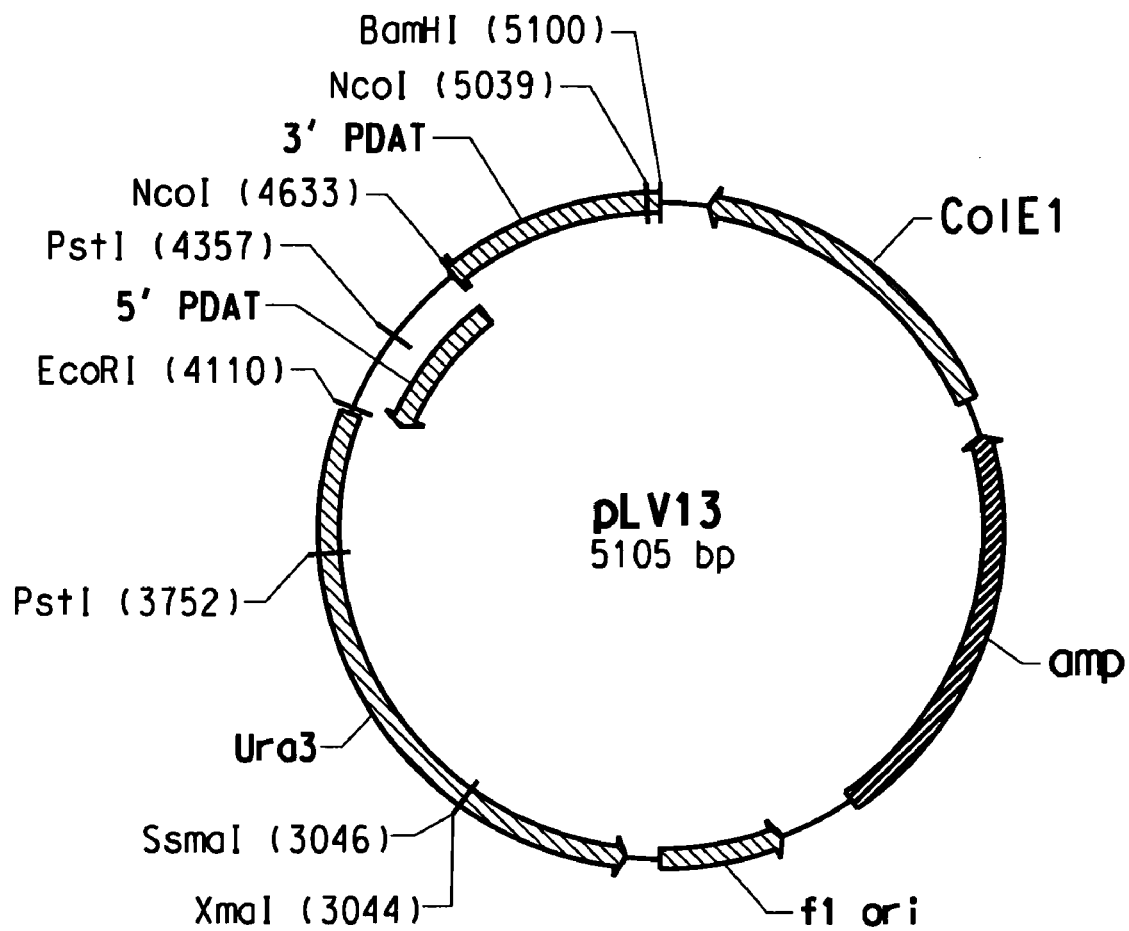
Figure 4C:
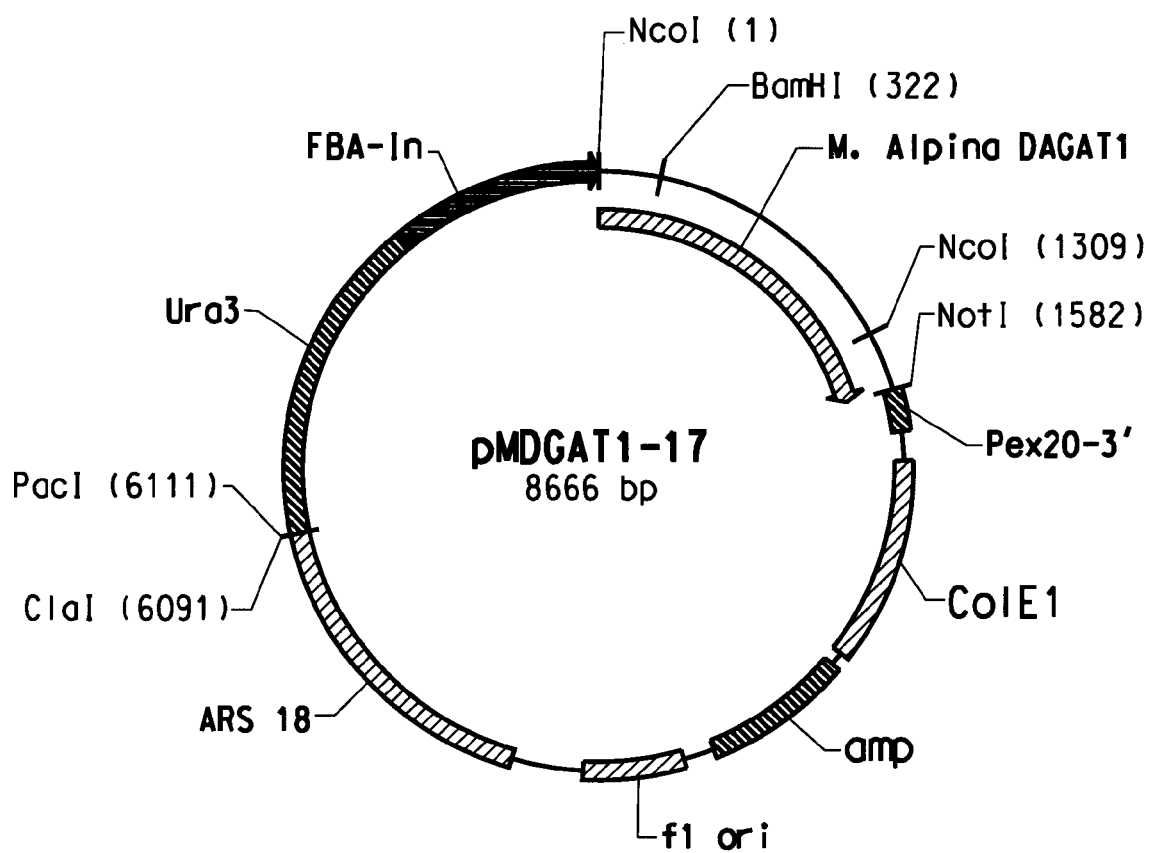
Figure 4D:
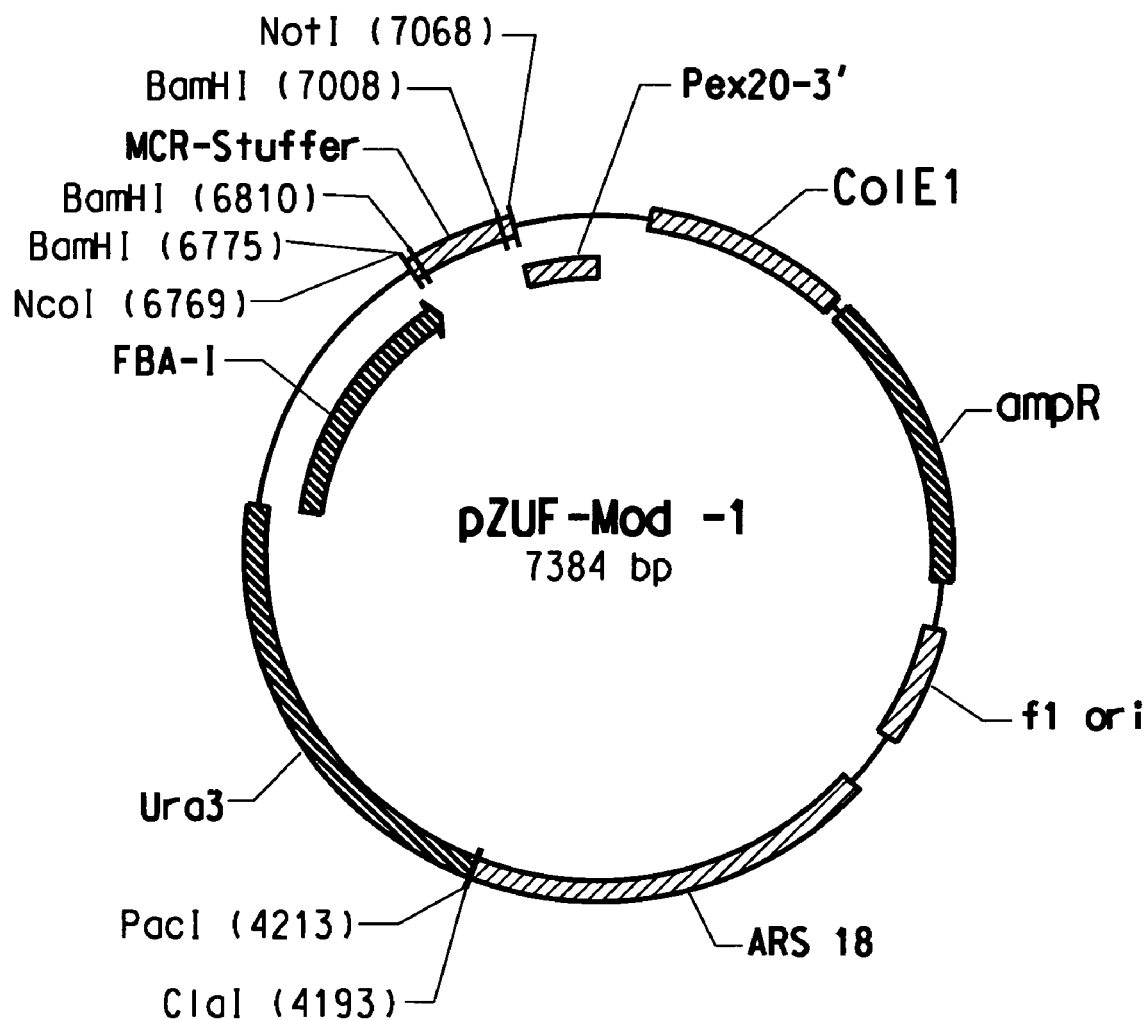

The term "ω-3/ω-6 fatty acid biosynthetic pathway" refers to a set of genes which, when expressed under the appropriate conditions encode enzymes that catalyze the production of either or both ω-3 and ω-6 fatty acids. Typically the genes involved in the ω-3/ω-6 fatty acid biosynthetic pathway encode some or all of the following enzymes: Δ12 desaturase, Δ6 desaturase, elongase(s), Δ5 desaturase, Δ17 desaturase, Δ15 desaturase, Δ9 desaturase, Δ8 desaturase and Δ4 desaturase. A representative pathway is illustrated in FIG. 2, providing for the conversion of oleic acid through various intermediates to DHA, which demonstrates how both ω-3 and ω-6 fatty acids may be produced from a common source. The pathway is naturally divided into two portions where one portion will generate ω-3 fatty acids and the other portion, only ω-6 fatty acids. That portion that only generates ω-3 fatty acids will be referred to herein as the ω-3 fatty acid biosynthetic pathway, whereas that portion that generates only ω-6 fatty acids will be referred to herein as the ω-6 fatty acid biosynthetic pathway.

The term "functional" as used herein in context with the ω-3/ω-6 fatty acid biosynthetic pathway means that some (or all of) the genes in the pathway express active enzymes. It should be understood that "ω-3/ω-6 fatty acid biosynthetic pathway" or "functional ω-3/ω-6 fatty acid biosynthetic pathway" does not imply that all the genes listed in the above paragraph are required, as a number of fatty acid products will only require the expression of a subset of the genes of this pathway.

The term "desaturase" refers to a polypeptide that can desaturate, i.e., introduce a double bond, in one or more fatty acids to produce a mono- or polyunsaturated fatty acid. Despite use of the omega-reference system throughout the specification in reference to specific fatty acids, it is more convenient to indicate the activity of a desaturase by counting from the carboxyl end of the substrate using the delta-system. Of particular interest herein are: Δ12 desaturases that desaturate a fatty acid between the $12^{th}$ and $13^{th}$ carbon atoms numbered from the carboxyl-terminal end of the molecule and that catalyze the conversion of oleic acid to LA; Δ15 desaturases that catalyze the conversion of LA to ALA; Δ17 desaturases that catalyze the conversion of ARA to EPA and/or DGLA to ETA; Δ6 desaturases that catalyze the conversion of LA to GLA and/or ALA to STA; Δ5 desaturases that catalyze the conversion of DGLA to ARA and/or ETA to EPA; Δ4 desaturases that catalyze the conversion of DPA to DHA; Δ8 desaturases that catalyze the conversion of EDA to DGLA and/or ETrA to ETA; and Δ9 desaturases that catalyze the conversion of palmitate to palmitoleic acid (16:1) and/or stearate to oleic acid (18:1).

The term "elongase" refers to a polypeptide that can elongate a fatty acid carbon chain to produce an acid that is 2 carbons longer than the fatty acid substrate that the elongase acts upon. This process of elongation occurs in a multi-step mechanism in association with fatty acid synthase, whereby CoA is the acyl carrier (Lassner et al., *The Plant Cell* 8:281-292 (1996)). Briefly, malonyl-CoA is condensed with a long-chain acyl-CoA to yield $CO_2$ and a β-ketoacyl-CoA (where the acyl moiety has been elongated by two carbon atoms). Subsequent reactions include reduction to β-hydroxyacyl-CoA, dehydration to an enoyl-CoA and a second reduction to yield the elongated acyl-CoA. Examples of reactions catalyzed by elongases are the conversion of GLA to DGLA, STA to ETA, and EPA to DPA. Accordingly, elongases can have different specificities. For example, a $C_{16/18}$ elongase will prefer a $C_{16}$ substrate, a $C_{18/20}$ elongase will prefer a $C_{18}$ substrate and a $C_{20/22}$ elongase will prefer a $C_{20}$ substrate. In like manner, a Δ9 elongase is able to catalyze the conversion of LA and ALA to EDA and ETrA, respectively.

The term "oleaginous" refers to those organisms that tend to store their energy source in the form of lipid (Weete, In: *Fungal Lipid Biochemistry*, $2^{nd}$ Ed., Plenum, 1980). Generally, the cellular oil content of these microorganisms follows a sigmoid curve, wherein the concentration of lipid increases until it reaches a maximum at the late logarithmic or early stationary growth phase and then gradually decreases during the late stationary and death phases (Yongmanitchai and Ward, *Appl Environ. Microbiol.* 57:419-25 (1991)).

The term "oleaginous yeast" refers to those microorganisms classified as yeasts that can make oil. Generally, the cellular oil or triacylglycerol content of oleaginous microorganisms follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.* 57:419-25 (1991)). It is not uncommon for oleaginous microorganisms to accumulate in excess of about 25% of their dry cell weight as oil. Examples of oleaginous yeast include, but are no means limited to, the following genera: *Yarrowia, Candida, Rhodotorula, Rhodosporidium, Cryptococcus, Trichosporon* and *Lipomyces*.

The term "fermentable carbon source" means a carbon source that a microorganism will metabolize to derive energy. Typical carbon sources of the invention include, but are not limited to: monosaccharides, oligosaccharides, polysaccharides, alkanes, fatty acids, esters of fatty acids, monoglycerides, carbon dioxide, methanol, formaldehyde, formate and carbon-containing amines.

The terms an "isolated nucleic acid fragment" an "isolated nucleic acid molecule" will be used interchangeably and will mean a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A nucleic acid molecule is "hybridizable" to another nucleic acid molecule, such as a cDNA, genomic DNA, or RNA molecule, when a single-stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, 2$^{nd}$ ed., Cold Spring Harbor Laboratory: Cold Spring Harbor, N.Y. (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washed with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least about 30 nucleotides. Furthermore, the skilled artisan will recognize that the temperature and wash solution salt concentration may be adjusted as necessary according to factors such as length of the probe.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.* 215:403-410 (1993)). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches partial or complete amino acid and nucleotide sequences encoding one or more particular yeast and fungal proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable of hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing, as well as those substantially similar nucleic acid sequences.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humania: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences is performed using the Clustal method of alignment (Higgins and Sharp, *CABIOS*. 5:151-153 (1989)) with default parameters (GAP PENALTY=10, GAP LENGTH PENALTY=10), unless otherwise specified. Default parameters for pairwise alignments using the Clustal method are: KTUPLE 1, GAP PENALTY=3, WINDOW=5 and DIAGONALS SAVED=5.

Suitable nucleic acid fragments (isolated polynucleotides of the present invention) encode polypeptides that are at least about 70% identical, preferably at least about 75% identical, and more preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

"Codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "codon-optimized", as it refers to genes or coding regions of nucleic acid molecules, refers to modification of codons such that the altered codons reflect the typical codon usage of the host organism without altering the polypeptide for which the DNA codes.

"Chemically synthesized", as related to a sequence of DNA, means that the component nucleotides were assembled in vitro. Manual chemical synthesis of DNA may be accomplished using well-established procedures; or automated chemical synthesis can be performed using one of a number of commercially available machines. "Synthetic genes" can be assembled from oligonucleotide building blocks that are chemically synthesized using procedures known to those skilled in the art. These building blocks are ligated and annealed to form gene segments that are then enzymatically assembled to construct the entire gene. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell, where sequence information is available. "Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

A "codon-optimized gene" is a gene having its frequency of codon usage designed to mimic the frequency of preferred codon usage of the host cell.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing sites, effector binding sites and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "3' non-coding sequences" or "transcription terminator" refers to DNA sequences located downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA" or "mRNA" refers to the RNA that is without introns and that can be translated into protein by the cell. "cDNA" refers to a double-stranded DNA that is complementary to, and derived from, mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; WO 99/28508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated and yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment(s) of the invention. Expression may also refer to translation of mRNA into a polypeptide.

"Transformation" refers to the transfer of a nucleic acid molecule into a host organism, resulting in genetically stable inheritance. The nucleic acid molecule may be a plasmid that replicates autonomously, for example; or, it may integrate into the genome of the host organism. Host organisms containing the transformed nucleic acid fragments are referred to as "transgenic" or "recombinant" or "transformed" organisms.

The terms "plasmid", "vector" and "cassette" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene(s) and having elements in addition to the foreign gene(s) that facilitate transformation of a particular host cell. "Expression cassette" refers to a specific vector containing a foreign gene(s) and having elements in addition to the foreign gene(s) that allow for enhanced expression of that gene in a foreign host.

The term "homologous recombination" refers to the exchange of DNA fragments between two DNA molecules (during cross over). The fragments which are exchanged are flanked by sites of identical nucleotide sequences between the two DNA molecules (i.e., "regions of homology"). The term "regions of homology" refer to stretches of nucleotide sequence on nucleic acid fragments that participate in homologous recombination that have homology to each other. Effective homologous recombination will generally take place where these regions of homology are at least about 10 bp in length where at least about 50 bp in length is preferred. Typically fragments that are intended for recombination contain at least two regions of homology where targeted gene disruption or replacement is desired.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.* 215:403-410 (1990)); 3.) DNASTAR (DNASTAR, Inc. Madison, Wis.); 4.) Sequencher (Gene Codes Corporation, Ann Arbor, Mich.); and 5.) the FASTA program incorporating the Smith-Waterman algorithm (W. R. Pearson, *Comput. Methods Genome Res.*, [Proc. Int. Symp.] (1994), Meeting Date 1992,111-20. Suhai, Sandor, Ed. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

The term "conserved domain" or "motif" means a set of amino acids conserved at specific positions along an aligned sequence of evolutionarily related proteins. While amino acids at other positions can vary between homologous proteins, amino acids that are highly conserved at specific positions indicate amino acids that are essential in the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family. Motifs that are universally found in DGAT1 enzymes (i.e., animal, plants and fungi) are provided as SEQ ID NOs:31-37; motifs found in DGAT1s that are specific to fungal organisms are provided as SEQ ID NOs:23-30.

Standard recombinant DNA and molecular cloning techniques used herein are well known in the art and are described by Sambrook, J., Fritsch, E. F. and Maniatis, T., *Molecular Cloning: A Laboratory Manual*, 2$^{nd}$ ed., Cold Spring Harbor Laboratory: Cold Spring Harbor, N.Y. (1989) (hereinafter "Maniatis"); by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience (1987).

Microbial Biosynthesis of Fatty Acids and Triacylglycerols

Figure 1:
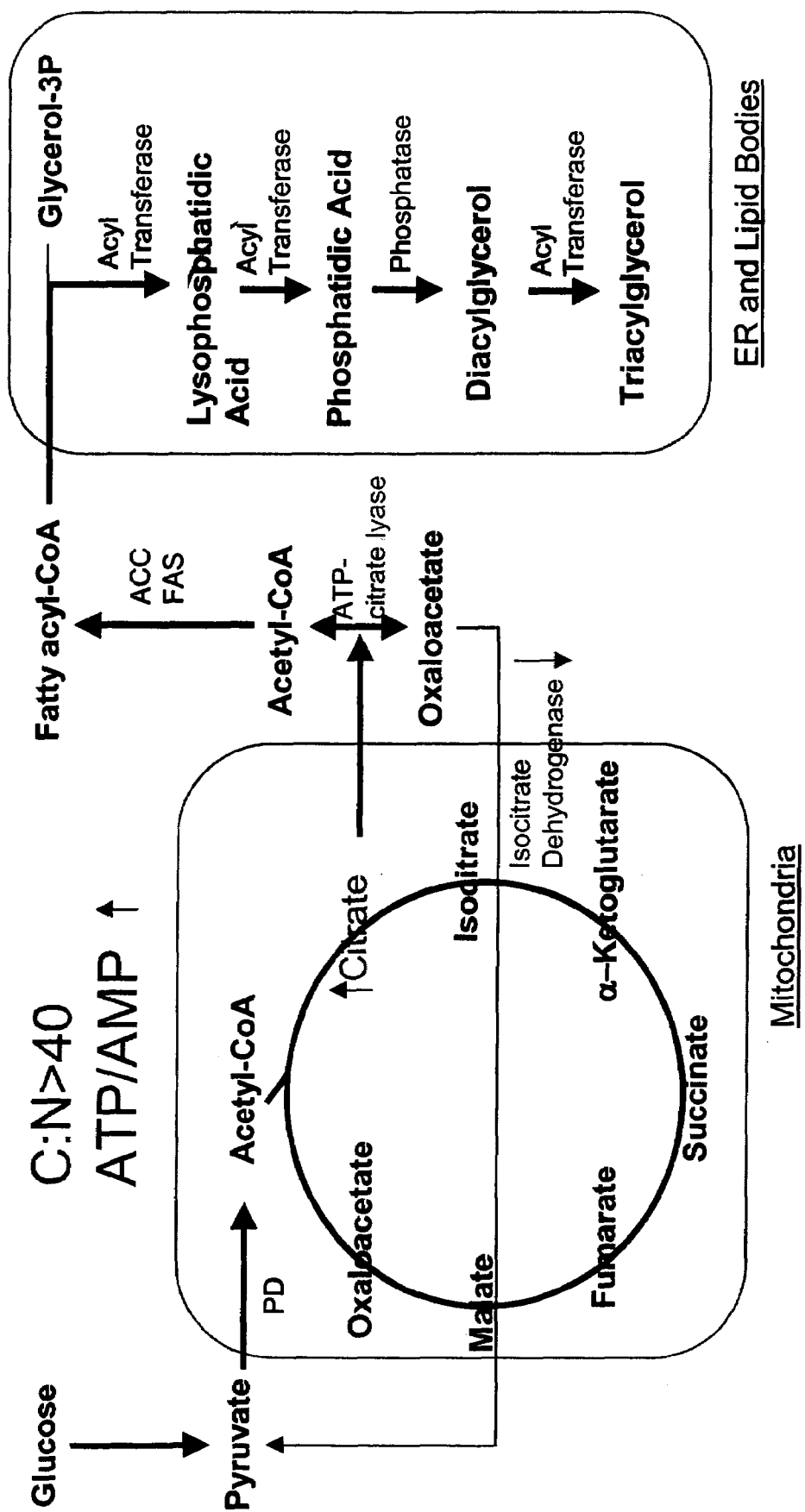
FIG. 1 shows a schematic illustration of the biochemical mechanism for lipid accumulation in oleaginous yeast.

In general, lipid accumulation in oleaginous microorganisms is triggered in response to the overall carbon to nitrogen ratio present in the growth medium (FIG. 1). When cells have exhausted available nitrogen supplies (e.g., when the carbon to nitrogen ratio is greater than about 40), the depletion of cellular adenosine monophosphate (AMP) leads to the cessation of AMP-dependent isocitrate dehydrogenase activity in the mitochondria and the accumulation of citrate, transport of citrate into the cytosol, and subsequent cleavage of the citrate by ATP-citrate lyase to yield acetyl-CoA and oxaloacetate. Acetyl-CoA is the principle building block for de novo biosynthesis of fatty acids. Although any compound that can effectively be metabolized to acetyl-CoA can serve as a precursor of fatty acids, glucose is the primary source of carbon in this type of reaction (FIG. 1). Glucose is converted to pyruvate via glycolysis, and pyruvate is then transported into the mitochondria where it can be converted to acetyl-CoA by pyruvate dehydrogenase ("PD"). Since acetyl-CoA can not be transported directly across the mitochondrial membrane into the cytoplasm, the two carbons from acetyl-CoA condense with oxaloacetate to yield citrate (catalyzed by citrate synthase). Citrate is transported directly into the cytoplasm, where it is cleaved by ATP-citrate lyase to regenerate acetyl-CoA and oxaloacetate. The oxaloacetate reenters the tricarboxylic acid cycle, via conversion to malate.

The synthesis of malonyl-CoA is the first committed step of fatty acid biosynthesis, which takes place in the cytoplasm. Malonyl-CoA is produced via carboxylation of acetyl-CoA by acetyl-CoA carboxylase ("ACC"). Fatty acid synthesis is catalyzed by a multi-enzyme fatty acid synthase complex ("FAS") and occurs by the condensation of eight two-carbon fragments (acetyl groups from acetyl-CoA) to form a 16-carbon saturated fatty acid, palmitate. More specifically, FAS catalyzes a series of 7 reactions, which involve the following (Smith, S. *FASEB J,* 8(15):1248-59 (1994)):

1. Acetyl-CoA and malonyl-CoA are transferred to the acyl carrier peptide (ACP) of FAS. The acetyl group is then transferred to the malonyl group, forming β-ketobutyryl-ACP and releasing $CO_2$.
2. The β-ketobutyryl-ACP undergoes reduction (via β-ketoacyl reductase) and dehydration (via β-hydroxyacyl dehydratase) to form a trans-monounsaturated fatty acyl group.
3. The double bond is reduced by NADPH, yielding a saturated fatty-acyl group two carbons longer than the initial one. The butyryl-group's ability to condense with a new malonyl group and repeat the elongation process is then regenerated.
4. When the fatty acyl group becomes 16 carbons long, a thioesterase activity hydrolyses it, releasing free palmitate (16:0).

Whereas palmitate synthesis occurs in the cytosol, formation of longer chain saturated and unsaturated fatty acid derivates occur in both the mitochondria and endoplasmic reticulum (ER), wherein the ER is the dominant system. Specifically, palmitate (16:0) is the precursor of stearic (18:0), palmitoleic (16:1) and oleic (18:1) acids through the action of elongases and desaturases. For example, palmitate and stearate are converted to their unsaturated derivatives, palmitoleic (16:1) and oleic (18:1) acids, respectively, by the action of a Δ9 desaturase.

TAGs (the primary storage unit for fatty acids) are formed by a series of reactions that involve: 1.) the esterification of one molecule of acyl-CoA to glycerol-3-phosphate via an acyltransferase to produce lysophosphatidic acid; 2.) the esterification of a second molecule of acyl-CoA via an acyltransferase to yield 1,2-diacylglycerol phosphate (commonly identified as phosphatidic acid); 3.) removal of a phosphate by phosphatidic acid phosphatase to yield 1,2-diacylglycerol (DAG); and 4.) the addition of a third fatty acid by the action of another acyltransferase (e.g., PDAT, DGAT1 or DGAT2) to form TAG (FIG. 1).

A wide spectrum of fatty acids can be incorporated into TAGs, including saturated and unsaturated fatty acids and short-chain and long-chain fatty acids. Some non-limiting examples of fatty acids that can be incorporated into TAGs by acyltransferases (e.g., DAG ATs or PDAT) include: capric (10:0), lauric (12:0), myristic (14:0), palmitic (16:0), palmitoleic (16:1), stearic (18:0), oleic (18:1), vaccenic (18:1), linoleic (18:2), eleostearic (18:3), γ-linolenic (18:3), α-linolenic (18:3), stearidonic (18:4), arachidic (20:0), eicosadienoic (20:2), dihomo-γ-linoleic (20:3), eicosatrienoic (20:3), arachidonic (20:4), eicosa-tetraenoic (20:4), eicosa-pentaenoic (20:5), behenic (22:0), docosa-pentaenoic (22:5), docosa-hexaenoic (22:6), lignoceric (24:0), nervonic (24:1), cerotic (26:0) and montanic (28:0) fatty acids. In preferred embodiments of the present invention, incorporation of PUFAs into TAG is most desirable.

Acyltransferases and Their Role in the Terminal Step of TAG Biosynthesis

Genes Encoding DGAT1

Historically, DGAT1 (responsible for the third acyl transferase reaction, wherein an acyl-CoA group is transferred from acyl-CoA to the sn-3 position of DAG to form TAG) was thought to be the only enzyme specifically involved in TAG synthesis. This enzyme was known to be homologous to acyl-CoA:cholesterol acyltransferases (ACATs); however, recent studies have identified a new family of DAG acyltransferase (DAG AT) enzymes that are unrelated to the ACAT gene family. Thus, nomenclature now distinguishes between the DAG AT enzymes that are related to the ACAT gene family (DGAT1 family) versus those that are unrelated (DGAT2 family) (Lardizabal et al., *J. Biol. Chem.* 276(42): 38862-28869 (2001)).

Many genes encoding DGAT1 enzymes have been identified through genetic means and the DNA sequences of some of these genes are publicly available. For example, some non-limiting examples include the following GenBank Accession Numbers: AY445635 (olive); AF384160 (mouse); NM_053437 (Norway rat); NM_174693 (cow); AY116586 (pig); AY327327 and AY327326 (*Toxoplasma gondii*); AF298815 (*Perilla frutescens*); and AF164434 (*Brassica napus*). Additionally, the patent literature provides many additional DNA sequences of DGAT1 genes (and/or details concerning several of the genes above and their methods of isolation). See, for example: U.S. Pat. No. 6,100,077 (human); U.S. Pat. No. 6,552,250 (*Brassica*); U.S. Pat. No. 6,344,548 (human, mouse, *Arabidopsis*); U.S. 2004/0088759A1 (plant); and U.S. 2004/0078836A1 (Farese et al.).

Genes Encoding DGAT2

Members of the DGAT2 family appear to be present in all major phyla of eukaryotes (fungi, plants, animals and basal eukaryotes). As such, many genes encoding DGAT2 enzymes have been identified through genetic means and the DNA sequences of some of these genes are publicly available. For example, some non-limiting examples include the following GenBank Accession Numbers: NC_001147 (locus NP_014888; *Saccharomyces cerevisiae*); NM_012079 (human); NM_127503, AF051849 and AJ238008 (*Arabidopsis thaliana*); NM_026384, NM_010046 and AB057816 (mouse); AY093657 (pig); AB062762 (rat); AF221132 (*Caenorhabditis elegans*); AF391089 and AF391090 (*Mortierella ramanniana*); AF129003 (*Nicotiana tabacum*); and, AF251794 and AF164434 (*Brassica napus*). Additionally, the patent literature provides many additional DNA sequences of DGAT2 genes (and/or details concerning several of the genes above and their methods of isolation). See, for example: US 2003/124126 (Cases et al.); WO 2001/034814 (Banas et al.); and US 2003/115632, US 2003/0028923 and US 2004/0107459 (Lardizabal et al.). The work of Lardizabal et al. includes DNA sequences of DGAT2s from, e.g., *Mortierella ramanniana, Neurospora crassa, Saccharomyces cerevisiae, Hordeum vulgare, Zea mays, Glycine max, Triticum aestivum, Drosophilia, Homo sapiens, Schizosaccharomyces pombe, Candida albicans* and *Arabidopsis thaliana*.

Most recently, a DGAT2 enzyme from the oleaginous yeast *Yarrowia lipolytica* has been isolated and characterized in co-pending U.S. patent application Ser. No. 10/882,760 (incorporated entirely herein by reference). Briefly, following cloning of a partial putative DGAT2 DNA fragment from *Y. lipolytica*, targeted disruption of the endogenous *Y. lipolytica* gene was carried out to test the identity of the fragment. Lower oil content in the disrupted strain confirmed that the native DGAT2 activity was eliminated. Subsequently, a full-length *Y. lipolytica* DGAT2 gene (2119 bp; SEQ ID NO:1) was assembled, which included three nested open reading frames: 1.) ORF 1: nucleotides +291 to +1835 of SEQ ID NO:1, corresponding to the protein encoded by SEQ ID NO:2 (514 amino acid residues); 2.) ORF 2: nucleotides +456 to +1835 of SEQ ID NO:1, corresponding to SEQ ID NO:3 (1380 bases) and the protein encoded by SEQ ID NO:4 (459 amino acid residues); and 3.) ORF 3: nucleotides +768 to +1835 of SEQ ID NO:1, corresponding to SEQ ID NO:5 (1068 bases) and the protein encoded by SEQ ID NO:6 (355 amino acid residues).

Genes Encoding PDAT

TAG synthesis can also occur in the absence of acyl-CoA, via the acyl-CoA-independent PDAT enzyme, as recently discovered by Dahlqvist et al. (*Proc. Nat Acad. Sci.* (*USA*) 97:6487-6492 (2000)) and Oelkers et al. (*J. Biol. Chem.* 275:15609-15612 (2000)). Specifically, PDAT removes an acyl group from the sn-2 position of a phosphotidylcholine substrate for transfer to the sn-3 position of DAG to produce TAG; and, although the function of PDAT is not as well characterized as DGAT2, PDAT has been postulated to play a major role in removing "unusual" fatty acids from phospholipids in some oilseed plants (Banas, A. et al., *Biochem. Soc. Trans.* 28(6):703-705 (2000)).

PDAT is structurally related to the lecithin:cholesterol acyltransferase (LCAT) family of proteins. Several genes encoding PDAT enzymes have been identified through genetic means and the DNA sequences of some of these genes are publicly available. For example, some non-limiting examples include the following GenBank Accession Numbers: P40345 (*Saccharomyces cerevisiae*); 094680 and NP_596330 (*Schizosaccharomyces pombe*); and, NP_190069 and AB006704 [gi:2351069] (*Arabidopsis thaliana*). Additionally, the patent literature provides many additional DNA sequences of PDAT genes (and/or details concerning several of the genes above and their methods of isolation); see, for example, WO 2000/060095 (Dahlqvist et al.).

And, particularly relevant to the disclosure herein, a PDAT enzyme from the oleaginous yeast *Yarrowia lipolytica* has been isolated and characterized in co-pending U.S. patent application Ser. No.10/882,760 in a manner similar to that described above for DGAT2. Again, lower oil content in a strain having a disruption in the putative PDAT gene confirmed that the native PDAT activity was eliminated. Subsequently, a full-length *Y. lipolytica* PDAT gene (2326 bp; SEQ ID NO:7) was assembled.

Genes Encoding ARE2

The process of sterol esterification in yeast was first studied by H. Yang et al. (*Science.* 272(5266):1353-1356 (1996)), wherein it was discovered that two genes (ARE1 and ARE2) encode ACAT-related enzymes that permit the esterification of cholesterol. The DNA sequences of only a few ARE2 genes are publicly available. For example, see GenBank Accession Numbers: Q876L2 (*Saccharomyces bayanus*), P53629 (*S. cerevisiae*) and Q10269 (*Schizosaccharomyces pombe*).

Interaction Between PDAT, DGAT1, DGAT2 and ARE2

In *S. cerevisiae*, four genes (i.e., ARE1, ARE2, DGA1 [encoding DGAT2] and LRO1 [encoding PDAT]), contribute to oil biosynthesis. PDAT and DGAT2 are responsible for up to approximately 95% of oil biosynthesis (Sandager, L. et al., *J. Biol. Chem.* 277(8):6478-6482 (2002); Oelkers et. al. *J. Biol. Chem.* 277:8877 (2002)).

Surprisingly, according to the work described in co-pending U.S. patent application Ser. No.10/882760 in *Yarrowia lipolytica*, PDAT and DGAT2 appeared to only be partially responsible for oil biosynthesis. Thus, it was apparent that at least one other DAG AT must play a role in TAG formation. As described in the Application herein, oil biosynthesis in the yeast *Yarrowia lipolytica* requires the activity of PDAT, DGAT1 and DGAT2, while ARE2 may additionally be a minor contributor to oil biosynthesis. This is in marked contrast to the enzymes responsible for oil biosynthesis in *S. cerevisiae*, where only DGAT2 and PDAT are the major DAG ATs.

Biosynthesis of Omega-3 and Omega-6 Polyunsaturated Fatty Acids

The metabolic process that converts LA to GLA, DGLA and ARA (the ω-6 pathway) and ALA to STA, ETA, EPA, DPA and DHA (the ω-3 pathway) involves elongation of the carbon chain through the addition of two-carbon units and desaturation of the molecule through the addition of double bonds (FIG. 2). This requires a series of desaturation and elongation enzymes. Specifically, oleic acid is converted to LA (18:2), the first of the ω-6 fatty acids, by the action of a Δ12 desaturase. Subsequent ω-6 fatty acids are produced as follows: 1.) LA is converted to GLA by the action of a Δ6 desaturase; 2.) GLA is converted to DGLA by the action of an elongase; and 3.) DGLA is converted to ARA by the action of a Δ5 desaturase. In like manner, linoleic acid (LA) is converted to ALA, the first of the ω-3 fatty acids, by the action of a Δ15 desaturase. Subsequent ω-3 fatty acids are produced in a series of steps similar to that for the ω-6 fatty acids. Specifically, 1.) ALA is converted to STA by the activity of a Δ6 desaturase; 2.) STA is converted to ETA by the activity of an elongase; and 3.) ETA is converted to EPA by the activity of a Δ5 desaturase. Alternatively, ETA and EPA can be produced from DGLA and ARA, respectively, by the activity of a Δ17 desaturase. EPA can be further converted to DHA by the activity of an elongase and a Δ4 desaturase.

In alternate embodiments, a Δ9 elongase is able to catalyze the conversion of LA and ALA to EDA and ETrA, respectively. A Δ8 desaturase then converts these products to DGLA and ETA, respectively.

Many microorganisms, including algae, bacteria, molds, fungi and yeasts, can synthesize PUFAs and omega fatty acids in the ordinary course of cellular metabolism. Particularly well-studied are fungi including *Schizochytrium aggregatm*, species of the genus *Thraustochytrium* and *Mortierella alpina*. Additionally, many dinoflagellates (Dinophyceaae) naturally produce high concentrations of PUFAs. As such, a variety of desaturase and elongase genes involved in PUFA production have been identified through genetic means and the DNA sequences of some of these genes are publicly available (non-limiting examples are as follows): AY131238, Y055118, AY055117, AF296076, AF007561, L11421, NM_031344, AF465283, AF465281, AF110510, AF465282, AF419296, AB052086, AJ250735, AF126799, AF126798 (Δ6 desaturases); AF199596, AF226273, AF320509, AB072976, AF489588, AJ510244, AF419297, AF07879, AF067654, AB022097 (Δ5 desaturases); AF489589.1, AY332747 (A4 fatty acid desaturases); AAG36933, AF110509, AB020033, ML13300, AF417244, AF161219, AY332747, MG36933, AF110509, AB020033, AAL13300, AF417244, AF161219, X86736, AF240777, AB007640, AB075526, AP002063 (Δ12 desaturases); NP_441622, BM18302, BM02924, ML36934 (Δ15 desaturases); AF338466, AF438199, E11368, E11367, D83185, U90417, AF085500, AY504633, NM_069854, AF230693 (Δ9 desaturases); and AX464731, NM_119617, NM_134255, NM_134383, NM_134382, NM_068396, NM_068392, NM_070713, NM_068746, NM_064685 (elongases).

Additionally, the patent literature provides many additional DNA sequences of genes (and/or details concerning several of the genes above and their methods of isolation) involved in PUFA production. See, for example: U.S. Pat.

No. 5,968,809 (Δ6 desaturases); U.S. Pat. No. 5,972,664 and U.S. Pat. No. 6,075,183 (Δ5 desaturases); WO 91/13972 and U.S. Pat. No. 5,057,419 (Δ9 desaturases); WO 93/11245 (Δ15 desaturases); WO 94/11516, U.S. Pat. No. 5,443,974 and WO 03/099216 (Δ12 desaturases); WO 00/12720 and U.S. 2002/0139974A1 (elongases); U.S. 2003/0196217 A1 (Δ17 desaturase); WO 00/34439 (Δ8 desaturases); and, WO 02/090493 (Δ4 desaturases). Each of these patents and applications are herein incorporated by reference in their entirety.

Depending upon the host cell, the availability of substrate, and the desired end product(s), several desaturases and elongases are of interest for use in production of PUFAs. Considerations for choosing a specific polypeptide having desaturase or elongase activity include: 1.) the substrate specificity of the polypeptide; 2.) whether the polypeptide or a component thereof is a rate-limiting enzyme; 3.) whether the desaturase or elongase is essential for synthesis of a desired PUFA; and/or 4.) co-factors required by the polypeptide. The expressed polypeptide preferably has parameters compatible with the biochemical environment of its location in the host cell. For example, the polypeptide may have to compete for substrate with other enzymes in the host cell. Analyses of the $K_M$ and specific activity of the polypeptide are therefore considered in determining the suitability of a given polypeptide for modifying PUFA production in a given host cell. The polypeptide used in a particular host cell is one that can function under the biochemical conditions present in the intended host cell but otherwise can be any polypeptide having desaturase or elongase activity capable of modifying the desired fatty acid substrate.

Sequence Identification of DGAT1 Acyltransferases

Despite the availability of several genes encoding DGAT1 (supra) that could be used for heterologous expression in oleaginous yeast (e.g., Yarrowia lipolytica), expression of a native enzyme is sometimes preferred over a heterologous (or "foreign") enzyme. This preference may occur because: 1.) the native enzyme is optimized for interaction with other enzymes and proteins in the cell; and 2.) heterologous genes are unlikely to share the same codon preference in the host organism. Knowledge of the sequences of a host organism's native DGAT1 also facilitates disruption of the homologous chromosomal genes by targeted disruption. And, as the present invention has shown, understanding of the complete complement of acyltransferase genes that enable TAG synthesis in an organism enables one to readily manipulate the oil content that the host organism produces in a variety of ways.

Comparison of the Yarrowia lipolytica DGAT1 nucleotide base (SEQ ID NO:13) and deduced amino acid (SEQ ID NO:14) sequences to public databases reveals that the most similar known sequences are about 55% identical to the amino acid sequence of DGAT1 reported herein over a length of 526 amino acids using the BLASTP method of alignment with a low complexity filter and the following parameters: Expect value=10, matrix=Blosum 62 (Altschul, et al., Nucleic Acids Res. 25:3389-3402(1997))).

Comparison of the Mortierella alpina DGAT1 nucleotide base (SEQ ID NO:17) and deduced amino acid (SEQ ID NO:18) sequences to public databases reveals that the most similar known sequences are about 49% identical to the amino acid sequence of DGAT1 reported herein over a length of 525 amino acids using the BLASTP method of alignment (Altschul, et al., supra). Furthermore, comparison of the Y. lipolytica DGAT1 to the M. alpina DGAT1 revealed the two proteins to be 32.4% identical.

Similarly, comparison of the Neurospora crassa DGAT1 amino acid (SEQ ID NO:19) sequence to the Yarrowia lipolytica DGAT1 amino acid (SEQ ID NO:14) reveals about 37% identity over a length of 533 amino acids; comparison of the Gibberella zeae PH-1 DGAT1 amino acid (SEQ ID NO:20) sequence to the Y. lipolytica DGAT1 amino acid (SEQ ID NO:14) reveals about 38.1% identity over a length of 499 amino acids; comparison of the Magnaporthe grisea DGAT1 amino acid (SEQ ID NO:21) sequence to the Y. lipolytica DGAT1 amino acid (SEQ ID NO:14) reveals about 36.2% identity over a length of 503 amino acids; and, comparison of the Aspergillus nidulans DGAT1 amino acid (SEQ ID NO:22) sequence to the Y. lipolytica DGAT1 amino acid (SEQ ID NO:14) reveals about 41.7% identity over a length of 458 amino acids.

More preferred DGAT1 amino acid fragments are at least about 70%-80% identical to the sequences herein (i.e., SEQ ID NOs:14, 18, 19, 20, 21, 22), where those sequences that are 85%-90% identical are particularly suitable and those sequences that are about 95% identical are most preferred. Similarly, preferred DGAT1 encoding nucleic acid sequences corresponding to the instant ORFs (i.e., SEQ ID NOs:13 and 17) are those encoding active proteins and which are at least about 70%-80% identical to the nucleic acid sequences encoding DGAT1 reported herein, where those sequences that are 85%-90% identical are particularly suitable and those sequences that are about 95% identical are most preferred.

Sequence Identification of an ARE2 Acyltransferase

Comparison of the Yarrowia lipolytica ARE2 nucleotide base (SEQ ID NO:15) and deduced amino acid (SEQ ID NO:16) sequences to public databases reveals that the most similar known sequences are about 44% identical to the amino acid sequence of ARE2 reported herein over a length of 543 amino acids using the BLASTP method of alignment with a low complexity filter and the following parameters: Expect value=10, matrix=Blosum 62 (Altschul, et al., Nucleic Acids Res. 25:3389-3402(1997)). More preferred ARE2 amino acid fragments are at least about 70%-80% identical to the sequences herein, where those sequences that are 85%-90% identical are particularly suitable and those sequences that are about 95% identical are most preferred. Similarly, preferred ARE2 encoding nucleic acid sequences corresponding to the instant ORFs are those encoding active proteins and which are at least about 70%-80% identical to the nucleic acid sequences encoding ARE2 reported herein, where those sequences that are 85%-90% identical are particularly suitable and those sequences that are about 95% identical are most preferred.

Isolation of Homologs

Each of the acyltransferase nucleic acid fragments of the instant invention may be used to isolate genes encoding homologous proteins from the same or other microbial species. Isolation of homologous genes using sequence-dependent protocols is well known in the art. Examples of sequence-dependent protocols include, but are not limited to: 1.) methods of nucleic acid hybridization; 2.) methods of DNA and RNA amplification, as exemplified by various uses of nucleic acid amplification technologies [e.g., polymerase chain reaction (PCR), Mullis et al., U.S. Pat. No. 4,683,202; ligase chain reaction (LCR), Tabor, S. et al., Proc. Acad. Sci. USA 82:1074 (1985); or strand displacement amplification (SDA), Walker, et al., Proc. Natl. Acad. Sci. U.S.A., 89:392 (1992)]; and 3.) methods of library construction and screening by complementation.

For example, genes encoding similar proteins or polypeptides to the DGAT1s and ARE2s described herein could be isolated directly by using all or a portion of the instant nucleic acid fragments as DNA hybridization probes to screen libraries from any desired yeast or fungus using methodology well known to those skilled in the art. Specific oligonucleotide probes based upon the instant nucleic acid sequences can be designed and synthesized by methods known in the art (Maniatis, supra). Moreover, the entire sequences can be used directly to synthesize DNA probes by methods known to the skilled artisan (e.g., random primers DNA labeling, nick translation or end-labeling techniques), or RNA probes using available in vitro transcription systems. In addition, specific primers can be designed and used to amplify a part of (or full-length of) the instant sequences. The resulting amplification products can be labeled directly during amplification reactions or labeled after amplification reactions, and used as probes to isolate full-length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotides as specific hybridization probes in the Diagnosis of Genetic Disorders", in *Human Genetic Diseases: A Practical Approach*, K. E. Davis Ed., (1986) pp 33-50, IRL: Herndon, Va.; and Rychlik, W., In *Methods in Molecular Biology*, White, B. A. Ed., (1993) Vol. 15, pp 31-39, PCR Protocols: Current Methods and Applications. Humania: Totowa, N.J.).

Generally two short segments of the instant sequences may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding microbial genes.

Alternatively, the second primer sequence may be based upon sequences derived from the cloning vector. For example, the skilled artisan can follow the RACE protocol (Frohman et al., *PNAS USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (e.g., BRL, Gaithersburg, Md.), specific 3' or 5' cDNA fragments can be isolated (Ohara et al., *PNAS USA* 86:5673 (1989); Loh et al., *Science* 243:217 (1989)).

Alternatively, the instant DGAT1 and ARE2 sequences may be employed as hybridization reagents for the identification of homologs. The basic components of a nucleic acid hybridization test include a probe, a sample suspected of containing the gene or gene fragment of interest, and a specific hybridization method. Probes of the present invention are typically single-stranded nucleic acid sequences that are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions that will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed. Optionally, a chaotropic agent may be added. The chaotropic agent stabilizes nucleic acids by inhibiting nuclease activity. Furthermore, the chaotropic agent allows sensitive and stringent hybridization of short oligonucleotide probes at room temperature (Van Ness and Chen, *Nucl. Acids Res*. 19:5143-5151 (1991)). Suitable chaotropic agents include guanidinium chloride, guanidinium thiocyanate, sodium thiocyanate, lithium tetrachloroacetate, sodium perchlorate, rubidium tetrachloroacetate, potassium iodide and cesium trifluoroacetate, among others. Typically, the chaotropic agent will be present at a final concentration of about 3 M. If desired, one can add formamide to the hybridization mixture, typically 30-50% (v/v).

Various hybridization solutions can be employed. Typically, these comprise from about 20 to 60% volume, preferably 30%, of a polar organic solvent. A common hybridization solution employs about 30-50% v/v formamide, about 0.15 to 1 M sodium chloride, about 0.05 to 0.1 M buffers (e.g., sodium citrate, Tris-HCl, PIPES or HEPES (pH range about 6-9)), about 0.05 to 0.2% detergent (e.g., sodium dodecylsulfate), or between 0.5-20 mM EDTA, FICOLL (Pharmacia Inc.) (about 300-500 kdal), polyvinylpyrrolidone (about 250-500 kdal) and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol glycine. Other additives may also be included, such as volume exclusion agents that include a variety of polar water-soluble or swellable agents (e.g., polyethylene glycol), anionic polymers (e.g., polyacrylate or polymethylacrylate) and anionic saccharidic polymers (e.g., dextran sulfate).

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

Availability of the instant nucleotide and deduced amino acid sequences facilitates immunological screening of DNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can then be used to screen DNA expression libraries to isolate full-length DNA clones of interest (Lerner, R. A. *Adv. Immunol.* 36:1 (1984); Maniatis, supra).

Gene Optimization For Improved Heterologous Expression

It may be desirable to modify the expression of the instant acyltransferases and/or PUFA biosynthetic pathway enzymes to achieve optimal conversion efficiency of each, according to the specific TAG composition that is desired within a specific host organism. As such, a variety of techniques can be utilized to improve and/or optimize the expression of a polypeptide of interest in an alternative host. Two such techniques include codon-optimization and mutagenesis of the gene.

Codon Optimization

As will be appreciated by one skilled in the art, it is frequently useful to modify a portion of the codons encoding a particular polypeptide that is to be expressed in a foreign host, such that the modified polypeptide uses codons that are preferred by the alternate host. Use of host-preferred codons can substantially enhance the expression of the foreign gene encoding the polypeptide.

In general, host-preferred codons can be determined within a particular host species of interest by examining codon usage in proteins (preferably those expressed in the largest amount) and determining which codons are used with highest frequency. Thus, the coding sequence for a polypeptide having acyltransferase activity can be synthesized in whole or in part using the codons preferred in the host species. All (or portions) of the DNA also can be synthesized to remove any destabilizing sequences or regions of secondary structure that would be present in the transcribed mRNA. All (or portions) of the DNA also can be synthesized to alter the base composition to one more preferable in the desired host cell.

Thus, for example, it may be desirable to modify a portion of the codons encoding the *Mortierella* polypeptide having DGAT1 activity, to enhance the expression of the gene in *Yarrowia lipolytica*, should the enzyme's substrate specificity be different than that of the *Y. lipolytica* DGAT1 disclosed herein. The codon usage profile and the consensus sequence around the 'ATG' translation initiation codon for this particular organism (i.e., *Y. lipolytica*) are taught in co-pending U.S. patent application Ser. No. 10/840,478 (herein incorporated entirely by reference); likewise, a method for rapid synthesis of genes optimized for expression in *Y. lipolytica* is also provided.

Mutagenesis

Methods for synthesizing sequences and bringing sequences together are well established in the literature. For example, in vitro mutagenesis and selection, site-directed mutagenesis, error prone PCR (Melnikov et al., *Nucleic Acids Research*, 27(4):1056-1062 (Feb. 15, 1999)), "gene shuffling" or other means can be employed to obtain mutations of naturally occurring acyltransferase genes. This would permit production of a polypeptide having acyltransferase activity in vivo with more desirable physical and kinetic parameters for function in the host cell (e.g., a longer half-life or a higher rate of synthesis of TAGs from fatty acids).

If desired, the regions of a DGAT1 or ARE2 polypeptide important for enzymatic activity can be determined through routine mutagenesis, expression of the resulting mutant polypeptides and determination of their activities. Mutants may include deletions, insertions and point mutations, or combinations thereof. A typical functional analysis begins with deletion mutagenesis to determine the N- and C-terminal limits of the protein necessary for function, and then internal deletions, insertions or point mutants are made to further determine regions necessary for function. Other techniques such as cassette mutagenesis or total synthesis also can be used. Deletion mutagenesis is accomplished, for example, by using exonucleases to sequentially remove the 5' or 3' coding regions. Kits are available for such techniques. After deletion, the coding region is completed by ligating oligonucleotides containing start or stop codons to the deleted coding region after the 5' or 3' deletion, respectively. Alternatively, oligonucleotides encoding start or stop codons are inserted into the coding region by a variety of methods including site-directed mutagenesis, mutagenic PCR or by ligation onto DNA digested at existing restriction sites. Internal deletions can similarly be made through a variety of methods including the use of existing restriction sites in the DNA, by use of mutagenic primers via site-directed mutagenesis or mutagenic PCR. Insertions are made through methods such as linker-scanning mutagenesis, site-directed mutagenesis or mutagenic PCR. Point mutations are made through techniques such as site-directed mutagenesis or mutagenic PCR.

Chemical mutagenesis also can be used for identifying regions of an acyltransferase polypeptide important for activity. A mutated construct is expressed, and the ability of the resulting altered protein to function as an acyltransferase is assayed. Such structure-function analysis can determine which regions may be deleted, which regions tolerate insertions, and which point mutations allow the mutant protein to function in substantially the same way as the native acyltransferase.

All such mutant proteins and nucleotide sequences encoding them that are derived from the DGAT1 and ARE2 genes described herein are within the scope of the present invention.

Microbial Production of Fatty Acids and Triacylglycerols

Microbial production of fatty acids and TAGs has several advantages over purification from natural sources such as fish or plants. For example:

1.) Many microbes are known with greatly simplified oil compositions compared with those of higher organisms, making purification of desired components easier;
2.) Microbial production is not subject to fluctuations caused by external variables, such as weather and food supply;
3.) Microbially produced oil is substantially free of contamination by environmental pollutants; and,
4.) Microbial oil production can be manipulated by controlling culture conditions, notably by providing particular substrates for microbially expressed enzymes, or by addition of compounds or genetic engineering approaches to suppress undesired biochemical pathways.

With respect to the production of ω-3 and/or ω-6 fatty acids in particular, and TAGs containing those PUFAs, additional advantages are incurred since microbes can provide fatty acids in particular forms that may have specific uses; and, recombinant microbes provide the ability to alter the naturally occurring microbial fatty acid profile by providing new biosynthetic pathways in the host or by suppressing undesired pathways, thereby increasing levels of desired PUFAs, or conjugated forms thereof, and decreasing levels of undesired PUFAs.

Thus, knowledge of the sequences of the present acyltransferase genes will be useful for manipulating fatty acid biosynthesis and accumulation in oleaginous yeasts, and particularly, in *Yarrowia lipolytica*. This may require metabolic engineering directly within the fatty acid or TAG biosynthetic pathways or additional manipulation of pathways that contribute carbon to the fatty acid biosynthetic pathway. Methods useful for manipulating biochemical pathways are well known to those skilled in the art.

Metabolic Engineering to Up-Regulate Genes and Biosynthetic Pathways Affecting Fatty Acid Synthesis and Oil Accumulation in Oleaginous Yeast It is expected that introduction of chimeric genes encoding the acyltransferases described herein, under the control of the appropriate promoters, will result in increased transfer of fatty acids to storage TAGs. As such, the present invention encompasses a method for increasing the TAG content in an oleaginous yeast comprising expressing at least one acyltransferase enzyme of the present invention in a transformed oleaginous yeast host cell producing a fatty acid, such that the fatty acid is transferred to the TAG pool.

Additional copies of acyltransferase genes (e.g., DGAT1, ARE2) may be introduced into the host to increase the transfer of fatty acids to the TAG fraction. Expression of the genes also can be increased at the transcriptional level through the use of a stronger promoter (either regulated or constitutive) to cause increased expression, by removing/deleting destabilizing sequences from either the mRNA or the encoded protein, or by adding stabilizing sequences to the mRNA (U.S. Pat. No. 4,910,141). Yet another approach to increase expression of heterologous genes is to increase the translational efficiency of the encoded mRNAs by replacement of codons in the native gene with those for optimal gene expression in the selected host microorganism.

In one specific embodiment, the present invention encompasses a method of increasing the ω-3 and/or ω-6 fatty acid content of TAGs in an oleaginous yeast, since it is possible to introduce an expression cassette encoding each of the enzymes necessary for ω-3 and/or ω-6 fatty acid biosynthesis into the organism (since naturally produced PUFAs in these organisms are limited to 18:2 (i.e., LA), and less commonly 18:3 (i.e., ALA) fatty acids). Thus, the method comprises:
 a) providing a transformed oleaginous yeast host cell possessing genes encoding a functional ω-3/ω-6 fatty acid biosynthetic pathway and at least one acyltransferase enzyme of the present invention;
 b) growing the yeast cells of step (a) in the presence of a fermentable carbon substrate, whereby the gene(s) of the ω-3/ω-6 fatty acid biosynthetic pathway and the acyltransferase(s) are expressed, whereby a ω-3 and/or ω-6 fatty acid is produced, and whereby the ω-3 and/or ω-6 fatty acid is transferred to TAGs.

A variety of PUFA products can be produced (prior to their transfer to TAGs), depending on the fatty acid substrate and the particular genes of the ω-3/ω-6 fatty acid biosynthetic pathway that are transformed into the host cell. As such, production of the desired fatty acid product can occur directly (wherein the fatty acid substrate is converted directly into the desired fatty acid product without any intermediate steps or pathway intermediates) or indirectly (wherein multiple genes encoding the PUFA biosynthetic pathway may be used in combination, such that a series of reactions occur to produce a desired PUFA). Specifically, for example, it may be desirable to transform an oleaginous yeast with an expression cassette comprising a Δ12 desaturase, Δ6 desaturase, an elongase, a Δ5 desaturase and a Δ17 desaturase for the overproduction of EPA. As is well known to one skilled in the art, various other combinations of the following enzymatic activities may be useful to express in a host in conjunction with the acyltransferases described herein: a Δ15 desaturase, a Δ4 desaturase, a Δ5 desaturase, a Δ6 desaturase, a Δ17 desaturase, a Δ9 desaturase, a Δ8 desaturase and/or an elongase(s) (see FIG. 2). The particular genes included within a particular expression cassette will depend on the host cell (and its PUFA profile and/or desaturase profile), the availability of substrate and the desired end product(s).

Thus, within the context of the present invention, it may be useful to modulate the expression of the TAG biosynthetic pathway by any one of the methods described above. For example, the present invention provides genes encoding key enzymes in the fatty acid biosynthetic pathway leading to the storage of TAGs. These genes encode the DGAT1 and ARE2 enzymes. It will be particularly useful to modify the expression levels of these genes in oleaginous yeasts to maximize production and accumulation of TAGs using various means for metabolic engineering of the host organism. In preferred embodiments, modification of the expression levels of these genes in combination with expression of ω-3/ω-6 biosynthetic genes can be utilized to maximize production and accumulation of preferred PUFAs in the TAG pool.

Metabolic Engineering to Down-Regulate Undesirable Genes and Biosynthetic Pathways Affecting Fatty Acid Synthesis and Oil Accumulation in Oleaginous Yeast In some embodiments, it may be useful to disrupt or inactivate a host organism's native DGAT1 and/or ARE2, based on the complete sequences described herein, the complement of those complete sequences, substantial portions of those sequences, codon-optimized acyltransferases derived therefrom, and those sequences that are substantially homologous thereto.

For gene disruption, a foreign DNA fragment (typically a selectable marker gene) is inserted into the structural gene to be disrupted in order to interrupt its coding sequence and thereby functionally inactivate the gene. Transformation of the disruption cassette into the host cell results in replacement of the functional native gene by homologous recombination with the non-functional disrupted gene (see, for example: Hamilton et al., *J. Bacteriol.* 171:4617-4622 (1989); Balbas et al., *Gene* 136:211-213 (1993); Gueldener et al., *Nucleic Acids Res.* 24:2519-2524 (1996); and Smith et al., *Methods Mol. Cell. Biol.* 5:270-277(1996)).

Antisense technology is another method of down-regulating genes when the sequence of the target gene is known. To accomplish this, a nucleic acid segment from the desired gene is cloned and operably linked to a promoter such that the anti-sense strand of RNA will be transcribed. This construct is then introduced into the host cell and the antisense strand of RNA is produced. Antisense RNA inhibits gene expression by preventing the accumulation of mRNA that encodes the protein of interest. The person skilled in the art will know that special considerations are associated with the use of antisense technologies in order to reduce expression of particular genes. For example, the proper level of expression of antisense genes may require the use of different chimeric genes utilizing different regulatory elements known to the skilled artisan.

Although targeted gene disruption and antisense technology offer effective means of down-regulating genes where the sequence is known, other less specific methodologies have been developed that are not sequence-based. For example, cells may be exposed to UV radiation and then screened for the desired phenotype. Mutagenesis with chemical agents is also effective for generating mutants and commonly used substances include chemicals that affect nonreplicating DNA (e.g., $HNO_2$ and $NH_2OH$), as well as agents that affect replicating DNA (e.g., acridine dyes, notable for causing frameshift mutations). Specific methods for creating mutants using radiation or chemical agents are well documented in the art. See, for example: Thomas D. Brock in *Biotechnology: A Textbook of Industrial Microbiology*, $2^{nd}$ ed. (1989) Sinauer Associates: Sunderland, Mass.; or Deshpande, Mukund V., *Appl. Biochem. Biotechnol.*, 36:227 (1992).

Another non-specific method of gene disruption is the use of transposable elements or transposons. Transposons are genetic elements that insert randomly into DNA but can be later retrieved on the basis of sequence to determine where the insertion has occurred. Both in vivo and in vitro transposition methods are known. Both methods involve the use of a transposable element in combination with a transposase enzyme. When the transposable element or transposon is contacted with a nucleic acid fragment in the presence of the transposase, the transposable element will randomly insert into the nucleic acid fragment. The technique is useful for random mutagenesis and for gene isolation, since the disrupted gene may be identified on the basis of the sequence of the transposable element. Kits for in vitro transposition are commercially available [see, for example: 1.) The Primer Island Transposition Kit, available from Perkin Elmer Applied Biosystems, Branchburg, N.J., based upon the yeast Ty1 element; 2.) The Genome Priming System, available from New England Biolabs, Beverly, Mass., based upon the bacterial transposon Tn7; and 3.) the EZ::TN Transposon Insertion Systems, available from Epicentre Technologies, Madison, Wis., based upon the Tn5 bacterial transposable element].

Thus, within the context of the present invention, it may be useful to disrupt one of the acyltransferase genes of the invention. For example, it may be necessary to disrupt genes and pathways that diminish the existing fatty acid pool and/or that hydrolyze TAGs to regulate (and/or maximize) TAG accumulation.

Expression Systems, Cassettes and Vectors

The genes and gene products of the instant sequences described herein may be produced in microbial host cells, particularly in the cells of oleaginous yeasts (e.g., *Yarrowia lipolytica*). Expression in recombinant microbial hosts may be useful for the transfer of various fatty acids to TAGs.

Microbial expression systems and expression vectors containing regulatory sequences that direct high level expression of foreign proteins are well known to those skilled in the art. Any of these could be used to construct chimeric genes for production of the gene products of the instant acyltransferase sequences. These chimeric genes could then be introduced into appropriate microorganisms via transformation to provide high level expression of the encoded enzymes.

Vectors or DNA cassettes useful for the transformation of suitable host cells are well known in the art. The specific choice of sequences present in the construct is dependent upon the desired expression products (supra), the nature of the host cell and the proposed means of separating transformed cells versus non-transformed cells. Typically, however, the vector or cassette contains sequences directing transcription and translation of the relevant gene(s), a selectable marker and sequences allowing autonomous replication or chromosomal integration. Suitable vectors comprise a region 5' of the gene that controls transcriptional initiation and a region 3' of the DNA fragment that controls transcriptional termination. It is most preferred when both control regions are derived from genes from the transformed host cell, although it is to be understood that such control regions need not be derived from the genes native to the specific species chosen as a production host.

Initiation control regions or promoters which are useful to drive expression of the instant ORFs in the desired host cell are numerous and familiar to those skilled in the art. Virtually any promoter capable of directing expression of these genes in the selected host cell is suitable for the present invention. Expression in a host cell can be accomplished in a transient or stable fashion. Transient expression can be accomplished by inducing the activity of a regulatable promoter operably linked to the gene of interest. Stable expression can be achieved by the use of a constitutive promoter operably linked to the gene of interest. As an example, when the host cell is yeast, transcriptional and translational regions functional in yeast cells are provided, particularly from the host species. The transcriptional initiation regulatory regions can be obtained, for example, from: 1.) genes in the glycolytic pathway, such as alcohol dehydrogenase, glyceraldehyde-3-phosphate-dehydrogenase (see U.S. patent application Ser. No. 10/869,630, incorporated herein by reference), phosphoglycerate mutase (see U.S. patent application Ser. No. 10/869,630), fructose-bisphosphate aldolase (see U.S. patent application Ser. No. 60/519,971, incorporated herein by reference), phosphoglucose-isomerase, phosphoglycerate kinase, glycerol-3-phosphate O-acyltransferase (see U.S. patent application Ser. No. 60/610,060), etc.; or, 2.) regulatable genes such as acid phosphatase, lactase, metallothionein, glucoamylase, the translation elongation factor EF1-α (TEF) protein (U.S. Pat. No. 6,265,185), ribosomal protein S7 (U.S. Pat. No. 6,265,185), etc. Any one of a number of regulatory sequences can be used, depending upon whether constitutive or induced transcription is desired, the efficiency of the promoter in expressing the ORF of interest, the ease of construction and the like.

Nucleotide sequences surrounding the translational initiation codon 'ATG' have been found to affect expression in yeast cells. If the desired polypeptide is poorly expressed in yeast, the nucleotide sequences of exogenous genes can be modified to include an efficient yeast translation initiation sequence to obtain optimal gene expression. For expression in yeast, this can be done by site-directed mutagenesis of an inefficiently expressed gene by fusing it in-frame to an endogenous yeast gene, preferably a highly expressed gene. Alternatively, one can determine the consensus translation initiation sequence in the host and engineer this sequence into heterologous genes for their optimal expression in the host of interest (see, e.g., U.S. patent application Ser. No. 10/840,478 for specific teachings applicable for *Yarrowia lipolytica*).

The termination region can be derived from the 3' region of the gene from which the initiation region was obtained or from a different gene. A large number of termination regions are known and function satisfactorily in a variety of hosts (when utilized both in the same and different genera and species from where they were derived). The termination region usually is selected more as a matter of convenience rather than because of any particular property. Preferably, the termination region is derived from a yeast gene, particularly *Saccharomyces*, *Schizosaccharomyces*, *Candida*, *Yarrowia* or *Kluyveromyces*. The 3'-regions of mammalian genes encoding γ-interferon and α-2 interferon are also known to function in yeast. Termination control regions may also be derived from various genes native to the preferred hosts. Optionally, a termination site may be unnecessary; however, it is most preferred if included.

As one of skill in the art is aware, merely inserting a gene into a cloning vector does not ensure that it will be successfully expressed at the level needed. In response to the need for a high expression rate, many specialized expression vectors have been created by manipulating a number of different genetic elements that control aspects of transcription, translation, protein stability, oxygen limitation and secretion from the host cell. More specifically, some of the molecular features that have been manipulated to control gene expression include: 1.) the nature of the relevant transcriptional promoter and terminator sequences; 2.) the number of copies of the cloned gene and whether the gene is plasmid-borne or integrated into the genome of the host cell; 3.) the final cellular location of the synthesized foreign protein; 4.) the efficiency of translation in the host organism; 5.) the intrinsic stability of the cloned gene protein within the host cell; and 6.) the codon usage within the cloned gene, such that its frequency approaches the frequency of preferred codon usage of the host cell. Each of these types of modifications are encompassed in the present invention, as means to further optimize expression of the acyltransferase enzymes.

Preferred Microbial Hosts for Recombinant Expression of Acyltransferases

Host cells for expression of the instant DGAT1 and ARE2 genes and nucleic acid fragments may include microbial hosts that grow on a variety of feedstocks, including simple or complex carbohydrates, organic acids and alcohols and/or hydrocarbons over a wide range of temperature and pH values. Although the genes described in the instant invention have been isolated for expression in an oleaginous yeast, and in particular *Yarrowia lipolytica*, it is contemplated that because transcription, translation and the protein biosynthetic apparatus is highly conserved, any bacteria, yeast, algae and/or filamentous fungus will be a suitable host for expression of the present nucleic acid fragments.

Preferred microbial hosts are oleaginous organisms, such as oleaginous yeasts. These oleaginous organisms are naturally capable of oil synthesis and accumulation, wherein the total oil content can comprise greater than about 25% of the cellular dry weight, more preferably greater than about 30% of the cellular dry weight and most preferably greater than about 40% of the cellular dry weight. Additionally, there is basis for the use of these organisms for the production of PUFAs, as seen in co-pending U.S. patent application Ser. No.10/840,579, herein incorporated entirely by reference.

Genera typically identified as oleaginous yeast include, but are not limited to: *Yarrowia, Candida, Rhodotorula, Rhodospordium, Cryptococcus, Trichosporon* and *Lipomyces*. More specifically, illustrative oil-synthesizing yeasts include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus, R. graminis*, and *Yarrowia lipolytica* (formerly classified as *Candida lipolytica*).

Most preferred is the oleaginous yeast *Yarrowia lipolytica*; and, in a further embodiment, most preferred are the *Y. lipolytica* strains designated as ATCC #20362, ATCC #8862, ATCC #18944, ATCC #76982, ATCC #90812 and/or LGAM S(7)1 (Papanikolaou S., and Aggelis G., *Bioresour. Technol.* 82(1):43-9 (2002)).

Transformation of Microbial Hosts

Once the DNA encoding a polypeptide suitable for expression in an oleaginous yeast has been obtained, it is placed in a plasmid vector capable of autonomous replication in a host cell or it is directly integrated into the genome of the host cell. Integration of expression cassettes can occur randomly within the host genome or can be targeted through the use of constructs containing regions of homology with the host genome sufficient to target recombination within the host locus. Where constructs are targeted to an endogenous locus, all or some of the transcriptional and translational regulatory regions can be provided by the endogenous locus.

Where two or more genes are expressed from separate replicating vectors, it is desirable that each vector has a different means of selection and should lack homology to the other construct(s) to maintain stable expression and prevent reassortment of elements among constructs. Judicious choice of regulatory regions, selection means and method of propagation of the introduced construct(s) can be experimentally determined so that all introduced genes are expressed at the necessary levels to provide for synthesis of the desired products.

Constructs comprising the gene of interest may be introduced into a host cell by any standard technique. These techniques include transformation (e.g., lithium acetate transformation [*Methods in Enzymology*, 194:186-187 (1991)]), protoplast fusion, biolistic impact, electroporation, microinjection, or any other method that introduces the gene of interest into the host cell. More specific teachings applicable for oleaginous yeasts (i.e., *Yarrowia lipolytica*) include U.S. Pat. Nos. 4,880,741 and 5,071,764 and Chen, D. C. et al. (*Appl Microbiol Biotechnol*. 48(2):232-235-(1997)).

For convenience, a host cell that has been manipulated by any method to take up a DNA sequence (e.g., an expression cassette) will be referred to as "transformed" or "recombinant" herein. The transformed host will have at least one copy of the expression construct and may have two or more, depending upon whether the gene is integrated into the genome, amplified or is present on an extra-chromosomal element having multiple copy numbers. The transformed host cell can be identified by selection for a marker contained on the introduced construct. Alternatively, a separate marker construct may be co-transformed with the desired construct, as many transformation techniques introduce many DNA molecules into host cells. Typically, transformed hosts are selected for their ability to grow on selective media. Selective media may incorporate an antibiotic or lack a factor necessary for growth of the untransformed host, such as a nutrient or growth factor. An introduced marker gene may confer antibiotic resistance, or encode an essential growth factor or enzyme, thereby permitting growth on selective media when expressed in the transformed host. Selection of a transformed host can also occur when the expressed marker protein can be detected, either directly or indirectly. The marker protein may be expressed alone or as a fusion to another protein. The marker protein can be detected by: 1.) its enzymatic activity (e.g., β-galactosidase can convert the substrate X-gal [5-bromo-4-chloro-3-indolyl-β-D-galactopyranoside] to a colored product; luciferase can convert luciferin to a light-emitting product); or 2.) its light-producing or modifying characteristics (e.g., the green fluorescent protein of *Aequorea victoria* fluoresces when illuminated with blue light). Alternatively, antibodies can be used to detect the marker protein or a molecular tag on, for example, a protein of interest. Cells expressing the marker protein or tag can be selected, for example, visually, or by techniques such as FACS or panning using antibodies.

For selection of yeast transformants, any marker that functions in yeast may be used. Desirably, resistance to kanamycin, hygromycin and the amino glycoside G418 are of interest, as well as ability to grow on media lacking uracil or leucine.

Following transformation, substrates suitable for the gene products of the instant sequences (and optionally other PUFA enzymes that are expressed within the host cell), may be produced by the host either naturally or transgenically, or they may be provided exogenously.

Fermentation Processes for Triacylglycerol Biosynthesis and Accumulation

The transformed microbial host cell is grown under conditions that optimize activity of fatty acid biosynthetic genes and acyltransferase genes. This leads to production of the greatest and the most economical yield of fatty acids, which can in turn be transferred to TAGs for storage. In general, media conditions that may be optimized include the type and amount of carbon source, the type and amount of nitrogen source, the carbon-to-nitrogen ratio, the oxygen level, growth temperature, pH, length of the biomass production phase, length of the oil accumulation phase and the time of cell harvest. Microorganisms of interest, such as oleaginous yeast, are grown in complex media (e.g., yeast extract-peptone-dextrose broth (YPD)) or a defined minimal media that lacks a component necessary for growth and thereby forces selection of the desired expression cassettes (e.g., Yeast Nitrogen Base (DIFCO Laboratories, Detroit, Mich.)).

Fermentation media in the present invention must contain a suitable carbon source. Suitable carbon sources may include, but are not limited to: monosaccharides (e.g., glucose, fructose), disaccharides (e.g., lactose, sucrose), oligosaccharides, polysaccharides (e.g., starch, cellulose or mixtures thereof), sugar alcohols (e.g., glycerol) or mixtures from renewable feedstocks (e.g., cheese whey permeate, cornsteep liquor, sugar beet molasses, barley malt). Additionally, carbon sources may include alkanes, fatty acids, esters of fatty acids, monoglycerides, diglycerides, triglycerides, phospholipids and various commercial sources of fatty acids including vegetable oils (e.g., soybean oil) and animal fats. Additionally, the carbon substrate may include one-carbon substrates (e.g., carbon dioxide, methanol, formaldehyde, formate, carbon-containing amines) for which metabolic conversion into key biochemical intermediates has been demonstrated. Hence it is contemplated that the source of carbon utilized in the present invention may encompass a wide variety of carbon-containing substrates and will only be limited by the choice of the host organism. Although all of the above mentioned carbon substrates and mixtures thereof are expected to be suitable in the present invention, preferred carbon substrates are sugars and/or fatty acids. Most preferred is glucose and/or fatty acids containing between 10-22 carbons.

Nitrogen may be supplied from an inorganic (e.g., $(NH_4)_2SO_4$) or organic source (e.g., urea, glutamate). In addition to appropriate carbon and nitrogen sources, the fermentation media must also contain suitable minerals, salts, cofactors, buffers, vitamins and other components known to those skilled in the art suitable for the growth of the microorganism and promotion of the enzymatic pathways necessary for fatty acid production. Particular attention is given to several metal ions (e.g., $Mn^{+2}$, $Co^{+2}$, $Zn^{+2}$, $Mg^{+2}$) that promote synthesis of lipids and PUFAs (Nakahara, T. et al., *Ind. Appl. Single Cell Oils*, D. J. Kyle and R. Colin, eds. pp 61-97 (1992)).

Preferred growth media in the present invention are common commercially prepared media, such as Yeast Nitrogen Base (DIFCO Laboratories, Detroit, Mich.). Other defined or synthetic growth media may also be used and the appropriate medium for growth of the particular microorganism will be known by one skilled in the art of microbiology or fermentation science. A suitable pH range for the fermentation is typically between about pH 4.0 to pH 8.0, wherein pH 5.5 to pH 7.0 is preferred as the range for the initial growth conditions. The fermentation may be conducted under aerobic or anaerobic conditions, wherein microaerobic conditions are preferred.

Typically, accumulation of high levels of fatty acids and TAGs in oleaginous yeast cells requires a two-stage process, since the metabolic state must be "balanced" between growth and synthesis/storage of fats. Thus, most preferably, a two-stage fermentation process is necessary for the production of oils in oleaginous yeast. In this approach, the first stage of the fermentation is dedicated to the generation and accumulation of cell mass and is characterized by rapid cell growth and cell division. In the second stage of the fermentation, it is preferable to establish conditions of nitrogen deprivation in the culture to promote high levels of lipid accumulation. The effect of this nitrogen deprivation is to reduce the effective concentration of AMP in the cells, thereby reducing the activity of the NAD-dependent isocitrate dehydrogenase of mitochondria. When this occurs, citric acid will accumulate, thus forming abundant pools of acetyl-CoA in the cytoplasm and priming fatty acid synthesis. Thus, this phase is characterized by the cessation of cell division followed by the synthesis of fatty acids and accumulation of TAGs.

Although cells are typically grown at about 30° C., some studies have shown increased synthesis of unsaturated fatty acids at lower temperatures (Yongmanitchai and Ward, *Appl. Environ. Microbiol.* 57:419-25 (1991)). Based on process economics, this temperature shift should likely occur after the first phase of the two-stage fermentation, when the bulk of the organisms' growth has occurred.

It is contemplated that a variety of fermentation process designs may be applied, where commercial production of fatty acids and TAGs using the instant acyltransferase genes is desired. For example, commercial production of TAGs containing PUFAs from a recombinant microbial host may be produced by a batch, fed-batch or continuous fermentation process.

A batch fermentation process is a closed system wherein the media composition is set at the beginning of the process and not subject to further additions beyond those required for maintenance of pH and oxygen level during the process. Thus, at the beginning of the culturing process the media is inoculated with the desired organism and growth or metabolic activity is permitted to occur without adding additional substrates (i.e., carbon and nitrogen sources) to the medium. In batch processes the metabolite and biomass compositions of the system change constantly up to the time the culture is terminated. In a typical batch process, cells moderate through a static lag phase to a high-growth log phase and finally to a stationary phase, wherein the growth rate is diminished or halted. Left untreated, cells in the stationary phase will eventually die. A variation of the standard batch process is the fed-batch process, wherein the substrate is continually added to the fermentor over the course of the fermentation process. A fed-batch process is also suitable in the present invention. Fed-batch processes are useful when catabolite repression is apt to inhibit the metabolism of the cells or where it is desirable to have limited amounts of substrate in the media at any one time. Measurement of the substrate concentration in fed-batch systems is difficult and therefore may be estimated on the basis of the changes of measurable factors such as pH, dissolved oxygen and the partial pressure of waste gases (e.g., $CO_2$). Batch and fed-batch culturing methods are common and well known in the art and examples may be found in Thomas D. Brock in *Biotechnology: A Textbook of Industrial Microbiology*, $2^{nd}$ ed., (1989) Sinauer Associates: Sunderland, Mass.; or Deshpande, Mukund V., *Appl. Biochem. Biotechnol.*, 36:227 (1992), herein incorporated by reference.

Commercial production of fatty acids using the instant genes may also be accomplished by a continuous fermentation process wherein a defined media is continuously added to a bioreactor while an equal amount of culture volume is removed simultaneously for product recovery. Continuous cultures generally maintain the cells in the log phase of growth at a constant cell density. Continuous or semi-continuous culture methods permit the modulation of one factor or any number of factors that affect cell growth or end product concentration. For example, one approach may limit the carbon source and allow all other parameters to moderate metabolism. In other systems, a number of factors affecting growth may be altered continuously while the cell concentration, measured by media turbidity, is kept constant. Continuous systems strive to maintain steady state growth and thus the cell growth rate must be balanced against cell loss due to media being drawn off the culture. Methods of modulating nutrients and growth factors for continuous culture processes, as well as techniques for maximizing the rate of product formation, are well known in the art of industrial microbiology and a variety of methods are detailed by Brock, supra.

Purification of Fatty Acids

Fatty acids, including PUFAs, may be found in the host microorganism as free fatty acids or in esterified forms such as acylglycerols, phospholipids, sulfolipids or glycolipids, and may be extracted from the host cell through a variety of means well-known in the art. One review of extraction techniques, quality analysis and acceptability standards for yeast lipids is that of Z. Jacobs (*Critical Reviews in Biotechnology* 12(5/6):463491 (1992)). A brief review of downstream processing is also available by A. Singh and O. Ward (*Adv. Appl. Microbiol.* 45:271-312 (1997)).

In general, means for the purification of fatty acids (including PUFAs) may include extraction with organic solvents, sonication, supercritical fluid extraction (e.g., using carbon dioxide), saponification and physical means such as presses, or combinations thereof. Of particular interest is extraction with methanol and chloroform in the presence of water (E. G. Bligh & W. J. Dyer, *Can. J. Biochem. Physiol.* 37:911-917 (1959)). Where desirable, the aqueous layer can be acidified to protonate negatively-charged moieties and thereby increase partitioning of desired products into the organic layer. After extraction, the organic solvents can be removed by evaporation under a stream of nitrogen. When isolated in conjugated forms, the products may be enzymatically or chemically cleaved to release the free fatty acid or a less complex conjugate of interest, and can then be subject to further manipulations to produce a desired end product. Desirably, conjugated forms of fatty acids are cleaved with potassium hydroxide.

If further purification is necessary, standard methods can be employed. Such methods may include extraction, treatment with urea, fractional crystallization, HPLC, fractional distillation, silica gel chromatography, high-speed centrifugation or distillation, or combinations of these techniques. Protection of reactive groups, such as the acid or alkenyl groups, may be done at any step through known techniques (e.g., alkylation, iodination). Methods used include methylation of the fatty acids to produce methyl esters. Similarly, protecting groups may be removed at any step. Desirably, purification of fractions containing GLA, STA, ARA, DHA and EPA may be accomplished by treatment with urea and/or fractional distillation.

Description of Preferred Embodiments

The ultimate goal of the work described herein is the development of an oleaginous yeast that accumulates TAGs enriched in ω-3 and/or ω-6 PUFAs. Toward this end, acyltransferases must be identified that function efficiently in oleaginous yeasts, to enable synthesis and high accumulation of preferred TAGs in storage lipid pools. Specifically, modification of the expression levels of these acyltransferases will enable increased transfer of fatty acids (and particularly, PUFAs) to TAGs. Thus, identification of efficient acyltransferases is necessary for the manipulation of the amount of ω-3/ω-6 PUFAs incorporated into the TAG fraction produced in host cells.

In the present invention, Applicants have isolated and cloned genes from *Yarrowia lipolytica* that encode DGAT1 and ARE2. This work was undertaken, following the surprising discovery that the *Y. lipolytica* DGAT2 and PDAT are only partially responsible for oil biosynthesis (based on analysis of a double knockout mutant; see co-pending U.S. patent application Ser. No. 10/882,760). Confirmation of the DGAT1 gene's activity was provided herein based upon lower oil content (total fatty acids as a % of dry cell weight) in *Yarrowia* strains wherein disruption of the native DGAT1 had occurred by targeted gene replacement through homologous recombination (Example 9). Additionally, over-expression of the DGAT1 and ARE2 genes of the invention are expected to increase oil content (total fatty acids as a % of dry cell weight), based on results obtained wherein the *Yarrowia* DGAT1 was overexpressed (Example 12).

Following identification of the *Y. lipolytica* DGAT1 (SEQ ID NOs:13 and 14), a proprietary database of *Mortierella alpina* cDNA sequences was searched to identify an orthologous gene(s). This lead to the identification of a bGAT1 homolog, whose full nucleotide sequence was thus determined (SEQ ID NO:17). Based on these two novel sequences, the Applicants were then able to identify a suite of unique fungal DGAT1 orthologs that are involved in the synthesis of TAGs. More specifically, these DGAT1s have been identified from *Neurospora crassa* (SEQ ID NO:19), *Gibberella zeae* PH-1 (SEQ ID NO:20), *Magnaporthe grisea* (SEQ ID NO:21) and *Aspergillus nidulans* (SEQ ID NO:22), based on comparison of the *Yarrowia* and *Mortierella* DNA sequences to the GenBank database using the BLAST algorithm, well known to those skilled in the art.

Analysis of these six DGAT1 sequences, when aligned with DGAT1 sequences from mouse (SEQ ID NO:169), soy (SEQ ID NO:170), *Arabidopsis* (SEQ ID NO:171), rice (SEQ ID NO:172), *Perilla* (SEQ ID NO:173) and wheat (SEQ ID NO:174), however, reveals unique characteristics that are specific for fungi and absent in DGAT1 s from the non-fungal organisms described above (i.e., fungal motifs #1-8, herein described as SEQ ID NOs:23-30). Furthermore, in a broader context, common motifs universally found in DGAT1 enzymes were also discovered (SEQ ID NOs:31-37). These unique fungal and universal conserved domains are between amino acids 97-105, 278-284, 334-341, 364-

374, 418-424, 415-424, 456-466 and 513-519, with respect to SEQ ID NO:14. As is well known to one of skill in the art, these motifs will therefore be diagnostic for DGAT1s and will permit rapid identification of novel DGAT1s. The motifs described herein are to be distinguished from the 'FxxPxYR' motif (SEQ ID NO:38) that was recently described by Lardizabal et al. (US 04/0107459 A1), which is preferably useful to identify DGAT2s of fungal origin.

The Applicants conclude that these DGAT1 and ARE2 acyltransferase genes are useful for expression in various microbial hosts, and particularly for over-expression in oleaginous yeasts (e.g., *Yarrowia lipolytica*). Additional benefits may result, since expression of the acyltransferases can also be put under the control of strong constitutive or regulated promoters that do not have the regulatory constraints of the native gene.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by: 1.) Sambrook, J., Fritsch, E. F. and Maniatis, T. *Molecular Cloning: A Laboratory Manual*; Cold Spring Harbor Laboratory: Cold Spring Harbor, N.Y. (1989) (Maniatis); 2.) T. J. Silhavy, M. L. Bennan, and L. W. Enquist, Experiments with Gene Fusions; Cold Spring Harbor Laboratory: Cold Spring Harbor, N.Y. (1984); and 3.) Ausubel, F. M. et al., Current Protocols in Molecular Biology, published by Greene Publishing Assoc. and Wiley-Interscience (1987).

Materials and methods suitable for the maintenance and growth of microbial cultures are well known in the art. Techniques suitable for use in the following Examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, Eds), American Society for Microbiology: Washington, D.C. (1994); or by Thomas D. Brock in *Biotechnology: A Textbook of Industrial Microbiology*, 2nd ed., Sinauer Associates: Sunderland, Mass. (1989). All reagents, restriction enzymes and materials used for the growth and maintenance of microbial cells were obtained from Aldrich Chemicals (Milwaukee, Wis.), DIFCO Laboratories (Detroit, Mich.), GIBCO/BRL (Gaithersburg, Md.) or Sigma Chemical Company (St. Louis, Mo.), unless otherwise specified.

*E. coli* TOP10 cells and *E. coli* Electromax DH10B cells were obtained from Invitrogen (Carlsbad, Calif.). Max Efficiency competent cells of *E. coli* DH5α were obtained from GIBCO/BRL (Gaithersburg, Md.). *E. coli* (XL1-Blue) competent cells were purchased from the Stratagene Company (San Diego, Calif.). *E. coli* strains were typically grown at 37° C. on Luria Bertani (LB) plates. General molecular cloning was performed according to standard methods (Sambrook et al., supra). Oligonucleotides were synthesized by Sigma-Genosys (Spring, Tex.).

All polymerase chain reactions (PCRs) were performed in a thermocyler using DNA polymerase in a buffer recommended by the manufacturer of the polymerase. Unless specified otherwise, amplification was carried out as follows: initial denaturation at 95° C. for 1 min, followed by 30 cycles of denaturation at 95° C. for 30 sec, annealing at 55° C. for 1 min, and elongation at 72° C. for 1 min. A final elongation cycle at 72° C. for 10 min was carried out, followed by reaction termination at 4° C. PCR products were cloned into Promega's pGEM-T-easy vector (Madison, Wis.), unless otherwise noted.

DNA sequence was generated on an ABI Automatic sequencer using dye terminator technology (U.S. Pat. No. 5,366,860; EP 272,007) using a combination of vector and insert-specific primers. Sequence editing was performed in Sequencher (Gene Codes Corporation, Ann Arbor, Mich.). All sequences represent coverage at least two times in both directions. Comparisons of genetic sequences were accomplished using DNASTAR software (DNASTAR, Inc., Madison, Wis.). The percent identities between these proteins were determined by the Megalign program of DNASTAR using Clustal W with the following parameters: gap penalty=10, gap length penalty=0.2, delay divergent seqs (%)=30, DNA transition weight=0.5 and protein weight matrix by Gonnet series.

The meaning of abbreviations is as follows: "sec" means second(s), "min" means minute(s), "h" means hour(s), "d" means day(s), "μl" means microliter(s), "mL" means milliliter(s), "L" means liter(s), "μM" means micromolar, "mM" means millimolar, "M" means molar, "mmol" means millimole(s), "μmole" mean micromole(s), "g" means gram(s), "μg" means microgram(s), "ng" means nanogram(s), "U" means unit(s), "bp" means base pair(s) and "kB" means kilobase(s).

Transformation and Cultivation of *Yarrowia lipolytica*

*Yarrowia lipolytica* strains ATCC #20362, #76982 and #90812 were purchased from the American Type Culture Collection (Rockville, Md.). *Y. lipolytica* strains were usually grown at 28° C. on YPD agar (1% yeast extract, 2% bactopeptone, 2% glucose, 2% agar).

Transformation of *Yarrowia lipolytica* was performed according to the method of Chen, D. C. et al. (*Appl. Microbiol Biotechnol*. 48(2):232-235 (1997)), unless otherwise noted. Briefly, *Yarrowia* was streaked onto a YPD plate and grown at 30° C. for approximately 18 hr. Several large loopfuls of cells were scraped from the plate and resuspended in 1 mL of transformation buffer containing: 2.25 mL of 50% PEG, average MW 3350; 0.125 mL of 2 M Li acetate, pH 6.0; 0.125 mL of 2 M DTT; and 50 μg sheared salmon sperm DNA. Then, approximately 500 ng of linearized plasmid DNA was incubated in 100 μl of resuspended cells, and maintained at 39° C. for 1 hr with vortex mixing at 15 min intervals. The cells were plated onto selection media plates and maintained at 30° C. for 2 to 3 days.

For selection of transformants, minimal medium ("MM") was generally used; the composition of MM is as follows: 0.17% yeast nitrogen base (DIFCO Laboratories, Detroit, Mich.) without ammonium sulfate or amino acids, 2% glucose, 0.1% proline, pH 6.1). Supplements of adenine, leucine, lysine and/or uracil were added as appropriate to a final concentration of 0.01% (thereby producing "MMA", "MMLe", "MMLy" and "MMU" selection media, each prepared with 20 g/L agar).

Alternatively, transformants were selected on 5-fluoro-orotic acid ("FOA"; also 5-fluorouracil-6-carboxylic acid monohydrate) selection media, comprising: 0.17% yeast nitrogen base (DIFCO Laboratories, Detroit, Mich.) without ammonium sulfate or amino acids, 2% glucose, 0.1% proline, 75 mg/L uracil, 75 mg/L uridine, 900 mg/L FOA (Zymo Research Corp., Orange, Calif.) and 20 g/L agar.

To promote oleaginous conditions, High Glucose Media ("HGM") was prepared as follows: 14 g/L $KH_2PO_4$, 4 g/L $K_2HPO_4$, 2 g/L $MgSO_4 \cdot 7H_2O$, 80 g/L glucose (pH 6.5).

Fatty Acid Analysis of *Yarrowia lipolytica*

For fatty acid analysis, cells were collected by centrifugation and lipids were extracted as described in Bligh, E. G. & Dyer, W. J. (*Can. J. Biochem. Physiol.* 37:911-917 (1959)). Fatty acid methyl esters were prepared by transesterification of the lipid extract with sodium methoxide (Roughan, G., and Nishida I. *Arch Biochem Biophys.* 276 (1):3846 (1990)) and subsequently analyzed with a Hewlett-Packard 6890 GC fitted with a 30-m×0.25 mm (i.d.) HP-INNOWAX (Hewlett-Packard) column. The oven temperature was from 170° C. (25 min hold) to 185° C. at 3.5° C./min.

For direct base transesterification, *Yarrowia* culture (3 mL) was harvested, washed once in distilled water, and dried under vacuum in a Speed-Vac for 5-10 min. Sodium methoxide (100 µl of 1%) was added to the sample, and then the sample was vortexed and rocked for 20 min. After adding 3 drops of 1 M NaCl and 400 µl hexane, the sample was vortexed and spun. The upper layer was removed and analyzed by GC as described above.

Example 1

Construction of Plasmids Suitable for Gene Expression in *Yarrowia lipolytica*

The present Example describes the construction of plasmids pY5, pY5-13, pY20 and pLV5.

Construction of Plasmid pY5

The plasmid pY5, a derivative of pINA532 (a gift from Dr. Claude Gaillardin, Insitut National Agronomics, Centre de biotechnologie Agro-Industrielle, laboratoire de Genetique Moleculaire et Cellularie INRA-CNRS, F-78850 Thiverval-Grignon, France), was constructed for expression of heterologous genes in Yarrowia lipolytica, as diagrammed in FIG. 3.

First, the partially-digested 3598 bp EcoRI fragment containing the ARS18 sequence and LEU2 gene of pINA532 was subcloned into the EcoRI site of pBluescript (Strategene, San Diego, Calif.) to generate pY2. The TEF promoter (Muller S. et al., *Yeast*, 14:1267-1283 (1998)) was amplified from *Y. lipolytica* genomic DNA by PCR using TEF5' (SEQ ID NO:39) and TEF3' (SEQ ID NO:40) as primers. PCR amplification was carried out in a 50 µl total volume containing: 100 ng *Yarrowia* genomic DNA, PCR buffer containing 10 mM KCl, 10 mM $(NH_4)_2SO_4$, 20 mM Tris-HCl (pH 8.75), 2 mM $MgSO_4$, 0.1% Triton X-100, 100 µg/mL BSA (final concentration), 200 µM each deoxyribonucleotide triphosphate, 10 pmole of each primer and 1 µl of PfuTurbo DNA polymerase (Stratagene). Amplification was carried out as follows: initial denaturation at 95° C. for 3 min, followed by 35 cycles of the following: 95° C. for 1 min, 56° C. for 30 sec, 72° C. for 1 min. A final extension cycle of 72° C. for 10 min was carried out, followed by reaction termination at 4° C. The 418 bp PCR product was ligated into pCR-Blunt to generate pIP-tef. The BamHI/EcoRV fragment of pIP-tef was subcloned into the BamHI/SmaI sites of pY2 to generate pY4.

The XPR2 transcriptional terminator was amplified by PCR using pINA532 as template and XPR5' (SEQ ID NO:41) and XPR3' (SEQ ID NO:42) as primers. The PCR amplification was carried out in a 50 µl total volume, using the components and conditions described above. The 179 bp PCR product was digested with SacII and then ligated into the SacII site of pY4 to generate pY5. Thus, pY5 (shown in FIG. 3) is useful as a *Yarrowia-E. coli* shuttle plasmid containing: a *Yarrowia* autonomous replication sequence (ARS18); a ColE1 plasmid origin of replication; an ampicillin-resistance gene ($Amp^R$) for selection in *E. coli*; a *Yarrowia* LEU2 gene (E.C. 1.1.1.85, encoding isopropylmalate isomerase) for selection in *Yarrowia*; the translation elongation promoter (TEF) for expression of heterologous genes in *Yarrowia*; and the extracellular protease gene terminator (XPR2) for transcriptional termination of heterologous gene expression in *Yarrowia*.

Construction of Plasmid pY5-13 pY5-13 was constructed as a derivative of pY5 to faciliate subcloning and heterologous gene expression in *Yarrowia lipolytica*. Specifically, pY5-13 was constructed by 6 rounds of site-directed mutagenesis using pY5 as template. Both SalI and ClaI sites were eliminated from pY5 by site-directed mutagenesis using oligonucleotides YL5 and YL6 (SEQ ID NOs:43 and 44) to generate pY5-5. A SalI site was introduced into pY5-5 between the LEU2 gene and the TEF promoter by site-directed mutagenesis using oligonucleotides YL9 and YL10 (SEQ ID NOs:45 and 46) to generate pY5-6. A PacI site was introduced into pY5-6 between the LEU2 gene and ARS18 using oligonucleotides YL7 and YL8 (SEQ ID NOs:47 and 48) to generate pY5-8. A NcoI site was introduced into pY5-8 around the translation start codon of the TEF promoter using oligonucleotides YL3 and YL4 (SEQ ID NOs:49 and 50) to generate pY5-9. The NcoI site inside the LEU2 gene of pY5-9 was eliminated using YL1 and YL2 oligonucleotides (SEQ ID NOs:51 and 52) to generate pY5-12. Finally, a BsiWI site was introduced into pY5-12 between the ColEI and XPR2 region using oligonucleotides YL61 and YL62 (SEQ ID NOs:53 and 54) to generate pY5-13.

Construction of Plasmids pY20 and pLV5

Plasmid pY20 (SEQ ID NO:55) is a derivative of pY5. It was constructed by inserting a Not I fragment containing a chimeric hygromycin resistance gene into the Not I site of pY5. Specifically, the *E. coli* hygromycin resistance gene (SEQ ID NO:56; "HPT"; Kaster, K. R. et al., *Nucleic Acids Res.* 11:6895-6911 (1983)) was PCR amplified for expression. The chimeric gene had the hygromycin resistance ORF under the control of the *Y. lipolytica* TEF promoter.

Plasmid pLV5 is a derivative of pY20. It was constructed by replacing the hygromycin resistant gene with the Yarrowia Ura3 gene. A 1.7 kB DNA fragment (SEQ ID NO:58) containing the *Yarrowia* Ura3 gene was PCR amplified using oligonucleotides KU5 and KU3 (SEQ ID NOs:60 and 61) as primers and *Yarrowia* genomic DNA as template.

Example 2

Cloning of a Partial *Yarrowia lipolytica* Acyl-CoA:Diacylglycerol Acyltransferase (DGAT2) Gene and Disruption of the Endogenous DGAT2 Gene The present Example describes the use of degenerate PCR primers to isolate a partial coding sequence of the *Yarrowia* lipolytica DGAT2 and the use of the partial sequence to disrupt the native gene in *Y. lipolytica*.

Cloning of a Partial Putative DGAT2 Sequence from *Yarrowia lipolytica* by PCR Using Degenerate PCR Primers and Chromosome Walking Genomic DNA was isolated from *Y. lipolytica* (ATCC #76982) using a DNeasy Tissue Kit (Qiagen, Catalog # 69504) and resuspended in kit buffer AE at a DNA concentration of 0.5 μg/μl. PCR amplifications were performed using the genomic DNA as template and several sets of degenerate primers designed to encode conserved amino acid sequences among different known DGAT2s (i.e., GenBank Accession Nos. NC_001147 *[Saccharomyces cerevisiae]* and AF3910890 and AF391090 *[Mortierella ramanniana]*). The best results were obtained with degenerate primers P7 and P8, as shown in the Table below.

TABLE 4

Degenerate Primers Used For
Amplification Of A Partial Putative DGAT2

| Primer Set | Description | Degenerate Nucleotide Sequence | Corresponding Amino Acid Sequence |
|---|---|---|---|
| P7 | (32) mers | 29-5'-AACTACATCTTCGGCTA YCAYCCNCAYGG-3' (SEQ ID NO:62) | NYIFGYHPHG (SEQ ID NO:63) |
| P8 | (48) mers | 29-5'-AGGGACTCGGAGGCGC CGCCNCANACDAT-3' (SEQ ID NO:64) | complementary to IVVGGASESL (SEQ ID NO:65) |

[Note: Abbreviations are standard for nucleotides and proteins. The nucleic acid degeneracy code used is as follows: Y = C/T; D = A/G/T; and N = A/C/G/T.]

The PCR was carried out in a RoboCycler Gradient 40 PCR machine (Stratagene) using the manufacturer's recommendations and Accuprime Taq polymerase (Invitrogen). Amplification was carried out as described in the General Methods.

The expected PCR product (ca. 264 bp) was detected by 4% NuSieve (FMC) agarose gel electrophoresis, isolated, purified, cloned into the TOPO® cloning vector (Invitrogen) and sequenced. The resultant sequence (contained within SEQ ID NO:1) had homology to known DGAT2s, based on BLAST program analysis (Basic Local Alignment Search Tool; Altschul, S. F. et al., *J. Mol. Biol.* 215:403-410 (1993)).

Using the 264 bp fragment as an initiation point, a 673 bp fragment was obtained by chromosome walking using the TOPO® Walker Kit (Invitrogen, Catalog #K8000-01). The chromosome walking was carried out in 6 steps, as described briefly below:

1.) Genomic DNA (5 μg) was digested with restriction enzymes Pst I or Sac I, leaving a 3' overhang;
2.) Digested DNA was treated with 0.1 U calf intestinal alkaline phosphatase to dephosphorylate DNA;
3.) Primer extension was performed, using the DGAT2 specific primer P80 (SEQ ID NO:66) and Taq polymerase;
4.) TOPO® Linker (1 μl) was added and the reaction was incubated at 37° C. for 5 min to ligate TOPO® Linker to the DNA;
5.) PCR was performed using the DGAT2 gene specific primer, P81 (SEQ ID NO:67) and LinkAmp primer 1 (SEQ ID NO:68); and
6.) The newly amplified fragment was sequenced with primer P81 and LinkAmp primer 1.

The sequence of the 673 bp fragment obtained by chromosome walking also showed homology to known DGAT2 sequences.

Targeted Disruption of the *Yarrowia lipolytica* DGAT2 Gene

Targeted disruption of the DGAT2 gene in *Y. lipolytica* ATCC #90812 and ATCC #76982 was carried out by homologous recombination-mediated replacement of the endogenous DGAT2 gene with a targeting cassette designated as plasmid pY21 DGAT2. pY21 DGAT2 was derived from plasmid pY20 (Example 1; SEQ ID NO:55). Specifically, pY21 DGAT2 was created by inserting a 570 bp Hind III/Eco RI fragment into similarly linearized pY20. The 570 bp DNA fragment contained (in 5' to 3' orientation): 3' homologous sequence from position +1090 to +1464 (of the coding sequence (ORF) in SEQ ID NO:1), a Bgl II restriction site and 5' homologous sequence from position +906 to +1089 (of the coding sequence (ORF) shown in SEQ ID NO:1). The fragment was prepared by PCR amplification of 3' and 5' sequences from the 673 bp DGAT2 PCR product obtained by chromosome walking using two pairs of PCR primers, P95 and P96 (SEQ ID NOs:69 and 70), and P97 and P98 (SEQ ID NOs:71 and 72), respectively.

pY21 DGAT2 was linearized by Bgl II restriction digestion and transformed into mid-log phase *Y. lipolytica* ATCC #90812 and ATCC #76982 cells, as described in the General Methods. The cells were plated onto YPD hygromycin selection plates and maintained at 30° C. for 2 to 3 days.

Four *Y. lipolytica* ATCC #76982 hygromycin-resistant colonies and fourteen *Y. lipolytica* ATCC #90812 hygromycin-resistant colonies were isolated and screened for targeted disruption by PCR. One set of PCR primers (P115 and P116 [SEQ ID NOs:73 and 74, respectively]) was designed to amplify a specific junction fragment following homologous recombination. Another pair of PCR primers (P115 and P112 [SEQ ID NO:75]) was designed to detect the native gene.

All (4 of 4) of the hygromycin-resistant colonies of ATCC #76982 strains were positive for the junction fragment and negative for the native fragment; and, 2 of the 14 hygromycin-resistant colonies of ATCC #90812 strains were positive for the junction fragment and negative for the native fragment. Thus, targeted integration was confirmed in these 6 strains. Disruption of the gene was further confirmed by GC analysis of total lipids of one of the disrupted strains, designated as "S-D2" (see Example 9).

Example 3

Cloning of a Partial *Yarrowia lipolytica* Phospholipid:Diacylglycerol Acyltransferase (PDAT) Gene and Disruption of the Endogenous PDAT Gene The present Example describes the use of degenerate PCR primers to isolate a partial coding sequence of *Y. lipolytica* PDAT and the use of the partial sequence to disrupt the native gene in *Y. lipolytica*.

Cloning of a Partial Putative PDAT Sequence From *Yarrowia lipolytica* by PCR Using Degenerate PCR Primers and Chromosome Walking Genomic DNA was isolated from *Y. lipolytica* (ATCC #76982) using a DNeasy Tissue Kit (Qiagen, Catalog #69504) and resuspended in kit buffer AE at a DNA concentration of 0.5 μg/μl. PCR amplifications were performed using genomic DNA as the template and several pairs of degenerate primers encoding conserved amino acid sequences in different known PDATs (GenBank Accession Nos. NP 190069 and AB006704 [(gi:2351069 *Arabidopsis thaliana*], and NP_596330 [*Schizosaccharomyces pombe*]; and the *Saccharomyces cerevisiae* Lro 1 gene [Dahlqvist et al., *Proc. Natl. Acad. Sci. USA* 97:6487 (2000)]). The best results were obtained with degenerate primers P26 and P27, as shown in the Table below.

TABLE 5

Degenerate Primers Used for Amplification Of A Partial Putative PDAT

| Primer Set | Description | Degenerate Nucleotide Sequence | Corresponding Amino Acid Sequence |
|---|---|---|---|
| P26 | (32) 29-mers | 5'-ATGCTGGACAAGGAG ACCGGNCTNGAYCC-3' (SEQ ID NO:76) | MLDKETGLDP (SEQ ID NO:77) |
| P27 | (16) 33-mers | 5'- CCAGATGACGTCGCCG CCCTTGGGNARCATNGA-3' (SEQ ID NO:78) | complementary to SMLPKGGEVIW (SEQ ID NO:79) |

[Note: Abbreviations are standard for nucleotides and proteins. The nucleic acid degeneracy code used is as follows: R = A/G; Y = C/T; and N = A/C/G/T.]

The PCR was carried out in a RoboCycler Gradient 40 PCR machine (Stratagene), using the amplification conditions described in the General Methods. The expected PCR product (ca. 600 bp) was detected by 4% NuSieve (FMC) agarose gel electrophoresis, isolated, purified, cloned into the TOPO® cloning vector (Invitrogen) and sequenced. The resultant sequence (contained within SEQ ID NO:7) had homology to known PDATs, based on BLAST program analysis (Altschul, S. F. et al., *J. Mol. Biol.* 215:403-410 (1993)).

Targeted Disruption of *Yarrowia lipolytica* PDAT Gene

Following the sequencing of this ca. 600 bp partial coding region for PDAT, a larger DNA fragment encoding this sequence was discovered in the public *Y. lipolytica* protein database of the "Yeast project *Genolevures*" (Center for Bioinformatics, LaBRI, Talence Cedex, France) (see also Dujon, B. et al., *Nature* 430 (6995):3544 (2004)). This allowed isolation of a 1008 bp genomic DNA fragment comprising a portion of the PDAT gene from *Y. lipolytica* ATCC #90812 using PCR primers P39 and P42 (SEQ ID NOs:80 and 81).

Targeted disruption of the PDAT gene in *Y. lipolytica* ATCC #90812 was carried out by homologous recombination-mediated replacement of the endogenous PDAT gene with a targeting cassette designated as pLV13 (SEQ ID NO:82). pLV13 was derived from plasmid pLV5 (Example 1). Specifically, pLV13 was created by inserting a 992 bp Bam HI/Eco RI fragment into similarly linearized pLV5. The 992 bp DNA fragment contained (in 5' to 3' orientation): 3' homologous sequence from position +877 to +1371 (of the coding sequence (ORF) in SEQ ID NO:7), a Bgl II restriction site and 5' homologous sequence from position +390 to +876 (of the coding sequence (ORF) in SEQ ID NO:7). The fragment was prepared by PCR amplification of 3' and 5' sequences from the 1008 bp PCR product described above, using PCR primers P39 and P41 (SEQ ID NOs:80 and 83) and P40 and P42 (SEQ ID NOs:84 and 81), respectively.

pLV13 was linearized by Bgl II restriction digestion and was transformed into mid-log phase *Y. lipolytica* ATCC #90812 cells by the lithium acetate method (General Methods). The cells were plated onto Bio101 DOB/CSM-Ura selection plates and maintained at 30° C. for 2 to 3 days.

Ten *Y. lipolytica* ATCC #90812 colonies were isolated and screened for targeted disruption by PCR. One set of PCR primers (P51 and P52 [SEQ ID NOs:85 and 86, respectively]) was designed to amplify the targeting cassette. Another set of PCR primers (P37 and P38 [SEQ ID NOs:87 and 88, respectively]) was designed to detect the native gene. Ten of the ten strains were positive for the junction fragment and 3 of the 10 strains were negative for the native fragment, thus confirming successful targeted integration in these 3 strains. Disruption of the gene was further confirmed by GC analysis of total lipids in one of the disrupted strains, designated as "S-P" (see Example 9).

Example 4

Construction of a *Yarrowia lipolytica* Double Knockout Strain Containing Disruptions in Both PDAT and DGAT2 Genes The present Example describes the creation of a double knockout strain that was disrupted in both PDAT and DGAT2 genes.

Specifically, the *Y. lipolytica* ATCC #90812 hygromycin-resistant "S-D2" mutant (containing the DGAT2 disruption from Example 2) was transformed with plasmid pLV13 (from Example 3) and transformants were screened by PCR, as described in Example 3. Two of twelve transformants were confirmed to be disrupted in both the DGAT2 and PDAT genes. Disruption of the gene was further confirmed by GC analysis of total lipids in one of the disrupted strains, designated as "S-D2-P" (see Example 9).

Example 5

Cloning of Full-Length *Yarrowia lipolytica* DGAT2 and PDAT Genes

The present Example describes the recovery of the genomic sequences flanking the disrupted DGAT2 and PDAT genes by plasmid rescue, using the sequence in the rescued plasmid to PCR the intact ORF of the native gene. The full-length genes and their deduced amino acid sequences are compared to other fungal DGAT2 and PDAT sequences, respectively.

Plasmid Rescue of *Yarrowia lipolytica* DGAT2 and PDAT Genes

Since the acyltransferase genes were disrupted by the insertion of the entire pY21 DGAT2 and pLV13 vectors that each contained an *E. coli* ampicillin-resistant gene and *E. coli* ori, it was possible to rescue the flanking PDAT and DGAT2 sequences in *E. coli*. For this, genomic DNA of *Y. lipolytica* strain "S-D2" (carrying the disrupted DGAT2 gene; Example 2) and *Y. lipolytica* strain "S-P" (carrying the disrupted PDAT gene; Example 3) was isolated using the DNeasy Tissue Kit. Specifically, 10 μg of the genomic DNA was digested with 50 U of the following restriction enzymes in a reaction volume of 200 μl: for DGAT2—Age I and Nhe I; for PDAT—Kpn I, Pac I and Sac I. Digested DNA was extracted with phenol:chloroform and resuspended in 40 μl deionized water. The digested DNA (10 μl) was self-ligated in a 200 μl ligation mixture containing 3 U T4 DNA ligase. Each ligation reaction was carried out at 16° C. for 12 hrs. The ligated DNA was extracted with phenol:chloroform and resuspended in 40 μl deionized water. Finally, 1 μl of the resuspended ligated DNA was used to transform *E. coli* by electroporation and plated on LB containing ampicillin (Ap). Ap-resistant transformants were isolated and analyzed for the presence of plasmids. The following insert sizes were found in the recovered or rescued plasmids (Tables 5 and 6):

TABLE 6

Insert Sizes Of Recovered DGAT2 Plasmids, According To Restriction Enzyme

| Enzyme | plasmid insert size (kB) |
|---|---|
| AgeI | 2.3 |
| NheI | 9.5 |

TABLE 7

Insert Sizes Of Recovered PDAT Plasmids, According To Restriction Enzyme

| Enzyme | plasmid insert size (kB) |
|---|---|
| Kpn I | 6.9 |
| Sac I | 5.4 |
| Sph I | 7.0 |

Sequencing of the DGAT2 rescued plasmids was initiated with sequencing primers P79 (SEQ ID NO:89) and P95 (SEQ ID NO:69). In contrast, sequencing of the PDAT plasmids was initiated with sequencing primers P84 (SEQ ID NO:90) and P85 (SEQ ID NO:91).

Based on the sequencing results, a full-length gene encoding the Y. lipolytica DGAT2 gene was assembled (2119 bp; SEQ ID NO:1). Specifically, the sequence encoded an open reading frame (ORF) of 1545 bases (nucleotides +291 to +1835 of SEQ ID NO:1), while the deduced amino acid sequence was 514 residues in length (SEQ ID NO:2). Since this ORF has an initiation codon ('ATG') at position 1, as well as at positions 56 and 160, it contains at least two additional nested (smaller) ORFs. Specifically, one ORF is 1380 bases long (nucleotides +456 to +1835 of SEQ ID NO:1, corresponding to SEQ ID NO:3), with a deduced amino acid sequence of 459 residues (SEQ ID NO:4); another ORF is 1068 bases long (nucleotides +768 to +1835 of SEQ ID NO:1, corresponding to SEQ ID NO:5) with a deduced amino acid sequence of 355 residues (SEQ ID NO:6).

The ORF encoded by SEQ ID NO:5 has a high degree of similarity to other known DGAT2 enzymes and because disruption in SEQ ID NO:5 eliminated DAG AT function of the native gene (see Example 9), the polypeptide of SEQ ID NO:6 has been identified as clearly having DGAT2 functionality.

Following sequencing and analysis of the DGAT2 protein described above, a Yarrowia lipolytica DGAT2 protein sequence was published within the public Y. lipolytica protein database of the "Yeast project Genolevures" (sponsored by the Center for Bioinformatics, LaBRI, bâtiment A30, UniversitéBordeaux 1, 351, cours de la Libération, 33405 Talence Cedex, France) (see also Dujon, B. et al., Nature 430 (6995):35-44 (2004)). Specifically, the sequence disclosed therein was identified as ORF YALI-CDS2240.1, encoding 514 amino acids, and the protein was reported to share some similarities with tr|Q08650 Saccharomyces cerevisiae YOR245C DGA1 acyl-CoA:diacylglycerol acyltransferase.

In a manner similar to that used to deduce the full-length sequence of DGAT2, a full-length gene encoding the Y. lipolytica PDAT gene was assembled (2326 bp; SEQ ID NO:7) based on sequencing results. Specifically, the sequence encoded an open reading frame of 1944 bases (nucleotides +274 to +2217 of SEQ ID NO:7), while the deduced amino acid sequence was 648 residues in length (SEQ ID NO:8).

Following sequencing and analysis of the PDAT protein described above, the Yarrowia lipolytica PDAT protein sequence was published as part of the public Y. lipolytica protein database of the "Yeast project Genolevures" (supra). The PDAT sequence disclosed therein was identified as ORF YALI-CDS1359.1, encoding 648 amino acids, and the protein was reported to share some similarities to sp|P40345 Saccharomyces cerevisiae YNR008w LRO1, a lecithin cholesterol acyltransferase-like gene which mediates diacylglycerol esterification.

Example 6

Identification of Additional Putative Yarrowia lipolytica DAG ATs

In order to identify additional DAG ATs in Yarrowia, the public Y. lipolytica protein database of the "Yeast project Genolevures" (supra) was searched using the Saccharomyces cerevisiae ARE1 (Sc AREL; GenBank Accession No. CAA42296) and ARE2 (Sc ARE2; GenBank Accession No. P53629) protein sequences (Yang, H. et al., Science. 272 (5266):1353-1356 (1996)). Both searches identified the following Y. lipolytica ORFs as the first and second hits, respectively:

(1) YALI-CDS2011.1: annotated as "similar to sp|P53629 Saccharomyces cerevisiae YNR019w ARE2 acyl-CoA sterol acyltransferase, hypothetical start"; 543 amino acids in length (SEQ ID NOs:9 and 10); and (2) YALI-CDS2141.1: annotated as "unnamed protein product; weakly similar to tr|Q9FUL6 Perilla frutescens Diacylglycerol acyltransferase (Pf DGAT1), hypothetical start"; 526 amino acids in length (SEQ ID NOs:11 and 12).

The percent identities between these proteins were determined by the Megalign program of DNASTAR using Clustal W according to the parameters described in the General Methods. The percent (%) identities are shown below, wherein the % identity is defined as percentage of amino acids that are identical between the two proteins:

TABLE 8

Percent Identities Between Known Acyltransferases And Yarrowia lipolytica ORFs

| | Sc ARE1 | Sc ARE2 | Pf DGAT1 |
|---|---|---|---|
| YALI-CDS2141.1 | 16.6 | 14.5 | 29.5 |
| YALI-CDS2011.1 | 32.6 | 33.8 | 18.4 |

Based on this comparison, YALI-CDS2141.1 and YALI-CDS2011.1 (designated herein as "Yl DGAT1" and "Yl ARE2", respectively) were candidates ORFs that were likely to encode proteins having DAG AT functionality in Yarrowia.

Following the analysis of the proteins described above, the Yarrowia lipolytica strain CLIB99 complete genome was published in GenBank as part of the Genolevures project. Thus, the ORF identified as YALI-CDS201 1.1 corresponds to GenBank Accession No. NC_006072, locus_tag= "YALI0F06578g" and the ORF identified as YALI- CDS2141.1 corresponds to GenBank Accession No. CR382130, locus_tag="YALI0D07986g".

Example 7

Cloning of a *Yarrowia lipolytica* Acyl-CoA:Diacylglycerol Acyltransferase (DGAT1) Gene and Disruption of the Endogenous DGAT1 Gene The present Example describes the use of degenerate PCR primers to isolate the full-length coding sequence of the *Yarrowia lipolytica* DGAT1 (encoded by ORF YALI-CDS201 1.1 (Example 6)) and the use of the sequence to disrupt the native gene in *Y. lipolytica*.

Cloning of a Putative DGAT1 Sequence from *Yarrowia lipolytica* by PCR Using Degenerate PCR Primers The full-length YI DGAT1 ORF was cloned by PCR using degenerate PCR primers P201 and P203 (SEQ ID NOs:92 and 93, respectively) and *Y. lipolytica* ATCC #76982 (from Example 2) genomic DNA as template. The degenerate primers were required, since the nucleotide sequence encoding YI DGAT1 was not known.

The PCR was carried out in a RoboCycler Gradient 40 PCR machine, using the components and thermocycler conditions described in the General Methods. The expected PCR product (ca. 1.6 kB) was detected by agarose gel electrophoresis, isolated, purified, cloned into the TOPO® cloning vector (Invitrogen), and partially sequenced to confirm its identity.

Targeted Disruption of the *Yarrowia lipolytica* DGAT1 Gene

Targeted disruption of the putative DGAT1 gene in *Y. lipolytica* ATCC #90812 was carried out by homologous recombination-mediated replacement of the endogenous DGAT1 gene with a targeting cassette (using the methodology described in Example 2). Specifically, the 1.6 kB isolated YI DGAT1 ORF (SEQ ID NO:13) was used as a PCR template molecule to construct a YI DGAT1 targeting cassette consisting of: 5' homologous YI DGAT1 sequence, the *Yarrowia* Leucine 2 (Leu2) gene, and 3' homologous YI DGAT1 sequence. For this, each portion of the targeting cassette was first individually amplified, using the primers set forth below:

Upper primer P214 and lower primer P215 (SEQ ID NOs:94 and 95, respectively), for amplification of the 5' homologous DGAT1 sequence;
Upper primer P216 and lower primer P217 (SEQ ID NOs:96 and 97, respectively), for amplification of the 3' homologous DGAT1 sequence; and,
Upper primer P218 and lower primer P219 (SEQ ID NOs:98 and 99, respectively), for amplification of the Leu2 gene (GenBank Accession No. AAA35244).

The PCRs were performed using Pfu Ultra polymerase (Stratagene, Catalog #600630), as described in the General Methods, and purified. The three correct-sized, purified fragments were mixed together as template molecules for a second PCR reaction using PCR primers P214 and P219 (SEQ ID NOs:94 and 99) to obtain the YI DGAT1 disruption cassette.

The targeting cassette was gel purified and used to transform mid-log phase wildtype *Y. lipolytica* (ATCC #90812). Transformation was performed as described in the General Methods.

Transformants were plated onto Bio1101 DOB/CSM-Leu selection plates and maintained at 30° C. for 2 to 3 days. Several leucine prototrophs were screened by PCR to confirm the targeted DGAT1 disruption. Specifically, one set of PCR primers (P226 and P227 [SEQ ID NOs:100 and 101, respectively]) was designed to amplify a junction between the disruption cassette and native target gene. Another set of PCR primers (P214 and P217 [SEQ ID NOs:94 and 97, respectively]) was designed to detect the native gene.

All of the leucine prototroph colonies were positive for the junction fragment and negative for the native fragment. Thus, targeted integration was confirmed in these strains. Disruption of the gene was further confirmed by GC analysis of total lipids of one of the disrupted strains, designated as "S-D1" (see Example 9).

In a similar manner, the DGAT1 targeting cassette was used to disrupt the DGAT1 gene in strains containing single disruptions in either PDAT ("S-P" from Example 3), DGAT2 ("S-D2" from Example 2), or double disruptions in PDAT and DGAT2 ("S-D2-P" from Example 4). This resulted in the creation of strains with double knockouts in DGAT1 and PDAT ("S-D1-P"), in DGAT2 and DGAT1 ("S-D2-D1") and triple knockouts in DGAT2, DGAT1 and PDAT ("S-D2-D1-P").

Example 8

Cloning of *Yarrowia lipolytica* Acyl-CoA:Sterol-Acyltransferase (ARE2) Gene and Disruption of the Endogenous ARE2 Gene The present Example describes the use of degenerate PCR primers to isolate the full-length coding sequence of the *Yarrowia lipolytica* ARE2 (encoded by ORF YALI-CDS2141.1 (Example 6)) and the use of the sequence to disrupt the native gene in *Y. lipolytica*.

Cloning of a Putative ARE2 Sequence from *Yarrowia lipolytica* by PCR Using Degenerate PCR Primers The full length YI ARE2 ORF was cloned by PCR using degenerate PCR primers P205 and P208 (SEQ ID NOs:102 and 103, respectively) and *Y. lipolytica* ATCC #76982 (from Example 2) genomic DNA as template. The degenerate primers were required, since the nucleotide sequence encoding YI ARE2 was not known. The PCR was performed using the protocol described in Example 7. A PCR product of the expected size was detected.

Targeted Disruption of the *Yarrowia lipolytica* ARE2 Gene (Prophetic)

Targeted disruption of the ARE2 gene in *Y. lipolytica* ATCC #90812 will be carried out by homologous recombination-mediated replacement of the endogenous ARE2 gene with a targeting cassette (as described in Example 7). Specifically, the ~1.6 kB isolated ORF encoding the putative YI ARE2 protein (SEQ ID NO:15) will be used as a PCR template molecule to construct a YI ARE2 targeting cassette consisting of: 5' homologous YI ARE2 sequence, the *Yarrowia* Leucine 2 (Leu2) gene, and 3' homologous YI ARE2 sequence. For this, each portion of the targeting cassette will be first individually amplified, as described in Example 7, using the primers set forth below:

Upper primer P220 and lower primer P221 (SEQ ID NOs:104 and 105, respectively), for amplification of the 5' homologous ARE2 sequence;
Upper primer P222 and lower primer P223 (SEQ ID NOs:106 and 107, respectively), for amplification of the 3' homologous ARE2 sequence; and,
Upper primer P224 and lower primer P225 (SEQ ID NOs:108 and 109, respectively), for amplification of the Leu2 gene.

Following purification, each of the correct-sized fragments will be mixed and utilized as template molecules in a PCR reaction using primers P220 and P223 to obtain the targeting cassette. Following gel purification of the product, the targeting cassette will be used to transform mid-log phase wildtype and mutant *Y. lipolytica* (ATCC #90812) strains containing single disruptions in PDAT ("S-P" from Example 3), DGAT2 ("S-D2" from Example 2), DGAT1 ("S-D1" from Example 7), double disruptions in PDAT and DGAT2 ("S-D2-P" from Example 4), double disruptions in PDAT and DGAT1 ("S-D1-P" from Example 7), double disruptions in DGAT1 and DGAT2 ("S-D1-D2" from Example 7) or triple disruptions in PDAT, DGAT2 and DGAT1 ("S-D1-D2-P" from Example 7). Transformation will be performed as described in the General Methods.

Transformants will be plated onto Bio101 DOB/CSM-Leu selection plates and maintained at 30° C. for 2 to 3 days. Several leucine prototrophs will be screened by PCR to confirm the targeted ARE2 disruption, using the methodology described in Example 7.

Example 9

Determination of TAG Content in Mutant and Wildtype *Yarrowia lipolytica* Strains (ATCC #90812)

The present Example describes a comparison of TAG content in wildtype and mutant *Y. lipolytica* ATCC #90812 containing: (1) single disruptions in PDAT, DGAT2 and DGAT1; (2) double disruptions in PDAT and DGAT2, DGAT1 and PDAT, and DGAT1 and DGAT2; and (3) triple disruptions in PDAT, DGAT2 and DGAT1.

Specifically, single colonies of wildtype and mutant *Y. lipolytica* containing single disruptions in PDAT ("S-P", from Example 3), DGAT2 ("S-D2", from Example 2), DGAT1 ("S-D1", from Example 7), double disruptions in PDAT and DGAT2 ("S-D2-P", from Example 4), DGAT1 and PDAT ("S-D1-P", from Example 7), DGAT1 and DGAT2 ("S-D1-D2", from Example 7), and triple disruptions ("S-D1-D2-P", from Example 7) were separately grown using conditions that induce oleaginy. One loopful of cells from each culture was each individually inoculated into 3 mL YPD medium and grown overnight on a shaker (300 rpm) at 30° C. The cells were harvested and washed once in 0.9% NaCl and resuspended in 50 mL of HGM. Cells were then grown on a shaker for 48 hrs. Cells were washed in water and the cell pellet was lyophilized. Twenty (20) mg of dry cell weight was used for total fatty acid by GC analysis and the oil fraction following TLC (infra) and GC analysis.

Thin Layer Chromatography (TLC)

The methodology used for TLC is described below in the following five steps: (1) The internal standard of 15:0 fatty acid (10 μl of 10 mg/mL) was added to 2 to 3 mg dry cell mass, followed by extraction of the total lipid using a methanol/chloroform method. (2) Extracted lipid (50 μl) was blotted across a light pencil line drawn approximately 1 inch from the bottom of a 5×20 cm silica gel 60 plate, using 25-50 μl micropipettes. (3) The TLC plate was then dried under $N_2$ and was inserted into a tank containing about ~100 mL 80:20:1 hexane:ethyl ether:acetic acid solvent. (4) After separation of bands, a vapor of iodine was blown over one side of the plate to identify the bands. This permitted samples on the other side of the plate to be scraped using a razor blade for further analysis. (5) Basic transesterification of the scraped samples and GC analysis was performed, as described in the General Methods.

Results from GC Analysis

GC results are shown below in Table 9. Cultures are described as the "S" strain (wildtype), "S-P" (PDAT knockout), "S-D1" (DGAT1 knockout), "S-D2" (DGAT2 knockout), "S-D1-D2" (DGAT1 and DGAT2 knockout), "S-P-D1" (PDAT and DGAT1 knockout), "S-P-D2" (PDAT and DGAT2 knockout) and "S-P-D1-D2" (PDAT, DGAT1 and DGAT2 knockout). Abbreviations utilized are: "WT"=wildtype; "FAs"=fatty acids; "dcw"=dry cell weight; and, "FAs % dcw, % WT"=FAs % dcw relative to the % in wildtype, wherein the "S" strain is wildtype.

TABLE 9

Lipid Content In *Yarrowia* ATCC #90812 Strains With Single, Double Or Triple Disruptions In PDAT, DGAT2 And DGAT1

| Strain | Residual DAG AT | dcw, mg | Total Fatty Acids | | | TAG Fraction | | |
|---|---|---|---|---|---|---|---|---|
| | | | FAs, μg | FAs % dcw | FAs % dcw, % WT | FAs, μg | FAs % dcw | FAs % dcw, % WT |
| S | D1, D2, P | 32.0 | 797 | 15.9 | 100 | 697 | 13.9 | 100 |
| S-D1 | D2, P | 78.8 | 723 | 13.6 | 86 | 617 | 11.6 | 83 |
| S-D2 | D1, P | 37.5 | 329 | 6.4 | 40 | 227 | 4.4 | 32 |
| S-P | D1, D2 | 28.8 | 318 | 6.0 | 38 | 212 | 4.0 | 29 |
| S-D1-D2 | P | 64.6 | 219 | 4.1 | 26 | 113 | 2.1 | 15 |
| S-D1-P | D2 | 76.2 | 778 | 13.4 | 84 | 662 | 11.4 | 82 |
| S-D2-P | D1 | 31.2 | 228 | 4.3 | 27 | 122 | 2.3 | 17 |
| S-D1-D2-P | None | 52.2 | 139 | 2.4 | 15 | 25 | 0.4 | 3 |

The results in Table 9 provide evidence that DGAT1 is a DAG AT, since its disruption resulted in lower oil content compared to the wild type strain. The results shown above also indicate the relative contribution of the three DAG ATs to oil biosynthesis. DGAT2 contributes the most, while PDAT and DGAT1 contribute equally but less than DGAT2. The residual oil content ca. 3% in the triple knockout strain may be the contribution of the Yl ARE2 (see Example 8).

Example 10

Generation of EPA-Producing *Yarrowia lipolytica* ATCC #20362 Strain MU and Strain Y2067U The present Example describes the construction of strain MU and strain Y2067U, each derived from *Yarrowia lipolytica* ATCC #20362, wherein each strain was capable of producing significant concentrations of EPA relative to the total lipids (FIG. 5). The affect of various acyltransferase knockouts and acyltransferase gene overexpression was examined in these EPA producing strains based on analysis of TAG content and/or fatty acid composition, as described in Examples 11, 12 and 15 (infra).

The development of strain MU herein required the construction of strain M4 (producing 8% DGLA), strain Y2034 (producing 10% ARA), strain E (producing 10% EPA), strain EU (producing 10% EPA) and strain M26 (producing 14%). The development of strain Y2067U first required the creation of a derivative of strain EU, designated as strain Y2067 (producing 15% EPA).

Construction of Strain M4 Producing 8% DGLA

Figure 6A:
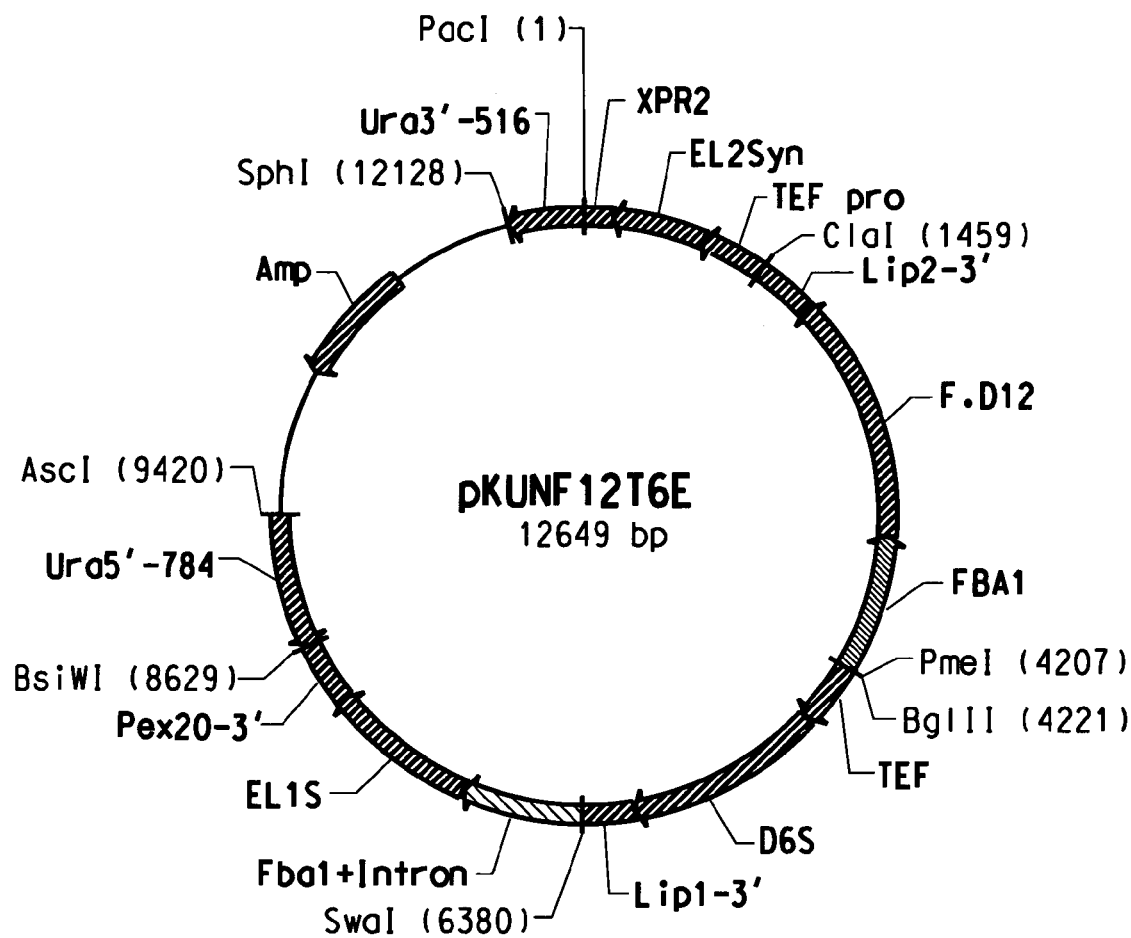

Construct pKUNF12T6E (FIG. 6A; SEQ ID NO:110) was generated to integrate four chimeric genes (comprising a Δ12 desaturase, a Δ6 desaturase and 2 elongases) into the Ura3 loci of wild type Yarrowia strain ATCC #20362, to thereby enable production of DGLA. The pKUNF12T6E plasmid contained the following components:

TABLE 10

Description of Plasmid pKUNF12T6E (SEQ ID NO: 110)

| RE Sites And Nucleotides Within SEQ ID NO: 110 | Description Of Fragment And Chimeric Gene Components |
|---|---|
| AscI/BsiWI (9420-8629) | 784 bp 5' part of Yarrowia Ura3 gene (GenBank Accession No. AJ306421) |
| SphI/PacI (12128-1) | 516 bp 3' part of Yarrowia Ura3 gene (GenBank Accession No. AJ306421) |
| SwaI/BsiWI (6380-8629) | FBAIN::EL1S:Pex20, comprising: FBAIN: FBAIN promoter (SEQ ID NO: 111; see also U.S. Patent Application No. 60/519971) EL1S: codon-optimized elongase 1 gene (SEQ ID NO: 112), derived from Mortierella alpina (GenBank Accession No. AX464731) Pex20: Pex20 terminator sequence from Yarrowia Pex20 gene (GenBank Accession No. AF054613) |
| BglII/SwaI (4221-6380) | TEF::Δ6S::Lip1, comprising: TEF: TEF promoter (GenBank Accession No. AF054508) Δ6S: codon-optimized Δ6 desaturase gene (SEQ ID NO: 114), derived from Mortierella alpina (GenBank Accession No. AF465281) Lip1: Lip1 terminator sequence from Yarrowia Lip1 gene (GenBank Accession No. Z50020) |
| PmeI/ClaI (4207-1459) | FBA::F.Δ12::Lip2, comprising: FBA: FBA promoter (SEQ ID NO: 116; see also U.S. Patent Application No. 60/519971) F.Δ12: Fusarium moniliforme Δ12 desaturase gene (SEQ ID NO: 117) Lip2: Lip2 terminator sequence from Yarrowia Lip2 gene (GenBank Accession No. AJ012632) |
| ClaI/PacI (1459-1) | TEF::EL2S::XPR, comprising: TEF: TEF promoter (GenBank Accession No. AF054508) EL2S: codon-optimized elongase gene (SEQ ID NO: 119), derived from Thraustochytrium aureum (U.S. Pat. No. 6,677,145) XPR: XPR terminator sequence of Yarrowia Xpr gene (GenBank Accession No. M17741) |

The pKUNF12T6E plasmid was digested with AscI/SphI, and then used for transformation of wild type Y. lipolytica ATCC #20362 according to the General Methods. The transformant cells were plated onto FOA selection media plates and maintained at 30° C. for 2 to 3 days. The FOA resistant colonies were picked and streaked onto MM and MMU selection plates. The colonies that could grow on MMU plates but not on MM plates were selected as Ura- strains. Single colonies of Ura-strains were then inoculated into liquid MMU at 30° C. and shaken at 250 rpm/min for 2 days.

The cells were collected by centrifugation, lipids were extracted, and fatty acid methyl esters were prepared by trans-esterification, and subsequently analyzed with a Hewlett-Packard 6890 GC.

GC analyses showed the presence of DGLA in the transformants containing the 4 chimeric genes of pKUNF12T6E (FIG. 6A), but not in the wild type Yarrowia control strain. Most of the selected 32 Ura- strains produced about 6% DGLA of total lipids. There were 2 strains (i.e., strains M4 and 13-8) that produced about 8% DGLA of total lipids.

Construction of Strain Y2034 Producing About 10% ARA

Figure 6B:
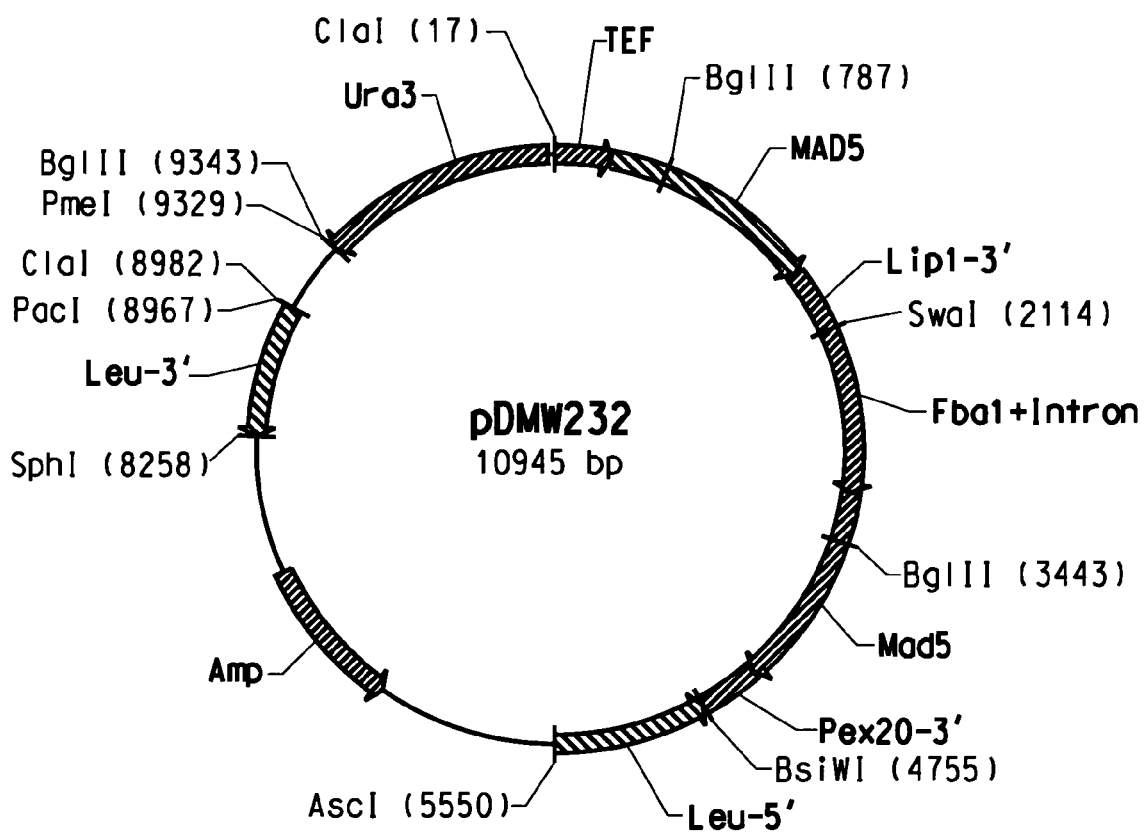

Constructs pDMW232 (FIG. 6B; SEQ ID NO:121) was generated to integrate two Δ5 chimeric genes into the Leu2 gene of Yarrowia strain M4. The plasmid pDMW232 contained the following components:

TABLE 11

Description of Plasmid pDMW232 (SEQ ID NO: 121)

| RE Sites And Nucleotides Within SEQ ID NO: 121 | Description Of Fragment And Chimeric Gene Components |
|---|---|
| AscI/BsiWI (5550-4755) | 788 bp 5' part of Yarrowia Leu2 gene (GenBank Accession No. AF260230) |
| SphI/PacI (8258-8967) | 703 bp 3' part of Yarrowia Leu2 gene (GenBank Accession No. AF260230) |
| SwaI/BsiWI (2114-4755) | FBAIN::MAΔ5::Pex20, comprising: FBAIN: FBAIN Promoter (SEQ ID NO: 111; see also U.S. Patent Application No. 60/519971) MAΔ5: Mortierella alpina Δ5 desaturase gene (SEQ ID NO: 122) (GenBank Accession No. AF067654) Pex20: Pex20 terminator sequence of Yarrowia Pex20 gene (GenBank Accession No. AF054613) |
| SwaI/ClaI (2114-17) | TEF::MAΔ5::Lip1, comprising: TEF: TEF promoter (GenBank Accession No. AF054508) MAΔ5: as described for FBAIN::MAΔ5::Pex20 (supra) Lip1: Lip1 terminator sequence of Yarrowia Lip1 gene (GenBank Accession No. Z50020) |
| PmeI/ClaI (5550-4755) | Yarrowia Ura3 gene (GenBank Accession No. AJ306421) |

Plasmid pDMW232 was digested with AscI/SphI, and then used to transform strain M4 according to the General Methods. Following transformation, the cells were plated onto MMLe plates and maintained at 30° C. for 2 to 3 days. The individual colonies grown on MMLe plates from each transformation were picked and streaked onto MM and MMLe plates. Those colonies that could grow on MMLe plates but not on MM plates were selected as Leu2- strains. Single colonies of Leu2- strains were then inoculated into liquid MMLe media at 30° C. and shaken at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed the presence of ARA in pDMW232 transformants, but not in the parental M4 strain. Specifically, among the 48 selected Leu2- transformants with pDMW232, there were 34 strains that produced less than 5% ARA, 11 strains that produced 6-8% ARA, and 3 strains that produced about 10% ARA of total lipids in the engineered Yarrowia. One of the strains that produced 10% ARA was named "Y2034".

Construction of Strain E, Producing About 10% EPA

Figure 6C:
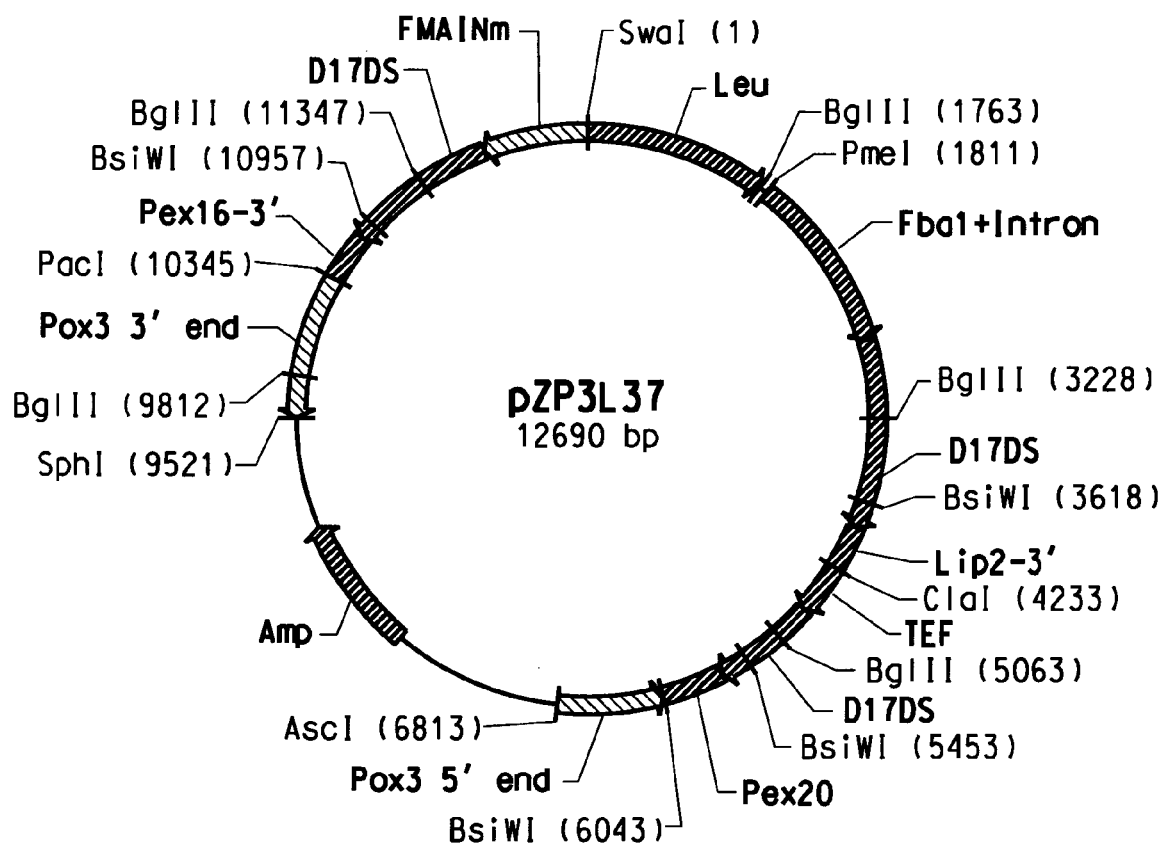

Construct pZP3L37 (FIG. 6C; SEQ ID NO:124) was created to integrate three synthetic Δ17 desaturase chimeric genes into the acyl-CoA oxidase 3 (i.e., POX3) gene of the Y2034 strain. The plasmid pZP3L37 contained the following components:

TABLE 12

Description of Plasmid pZP3L37 (SEQ ID NO: 124)

| RE Sites And Nucleotides Within SEQ ID NO: 124 | Description Of Fragment And Chimeric Gene Components |
|---|---|
| AscI/BsiWI (6813-6043) | 763 bp 5' part of *Yarrowia* Pox3 gene (GenBank Accession No. AJ001301) |
| SphI/PacI (9521-10345) | 818 bp 3' part of *Yarrowia* Pox3 gene (GenBank Accession No. AJ001301) |
| ClaI/BsiWI (4233-6043) | TEF::Δ17S::Pex20, comprising: TEF: TEF promoter (GenBank Accession No. AF054508) Δ17S: codon-optimized Δ17 desaturase gene (SEQ ID NO: 125), derived from *S. diclina* (US 2003/0196217 A1) Pex20: Pex20 terminator sequence of *Yarrowia* Pex20 gene (GenBank Accession No. AF054613) |
| ClaI/PmeI (4233-1811) | FBAIN::Δ17S::Lip2, comprising: FBAIN: FBAIN promoter (SEQ ID NO: 111; see also U.S. Patent Application No. 60/519971) Δ17S: SEQ ID NO: 125 (supra) Lip2: Lip2 terminator sequence of *Yarrowia* Lip2 gene (GenBank Accession No. AJ012632) |
| PmeI/SwaI (1811-1) | *Yarrowia* Leu2 gene (GenBank Accession No. AF260230) |
| PacI/SwaI (10345-1) | FBAINm::Δ17S::Pex16, comprising: FBAINm: FBAINm promoter (SEQ ID NO: 127; see also U.S. Patent Application No. 60/519971) Δ17S: SEQ ID NO: 125 (supra) Pex16: Pex16 terminator sequence of *Yarrowia* Pex16 gene (GenBank Accession No. U75433) |

Plasmid pZP3L37 was digested with AscI/SphI, and then used to transform strain Y2034 according to the General Methods. Following transformation, the cells were plated onto MM plates and maintained at 30° C. for 2 to 3 days. A total of 48 transformants grown on the MM plates were picked and re-streaked onto fresh MM plates. Once grown, these strains were individually inoculated into liquid MM at 30° C. and shaken at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed the presence of EPA in most of the transformants with pZP3L37, but not in the parental strain (i.e., Y2034). Among the 48 selected transformants with pZP3L37, there were 18 strains that produced less than 2% EPA, 14 strains that produced 2-3% EPA, and 1 strain that produced about 7% EPA of total lipids in the engineered *Yarrowia*.

The strain that produced 7% EPA was further analyzed after culturing the strain as follows ("two-stage growth conditions"). First, cells were grown in triplicate in liquid MM at 30° C. with shaking at 250 rpm/min for 48 hrs. The cells were collected by centrifugation and the liquid supernatant was extracted. The pelleted cells were resuspended in HGM and grown for 72 hrs at 30° C. with shaking at 250 rpm/min. The cells were again collected by centrifugation and the liquid supernatant was extracted.

GC analyses showed that the engineered strain produced about 10% EPA of total lipids after the two-stage growth. The strain was designated as the "E" strain.

Construction of Strain EU Producing About 10% EPA

Strain EU (Ura⁻) was created by identifying mutant cells of strain E that were 5-FOA resistant. Specifically, one loop of *Yarrowia* E strain cells were inoculated into 3 mL YPD medium and grown at 30° C. with shaking at 250 rpm for 24 hrs. The culture with diluted with YPD to an $OD_{600}$ of 0.4 and then incubated for an additional 4 hrs. The culture was plated (100 μl/plate) onto FOA selection plates and maintained at 30° C. for 2 to 3 days. A total of 16 FOA resistant colonies were picked and streaked onto MM and FOA selection plates. From these, 10 colonies grew on FOA selection plates but not on MM plates and were selected as potential Ura⁻ strains.

Figure 6D:
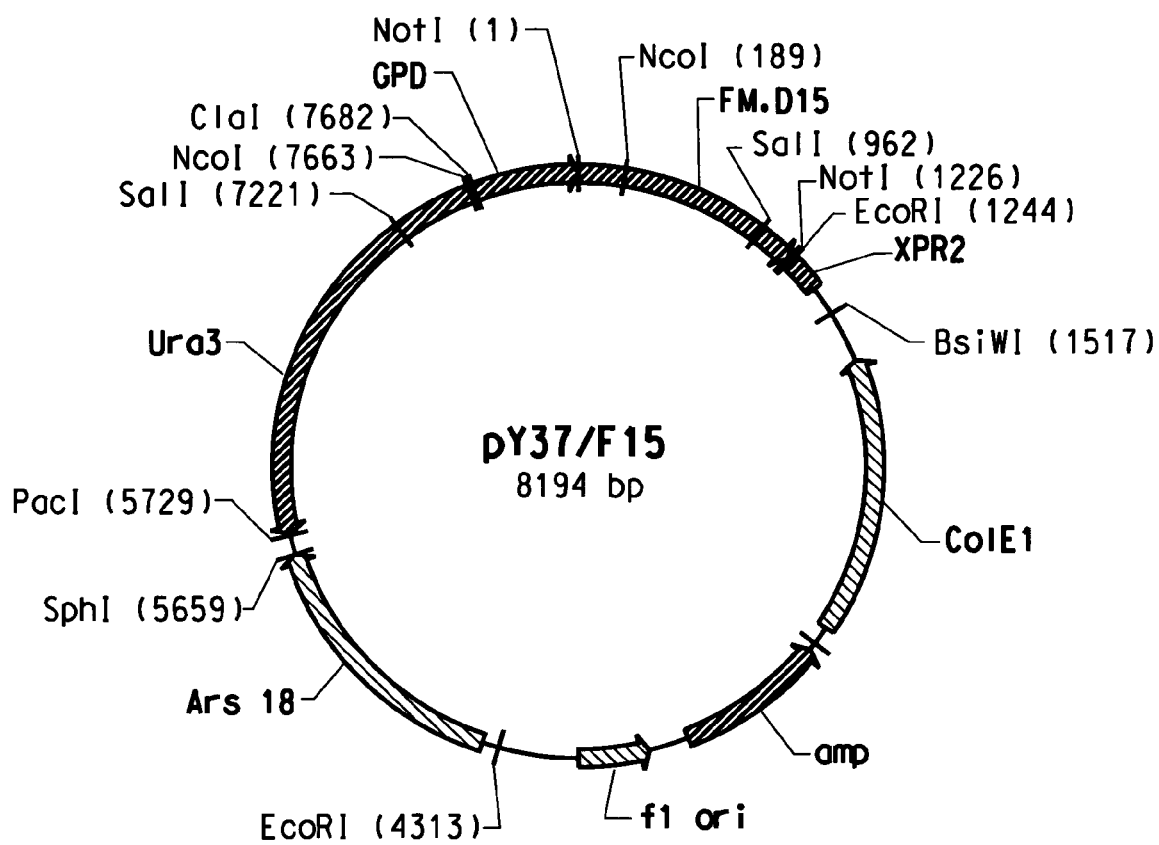
Figure 6E:
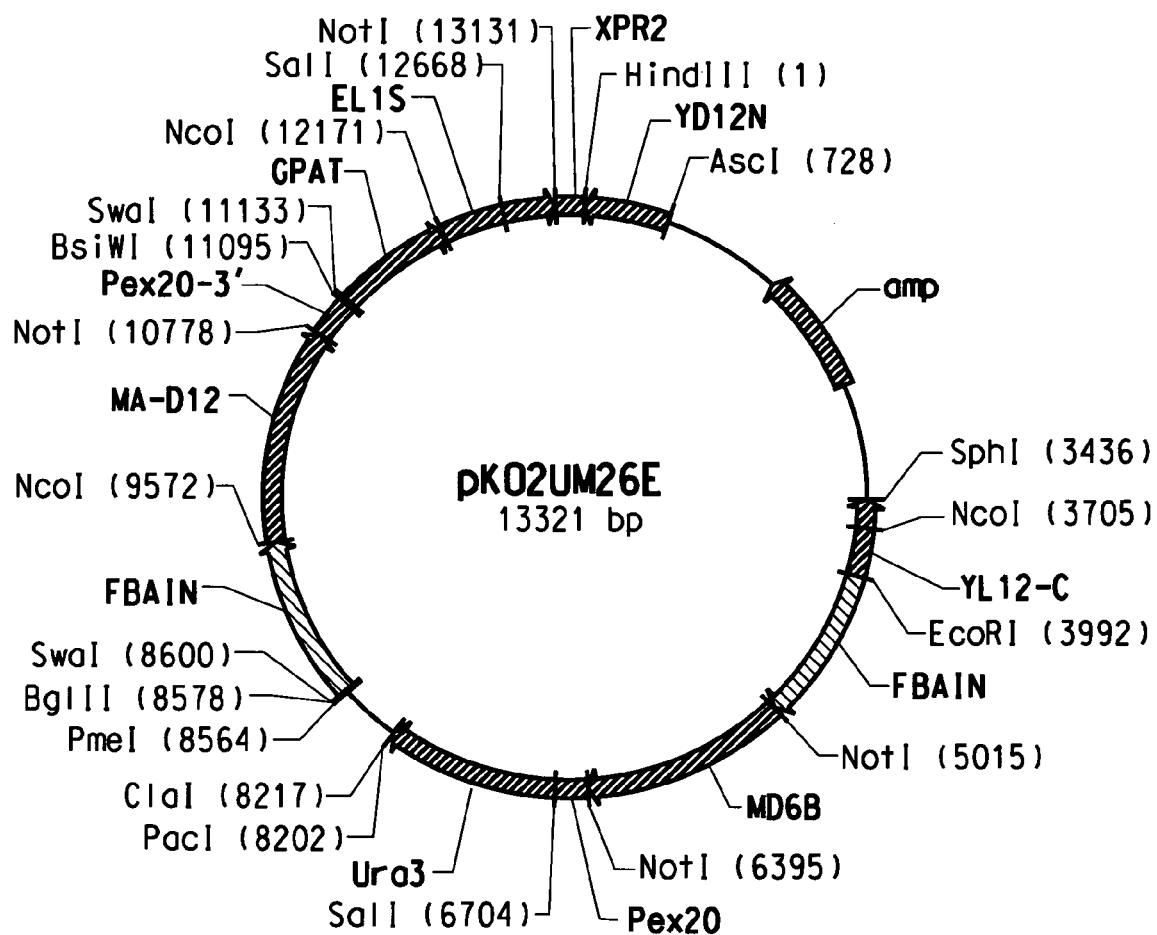

One of these strains was used as host for transformation with pY37/F15, comprising a chimeric GPD::*Fusarium moniliforme* Δ15::XPR2 gene and a Ura3 gene as a selection marker (FIG. 6D; SEQ ID NO:128). After three days of selection on MM plates, hundreds of colonies had grown on the plates and there was no colony growth of the transformation control that carried no plasmid. This 5-FOA resistant strain was designated as strain "EU".

Single colonies of the EU strain were then inoculated into liquid MMU additionally containing 0.1 g/L uridine and cultured for 2 days at 30° C. with shaking at 250 rpm/min. The cells were collected by centrifugation, lipids were extracted, and fatty acid methyl esters were prepared by trans-esterification and subsequently analyzed with a Hewlett-Packard 6890 GC. GC analyses showed that the EU strain produced about 10% EPA of total lipids.

Construction of Strain M26, Producing 14% EPA

Construct pZKO2UM26E (FIG. 6E, SEQ ID NO:129) was used to integrate a cluster of three chimeric genes (comprising an elongase, a Δ6 desaturase and a Δ12 desaturase) and a Ura3 gene into the *Yarrowia* Δ12 desaturase gene site of strain EU. Plasmid pKO2UM26E contained the following components:

TABLE 13

Description of Plasmid pKO2UM26E (SEQ ID NO: 129)

| RE Sites And Nucleotides Within SEQ ID NO: 129 | Description Of Fragment And Chimeric Gene Components |
|---|---|
| HindIII/AscI (1-728) | 728 bp 5' part of *Yarrowia* Δ12 desaturase gene (SEQ ID NO: 130) |
| SphI/EcoRI 3436-3992) | 556 bp 3' part of *Yarrowia* Δ12 desaturase gene (SEQ ID NO: 130) |
| BsiWI/HindIII (11095-1) | GPAT::EL1S::XPR, comprising: GPAT: GPAT promoter (SEQ ID NO: 132; see also U.S. Patent Application No. 60/610060) EL1S: codon-optimized elongase 1 gene (SEQ ID NO: 112), derived from *Mortierella alpina* (GenBank Accession No. AX464731) XPR: terminator sequence of *Yarrowia* Xpr2 gene (GenBank Accession No. M17741) |
| BglII/BsiWI (8578-11095) | FBAIN::M.Δ12.Pex20, comprising: FBAIN: FBAIN promoter (SEQ ID NO: 111; see also U.S. Patent Application No. 60/519971) M.Δ12: *Mortieralla isabellina* Δ12 desaturase gene (GenBank Accession No. AF417245; SEQ ID NO: 133) Pex20: Pex20 terminator sequence of *Yarrowia* Pex20 gene (GenBank Accession No. AF054613) |

TABLE 13-continued

Description of Plasmid pKO2UM26E (SEQ ID NO: 129)

| RE Sites And Nucleotides Within SEQ ID NO: 129 | Description Of Fragment And Chimeric Gene Components |
|---|---|
| SalI/PacI (6704-8202) | Yarrowia Ura3 gene (GenBank Accession No. AJ306421) |
| EcoRI/SalI (3992-6704) | FBAIN::M.Δ6B::Pex20, comprising: FBAIN: FBAIN promoter (SEQ ID NO: 111; see also U.S. Patent Application No. 60/519971) M.Δ6B: *Mortieralla alpina* Δ6 desaturase gene "B" (GenBank Accession No. AB070555; SEQ ID NO: 135) Pex20: Pex20 terminator sequence of *Yarrowia* Pex20 gene (GenBank Accession No. AF054613) |

The plasmid pKO2UM26E was digested with SphI/AscI, and then used to transform EU strain according to the General Methods. Following transformation, cells were plated onto MM plates and maintained at 30° C. for 2 to 3 days.

A total of 48 transformants grown on MM plates were picked and re-streaked onto fresh MM plates. Once grown, these strains were individually inoculated into liquid MM at 30° C. and grown with shaking at 250 rpm/min for 1 day. The cells were collected by centrifugation, lipids were extracted, and fatty acid methyl esters were prepared by trans-esterification, and subsequently analyzed with a Hewlett-Packard 6890 GC.

GC analyses showed that EPA was produced in almost all transformants with pKO2UM26E after one-day growth in MM media. Among the 48 selected transformants, 5 strains produced less than 4% EPA, 23 strains produced 4-5.9% EPA, 9 strains produced 6-6.9% EPA and 11 strains produced 7-8.2% EPA of total lipids in the engineered *Yarrowia*. The strain that produced 8.2% EPA was selected for further analysis using a two-stage growth procedure (i.e., 48 hrs MM+96 hrs in HGM). GC analyses showed that the engineered strain produced about 14% EPA of total lipids. The strain was designated as strain "M26". The final genotype of the M26 strain with respect to wildtype *Yarrowia lipolytica* ATCC #20362 was as follows: Pox3-, Y.Δ12-, FBA::F.Δ12::Lip2, FBAIN::MΔ12::Pex20, TEF.::Δ6S::Lip1, FBAIN::Δ6B::Pex20, FBAIN::E1S::Pex20; GPAT::E1S::Xpr, TEF::E2S::Xpr;

FBAIN::MAΔ5::Pex20, TEF::MAΔ5::Lip1, FBAIN::Δ17S::Lip2,

FBAINm::Δ17S::Pex16 and TEF::Δ17S::Pex20.

Construction of Strain MU, Producing EPA

Strain MU was a Ura auxotroph of strain M26. This strain was made by transforming strain M26 with 5 μg of plasmid pZKUM (FIG. 7A; SEQ ID NO:137) that had been digested with PacI and HincII. Transformation was performed using the Frozen-EZ Yeast Transformation kit (Zymo Research Corporation, Orange, Calif.) and transformants were selected by plating 100 μl of the transformed cell mix on an agar plate with the following medium: 6.7 g/L yeast Nitrogen Base (DIFCO Laboratories, Detroit, Mich.), 20 g/L dextrose, 50 mg/L uracil and 800 mg/L FOA. After 7 days, small colonies appeared that were plated on MM and MMU agar plates. All were Ura auxotrophs. One of the strains was designated "MU".

Construction of Strain Y2067 Producing about 15% EPA

Figure 7A:
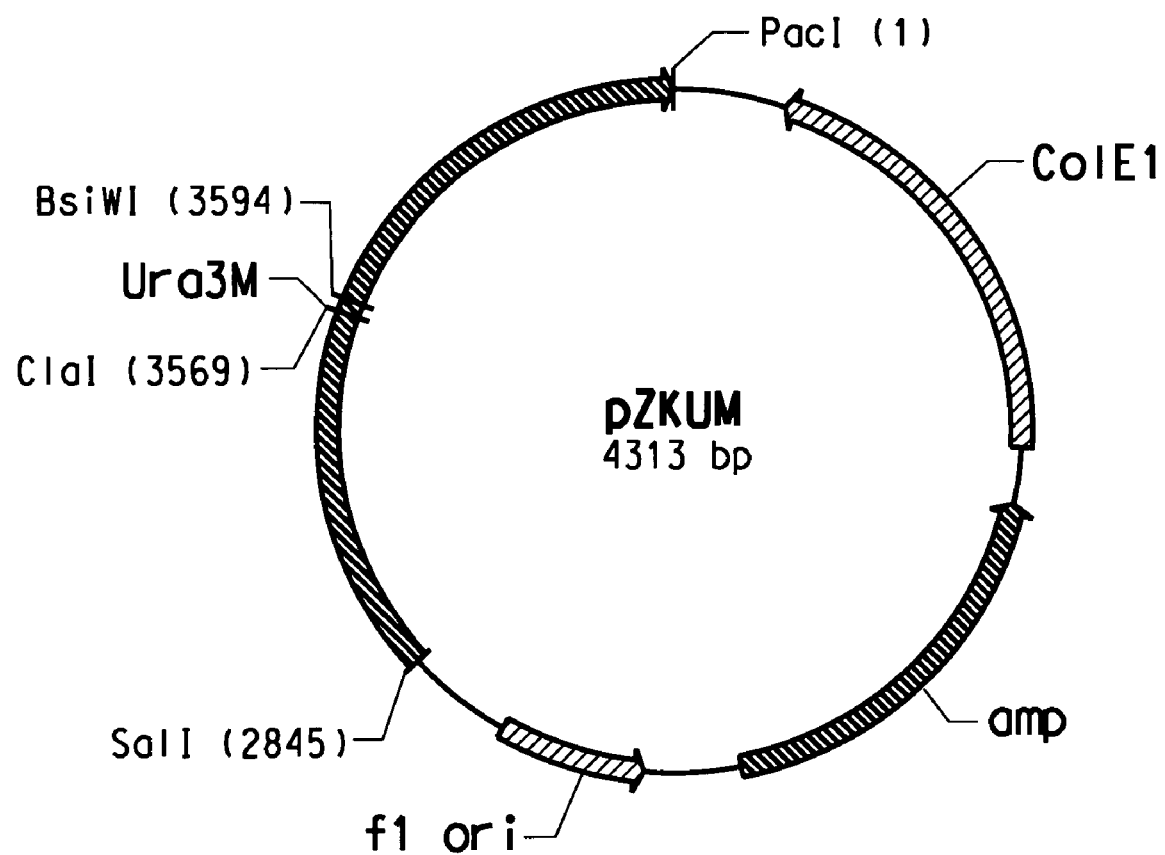
Figure 7B:
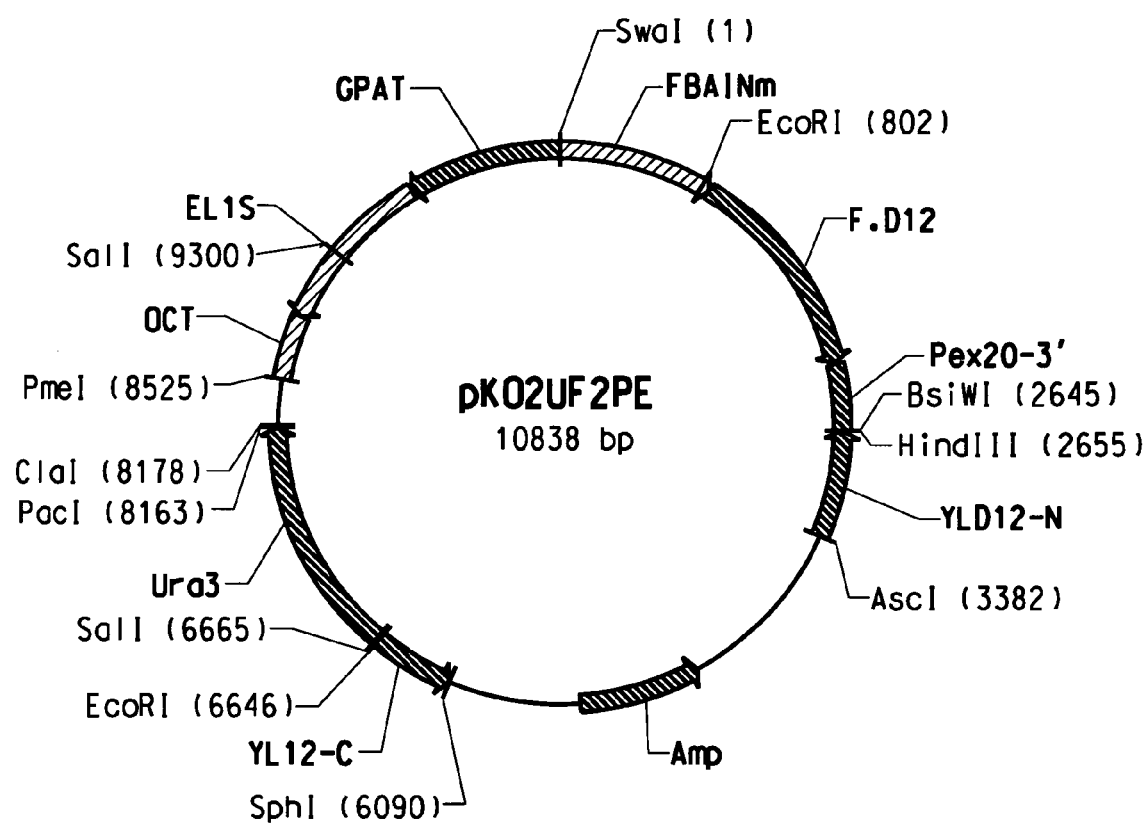

Plasmid pKO2UF2PE (FIG. 7B; SEQ ID NO:138) was created to integrate a cluster containing two chimeric genes (comprising a heterologous Δ12 desaturase and an elongase) and a Ura3 gene into the native *Yarrowia* Δ12 desaturase gene of strain EU (supra). Plasmid pKO2UF2PE contained the following components:

TABLE 14

Description of Plasmid pKO2UF2PE (SEQ ID NO: 138)

| RE Sites And Nucleotides Within SEQ ID NO: 138 | Description Of Fragment And Chimeric Gene Components |
|---|---|
| AscI/BsiWI (3382-2645) | 730 bp 5' part of *Yarrowia* Δ12 desaturase gene (SEQ ID NO: 130) |
| SphI/EcoRI (6090-6646) | 556 bp 3' part of *Yarrowia* Δ12 desaturase gene (SEQ ID NO: 130) |
| SwaI/BsiWI/ (1-2645) | FBAINm::F.Δ12DS::Pex20, comprising: FBAINm: FBAINm promoter (SEQ ID NO: 127; see also U.S. Patent Application No. 60/519971) F.Δ12: *Fusarium moniliforme* Δ12 desaturase gene (SEQ ID NO: 117) Pex20: Pex20 terminator sequence of *Yarrowia* Pex20 gene (GenBank Accession No. AF054613) |
| SwaI/PmeI (1-8525) | GPAT::EL1S::OCT, comprising: GPAT: GPAT promoter (SEQ ID NO: 132; see also U.S. Patent Application No. 60/610060) EL1S: codon-optimized elongase 1 gene (SEQ ID NO: 112), derived from *Mortierella alpina* (GenBank Accession No. AX464731) OCT: OCT terminator sequence of *Yarrowia* OCT gene (GenBank Accession No. X69988) |
| EcoRI/PacI (6646-8163) | *Yarrowia* Ura3 gene (GenBank Accession No. AJ306421) |

Plasmid pKO2UF2PE was digested with AscI/SphI and then used to transform strain EU according to the General Methods (although strain EU was streaked onto a YPD plate and grown for approximately 36 hr prior to suspension in transformation buffer [versus 18 hrs]). Following transformation, cells were plated onto MM plates and maintained at 30° C. for 2 to 3 days. A total of 72 transformants grown on MM plates were picked and re-streaked separately onto fresh MM plates. Once grown, these strains were individually inoculated into liquid MM at 30° C. and shaken at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed the presence of EPA in almost all of the transformants with pKO2UF2PE. More specifically, among the 72 selected transformants, there were 17 strains that produced 8-9.9% EPA, 27 strains that produced 10-10.9% EPA, 16 strains that produced 11-11.9% EPA, and 7 strains that produced 12-12.7% EPA of total lipids in the engineered *Yarrowia*. The strain that produced 12.7% EPA was further analyzed by using two-stage growth conditions.

GC analyses showed that the engineered strain produced about 15% EPA of total lipids after the two-stage growth. The strain was designated as strain "Y2067".

Construction of Strain Y2067U Producing about 14% EPA with Ura-Phenotype

Figure 7C:
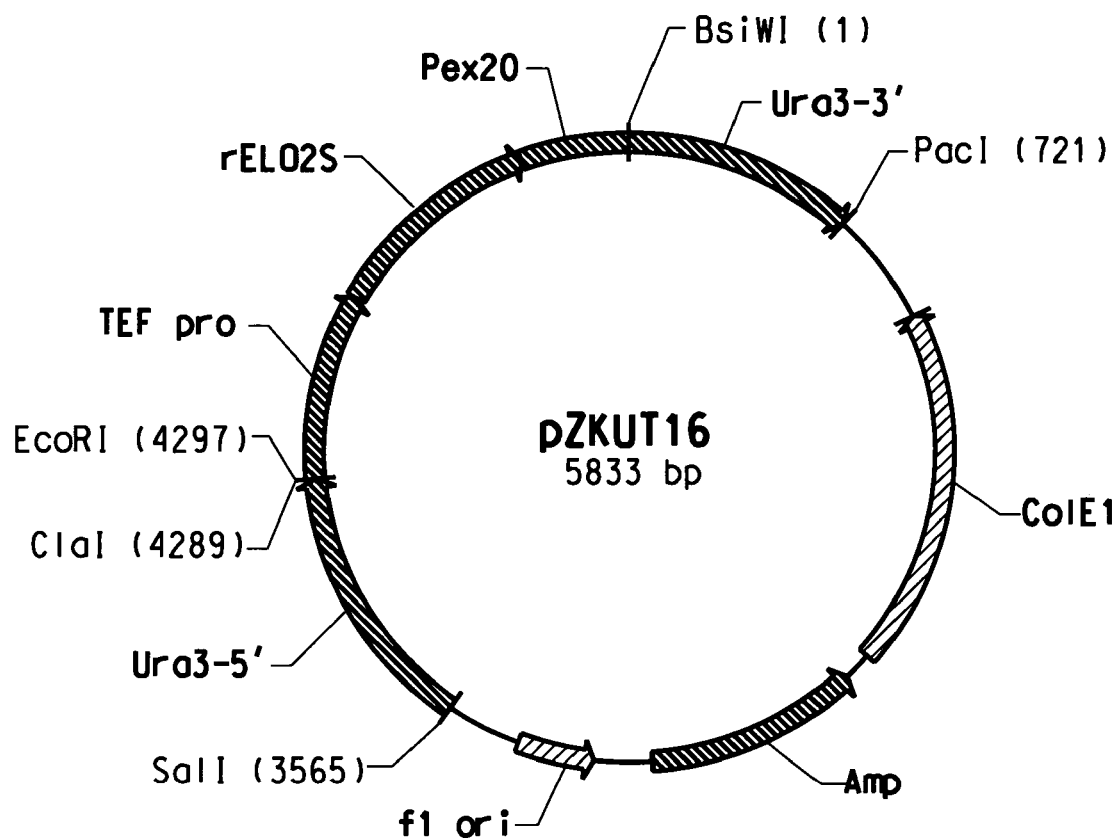

In order to disrupt the Ura3 gene in Y2067 strain, construct pZKUT16 (FIG. 7C; SEQ ID NO:139) was created to integrate a TEF::rELO2S::Pex20 chimeric gene into the Ura3 gene of strain Y2067. rELO2S is a codon-optimized rELO gene encoding a rat hepatic enzyme that elongates 16:0 to 18:0. The plasmid pZKUT16 contained the following components:

TABLE 15

Description of Plasmid pZKUT16 (SEQ ID NO: 139)

| RE Sites And Nucleotides Within SEQ ID NO: 139 | Description Of Fragment And Chimeric Gene Components |
|---|---|
| BsiWI/PacI (1-721) | 721 bp 5' part of Yarrowia Ura3 gene (GenBank Accession No. AJ306421) |
| SalI/ClaI (3565-4289) | 724 bp 3' part of Yarrowia Ura3 gene (GenBank Accession No. AJ306421) |
| ClaI/BsiWI (4289-1) | TEF::rELO2S::Pex20, comprising: TEF: TEF Promoter (GenBank Accession No. AF054508) rELO2S: codon-optimized rELO2 elongase gene (SEQ ID NO: 140), derived from rat (GenBank Accession No. AB071986) Pex 20: Pex20 terminator sequence of Yarrowia Pex20 gene (GenBank Accession No. AF054613) |

The plasmid pZKUT16 was digested with SalI/PacI, and then used to transform Y2067 strain according to the General Methods. Following transformation, cells were plated onto FOA selection plates and maintained at 30° C. for 2 to 3 days.

A total of 24 transformants grown on FOA plates were picked and re-streaked onto MM plates and FOA plates, separately. The strains that could grow on FOA plates, but not on MM plates, were selected as Ura-strains. A total of 10 Ura-strains were individually inoculated into liquid MMU media at 30° C. and grown with shaking at 250 rpm/min for 1 day. The cells were collected by centrifugation, lipids were extracted, and fatty acid methyl esters were prepared by trans-esterification, and subsequently analyzed with a Hewlett-Packard 6890 GC.

GC analyses showed the presence of 5 to 7% EPA in all of the transformants with pZKUT16 after one day growth in MMU media. The strain that produced 6.2% EPA was further analyzed using two-stage growth conditions (48 hrs MM+96 hrs in HGM). GC analyses showed that the engineered strain produced about 14% EPA of total lipids. The strain was designated as strain "Y2067U". The final genotype of this strain with respect to wildtype Yarrowia lipolytica ATCC #20362 was as follows: Ura3-, Pox3-, Y.Δ12-, FBA::F.Δ12::Lip2, FBAINm::F. Δ12::Pex20, TEF::Δ6S::Lip1, FBAIN::E1S::Pex20; GPAT::E1S::Oct, TEF::E2S::Xpr; FBAIN::MAΔ5::Pex20, TEF::MAΔ5::Lip1, FBAIN::Δ17S::Lip2, FBAINm::Δ17S::Pex16, TEF::Δ17S::Pex20 and TEF::rELO2S::Pex20.

Example 11

Determination of TAG Content in Mutant and Wildtype *Yarrowia lipolytica* Strain MU Engineered for EPA Biosynthesis The present Example describes TAG content and fatty acid composition in various acyltransferase knockout strains of strain MU (an engineered strain of *Yarrowia lipolytica* ATCC #20362, capable of producing greater than 10% EPA). More specifically, single disruptions in PDAT, DGAT2 and DGAT1 and double disruptions in PDAT and DGAT2 were created in strain MU. Lipid content and composition is compared in each of these strains, following growth in 4 different growth conditions.

More specifically, single disruptions in PDAT, DGAT2, DGAT1 were created in strain MU (supra, Example 10), using the methodology described in Examples 2, 3, and 7 (with the exception that selection for the DGAT1 disruption relied on the URA3 gene). This resulted in single knockout strains identified as "MU-D1" (disrupted in DGAT1), "MU-D2" (disrupted in DGAT2) and "MU-P" (disrupted in PDAT). Individual knockout strains were confirmed by PCR. Additionally, the MU-D2 strain was disrupted for the PDAT gene and the disruption confirmed by PCR. The resulting double knockout strain was designated "MU-D2-P".

The MU-D1, MU-D2, MU-P and M-D2-P knockout strains were analyzed to determine each knockout's effect on lipid content and composition, as described below. Furthermore, the growth conditions promoting oleaginy were also explored to determine their effect on total lipid content. Thus, in total, four different experiments were conducted, identified as "Experiment A", "Experiment B", "Experiment C" and "Experiment E". Specifically, three loops of cells from plates containing each strain above were inoculated into MMU [3 mL for Experiments B and C; and 50 mL for Experiments A and E] and grown in a shaker at 30° C. for 24 hrs (for Experiments A, B and C) or 48 hrs (for Experiment E). Cells were harvested, washed once in HGM, resuspended in either HGM (50 mL for Experiments A and E; and 3 mL for Experiment B) or HGM with uracil ("HGMU") (3 mL for Experiment C) and cultured as above for 4 days. One aliquot (1 mL) was used for lipid analysis by GC as described according to the General Methods, while a second aliquot was used for determining the culture OD at 600 nm. The remaining culture in Experiments A and E was harvested, washed once in water and lyophilized for dry cell weight (dcw) determination. In contrast, the dcw in Experiments B and C were determined from their $OD_{600}$ using the equation showing their relationship. The fatty acid compositions of each of the different strains in Experiments A, B, C and E were also determined.

The results are shown in Table 16 below. Cultures are described as the "MU" strain (the parent EPA producing strain), "MU-P" (PDAT knockout), "MU-D1" (DGAT1 knockout), "MU-D2" (DGAT2 knockout) and "MU-D2-P" (DGAT2 and PDAT knockouts). Abbreviations utilized are: "WT"=wildtype (i.e., MU); "OD"=optical density; "dcw"=dry cell weight; "TFAs"=total fatty acids; and, "TFAs % dcw, % WT"=TFAs % dcw relative to the wild type ("MU") strain. Fatty acids are identified as 16:0, 16:1, 18:0, 18:1 (oleic acid), 18:2 (LA), GLA, DGLA, ARA, ETA and EPA; and the composition of each is presented as a % of the total fatty acids.

TABLE 16

Lipid And EPA Content In *Yarrowia* Strain MU With Various Acyltransferase Disruptions

| Expt | Strain | Residual DAG AT | 1st Phase Growth Condition | 2nd Phase Growth Condition | OD | dcw (mg) | TFAs (µg) | TFAs % dcw | TFAs % dcw, % WT |
|---|---|---|---|---|---|---|---|---|---|
| A | MU | D1, D2, P | 1 day, | 4 days, | 4.0 | 91 | 374 | 20.1 | 100 |
| A | MU-D2 | D1, P | 50 mL | 50 mL | 3.1 | 75 | 160 | 10.4 | 52 |
| A | MU-D1 | D2, P | MMU | HGM | 4.3 | 104 | 217 | 10.2 | 51 |
| A | MU-P | D1, D2 | | | 4.4 | 100 | 238 | 11.7 | 58 |
| B | MU | D1, D2, P | 1 day, | 4 days, | 5.9 | 118 | 581 | 24.1 | 100 |
| B | MU-D2 | D1, P | 3 mL | 3 mL | 4.6 | 102 | 248 | 11.9 | 50 |
| B | MU-D1 | D2, P | MMU | HGM | 6.1 | 120 | 369 | 15.0 | 62 |
| B | MU-P | D1, D2 | | | 6.4 | 124 | 443 | 17.5 | 72 |
| C | MU | D1, D2, P | 1 day, | 4 days, | 6.8 | 129 | 522 | 19.9 | 100 |
| C | MU-D2 | D1, P | 3 mL | 3 mL | 5.6 | 115 | 239 | 10.2 | 51 |
| C | MU-D1 | D2, P | MMU | HGMU | 6.9 | 129 | 395 | 15.0 | 75 |
| C | MU-P | D1, D2 | | | 7.1 | 131 | 448 | 16.8 | 84 |
| E | MU | D1, D2, P | 2 days, | 4 days, | 4.6 | 89 | 314 | 17.3 | 100 |
| E | MU-D2 | D1, P | 50 mL | 50 mL | 2.8 | 62 | 109 | 8.5 | 49 |
| E | MU-P | D2, P | MM | HGM | 5.0 | 99 | 232 | 11.5 | 66 |
| E | MU-D2-P | D1 | | | 4.2 | 98 | 98 | 4.9 | 28 |

| Expt | % 16:0 | % 16:1 | % 18:0 | % 18:1 | % 18:2 | % GLA | % DGLA | % ARA | % ETA | % EPA |
|---|---|---|---|---|---|---|---|---|---|---|
| A | 17 | 10 | 2 | 18 | 10 | 22 | 7 | 1 | 3 | 9.7 |
| A | 16 | 12 | 0 | 8 | 9 | 23 | 7 | 0 | 8 | 17.4 |
| A | 15 | 10 | 2 | 11 | 10 | 22 | 7 | 0 | 7 | 17.4 |
| A | 16 | 9 | 2 | 11 | 7 | 24 | 7 | 1 | 6 | 17.5 |
| B | 17 | 9 | 3 | 18 | 10 | 22 | 8 | 1 | 3 | 9.1 |
| B | 16 | 10 | 0 | 7 | 10 | 24 | 7 | 1 | 7 | 17.8 |
| B | 18 | 9 | 3 | 14 | 11 | 20 | 7 | 1 | 5 | 12.0 |
| B | 15 | 8 | 3 | 16 | 10 | 25 | 6 | 1 | 4 | 11.9 |
| C | 16 | 10 | 2 | 13 | 11 | 21 | 10 | 1 | 4 | 12.6 |
| C | 17 | 9 | 1 | 6 | 11 | 21 | 8 | 1 | 7 | 18.9 |
| C | 15 | 9 | 2 | 12 | 12 | 20 | 10 | 1 | 5 | 13.5 |
| C | 17 | 8 | 3 | 14 | 11 | 20 | 10 | 1 | 4 | 11.3 |
| E | 16 | 12 | 2 | 18 | 9 | 22 | 7 | 1 | 4 | 11.2 |
| E | 14 | 12 | 1 | 6 | 8 | 25 | 6 | 0 | 7 | 20.0 |
| E | 16 | 10 | 2 | 14 | 7 | 24 | 7 | 1 | 5 | 15.8 |
| E | 18 | 10 | 0 | 7 | 12 | 20 | 5 | 0 | 6 | 22.5 |

The data showed that the lipid content within the transformed cells varied according to the growth conditions. Furthermore, the contribution of each acyltransferase on lipid content also varied. Specifically, in Experiments B, C and E, DGAT2 contributed more to oil biosynthesis than either PDAT or DGAT1. In contrast, as demonstrated in Experiment A, a single knockout in DGAT2, DGAT1 and PDAT resulted in approximately equivalent losses in lipid content (i.e., 48%, 49% and 42% loss, respectively [see "TFAs % dcw, % WT"]).

Example 12

Sequencing of *Yarrowia lipolytica* DGAT1 and ORF Expression Under the Control of a *Yarrowia* Promoter The present Example describes the sequencing of YI DGAT1 and the over-expression of a chimeric gene comprising the *Yarrowia lipolytica* TEF promoter, YI DGAT1, and *Yarrowia lipolytica* peroxin (Pex20) terminator (i.e., a TEF::YI DGAT1::Pex20 gene) in a wild type *Yarrowia* strain.

Sequencing of the *Y. lipolytica* DGAT1

First, the ORF of *Y. lipolytica* DGAT1 was PCR-amplified using degenerate primers P201 and P203 (SEQ ID NOs:92 and 93) and genomic DNA of *Y. lipolytica* ATCC #90812 as template (from Example 2). The PCR was performed using the Expand High Fidelity PCR System of Roche Applied Sciences (Indianapolis, Ind.), as described in the General Methods.

The expected 1.6 kB fragment was isolated by standard agarose gel electrophoresis, purified, and cloned into pCR4-TOPO vector from Invitrogen (Carlsbad, Calif.) to yield plasmid pYAP42-23. Plasmid pYAP42-23 was transformed into *E. coli* XL2; and, transformants comprising pYAP42-23 were confirmed by plasmid miniprep analysis and restriction enzyme digestions with either NotI or NcoI. The DNA insert in plasmid pYAP42-23 was sequenced according to the methodology described in the General Methods using sequencing primers T7, T3, P239 (SEQ ID NO:142) and P240 (SEQ ID NO:143), to obtain the complete nucleotide sequence of the YI DGAT1 ORF.

The nucleotide sequence of the YI DGAT1 ORF is provided as SEQ ID NO:13; the translated product has the amino acid sequence provided in SEQ ID NO:14. The resultant sequence was compared to other known proteins, based on BLAST program analysis (Basic Local Alignment Search Tool; Altschul, S. F. et al., *J. Mol. Biol.* 215:403-410 (1993)). In particular, SEQ ID NO:13 was identical to the YI DGAT1 partial sequence that was obtained in Example 7, except for the presence of 6 silent mutations in the region of the degenerate PCR primers. These mutations included: an A-to-G mutation at position 6; an A-to-G mutation at position 21; an A-to-G mutation at position 24; a T-to-C mutation at position 1548; a C-to-T mutation at position 1552; and a T-to-C mutation at position 1557. Since these mutations resulted from the use of degenerate PCR primers, the deduced amino acid sequence of SEQ ID NO:13, i.e., SEQ ID NO:14 is identical to ORF YALI-CDS2141.1 (SEQ ID NO:12, corresponding to GenBank Accession No. NC_006072, locus_tag="YALI0F06578g").

Construction of a *Y. lipolytica* DGAT1 Chimeric Gene

Figure 7D:
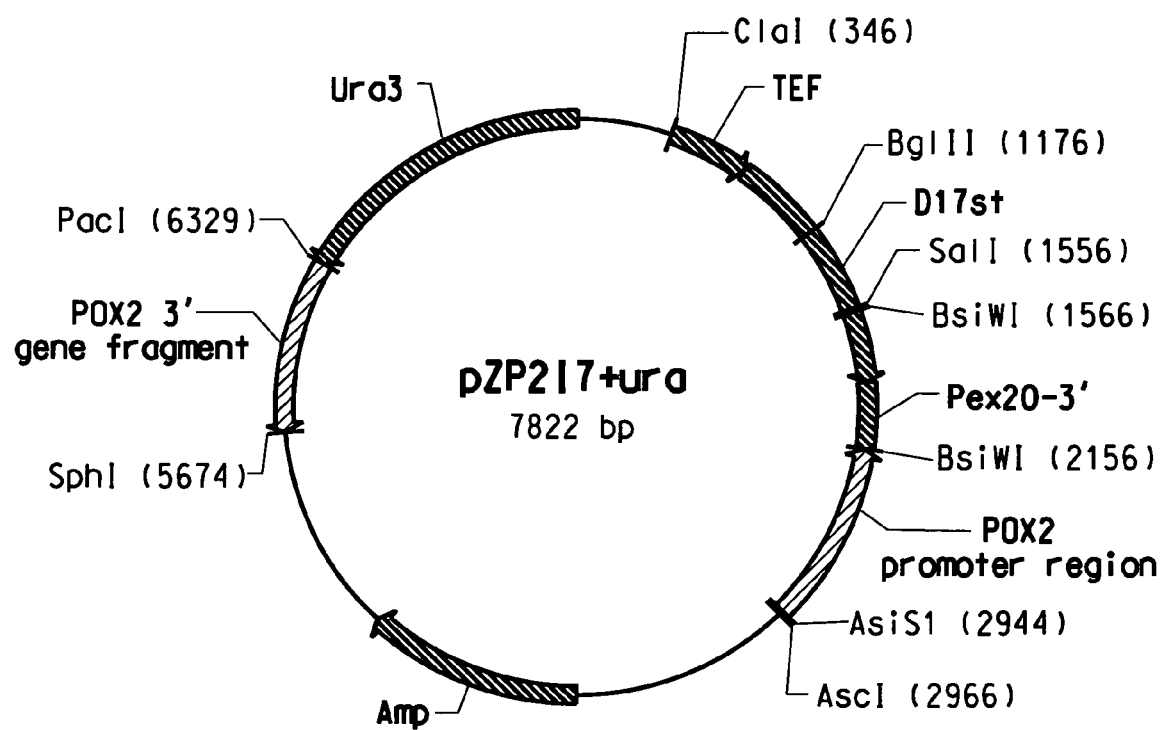

Plasmid pYAP23-42 was digested with NcoI and Not I for 1 hr and the 1.6 kB fragment containing YI DGAT1 was isolated and inserted into NcoI- and Not I-digested pZP217+ Ura (SEQ ID NO:144; FIG. 7DA), such that the ORF was cloned under the control of the TEF promoter and the PEX20-3' terminator region in an integrating vector targeted into the *Yarrowia* POX2 gene. Correct transformants were confirmed by miniprep analysis and the resultant plasmid was designated as "pYDA1".

Plasmids pZP217+Ura and pYDA1 were transformed into strain "MU-D2" of *Y. lipolytica* (supra; Example 11), according to the General Methods. Transformants were plated onto MM and single colonies were picked, purified, and analyzed to determine the effect of the overexpressed DGAT1 on lipid content. Specifically, lipid content was analyzed in the following cultures: "MU" ("wildtype"), MU-D2 transformed with pZP217+Ura, and MU-D2 transformed with pYDA1 (clones #5, 6, 7 and 16). Several loops of cells from each of the strains above were inoculated into 50 mL MM and grown in a shaker at 30° C. for 48 hrs. Cells were harvested, washed once in HGM, resuspended in 30 mL HGM medium, and grown as above for another 4 days. After growth, 100 µL aliquots from each culture were used to determine absorbance at 600 nm ($OD_{600}$) and a 1 mL aliquot was used for GC analysis. For this, the 1 mL sample was harvested, washed once in water, spun down, and the pellet used for lipid determination following direct transesterification by base method and GC analysis (as described in the General Methods). The remaining culture was harvested, washed once in water and lyophilized to obtain the dry cell weight.

The results are shown in the Table below. Cultures are described as the "MU" strain ("wildtype") and "MU-D2" (DGAT2 knockout). Abbreviations utilized are: "WT"=wildtype (i.e., strain MU-D2 having a DGAT2 knockout); "OD"=optical density; "dcw"=dry cell weight; "TFAs"=total fatty acids; and, "TFAs % dcw, % WT"=TFAs % dcw relative to the wild type ("MU-D2") strain.

TABLE 17

Lipid Content In *Yarrowia* Strains Engineered To Produce EPA And Overexpressing DGAT1

| Strain | OD | dcw, mg | TFAs, µg | TFAs % dcw | TFAs % dcw, % WT |
|---|---|---|---|---|---|
| MU | 2.1 | 33 | 195 | 17.0 | |
| MU-D2 + pZP2I7 + Ura | 1.8 | 31 | 82 | 7.7 | 100 |

TABLE 17-continued

Lipid Content In *Yarrowia* Strains Engineered To Produce EPA And Overexpressing DGAT1

| Strain | OD | dcw, mg | TFAs, µg | TFAs % dcw | TFAs % dcw, % WT |
|---|---|---|---|---|---|
| MU-D2 + pYDA1, clone #5 | 2.1 | 31 | 192 | 17.8 | 231 |
| MU-D2 + pYDA1, clone #6 | 1.3 | 22 | 338 | 21.3 | 278 |
| MU-D2 + pYDA1, clone #7 | 4.4 | 72 | 146 | 5.9 | 76 |
| MU-D2 + pYDA1, clone #16 | 2.2 | 34 | 195 | 16.9 | 220 |

In general, the results showed that overexpression of DGAT1 was able to compensate for the lack of DGAT2 activity in strain MU-D2, to result in lipid content approximately equal or greater than in strain MU (i.e., MU-D2+ pYDA1, clones #5, 6 and 16 have a lipid content (measured as TFAs % dcw) approximately equal to or greater than that of strain MU). This lipid content in MU-D2+pYDA1, clones #5, 6 and 16 was greater than double that of the control strain, MU-D2+pZP217+Ura. These results provide further confirmation that the *Yarrowia* DGAT1 encodes a functional DAG AT involved in oil biosynthesis.

Transformant MU-D2 +pYDA1, clone #7 did not show an increase in lipid content comparable to clones #5, 6 and 16. However, since these chromosomal integrations are generally random, such variation is to be expected.

Example 13

Construction and Sequencing of a *Mortierella alpina* cDNA Library

The present Example describes the construction of a cDNA library of *Mortierella alpina* and subsequent sequencing of the library.

Synthesis of *M. alpina* cDNA

*M. alpina* cDNA was synthesized using the BD-Clontech Creator Smart® cDNA library kit (Mississauga, ON, Canada), according to the manufacturer's protocol.

Specifically, *M. alpina* strain ATCC #16266 was grown in 60 mL YPD medium (2% Bacto-yeast extract, 3% Bactor-peptone, 2% glucose) for 3 days at 23° C. Cells were pelleted by centrifugation at 3750 rpm in a Beckman GH3.8 rotor for 10 min and resuspended in 6×0.6 mL Trizole reagent (Invitrogen). Resuspended cells were transferred to six 2 mL screw cap tubes each containing 0.6 mL of 0.5 mm glass beads. The cells were homogenized at the HOMOG-ENIZE setting on a Biospec (Bartlesville, Okla.) mini bead beater for 2 min. The tubes were briefly spun to settle the beads. Liquid was transferred to 4 fresh 1.5 mL microfuge tubes and 0.2 mL chloroform/isoamyl alcohol (24:1) was added to each tube. The tubes were shaken by hand for 1 min and let stand for 3 min. The tubes were then spun at 14,000 rpm for 10 min at 4° C. The upper layer was transferred to 4 new tubes. Isopropyl alcohol (0.5 mL) was added to each tube. Tubes were incubated at room temperature for 15 min, followed by centrifugation at 14,000 rpm and 4° C. for 10 min. The pellets were washed with 1 mL each of 75% ethanol, made with RNase free water and air-dried. The total RNA sample was then redissolved in 500 µl of water, and the amount of RNA was measured by A260 nm using 1:50 diluted RNA sample. A total of 3.14 mg RNA was obtained.

This total RNA sample was further purified with the Qiagen RNeasy total RNA Midi kit following the manufacturer's protocol. Thus, the total RNA sample was diluted to 2 mL and mixed with 8 mL of buffer RLT with 80 µl of β-mercaptoethanol and 5.6 mL 100% ethanol. The sample was divided into 4 portions and loaded onto 4 RNeasy midid columns. The columns were then centrifuged for 5 min at 4500×g. To wash the columns, 2 mL of buffer RPE was loaded and the columns centrifuged for 2 min at 4500×g. The washing step was repeated once, except that the centrifugation time was extended to 5 min. Total RNA was eluted by applying 250 µl of RNase free water to each column, waiting for 1 min and centrifuging at 4500×g for 3 min.

PolyA(+)RNA was then isolated from the above total RNA sample, following Pharmacia's kit protocol. Briefly, 2 oligo-dT-cellulose columns were used. The columns were washed twice with 1 mL each of high salt buffer. The total RNA sample from the previous step was diluted to 2 mL total volume and adjusted to 10 mM Tris/HCl, pH 8.0, 1 mM EDTA. The sample was heated at 65° C. for 5 min, then placed on ice. Sample buffer (0.4 mL) was added and the sample was then loaded onto the two oligo-dT-cellulose columns under gravity feed. The columns were centrifuged at 350×g for 2 min, washed 2× with 0.25 mL each of high salt buffer, each time followed by centrifugation at 350×g for 2 min. The columns were further washed 3 times with low salt buffer, following the same centrifugation routine. Poly (A)+RNA was eluted by washing the column 4 times with 0.25 mL each of elution buffer preheated to 65° C., followed by the same centrifugation procedure. The entire purification process was repeated once. Purified poly(A)+RNA was obtained with a concentration of 30.4 ng/µl.

cDNA was generated, using the LD-PCR method specified by BD-Clontech and 0.1 µg of polyA(+) RNA sample. Specifically, for $1^{st}$ strand cDNA synthesis, 3 µl of the poly(A)+RNA sample was mixed with 1 µl of SMART IV oligo nucleotide (SEQ ID NO:145) and 1 µl of CDSIII/3' PCR primer (SEQ ID NO:146). The mixture was heated at 72° C. for 2 min and cooled on ice for 2 min. To the tube was added the following: 2 µl first strand buffer, 1 µl 20 mM DTT, 1 µl 10 mM dNTP mix and 1 µl Powerscript reverse transcriptase. The mixture was incubated at 42° C. for 1 hr and cooled on ice.

The $1^{st}$ strand cDNA synthesis mixture was used as template for the PCR reaction. Specifically, the reaction mixture contained the following: 2 µl of the $1^{st}$ strand cDNA mixture, 2 µl 5'-PCR primer (SEQ ID NO:147), 2 µl CDSIII/3'-PCR primer (SEQ ID NO:146), 80 µl water, 10 µl 10× Advantage 2 PCR buffer, 2 µl 50× dNTP mix and 2 µl 50× Advantage 2 polymerase mix. The thermocycler conditions were set for 95° C. for 20 sec, followed by 14 cycles of 95° C. for 5 sec and 68° C. for 6 min on a GenAmp 9600 instrument. PCR product was quantitated by agarose gel electrophoresis and ethidium bromide staining.

Seventy-five µl of the above PCR products (cDNA) were mixed with 3 µl of 20 µg/µl proteinase K supplied with the kit. The mixture was incubated at 45° C. for 20 min, then 75 µl of water was added and the mixture was extracted with 150 µl phenol:chloroform:isoamyl alcohol mixture (25:24:1). The aqueous phase was further extracted with 150 µl chloroform:isoamyl alcohol (25:1). The aqueous phase was then mixed with 15 µl of 3 M sodium acetate, 2 µl of 20 µg/µl glycogen and 400 µl of 100% ethanol. The mixture was immediately centrifuged at room temperature for 20 min at 14000 rpm in a microfuge. The pellet was washed once with 150 µl of 80% ethanol, air dried and dissolved in 79 µl of water.

Dissolved cDNA was subsequently digested with SfiI (79 µl of the cDNA was mixed with 10 µl of 10× SfiI buffer, 10 µl of SfiI enzyme and 1 µl of 100× BSA and the mixture was incubated at 50° C. for 2 hrs). Xylene cyanol dye (2 µl of 1%) was added. The mixture was then fractionated on the Chroma Spin-400 column provided with the kit, following the manufacturer's procedure exactly. Fractions collected from the column were analyzed by agarose gel electrophoresis. The first three fractions containing cDNA were pooled and cDNA precipitated with ethanol. The precipitated cDNA was redissolved in 7 µl of water, and ligated into kit-supplied PDNR-LIB.

Library Sequencing

The ligation products were used to transform *E. coli* XL-1 Blue electroporation competent cells (Stratagene). An estimated total of $2 \times 10^6$ colonies was obtained. Sequencing of the cDNA library was carried out by Agencourt Bioscience Corporation (Beverly, Mass.), using an M13 forward primer (SEQ ID NO:148).

Example 14

Identification and Cloning of a *Mortierella alpina* Diacylglycerol Acyltransferase (DGAT1) Gene The present Example describes the identification of a putative *M. alpina* DGAT1 within one of 9,984 cDNA sequences. Specifically, the *Y. lipolytica* DGAT1 protein sequence (Example 7, SEQ ID NO:14) was used as a query sequence against each of the *M. alpina* cDNA sequences using BLAST program analysis (Basic Local Alignment Search Tool; Altschul, S. F. et al., *J. Mol. Biol.* 215:403-410 (1993)). One cDNA fragment bore significant homology to the *Y. lipolytica* DGAT1 and thus was tentatively identified as the *M. alpina* DGAT1 (SEQ ID NO:175). Subsequent BLAST analyses with SEQ ID NO:175 as the query against publically available sequence databases confirmed the cDNA's significant degree of similarity with the DGAT1s from several other species. Rapid amplification of cDNA ends (RACE) technology and genome walking were then used to isolate the entire *Mortierella alpina* coding sequence thereof.

Isolation of Genomic DNA

Genomic DNA was isolated from *Mortierella alpina* (ATCC #16266) using a QiaPrep Spin Miniprep Kit (Qiagen, Catalog #627106). Cells grown on a YPD agar plate were scraped off and resuspended in 1.2 mL kit buffer P1. The resuspended cells were placed into two 2.0 mL screw cap tubes, each containing 0.6 mL glass beads (0.5 mm diameter). The cells were homogenized at the HOMOGENIZE setting on a Biospec (Bartlesville, Okla.) mini bead beater for 2 min. The tubes were then centrifuged at 14,000 rpm in an Eppendorf microfuge for 2 min. The supernatant (0.75 mL) was transferred to three 1.5 mL microfuge tubes. Equal volumes of kit buffer P2 were added to each tube. After mixing the tubes three times by inversion, 0.35 mL of buffer N3 was added to each tube. The contents was mixed again by inverting the tubes 5 times. The mixture was centrifuged at 14,000 rpm in an Eppendorf microfuge for 5 min. The supernatant from each tube was transferred into a separate kit spin column. The columns were centrifuged for 1 min at 14,000 rpm, washed once with buffer PE and centrifuged at 14,000 rpm for 1 min again, followed by a final centrifugation at 14,000 rpm for 1 min. Buffer EB (50 µl) was added to each column and let stand for 1 min. The genomic DNA was then eluted by centrifugation at 14,000 rpm for 1 min.

Cloning of the 5'-End Region of the Putative DGAT1 Gene

A Clontech Universal GenomeWalker™ kit (Palo Alto, Calif.) was utilized to obtain a piece of genomic DNA corresponding to the 5'-end region of the *M. alpina* DGAT1. Based on the partial DGAT1 gene sequence available (SEQ ID NO:149), the following primers were synthesized for use in the cloning: MARE2-N1 and MARE2-N2 (SEQ ID NOs:150 and 151).

Briefly, 2.5 μg each of *M. alpina* genomic DNA was digested with DraI, EcoRV, PvuII or StuI individually, the digested DNA samples were purified using Qiagen Qiaquick PCR purification kits and eluted with 30 μl each of kit buffer EB, and the purified samples were then ligated with Genome Walker adaptor (SEQ ID NOs:152 [top strand] and 153 [bottom strand]), as shown below:

```
5'-GTAATACGACTCACTATAGGGCACGCGTGGTCGACGGCCCGGGCT
GGT-3'

3'-H2N-CCCGACCA-5'
```

Specifically, each ligation reaction mixture contained 1.9 μl of 25 μM Genome Walker adaptor, 1.6 μl 10× ligation buffer, 0.5 μl T4 DNA ligase and 4 μl of one of the purified digested genomic DNA samples. The reaction mixtures were incubated at 16° C. overnight. The reaction was terminated by incubation at 70° C. for 5 min. Then, 72 μl of 10 mM TrisHCl, 1 mM EDTA, pH 7.4 buffer was added to each ligation reaction mix.

Four PCR reactions were then carried out using each of the ligation products as templates. Each PCR reaction mixture contained 1 μl of ligation mixture, 1 μl of 20 μM MARE2-N1 (SEQ ID NO:150),2 μl of 10 μM kit primer AP1 (SEQ ID NO:154), 21 μl water and 25 μl ExTaq premix Taq 2× PCR solution (TaKaRa Bio Inc., Otsu, Shiga, 520-2193, Japan). PCR amplifications were carried out as follows: 30 cycles of denaturation at 94° C. for 30 sec, annealing at 55° C. for 30 sec, and elongation at 72° C. for 90 sec. A final elongation cycle at 72° C. for 7 min was carried out, followed by reaction termination at 4° C.

Second PCR reactions were then carried out using 1 μl of 1:50 diluted first PCR product as template, 1 μl of 20 μM MARE2-N2 (SEQ ID NO:151), 2 μl of 10 μM kit primer AP2 (SEQ ID NO:155), 21 μl water and 25 μl of ExTaq premix Taq 2× PCR solution (TaKaRa). PCR reaction was carried out for 30 cycles using the same conditions described above.

A ~1.6 kb PCR product was observed when the DraI-digested and adaptor-ligated genomic DNA was used as template. This fragment was purified using a Qiagen PCR purification kit, ligated into pCR2.1-TOPO, and sequenced. Analysis of the sequence (SEQ ID NO:156) showed that this DNA fragment was the 5'-end extension of the DGAT1 cDNA fragment.

Cloning of the 3'-End Region of the Putative DGAT1 Gene

To clone the 3'-region of the putative DGAT1 gene by RACE, the following primers were synthesized: ARE-N3-1 and ARE-N3-2 (SEQ ID NOs:157 and 158, respectively).

3'-end RACE was carried out using InVitrogen's 3'-end RACE kit, following the manufacturer's protocol. Briefly, 90 ng of *M. alpina* polyA(+)RNA sample in 11 μl of water were mixed with 1 μl of 10 μM Adaptor primer (AP, SEQ ID NO:159) solution. The mixture was heated at 70° C. for 10 min and cooled on ice for 2 min. Then, 2 μl each of 10× PCR buffer, 25 mM MgCl₂ and 0.1 M DTT, and 1 μl of 10 mM dNTP mix were added. The reaction mixture was heated to 42° C. for 3 min and then kit-supplied Superscript II reverse transcriptase (1 μl) was added. The reaction was allowed to proceed for 50 min at 42° C. Afterward, the reaction mixture was heated to 70° C. for 15 min and cooled on ice for 2 min. RNaseH (1 μl) from the kit was added and the entire mixture was incubated at 37° C. for 20 min.

The reaction mixture (2 μl) was used directly as PCR template. The PCR reaction mixture contained 1 μl of 20 μM ARE-N3-1 (SEQ ID NO:157), 2 μl of 10 uM kit primer UAP (SEQ ID NO:160), 25 μl of ExTaq premix Taq 2× PCR solution (TaKaRa) and 20 μl of water. PCR amplification was performed as previously described above. Diluted PCR reaction mixture (1 μl of a 1:10 dilution) was then used as template for a second round of PCR using the same conditions, except with primer ARE-N3-2 (SEQ ID NO:158) replacing primer AREN3-1.

A ca. 300 bp fragment was obtained from the PCR. After purification with Qiagen's QiaQuick PCR purification kit, the fragment was cloned into pCR2.1-TOPO and sequenced. Sequence analysis verified that the sequence encoded the 3'-end of the DGAT1 cDNA, including the polyA tail (SEQ ID NO:161).

Complete Assembly of the Nucleotide Sequence Encoding *M. alpina*'s DGAT1

Assembly of the sequence of the 5'-region (SEQ ID NO:156), the original cDNA fragment (SEQ ID NO:149) and the 3'-region (SEQ ID NO:161) yielded the entire *M. alpina* DGAT1 coding sequence (SEQ ID NO:17). The 5'-region genomic sequence included an intron (nucleotide bases 449 to 845 within SEQ ID NO:17).

Example 15

Expression of *Mortierella alpina* DGAT1 in *Yarrowia lipolytica* Strain Y2067U Engineered to Produce Polyunsaturated Fatty Acids The present Example describes the expression of the *M. alpina* DGAT1 in *Y. lipolytica* strain Y2067U (supra, Example 10), and the effect of MDGAT1 expression on the final concentration of EPA and other PUFAs produced.

The *M. alpina* DGAT1 ORF was cloned as follows. First, to aid the cloning of the cDNA, the sequence of the second codon of the DGAT1 was changed from 'ACA' to 'GCA', resulting in an amino acid change of threonine to alanine. This was accomplished by amplifying the complete coding region of the *M. alpina* DGAT1 ORF with primers MACAT-F1 and MACAT-R (SEQ ID NOs:162 and 163, respectively). Specifically, the PCR reaction mixture contained 1 μl each of a 20 μM solution of primers MACAT-F1 and MACAT-R, 1 μl of *M. alpina* cDNA (supra, Example 13), 22 μl water and 25 μl ExTaq premix 2× Taq PCR solution (TaKaRa Bio Inc., Otsu, Shiga, 520-2193, Japan). Amplification was carried out as follows: initial denaturation at 94° C. for 150 sec, followed by 30 cycles of denaturation at 94° C. for 30 sec, annealing at 55° C. for 30 sec and elongation at 72° C. for 90 sec. A final elongation cycle at 72° C. for 10 min was carried out, followed by reaction termination at 4° C. A ~1600 bp DNA fragment was obtained from the PCR reaction. It was purified using Qiagen's PCR purification kit according to the manufacturer's protocol.

Figure 7E:
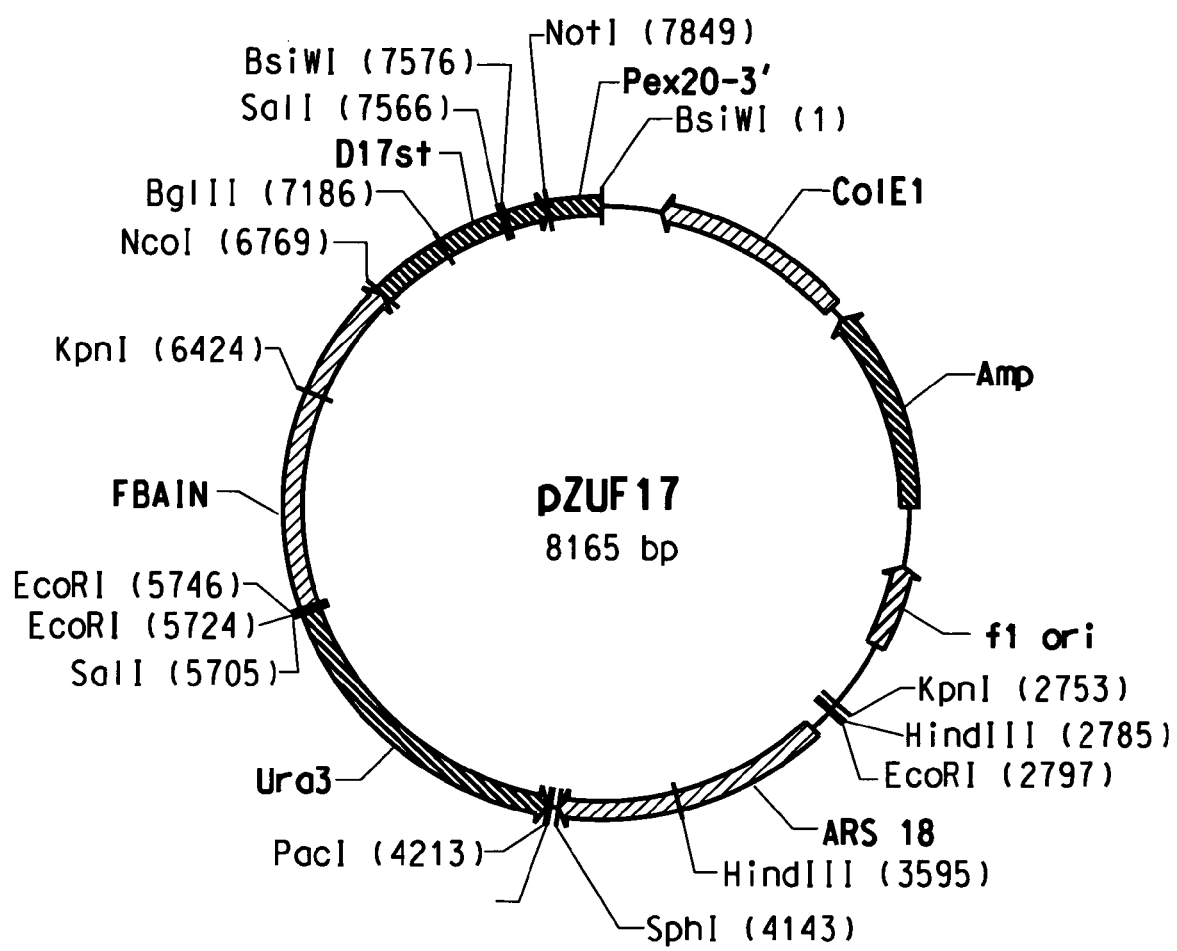

The *M. alpina* DGAT1 ORF was to be inserted into Nco I- and Not I-digested plasmid pZUF17 (SEQ ID NO:164; FIG. 7E), such that the ORF was cloned under the control of the FBAIN promoter (SEQ ID NO:111) and the PEX20-3' terminator region. However, since the DGAT1 ORF contained an internal NcoI site, it was necessary to perform two separate restriction enzyme digestions for cloning. First, ~2 µg of the purified PCR product was digested with BamHI and Nco I. The reaction mixture contained 20 U of each enzyme (Promega) and 6 µl of restriction buffer D in a total volume of 60 µl. The mixture was incubated for 2 hrs at 37° C. A ~320 bp fragment was separated by agarose gel electrophoresis and purified using a Qiagen Qiaex II gel purification kit. Separately, ~2 µg of the purified PCR product was digested with BamHI and Not I using identical reaction conditions to those above, except Nco I was replaced by Not I. A ~1280 bp fragment was isolated and purified as above. Finally, ~3 µg of pZUF17 was digested with Nco I and Not I and purified as described above, generating a ~7 kB fragment.

The ~7 kB Nco I/Not I pZUF17 fragment, the ~320 bp Nco I/BamHI DGAT1 fragment and the ~1280 bp BamHI/Not I DGAT1 fragment were ligated together in a three-way ligation incubated at room temperature overnight. The ligation mixture contained 100 ng of the 7 kB fragment and 200 ng each of the 320 bp and 1280 bp fragments, 2 µl ligase buffer, and 2 U T4 DNA ligase (Promega) in a total volume of 20 µl. The ligation products were used to transform E. coli Top10 chemical competent cells (Invitrogen) according to the manufacturer's protocol. Individual colonies (12 total) from the transformation were used to inoculate cultures for miniprep analysis. Restriction mapping and sequencing showed that 5 out of the 12 colonies harbored the desired plasmid, which was named "pMDGAT1-17" (FIG. 4C; SEQ ID NO:165).

"Control" vector pZUF-MOD-1 (SEQ ID NO:168) was prepared as follows. First, primers pzuf-mod1 (SEQ ID NO:166) and pzuf-mod2 (SEQ ID NO:167) were used to amplify a 252 bp "stuffer" DNA fragment using pDNR-LIB (ClonTech, Palo Alto, Calif.) as template. The amplified fragment was purified with a Qiagen QiaQuick PCR purification kit, digested with NcoI and NotI using standard conditions, and then purified again with a QiaQuick PCR purification kit. This fragment was ligated into similarly digested NcoI/NotI-cut pZUF17 vector (SEQ ID NO:164; FIG. 10E) and the resulting ligation mixture was used to transform E. coli Top10 cells (Invitrogen). Plasmid DNA was purified from 4 resulting colonies, using a Qiagen QiaPrep Spin Miniprep kit. The purified plasmids were digested with NcoI and NotI to confirm the presence of the ~250 bp fragment. The resulting plasmid was named "pZUF-MOD-1" (FIG. 4D; SEQ ID NO:168).

Y. lipolytica strain Y2067U (from Example 10, producing 14% EPA of total lipids) was transformed with pMDGAT1-17 and pZUF-MOD-1, respectively, according to the General Methods. Transformants were grown for 2 days in synthetic MM supplemented with amino acids, followed by 4 days in HGM. The fatty acid profile of two transformants containing pMDGAT1-17 and two transformants containing pZUF-MOD-1 are shown below in Table 18, based on GC analysis (as described in the General Methods). Fatty acids are identified as 18:0, 18:1 (oleic acid), 18:2 (LA), GLA, DGLA, ARA, ETA and EPA; and the composition of each is presented as a % of the total fatty acids.

TABLE 18

Lipid Content In Yarrowia Strain Y2067U Engineered To Overexpress M. alpina DGAT1

| Strain | Total Fatty Acids | | | | | | | |
|---|---|---|---|---|---|---|---|---|
| | 18:0 | 18:1 | 18:2 | GLA | DGLA | ARA | ETA | EPA |
| Y2067U + pZUF-MOD-1 #1 | 1.31 | 6.92 | 12.03 | 23.11 | 5.72 | 1.05 | 3.80 | 13.20 |
| Y2067U + pZUF-MOD-1 #2 | 1.39 | 6.83 | 12.15 | 21.99 | 5.83 | 1.07 | 3.82 | 13.47 |
| Y2067U + pMDGAT1-17 #1 | 0.89 | 7.13 | 10.87 | 24.88 | 5.82 | 1.19 | 3.97 | 14.09 |
| Y2067U + pMDGAT1-17 #2 | 0.86 | 7.20 | 10.25 | 22.42 | 6.35 | 1.26 | 4.38 | 15.07 |

As demonstrated above, expression of the M. alpina DGAT1 from plasmid PMDGATI-17 increased the EPA concentration from ~13.3% in the "control" strains to ~14.1% ("Y2067U+pMDGAT1-17 #1") and ~15.1% ("Y2067U+pMDGAT1-17 #2"), respectively.

Example 16

Identification of DGAT1 Fungal Homologs

The present Example describes the use of the Yarrowia lipolytica and Mortierella alpina DGAT1 sequences (SEQ ID NOs:13 and 17, respectively) to identify orthologous proteins in other fungi.

Orthologous DGAT1 fungal proteins were identified by conducting BLAST searches for similarity to sequences contained in the BLAST "nr" database (comprising all non-redundant GenBank CDS translations, sequences derived from the 3-dimensional structure Brookhaven Protein Data Bank, the SWISS-PROT protein sequence database, EMBL and DDBJ databases). The Yarrowia lipolytica and Mortierella alpina DGAT1 sequences (SEQ ID NOs:13 and 17) were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database, using the BLASTX algorithm (Gish, W. and States, D. J. Nature Genetics 3:266-272 (1993)) provided by the NCBI. These searches resulted in the identification of 4 orthologous proteins (as shown below in Table 19). Table 19 additionally shows the results of sequence comparisons between the Yarrowia lipolytica DGAT1 sequence (SEQ ID NO:13) with each of the DGAT1 proteins disclosed herein, in terms of the observed "% Ident." (defined as the percentage of amino acids that are identical between the two proteins).

TABLE 19

Comparison Of *Yarrowia lipolytica* DGAT1 To Orthologous DGAT1s From Fungi

| Organism | Abbreviation | % Ident | GenBank Accession No., Reference and Annotation | SEQ ID NO |
|---|---|---|---|---|
| *Mortierella alpina* | Ma DGAT1 | 32.4 | — | 18 |
| *Neurospora crassa* strain OR74A | Nc DAGAT1 | 37.0 | XP_322121; gi\|32403016\|ref\| XP_322121.1\|hypothetical protein; gi\|28918105\|gb\| EAA27786.1\|hypothetical protein | 19 |
| *Gibberella zeae* PH-1 | Fm DAGAT1 | 38.1 | EAA77624; gi\|42554781\|gb\| EAA77624.1\|hypothetical protein FG06688.1 | 20 |
| *Magnaporthe grisea* 70-15 | Mg DAGAT1 | 36.2 | EAA52634; gi\|38106308\| gb\|EAA52634.1\|hypothetical protein MG05326.4 | 21 |
| *Aspergillus nidulans* FGSC A4 | An DAGAT1 | 41.7 | EAA57945; gi\|40738755\|gb\|EAA57945.1\| hypothetical protein AN6159.2 | 22 |

Example 17

Identification of Universal and Fungal DGAT1 Motifs

The present Example describes the use of the DGAT1 sequences of the present invention, in conjunction with other known DGAT1 sequences, to identify fungal and universal DGAT1 motifs.

To identify motifs (i.e., a set of amino acids conserved at specific positions along an aligned sequence of evolutionarily related proteins) that are indicative of a DGAT1 protein, it was first necessary to generate an alignment of DGAT1 sequences. For this, the following fungal sequences were used: SEQ ID NOs:14, 18, 19, 20, 21 and 22. Additionally, DGAT1 orthologs from 6 non-fungal sources were also included in the comparative alignment: mouse (Mm DGAT1; GenBank Accession No. AF384160, corresponding to SEQ ID NO:169 herein); soy (Gm DGAT1; SEQ ID NO:16 of US20040088759A1, corresponding to SEQ ID NO:170 herein); *Arabidopsis* (At DGAT1; SEQ ID NO:2 of US20040088759A1, corresponding to SEQ ID NO:171 herein); rice (Os DGAT1; SEQ ID NO:14 of US20040088759A1, corresponding to SEQ ID NO:172 herein); wheat (Ta DGAT1; SEQ ID NO:22 of US20040088759A1, corresponding to SEQ ID NO:174 herein); and *Perilla frutescens* (Pf; GenBank Accession No. AF298815, corresponding to SEQ ID NO:173 herein).

Alignment was done using the Megalign program of DNASTAR using Clustal W with the following parameters: gap penalty=10, gap length penalty=0.2, delay divergent seqs (%)=30, DNA transition weight=0.5 and protein weight matrix by Gonnet series. The results of this alignment are shown in FIG. 8a, 8b, 8c, 8d, 8e, 8f, 8g and 8h. Based on analysis of the alignment, 8 motifs were identified as unique to fungal DGAT1 sequences. Additionally, 7 motifs that were universally present in DGAT1 sequences from plants, animals and fungi were also deduced.

TABLE 20

Fungal and Universal DGAT1 Motifs

| Motif | Alignment Position* | Fungal Motif Sequence and SEQ ID NO | Universal Motif Sequence and SEQ ID NO |
|---|---|---|---|
| #1 | 97–104 | (F/Y)xGFxN(L/I)**(M/G)** (SEQ ID NO:23) | xxGxxNxx (SEQ ID NO:31) |
| #2 | 278–284 | (P/Q)YPxN(I/V)T (SEQ ID NO:24) | n/a |
| #3 | 334–340 | QYAxPx**(L/M)** (SEQ ID NO:25) | Q(Y/W)xxPxx (SEQ ID NO:32) |
| #4 | 364–374 | KL(A/S)**(T/S)x₁S**XX (I/V)WL (wherein x₁ can not be P) (SEQ ID NO:26) | KL(A/S)xxxxxxWL (SEQ ID NO:33) |
| #5 | 418–424 | PV**(Y/N)(Q/T/I)(Y/F)** (F/M)**(K/R)** (SEQ ID NO:27) | PVxxxxx (SEQ ID NO:34) |
| #6 | 415–424 | WN(K/R/S)PV(Y/N)x₁ (Y/F)(F/M)(K/R) (wherein x₁ can not be K) (SEQ ID NO:28) | WNxPVxxxxx (SEQ ID NO:35) |
| #7 | 456–466 | LxGxPTHxx**(I/Y)G** (SEQ ID NO:29) | xxxxPxxxxxx (SEQ ID NO:36) |
| #8 | 513–519 | A(L/F)(L/M)Y(F/Y)X (A/H) (SEQ ID NO:30) | x(L/F)(L/M)Yxxx (SEQ ID NO:37) |

*[Note: Alignment positions are with respect to that of the *Yarrowia lipolytica* DGAT1, herein identified as SEQ ID NO:14. Those residues shown in bold-type face and underlined are conserved only in fungal DGAT1 sequences.]

These motifs, located at positions 97-104, 278-284, 334-340, 364-374, 418-424, 415-424, 456-466 and 513-519 (wherein the alignment positions are with respect to SEQ ID NO:14) in a sequence alignment of a family of protein homologues, have a high degree of conservation among DGAT1 proteins; as such, it is expected that the amino acids residues located therein are essential in the structure, the stability, or the activity of the protein. Based on the sequence conservation observed, one skilled in the art will know how to use the motifs provided as SEQ ID NOs:23-37 as an identifier, or "signature", to determine if a protein with a newly determined sequence belongs to the DGAT1 protein family described herein.

What is claimed is:

1. An isolated nucleic acid molecule encoding a diacylglycerol acyltransferase-1 enzyme, selected from the group consisting of:

(a) an isolated nucleic acid molecule encoding the amino acid sequence as set forth in SEQ ID NO: 18; and (b) an isolated nucleic acid molecule that hybridizes with (a) under the following hybridization conditions: 0.1× SSC, 0.1% SDS, 65° C. and washed with 2×SSC, 0.1% SDS followed by 0.1×SSC, 0.1% SDS; and encodes a protein having diacylglycerol acyltransferase activity or an isolated nucleic acid molecule that is completely complementary to (a) or (b).

2. The isolated nucleic acid molecule of claim 1 as set forth in SEQ ID NO: 17.

3. A chimeric gene comprising the isolated nucleic acid molecule of claim 1 operably linked to suitable regulatory sequences.

4. An isolated transformed host cell comprising the chimeric gene of claim 3.

5. The transformed host cell of claim 4, selected from the group consisting of algae, bacteria, molds, fungi and yeasts.

6. The transformed host cell of claim 5, wherein the yeast is an oleaginous yeast.

7. The transformed host cell of claim 6, wherein the oleaginous yeast cell is selected from the group consisting of *Yarrowia, Candida, Rhodotorula, Rhodosporidium, Cryptococcus, Trichosporon* and *Lipomyces*.

8. The transformed host cell of claim 7, wherein the host cell is *Yarrowia lipolytica*.

* * * * *